(12) United States Patent
Gill et al.

(10) Patent No.: US 12,065,678 B2
(45) Date of Patent: Aug. 20, 2024

(54) CONSTRUCTS, COMPOSITIONS AND METHODS THEREOF HAVING IMPROVED GENOME EDITING EFFICIENCY AND SPECIFICITY

(71) Applicant: DANMARKS TEKNISKE UNIVERSITET, KGS Lyngby (DK)

(72) Inventors: Ryan T. Gill, Denver, CO (US); Tanya Warnecke, Boulder, CO (US); Dominika Joanna Jedrzejczyk, Copenhagen (DK)

(73) Assignee: Danmarks Tekniske Universitet, Lyngby (DK)

( * ) Notice: Subject to any disclaimer, the term of this patent is extended or adjusted under 35 U.S.C. 154(b) by 0 days.

(21) Appl. No.: 18/142,013

(22) Filed: May 1, 2023

(65) Prior Publication Data
US 2023/0340438 A1    Oct. 26, 2023

Related U.S. Application Data

(63) Continuation of application No. 17/780,002, filed as application No. PCT/US2020/061850 on Nov. 23, 2020.

(60) Provisional application No. 62/941,392, filed on Nov. 27, 2019.

(51) Int. Cl.
*C12N 9/22* (2006.01)
*C12N 15/11* (2006.01)
*C12N 15/90* (2006.01)

(52) U.S. Cl.
CPC ............. *C12N 9/22* (2013.01); *C12N 15/11* (2013.01); *C12N 15/90* (2013.01); *C12N 15/902* (2013.01); *C12N 15/907* (2013.01); *C12N 2310/20* (2017.05); *C12N 2800/80* (2013.01)

(58) Field of Classification Search
CPC ........ C12N 9/22; C12N 15/11; C12N 15/902; C12N 15/907; C12N 2310/20; C12N 2800/80
See application file for complete search history.

(56) References Cited

U.S. PATENT DOCUMENTS

| | | |
|---|---|---|
| 8,697,359 B1 | 4/2014 | Zhang |
| 2014/0068797 A1 | 3/2014 | Doudna et al. |
| 2016/0208243 A1 | 7/2016 | Zhang et al. |
| 2018/0155716 A1 * | 6/2018 | Zhang ............... C12N 9/22 |

FOREIGN PATENT DOCUMENTS

| | | | |
|---|---|---|---|
| WO | 2016115179 A1 | 7/2016 | |
| WO | 2017106657 A1 | 6/2017 | |
| WO | 2018013990 A1 | 1/2018 | |
| WO | 2018226972 A2 | 12/2018 | |
| WO | WO-2019157326 A1 * | 8/2019 | ........... C12N 15/102 |

OTHER PUBLICATIONS

International Searching Authority/US, International Search Report and Written Opinion for PCT/US20/61850, mailed Mar. 10, 2021, 11 Pages.
Zetsche, Bernd et al., pf1 is a single RNA-guided endonuclease of a Class 2 CRISPR-Cas system Cell Oct. 22, 2015; 163(3):759-71.

* cited by examiner

*Primary Examiner* — Celine X Qian
*Assistant Examiner* — Tiffany Nicole Grooms
(74) *Attorney, Agent, or Firm* — N.V. Nederlandsch Octrooibureau

(57) ABSTRACT

Embodiments disclosed herein include novel nucleic acid-guided nucleases, novel guide nucleic acids, and novel targetable nuclease systems, and methods of use. In some embodiments, engineered non-naturally occurring nucleic acid-guided nucleases, can be used with known guide nucleic acids in a targetable nuclease system. In certain embodiments, targetable nuclease systems can be used to edit targeted genomes of humans and other species. In some embodiments, methods include, but are not limited to, recursive genetic engineering and trackable genetic engineering methods.

19 Claims, 13 Drawing Sheets
Specification includes a Sequence Listing.

sequences of gRNAs used DNMT1 *in vitro* cleavage assay predicted – cognate gRNAs:

| | | |
|---|---|---|
| ABW1: | GUCUAAAGACCAUAUGAAUUCUACUUUCGUAGAUCGAUGGUCCAUGUCUGUUA | SEQ ID NO: 140 |
| ABW2: | GUCUAAAGGCCUAUAUAAAUUCUACUGUCGUAGAUCGAUGGUCCAUGUCUGUUA | SEQ ID NO: 141 |
| ABW3: | GUCUAUACAGAGACACUUUAAUUCUACUAUUGUAGAUCUGAUGGUCCAUGUCUGUUA | SEQ ID NO: 142 |
| ABW4: | GUCUGAAAGACACAAGUAUAUAAUUCUACUAUUGUAGAUCGAUGUUCCAUGUCUCGUUA | SEQ ID NO: 143 |
| ABW5: | GGCUAUAAGCCUUGUAUAAAUUCUACUAUUGUAGAUCUGAUGGUCCAUGUCUGUUA | SEQ ID NO: 144 |
| ABW6: | GUUGAAACUGUAAGCGAAUGUCUACUUGGUAGAUCUGAUGGUCCAUGUCUGUUA | SEQ ID NO: 145 |
| ABW7: | GCAUGAGAACCAUCUAUUCUAAGGUACUCCAAACCUGAUCUGAUGGUCCAUGUCUCGUUA | SEQ ID NO: 146 |
| ABW8: | GUUGAGUAACCUUAAAUAAUUCUACUGUUGUAGAUCUGAUGGUCCAUGUCUGUUA | SEQ ID NO: 147 |
| ABW9: | AUCUACAACAGUAGAAUUUAAGCUAAGAAUUCUAGACCUGAUGGUCCAUGUCUGUUA | SEQ ID NO: 148 |

Control gRNA: UAAUUCUACUCUGUAGAUCUGAUGGUCCAUGUCUGUUA  SEQ ID NO: 149

STAR gRNA: UAAUUCUACUC – UUGUAGAUCUGAUGGUCCAUGUCUGUUA  SEQ ID NO: 150
dnmt1_s1_1               dnmt1_s1_2

\*  \*   \*DNMT1 amplicon targeting fragments are underlined

\*\* Positive Control

FIG. 2

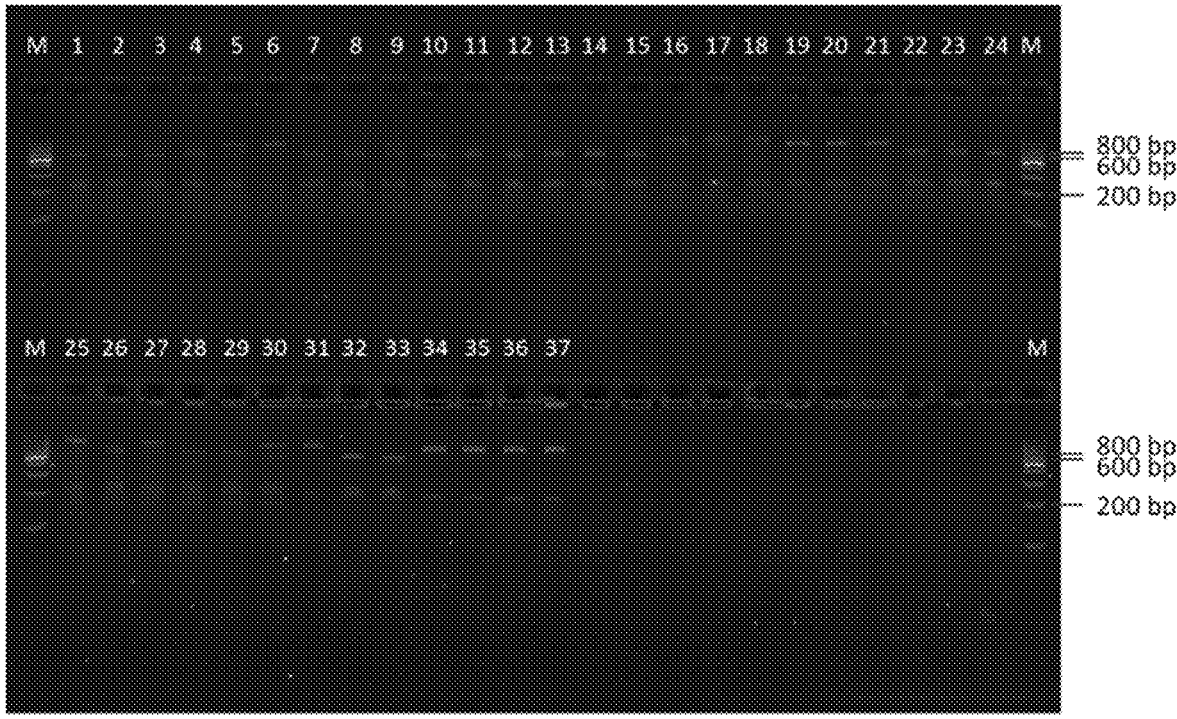

legend:
M. size marker (100bp)
1. ABW1 + cognate gRNA
2. ABW1 + control gRNA
3. ABW1 + STAR gRNA (s1_1_2)
4. ABW2 + cognate gRNA
5. ABW2 + control gRNA
6. ABW2 + STAR gRNA (s1_1_2)
7. ABW3 + control gRNA
8. ABW3 + control gRNA
9. ABW3 + STAR gRNA (s1_1_2)
10. ABW4 + cognate gRNA
11. ABW4 + control gRNA
12. ABW4 + STAR gRNA (s1_1_2)
13. ABW5 + cognate gRNA
14. ABW5 + control gRNA
15. ABW5 + STAR gRNA (s1_1_2)
16. ABW6 + cognate gRNA
17. ABW6 + control gRNA
18. ABW6 + STAR gRNA (s1_1_2)
19. ABW7 + cognate gRNA
20. ABW7 + control gRNA
21. ABW7 + STAR gRNA (s1_1_2)
22. ABW8 + cognate gRNA
23. ABW8 + control gRNA
24. ABW8 + STAR gRNA (s1_1_2)
25. ABW9 + cognate gRNA
26. ABW9 + control gRNA
27. ABW9 + STAR gRNA (s1_1_2)
28. nuclease positive control + cognate gRNA
29. nuclease positive control + control gRNA
30. nuclease positive control + STAR gRNA (s1_1_2)
31. uncut DNA
32. cutting positive control + control gRNA
33. cutting positive control + STAR gRNA (s1_1_2)
34. cutting negative control (STAR s1_1)
35. cutting negative control (STAR s1_2)
36. cutting negative control (nuclease only)
37. cutting negative control (gRNA only)

*active nucleases are underlined

FIG. 5 molar ratio
nuclease : gRNA : target DNA
20 : 60 : 1
10 : 30 : 1
5 : 10 : 1
2.5 : 7.5 : 1
1.25 : 3.75 : 1
0.625 : 1.875 : 1

M = GeneRuler Low Range DNA Ladder

FIG. 8

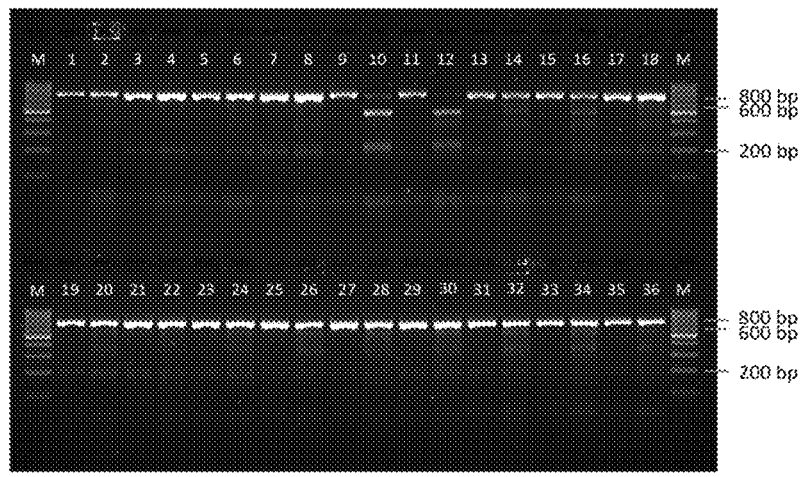

*active nucleases are underlined

M   size marker (100bp)
1.  editing negative control #1
2.  T7 treated editing negative control #1
3.  editing negative control #2
4.  T7 treated editing negative control #2
5.  editing negative control #3
6.  T7 treated editing negative control #3
7.  editing negative control #4
8.  T7 treated editing negative control #4
9.  editing positive control #1
10. T7 treated editing positive control #1
11. editing positive control #2
12. T7 treated editing positive control #2
13. ABW1 + cognate gRNA
14. T7 treated ABW1 + cognate gRNA
15. ABW1 + control gRNA
16. T7 treated ABW1 + control gRNA
17. ABW2 + cognate gRNA
18. T7 treated ABW2 + cognate gRNA
19. ABW2 + control gRNA
20. T7 treated ABW2 + control gRNA
21. ABW3 + cognate gRNA
22. T7 treated ABW3 + cognate gRNA
23. ABW3 + control gRNA
24. T7 treated ABW3 + control gRNA
25. ABW4 + cognate gRNA
26. T7 treated ABW4 + cognate gRNA
27. ABW4 + control gRNA
28. T7 treated ABW4 + control gRNA
29. ABW5 + cognate gRNA
30. T7 treated ABW5 + cognate gRNA
31. ABW5 + control gRNA
32. T7 treated ABW5 + control gRNA
33. ABW8 + cognate gRNA
34. T7 treated ABW8 + cognate gRNA
35. ABW8 + control gRNA
36. T7 treated ABW8 + control gRNA

FIG. 9

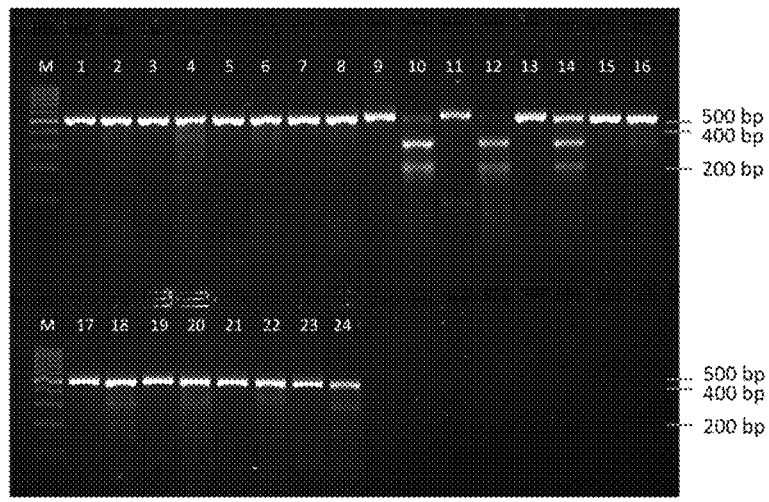

*active nucleases are <u>underline</u>

- M   size 100bp)
1. editing negative control #1
2. T7 treated editing negative control #1
3. editing negative control #2
4. T7 treated editing negative control #2
5. editing negative control #3
6. T7 treated editing negative control #3
7. editing negative control #4
8. T7 treated editing negative control #4
9. <u>editing positive control #1</u>
10. <u>T7 treated editing positive control #1</u>
11. <u>editing positive control #2</u>
12. <u>T7 treated editing positive control #2</u>
13. <u>ABW1 + control gRNA</u>
14. <u>T7 treated ABW1 + control gRNA</u>
15. <u>ABW2 + control gRNA</u>
16. <u>T7 treated ABW2 + control gRNA</u>
17. <u>(ABW3 + control gRNA</u>
18. <u>T7 treated ABW3 + control gRNA</u>
19. <u>ABW4 + control gRNA</u>
20. <u>T7 treated ABW4 + control gRNA</u>
21. ABW5 + control gRNA
22. T7 treated ABW5 + control gRNA
23. <u>ABW8 + control gRNA</u>
24. <u>T7 treated ABW8 + control gRNA</u>

CONSTRUCTS, COMPOSITIONS AND METHODS THEREOF HAVING IMPROVED GENOME EDITING EFFICIENCY AND SPECIFICITY

PRIORITY

This application is a continuation of U.S. application Ser. No. 17/780,002, filed on May 25, 2022, which is a National Stage Entry of PCT/US2020/061850, filed Nov. 23, 2020, which claims priority to U.S. Provisional Application No. 62/941,392, filed Nov. 27, 2019. This provisional application is incorporated herein by reference in its entirety for all purposes.

STATEMENT REGARDING SEQUENCE LISTING

The instant application contains a Sequence Listing which has been submitted via XML copy created on Nov. 29, 2023 referred to as 'ARTN-013_USNTL-CON-T1_SL.xml' having 152 sequences, and is 633, 149 bytes in size.

FIELD

Some embodiments disclosed herein concern novel nucleic acid-guided nucleases, guide nucleic acids (e.g. gRNAs), and targetable nuclease systems, and methods of use. In other embodiments, methods for making and using engineered non-naturally occurring nucleic acid-guided nucleases, guide nucleic acids, and targetable nuclease systems are disclosed. In some embodiments, targetable nuclease systems can be used to edit mammalian such as human genomes or genomes of other species.

BACKGROUND

CRISPR is an abbreviation of Clustered Regularly Interspaced Short Palindromic Repeats. In a palindromic repeat, the sequence of nucleotides is the same in both directions. Each of these palindromic repetitions is followed by short segments of spacer DNA. Small clusters of Cas (CRISPR-associated system) genes are located next to CRISPR sequences. The CRISPR/Cas system is a prokaryotic immune system that can confer resistance to foreign genetic elements such as those present within plasmids and phages providing the prokaryote a form of acquired immunity. RNA harboring a spacer sequence assists Cas (CRISPR-associated) proteins to recognize and cut exogenous DNA. CRISPR sequences, found in approximately 50% of bacterial genomes and nearly 90% of sequenced archaea, select for efficient and robust metabolic and regulatory networks that prevent unnecessary metabolite biosynthesis and optimally distribute resources to maximize overall cellular fitness. The complexity of these networks with limited approaches to understand their structure and function, and the ability to re-program cellular networks to modify these systems for a diverse range of applications have complicated advances in this space. Certain approaches to re-program cellular networks are directed to modifying single genes of complex pathways but as a consequence of modifying single genes, unwanted modifications to the genes or other genes can result, getting in the way of identifying changes necessary to achieve a particular endpoint as well as complicating the endpoint sought by the modification.

CRISPR-Cas driven genome editing and engineering has dramatically impacted biology and biotechnology in general. CRISPR-Cas editing systems require a polynucleotide guided nuclease, a guide polynucleotide (e.g. a guide RNA (gRNA)) that directs by homology the nuclease to cut a specific region of the genome, and, optionally, a donor DNA cassette that can be used to repair the cut dsDNA and thereby incorporate programmable edits at the site of interest. The earliest demonstrations and applications of CRISPR-Cas editing used Cas9 nucleases and associated gRNA. These systems have been used for gene editing in a broad range of species encompassing bacteria, plants, to higher order mammalian systems such as animals and in certain cases, humans. It is well established, however, that key editing parameters such as protospacer adjacent motif (PAM) specificity, editing efficiency, and off-target rates, among others, are species, loci, and nuclease dependent. There is increasing interest in identifying and rapidly characterizing novel nuclease systems that can be exploited to broaden and improve overall editing capabilities.

One version of the CRISPR/Cas system, CRISPR/Cas9, has been modified to provide useful tools for editing targeted genomes. By delivering the Cas9 nuclease complexed with a synthetic guide RNA (gRNA) into a cell, the cell's genome can be cut/edited at a predetermined location, allowing existing genes to be removed and/or new ones added. These systems are useful but have some important limitations regarding efficiency and accuracy of targeted editing, imprecise editing complications, as well as, impediments when used for commercially relevant situations such as gene replacement. Therefore, a need exists for improved nucleic acid guided nuclease systems for directed and accurate editing with improved efficiency.

SUMMARY

Some embodiments disclosed herein concern novel and improved nucleic acid-guided nucleases and guide nucleic acids (e.g. gRNAs) of use to target genomes such as mammalian genomes for improved genome editing and reduced off-targeting. In certain embodiments, eukaryotic or prokaryotic genomes can be edited using targeted systems disclosed herein. In other embodiments, systems for using these novel nucleic acid-guided nucleases with known gRNAs or with novel gRNAs disclosed herein are contemplated. In addition, it is contemplated that known nucleic acid-guided nucleases can be used in systems for genome editing that include novel guide nucleic acids (e.g. gRNAs) disclosed in the instant application.

In other embodiments, methods for making and using engineered non-naturally occurring nucleic acid-guided nucleases, guide nucleic acids, and targetable nuclease systems are disclosed. In some embodiments, targetable nuclease systems can be used to edit human genomes or genomes of other species. In some embodiments, nucleic acid-guided nucleases of use in compositions, methods and systems disclosed herein can be represented by the amino acid sequence represented by one or more of SEQ ID NO: 94 (ABW8), 29 (ABW3), 81 (ABW7), 107 (ABW9), 3 (ABW1), 16 (ABW2), 42 (ABW4), 55 (ABW5), and 68 (ABW6). In other embodiments, nucleic acid-guided nucleases can be represented by the polynucleotides encoding polypeptides represented by one or more of SEQ ID NO: 95-104 (ABW8 variants 1-10), 30-39 (ABW3 variants 1-10), 82-91 (ABW7 variants 1-10), 108-117 (ABW9 variants 1-10), 4-13 (ABW1 variants 1-10), 17-26 (ABW2 variants 1-10), 43-52 (ABW4 variants 1-10), 56-65 (ABW5 variants 1-10), and 69-78 (ABW6 variants 1-10). In other embodiments, gRNAs of use in compositions and methods disclosed herein can be represented by gRNAs represented by SEQ ID NO: 125, 120, 124, 126, 118, 119, 121, 122, 123, 127 and 128 and can be a split gRNA of use as a synthetic tracrRNA and crRNA.

In some embodiments, a nucleic acid-guided nuclease system can include, but is not limited to, an engineered nucleic acid-guided nuclease; and an engineered guide polynucleotide (gRNA) for complexing with the nucleic acid-guided nuclease, wherein the engineered guide polynucleotide has an amino acid sequence selected from SEQ ID NO: 3, 16, 29, 42, 55, 68, 81, 94 and 107. In certain methods, the target region is eukaryotic genome. In other embodiments, the target region a mammalian genome. In other embodiments, a nucleic acid-guided nuclease system can include an engineered nucleic acid-guided nuclease, wherein the engineered nucleic acid-guided nuclease has a nucleic acid sequence represented by SEQ ID NO: 4-13, 17-26, 30-39, 43-52, 56-65, 69-78, 82-91, 95-104 and 108-117 and an engineered guide polynucleotide for complexing with the nucleic acid-guided nuclease. In certain embodiments, the target region is a eukaryotic genome. In other embodiments, the target region a mammalian genome. In certain embodiments, the targeted genome is a prokaryotic genome. In some embodiments, mammalian genomes can include, pets, livestock or other animals. In certain embodiments, mammalian genomes contemplated to be edited by systems disclosed herein can include human genomes for example, adult, children, infant and/or fetal genomes.

In other embodiments, a nucleic acid-guided nuclease system disclosed herein can include, but is not limited to, an engineered nucleic acid-guided nuclease, wherein the engineered nucleic acid-guided nuclease has an amino acid sequence represented by SEQ ID NO: 3, 16, 29, 42, 55, 68, 81, 94 and 107; and an engineered guide polynucleotide for complexing with the nucleic acid-guided nuclease, wherein the engineered guide polynucleotide includes a nucleic acid sequence represented by SEQ ID NO: 118 to SEQ ID NO: 126 or SEQ ID NO: 128. In other embodiments, the engineered polynucleotide (gRNA) represented by SEQ ID NO: 125, 120, 124, 126, 118, 119, 121, 122, 123, 127 and 128 and can be a split gRNA of use as a synthetic tracrRNA and cfRNA. In certain methods, the target region is a eukaryotic genome. In other embodiments, the target region is a mammalian genome (e.g. animal or human genome). In certain embodiments, the targeted genome is a prokaryotic genome.

In other embodiments, methods for modifying a genome are disclosed. In accordance with these embodiments, methods can include, but are not limited to, contacting a targeted genome with an engineered nucleic acid-guided nuclease; and an engineered guide polynucleotide for complexing with the nucleic acid-guided nuclease, wherein the engineered guide polynucleotide includes a nucleic acid sequence represented by SEQ ID NO: 125, 120, 124, 126, 118, 119, 121, 122, 123, 127 and 128; and allowing the nuclease and gRNA to modify the targeted genome. In some embodiments, the engineered polynucleotide (gRNA) disclosed herein can be split into fragments encompassing a synthetic tracrRNA and crRNA of use in methods for targeting a genome. In other embodiments, methods can further include contacting the targeted genome with a novel engineered nucleic acid-guided nuclease wherein the engineered nucleic acid-guided nuclease has an amino acid sequence represented by SEQ ID NO: 3, 16, 29, 42, 55, 68, 81, 94 and 107 or wherein the engineered nucleic acid-guided nuclease has nucleic acid sequence represented by SEQ ID NO: 4-13, 17-26, 30-39, 43-52, 56-65, 69-78, 82-91, 95-104 and 108-117. In other embodiments, the engineered guide nucleic acid and an editing sequence are provided as a single nucleic acid. In other embodiments, the editing sequence further includes a protospacer adjacent motif (PAM) site or a mutation in a protospacer adjacent motif (PAM) site.

In other embodiments, kits are contemplated. In some embodiments, the kit can include an engineered nucleic acid-guided nuclease and a gRNA having a nucleic acid sequence represented by SEQ ID NO: 125, 120, 124, 126, 118, 119, 121, 122, 123, 127 and 128 and a container. In other embodiments, a kit can include an engineered nucleic acid-guided nuclease having a polypeptide sequence represented by SEQ ID NO: 3, 16, 29, 42, 55, 68, 81, 94 and 107 or an engineered nucleic acid-guided nuclease having a nucleic acid sequence represented by SEQ ID NO: 4-13, 17-26, 30-39, 43-52, 56-65, 69-78, 82-91, 95-104 and 108-117; and a container.

Other embodiments include methods of modifying a target region in the genome of a cell, the method includes, but is not limited to, contacting a cell with: a non-naturally occurring nucleic-acid-guided nuclease encoded by a nucleic acid having at least 80% identity to one or more of SEQ ID NO: 4-13, 17-26, 30-39, 43-52, 56-65, 69-78, 82-91, 95-104 and/or 108-117; an engineered guide nucleic acid capable of complexing with the nucleic acid-guided nuclease; and an editing sequence encoding a nucleic acid complementary to said target region having a change in sequence relative to the target region; and permitting the nuclease, guide nucleic acid, and editing sequence to create an edited region in a targeted region of the genome of the cell. In other embodiments, a non-naturally occurring nucleic-acid-guided nuclease encodes an amino acid sequence represented by at least 80% identity to SEQ ID NO: 3, 16, 29, 42, 55, 68, 81, 94 and/or 107. In some embodiments, an engineered guide nucleic acid (e.g. gRNA) and the editing sequence are provided as a single nucleic acid construct. In some embodiments, the engineered polynucleotide (gRNA) disclosed herein can be split into fragments encompassing a synthetic tracrRNA and crRNA of use in methods for targeting a genome. In other embodiments, the single nucleic acid construct can include a protospacer adjacent motif (PAM) site and/or a mutation in a protospacer adjacent motif (PAM) site. In some aspects, the nucleic acid-guided nuclease is encoded by a nucleic acid with at least 85% identity to one or more of SEQ ID NO: 4-13, 17-26, 30-39, 43-52, 56-65, 69-78, 82-91, 95-104 and/or 108-117. In some embodiments, the nucleic acid-guided nuclease is encoded by a nucleic acid having at least 85% identity to SEQ ID NO: 125, 120, 124, 126, 118, 119, 121, 122, 123, 127 and 128.

In yet other embodiments, nucleic acid-guided nuclease systems are disclosed that include, but are not limited to, a non-naturally occurring nuclease encoded by a nucleic acid having at least 80% identity to one or more of SEQ ID NO: 4-13, 17-26, 30-39, 43-52, 56-65, 69-78, 82-91, 95-104 and/or 108-117; a known engineered guide nucleic acid capable of complexing with the nucleic acid-guided nuclease or a novel engineered guide nucleic acid capable of complexing with the nucleic acid-guided nuclease having at least 85% identity to SEQ ID NO: 125, 120, 124, 126, 118, 119, 121, 122, 123, 127 or 128 and an editing sequence, wherein the system can edit a targeted genome in the target region of the genome of the cell facilitated by the nuclease, the engineered guide nucleic acid, and the editing sequence. In some aspects, the nucleic acid-guided nuclease is encoded by a nucleic acid with at least 85% identity to one or more of SEQ ID NO: 4-13, 17-26, 30-39, 43-52, 56-65, 69-78, 82-91, 95-104 and/or 108-117. In some embodiments, the nucleic acid-guided nuclease can be codon optimized for the cell to be edited. In other aspects, the engineered guide nucleic acid and the editing sequence are provided as a single nucleic acid. In some aspects, the single nucleic acid further comprises a wild type or mutated proto-spacer adjacent motif (PAM) site.

In other embodiments, compositions disclosed herein can include a non-naturally occurring nuclease encoded by a nucleic acid having at least 75% identity to one or more of SEQ ID NO: 4-13, 17-26, 30-39, 43-52, 56-65, 69-78, 82-91, 95-104 and/or 108-117. In some aspects, the nucleic acid has at least 80% identity to one or more of SEQ ID NO: 4-13, 17-26, 30-39, 43-52, 56-65, 69-78, 82-91, 95-104 and/or 108-117. In some embodiments, the nucleic acid has at least 90% identity to one or more of SEQ ID NO: 4-13, 17-26, 30-39, 43-52, 56-65, 69-78, 82-91, 95-104 and/or 108-117. In certain embodiments, the nuclease can be codon optimized for use in cells from a particular organism. In certain embodiments, the nuclease is codon optimized for a human genome. In other embodiments, the nuclease is codon optimized for a mammalian genome such as a pet, livestock or other mammal. In certain embodiments, a nuclease disclosed herein can be codon optimized for a bird or fish. In other embodiments, a nuclease disclosed herein can be codon optimized for a plant. In other embodiments, a nuclease disclosed herein can be codon optimized for a prokaryotic genome.

BRIEF DESCRIPTION OF THE FIGURES

The following drawings form part of the present specification and are included to further demonstrate certain embodiments of the present disclosure. Certain embodiments can be better understood by reference to one or more of these drawings in combination with the detailed description of specific embodiments presented herein.

FIG. 2 is an exemplary image illustrating novel guide polynucleotide sequences (e.g. guide RNA (gRNAs)) used in a DNMT1 amplicon in vitro cleavage assay to assess the efficiently of ABW nucleases of some embodiments disclosed herein.

FIG. 5 is an exemplary image illustrating an in vitro cleavage assay to assess the efficiently of ABW nucleases and STAR gRNA of some embodiments disclosed herein.

FIG. 8 is an exemplary image illustrating a T7 endonuclease assay to assess the efficiently of ABW nuclease editing of the DNMT1 gene in Jurkat cells of some embodiments disclosed herein.

FIG. 9 is an exemplary image illustrating a T7 endonuclease assay to assess the efficiently of ABW nuclease editing of the TRAC gene in Jurkat cells of some embodiments disclosed herein.

DETAILED DESCRIPTION

Figure 1:
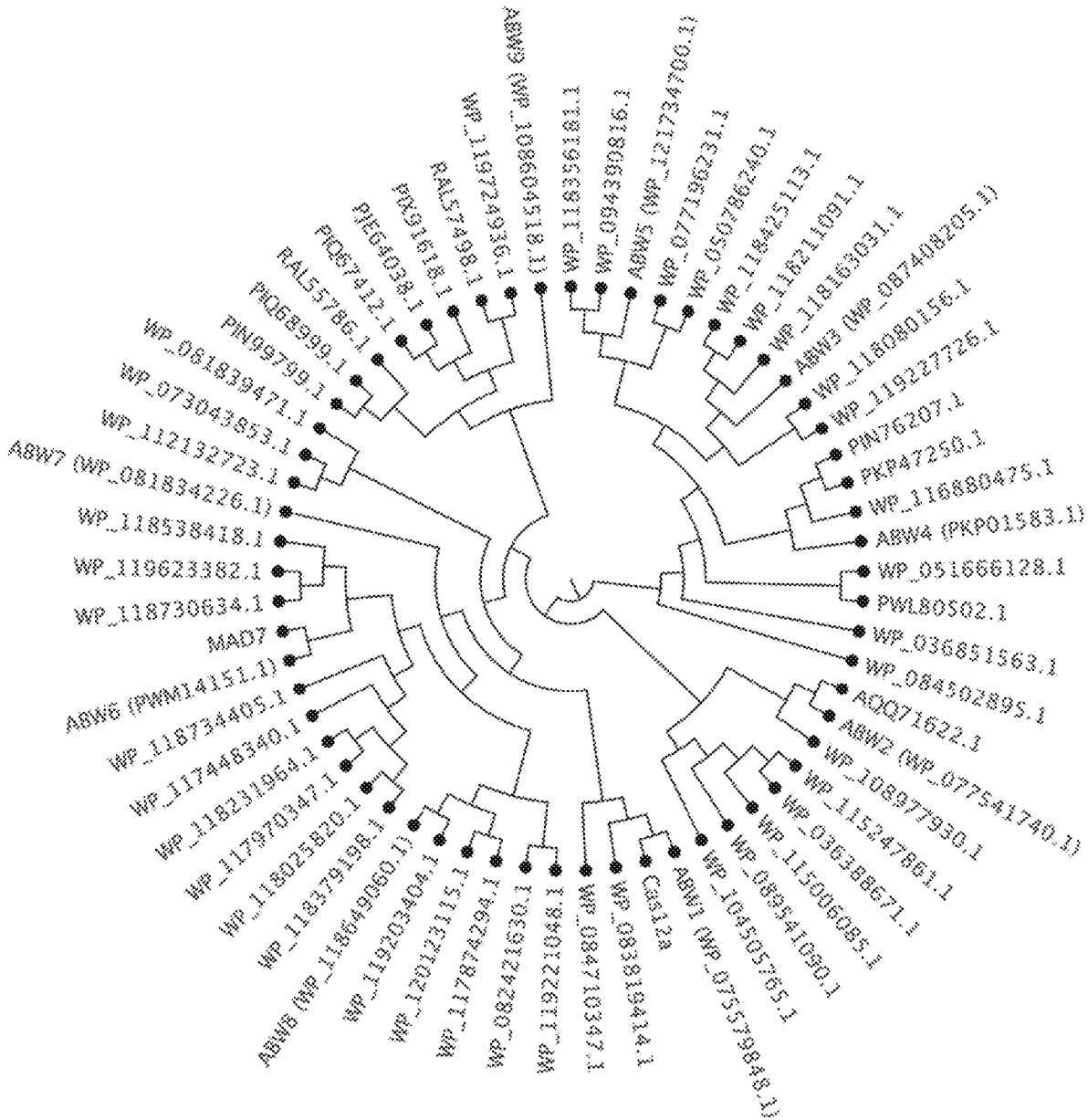
FIG. 1 is an exemplary image illustrating a circular phylogram representing some evolutionary relationships among novel engineered nucleases of some embodiments disclosed herein.

In the following sections, various exemplary compositions and methods are described in order to detail various embodiments of the disclosure. It will be obvious to one of skill in the relevant art that practicing the various embodiments does not require the employment of all or even some of the details outlined herein, but rather that concentrations, times and other details can be modified through routine experimentation. In some cases, well-known methods or components have not been included in the description.

As used herein, the term "modulating" and "manipulating" of genome editing can mean an increase, a decrease, upregulation, downregulation, induction, a change in editing activity, a change in binding, a change cleavage or the like, of one or more of targeted genes or gene clusters of certain embodiments disclosed herein.

In certain embodiments of the present disclosure, there can be employed conventional molecular biology, microbiology, and recombinant DNA techniques within the skill of the art. Such techniques are explained fully in the literature and understood by those of skill in the art.

In other embodiments, primers used herein for preparation per conventional techniques can include sequencing primers and amplification primers. In some embodiments, plasmids and oligomers used in conventional techniques can include synthesized oligomers and oligomer cassettes.

In some embodiments disclosed herein, nucleic acid-guided nuclease systems and methods of use are provided. A nuclease system can include transcripts and other elements involved in the expression of an engineered nuclease disclosed herein, which can include sequences encoding a novel engineered nucleic acid-guided nuclease protein and a guide sequence (gRNA) or a novel gRNA as disclosed herein. In some embodiments, nucleic acid-guided nuclease systems can include at least one CRISPR-associated nucleic acid guided nuclease construct, the disclosure of which are provided herein. In other embodiments, nucleic acid-guided nuclease systems can include at least one known guide sequence (gRNA) or at least one novel gRNA. In some embodiments, an engineered nucleic acid-guided nuclease of the instant invention can be used in systems for editing a gene of interest in humans or other species.

Bacterial and archaeal targetable nuclease systems have emerged as powerful tools for precision genome editing. However, naturally occurring nucleases have some limitations including expression and delivery challenges due to the nucleic acid sequence and protein size. In certain embodiments, novel engineered nucleic acid-guided nuclease constructs disclosed herein can be created for altered targeting of a targeted gene and/or increased efficiency and/or accuracy of targeted gene editing in a subject.

In accordance with these embodiments, it is known that Cas12a is a single RNA-guided CRISPR/Cas endonuclease capable of genome editing having differing features when compared to Cas9. Compared to other known Cas nucleases, Cas12a nucleases can process gRNAs from a transcribed CRISPR array lacking accessory factors (e.g. tracrRNA), recognize T-rich PAMs located 5' of the displaced strand of target DNA, utilize a RuvC endonucleolytic domain to nick both strands of target DNA, and/or can non-specifically cleave single-stranded DNA upon target recognition. In certain embodiments, a Cas12a-based system disclosed herein can allow for fast and reliable introduction of donor DNA into a genome. In some embodiments, a Cas12a-based system disclosed herein can broaden genome editing. CRISPR/Cas12a genome editing has been evaluated in human cells as well as other organisms including plants.

It is known that a Cas12a nuclease recognizes T-rich protospacer adjacent motif (PAM) sequences (e.g. 5'-TTTN-3' (AsCas12a, LbCas12a) and 5'-TTN-3' (FnCas12a); whereas, the comparable sequence for SpCas9 is NGG. The PAM sequence of Cas12a is located at the 5' end of the target DNA sequence, where it is at the 3' end for Cas9. In addition, Cas12a is capable of cleaving DNA distal to its PAM around the +18/+23 position of the protospacer. This cleavage creates a staggered DNA overhang (e.g. sticky ends), whereas Cas9 cleaves close to its PAM after the 3' position of the protospacer at both strands and creates blunt ends. In certain methods, creating altered recognition of nucleases can provide an improvement over Cas9 or Cas12a to improve accuracy. Further, Cas12a is guided by a single crRNA and does not require a tracrRNA, resulting in a shorter gRNA sequence than the gRNA used by Cas9.

It is also known that Cas12a displays additional ribonuclease activity that functions in crRNA processing. Cas12a is used as an editing tool for different species (e.g. *S. cerevisiae*), allowing the use of an alternative PAM sequence compared with the one recognized by CRISPR/Cas9. Novel nucleases disclosed herein can further recognize the same or alternative PAM sequences. These novel nucleases can provide an alternative system for multiplex genome editing as compared with known multiplex approaches and can be used as an improved system in mammalian gene editing.

Well-known Cas12a protein-RNA complexes recognize a T-rich PAM and cleavage leads to a staggered DNA double-stranded break. Cas12a-type nuclease interacts with the pseudoknot structure formed by the 5'-handle of crRNA. A guide RNA segment, composed of a seed region and the 3' terminus, possesses complementary binding sequences with the target DNA sequences. Cas 12a type nucleases characterized to date have been demonstrated to work with a single gRNA and to process gRNA arrays. While Cas 12a-type and Cas9 nuclease systems have proven highly impactful, neither system has been demonstrated to function as predictably as is desired to enable the full range of applications envisioned for gene-editing technologies.

In the current state, a range of efforts have attempted to engineer improved CRISPR editing systems having increased efficiency and accuracy, which have included engineering of the PAM specificity, stability, and sequence of the gRNA and- or the nuclease. For example, chemical modifications of CRISPR/Cas9 gRNA expected to increase gRNA stability was found to lead to a 3.8-fold higher indel frequencies in human cells. In addition, other studies included structure-guided mutagenesis of Cas12a and screened to identify variants with an increased range of recognized PAM sequences. These engineered AsCas12a recognized TYCV and TATV PAMs in addition to the established TTTV sequence, with enhanced activities in vitro and in tested human cells.

In other embodiments, Cas12a-like nucleases and engineered gRNAs disclosed herein are contemplated of use in bacteria, yeast, Archaea, and other prokaryotes. In other embodiments, engineered designer nucleases are contemplated of use in eukaryotes such as mammals as well as of use in birds and fish. In other embodiments, engineered designer nucleases are contemplated of use in plants. In accordance with these embodiments, these constructs are created in order to alter certain features of the wild-type gRNA sequences while preserving other desirable features compared to the control the gRNAs are derived from.

In certain embodiments, engineered gRNA constructs of embodiments disclosed herein can be created from Cas12as gRNAs known in the art or not yet discovered and can include, but are not limited to, *Acidaminococcus massiliensis* sp. (e.g. AM_Cas12a strain Marseille-P2828), *Sedimentisphaera cyanobacteriorum* sp. (SC_Cas12a, strain L21-RPul-D3), *Barnesiella* sp. An22 (B_Cas12a; An22 An22), *Bacteroidetes bacterium HGW-Bacteroidetes*-6 sp. XS5, (BB_Cas12a, 08E140C01), *Parabacteroides distasonis* sp. (PD_Cas12a, strain 8-P5) *Collinsella tanakaei* sp. (CT_Cas12a, isolate CIM:MAG 294), *Lachnospiraceae bacterium* MC2017 sp. (LB_Cas12a, T350), *Coprococcus* sp. AF16-5 (Co_Cas12a, AF16-5 AF16-5.Scaf1), or *Catenovulum* sp. CCB-QB4 (Ca_Cas12a, species CCB-QB4) *Eubacterium rectale*, (a positive control is a derivative of this Cas12a), *Flavobacterium branchiophilum* (FB_Cas12a), and/or a synthetic construct (SC_Cas12a) or similar. In certain embodiments, constructs can include 60% or less identity to a known Cas12a to create a novel nuclease. In certain embodiments, novel Cas12a derived constructs can include constructs with reduced off-targeting rates and/or improved editing functions compared to a control or wild-type Cas12a nuclease.

In some embodiments, off-targeting rates for nuclease constructs disclosed herein can be reduced compared to a control for improved editing. For example, off-targeting rates can be readily tested. In accordance with these embodiments, a wild-type gRNA plasmid can be used to assess baseline off-target editing compared to experimentally designed gRNAs to assess accuracy of novel nucleases compared to control Cas12a nucleases or other nucleases known in the art as a positive control (e.g. MAD7). In certain methods, spacer mutations can be introduced to a plasmid to test when a substitution gRNA sequence is created or a deletion or insertion mutant. Each of these plasmid constructs can be used to test genome editing accuracy and efficiency, for example, with deletions, substitutions or insertions.

In certain embodiments, spacer mutations can be introduced to a plasmid to test when a substitution gRNA sequence is created or a deletion or insertion mutant is created. Each of these plasmid constructs can be used to test genome editing accuracy and efficiency, for example, having a deletion, substitution or insertion. Alternatively, in some embodiments, nuclease constructs created by compositions and methods disclosed herein can be tested for optimal genome editing time on a select target by observing editing efficiencies over predetermined time periods. In accordance with these embodiments, nuclease constructs created by compositions and methods disclosed herein can be tested for optimal genome editing windows to optimize editing efficiency and accuracy.

In some embodiments, nuclease constructs created by compositions and methods disclosed herein having optimal genome editing efficiency and accuracy are an improvement over control nuclease constructs. In some embodiments, nuclease constructs created by compositions and methods disclosed herein can have at least a 10% increase, a 15% increase, a 20% increase or more in enzymatic activity, efficiency and/or accuracy compared to control nucleases. In other embodiments, nuclease constructs created by compositions and methods disclosed herein can have about 10% to about 99.5% or more increase in enzymatic activity and/or editing efficiency and/or editing accuracy compared to nucleases having a native sequence compared to nucleases disclosed herein. In some embodiments, nuclease constructs disclosed herein having increased enzymatic activity and/or editing efficiency compared to control nuclease sequences can have a polypeptide sequence having at least 85% homology to the polypeptide represented by SEQ ID NO: 94 (ABW8), 29 (ABW3), 81 (ABW7), 107 (ABW9), 3 (AWBW1), 16 (AWBW2), 42 (AWBW4), 55 (AWBW5), and/or 68 (AWBW6). In some embodiments, nuclease constructs herein having increased enzymatic activity and/or editing efficiency and/or accuracy compared to control nuclease sequences can have a polynucleotide sequence at least 85% homologous to the polynucleotide encoding the polypeptide having a polynucleotide represented by SEQ ID NO: 95-104 (ABW8 variants 1-10), 30-39 (ABW3 variants 1-10), 82-91 (ABW7 variants 1-10), 108-117 (ABW9 variants 1-10), 4-13 (ABW1 variants 1-10), 17-26 (ABW2 variants 1-10), 43-52 (ABW4 variants 1-10), 56-65 (ABW5 variants 1-10), and/or 69-78 (ABW6 variants 1-10).

In some embodiments, nuclease constructs herein having a polypeptide of at least 85% homology to the polypeptide represented SEQ ID NO: 94 (ABW8) can have increased activity and/or editing accuracy compared to other nuclease constructs. In some embodiments, nuclease constructs herein having a polypeptide of at least 85% homology to the polypeptide represented by SEQ ID NO: 94 (ABW8), 29 (ABW3), 81 (ABW7) and/or 107 (ABW9) can have increased enzymatic activity and/or editing efficiency and/or accuracy compared to other nuclease constructs such as control nuclease constructs or native sequence-containing nucleases.

In some embodiments, nuclease constructs disclosed herein having a polynucleotide encoding a polypeptide having a polynucleotide of at least 85% homology to a polynucleotide represented by SEQ ID NO: 95-104 (ABW8 variants 1-10) can have increased enzymatic activity and/or editing efficiency and/or accuracy compared to control nuclease constructs or nuclease constructs having native sequences. In some embodiments, nuclease constructs disclosed herein having a polynucleotide encoding a polypeptide of at least 85% homology to a polynucleotide represented by SEQ ID NO: 95-104 (ABW8 variants 1-10), 30-39 (ABW3 variants 1-10) or 82-91 (ABW7 variants 1-10) can have increased activity (e.g. editing and/or efficiency) compared to control nuclease constructs or other nuclease constructs.

Examples of target polynucleotides for use with engineered nucleic acid guided nucleases disclosed herein can include a sequence/gene or gene segment associated with a signaling biochemical pathway, e.g., a signaling biochemical pathway-associated gene or polynucleotide. Other embodiments contemplated herein concern examples of target polynucleotides related to a disease-associated genes or polynucleotides.

A "disease-associated" or "disorder-associated" gene or polynucleotide can refer to any gene or polynucleotide which results in a transcription or translation product at an abnormal level compared to a control or results in an abnormal form in cells derived from disease-affected tissues compared with tissues or cells of a non-disease control. It can be a gene that becomes expressed at an abnormally high level; it can be a gene that becomes expressed at an abnormally low level, or where the gene contains one or more mutations and where altered expression or expression directly correlates with the occurrence and/or progression of a health condition or disorder. A disease or disorder-associated gene can refer to a gene possessing mutation(s) or genetic variation that are directly responsible or is in linkage disequilibrium with a gene(s) that is responsible for the cause or progression of a disease or disorder. The transcribed or translated products can be known or unknown, and can be at a normal or abnormal level.

It is understood by one of skill in the relevant art that examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web.

Genetic Disorders contemplated herein can include, but are not limited to:

Neoplasia: Genes linked to this disorder: PTEN; ATM; ATR; EGFR; ERBB2; ERBB3; ERBB4; Notch1; Notch2; Notch3; Notch4; AKT; AKT2; AKT3; HIF; HIFI a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MENI; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc;

Age-related Macular Degeneration: Genes linked to these disorders Abcr; Cc12; Cc2; cp (cemloplasmin); Timp3; cathepsinD; Vldlr; Ccr2;

Schizophrenia Disorders: Genes linked to this disorder: Neuregulinl (Nrgl); Erb4 (receptor for Neuregulin); Complexinl (Cp1×1); Tphl Tryptophan hydroxylase; Tph2 Tryptophan hydroxylase 2; Neurexin 1; GSK3; GSK3a; GSK3b;

Trinucleotide Repeat Disorders: Genes linked to this disorder: 5 HTT (Huntington's Dx); SBMA/SMAXI/AR (Kennedy's Dx); FXN/X25 (Friedrich's Ataxia); ATX3 (Machado-Joseph's Dx); ATXNI and ATXN2 (spinocerebellar ataxias); DMPK (myotonic dystrophy); Atrophin-1 and Atnl (DRPLA Dx); CBP (Creb-BP—global instability); VLDLR (Alzheimer's); Atxn7; Atxn10;

Fragile X Syndrome: Genes linked to this disorder: FMR2; FXR1; FXR2; mGLURS;

Secretase Related Disorders: Genes linked to this disorder: APH-1 (alpha and beta); Presenil n (Psenl); nicastrin (Ncstn); PEN-2;

Others: Genes linked to this disorder: Nosl; Paipl; Nati; Nat2;

Prion—related disorders: Gene linked to this disorder: Prp;

ALS: Genes linked to this disorder: SOD1; ALS2; STEX; FUS; TARDBP; VEGF (VEGF-a; VEGF-b; VEGF-c);

Drug addiction: Genes linked to this disorder: Prkce (alcohol); Drd2; Drd4; ABAT (alcohol); GRIA2; GrmS; Grinl; Htrlb; Grin2a; Drd3; Pdyn; Grial (alcohol);

Autism: Genes linked to this disorder: Mecp2; BZRAP1; MDGA2; SemaSA; Neurexin 1; Fragile X (FMR2 (AFF2); FXR1; FXR2; MglurS);

Alzheimer's Disease Genes linked to this disorder: E1; CHIP; UCH; UBB; Tau; LRP; PICALM; Clusterin; PS1; SORLI; CR1; Vldlr; Ubal; Uba3; CHIP28 (Aqp1, Aquaporin 1); Uchll; Uch13; APP;

Inflammation and Immune-related disorders Genes linked to this disorder: IL-10; IL-1 (IL-1a; IL-1b); IL-13; IL-17 (IL-17a (CTLA8); IL-17b; IL-17c; IL-17d; IL-17f); 11-23; Cx3crl; ptpn22; TNFa; NOD2/CARD15 for IBD; IL-6; IL-12 (IL-12a; IL-12b); CTLA4; Cx3c11, AAT deficiency/ mutations, AIDS (KIR3DL1, NKAT3, NKB1, ANIB11, KIR3DS1, IFNG, CXCL12, SDF1); Autoimmune lymphoproliferative syndrome (TNFRSF6, APT1, FAS, CD95, ALPSIA); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD4OLG, HIGMI, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), 11-23, Cx3crl, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLREIC, ARTEMIS, SCIDA, RAGI, RAG2, ADA, PTPRC, CD45, LCA, IL7R, CD3D, T3D, IL2RG, SCIDX1, SCIDX, IMD4);

Parkinson's, Genes linked to this disorder: x-Synuclein; DJ-1; LRRK2; Parkin; PINK1;

Blood and coagulation disorders: Genes linked to these disorders: Anemia (CDANI, CDA1, RPS19, DBA, PKLR, PK1, NT5C3, UMPH I, PSNI, RHAG, RH50A, NRAMP2, SPTB, ALAS2, ANH I, ASB, ABCB7, ABC7, ASAT); Bare lymphocyte syndrome (TAPBP, TPSN, TAP2, ABCB3, PSF2, RINGI 1, MHC2TA, C2TA, RFX5, RFXAP, RFX5), Bleeding disorders (TBXA2R, P2RX I, P2X I); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FAI, FA, FAA, FAAP95, FAAP90, FLJ34064, FANCB, FANCC, FACC, BRCA2, FANCDI, FANCD2, FANCD, FACD, FAD, FANCE, FACE, FANCF, XRCC9, FANCG, BRIP1, BACHI, FANCJ, PHF9, FANCL, FANCM, ICIAA 1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1);

Cell dysregulation and oncology disorders: Genes linked to these disorders: B-cell non-Hodgkin lymphoma (BCL7A, BCL7); Leukemia (TALI TCL5, SCL, TAL2, FLT3, NBS 1, NBS, ZNFNIAI, IKI, LYF1, HOXD4, HOX4B, BCR, CML, PHL, ALL, ARNT, KRAS2, RASK2, GMPS, AFIO, ARHGEFI2, LARG, KIAA0382, CALM, CLTH, CEBPA, CEBP, CHIC2, BTL, FLT3, KIT, PBT, LPP, NPMI, NUP214, D9S46E, CAN, CAIN, RUNX 1, CBFA2, AMLI, WHSC 1 LI, NSD3, FLT3, AFIQ, NPM 1, NUMAI, ZNF145, PLZF, PML, MYL, STAT5B, AFI 0, CALM, CLTH, ARLI 1, ARLTS1, P2RX7, P2X7, BCR, CML, PHL, ALL, GRAF, NFI, VRNF, WSS, NFNS, PTPNI 1, PTP2C, SHP2, NS 1, BCL2, CCNDI, PRADI, BCLI, TCRA, GATAI, GF1, ERYF1, NFE1, ABLI, NQO1, DIA4, NMORI, NUP214, D9S46E, CAN, CAIN);

Metabolic, liver, kidney disorders: Genes linked to these disorders: Amyloid neuropathy (TTR, PALS); Amyloidosis (APOA1, APP, AAA, CVAP, ADI, GSN, FGA, LYZ, UR, PALS); Cirrhosis (KATI 8, KRT8, CaHIA, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPS, AGL, GDE, GBEI, GYS2, PYGL, PFKM); Hepatic adenoma, 142330 (TCF1, HNFIA, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXINI, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHDI, ARPKD, PKD2, PKD4, PKDTS, PRKCSH, G19P1, PCLD, SEC63);

Muscular/Skeletal Disorders: Genes linked to these disorders: Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMDIA, HGPS, LGMD1B, LMNA, LMN1, EMD2, FPLD, CMDIA); Facioscapulohumeral muscular dystrophy (FSHMDIA, FSHDIA); Muscular dystrophy (FKRP, MDCIC, LGMD2I, *LAMA*2, LAMM, LARGE, KIAA0609, MDCID, FCMD, TTID, MYOT, CAPN3, CANP3, DYSF, LGMD2B, SCGC, LGMD2C, DMDA1, SCG3, SGCA, ADL, DAG2, LGMD2D, DMDA2, SGCB, LGMD2E, SGCD, SGD, LGMD2F, CMDIL, TCAP, LGMD2G, CMDIN, TRIM32, HT2A, LGMD2H, FKRP, MDCIC, LGMD2I, TTN, CMDIG, TMD, LGMD2J, POMTI, CAV3, LGMDIC, SEPNI, SELN, RSMDI, PLECI, PLTN, EBS1); Osteopetrosis (LAPS, BMND1, LRP7, LR3, OPPG, VBCH2, CLCN7, CLC7, OPTA2, OSTMI, GL, TCIRGI, TIRC7, 0C116, OPTB1); Muscular atrophy (VAPB, VAPC, ALS8, SMNI, SMA1, SMA2, SMA3, SMA4, BSCL2, SPG17, GARS, SMAD1, CMT2D, HEXB, IGHMBP2, SMUBP2, CATF1, SMARDI);

Neurological and Neuronal disorders: Genes linked to these disorders: ALS (SOD1, ALS2, STEX, FUS, TARDBP, VEGF (VEGF-a, VEGF-b, VEGF-c); Alzheimer disease (APP, AAA, CVAP, ADI, APOE, AD2, PSEN2, AD4, STM2, APBB2, FE65L1, NOS3, PLAU, URK, ACE, DCPI, ACEI, MPO, PACIP1, PAXIPIL, PTIP, A2M, BLMH, BMH, PSENI, AD3); Autism (Mecp2, BZRAP I, MDGA2, Sema5A, Neurex 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURRI, NOT, TINUR, SNCAIP, TBP, SCA17, SNCA, NACP, PARKI, PARK4, DJI, PARK7, LRRK2, PARKS, PINK1, PARK6, UCHLI, PARKS, SNCA, NACP, PARKI, PARK4, PRKN, PARK-2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulinl (Nrgl), Erb4 (receptor for Neuregulin), Complexinl (Cp1×1), Tphl Tryptophan hydroxylase, Tph2, Tryptophan hydroxylase 2, Neurexin 1, GSK3, GSK3a, GSK3b, 5-HTT (S1c6a4), COMT, DRD (Drd 1a), SLC6A3, DAOA, DTNBP1, Dao (Daol)); Secretase Related Disorders (APH-1 (alpha and beta), Preseni I in (Psenl), nicastrin, (Ncstn), PEN-2, Nosl, Parpl, Natl, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXNI and ATXN2 (spinocerebellar ataxias), DMPK (myotonic dystrophy), Atrophin-1 and Atnl (DRPLA Dx), CBP (Creb-BP-global instability), VLDLR (Alzheimer's), Atxn7, Atxn10);

Occular-related disorders: Genes linked to these disorders: Age-related macular degeneration (Aber, Cc12, Cc2, cp (ceruloplasmin), Timp3, cathepsinD, Vld1r, Ccr2); Cataract (CRYAA, CRYA1, CRYBB2, CRYB2, PITX3, BFSP2, CP49, CP47, CRYAA, CRYA1, PAX6, AN2, MGDA, CRYBAI, CRYBI, CRYGC, CRYG3, CCL, LIM2, MP19, CRYGD, CRYG4, BFSP2, CP49, CP47, HSF4, CTM, HSF4, CTM, MIP, AQPO, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAEI, GJA3, CX46, CZP3, CAE3, CCM1, CAM, KRITI); Corneal clouding and dystrophy (APOA1, TGFBI, CSD2, CDGGI, CSD, BIGH3, CDG2, TACSTD2, TROP2, MISI, VSX1, RINX, PPCD, PPD, KTCN, COL8A2, FECD, PPCD2, PIP5K3, CFD); Cornea plana congenital (KERA, CNA2); Glaucoma (MYOC, TIGR, GLCIA, JOAG, GPOA, OPTN, GLCIE, FIP2, HYPL, NRP, CYPIB1, GLC3A, OPAL, NTG, NPG, CYPIB1, GLC3A); Leber congenital amaurosis (CRB1, RP12, CRX, CORD2, CRD, RPGRIPI, LCA6, CORD9, RPE65, RP20, AIPLI, LCA4, GUCY2D, GUC2D, LCAI, CORD6, RDH12, LCA3); Macular dystrophy (ELOVL4, ADMD, STGD2, STGD3, RDS, RP7, PRPH2, PRPH, AVMD, AOFMD, VMD2);

P13K/AKT Cellular Signaling disorders: Genes linked to these disorders: PRKCE; ITGAM; ITGA5; IRAK1; PRKAA2; EIF2AK2; PTEN; EIF4E; PRKCZ; GRK6; MAPKI; TSC1; PLKI; AKT2; IKBKB; PIK3CA; CDK8; CDKNIB; NFKB2; BCL2; PIK3CB; PPP2RIA; MAPK8; BCL2L1; MAPK3; TSC2; ITGAI; KRAS; EIF4EBP1; RELA; PRKCD; NOS3; PRKAAI; MAPK9; CDK2; PPP2CA; PIMI; ITGB7; YWHAZ; ILK; TP53; RAF1; IKBKG; RELB; DYRKIA; CDKNIA; ITGB1; MAP2K2; JAKI; AKTI; JAK2; PIK3R1; CHUK; PDPK1; PPP2R5C; CTNNB1; MAP2K1; NFKB1; PAK3; ITGB3; CCNDI; GSK3A; FRAP1; SFN; ITGA2; TTK; CSNKIA1; BRAF; GSK3B; AKT3; FOXO1; SOK; HS P90AAI; RP S 6KB1;

ERK/MAPK Cellular Signaling disorders: Genes linked to these disorders: PRKCE; ITGAM; ITGA5; HSPB1; IRAK1; PRKAA2; EIF2AK2; RACI; RAPIA; TLNI; EIF4E; ELK1; GRK6; MAPKI; RAC2; PLK1; AKT2; PIK3CA; CDK8; CREB1; PRKCI; PTK2; FOS; RPS6KA4; PIK3CB; PPP2RIA; PIK3C3; MAPK8; MAPK3; ITGAI; ETSI; KRAS; MYCN; EIF4EBP1; PPARG; PRKCD; PRKAAI; MAPK9; SRC; CDK2; PPP2CA; PIM1; PIK3C2A; ITGB7; YWHAZ; PPPICC; KSR1; PXN; RAF1; FYN; DYRKIA; ITGB1; MAP2K2; PAK4; PIK3R1; STAT3; PPP2R5C; MAP2K1; PAK3; ITGB3; ESRI; ITGA2; MYC; TTK; CSNKIAI; CRKL; BRAE; ATF4; PRKCA; SRF; STATI; SGK;

Glucocorticoid Receptor Cellular Signaling disorders: Genes linked to these disorders: RAC1; TAF4B; EP300; SMAD2; TRAF6; PCAF; ELK1; MAPKI; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKNIC; TRAF2; SERPINE1; NCOA3; MAPK14; TNF; RAF1; IKBKG; MAP3K7; CREBBP; CDKNIA; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP 1; STATI; IL6; HSP90AA1;

Axonal Guidance Cellular Signaling disorders: Genes linked to these disorders: PRKCE; ITGAM; ROCK1; ITGA5; CXCR4; ADAM12; IGF1; RAC1; RAPIA; E1 F4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GUI; WNT5A; ADAM10; MAP2K1; PAK3; ITGB3; CDC42; VEGFA; ITGA2; EPHA8; CRKL; RND1; GSK3B; AKT3; PRKCA;

Ephrin Recptor Cellular Signaling disorders: Genes linked to these disorders: PRKCE; ITGAM; ROCK1; ITGA5; CXCR4; IRAK1; PRKAA2; EIF2AK2; RAC1; RAPIA; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIMI; ITGB7; PXN; RAF1; FYN; DYRKIA; ITGB1; MAP2K2; PAK4; AKTI; JAK2; STAT3; ADAM10; MAP2K1; PAK3; ITGB3; CDC42; VEGFA; ITGA2; EPHA8; TTK; CSNKIA1; CRKL; BRAF; PTPN13; ATF4; AKT3; SGK;

Actin Cytoskeleton Cellular Signaling disorders: Genes linked to these disorders: ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPPICC; PXN; VIL2; RAF1; GSN; DYRKIA; ITGB1; MAP2K2; PAK4; PIP5KIA; PIK3R1; MAP2K1; PAK3; ITGB3; CDC42; APC; ITGA2; TTK; CSNKIA1; CRKL; BRAF; VAV3; SGK;

Huntington's Disease Cellular Signaling disorders: Genes linked to these disorders: PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKC1; HS PA5; REST; GNAQ; PIK3CB; PIK3C3; MAPK8; IGF1R; PRKDI; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3;

Apoptosis Cellular Signaling disorders: Genes linked to these disorders: PRKCE; ROCK1; BID; IRAK1; PRKAA2; EIF2AK2; BAK1; BIRC4; GRK6; MAPKI; CAPNS1; PLKI; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAAI; MAPK9; CDK2; PIMI; TP53; TNF; RAF1; IKBKG; RELB; CASP9; DYRKIA; MAP2K2; CHUK; APAF1; MAP2K1; NFKB1; PAK3; LMNA; CASP2; BIRC2; TTK; CSNKIA1; BRAF; BAX; PRKCA; SGK; CASP3: BTRC3: PARPI;

B Cell Receptor Cellular Signaling disorders: Genes linked to these disorders: RACI; PTEN; LYN; ELK1; MAPK1; RAC2; PTPN11; AKT2; IKBKB; PIK3CA; CREBI; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGRI; PIK3C2A; BTK; MAPK14; RAF1; IKBKG; RELB; MAP3K7; MAP2K2; AKTI; PIK3R1; CHUK; MAP2K1; NFKB1; CDC42; GSK3A; FRAP1; BCL6; BCL10; JUN; GSK3B; ATF4; AKT3; VAV3; RPS6KB1;

Leukocyte Extravasation Cellular Signaling disorders: Genes linked to these disorders: ACTN4; CD44; PRKCE; ITGAM; ROCK1; CXCR4; CYBA; RACI; RAPIA; PRKCZ; ROCK2; RAC2; PTPN11; MMP14; PIK3CA; PRKCI; PTK2; PIK3CB; CXCL12; PIK3C3; MAPK8; PRKDI; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDNI; CDC42; FUR; ITK; CRKL; VAV3; CTTN; PRKCA; MMPI; MMP9;

Integrin Cellular Signaling disorders: Genes linked to these disorders: ACTN4; ITGAM; ROCK1; ITGA5; RACI; PTEN; RAPIA; TLNI; ARHGEF7; MAPKI; RAC2; CAPNS1; AKT2; CAPN2; PIK3CA; PTK2; PIK3CB; PIK3C3; MAPK8; CAV1; CAPN1; ABL1; MAPK3; ITGAI; KRAS; RHOA; SRC; PIK3C2A; ITGB7; PPPICC; ILK; PXN; VASP; RAF1; FYN; ITGB1; MAP2K2; PAK4; AKTI; PIK3R1; TNK2; MAP2K1; PAK3; ITGB3; CDC42; RND3; ITGA2; CRKL; BRAF; GSK3B; AKT3;

Acute Phase Response Cellular Signaling disorders: Genes linked to these disorders: IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKTI; JAK2; PIK3R1; CHUK; STAT3; MAP2K1; NFKB1; FRAP1; CEBPB; JUN; AKT3; ILIRI; IL6;

PTEN Cellular Signaling disorders: Genes linked to these disorders: ITGAM; ITGA5; RAC1; PTEN; PRKCZ; BCL2L11; MAPKI; RAC2; AKT2; EGFR; IKBKB; CBL; PIK3CA; CDKNIB; PTK2; NFKB2; BCL2; PIK3CB; BCL2L1; MAPK3; ITGAI; KRAS; ITGB7; ILK; PDGFRB; INSR; RAF1; IKBKG; CASP9; CDKNIA; ITGB1; MAP2K2; AKTI; PIK3R1; CHUK; PDGFRA; PDPK1; MAP2K1; NFKB1; ITGB3; CDC42; CCND1; GSK3A; ITGA2; GSK3B; AKT3; FOXO1; CASP3;

p53 Cellular Signaling disorders: Genes linked to these disorders: RPS6KB1 PTEN; EP300; BBC3; PCAF; FASN; BRCA1; GADD45A; BIRC5; AKT2; PIK3CA; CHEKI; TP53INP1; BCL2; PIK3CB; PIK3C3; MAPK8; THBS 1; ATR; BCL2L1; E2F1; PMAIP1; CHEK2; TNFASF10B; TP73; RB1; HDAC9; CDK2; PIK3C2A; MAPK14; TP53; LRDD; CDKNIA; HIPK2; AKT1; PIK3R1; RAM2B; APAF1; CTNNB1; SIRTI; CCNDI; PRKDC; ATM; SFN; CDKN2A; JUN; SNAI2; GSK3B; BAX; AKT3;

Aryl Hydrocarbon Receptor Cellular Signaling disorders: Genes linked to these disorders: HSPB1; EP300; FASN; TGM2; RXRA; MAPKI; NQO1; NCOR2; SP1; ARNT; CDKNIB; FOS; CHEK1; SMARCA4; NFKB2; MAPK8; ALDHIA1; ATR; E2F1; MAPK3; NRIPI; CHEK2; RELA; TP73; GSTP1; RB1; SRC; CDK2; AHR; NFE2L2; NCOA3; TP53; TNF; CDKNIA; NCOA2; APAF1; NFKB1; CCND1; ATM; ESRI; CDKN2A; MYC; JUN; ESR2; BAX; IL6; CYPIB1; HSP90AA1;

Xenobiotic Metabolism Cellular Signaling disorders: Genes linked to these disorders: PRKCE; EP300; PRKCZ; RXRA; MAPK1; NQO1; NCOR2; PIK3CA; ARNT; PRKCI; NFKB2; CAMK2A; PIK3CB; PPP2RIA; PIK3C3; MAPK8; PRKDI; ALDHIA1; MAPK3; NRIPI; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1;

SAPL/JNK Cellular Signaling disorders: Genes linked to these disorders: PRKCE; IRAK1; PRKAA2; EIF2AK2; RACI; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRKIA; MAP2K2; PIK3R1; MAP2K1; PAK3; CDC42; JUN; TTK; CSNKIA1; CRKL; BRAF; SGK;

PPAr/RXR Cellular Signaling disorders: Genes linked to these disorders: PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IASI; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBAI; SMAD4; JUN; ILIR1; PRKCA; IL6; HSP90AA1; ADIPOO;

NF-KB Cellular Signaling disorders: Genes linked to these disorders: IRAK1; EIF2AK2; EP300; INS; MYD88; PRKCZ: TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4: PDGFRB; TNF; INSR; LCK; IKBKG; RELB; MAP3K7; CREBBP; AKTI; PIK3R1; CHUK; PDGFRA; NFKB1; TLR2; BCL10; GSK3B; AKT3; TNFAIP3; ILIR1;

Neuregulin Cellular Signaling disorders: Genes linked to these disorders: ERBB4; PRKCE; ITGAM; ITGA5: PTEN; PRKCZ; ELK1; MAPK1; PTPN11; AKT2; EGFR; ERBB2; PRKCI; CDKNIB; STAT5B; PRKD1; MAPK3; ITGA1; KRAS; PRKCD; STAT5A; SRC; ITGB7; RAF1; ITGB1; MAP2K2; ADAM17; AKTI; PIK3R1; PDPK1; MAP2K1; ITGB3; EREG; FRAP1; PSEN1; ITGA2; MYC; NRG1; CRKL; AKT3; PRKCA; HS P90AA1; RPS6KB1;

Wnt and Beta catenin Cellular Signaling disorders: Genes linked to these disorders: CD44; EP300; LRP6; DVL3; CSNKIE; GJA1; SMO; AKT2; *PINI*; CDH1; BTRC;

GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LAPS; CTNNB1; TGFBR1; CCND1; GSK3A; DVL1; APC; CDKN2A; MYC; CSNK1A1; GSK3B; AKT3; SOX2;

Insulin Receptor Signaling disorders: Genes linked to these disorders: PTEN; INS; EIF4E; PTPN1; PRKCZ; MAPK1; TSC1; PTPN11; AKT2; CBL; PIK3CA; PRKCI; PIK3CB; PIK3C3; MAPK8; IASI; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1;

IL-6 Cellular Signaling disorders: Genes linked to these disorders: HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6;

Hepatic Cholestasis Cellular Signaling disorders: Genes linked to these disorders: PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESRI; SREBF1; FGFR4; JUN; IL1R1; PRKCA; IL6;

IGF-1 Cellular Signaling disorders: Genes linked to these disorders: IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1;

NRF2-mediated Oxidative Stress Response Signaling disorders: Genes linked to these disorders: PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1;

Hepatic Fibrosis/Hepatic Stellate Cell Activation Signaling disorders: Genes linked to these disorders: EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9;

PPAR Signaling disorders: Genes linked to these disorders: EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1;

Fc Epsilon RI Signaling disorders: Genes linked to these disorders: PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA;

G-Protein Coupled Receptor Signaling disorders: Genes linked to these disorders: PRKCE; RAPIA; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA;

Inositol Phosphate Metabolism Signaling disorders: Genes linked to these disorders: PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK;

PDGF Signaling disorders: Genes linked to these disorders: EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 VEGF Signaling disorders: Genes linked to these disorders: ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA;

Natural Killer Cell Signaling disorders: Genes linked to these disorders: PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA;

Cell Cycle: G1/S Checkpoint Regulation Signaling disorders: Genes linked to these disorders: HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6;

T Cell Receptor Signaling disorders: Genes linked to these disorders: RAC1; ELK1; MAPK1; IKBKB; CBL; PIK3CA; FOS; NFKB2; PIK3CB; PIK3C3; MAPK8; MAPK3; KRAS; RELA, PIK3C2A; BTK; LCK; RAF1; IKBKG; RELB; FYN; MAP2K2; PIK3R1; CHUK; MAP2K1; NFKB1; ITK; BCL10; JUN; VAV3;

Death Receptor disorders: Genes linked to these disorders: CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3;

FGF Cell Signaling disorders: Genes linked to these disorders: RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF;

GM-CSF Cell Signaling disorders: Genes linked to these disorders: LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1;

Amyotrophic Lateral Sclerosis Cell Signaling disorders: Genes linked to these disorders: BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX;

AKT3; CASP3; BIRC3 PTPNI; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKNIA; MAP2K2; JAK1; AKTI; JAK2; PIK3R1; STAT3; MAP2K1; FRAP1; AKT3; STAT1;

JAK/Stat Cell Signaling disorders: Genes linked to these disorders: PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKNIA; MAP2K2; JAK1; AKTI; JAK2; PIK3R1; STAT3; MAP2K1; FRAP1; AKT3; STATI;

Nicotinate and Nicotinamide Metabolism Cell Signaling disorders: Genes linked to these disorders: PRKCE; IRAK1; PRKAA2; EIF2AK2; GRK6; MAPK1; PLK1; AKT2; CDK8; MAPK8; MAPK3; PRKCD; PRKAAI; PBEF1; MAPK9; CDK2; PIM1; DYRKIA; MAP2K2; MAP2K1; PAK3; NT5E; TTK; CSNKIAI; BRAF; SGK;

Chemokine Cell Signaling disorders: Genes linked to these disorders: CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPPICC; MAPK14; NOX1; RAF1; MAP2K2; MAP2K1; JUN; CCL2; PRKCA;

IL-2 Cell Signaling disorders: Genes linked to these disorders: ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKTI; PIK3R1; MAP2K1; JUN; AKT3;

Synaptic Long Term Depression Signaling disorders: Genes linked to these disorders: PRKCE; IGF1; PRKCZ; PRDX6; LYN; MAPKI; GNAS; PRKCI; GNAQ; PPP2RIA; IGFIR; PRKDI; MAPK3; KRAS; GRN; PRKCD; NOS3; NOS2A; PPP2CA; YWHAZ; RAF1; MAP2K2; PPP2R5C; MAP2K1; PRKCA;

Estrogen Receptor Cell Signaling disorders: Genes linked to these disorders: TAF4B; EP300; CARMI; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESRI; ESR2;

Protein Ubiquitination Pathway Cell Signaling disorders: Genes linked to these disorders: TRAF6; SMURF1; BIRC4; BRCAI; UCHLI; NEDD4; CBL; UBE21; BTRC; HSPA5; USP7; USP10; FBXW7; USP9X; STUB1; USP22; B2M; BIRC2; PARK2; USP8; USP1; VHL; HSP90AA1; BIRC3;

IL-10 Cell Signaling disorders: Genes linked to these disorders: TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; ILIR1; IL6;

VDR/RXR Activation Signaling disorders: Genes linked to these disorders: PRKCE; EP300; PRKCZ; RXRA; GADD45A; HES1; NCOR2; SP1; PRKCI; CDKNIB; PRKD1; PRKCD; RUNX2; KLF4; YY1; NCOA3; CDKNIA; NCOA2; SPP1; LAPS; CEBPB; FOXO1; PRKCA;

TGF-beta Cell Signaling disorders: Genes linked to these disorders: EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5;

Toll-like Receptor Cell Signaling disorders: Genes linked to these disorders: IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN;

p38 MAPK Cell Signaling disorders: Genes linked to these disorders: HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; ILIR1; SRF; STATI; and Neurolrophin/TRK Cell Signaling disorders: Genes linked to these disorders: NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4.

Other cellular dysfunction disorders linked to a genetic modification are contemplated herein for example, FXR/RXR Activation, Synaptic Long Term Potentiation, Calcium Signaling EGF Signaling, Hypoxia Signaling in the Cardiovascular System, LPS/IL-1 Mediated Inhibition of RXR Function LXR/RXR Activation, Amyloid Processing, IL-4 Signaling, Cell Cycle: G2/M DNA Damage Checkpoint Regulation, Nitric Oxide Signaling in the Cardiovascular System Purine Metabolism, cAMP-mediated Signaling, Mitochondrial Dysfunction Notch Signaling Endoplasmic Reticulum Stress Pathway Pyrimidine Metabolism, Parkinson's Signaling Cardiac & Beta Adrenergic Signaling Glycolysis/Gluconeogenesis Interferon Signaling Sonic Hedgehog Signaling Glycerophospholipid Metabolism, Phospholipid Degradation, Tryptophan Metabolism Lysine Degradation Nucleotide Excision Repair Pathway, Starch and Sucrose Metabolism, Aminosugars Metabolism Arachidonic Acid Metabolism, Circadian Rhythm Signaling, Coagulation System Dopamine Receptor Signaling, Glutathione Metabolism Glycerolipid Metabolism Linoleic Acid Metabolism Methionine Metabolism Pyruvate Metabolism Arginine and Praline Metabolism, Eicosanoid Signaling Fructose and Mannose Metabolism, Galactose Metabolism Stilbene, Coumarine and Lignin Biosynthesis Antigen Presentation Pathway, Biosynthesis of Steroids Butanoate Metabolism Citrate Cycle Fatty Acid Metabolism Glycerophospholipid Metabolism, Histidine Metabolism Inositol Metabolism Metabolism of Xenobiotics by Cytochrome p450, Methane Metabolism, Phenylalanine Metabolism, Propanoate Metabolism Selenoamino Acid Metabolism Sphingolipid Metabolism Aminophosphonate Metabolism, Androgen and Estrogen Metabolism Ascorbate and Aldarate Metabolism, Bile Acid Biosynthesis Cysteine Metabolism Fatty Acid Biosynthesis Glutamate Receptor Signaling, NRF2-mediated, Oxidative Stress Response Pentose Phosphate Pathway, Pentose and Glucuronate Interconversions, Retinol Metabolism Riboflavin Metabolism Tyrosine Metabolism Ubiquinone Biosynthesis Valine, Leucine and Isoleucine Degradation Glycine, Serine and Threonine Metabolism Lysine Degradation Pain/Taste, or Mitochondrial Function Developmental Neurology or combinations thereof.

Nucleic acid-guided nucleases disclosed herein can encompass a native sequence, an engineered sequence, or engineered nucleotide sequences of synthetized variants. Non-limiting examples of types of engineering that can be done to obtain a non-naturally occurring nuclease system are as follows. Engineering can include codon optimization to facilitate expression or improve expression in a host cell, such as a heterologous host cell. Engineering can reduce the size or molecular weight of the nuclease in order to facilitate expression or delivery. Engineering can alter PAM selection in order to change PAM specificity or to broaden the range of recognized PAMs. Engineering can alter, increase, or decrease stability, processivity, specificity, or efficiency of a targetable nuclease system. Engineering can alter, increase, or decrease protein stability. Engineering can alter, increase, or decrease processivity of nucleic acid scanning. Engineering can alter, increase, or decrease target sequence specificity. Engineering can alter, increase, or decrease nuclease activity. Engineering can alter, increase, or decrease editing efficiency. Engineering can alter, increase, or decrease transformation efficiency. Engineering can alter, increase, or decrease nuclease or guide nucleic acid expression. As used herein, a non-naturally occurring nucleic acid sequence can be an engineered sequence or engineered nucleotide sequences of synthetized variants. Such non-naturally occurring nucleic acid sequences can be amplified, cloned, assembled, synthesized, generated from synthesized oligonucleotides or dNTPs, or otherwise obtained using methods known by those skilled in the art. Examples of non-naturally occurring nucleic acid sequences which are disclosed herein include those for nucleic acid-guided nucleases with engineered sequences (e.g., SEQ ID NO: 4-13, 17-26, 30-39, 43-52, 56-65, 69-78, 82-91, 95-104 and 108-117) and those for nucleic acid-guided nucleases with engineered nucleotide sequences of synthetized variants (e.g., SEQ ID NO: 125, 120, 124, 126, 118, 119, 121, 122, 123, 127 and 128).

Disclosed herein are nucleic acid-guided nucleases. Subject nucleases are functional in vitro, or in prokaryotic, archaeal, or eukaryotic cells for in vitro, in vivo, or ex vivo applications. Suitable nucleic acid-guided nucleases can be from an organism from a genus which includes but is not limited to Thiomicrospira, Succinivibrio, Candidatus, Porphyromonas, Acidaminococcus, Acidomonococcus, Barnesiella, Prevotella, Smithella, Moraxella, Synergistes, Francisella, Leptospira, Catenibacterium, Kandleria, Clostridium, Dorea, Coprococcus, Enterococcus, Fructobacillus, Weissella, Pediococcus, Collinsella, Corynebacter, Sutterella, Legionella, Treponema, Roseburia, Filifactor, Lachnospiraceae, Eubacterium, Sedimentisphaera, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Parabacteroides, Staphylococcus, Nitratifractor, Mycoplasma, Alicyclobacillus, Brevibacilus, Bacillus, Bacteroidetes, Brevibacilus, Carnobacterium, Clostridiaridium, Clostridium, Desulfonatronum, Desulfovibrio, Helcococcus, Leptotrichia, Listeria, Methanomethyophilus, Methylobacterium, Opitutaceae, Paludibacter, Rhodobacter, Sphaerochaeta, Tuberibacillus, Oleiphilus, Omnitrophica, Parcubacteria, and Campylobacter. Species of organism of such a genus can be as otherwise herein discussed. Suitable gRNAs can be from an organism from a genus or unclassified genus within a kingdom which includes but is not limited to Firmicute, Actinobacteria, Bacteroidetes, Proteobacteria, Spirochates, and Tenericutes. Suitable gRNAs can be from an organism from a genus or unclassified genus within a phylum which includes but is not limited to Erysipelotrichia, Clostridia, Bacilli, Actinobacteria, Bacteroidetes, Catenovulum, Coprococcus, Flavobacteria, Alphaproteobacteria, Betaproteobacteria, Gammaproteobacteria, Deltaproteobacteria, Epsilonproteobacteria, Spirochaetes, and Mollicutes. Suitable gRNAs can be from an organism from a genus or unclassified genus within an order which includes but is not limited to Clostridiales, Lactobacillus, Actinomycetales, Bacteroidales, Flavobacteriales, Rhizobiales, Rhodospirillales, Burkholderiales, Neisseriales, Legionellales, Nautiliales, Campylobacterales, Spirochaetales, Mycoplasmatales, and Thiotrichales. Suitable gRNAs can be from an organism from a genus or unclassified genus within a family which includes but is not limited to, Lachnospiraceae, Enterococcaceae, Leuconostocaceae, Lactobacilluseae, Streptococcaceae, Peptostreptococcaceae, Staphylococcaceae, Eubacteriaceae, Corynebactrineae, Bacteroidaceae, Flavobacterium, Cryomoorphaceae, Rhodobiaceae, Rhodospirillaceae, Acetobacteraceae, Sutterellaceae, Neisseriaceae, Legionellaceae, Nautiliaceae, Campylobacteraceae, Spirochaetaceae, Mycoplasmataceae, Pisciririckettsiaceae, and Francisellaceae. In some embodiments, suitable gRNAs can be from an organism from a genus or unclassified genus within a family which includes Acidaminococcus, Sedimentisphaera, Barnesiella sp., Bacteroidetes, Parabacteroides, Lachnospiraceae, Coprococcus sp., Catenovulum sp., and Collinsella. Other nucleic acid-guided nucleases have been described in US Patent Application Publication No. US20160208243 filed Dec. 18, 2015, US Application Publication No. US20140068797 filed Mar. 15, 2013, U.S. Pat. No. 8,697,359 filed Oct. 15, 2013, and Zetsche et al., Cell 2015 Oct. 22; 163(3):759-71, each of which are incorporated herein by reference in their entirety.

Some nucleic acid-guided nucleases suitable for use in the methods, systems, and compositions of the present disclosure can include, but are not limited to, those derived from an organism such as, but not limited to, Thiomicrospira sp. XS5, Eubacterium rectale, Succinivibrio dextrinosolvens, Candidatus Methanoplasma termitum, Candidatus Methanomethylophilus alvus, Porphyromonas crevioricanis, Flavobacterium branchiophilum, Acidaminococcus Sp., Acidomonococcus sp., Lachnospiraceae bacterium COE1, Prevotella brevis ATCC 19188, Smithella sp. SCADC, Moraxella bovoculi, Synergistes jonesii, Bacteroidetes oral taxon 274, Francisella tularensis, Leptospira inadai serovar Lyme str. 10, Acidomonococcus sp. crystal structure (5B43) S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis 1, Prevotella albensis, Lachnospiraceae bacterium MC2017 1, Butyrivibrio proteoclasticus, Butyrivibrio proteoclasticus B316, Peregrinibacteria bacterium GW2011_GWA2_33_10, Parcubacteria bacterium GW2011_GWC2_44_17, Smithella sp. SCADC, Acidaminococcus sp. BV3L6, Lachnospiraceae bacterium MA2020, Candidatus Methanoplasma termitum, Eubacterium eligens, Moraxella bovoculi 237, Leptospira inadai, Lachnospiraceae bacterium ND2006, Porphyromonas crevioricanis 3, Prevotella disiens, Porphyromonas macacae, Catenibacterium sp. CAG: 290, Kandleria vitulina, Clostridiales bacterium KA00274, Lachnospiraceae bacterium 3-2, Dorea longicatena, Coprococcus catus GD/7, Enterococcus columbae DSM 7374, Fructobacillus sp. EFB-NI, Weissella halotolerans, Pediococcus acidilactici, Lactobacillus curvatus, Streptococcus pyogenes, Lactobacillus versmoldensis, Filifactor alocis ATCC 35896, Alicyclobacillus acidoterrestris, Alicyclobacillus acidoterrestris ATCC 49025, Desulfovibrio inopinatus, Desulfovibrio inopinatus DSM 10711, Oleiphilus sp. Oleiphilus sp. HI0009, Candidtus kefeldibacteria, Parcubacteria CasY.4, Omnitrophica WOR 2 bacterium GWF2, Bacillus sp. NSP2.1, Bacillus thermoamylovorans, Catenovulum sp. CCB-QB4, Coprococcus sp. AF16-5, Lachnospiraceae bacterium MC2017, Collinsella tanakaei, Parabacteroides distasonis, Bacteroidetes bacterium HGW-Bacteroidetes-6, Barnesiella sp. An22, Sedimentisphaera cyanobacteriorum, and Acidaminococcus massiliensis.

In some embodiments, a nucleic acid-guided nuclease disclosed herein includes an amino acid sequence having at least 50% amino acid identity to any one of SEQ ID NO: 3, 16, 29, 42, 55, 68, 81, 94 and/or 107. In some embodiments, a nucleic acid-guided nuclease disclosed herein includes a polypeptide having an amino acid sequence of about 60%, about 65%, or about 75%, or about 85%, or about 95%, or about 99% or about 99.5% identity to about 100% to amino acid sequences of one or more of SEQ ID NO: 3, 16, 29, 42, 55, 68, 81, 94 and/or 107. In some embodiments, a nucleic acid-guided nuclease disclosed herein includes an amino acid sequence having about 85%, about 90%, or about 95%, or about 99%, or about 99.5% or about 100%, amino acid identity to any one of SEQ ID NO: 3, 16, 29, 42, 55, and/or 94.

In some embodiments, a guide RNA (gRNA) disclosed herein includes a nucleic acid sequence of at least 50% amino acid identity to any one of SEQ ID NO: 125, 120, 124, 126, 118, 119, 121, 122, 123, 127 and 128. In some embodiments, a gRNA disclosed herein includes a nucleic acid sequence of at least 10%, 20%, 30%, 40%, 50%, 60%, 65%, 70%, 75%, 80%, 85%, 90%, 95%, greater than 95%, or 100% nucleic acid identity to any one of SEQ ID NO: 125, 120, 124, 126, 118, 119, 121, 122, 123, 127 and 128. In some embodiments, a gRNA disclosed herein includes a nucleic acid sequence of at least 50%, or about 60%, about 65%, or about 75%, or about 85%, or about 95%, or about 99% or about 99.5% identity to about 100% to, nucleic acid identity to any one of SEQ ID NO: 125, 120, 124, 126, 118, 119, 121, 122, 123, 127 and 128. In some embodiments, the engineered polynucleotide (gRNA) can be split into fragments encompassing a synthetic tracrRNA and crRNA. In some embodiments, a crRNA disclosed herein can include a nucleic acid sequence of at least 50%, or about 60%, about 65%, or about 75%, or about 85%, or about 95%, or about 99% or about 99.5% identity to about 100% to, nucleic acid identity to any one of SEQ ID NO: 129-139. In some embodiments, a crRNA disclosed herein can include a nucleic acid sequence of at least 50%, or about 60%, or about 65%, or about 75%, or about 85%, or about 95%, or about 99% or about 99.5% identity to about 100% to, nucleic acid identity to any one of SEQ ID NO: 129-137.

In some embodiments, gRNA disclosed herein can include a nucleic acid sequence of at least 50% nucleic acid identity to SEQ ID NO: 127. In other embodiments, a gRNA disclosed herein can include a nucleic acid sequence of about 10%, 20%, 30%, 40%, 50%, 60%, 65%, 70%, 75%, 80%, 85%, 90%, 95%, greater than 95%, or 100% nucleic acid identity to SEQ ID NO: 127. In some embodiments, a gRNA disclosed herein includes a nucleic acid sequence of at least 50%, or about 60%, about 65%, or about 75%, or about 85%, or about 95%, or about 99% or about 99.5% identity to about 100%, nucleic acid identity to SEQ ID NO: 127.

In some embodiments, a nucleic acid-guided nuclease disclosed herein includes a nucleic acid sequence of at least 50% nucleic acid sequence identity to any one of SEQ ID NO: 4-13, 17-26, 30-39, 43-52, 56-65, 69-78, 82-91, 95-104 and/or 108-117. In some embodiments, a nucleic acid-guided nuclease disclosed herein includes a nucleic acid sequence of about 60%, or about 65%, or about 70%, or about 75%, or about 80%, or about 85%, or about 90%, or about 95%, greater than 95%, or 100% amino acid identity to any one of SEQ ID NO: 4-13, 17-26, 30-39, 43-52, 56-65, 69-78, 82-91, 95-104 and/or 108-117. In some embodiments, a nucleic acid-guided nuclease disclosed herein includes a nucleic acid sequence of about 60%, 65%, 70%, 75%, 80%, 85%, 90%, 95%, greater than 95%, nucleic acid identity to any one of SEQ ID NO: 4-13, 17-26, 30-39, 43-52, 56-65, and/or 95-104.

In some instances, a nucleic acid-guided nuclease disclosed herein is encoded from a nucleic acid sequence. Such a nucleic acid can be codon optimized for expression in a desired host cell. Suitable host cells can include, as non-limiting examples, prokaryotic cells such as *E. coli, P. aeruginosa, B. subtilus,* and *V. natriegens,* and *S. cerevisiae,* eukaryotic cells, plant cells, insect cells, nematode cells, amphibian cells, fish cells, or mammalian cells, including human cells.

A nucleic acid sequence encoding a nucleic acid-guided nuclease can be operably linked to a promoter. Such nucleic acid sequences can be linear or circular. The nucleic acid sequences can be encompassed on a larger linear or circular nucleic acid sequence that comprises additional elements such as an origin of replication, selectable or screenable marker, terminator, other components of a targetable nuclease system, such as a guide nucleic acid, or an editing or recorder cassette as disclosed herein. In some aspects, nucleic acid sequences can include a at least one glycine, at least one 6X histidine tag (SEQ ID NO: 151), and/or at least one 3×nuclear localization signal tag. Larger nucleic acid sequences can be recombinant expression vectors, as are described in more detail later.

gRNAs

In general, a guide polynucleotide can complex with a compatible nucleic acid-guided nuclease and can hybridize with a target sequence, thereby directing the nuclease to the target sequence. A subject nucleic acid-guided nuclease capable of complexing with a guide polynucleotide can be referred to as a nucleic acid-guided nuclease that is compatible with the guide polynucleotide. In addition, a guide polynucleotide capable of complexing with a nucleic acid-guided nuclease can be referred to as a guide polynucleotide or a guide nucleic acid that is compatible with the nucleic acid-guided nucleases. In some embodiments, an engineered polynucleotide (gRNA) disclosed herein can be split into fragments encompassing a synthetic tracrRNA and crRNA. Examples of gRNA can include, but are not limited to, gRNAs represented in Table 1.

TABLE 1

Exemplary gRNAs

| gRNA SEQ. ID NO. | gRNA Nucleotide Sequence | compatible nucleic acid-guided nuclease |
|---|---|---|
| 118 | GUCUAAAAGACCAUAUGAAUUUCUACUU UCGUAGAUNNNNNNNNNNNNNNNNNNNNN | ABW1 |
| 119 | GUCUAAAGGCCUUAUAAAAUUUCUACUG UCGUAGAUNNNNNNNNNNNNNNNNNNNNN | ABW2 |
| 120 | GUCUAUACAGACACUUUAAUUUCUACUA UUGUAGAUNNNNNNNNNNNNNNNNNNNNN | ABW3 |
| 121 | GUCUGAAAGACAAGUAUAAUUUCUACUA UUGUAGAUNNNNNNNNNNNNNNNNNNNNN | ABW4 |
| 122 | GGCUAUAAGCCUUGUAUAAUUUCUACUA UUGUAGAUNNNNNNNNNNNNNNNNNNNNN | ABW5 |
| 123 | GUUGAAACUGUAAGCGGAAUGUCUACUU GGGUAGAUNNNNNNNNNNNNNNNNNNNNN | ABW6 |
| 124 | GCAUGAGAACCAUGCAUUUCUAAGGUAC UCCAAAACNNNNNNNNNNNNNNNNNNNNN | ABW7 |
| 125 | GUUGAGUAACCUUAAAUAAUUUCUACUG UUGUAGAUNNNNNNNNNNNNNNNNNNNNN | ABW8 |
| 126 | AUCUACAACAGUAGAAAUUUAAGCUAAG GCUUAGACNNNNNNNNNNNNNNNNNNNNN | ABW9 |

TABLE 1-continued

Exemplary gRNAs

| gRNA SEQ. ID NO. | gRNA Nucleotide Sequence | compatible nucleic acid-guided nuclease |
|---|---|---|
| 127 | UAAUUCUACUCUUGUAGAUNNNNNNNN NNNNNNNNNNNN | Cas12A |
| 128 | UAAUUUCUACUC-UUGUAGAUNNNNNNNNNNNNNNNNNNNN | STAR |

A guide polynucleotide can be DNA. A guide polynucleotide can be RNA. A guide polynucleotide can include both DNA and RNA. A guide polynucleotide can include modified or non-naturally occurring nucleotides. In cases where the guide polynucleotide comprises RNA, the RNA guide polynucleotide can be encoded by a DNA sequence on a polynucleotide molecule such as a plasmid, linear construct, or editing cassette as disclosed herein.

A guide polynucleotide can comprise a guide sequence. A guide sequence is a polynucleotide sequence having sufficient complementarity with a target polynucleotide sequence to hybridize with the target sequence and direct sequence-specific binding of a complexed nucleic acid-guided nuclease to the target sequence. The degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment can be determined with the use of any suitable algorithm for aligning sequences. In some embodiments, a guide sequence can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In other embodiments, a guide sequence can be less than about 75, 50, 45, 40, 35, 30, 25, 20 nucleotides in length. Preferably the guide sequence is 10-30 nucleotides long. The guide sequence can be 15-20 nucleotides in length. The guide sequence can be 15 nucleotides in length. The guide sequence can be 16 nucleotides in length. The guide sequence can be 17 nucleotides in length. The guide sequence can be 18 nucleotides in length. The guide sequence can be 19 nucleotides in length. The guide sequence can be 20 nucleotides in length.

A guide polynucleotide can include a scaffold sequence. In general, a "scaffold sequence" can include any sequence that has sufficient sequence to promote formation of a targetable nuclease complex, wherein the targetable nuclease complex includes, but is not limited to, a nucleic acid-guided nuclease and a guide polynucleotide can include a scaffold sequence and a guide sequence. Sufficient sequence within the scaffold sequence to promote formation of a targetable nuclease complex can include a degree of complementarity along the length of two sequence regions within the scaffold sequence, such as one or two sequence regions involved in forming a secondary structure. In some cases, the one or two sequence regions are included or encoded on the same polynucleotide. In some cases, the one or two sequence regions are included or encoded on separate polynucleotides. Optimal alignment can be determined by any suitable alignment algorithm, and can further account for secondary structures, such as self-complementarity within either the one or two sequence regions. In some embodiments, the degree of complementarity between the one or two sequence regions along the length of the shorter of the two when optimally aligned can be about or more than about 25%, 30%, 40%, 50%, 60%, 70%, 80%, 90%, 95%, 97.5%, 99%, or higher. In some embodiments, at least one of the two sequence regions can be about or more than about 5, 6, 7, 8, 9, 10, 11, 12, 13, 14, 15, 16, 17, 18, 19, 20, 25, 30, 40, 50, or more nucleotides in length.

A scaffold sequence of a subject guide polynucleotide can comprise a secondary structure. A secondary structure can comprise a pseudoknot region. In some cases, binding kinetics of a guide polynucleotide to a nucleic acid-guided nuclease is determined in part by secondary structures within the scaffold sequence. In some cases, binding kinetics of a guide polynucleotide to a nucleic acid-guided nuclease is determined in part by nucleic acid sequence with the scaffold sequence. In some aspects, the invention provides a nuclease that binds to a guide polynucleotide can include a conserved scaffold sequence. For example, the nucleic acid-guided nucleases for use in the present disclosure can bind to a conserved pseudoknot region.

An engineered guide polynucleotide, or engineered gRNA, can be the sequence of any one of SEQ ID NO: 125, 120, 124, 126, 118, 119, 121, 122, 123, 127 and 128 or another suitable known gRNA. In some embodiments, the engineered polynucleotide (gRNA) can be split into fragments encompassing a synthetic tracrRNA and crRNA. In some examples, any one of SEQ ID NO: 125, 120, 124, 126, 118, 119, 121, 122, 123, 127 and 128 can be split into fragments encompassing a synthetic tracrRNA and crRNA.

As used herein, "guide nucleic acid" or "guide polynucleotide" can refer to one or more polynucleotides and can include 1) a guide sequence capable of hybridizing to a target sequence and 2) a scaffold sequence capable of interacting with or complexing with a nucleic acid-guided nuclease as described herein. A guide nucleic acid can be provided as one or more nucleic acids. In some embodiments, the guide sequence and the scaffold sequence are provided as a single polynucleotide. In other aspects, guide nucleic acid can include at least one amplicon targeting fragments.

A guide nucleic acid can be compatible with a nucleic acid-guided nuclease when the two elements can form a functional targetable nuclease complex capable of cleaving a target sequence. In certain methods, a compatible scaffold sequence for a compatible guide nucleic acid can be found by scanning sequences adjacent to a native nucleic acid-guided nuclease loci. For example, native nucleic acid-guided nucleases can be encoded on a genome within proximity to a corresponding compatible guide nucleic acid or scaffold sequence.

Nucleic acid-guided nucleases can be compatible with guide nucleic acids that are not found within the nucleases endogenous host. Such orthogonal guide nucleic acids can be determined by empirical testing. Orthogonal guide nucleic acids can come from different bacterial species or be synthetic or otherwise engineered to be non-naturally occurring.

Orthogonal guide nucleic acids that are compatible with a common nucleic acid-guided nuclease can comprise one or more common features. Common features can include sequence outside a pseudoknot region. Common features can include a pseudoknot region. Common features can include a primary sequence or secondary structure.

A guide nucleic acid can be engineered to target a desired target sequence by altering the guide sequence such that the guide sequence is complementary to the target sequence, thereby allowing hybridization between the guide sequence and the target sequence. A guide nucleic acid with an engineered guide sequence can be referred to as an engineered guide nucleic acid. Engineered guide nucleic acids are often non-naturally occurring and are not found in nature.

Engineered guide nucleic acids can be formed using a Synthetic Tracr RNA (STAR) system. STAR, when combined with a Cas12a protein, can form at least one ribonucleoprotein (RNP) complex that targets a specific genomic locus. STAR takes advantage of the natural properties of the CRISPR (Clustered Regularly Interspaced Short Palindromic Repeats) where the CRISPR system functions much like an immune system against invading viruses and plasmid DNA. Short DNA sequences (spacers) from invading viruses are incorporated at CRISPR loci within the bacterial genome and serve as "memory" of previous infections. Reinfection triggers complementary mature CRISPR RNA (crRNA) to find a matching viral sequence. Together, the crRNA and trans-activating crRNA (tracrRNA) guide CRISPR-associated (Cas) nuclease to cleave double-strand breaks in "foreign" DNA sequences. The prokaryotic CRISPR "immune system" has been engineered to function as an RNA-guided, mammalian genome editing tool that is simple, easy and quick to implement. STAR (which includes synthetic crRNA and tracrRNA) when combined with Cas12a protein can form ribonucleoprotein (RNP) complexes that target a specific genomic locus. Engineered guide nucleic acids formed with the RNA (STAR) system can result in a split gRNA. An example of a split gRNA for use as disclosed herein can include the sequence represented by SEQ ID NO: 128.

In some embodiments, a ribonucleoprotein (RNP) complex of use herein can include at least one nuclease disclosed herein. In some aspects, a RNP complex can include at least one nuclease having an amino acid sequence of about 75%, about 85%, about 95%, about 99%, or is identical to one or more sequences of SEQ ID NOs: 4-13, 17-26, 30-39, 43-52, 56-65, 69-78, 82-91, 95-104 and 108-117. In some embodiments, an RNP complex including a nuclease disclosed herein can further include at least one STAR gRNA. In another embodiment, an RNP complex including a nuclease disclosed herein can further include at least one non-STAR gRNA. In other embodiments, an RNP complex including a nuclease disclosed herein can further include at least one polynucleotide. In certain embodiments, a polynucleotide included in an RNP complex disclosed herein can be greater than about 50 nucleotides in length. In other embodiments, a polynucleotide included in a RNP complex disclosed herein can be about 50, to about 100, to about 150, to about 200, to about 250, to about 300, to about 350, to about 400, to about 450 to about 500, to about 750, to about 1000 nucleotides, or greater than 1000 nucleotides in length. In some embodiments, more than one nuclease can be included in an RNP complex contemplated herein in order to affect overall editing efficiency of the complex on a targeted genome. In certain embodiments, more than one gRNA can be added to the RNP complex to allow for multiplexed editing of more than one site in a single transfection. In certain embodiments, more than one DNA template can be added to an RNP complex to allow for multiplexed editing at one or more sites based on a desired repair outcome of a targeted genome.

Nuclease Systems

Other embodiments disclosed herein concern targetable nuclease systems. In certain embodiments, a targetable nuclease system can include a nucleic acid-guided nuclease and a compatible guide nucleic acid (also referred to interchangeably herein as "guide polynucleotide" and "gRNA"). A targetable nuclease system herein can include a novel nucleic acid-guided nuclease or a polynucleotide sequence encoding the novel nucleic acid-guided nuclease disclosed herein. In other embodiments, a targetable nuclease system can include a guide nucleic acid or a polynucleotide sequence encoding the guide nucleic acid and a known or novel gRNA.

In accordance with these embodiments, a targetable nuclease system as disclosed herein can be characterized by elements that promote the formation of a targetable nuclease complex at the site of a target sequence (e.g. eukaryotic genome sequence for editing), where the targetable nuclease complex includes at least a nucleic acid-guided nuclease and a guide nucleic acid. A guide nucleic acid (gRNA) together with a nucleic acid-guided nuclease forms a targetable nuclease complex capable of binding to a target sequence within a target polynucleotide, as determined by the guide sequence of the guide nucleic acid.

In certain embodiments, to generate a double stranded break in the target sequence, a targetable nuclease complex can bind to a target sequence as determined by the guide nucleic acid (gRNA), and the nuclease recognizes a protospacer adjacent motif (PAM) sequence adjacent to the target sequence in order to cut the target sequence. In some embodiments, a targetable nuclease complex can include a nucleic acid-guided nuclease encoded by one or more of SEQ ID NO: 4-13, 17-26, 30-39, 43-52, 56-65, 69-78, 82-91, 95-104 and 108-117 and a compatible guide nucleic acid. In other embodiments, a targetable nuclease complex can include a nucleic acid-guided nuclease encoded by one or more of a nuclease represented by SEQ ID NO: 3, 16, 29, 42, 55, 68, 81, 94 and 107 and a compatible guide nucleic acid. In yet other embodiments, a targetable nuclease complex can include a nucleic acid-guided nuclease and a compatible guide nucleic acid represented by SEQ ID NO: 125, 120, 124, 126, 118, 119, 121, 122, 123, 127 and 128. In other embodiments, a targetable nuclease complex can include a nucleic acid-guided nuclease according to one or more of SEQ ID NO: 4-13, 17-26, 30-39, 43-52, 56-65, 69-78, 82-91, 95-104 and 108-117 and a compatible guide nucleic acid represented by SEQ ID NO: 125, 120, 124, 126, 118, 119, 121, 122, 123, 127 and 128. In accordance with these embodiments, the guide nucleic acid can include a scaffold sequence compatible with the nucleic acid-guided nuclease. In other embodiments, the guide sequence can be engineered to be complementary to any desired target sequence for efficient editing of the target sequence. In other embodiments, the guide sequence can be engineered to hybridize to any desired target sequence. In some embodiments, the target nucleic acid sequence has 20 nucleotides in length. In some embodiments, the target nucleic acid has less than 20 nucleotides in length. In some embodiments, the target nucleic acid has more than 20 nucleotides in length. In some embodiments, the target nucleic acid has at least: 5, 10, 15, 16, 17, 18, 19, 20, 21, 22, 23, 24, 25, 30 or more nucleotides in length. In some embodiments, the target nucleic acid has at most: 5, 10, 15, 16, 17, 18, 19, 20, 21, 22, 23, 24, 25, 30 or more nucleotides in length.

In some embodiments, a target sequence of a targetable nuclease complex can be any polynucleotide endogenous or exogenous to a prokaryotic or eukaryotic cell, or in an in vitro system for verification or otherwise. In other embodiments, a target sequence can be a polynucleotide residing in the nucleus of the eukaryotic cell. A target sequence can be a sequence coding a gene product (e.g., a protein) or a non-coding sequence (e.g., a regulatory polynucleotide or a junk DNA). It is contemplated herein that the target sequence should be associated with a PAM; that is, a short sequence recognized by a targetable nuclease complex. In some embodiments, sequence and length requirements for a PAM differ depending on the nucleic acid-guided nuclease selected. In certain embodiments, PAM sequences can be about 2-5 base pair sequences adjacent the target sequence or longer, depending on the PAM desired. Examples of PAM sequences are given in the Examples section below, and the skilled person will be able to identify further PAM sequences for use with a given nucleic acid-guided nuclease as these are not intended to limit this aspect of the inventions. Further, engineering of a PAM Interacting (PI) domain can allow programming of PAM specificity, improve target site recognition fidelity, and increase the versatility of a nucleic acid-guided nuclease genome engineering platform. Nucleic acid-guided nucleases can be engineered to alter their PAM specificity, for example as previously described.

In some embodiments, at least one PAM site can be a nucleotide sequence in close proximity to a target sequence. In accordance with these embodiments, a nucleic acid-guided nuclease can only cleave a target sequence if at least one corresponding PAM is present as selected herein. In certain embodiments, PAM sites can be nucleic acid-guided nuclease-specific and can be different between two different nucleic acid-guided nucleases. In accordance with these embodiments, a PAM can be positioned or located 5' of a target sequence, 3' of a target sequence, consecutively or combination. A PAM can be upstream of a target sequence, downstream of a target sequence, repeated or a combination. A PAM can be 1, 2, 3, 4, 5, 6, 7, 8, 9, 10 or more nucleotides in length. In some embodiments, a PAM is between 2-6 nucleotides in length. In some embodiments, a PAM sequence for use herein can be 5'-TTN-3'. In other embodiments, a PAM sequence for use herein can be 5'-TTTN-3'. In certain embodiments, a PAM sequence for use herein can be different than the 5'-TTN-3' or 5'-TTTN-3' sequence described above. In some embodiments, a PAM sequence for use herein can depend on (or for example, correspond to) one or more of nucleases disclosed herein (e.g. matching or pairing for efficient editing). In some embodiments, various methods (e.g., in silico and/or wet lab methods) for identification of an appropriate PAM sequence are known in the art and can be used herein.

In some embodiments disclosed herein, a PAM can be provided on a separate oligonucleotide. In accordance with these embodiments, providing PAM on an adjacent or separate oligonucleotide allows cleavage of a neighboring target sequence that otherwise would not be able to be cleaved or edited because no adjacent PAM is present on the targeted sequence itself.

Polynucleotide sequences encoding a component of a targetable nuclease system can include one or more vectors. The term "vector" as used herein can refer to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Other vectors (e.g., non-episomal mammalian vectors) can be integrated into the genome of a host cell upon introduction into the host cell. Recombinant expression vectors can include a nucleic acid of the invention in a form suitable for expression of the nucleic acid in a host cell, can mean that the recombinant expression vectors include one or more regulatory elements, which can be selected on the basis of the host cells to be used for expression, that is operatively-linked to the nucleic acid sequence to be expressed.

In some embodiments, a regulatory element can be operably linked to one or more elements of a targetable nuclease system so as to drive expression of the one or more components of the targetable nuclease system.

In some embodiments, a vector can include a regulatory element operably linked to a polynucleotide sequence encoding a nucleic acid-guided nuclease. The polynucleotide sequence encoding the nucleic acid-guided nuclease can be codon optimized for expression in particular cells, such as prokaryotic or eukaryotic cells. Eukaryotic cells can be yeast, fungi, algae, plant, animal, or human cells. Eukaryotic cells can be those derived from a particular organism, such as a mammal, including but not limited to human, mouse, rat, rabbit, dog, or non-human mammal including non-human primate. Plant cells can include, without limitation, cells from seeds, suspension cultures, embryos, meristematic regions, callus tissue, leaves, roots, shoots, gametophytes, sporophytes, pollen and microspores.

As used herein, 'codon optimization' can refer to a process of modifying a nucleic acid sequence for enhanced expression in the host cells of interest by replacing at least one codon or more of the native sequence with codons that are more frequently or most frequently used in the genes of that host cell while maintaining the native amino acid sequence. Various species exhibit particular bias for certain codons of a particular amino acid. As contemplated herein, genes can be tailored for optimal gene expression in a given organism based on codon optimization. Codon usage tables are readily available, for example, at the "Codon Usage Database."

In some embodiments, a nucleic acid-guided nuclease and one or more guide nucleic acids can be delivered either as DNA or RNA. Delivery of a nucleic acid-guided nuclease and guide nucleic acid both as RNA (unmodified or containing base or backbone modifications) molecules can be used to reduce the amount of time that the nucleic acid-guided nuclease persist in the cell (e.g. reduced half-life). This can reduce the level of off-target cleavage activity in the target cell. Since delivery of a nucleic acid-guided nuclease as mRNA takes time to be translated into protein, an aspect herein can include delivering a guide nucleic acid several hours following the delivery of the nucleic acid-guided nuclease mRNA, to maximize the level of guide nucleic acid available for interaction with the nucleic acid-guided nuclease protein. In other cases, the nucleic acid-guided nuclease mRNA and guide nucleic acid can be delivered concomitantly. In other examples, the guide nucleic acid can be delivered sequentially, such as 0.5, 1, 2, 3, 4, or more hours after the nucleic acid-guided nuclease mRNA.

In some embodiments, guide nucleic acid in the form of RNA or encoded on a DNA expression cassette can be introduced into a host cell that includes a nucleic acid-guided nuclease encoded on a vector or chromosome. The guide nucleic acid can be provided in the cassette having one or more polynucleotides, which can be contiguous or noncontiguous in the cassette. In some embodiments, the guide nucleic acid can be provided in the cassette as a single contiguous polynucleotide. In other embodiments, a tracking agent can be added to the guide nucleic acid in order to track distribution and activity.

In other embodiments, a variety of delivery systems can be used to introduce a nucleic acid-guided nuclease (e.g. DNA or RNA or other nucleic acid construct) and guide nucleic acid (e.g. DNA or RNA or other nucleic acid construct) into a host cell. In accordance with these embodiments, systems of use for embodiments disclosed herein can include, but are not limited to, yeast systems, lipofection systems, microinjection systems, biolistic systems, virosomes, liposomes, immunoliposomes, polycations, lipid: nucleic acid conjugates, virions, artificial virions, viral vectors, electroporation, cell permeable peptides, nanoparticles, nanowires, exosomes. Molecular trojan horse liposomes or similar can be used to deliver an engineered nuclease and guide nuclease for example, across the blood brain barrier.

In some embodiments, an editing template can also be provided. In accordance with these embodiments, an editing template can be a component of a vector as described herein, contained in a separate vector, or provided as a separate polynucleotide, such as an oligonucleotide, linear polynucleotide, or synthetic polynucleotide. In some embodiments, an editing template is on the same polynucleotide as a guide nucleic acid. In other embodiments, an editing template is designed to serve as a template in homologous recombination, such as within or near a target sequence nicked or cleaved by a nucleic acid-guided nuclease as a part of a complex for editing as disclosed herein. An editing template polynucleotide can be of any suitable length, such as about or less or more than about 5, 10, 15, 20, 25, 50, 75, 100, 150, 200, 500, 1000, or more nucleotides in length. In some embodiments, an editing template polynucleotide can be complementary to a portion of a polynucleotide that can include the target sequence or be adjacent or in close proximity to a target sequence for editing. In accordance with these embodiments, when optimally aligned, an editing template polynucleotide can overlap with one or more nucleotides of a target sequences (e.g. about or more than about 1, 5, 10, 15, 20, 25, 30, 35, 40, or more nucleotides). In some embodiments, when optimally aligned, an editing template sequence and a polynucleotide can include a target sequence optimally aligned, where the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, methods are provided for delivering one or more polynucleotides, such as or one or more vectors or linear polynucleotides as described herein, one or more transcripts thereof, and/or one or proteins transcribed therefrom, to a host cell. In some aspects, the invention further provides cells produced by such methods, and organisms can include or produced from such cells. In some embodiments, an engineered nuclease in combination with (and optionally complexed with) a guide nucleic acid is delivered to a cell.

In certain embodiments, conventional viral and non-viral based gene transfer methods can be used to introduce nucleic acids in cells, such as prokaryotic cells, eukaryotic cells, plant cells, mammalian cells, or target tissues. Such methods can be used to administer nucleic acids encoding components of an engineered nucleic acid-guided nuclease system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. Any gene therapy method known in the art is contemplated of use herein. Methods of non-viral delivery of nucleic acids include are contemplated herein. Adeno-associated virus ("AAV") vectors can also be used to transduce cells with target nucleic acids, e.g., in the in vitro production of nucleic acids and peptides, and for in vivo and ex vivo gene therapy procedures.

In some embodiments, a host cell is transiently or non-transiently transfected with one or more vectors, linear polynucleotides, polypeptides, nucleic acid-protein complexes, or any combination thereof as described herein. In some embodiments, a cell can be transfected in vitro, in culture, or ex vivo. In some embodiments, a cell can be transfected as it naturally occurs in a subject. In some embodiments, a cell that is transfected can be taken from a subject. In some embodiments, the cell is derived from cells taken from a subject, such as a cell line.

In some embodiments, a cell transfected with one or more vectors, linear polynucleotides, polypeptides, nucleic acid-protein complexes, or any combination thereof as described herein is used to establish a new cell line can include one or more transfection-derived sequences. In some embodiments, a cell transiently transfected with the components of an engineered nucleic acid-guided nuclease system as described herein (such as by transient transfection of one or more vectors, or transfection with RNA), and modified through the activity of an engineered nuclease complex, is used to establish a new cell line can include cells containing the modification but lacking any other exogenous sequence.

In some embodiments, one or more vectors described herein are used to produce a non-human transgenic cell, organism, animal, or plant. In some embodiments, the transgenic animal is a mammal, such as a mouse, rat, or rabbit. Methods for producing transgenic cells, organisms, plants, and animals are known in the art, and generally begin with a method of cell transformation or transfection, such as described herein.

In certain embodiments, an engineered nuclease complex, "target sequence" can refer to a sequence to which a guide sequence is designed to have complementarity, where hybridization between a target sequence and a guide sequence promotes the formation of an engineered nuclease complex. A target sequence can include any polynucleotide, such as DNA, RNA, or a DNA-RNA hybrid. A target sequence can be located in the nucleus or cytoplasm of a cell. A target sequence can be located in vitro or in a cell-free environment. A target sequence can be eukaryotic or prokaryotic target sequence.

In some embodiments, formation of an engineered nuclease complex can include a guide nucleic acid hybridized to a target sequence and complexed with one or more engineered nucleases as disclosed herein leading to cleavage of one or both strands in or near (e.g. within 1, 2, 3, 4, 5, 6, 7, 8, 9, 10, 20, 50, or more base pairs from) of the target sequence. In certain embodiments, cleavage can occur within a target sequence, 5' of the target sequence, upstream of a target sequence, 3' of the target sequence, or downstream of a target sequence.

In some embodiments, one or more vectors driving expression of one or more components of a targetable nuclease system can be introduced into a host cell or used in vitro such formation of a targetable nuclease complex at one or more target sites. In some embodiments, a nucleic acid-guided nuclease and a guide nucleic acid could each be operably linked to separate regulatory elements on separate vectors. In other embodiments, two or more of the elements expressed from the same or different regulatory elements, can be combined in a single vector, with one or more additional vectors providing any components of the targetable nuclease system not included in the first vector. Targetable nuclease system elements that are combined in a single vector can be arranged in any suitable orientation, such as one element located 5' with respect to ("upstream" of) or 3' with respect to ("downstream" of) a second element. In some embodiments, the coding sequence of one element can be located on the same or opposite strand of the coding sequence of a second element, and oriented in the same or opposite direction. In other embodiments, a single promoter drives expression of a transcript encoding a nucleic acid-guided nuclease and one or more guide nucleic acids. In certain embodiments, a nucleic acid-guided nuclease and one or more guide nucleic acids are operably linked to and expressed from the same promoter. In other embodiments, one or more guide nucleic acids or polynucleotides encoding the one or more guide nucleic acids are introduced into a cell or in vitro environment already can include a nucleic acid-guided nuclease or polynucleotide sequence encoding the nucleic acid-guided nuclease.

In certain methods, when multiple different guide sequences are used, a single expression construct can be used to target nuclease activity to multiple different, corresponding target sequences (to the selected guide sequences etc.) within a cell or cells within a tissue, ex vivo or in vitro. For example, a single vector can include about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors can be provided, and optionally delivered to a cell or in vitro.

In other embodiments, methods and compositions disclosed herein can include more than one guide nucleic acid, such that each guide nucleic acid has a different guide sequence, thereby targeting a different target sequence. In accordance with these embodiments, multiple guide nucleic acids can be using in multiplexing, wherein multiple targets are targeted simultaneously. Additionally, or alternatively, multiple guide nucleic acids can be introduced into a population of cells or cells within a tissue, such that each cell in a population of cells receives a different or random guide nucleic acid, thereby targeting multiple different target sequences across a population of cells for optimal editing outcomes in some embodiments disclosed herein. In certain embodiments, the collection of subsequently altered cells can be referred to as a library.

In other embodiments, methods and compositions disclosed herein can include multiple different nucleic acid-guided nucleases, each with one or more different corresponding guide nucleic acids, thereby allowing targeting of different target sequences by different nucleic acid-guided nucleases. In some embodiments, each nucleic acid-guided nuclease can correspond to a distinct plurality of guide nucleic acids, allowing two or more non-overlapping, partially overlapping, or completely overlapping multiplexing events to occur.

In some embodiments, nucleic acid-guided nucleases herein can have DNA cleavage activity or RNA cleavage activity. In some embodiments, the nucleic acid-guided nuclease directs cleavage of one or both strands at the location of a target sequence, such as within the target sequence and/or within the complement of the target sequence. In certain embodiments, the nucleic acid-guided nuclease directs cleavage of one or both strands within about 1, 2, 3, 4, 5, 6, 7, 8, 9, 10, 15, 20, 25, 50, 100, 200, 500, or more base pairs from the first or last nucleotide of a target sequence.

In some embodiments, methods of modifying a target sequence in vitro, or in a prokaryotic or eukaryotic cell, which can be in vivo, ex vivo, or in vitro are disclosed. In some embodiments, the method includes sampling a cell or population of cells such as prokaryotic cells, or those from a human or non-human animal or plant (including micro-algae), and modifying the cell or cells. Culturing can occur at any stage in vitro or ex vivo. The cell or cells can be re-introduced into the host, such as a non-human animal or plant (including micro-algae). In some embodiments, compositions and methods disclosed herein can be used to improve resistance in a plant to microbes or changes in climate. In some embodiments, for re-introduced cells, they can include stem cells or other progenitor cells.

In some embodiments, methods can include allowing a targetable nuclease complex to bind to the target sequence to effect cleavage of the target sequence, thereby modifying the target sequence, wherein the targetable nuclease complex includes a nucleic acid-guided nuclease complexed with a guide nucleic acid wherein the guide sequence of the guide nucleic acid is hybridized to a target sequence within a target polynucleotide. In other embodiments, methods of modifying expression of a target polynucleotide in in vitro or in a prokaryotic or eukaryotic cell are provided. In some embodiments, methods herein can include allowing a targetable nuclease complex to bind to a target sequence with the target polynucleotide such that the binding results in increased or decreased expression of the target polynucleotide. In accordance with these embodiments, the targetable nuclease complex can include a nucleic acid-guided nuclease complexed with a guide nucleic acid, where the guide sequence of the guide nucleic acid is hybridized to a target sequence within the target polynucleotide.

In some embodiments, kits are provided containing one or more of the elements disclosed in the above methods and compositions and at least one container. Elements can be provided individually or in combinations, and can be provided in any suitable container, such as a vial, a bottle, or a tube. In some embodiments, kits can include instructions in one or more languages, for example in more than one language. In some embodiments, kits can include components of novel nucleases and/or gRNAs disclosed herein or compositions for making these components. In other embodiments, kits contemplated herein can include all components and containers needed for performing an efficient editing of a target genome.

In some embodiments, a kit contemplated herein includes one or more reagents for use in a process utilizing one or more of the elements described herein. Reagents can be provided in any suitable container. For example, a kit can provide one or more reaction or storage buffers. Reagents can be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In other embodiments, the buffer has a pH from about 7 to about 10. In other embodiments, the kit includes one or more oligonucleotides corresponding to a guide sequence for insertion into a vector so as to operably link the guide sequence and a regulatory element. In some embodiments, the kit includes an editing template.

In some embodiments, a targetable nuclease complex has a wide variety of utility including modifying (e.g., deleting, inserting, translocating, inactivating, activating) a target sequence in a multiplicity of cell types. In some embodiments, a targetable nuclease complex can have a broad spectrum of applications in, e.g., biochemical pathway optimization, genome-wide studies, genome engineering, gene therapy, drug screening, disease diagnosis, and prognosis. An exemplary targetable nuclease complex includes a nucleic acid-guided nuclease as disclosed herein complexed with a guide nucleic acid, wherein the guide sequence of the guide nucleic acid can hybridize to a target sequence within the target polynucleotide. A guide nucleic acid can include a guide sequence linked to a scaffold sequence. A scaffold sequence can include one or more sequence regions with a degree of complementarity such that together they form a secondary structure.

In some embodiments, an editing template polynucleotide can include a sequence to be integrated (e.g., a mutated gene). In accordance with these embodiments, a sequence for integration can be a sequence endogenous or exogenous to the cell. Examples of a sequence to be integrated include polynucleotides encoding a protein or a non-coding RNA (e.g., a microRNA). In certain embodiments, the sequence for integration can be operably linked to an appropriate control sequence or sequences. Alternatively, the sequence to be integrated can provide a regulatory function. In certain embodiments, sequences to be integrated can be a mutated or variant of an endogenous wild-type sequence. In other embodiments, sequences to be integrated can be a wild-type version of an endogenous mutated sequence. Additionally, or alternatively, sequences to be integrated can be a variant or mutated form of an endogenous mutated or variant sequence.

An upstream or downstream sequence can encompass from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence has about 15 bp to about 50 bp, about 30 bp to about 100 bp, about 200 bp to about 2000 bp, about 600 bp to about 1000 bp, or more particularly about 700 bp to about 1000 bp.

In some methods, the editing template polynucleotide can further include a marker. In accordance with these embodiments, a marker can make it easy to screen for targeted integrations in order to assess efficiency and accuracy. Examples of suitable markers include, but are not limited to, restriction sites, fluorescent proteins, or selectable markers. In some embodiments, exogenous polynucleotide templates disclosed herein can be constructed using recombinant techniques.

In some embodiments, methods for modifying a target polynucleotide by integrating an editing template polynucleotide, can be by introducing a double-stranded break into the genome sequence by an engineered nuclease complex, the break can be repaired via homologous recombination using an editing template such that a desired template is integrated into the target polynucleotide. The presence of a double-stranded break can increase the efficiency of integration of the editing template for directed outcome.

In other embodiments, methods are disclosed for modifying expression of a polynucleotide in a cell. In accordance with these embodiments, some methods can include increasing or decreasing expression of a target polynucleotide by using a targetable nuclease complex that binds to the target polynucleotide.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, an amount of the amplified products can be determined by quantifying the fluorescence of the intercalated dye using conventional optical systems in the art. DNA-binding dye suitable for this application include, but are not limited to, SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and others known by one of skill in the art.

In some embodiments, other fluorescent labels such as sequence specific traceable probes can be employed in the amplification reaction to facilitate the detection and quantification of the amplified products. Probe-based quantitative amplification relies on the sequence-specific detection of a desired amplified product. In these methods, fluorescent, target-specific probes (e.g., TaqMan™ probes) can be used resulting in increased specificity and sensitivity of detection and quantitative analysis. Methods for performing probe-based quantitative amplification are well known in the art and contemplated of use herein.

In certain embodiments, an agent-induced change in expression of sequences associated with a signaling biochemical pathway can also be determined by examining the corresponding gene products. Determining protein levels can involve (a) contacting the protein contained in a biological sample with an agent that specifically binds to a protein associated with a signaling biochemical pathway; and (b) identifying an agent:polypeptide complex so formed. In one aspect of this embodiment, the agent that specifically binds a protein associated with a signaling biochemical pathway can be an antibody, such as a monoclonal antibody.

In some embodiments, the amount of agent:polypeptide complexes formed during the binding reaction can be quantified by standard quantitative assays. As disclosed above, the formation of agent:polypeptide complex can be measured directly by the amount of label remained at the site of binding. In an alternative, the protein associated with a signaling biochemical pathway is tested for its ability to compete with a labeled analog for binding sites on the specific agent. In this competitive assay, the amount of label captured is inversely proportional to the amount of protein sequences associated with a signaling biochemical pathway present in a test sample.

In other embodiments, a number of techniques for protein analysis based on the general principles outlined above are available in the art. They include, but are not limited to, radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays, and SDS-PAGE.

In some embodiments, methods herein can be used to discern the expression pattern of a protein associated with a signaling biochemical pathway in different bodily tissue, in different cell types, and/or in different subcellular structures. These studies can be performed with the use of tissue-specific, cell-specific or subcellular structure specific antibodies capable of binding to protein markers that are preferentially expressed in certain tissues, cell types, or subcellular structures.

In some embodiments, an altered expression of a gene associated with a signaling biochemical pathway can also be determined by examining a change in activity of the gene product relative to a control cell. The assay for an agent-induced change in the activity of a protein associated with a signaling biochemical pathway will dependent on the biological activity and/or the signal transduction pathway that is under investigation. For example (but not limited to), where the protein is a kinase, a change in its ability to phosphorylate the downstream substrate(s) can be determined by a variety of assays known in the art. Representative assays include but are not limited to immunoblotting and immunoprecipitation with antibodies such as anti-phosphotyrosine antibodies that recognize phosphorylated proteins. In addition, kinase activity can be detected by high throughput chemiluminescent assays.

In certain embodiments, where the protein associated with a signaling biochemical pathway is part of a signaling cascade leading to a fluctuation of intracellular pH condition, pH sensitive molecules such as fluorescent pH dyes can be used as the reporter molecules. In another example, where the protein associated with a signaling biochemical pathway is an ion channel, fluctuations in membrane potential and/or intracellular ion concentration can be monitored. A number of commercial kits and high-throughput devices are particularly suited for a rapid and robust screening for modulators of ion channels. Representative instruments include FLIPR™ (Molecular Devices, Inc.) and VIPR (Aurora Biosciences). These instruments are capable of detecting reactions in over 1000 sample wells of a microplate simultaneously, and providing real-time measurement and functional data within a second or even a millisecond.

In practicing any of the methods disclosed herein, a suitable vector can be introduced to a cell, tissue, organism, or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector can be introduced into an embryo by microinjection. The vector or vectors disclosed herein can be microinjected into the nucleus or the cytoplasm of the embryo. In some methods, the vector or vectors can be introduced into a cell by nucleofection.

In some embodiments, a target polynucleotide of a targetable nuclease complex can be any polynucleotide endogenous or exogenous to the host cell. For example, the target polynucleotide can be a polynucleotide residing in the nucleus of the eukaryotic cell, the genome of a prokaryotic cell, or an extrachromosomal vector of a host cell. The target polynucleotide can be a sequence coding a gene product (e.g., a protein) or a non-coding sequence (e.g., a regulatory polynucleotide or a junk DNA).

Some embodiments disclosed herein relate to use of an engineered nucleic acid guided nuclease system disclosed herein; for example, in order to target and knock out genes, amplify genes and/or repair particular mutations associated with DNA repeat instability and a medical disorder. This nuclease system can be used to harness and to correct these defects of genomic instability. In other embodiments, engineered nucleic acid guided nuclease systems disclosed herein can be used for correcting defects in the genes associated with Lafora disease. Lafora disease is an autosomal recessive condition which is characterized by progressive myoclonus epilepsy which can start as epileptic seizures in adolescence. This condition causes seizures, muscle spasms, difficulty walking, dementia, and eventually death.

In yet another aspect of the invention, the engineered/novel nucleic acid guided nuclease system disclosed herein can be used to correct genetic-eye disorders that arise from several genetic mutations.

In other embodiments, methods herein can be used to correct defects associated with a wide range of genetic diseases which are described, but not limited to those on the website of the National Institutes of Health under the topic subsection Genetic Disorders. Certain genetic disorders of the brain can include, but are not limited to, Adrenoleukodystrophy, Agenesis of the Corpus Callosum, Aicardi Syndrome, Alpers' Disease, glioblastoma, Alzheimer's, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly or other brain disorder scontributed to by genetically-linked causation.

In some embodiments, a genetically-linked disorder can be a neoplasia. In some embodiments, where the condition is neoplasia, targeted genes can include one or more genes listed above. In some embodiments, a health condition contemplated herein can be Age-related Macular Degeneration or a Schizophrenic-related Disorder. In other embodiments, the condition can be a Trinucleotide Repeat disorder or Fragile X Syndrome. In other embodiments, the condition can be a Secretase-related disorder. In some embodiments, the condition can be a Prion-related disorder. In some embodiments, the condition can be ALS. In some embodiments, the condition can be a drug addiction related to prescription or illegal substances. In accordance with these embodiments, addiction-related proteins can include ABAT for example.

In some embodiments, the condition can be Autism. In some embodiments, the health condition can be an inflammatory-related condition, for example, over-expression of a pro-inflammatory cytokine. Other inflammatory condition-related proteins can include one or more of monocyte chemoattractant protein-1 (MCP1) encoded by the Ccr2 gene, the C C chemokine receptor type 5 (CCR5) encoded by the Ccr5 gene, the IgG receptor IIB (FCGR2b, also termed CD32) encoded by the Fcgr2b gene, or the Fc epsilon R1g (FCER1g) protein encoded by the Fcer1g gene, or other protein having a genetic-link to these conditions.

In some embodiments, the condition can be Parkinson's Disease. In accordance with these embodiments, proteins associated with Parkinson's disease can include, but are not limited to, a-synuclein, DJ-1, LRRK2, PINK1, Parkin, UCHLI, Synphilin-1, and NURR1.

Cardiovascular-associated proteins that contribute to a cardiac disorder, can include, but are not limited to, IL 1b (interleukin 1-beta), XDH (xanthine dehy-drogenase), TP53 (tumor protein p53), PTGIS (prostaglandin 12 (prostacyclin) synthase), MB (myoglobin), IL4 (interleukin 4), ANGPTI (angiopoietin 1), ABCG8 (ATP-binding cas-sette, sub-family G (WHITE), member 8), or CTSK (cathepsin K), or other known contributors to these conditions.

In certain embodiments, the condition can be Alzheimer's disease. In accordance with these embodiments, Alzheimer's disease associated proteins can include very low density lipoprotein receptor protein (VLDLR) encoded by the VLDLR gene, ubiquitin-like modifier activating enzyme 1 (UBA1) encoded by the UBA1 gene, or for example, NEDD8-activating enzyme E1 catalytic subunit protein (UBEIC) encoded by the UBA3 gene or other genetically-related contributor.

In other embodiments, the condition can be an Autism Spectrum Disorder. In accordance with these embodiments, proteins associated Autism Spectrum Disorders can include the benzodiazapine receptor (peripheral) associated protein 1 (BZRAP1) encoded by the BZRAPI gene, the AF4/FMR2 family member 2 protein (AFF2) encoded by the AFF2 gene (also termed MFR2), the fragile X mental retardation autosomal homolog 1 protein (FXR1) encoded by the FXR1 gene, or the fragile X mental retardation autosomal homolog 2 protein (FXR2) encoded by the FXR2 gene, or other genetically-related contributor.

In some embodiments, the condition can be Macular Degeneration. In accordance with these embodiments, proteins associated with Macular Degeneration can include, but are not limited to, the ATP-binding cassette, sub-family A (ABC1) member 4 protein (ABCA4) encoded by the ABCR gene, the apolipoprotein E protein (APOE) encoded by the APOE gene, or the chemokine (CC motif) L1g and 2 protein (CCL2) encoded by the CCL2 gene, or other genetically-related contributor.

In certain embodiments, the condition can be Schizophrenia. In accordance with these embodiments, proteins associated with Schizophrenia In accordance with these embodiments, proteins associated with Schizophrenia y include NRG1, ErbB4, CPLX1, TPH1, TPH2, NRXN1, GSK3A, BDNF, DISCI, GSK3B, and combinations thereof.

In other embodiments, the condition can be tumor suppression. In accordance with these embodiments, proteins associated with tumor suppression can include ATM (ataxia telangiectasia mutated), ATR (ataxia telangiectasia and Rad3 related), EGFR (epidermal growth factor receptor), ERBB2 (v-erb-b2 erythroblastic leukemia viral oncogene homolog 2), ERBB3 (v-erb-b2 erythroblastic leukemia viral oncogene homolog 3), ERBB4 (v-erb-b2 erythroblastic leukemia viral oncogene homolog 4), Notch 1, Notch2, Notch 3, or Notch 4 or other genetically-related contributor.

In yet other embodiments, the condition can be a secretase disorder. In accordance with these embodiments, proteins associated with a secretase disorder can include PSENEN (presenilin enhancer 2 homolog (*C. elegans*)), CTSB (cathepsin B), PSENI (presenilin 1), APP (amyloid beta (A4) precursor protein), APHIB (anterior pharynx defective 1 homolog B (*C. elegans*)), PSEN2 (presenilin 2 (Alzheimer disease 4)), or BACE1 (beta-site APP-cleaving enzyme 1), or other genetically-related contributor.

In certain embodiments, the condition can be Amyotrophic Lateral Sclerosis. In accordance with these embodiments, proteins associated with can include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof or other genetically-related contributor.

In some embodiments, the condition can be a prion disease disorder. In accordance with these embodiments, proteins associated with a prion diseases disorder can include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof or other genetically-related contributor. Examples of proteins related to neurodegenerative conditions in prion disorders can include A2M (Alpha-2-Macro-globulin), AATF (Apoptosis antagonizing transcription factor), ACPP (Acid phosphatase prostate), ACTA2 (Actin alpha 2 smooth muscle aorta), ADAM22 (ADAM metallopeptidase domain), ADORA3 (Adenosine A3 receptor), or ADRA1D (Alpha-ID adrenergic receptor for Alpha-1D adrenoreceptor), or other genetically-related contributor.

In some embodiments, the condition can be an immunodeficiency disorder. In accordance with these embodiments, proteins associated with an immunodeficiency disorder can include A2M [alpha-2-macroglobulin]; AANAT [arylalkylamine N-acetyltransferase]; ABCA1 [ATP-binding cassette, sub-family A (ABC1), member 1]; ABCA2 [ATP-binding cassette, sub-family A (ABC1), member 2]; or ABCA3 [ATP-binding cassette, sub-family A (ABC 1), member 3]; or other genetically-related contributor.

In certain embodiments, the condition can be an immunodeficiency disorder. In accordance with these embodiments, proteins associated with an immunodeficiency disorder can include Trinucleotide Repeat Disorders include AR (androgen receptor), FMRI (fragile X mental retardation 1), HTT (huntingtin), or DMPK (dystro-phia myotonica-protein kinase), FXN (frataxin), ATXN2 (ataxin 2), or other genetically-related contributor.

In some embodiments, the condition can be a Neurotransmission Disorders. In accordance with these embodiments, proteins associated with a Neurotransmission Disorders can include SST (somatostatin), NOS1 (nitric oxide synthase 1 (neuronal)), ADRA2A (adrenergic, alpha-2A-, receptor), ADRA2C (adrenergic, alpha-2C-, receptor), TACR1 (tachykinin receptor 1), or HTR2c (5-hydrox-ytryptamine (serotonin) receptor 2C), or other genetically-related contributor. In other embodiments, neurodevelopmental-associated sequences can include, but are not limited to, A2BP1 [ataxin 2-binding protein 1], AADAT [aminoadipate aminotransferase], AANAT [arylalkylamine N-acetyltransferase], ABAT [4-aminobutyrate aminotrans-ABCA1 [ATP-binding cassette, sub-family A (ABC1), member 1], or ABCA13 [ATP-binding cassette, sub-family A (ABC1), member 13], or other genetically-related contributor.

In yet other embodiments, genetic health conditions targeted for genome editing to treat a condition in a subject can include, but are not limited to Aicardi-Goutieres Syndrome; Alexander Disease; Allan-Herndon-Dudley Syndrome; POLG-Related Disorders; Alpha-Mannosidosis (Type II and III); Alstrom Syndrome; Angelman; Syndrome; Ataxia-Telangiectasia; Neuronal Ceroid-Lipofuscinoses; Beta-Thalassemia; Bilateral Optic Atrophy and (Infantile) 3 Optic Atrophy Type 1; Retinoblastoma (bilateral); Canavan Disease; Cerebrooculofacioskeletal Syndrome 1 [COFS1]; Cerebrotendinous Xanthomatosis; Cornelia de Lange Syndrome; MAPT-Related Disorders; Genetic Prion Diseases; Dravet Syndrome; Early-Onset Familial Alzheimer Disease; 4 Friedreich Ataxia [FRDA]; Fryns Syndrome; Fucosidosis; Fukuyama Congenital Muscular Dystrophy; Galactosialido-sis; Gaucher Disease; Organic Acidemias; Hemophagocytic Lymphohistiocytosis; Hutchinson-Gilford Progeria Syndrome; Mucolipidosis II; Infantile Free Sialic Acid Storage 4 Disease; PLA2G6-Associated Neurodegeneration; Jervell and Lange-Nielsen Syndrome; Junctional Epidermolysis Bullosa; Huntington Disease; Krabbe Disease (Infantile); Mitochondrial DNA-Associated Leigh Syndrome and NARP; Lesch-Nyhan Syndrome; LIST-Associated Lissen-5 cephaly; Lowe Syndrome; Maple Syrup Urine Disease; MECP2 Duplication Syndrome; ATP7A-Related Copper Transport Disorders; LAMA2-Related Muscular Dystrophy; Arylsulfatase A Deficiency; Mucopolysaccharidosis Types I, II or III; Peroxisome Biogenesis Disorders, Zellweger Syndrome Spectrum; Neurodegeneration with Brain Iron Accumulation Disorders; Acid Sphingomyelinase Deficiency; Niemann-Pick Disease Type C; Glycine Encephalopathy; ARX-Related Disorders; Urea Cycle Disorders; COL1A1/2-Related Osteogenesis Imperfecta; Mitochondrial DNA Deletion Syndromes; PLP1-Related Disorders; Perry Syndrome; Phelan-McDermid Syndrome; Glycogen Storage Disease Type II (Pompe Disease) (Infantile); MAPT-Related Disorders; MECP2-Related Disorders; Rhizomelic Chondrodys-plasia Punctata Type 1; Roberts Syndrome; Sandhoff Disease; Schindler Disease Type 1; Adenosine Deaminase Deficiency; Smith-Lemli-Opitz Syndrome; Spinal Muscular Atrophy; Infantile-Onset Spinocerebellar Ataxia; Hexosaminidase A Deficiency; Thanatophoric Dysplasia Type 1; Collagen Type VI-Related Disorders; Usher Syndrome Type I; Congenital Muscular Dystrophy; Wolf-Hirschhorn Syndrome; Lysosomal Acid Lipase Deficiency; and Xeroderma Pigmentosum.

In other embodiments, genetic disorders in animals targeted by editing systems disclosed herein can include, but are not limited to, Hip Dysplasia, Urinary Bladder conditions, epilepsy, cardiac disorders, Degenerative Myelopathy, Brachycephalic Syndrome, Glycogen Branching Enzyme Deficiency (GBED), Hereditary Equine Regional Dermal Asthenia (HERDA), Hyperkalemic Periodic Paralysis Disease (HYPP), Malignant Hyperthermia (MH), Polysaccharide Storage Myopathy—Type 1 (PSSM1), junctional epdiermolysis bullosa, cerebellar abiotrophy, lavender foal syndrome, fatal familial insomnia, or other animal-related genetic disorder.

In some embodiments, nuclease and/or gRNA sequences of use in compositions and methods disclosed herein can include sequences having homologous substitution (for example, substitution and replacement are both used herein to mean the interchange of an existing amino acid residue or nucleotide, with an alternative residue or nucleotide) that can occur in the case of amino acids such as basic for basic, acidic for acidic, polar for polar, etc. Non-homologous substitutions are also contemplated; for example, from one class of residue to another or alternatively involving the inclusion of non-naturally occurring amino acids such as ornithine (hereinafter referred to as Z), diamin-obutyric acid ornithine (hereinafter referred to as B), nor-leucine ornithine (hereinafter referred to as 0), pyridylala-nine, thienylalanine, naphthylalanine and phenylglycine.

In certain embodiments disclosed herein, engineered nucleic acid guided nuclease constructs can recognize a protospacer adjacent motif (PAM) sequence other than TTTN or in addition to TTTN. In other embodiments, engineered nucleic acid guided nuclease constructs disclosed herein can be further mutated to improve targeting efficiency or can be selected from a library for particular targeted features. Other embodiments disclosed herein concern vectors including constructs disclosed herein of use for further analysis and to select for improved genome editing features.

Other embodiments include kits for packaging and transporting nucleic acid guided nuclease constructs and/or novel gRNAs disclosed herein or known gRNAs disclosed herein and further include at least one container.

As will be apparent, it is envisaged that the present system can be used to target any polynucleotide sequence of interest. Some examples of conditions or diseases that might be use fully treated using the present system are included in the figures and tables herein and examples of genes currently associated with those conditions are also provided there. However, the genes exemplified are not exhaustive. Additional objects, advantages, and novel features of this disclosure will become apparent to those skilled in the art upon review of the following examples in light of this disclosure. The following examples are not intended to be limiting.

EXAMPLES

The following examples are included to demonstrate preferred embodiments of the disclosure. It should be appreciated by those of skill in the art that the techniques disclosed in the examples that follow represent techniques discovered by the inventors to function well in the practice of the present disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present disclosure.

Example 1

In one exemplary method, selection criteria used was set to identify sequences with <60% AA sequence similarity to Cas12a, <60% AA sequence similarity to MAD7 (positive control nuclease), and >80% query cover. After some screening rounds, nine nucleases were identified and referenced herein as ABW 1-9 for further study.

In one exemplary method, ABW (as referred to herein) nucleic acid guided nuclease constructs were compared to native amino acid sequences of Cas12a nucleases from different organisms for homology. Exemplary results are provided in Tables 1-2 below:

TABLE 1

Percent identity between amino acid sequences of ABW nucleases and native Cas12a nucleases.

| | Percent Identity Between Amino Acid Sequences | | |
|---|---|---|---|
| | AsCpf1 (WP_021736722.1) | FnCpf1 (WP_003040289.1) | EeCpf1 (WP_055225123.1) |
| ABW1 (WP_075579848.1) SEQ ID NO: 1 | 48.81 | 34.75 | 32.22 |
| ABW2 (WP_077541740.1) SEQ ID NO: 14 | 34.14 | 37.25 | 30.23 |
| ABW3 (WP_087408205.1) SEQ ID NO: 27 | 33.75 | 42.64 | 35.66 |
| ABW4 (PKP01583.1) SEQ ID NO: 40 | 34.96 | 41.17 | 33.65 |

TABLE 1-continued

Percent identity between amino acid sequences of ABW nucleases and native Cas12a nucleases.

| | Percent Identity Between Amino Acid Sequences | | |
|---|---|---|---|
| | AsCpf1 (WP_021736722.1) | FnCpf1 (WP_003040289.1) | EeCpf1 (WP_055225123.1) |
| ABW5 (WP_121734700.1) SEQ ID NO: 53 | 33.02 | 42.80 | 35.05 |
| ABW6 (PWM14151.1) SEQ ID NO: 66 | 32.64 | 33.28 | 52.45 |
| ABW7 (WP_081834226.1) SEQ ID NO: 79 | 23.28 | 22.80 | 26.39 |
| ABW8 (WP_118649060.1) SEQ ID NO: 92 | 31.65 | 35.39 | 48.69 |
| ABW9 (WP_108604518.1) SEQ ID NO: 105 | 30.67 | 32.36 | 34.29 |

TABLE 2

Percent identity between amino acid sequences of ABW nucleases and native Cas12a nucleases. NCBI references are provided for each sequence.

| | Percent Identity Amino Acid Between Sequences | | | | | | | | | | | |
|---|---|---|---|---|---|---|---|---|---|---|---|---|
| | AsCpf1 | FnCpf1 | EeCpf1 | ABW1 | ABW2 | ABW3 | ABW4 | ABW5 | ABW6 | ABW7 | ABW8 | ABW9 |
| AsCpf1 (WP_021736722.1) | 100.0 | | | | | | | | | | | |
| FnCpf1 (WP_003040289.1) | 31.33 | 100.0 | | | | | | | | | | |
| EeCpf1 (WP_055225123.1) | 28.98 | 32.74 | 100.0 | | | | | | | | | |
| ABW1 (WP_075579848.1) SEQ ID NO: 1 | 48.81 | 31.80 | 28.82 | 100.0 | | | | | | | | |
| ABW2 (WP_077541740.1) SEQ ID NO: 14 | 30.55 | 32.68 | 26.24 | 30.65 | 100.0 | | | | | | | |
| ABW3 (WP_087408205.1) SEQ ID NO: 27 | 30.30 | 41.33 | 31.74 | 30.29 | 33.07 | 100.0 | | | | | | |
| ABW4 (PKP01583.1) SEQ ID NO: 40 | 31.10 | 39.52 | 29.23 | 31.56 | 33.54 | 46.88 | 100.0 | | | | | |
| ABW5 (WP_121734700.1) SEQ ID NO: 53 | 29.67 | 42.18 | 30.70 | 29.44 | 31.58 | 53.86 | 45.85 | 100.0 | | | | |
| ABW6 (PWM14151.1) SEQ ID NO: 66 | 28.18 | 29.60 | 51.21 | 28.12 | 25.15 | 29.03 | 27.48 | 27.71 | 100.0 | | | |
| ABW7 (WP_081834226.1) SEQ ID NO: 79 | 16.23 | 15.69 | 16.63 | 17.32 | 16.81 | 16.10 | 15.69 | 15.57 | 16.40 | 100.0 | | |
| ABW8 (WP_118649060.1) SEQ ID NO: 92 | 27.69 | 30.66 | 48.10 | 28.31 | 26.13 | 30.51 | 28.46 | 30.69 | 43.48 | 15.59 | 100.0 | |
| ABW9 (WP_108604518.1) SEQ ID NO: 105 | 23.71 | 27.11 | 23.60 | 24.42 | 27.71 | 26.83 | 29.72 | 26.78 | 22.90 | 19.59 | 23.59 | 100.0 |

The nucleotide sequences of the ABW nucleases were compared to Cas 12a nucleotide sequences from different organism. The exemplary results are provided in Table 3 below:

TABLE 3

Percent identity between nucleotide sequences of native ABW nucleases and native Cas12a nucleases. NCBI references are provided for each sequence.

| | Percent Identity Between Nucleotide Sequences | | | | | | | | | | |
|---|---|---|---|---|---|---|---|---|---|---|---|
| | AsCpf1 | FnCpf1 | EeCpf1 | ABW1 | ABW2 | ABW3 | ABW4 | ABW5 | ABW6 | ABW7 | ABW8 | ABW9 |
| AsCpf1 (NZ_AWUR01000016.1: 24220-28143) | 100.0 | | | | | | | | | | | |
| FnCpf1 (NC_008601.1:c1477344-1473442) | 38.63 | 100.0 | | | | | | | | | | |
| EeCpf1 (NZ_CYYW01000037.1: 2537-6328) | 40.14 | 42.32 | 100.0 | | | | | | | | | |
| ABW1 (NZ LT608315.1:1257961-1261869) SEQ ID NO: 2 | 55.81 | 39.71 | 39.41 | 100.0 | | | | | | | | |
| ABW2 (NZ_CP019633.1:c2931404-2927472) SEQ ID NO: 15 | 37.89 | 49.37 | 37.06 | 38.69 | 100.0 | | | | | | | |
| ABW3 (NZ_NFJR01000003.1: 227868-231620) SEQ ID NO: 28 | 37.92 | 42.91 | 38.30 | 36.79 | 40.46 | 100.0 | | | | | | |
| ABW4 (PHDB01000067.1:9586-13488) | 38.39 | 46.28 | 39.66 | 38.57 | 41.85 | 53.33 | 100.0 | | | | | |
| ABW5 (NZ_RAYI01000001.1: 346670-350428) SEQ ID NO: 41 | 36.37 | 45.11 | 40.19 | 36.86 | 39.39 | 56.35 | 51.47 | 100.0 | | | | |
| ABW6 (QALK01000061.1:4314-8129) SEQ ID NO: 67 | 38.86 | 39.54 | 59.26 | 38.16 | 36.16 | 37.35 | 37.34 | 37.95 | 100.0 | | | |
| ABW7 (NZ_KL370807.1:41505-45212) SEQ ID NO: 80 | 31.57 | 32.61 | 31.46 | 31.61 | 36.39 | 30.69 | 30.42 | 32.26 | 33.41 | 100.0 | | |
| ABW8 (NZ_QUGZ01000001.1: 63017-66937) SEQ ID NO: 93 | 38.41 | 40.96 | 54.85 | 38.07 | 31.46 | 36.72 | 38.83 | 39.23 | 52.67 | 32.68 | 100.0 | |
| ABW9 (NZ_CP026604.1:c5177923-5173532) SEQ ID NO: 106 | 33.37 | 39.95 | 36.01 | 33.00 | 36.62 | 39.28 | 44.53 | 40.78 | 34.30 | 29.21 | 34.81 | 100.0 |

In other methods, circular phylogram was prepared to assess the evolutionary relationship among the ABW1-ABW9 nucleases identified in the final round of screening. The result is illustrated in FIG. 1.

Following this comparison of these nucleases, the nine type V CRISPR-associated protein Cas12a (ABW) nucleases were subjected to nuclease engineering. Briefly, codon optimization was performed using the Codon Optimization Tool, as known in the art, providing the amino acid sequence of the nuclease as an input, choosing gene as a product type, and Escherichia coli B as an organism. The IDT Codon Optimization Tool was developed to optimize a DNA or protein sequence from one organism for expression in another by reassigning codon usage based on the frequencies of each codon's usage in the new organism. For example, valine is encoded by 4 different codons (GUG, GUU, GUC, and GUA). In human cell lines, however, the GUG codon is preferentially used (46% use vs. 18, 24, and 12%, respectively). The codon optimization tool takes this information into account and assigns valine codons with those same frequencies. In addition, the tool algorithm eliminated codons with less than 10% frequency and re-normalized the remaining frequencies to 100%. Moreover, the optimization tool reduced complexities that could interfere with manufacturing and downstream expression, such as repeats, hairpins, and extreme GC content. Exemplary engineered ABW nucleases disclosed herein are provided in Table 4.

TABLE 4

Sequences of exemplary engineered ABW nucleases

| | Engineered Amino Acid Sequence | Engineered Nucleotide Sequence |
|---|---|---|
| ABW1 | MGHHHHHHSSGLVPRGSGTMAA FDKFIHQYQVSKTLRFALIPQG KTLENTKNNVLQEDDERQKNYE KVKPILDRIYKVFAEESLKDCS VDWNDLNACLDAYQKNPSADKR QKVKAAQDALRDEIAGYFTGKQ YANGKNKNAVKEKEQAELYKDI FSKKIFDGTVTNNKLPQVNLSA EETELLGCFDKFTTYFVGFYQN RENVFSGEDIATAIPHRIVQDN FPKFRENCRIYQDLIKNEPALK PLLQQAAAVMAQNPKGIYQPR KSLDDIFVIPFYNHLLLQDDID YFNQILGGISGAAGQKKIQGLN ETINLFMQQHPQEADKLKKKKI RHRFIPLYKQILSDRTSFSFIP EAFSNSQEALDGIETFKKSLKK NDTFGALERLIQNLASLDLKYV YLSNKKVNEISQALYGEWHCIQ DVLKQDFSLESLIQINPQNSSN GFLATLTDEGKKRISQCRNVLG NPLPVKLADDQDKAQVKNQLDT LLAAVHYLEWFKADPDLETDPN FTVPPEKIWEELVPLLSLYSKV RNFVTKKPYSTAKFKLNFANPT LADGWDIHKESDNGALLFEKGG LYYLGIMNPKDKPNFKSYQGAE PYYQKMVYRFFPDCSKTIPKCS TQRKDVKKYFEDHPQATSYQIH DSKKEKFRQDFFEIPREIYELN NTTYGTGKSKYKKFQTQYYQKT QDKSGYQKALRKWIDFSKKFLQ TYVSTSIFDFKGLRPSKDYQDL GEFYKDVNSRCYRVTFEKIRVQ DIHEAVKNGQLYLFQLYNKDFS PKSHGLPNLHTLYWKAVFDPEN LKDPIVKLNGQAELFYRPKSNM QIIQHKTGEEIVNKKLKDGTPV PDDIYREISAYVQGKCQGNLSP EAEKWLPSVTIKKAAHDITKDR RFTEDKFFFHVPITLNYQSSGK PTAFNSQVNDFLTEHPETNIIG IDRGERNLIYAVVITPDGKILE QKSFNVIHDFDYHESLSQREKQ RVAARQAWTAIGRIKDLKEGYL SLVVHEIAQMMIKYQAVVVLEN LNTGPFKRVRGGISEKAVYQFE KMLIEKLNFLVFKDRAINQEGG VLKAYQLTDSFTSFAKLGNQSG FLFYIPSAYTSKIDPGTGFVDP FIWSHVTASEENRNEFLKGFDS LKYDAQSSAFVLHFKMKSNKQF QKNNVEGFMPEWDICFEKNEEK ISLQGSKYTAGKRIIFDSKKKQ YMECFPQNELMKALQDVGITWN TGNDIWQDVLKQASTDTGFRHR MINLIRSVLQMRSSNGATGEDY INSPVMDLDGRFFDTRAGIRDL PLDADANGAYHIALKGRMVLER IRSQKNTAIKNTDWLYAIQEER NGAPKRPAATKKAGQAKKKKAS GSGAGSPKKKRKVEDPKKKRKV (SEQ ID NO: 3) | ATGGGCCACCATCATCATCATCATAGCAGCGGCCTGGTGCCGC GCGGCAGCGGTACCATGGCGGCGTTCGATAAGTTCATCCATCA ATATCAAGTAAGCAAAACCCTCCGTTTTGCACTTATTCCGCAG GGGAAAACCTTGGAGAATACAAAAAATAACGTACTCCAGGAAG ATGATGAGCGTCAGAAAAATTACGAAAAAGTCAAACCTATCCT TGATCGTATTTATAAGGTATTCGCTGAGGAAAGCCTGAAAGAT TGCAGCGTTGACTGGAATGACCTCAATGCATGTCTGGATGCTT ACCAAAAAAATCCTAGCGCGGATAAGCGTCAGAAGGTGAAAGC CGCGCAGGACGCGTTGCGGGACGAAATTGCCGGTTATTTTACA GGGAAACAATACGCGAACGGGAAGAACAAAAATGCCGTTAAGG AGAAAGAGCAGGCAGAATTGTATAAGGATATCTTTAGCAAAAA GATCTTTGATGGGACCGTAACGAACAACAAATTGCCACAGGTC AACCTTTCAGCCGAAGAAACAGAGTTATTAGGCTGTTTTGATA AATTCACAACATATTTCGTCGGCTTTTACCAGAACCGTGAGAA CGTATTTTCAGGGGAGGATATTGCTACAGCTATTCCGCATCGG ATCGTCCAGGATAATTTTCCTAAATTCCGGGAAAACTGTCGGA TTTATCAGGACTTAATCAAAAATGAACCTGCCCTTAAACCGCT GCTTCAGCAAGCAGCGGCCGCGGTGATGGCCCAGAATCCAAAG GGGATCTATCAACCACGTAAGAGTCTGGACGATATTTTTGTCA TTCCGTTTTATAACCATCTCCTTCTTACAGGATGATATTGATA TTTCAATCAAATCTTAGGCGGCATTTCGGGGGCAGCCGGTCAG AAAAAAATCCAGGGTTTAAATGAAACAATTAATCTGTTTATGC AACAGCACCCACAAGAAGCCGATAAGTTAAAGAAAAAAAAGAT TCGTCATCGGTTTATTCCGCTGTATAAACAAATTCTCTCTGAC CGTACGCTTTCTCGTTCATCCCTGAAGCTTTTTCCAATTCTC AGGAAGCGTTAGACGGCATTGAGACATTCAAAAAGTCTCTTAA GAAGAATGACACATTCGGCGCGTTGGAGCGGCTGATTCAAAAT CTTGCTTCCCTGGACCTGAAATACGTGTATTTATCGAACAAGA AGGTCAATGAGATTTCGCAGGCATTATACGGCGAATGGCACTG CATCCAAGACGTCCTCAAGCAAGATTTCAGCCTTGAGAGCCTG ATCCAGATCAACCCACAAAATTCTAGCAATGGTTTCCTGGCCA CACTTACCGACGAAGGCAAGAAACGTATCTCCCAATGTCGTAA CGTACTGGGGAATCCTCTTCCAGTCAAGCTTGCGGATGATCAA GACAAAGCGCAAGTCAAAAACCAATTGGATACATTACTGGCTG CTGTACACTATCTCGAGTGGTTCAAGGCAGATCCAGACCTGGA AACAGACCCTAACTTCACTGTTCCTTTCGAAAAGATCTGGGAG GAATTGGTTCCTTTACTTTCACTGTACTCTAAAGTTCGGAATT TTGTTACAAAGAAGCCATATTCTACAGCTAAATTTAAACTGAA CTTTGCTAACCCGACATTAGCGGATGGGTGGGATATTCACAAG GAAAGTGATAACGGCGCGCTCCTGTTTGAAAAGGGTGGTTTGT ATTACTTGGGTATCATGAACCCTAAAGATAAGCCTAATTTTAA ATCCTATCAGGGTGCAGAGCCATACTATCAGAAGATGGTGTAC CGTTTTTTCCTGACTGTTCGAAGACCATCCCAAAATGCAGCA CCCAACGTAAGGATGTAAAAAAGTACTTCGAAGACCACCCTCA AGCGACCTCATCACGACGCTCACGACTCAAAGAAAGAGAAGTTT CGTCAGGATTTTTTTGAGATCCCTCGGGAGATTTACGAGCTTA ATAACACCACATACGGCACAGGTAAGTCTAAATATAAAAAATT CCAGACCCAGTATTACCAGAAGACTCAGGATAAGTCAGGCTAT CAGAAAGCACTTCGCAAATGGATTGACTTTTCCAAAAAGTTTC TTCAAACATACGTCAGTACTTCCATTTTTGATTTCAAAGGTCT CCGTCCTTCGAAGGATTATCAGGACTTAGGCGAGTTCTATAAA GACGTTAATTCGCGTTGTTACCGTGTGACGTTCGAGAAAATTC GCGTACAGGACATCCACGAAGCAGTCAAAAATGGGCAACTGTA TCTCTTCCAATTATATAATAAGGACTTCTCACCTAAAAGCCAT GGGTTGCCTAATCTTCACACTCTCTATTGGAAAGCCGTGTTCG ATCCTGAGAACTTGAAGGACCCTATCGTAAAACTTAATGGCCA AGCTGAGTTATTCTATCGGCCGAAATCCAACATGCAAATCATC CAACATAAGACCGGGGAGGAGATTGTGAACAAAAAGCTGAAGG ACGGCACCCCGGTTCCTGATGATATCTACCGCGAAATCAGTGC TTACGTCCAGGGGAAATGTCAAGGCAACTTATCCCCGGAGGCA GAGAAGTGGCTCCCAAGTGTCACAATCAAGAAAGCCGCCCATG ATATCACAAAGGATCGTCGCTTTACCGAAGATAAGTTTTTCTT TCATGTCCCTATTACACTGAACTATCAGAGTTCAGGCAAGCCG ACGGCATTCAACTCGCAAGTAAACGATTTCTTGACCGAGCACC CTGAGACAAATATCATCGGCATTGATCGGGGTGAACGTAACTT GATTTATGCCGTTGTAATCACTCCAGATGGCAAGATTCTCGAA CAGAAATCTTTTAACGTGATCCACGACTTTGATTATCATGAAT CCCTGTCCCAGCGGGAAAAACAGCGGGTAGCAGCGCGTCAGGC TTGGACAGCGATTGGTCGCATCAAGGATCTCAAGGAAGGTTAC CTGTCGCTTGTGGTGCACGAAATTGCTCAAATGATGATCAAAT ACCAAGCAGTCGTCGTATTAGAAAACCTCAACACGGGCTTTAA GCGTGTGCGCGGTGGTATCAGTGAGAAGGCCGTCTACCAACAG TTCGAAAAAATGTTGATTGAAAAATTGAACTTCCTGGTATTTA AAGATCGGGCAATCAATCAGGAAGGCGGGGTTCTCAAAGCTTA CCAGCTGACAGACTCGTTTACGTCTTTTGCAAAGTTAGGTAAC |

TABLE 4-continued

Sequences of exemplary engineered ABW nucleases

| Engineered Amino Acid Sequence | Engineered Nucleotide Sequence |
|---|---|
| | CAGTCCGGTTTCCTGTTCTACATCCCGTCCGCCTACACCAGCA<br>AAATCGACCCTGGTACGGGCTTCGTCGATCCTTTTATCTGGTC<br>TCACGTGACCGCTTCTGAGGAAAATCGGAATGAATTTTTAAAG<br>GGCTTTGATAGCTTGAAATATGACGCCCAATCATCCGCCTTTG<br>TACTGCATTTCAAGATGAAATCCAATAAGCAATTTCAGAAGAA<br>CAATGTTGAAGGTTTCATGCCGGAATGGGATATCTGCTTCGAG<br>AAAAACGAGGAAAAGATTTCCTTGCAGGGTAGTAAGTATACAG<br>CCGGTAAACGCATTATTTTCGACTCCAAAAAGAAGCAATACAT<br>GGAGTGCTTCCCGCAGAATGAGCTCATGAAAGCACTGCAGGAC<br>GTAGGCATCACCTGGAACACGGGCAACGATATCTGGCAGGATG<br>TCCTTAAACAAGCGAGCACAGATACAGGGTTTCGTCACCGGAT<br>GATCAACCTGATCCGTTCAGTGCTCCAGATGCGGTCCAGTAAT<br>GGTGCGACCGGGGAGGATTACATCAATTCACCTGTGATGGATC<br>TGGACGGCCGTTTTTTCGACACTCGGGCGGGGATTCGTGATCT<br>GCCATTGGATGCCGACGCCAACGGCGCATACCACATCGCTTTA<br>AAAGGGCGTATGGTACTCGAACGCATTCGCTCCCAAAAGAATA<br>CCGCGATTAAGAACACTGACTGGTTATACGCAATCCAAGAGGA<br>ACGTAACGGCGCGCCAAAAAGGCCGGCGGCCACGAAAAGGCC<br>GGCCAGGCAAAAAAGAAAAAGGCTAGCGGCAGCGGCGCCGGAT<br>CCCCAAAGAAGAAAAGGAAGGTTGAAGACCCCAAGAAAAAGAG<br>GAAGGTGTGATAA (SEQ ID NO: 4) |
| ABW2 | MGHHHHHHSSGLVPRGSGTMKE<br>FTNQYSLTKTLRFELRPVGETA<br>EKIEDFKSGGLKQTVEKDRERT<br>EAYKQLKEVIDSYHRDFIEQAF<br>ARQQTLSEEDFKQTYQLYKEAQ<br>KEKDGETLTKQYEHLRKKIAAM<br>FSKATKEWAVMGENNELIGKNK<br>ESKLYQWLEKNYRAGRIEKEEF<br>DHNAGLIEYFEKFSTYFVGFDK<br>NRANMYSKEAKATAISFRTINE<br>NMVKHFDNCQRLEKIKSKYPDL<br>AEELKDFEEFFKPSYFINCMNQ<br>SGIDYYNISAIGGKDEKDQKAN<br>MKINLFTQKNHLKGSDKPPFFA<br>KLYKQILSDREKSVVIDEFEKD<br>SELTEALKNVFSKDGLINEEFF<br>TKLKSALENFMLPEYQGQLYIR<br>NAFLTKISANIWGSGSWGIIKD<br>AVTQAAENNFTRKSDKEKYAKK<br>DFYSIAELQQAIDEYIPTLENG<br>VQNASLIEYFRKMNYKPRGSEE<br>DAGLIEEINNNLRQAGIVLNQA<br>ELGSGKQREENIEKIKNLLDSV<br>LNLERFLKPLYLEKEKMRPKAA<br>NLNKDFCESFDPLYEKLKTFFK<br>LYNKVRNYATKKPYSKDKFKIN<br>FDTATLLYGWSLDKETANLSVI<br>FRKREKFYLGIINRYNSQIFNY<br>KIAGSESEKGLERKRSLQQKVL<br>AEEGEDYFEKMVYHLLLGASKT<br>IPKCSTQLKEVKAHFQKSSEDY<br>IIQSKSFAKSLTLTKEIFDLNN<br>LRYNTETGEISSELSDTYPKKF<br>QKGYLTQTGDVSGYKTALHKWI<br>DFCKEFLRCYRNTEIFTFHFKD<br>TKEYESLDEFLKEVDSSGYEIS<br>FDKIKASYINEKVNAGELYLFE<br>IYNKDFSEYSKGKPNLHTIYWK<br>SLFETQNLLDKTAKLNGKAEIF<br>FRPRSIKHNDKIIHRAGETLKN<br>KNPLNEKPSSRFDYDITKDRRF<br>TKDKFFLHCPITLNFKQDKPVR<br>FNEQVNLYLKDNPDVNIIGIDR<br>GERHLLYYTLINQNGEILQQGS<br>LNRIGEEESRPTDYHRLLDERE<br>KQRQQARETWKAVEGIKDLKAG<br>YLSRVVHKLAGLMVQNNAIVVL<br>EDLNKGFKRGRFAVEKQVYQNF<br>EKALIQKLNYLVFKEVNSKDAP<br>GHYLKAYQLTAPFISFEKLGTQ<br>SGFLFYVRAWNTSKIDPATGFT<br>DQIKPKYKNQKQAKDFMSSFDS<br>VRYNRKENYFEFEADFEKLAQK | ATGGGCCACCATCATCATCATCATAGCAGCGGCCTGGTGCCGC<br>GCGGCAGCGGTACCATGAAGGAGTTTACCAACCAATATTCCTT<br>AACCAAGACCCTCGGTTCGAGTTGCCGGCCAGTCGGCGAAACA<br>GCAGAAAAGATCGAAGATTTTAAATCGGGCGGGCTCAAGCAAA<br>CAGTGGAAAAGGATCGTGAGCGTACAGAAGCGTATAAGCAGTT<br>GAAAGAGGTTATTGACTCCTATCATCGTGACTTCATTGAGCAA<br>GCTTTTGCGCGCCAGCAGACGCTGTCCGAGGAGGATTTTAAAC<br>AAACATATCAACTGTACAAAGAGGCCCAGAAAGAGAAGGATGG<br>GGAAACATTAACAAAGCAGTACGAGCATTTACGGAAGAAAATC<br>GCAGCTATGTTCAGCAAGGCTACGAAGGAATGGGCCGTTATGG<br>GGGAGAATAACGAATTGATCGGGAAAAACAAAGAGTCAAAGTT<br>GTATCAGTGGCTGGAGAAGAACTACCGCGCAGGTCGCATCGAA<br>AAAGAGGAATTCGACCATAATGCGGGCTTAATCGAATACTTCG<br>AGAAATTTTCCACATATTTCGTAGGTTTTGACAAAAATCGTGC<br>GAATATGTATTCAAAGGAGGCAAAGGCGACCGCAATTTCCTTC<br>CGGACGATTAATGAGAACATGGTCAAGCATTTCGATAATTGCC<br>AGCGGCTCGAGAAGATTAAATCTAAATATCCTGATTTGGCCGA<br>GGAGCTGAAGGATTTTGAGGAGTTTTTTAAACCTAGCTATTTC<br>ATTAATTGTATGAATCAATCGGGTATCGACTACTACAATATCA<br>GCGCGATCGGCGGTAAGGATGAAAAGGATCAGAAAGCGAATAT<br>GAAGATCAACCTTTTCACGCAAAAAAATCATTTAAAGGGCAGT<br>GATAAACCACCATTTTTTGCTAAGCTCTACAAGCAAATTTTGA<br>GTGACCGGGAGAAGTCCGTGGTAATCGACGAGTTCGAAAAGGA<br>CAGCGAATTGACAGAGGCACTCAAAAACGTGTTTTCCAAGGAC<br>GGTTTGATCAATGAGGAGTTTTTTACAAAGTTAAAAGTGCAT<br>TAGAAAATTTTATGTTGCCTGAATATCAAGGTCAACTCTACAT<br>CCGTAACGCTTTCCTTACGAAGATCAGCGCAAACATTTGGGGC<br>TCTGGTTCTTGGGGCATCATCAAGGACGCAGTTACCCAGGCTG<br>CGGAAACAATTTCACGCGTAAGTCTGACAAGGAAAAGTATGC<br>CAAGAAAGACTTCTATTCCATTGCTGAACTCCAGCAGGCTATT<br>GATGAATACATTCCTACTCTGGAGAACGGGGTTCAAAACGCAT<br>CACTCATCGAGTACTTTCGCAAAATGAATTACAAACCACGCGG<br>TTCTGAAGAAGACGCAGGCTTGATCGAAGAATTAATAACAAC<br>CTGCGTCAGGCTGGGATCGTCCTGAATCAAGCCGAGCTGGGGT<br>CTGGTAAGCAGCGGGAAGAGAATATTGAAAAAATTAAGAACTT<br>ATTAGATTCGGTTTTGAATCTCGAACGTTTCTTAAAGCCACTT<br>TACTTGGAGAAAGAGAAAATGCGTCCAAAAGCTGCTAACCTGA<br>ATAAGGATTTTTGTGAGTCATTTGATCCACTTTACGAGAAACT<br>GAAAACGTTTTTCAAGCTCTACAATAAAGTACGTAACTACGCA<br>ACAAAGAAACCATACTCAAAGGACAAATTTAAGATCAATTTTG<br>ATACCGCTACGTTATTATATGGGTGGAGTTTGGATAAGGAAAC<br>CGCGAATCTCAGCGTCATTTTCCGTAAACGCGAAAAATTCTAT<br>TTGGGTATCATCAACCGGTACAATAGCCAGATTTTCAATTATA<br>AGATTGCGGGCAGTGAGAGCGAGAAAGGTAGAGCGTAAGCG<br>GTCGCTCAGCAAAAGGTGCTTGCAGAGGAGGGTGAAGATTAT<br>TTTGAGAAATGGTATACCACCTGCTGCTTGGCGCGTCGAAAA<br>CTATTCCGAAATGCTCGACACAGTTGAAAGAAGTAAAAGCACA<br>CTTTCAAAAGTCATCAGAAGATTATATTATCCAATCCAAATCA<br>TTTGCAAAGTCATTAACATTAACAAAAGAGATCTTTGACTTAA<br>ATAATCTGCGGTATAACACAGAAACGGGCGAATTAGTTCCGA<br>GCTTTCTGATACATATCCGAAGAAGTTCCAGAAGGGGTATCTC<br>ACACAAACAGGCGACGTTTCGGGTTACAAAACTGCTCTGCATA<br>AGTGGATTGATTTCTGCAAAGAGTTCTTGCGTTGCTATCGTAA |

TABLE 4-continued

Sequences of exemplary engineered ABW nucleases

| Engineered Amino Acid Sequence | Engineered Nucleotide Sequence |
|---|---|
| PKGRTRWTICSYGQERYSYSPK ERKFVKHNVTQNLAELFNSEGI SFDSGQCFKDEILKVEDASFFK SIIFNLRLLLKLRHTCKNAEIE RDFIISPVKGNNSSFFDSRIAE QENITSIPQNADANGAYNIALK GLMNLHNISKDGKAKLIKDEDW IEFVQKRKFAAAKRPAATKKAG QAKKKKASGSGAGSPKKKRKVE DPKKKRKV (SEQ ID NO: 16) | TACGGAGATCTTCACGTTCCATTTCAAGGACACGAAGGAGTAC GAGTCGTTAGATGAGTTCTTGAAAGAAGTGGATAGTTCAGGTT ATGAGATTTCATTCGATAAGATCAAAGCCTCTTATATCAACGA GAAGGTTAATGCAGGCGAGCTGTACTTGTTCGAGATCTATAAT AAAGATTTCTCCGAGTATTCCAAAGGTAAGCCAAATCTGCATA CCATTTATTGGAAAAGTCTCTTCGAGACTCAAAACTTGCTGGA TAAAACAGCGAAACTCAACGGCAAGGCAGAGATCTTCTTCCGG CCACGTTCGATCAAACAACAACGACAAAATCATCCACCGTGCGG GCGAAACACTTAAGAATAAAAACCCGCTCAATGAAAAGCCTAG TTCGCGTTTCGATTACGATATTACGAAAGATCGTCGTTTTACG AAAGACAAATTTTTTTTACACTGCCCTATTACGTTAAACTTTA AGCAGGACAAGCCTGTTCGCTTTAATGAACAAGTCAACTTATA CTTAAAAGACAATCCAGACGTGAATATTATCGGTATCGATCGT GGTGAGCGTCACTTGCTTTATTACACTTTGATCAATCAGAATG GTGAGATCTTACAGCAGGGTTCACTTAATCGCATTGGTGAGGA AGAATCTCGGCCTACGGACTACCATCGGTTACTCGATGAGCGT GAAAAGCAGCGTCAACAAGCACGGAGACGTGGAAAGCAGTAG AAGGGATTAAGGACTTAAAAGCTGGGTATCTTTCACGGGTTGT ACATAAACTTGCAGGTTTAATGGTACAAAACAACGCAATTGTC GTTCTGGAAGATCTTAACAAGGGTTTTAAGCGCGGTCGTTTCG CTGTTGAGAAACAGGTGTACCAGAACTTCGAAAAAGCACTTAT TCAAAAGCTTAACTATTTAGTGTTCAAGGAGGTCAACTCTAAA GACGCCCCTGGCCACTATTTGAAGGCATATCAGCTTACGGCCC CTTTCATCTCGTTCGAAAAATTGGGTACTCAGAGCGGTTTCCT TTTTTATGTGCGCGCATGGAATACCTCGAAGATCGACCCGGCG ACGGGTTTTACCGACCAAATCAAACCAAAGTATAAAACCAAA AACAAGCTAAAGACTTCATGTCAAGCTTCGACTCTGTCCGGTA CAACCGCAAGGAAAATTATTTTGAATTCGAGGCGGACTTTGAA AAACTGGCACAGAAACCTAAGGGGCGCACCCGCTGGACGATTT GTTCCTATGGCCAGGAACGGTACTCTTACTCCCAAAAGAACG GAAGTTTGTAAAGCACAACGTTACACAAAATCTTGCTGAGCTT TTTAATTCAGAGGGTATCTCGTTCGACTCCGGGCAGTGTTTCA AGGATGAGATCCTGAAGGTCGAGGATGCCAGTTTCTTTAAGTC TATTATTTTCAATCTTCGCCTCCTTCTCAAGCTTCGTCACACT TGCAAGAACGCCGAGATCGAACGTGATTTCATCATTTCTCCTG TCAAGGGGAACAATTCGTCCTTTTTTGACTCCCGTATTGCCGA ACAAGAAAATATCACCAGCATTCCACAGAATGCTGATGCAAAC GGTGCATACAACATCGCGCTGAAGGGCCTGATGAACCTCCATA ATATCTCTAAGGACGGCAAGGCAAAATTAATTAAGGATGAAGA TTGGATCGAATTTGTCCAAAAACGCAAGTTCGCGGCCGCAAAA AGGCCGGCGGCCACGAAAAAGCCGGCCAGGCAAAAAAGAAAA AGGCTAGCGGCAGCGGCGCCGGATCCCCAAAGAAGAAAAGGAA GGTTGAAGACCCCAAGAAAAAGAGGAAGGTGTGATAA (SEQ ID NO: 17) |
| ABW3 MGHHHHHHSSGLVPRGSLQMKT LSDFTNLFPLSKTLRFKLIPIG NTLKNIEASGILDEDRHRAESY VKVKAIIDEYHKAFIDRVLSDT CLQTESIGKHNSLEEFFFYYQI GAKSEQQKKTFKKIQDALRKQI ADSLTKDKHFSRIDKKELIQED LIQFVRDGEDAAEKTSLISEFQ NFTVYFTGFHENRQNMYSPDEK STAIAYRLINENLPKFVDNMKV FDRIAASELASCFDELYHNFEE YLQVERLHDIFSLDYFNLLLTQ KHIDVYNALIGGKATETGEKIK GLNEYINLYNQRHKQEKLPKFK MLFKQILTDREAISWLPRQFDD NSQLLSAIEQCYNHLSTYTLKD GSLKYLLENLHTYDTEKIFIRN DSLLTEISQRHYGSWSILPEAI KRHLERANPQKRRETYEAYQSR IEKAFKAYPGFSIAFLNGCLTE TGKESPSIESYFESLGAVETET SQQENWFARIANAYTDFREMQN RLHATDVPLAQDAEAVARIKKL LDALKGLQLFIKPLLDTGEEAE KDERFYGDFTEFWNELDTITPL YNMVRNYLTRKPYSEEKIKLNF QNPTLLNGWDLNKEVDNTSVIL RRNGRYYLAIMHRNHRRVFSQY PGTERGDCYEKMEYKLLPGANK MLPKVFFSKSRIDEFNPSEELL | ATGGGCCACCATCATCATCATCATAGCAGCGGCCTGGTGCCGC GCGGCAGCCTGCAGATGAAGACCTTGTCTGATTTTACCAATCT GTTCCCTTTATCTAAGACTCTCCGTTTCAAGCTGATTCCAATC GGCAACACGCTCAAGAACATTGAAGCTAGTGGCATCCTTGACG AGGATCGCCACCGCGCGGAGTCCTATGTCAAGGTCAAGGCCAT CATCGACGAATATCATAAAGCTTTCATCGATCGGGTCCTGTCG GATACTTGCCTCCAGACGGAATCTATCGGCAAACACAACAGTC TCGAGGAATTCTTTTTCTACTACCAAATTGGTGCAAAAAGTGA ACAGCAGAAAAAGACGTTTAAAAAGATTCAAGACGCCTTGCGC AAACAAATCGCAGATAGCCTCACCAAGGACAAACATTTTTCAC GGATTGATAAAAAAGAATTGATCCAAGAGGATTTGATCCAGTT TGTGCGCGATGGGGAGGATGCCGCTGAAAAGACGTCTCTGATT TCCGAATTTCAAAATTTCACAGTTTATTTTACCGGGTTTCATG AGAATCGCCAGAACATGTACAGTCCGGACGAGAAGTCCACGGC CATCGCATATCGCTTAATTAACGAGAATCTCCCAAAATTCGTA GACAACATGAAAGTTTTTGACCGTATCGCGGCGTCCGAATTGG CATCGTGTTTCGACGAATTATACCACAATTGTCGAGGAATACCT CCAAGTGGAGCGGTTACATGATATCTTTAGTTTGGACTATTTC AATCTGCTTCTCACGCAGAAACATATCGACGTCTATAATGCTC TGATCGGTGGGAAGGCAACCGAAACCGGGGAAAAGATCAAGGG CTTAAATGAATACATCAATCTCTACAATCAACGTCACAAGCAG GAAAAACTGCCAAAATTCAAGATGTTATTCAAGCAAATTCTTA CCGACCGTGAGGCAATCAGCTGGTTGCCACGCCAATTTGACGA TAATAGTCAGTTACTCTCAGCCATTGAACAGTGTTATAACCAC CTTTCGACCTACACACTCAAGGATGGGTCACTCAAAATACCTGT TAGAAAACCTGCATACATACGATACTGAAAAGATCTTCATCCG CAATGACAGTTTACTTACGGAAATCTCCCAACGGCATTACGGT TCGTGGTCGATTTTACCAGAAGCTATCAAACGTCATCTCGAGC GCGCGAACCCGCAAAACGGCGCGAAACATACGAGGCCTATCA ATCTCGCATTGAGAAGGCCTTTAAGGCATATCCGGGGTTTTCA |

TABLE 4-continued

Sequences of exemplary engineered ABW nucleases

| | Engineered Amino Acid Sequence | Engineered Nucleotide Sequence |
|---|---|---|
| | ARYQQGTHKKGENFNLHDCHAL IDFFKDSIEKHEEWRNFHFKFS DTSSYTDMSGFYREIETQGYKL SFVPVACEYIDELVRDGKIFLF QIYNKDFSTYSKGKPNMHTLYW EMLFDERNLMNVVYKLNGQAEI FFRKASLSARHPEHPAGLPIKK KQAPTEESCFPYDLIKNKRYTV DQFQFHVPITINFKATGTSNIN PSVTDYIRTADDLHIIGIDRGE RHLLYLVVIDSQGRICEQFSLN EIVTQYQGHQYRTDYHALLQKK EDERQKARQSWQSIENIKELKE GYLSQVVHKVSELMIKYKAIVV LEDLNAGFKRSRQKVEKQVYQK FEKMLIDKLNYLVFKTAEADQP GGLLHAYQLTNKFESFKKMGKQ SGFLFYIPAWNTSKIDPTTGFV NLFDTRYENVDKSRAFFGKFDS IRYRADKGTFEWTFDYNNFHKK AEGTRSSWCLSSHGNRVRTFRN PAKNQWDNEEIDLTQAFRDLF EAWGIEITSNLKEAICNQSEKK FFSELFELFKLMIQLRNSVTGT NIDYMVSPVENHYGTFFDSRTC DSSLPANADANGAYNIARKGLM LARRIQATPENDPISLTLSNKE WLRFAQGLDETTTYEAAAKRPA ATKKAGQAKKKKASGSGAGSPK KKRKVEDPKKKRKV (SEQ ID NO: 29) | ATTGCTTTCCTCAATGGGTGTTTAACAGAGACAGGTAAGGAGT CGCCATCCATCGAAAGCTATTTTGAAAGTCTGGGTGCTGTCGA AACAGAGACCTCTCAGCAGGAAAACTGGTTTGCCCGCATCGCA AACGCTTATACGGACTTTCGTGAAATGCAAAATCGGCTGCACG CCACTGACGTGCCGTTGGCTCAAGACGCTGAGGCAGTGGCCCG GATCAAGAAGCTGTTAGATGCACTGAAAGGCCTGCAATTATTC ATTAAGCCTCTTTTGGATACTGGCGAAGAAGCAGAGAAAGATG AACGGTTCTATGGGGACTTTACCGAATTCTGGAACGAGTTAGA CACTATCACGCATTGTACAATATGGTACGGAACTATCTCACG CGTAAGCCTTATAGTGAAGAAAAATCAAGCTCAATTTCCAGA ATCCGACATTACTGAACGGTTGGGATTTGAACAAAGAGGTAGA TAATACATCTGTCATCCTCCGCCGGAATGGTCGTTATTATCTT GCCATCATGCACCGCAACCACCGGCGTGTATTTTCACAGTATC CAGGCACAGAACGTGGCGATTGTTATGAGAAAATGGAATATAA ACTGCTTCCGGGCGCCAACAAGATGCTCCCAAAAGTCTTCTTC TCTAAATCACGCATCGATGAATTCAACCCTAGCAGAGAATTAT TAGCACGTTACCAGCAAGGTACCCACAAGAAGGGTGAGAATTT TAATTTACACGACTGCCATGCCTTGATTGATTTTTTTAAAGAC TCTATTGAGAAACATGAAGAATGGCGTAACTTTCATTTTAAAT TTAGTGATACCTCCAGTTACACCGACATGAGCGGCTTTTATCG TGAAATCGAAACACAGGGTTACAAGTTGTCATTTGTGCCAGTG GCGTGTGAATACATCGATGAGTTGGTACGTGATGGCAAAATCT TTTTGTTCCAGATCTATAATAAGGACTTTTCGACCTACTCTAA GGGCAAGCCAAATATGCACACTCTTTATTGGGAAATGCTTTTC GACGAGCGGAACCTGATGAACGTGGTGTATAAACTCAATGGCC AAGCAGAGATCTTTTTTCGTAAAGCATCACTGAGCGCACGTCA CCCTGAGCACCCGGCAGGGTTGCCAATTAAAAAAAAACAGGCC CCGACGGAAGAATCCTTGTTTCCCATATGATCTCATTAAGAATA AGCGGTATACAGTTGACCAGTTTCAGTTTCACGTGCCAATTAC TATTAATTTTAAAGCAACTGGGACTTCAAATATCAACCCGTCG GTCACTGATTATATTCGTACGGCCGATGACCTCCATATCATTG GCATTGATCGCGGTGAGCGCCATTTACTTTATTTAGTGGTGAT TGACTCACAAGGGCGCATCTGTGAACAGTTTTCCTTAAACGAG ATCGTAACGCAATACCAAGGTCACCAGTACCGTACAGATTATC ATGCTCTCTTGCAGAAAAAGAGGATGAACGGCAAAAGCTCG CCAGTCTTGGCAATCGATCGAAAACATCAAGGAATTAAAAGAG GGGTATCTGAGCCAAGTAGTGCACAAGGTTTCTGAACTGATGA TCAAATATAAAGCAATTGTGGTGTTGGAAGATTTAAATGCTGG GTTCAAGCGGAGTCGGCAGAAGGTTGAAAAGCAAGTGTATCAA AAATTTGAGAAGATGCTGATCGACAAACTTAACTATCTTGTGT TCAAGACCGCAGAAGCTGACCAACCTGGCGGCCTCCTGCACG ATACCAATTAACAAATAAATTTGAGTCATTCAAGAAAATGGGG AAGCAAAGTGGCTTCCTCTTCTACATTCCTGCATGGAACACGT CTAAAATCGACCCGACCACGGGCTTTGTCAACCTTTTTGATAC CCGGTATGAGAACGTAGACAAATCCCGTGCCTTCTTCGGCAAA TTCGATAGCATCCGCTACCGTGCGGACAAGGGCACGTTCGAGT GGACGTTCGATTATAATAACTTTCACAAAAAGGCCGAAGGTAC GCGGTCGAGCTGGTGTTTGTCTTCTCATGGTAACCGGGTCCGT ACTTTCCGCAATCCTGCGAAAAACAACCAATGGGACAACGAAG AGATCGACTTAACACAAGCGTTCCGCGATCTGTTTGAAGCTTG GGGGATCGAGATACTTCGAACTTAAAAGAGGCCATTTGCAAC CAGTCTGAGAAGAAATTCTTTTCTGAGCTTTTCGAACTGTTCA AACTTATGATCCAGCTGCGGAACTCAGTGACAGGCACGAATAT CGACTATATGGTGAGCCCAGTCGAGAATCACTACGGCACGTTC TTCGATTCGCGCACATGCGATTCGTCTCTGCCGGCTAACGCTG ACGCTAATGGTGCTTATAATATTGCCCGTAAGGGGTTAATGCT GGCTCGCCGCATTCAGGCTACCCCTGAGAATGATCCGATCTCC TTAACATTGAGCAACAAAGAGTGGTTACGCTTTGCACAGGGC TCGATGAGACAACAACCTACGAGGCGGCCGCAAAAAGGCCGGC GGCCACGAAAAAGGCCGGCCAGGCAAAAAGAAAAAGGCTAGC GGCAGCGGCGCCGGATCCCCAAAGAAGAAAAGGAAGGTTGAAG ACCCCAAGAAAAAGAGGAAGGTGTGATAA (SEQ ID NO: 30) |
| ABW4 | MGHHHHHHSSGLVPRGSGTMKN MESFINLYPVSKTLRFELKPIG KTLETFSRWIEELKEKEAIELK ETGNLLAQDEHRAESYKKVKKI LDEYHKWFITESLQNTKLNGLD VFYHNYMLPKKEDHEKKAFASC QDNLRKQIVNAFRQETGLFNKL SGKELFKDSKEEVALLKAIVPY FDNKTLENIGVKSNEGALLLIE EFKDFTTYFGGFHENRKNMYSD EAKSTAVAFRLIHENLPRFIDN | ATGGGCCACCATCATCATCATCATAGCAGCGGCCTGGTGCCGC GCGGCAGCGGTACCATGAAGAACATGGAGTCTTTTATTAATTT ATATCCGGTTTCGAAAACTTTACGTTTTGAGTTAAAGCCTATT GGCAAAACACTCGAAACTTTCTCCCGCTGGATCGAAGAGTTGA AAGAGAAAGAGGCTATTGAGCTGAAAGAAACTGGCAACCTGTT GGCGCAGGATGAGCATCGGGCCGAGTCTTATAAGAAGGTCAAA AAAATTCTTGACGAATATCATAAATGGTTCATCACTGAAAGCC TCCAGAACACAAGTTAAATGGGTTGGACGTTTTTATCATAA CTATATGCTCCCGAAGAAGGAGGACCATGAGAAGAAAGCTTTT GCTTCGTGTCAAGATAATCTCCGTAAGCAAATTGTAAACGCGT TTCGTCAAGAAACCGGTTTATTTAACAAACTGTCAGGCAAAGA |

TABLE 4-continued

Sequences of exemplary engineered ABW nucleases

| Engineered Amino Acid Sequence | Engineered Nucleotide Sequence |
|---|---|
| KKVFEEKIMNSELKDKFPEILK ELEQILQVNEIEEMFQLDYFND TLIQNGIDVYNHLIGGYAEEGK KKIQGLNEHINLYNQIQKEKNK RIPRLKPLYKQILSDRETASFV TEAFENDGELLESLEKSYRLLQ QEVFTPEGKEGLANLLAAIAES ETHKIFLKNDLGLTEISQQIYE SWSLIEEAWNKQYDNKQKKVTE TETYVDNRKKAFKSIKSFSIAE VEEWVKALGNEKHKGKSVATYF KSLGKTDEKVSLIEQVENNYNI IKDLLNTPYPPSKDLAQQKDDV EKIKNYLDSLKALQRFIKPLLG SGEESDKDAHFYGEFTAFWDVL DKVTPLYNKVRNYMTKKPYSTE KFKLNFENSYFLNGWAQDYETK AGLIFLKDGNYFLAINNKKLDE KEKKQLKTNYEKNPAKRIILDF QKPDNKNIPRLFIRSKGDNFAP AVEKYNLPISDVIDIYDEGKFK TEYRKINEPEYLKSLHKLIDYF KLGFSKHESYKHYSFSWKKTHE YENIAQFYHDVEVSCYQVLDEN INWDSLMEYVEQNKLYLFQIYN KDFSPNSKGTPNMHTLYWKMLF NPDNLKDVVYKLNGQAEVFYRK ASIKKENKIVHKANDPIDNKNE LNKKKQNTFEYDIVKDKRYTVD KFQFHVPITLNFKAEGLNNLNS KVNEYIKECDDLHIIGIDRGER HLLYLSLIDMKGNIVKQFSLNE IVNEHKGNTYRTNYHNLLDKRE KEREKERESWKTIETIKELKEG YISQVVHKITQLMIEYNAIVVL EDLNFGFKRGRFKVEKQVYQKF EKMLIDKLNYLVDKKKEANESG GTLKAYQLTDSYADFMKYKKKQ CGFLFYVPAWNTSKIDPTTGFV NLFDTHYVNVSKAQEFFSKFKS IRYNAANNYFEFEVTDYFSFSG KAEGTKQNWIICTHGTRIINFR NPEKNSQWDNKEVVITDEFKKL FEKHGIDYKNSSDLKGQIASQS EKAFFHNEKKDTKDPDGLLQLF KLALQMRNSFIKSEEDYLVSPV MNDEGEFFDSRKAQPNQPENAD ANGAYNIAMKGKWVVKQIRESE DLDKLKLAISNKEWLNFAQRSA AAKRPAATKKAGQAKKKKASGS GAGS PKKKRKVEDPKKKRKV (SEQ ID NO: 42) | ACTGTTTAAAGATTCGAAGGAAGAGGTTGCACTGTTGAAAGCC ATTGTACCGTATTTCGATAACAAGACTCTGGAAAACATTGGTG TTAAGAGTAATGAAGGGGCTCTCCTTTTAATTGAAGAGTTCAA GGATTTTACCACGTATTTCGGTGGCTTCCATGAGAATCGCAAA AATATGTATAGCGACGAAGCAAATCAACAGCGGTTGCCTTTC GTCTTATTCACGAAAATTTGCCGCGCTTCATTGACAATAAGAA GGTCTTCGAAGAGAAAATCATGAATAGTGAATTAAAGGATAAA TTTCCAGAGATTTTGAAGGAGCTGGAACAGATTCTGCAAGTCA ACGAGATTGAAGAGATGTTTCAGCTCGACTATTTTAACGACAC ATTGATCCAGAATGGCATCGATGTCTATAACCATTTGATCGGC GGCTACGCCGAGGAAGGCAAGAAAAAAATTCAAGGGCTTAACG AGCATATTAACCTCTATAACCAGATCCAGAAGGAGAAGAATAA GCGTATCCCGCGGCTGAAACCACTCTATAAGCAAATTTTGAGT GATCGCGAAACCGCCTCATTGTTATCGAGGCGTTTGAGAACG ATGGCGAGTTATTAGAATCATTGGAGAAGTCATATCGCTTACT GCAGCAGGAGGTCTTTACGCCTGAAGGTAAAGAAGGTCTGGCG AATTTACTCGCAGCAATCGCTGAAAGCGAGACACACAAGATCT TTCTGAAGAACGACTTGGGTCTCACCGAGATCTCTCAACAAAT TTATGAATCATGGTCGCTGATTGAAGAGGCATGGAATAAACAA TATGACAACAAACAGAAGAAAGTTACGGAGACAGAGACATATG TGGACAATCGGAAAAAGGCTTTCAAGTCCATCAAGAGCTTTAG CATCGCAGAGGTTGAGGAATGGGTGAAAGCACTTGGGAATGAG AAACACAAGGGCAAAAGCGTGGCAACCTATTTTAAAAGTCTCG GGAAGACTGACGAAAAAGTTAGCCTTATTGAACAGGTAGAGAA CAATTATAATATCATCAAGGACCTTTTGAACACACCGTATCCT CCTTCGAAGGACTTGGCCCAGCAAAAAGATGACGTTGAAAAAA TCAAAAATTATTTGGACTCTCTGAAGGCCCTCCAGCGGTTCAT TAAGCCATTGTTGGGTAGCGGGGAGGAATCCGATAAAGATGCG CACTTTTATGGTGAGTTTACCGCTTTCTGGGATGTGCTCGACA AAGTAACCCCACTCTACAATAAAGTCCGCAACTATATGACTAA GAAACCTTATAGCACAGAGAAATTTAAGCTGAATTTTGAAAAT AGTTACTTTTTGAATGGTTGGGCACAGGACTACGAGACAAAAG CGGGGCTTATCTTCTTGAAGGACGGCAATTACTTCCTTGCCAT CAATAATAAGAAATTAGATGAAAAGGAGAAAAAACAGCTCAAG ACTAATTATGAGAAGAATCCTGCGAAGCGTATCATCTTAGACT TTCAGAAGCCAGACAATAAGAACATTCCTCGCTTGTTCATTCG CAGTAAAGGCGACAATTTCGCTCCTGCAGTAGAAAAGTATAAT CTTCCGATCTCTGACGTTATTGACATCTATGACGAGGGGAAGT TTAAGACTGAGTATCGCAAAATTAACGAGCCGGAATATCTCAA ATCTCTCCATAAGCTGATTGACTACTTCAAACTTGGGTTCTCC AAGCATGAATCCTACAAGCATTATTCTTTCTCATGGAAGAAAA CACATGAGTATGAGAACATCGCCCAGTTTTACCACGACGTGGA GGTCTCTTGCTATCAGGTGCTCGACGAAAATATTAACTGGGAT TCCCTCATGGAGTATGTAGAACAGAACAAATTGTACTTGTTCC AGATTTATAACAAAGACTTCTCCCCAAACTCGAAAGGCACTCC GAATATGCACACTTTGTACTGGAAGATGTTGTTTAATCCGGAT AATCTTAAGGACGTGGTCTATAAGCTGAACGGTCAGGCTGAAG TATTCTACCGGAAGGCGAGTATTAAGAAAGAAAACAAGATTGT CCACAAGGCGAACGACCCTATTGACAATAAAAACGAGTTGAAT AAGAAAAAGCAAAATACATTTGAATACGACATCGTCAAAGATA AACGGTATACAGTGGATAAGTTTCAATTCCATGTTCCTATCAC GCTCAACTTTAAAGCTGAAGGCCTGAATAACTTGAATAGCAAA GTTAACGAATACATCAAAGAGTGTGACGACCTTCACATTATTG GCATCGACCGGGGTGAACGGCACCTCTTGTATCTGAGCCTCAT CGATATGAAAGGTAACATTGTAAAGCAATTTAGTCTTAACGAG ATCGTTAATGAGCACAAGGGGAACACGTACCGCACGAACTATC ATAACCTCTTGGACAAACGTGAAAAGGAACGTGAAAAAGAGCG CGAGTCATGGAAAACCATTGAGACCATCAAAGAGCTGAAAGAA GGCTATATTAGTCAAGTAGTACATAAAATCACTCAGTTAATGA TCGAATATAATGCGATCGTTGTACTCGAAGACCTGAATTTCGG CTTCAAACGCGGCCGGTTCAAGGTGGAGAAGCAAGTGTATCAA AAATTTGAGAAGATGTTAATTGATAAACTGAACTACTTGGTCG ATAAGAAGAAGGAAGCCAATGAGAGTGGCGGGACACTCAAAGC CTACCAGCTTACCGATAGTTACGCTGACTTCATGAAGTACAAG AAAAAGCAATGCGGCTTCCTGTTTTATGTCCCGGCCTGGAACA CTTCCAAAATCGATCCTACTACTGGGTTCGTGAATCTGTTTGA CACACATTATGTCAATGTTAGTAAGGCCCAGGAATTTTTCTCG AAATTCAAGTCAATTCGCTACAACGCGGCCAACAACTATTTCG AGTTTGAAGTAACAGATTATTTTCCTTCAGTGGTAAAGCTGAA GGGCACCAAGCAGAATTGGATCATTTGCACCCATGGCACCCGC ATTATCAATTTTCGTAACCCGGAAAAAAATTCGCAGTGGGATA ATAAGGAAGTAGTGATCACAGATGAATTCAAGAAACTGTTTGA GAAGCACGGCATTGACTACAAAAATAGTTCCGACCTCAAGGGG CAGATCGCCTCTCAATCGGAGAAGGCGTTTTTTCATAACGAAA AAAAAGATACAAAGGACCCAGATGGCCTTCTGCAGCTTTTTAA |

TABLE 4-continued

Sequences of exemplary engineered ABW nucleases

| | Engineered Amino Acid Sequence | Engineered Nucleotide Sequence |
|---|---|---|
| | | ACTGGCGCTGCAGATGCGGAACTCTTTCATTAAGAGCGAAGAG GACTACTTAGTATCTCCTGTGATGAACGACGAAGGTGAATTCT TTGACTCGCGCAAAGCCCAGCCTAATCAGCCAGAGAACGCTGA TGCTAATGGGGCGTACAATATTGCAATGAAAGGGAAATGGGTT GTTAAGCAAATCCGCGAATCGGAGGACCTCGACAAGCTGAAAC TGGCAATCTCAAATAAAGAATGGTTGAACTTCGCCCAGCGCTC CGCGGCCGCAAAAGGCCGGCGGCCACGAAAAAGGCCGGCCAG GCAAAAAAGAAAAAGGCTAGCGGCAGCGGCGCCGGATCCCCAA AGAAGAAAGGAAGGTTGAAGACCCCAAGAAAAAGAGGAAGGT GTGATAA (SEQ ID NO: 43) |
| ABW5 | MGHHHHHHSSGLVPRGSGTMKN ILEQFVGLYPLSKTLRFELKPL GKTLEHIEKKGLIAQDEQRAEE YKLVKDIIDRYHKAFIHMCLKH FKLKMYSEQGYDSLEEYRKLAS ISKRNEKEEQQFDKVKENLRKQ IVDAFKNGGSYDDLFKKELIQK HLPRFIEGEEEKRIVDNFNKFT TYFTGFHENRKNMYSDEKESTA IAYRLIHENLPLFLDNMKSFAK IAESEVAARFTEIETAYRTYLN VEHISELFTLDYFSTVLTQEQI EVYNNIIGGRVDDDNVKIQGLN EYVNLYNQQQKDRSKRLPLLKS LYKMILSDRIAISWLPEEFKSD KEMIEAINNMHDDLKDILAGDN EDSLKSLLQHIGQYDLSKIYIA NNPGLTDISQQMFGCYDVFTNG IKQELRNSITPSKKEKADNEIY EERINKMFKSEKSFSIAYLNSL PHPKTDAPQKNVEDYFALLGTC NQNDEQPINLFAQIEMARLVAS DILAGRHVNLNQSENDIKLIKD LLDAYKALQHFVKPLLGSGDEA EKDNEFDARLRAAWNALDIVTP LYNKVRNWLTRKPYSTEKIKLN FENAQLLGGWDQNKEPDCTSVL LRKDGMYYLAIMDKKANHAFDC DCLPSDGACFEKIDYKLLPGAN KMLPKVFFSKSRIKEFSPSESI IAAYKKGTHKKGPNFSLSDCHR LIDFFKASIDKHEDWSKFRFRF SDTKTYEDISGFYREVEQQGYM LGFRKVSEAFVNKLVDEGKLYL FHIWNKDFSKHSKGTPNLHTIY WKMLFDEKNLTDVIYKLNGQAE VFYRKKSLDLNKTTTHKAHAPI TNKNTQNAKKGSVFDYDIIKNR RYTVDKFQFHVPITLNFKATGR NYINEHTQEAIRNNGIEHIIGI DRGERHLLYLSLIDLKGNIVKQ MTLNDIVNEYNGRTYATNYKDL LATREGERTDARRNWQKIENIK EIKEGYLSQVVHILSKMMVDYK AIVVLEDLNTGFMRNRQKIERQ VYEKPEKMLIDKLNCYVDKQKD ADETGGALHPLQLTNKFESFRK LGKQSGWLFYIPAWNTSKIDPV TGFVNMLDTRYENADKARCFFS KFDSIRYNADKDWFEFAMDYSK FTDKAKDTYTWWTLCSYGTRIK TFRNPAKNNLWDNEEVVLTDEF KKVFAAAGIDVHENLKEAICAL TDKKYLEPLMRLMTLLVQMRNS ATNSETDYLLSPVADESGMFYD SREGKETLPKDADANGAYNIAR KGLWTIRRIQATNCEEKVNLVL SNREWLQFAQQKPYLNDAAAKR PAATKKAGQAKKKKASGSGAGS PKKKRKVEDPKKKRKV (SEQ ID NO: 55) | ATGGGCCACCATCATCATCATCATAGCAGCGGCCTGGTGCCGC GCGGCAGCGGTACCATGAAGAACATCTTAGAGCAGTTTGTCGG CTTATATCCGTTGTCTAAAACACTTCGGTTTGAGCTTAAACCT TTGGGTAAGACGTTGGAACATATTGAGAAAAAGGCTTGATTG CCCAAGACGAACAGCGGGCGGTACAAATTGGTTAAAGA TATTATTGATCGCTACCACAAGGCTTTTATTCATATGTGCTTA AAACATTTTAAGCTCAAGATGTACAGTGAACAAGGGTATGATA GCTTGGAGGAGTACCGCAAGCTTGCGTCAATTTCCAAACGCAA CGAGAAAGAGGAGCAGCAATTTGACAAGTCAAGGAAAATCTT CGTAAGCAAATTGTCGACGCGTTTAAAAATGGCGGGAGTTATG ATGATCTGTTTAAGAAAGAATTGATCCAGAAACACCTCCCACG TTTTATTGAGGGTGAAGAAGAAAAACGTATCGTTGACAACTTC AACAAGTTCACGACCTATTTTACTGGTTTTCATGAAAATCGCA AGAATATGTATAGTGACGAAAAGGAATCGACGGCTATTGCTTA TCGTCTCATTCACGAAAACTTGCCATTGTTTTTGGATAACATG AAGAGCTTCGCTAAGATCGCCGAATCGGAAGTGGCTGCTCGTT TTACCGAAATCGAAACCGCTTACCGGACATACTTGAACGTAGA ACACATTAGTGAACTGTTCACCCTCGACTATTTTAGCACGGTT TTGACGCAAGAACAAATCGAAGTATATAATAACATTATCGGCG GGCGCGTCGACGACGACAACGTAAAGATCCAAGGGTTGAATGA GTACGTAAATTTATATAATCAGCAGCAGAAGGACCGGTCTAAG CGCTTACCGCTTCTTAAGTCCCTCTACAAAATGATCTTATCCG ATCGTATTGCAATTTCGTGGTTACCTGAGGAGTTCAAATCCGA TAAGGAGATGATTGAAGCAATTAACAACATGCATGACGACCTG AAGGACATTCTGGCAGGCGACAACGAAGACTCGCTTAAGTCCT TACTGCAGCATATTGGCCAATACGATCTCTCGAAAATCTACAT TGCGAACAATCCGGGCCTGACAGATATCTCACAACAAATGTTC GGGTGTTATGACGTCTTTACTAATGGGATCAAGCAGGAGCTCC GGAACAGTATTACCCCTTCAAAAAAGGAGAAAGCCGATAACGA AATCTACGAGGAGCGGATTAACAAAATGTTTAAAAGTGAGAAG AGTTTCTCAATTGCCTACCTGAATTCGTTGCCGCACCCAAAGA CGGATGCGCCTCAAAAAAATGTTGAGGATTATTTTGCTCTCCT GGGGACTTGCAATCAAAACGATGAACAGCCGATTAATTTGTTT GCCCAAATTGAGATGGCACGCTTAGTCGCCTCTGATATTCTCG CAGGCCGGCACGTTAATTTGAACCAATCTGAGAATGATATCAA GTTAATCAAGGATCTGTTAGATGCTTACAAGGCTCTGCAGCAT TTCGTCAAACCACTCCTTGGCTCGGGTGACGAGGCTGAGAAAG ATAACGAGTTCGATGCACGCCTCCGTGCGGCTTGGAATGCGTT GGACATTGTTACACCACTCTATAACAAGGTTCGGAACTGGCTG ACCCGCAAACCATATTCTACAGAAAAAATCAAGCTTAATTTCG AAAACGCCCAACTTCTGGGGGTTGGGATCAGAACAAAGAACC GGATTGCACATCAGTCCTCCTTCGGAAGGATGGGATGTACTAT TTAGCGATCATGGATAAAAAGGCGAATCACGCCTTTGACTGTG ACTGCTTACCGTCTGACGGGGCCTGTTTCGAGAAAATTGACTA CAAGCTGCTCCCGGGCGCGAATAAAATGTTGCCGAAAGTTTTT TTTTCTAAAAGCCGCATCAAAGAATTTTCCCCTTCGGAATCGA TCATCGCTGCTTATAAAAAGGGCACTCATAAAAAAGGGCCGAA TTTCAGTCTCTCTGATTGTCATCGCTTGATTGACTTTTTTAAG GCTAGCATTGATAAGCACGAAGATTGGTCAAAATTTCGTTTTC GCTTCTCAGATACCAAAACGTATGAAGACATCAGTGGTTTCTA CCGTGAAGTAGAACAGCAAGGCTATATGCTTGGGTTTTCGTAAA GTCTCTGAGGCCTTTGTGAATAAACTCGTTGATGAAGGTAAGT TATACTTATTCCATATCTGGAACAAGACTTTAGTAAGCACTC CAAAGGTACACCTAATCTCCACACTATTTATTGGAAAATGCTC TTCGATGAGAAAATCTCACTGACCGATGTCATCTACAAACTGAATG GCAGGCTGAAGTATTCTACCGTAAAAAAGTCTGGATCTTAA TAAGACAACTACTCACAAGGCACATGCCCAATCACCAATAAA AATACCCAAAACGCAAAGAAGGGTAGTGTTTTCGATTACGATA TCATCAAAAATCGTCGCTACACAGTGGACAAATTCCAGTTCCA CGTCCCTATCACCTTAAATTTTAAGGCAACAGGTCGTAATTAC ATTAATGAGCACACTCAAGAGGCAATCCGTAATAATGGCATCG AACATATCATTGGCATCGACCGTGGGGAGCGTCACTTGCTTTA CTTGTCGCTCATTGATCTGAAGGGTAATATCGTCAAGCAGATG ACCCTTAATGATATTGTCAATGAATATAATGGTCGGACTTATG |

TABLE 4-continued

Sequences of exemplary engineered ABW nucleases

| Engineered Amino Acid Sequence | Engineered Nucleotide Sequence |
|---|---|
| | CGACGAACTACAAGGACTTGCTGGCAACACGGGAGGGTGAGCG<br>TACGGACGCTCGGCGCAACTGGCAGAAGATTGAAATATTAAA<br>GAAATCAAGGAAGGTTACCTTAGCCAGGTGGTGCACATCTTGA<br>GTAAAATGATGGTCGACTACAAGGCTATCGTTGTTCTGGAAGA<br>CTTGAATACAGGCTTCATGCGGAATCGTCAAAAAATCGAACGT<br>CAAGTATATGAGAAGTTCGAAAAAATGTTAATTGACAAGCTGA<br>ACTGCTATGTTGACAAACAAAAGGATGCTGACGAGACGGGCGG<br>TGCCCTCCACCCGCTGCAGCTGACAAACAAATTTGAGTCGTTT<br>CGTAAGTTAGGTAAGCAGAGTGGTTGGCTTTTTTACATCCCAG<br>CATGGAACACTTCGAAAATCGACCCAGTTACTGGGTTCGTGAA<br>CATGTTAGACACGCGCTACGAGAACGCCGATAAGGCGCGGTGT<br>TTCTTCTCGAAATTCGATTCCATCCGGTATAACGCTGACAAAG<br>ATTGGTTTGAGTTTGCTATGGATTACAGTAAGTTCACTGATAA<br>AGCGAAAGATACTTACACGTGGTGGACTCTGTGTTCCTATGGG<br>ACGCGTATTAAAACTTTTCGTAATCCGGCTAAGAATAATTTGT<br>GGGATAATGAGGAGGTTGTCCTTACTGATGAGTTCAAGAAAGT<br>TTTCGCAGCGGCAGGTATTGATGTCCATGAGAACCTTAAGGAA<br>GCGATCTGTGCTCTGACAGATAAAAAGTATCTTGAACCACTCA<br>TGCGTCTCATGACCCTGCTCGTTCAAATGCGGAACTCTGCTAC<br>TAACTCCGAAACAGACTATTTACTTTCACCAGTTGCTGACGAG<br>TCAGGGATGTTCTATGACTCCCGCGAAGGGAAGGAAACACTGC<br>CAAAAGATGCGGACGCCAACGGTGCATATAACATTGCCCGTAA<br>GGGCCTCTGGACCATCCGGCGGATTCAAGCCACCAACTGTGAG<br>GAGAAAGTTAACTTAGTCCTCAGTAATCGTGAATGGTTGCAGT<br>TTGCCCAGCAGAAACCATATCTGAATGATGCGGCCGCAAAAAG<br>GCCGGCGGCCACGAAAAAGGCCGGCCAGGCAAAAAAGAAAAAG<br>GCTAGCGGCAGCGGCGCCGGATCCCCAAAGAAGAAAAGGAAGG<br>TTGAAGACCCCAAGAAAAGAGGAAGGTGTGATAA (SEQ ID NO: 56) |
| ABW 6 | MGHHHHHHSSGLVPRGSGTMIY<br>RENFKRKKEKIEMNTGFNDFTN<br>LSSVTKTLCNRLIPTEITAKYI<br>KEHGVIEADQERNMMSQELKNI<br>LNDFYRSFLNENLVKVHELDFK<br>PLFTEMKKYLETKDNKEALEKA<br>QDDMRKAIHDIFESDDRYKKMF<br>KAEITASILPEFILHNGAYSAE<br>EKEEKMQVVKMFNGPMTSFSAF<br>FTNRENCFSKEKISSSACYRIV<br>DDNAKIHFDNIRIYKNIANKFD<br>YEIEMIEKIEEAAGGADIRNIF<br>SYNFDHFAFNHFVSQDDISFYN<br>YVVGGINKFMNLYCQATKEKLS<br>PYKLRHLHKQILCIEESLYDVP<br>AKFNCDEDVYAAVNDFLNNVRT<br>KSVIERLQMLGKNADSYDLDKI<br>YISKKHFTNISQTLYRDFSVIN<br>TALTMSYIDTLPGKGKTKEKKA<br>ASMAKNTELISLGEIDKLVDKY<br>NLCPDKAASTRSLIRSISDIVA<br>DYKANPLTMNSGIPLAENETEI<br>AVLKEAIEPFMDIFRWCAKFKT<br>DEPVDKDTDFYTELEDINDEIH<br>SIVSLYNRTRNYVTKKPYNTDK<br>FGLYFGTSSFASGWSESKEFTN<br>NAILLAKDDKFYLGVFNAKNKP<br>AKSIIKGHDTIQDGDYKKMVYS<br>LLTGPNKMLPHMFISSSKAVPV<br>YGLTDELLSDYKKGRHLKTSKN<br>FDIDYCHKLIDYFKHCLALYTD<br>WDCFNFKFSDTESYNDIGEFYK<br>EVAEQGYYMNWTYIGSDDIDSL<br>QENGQLYLFQIYNKDFSEKSFG<br>KPSKHTAILRSLFSDENVADPV<br>IKLCGGTEVFFRPKSIKTPVVH<br>KKGSILVSKTYNAQEMDENGNI<br>ITVRKCVPDDVYMELYGYYNNS<br>GTPLSAEALKYKDIVDHRTAPY<br>DIIKDRRYTEDEFFINMPVSLN<br>YKAENRRVNVNEMALKYIAQTK<br>DTYIIGIDRGERNLLYVSVIDT<br>DGNIVEQKSLNIINNVDYQAKL<br>KQVEIMRKLARQNWKQGVKIAD<br>LKKGYLSQAVHEVAELVIKYNG | ATGGGCCACCATCATCATCATCATAGCAGCGGCCTGGTGCCGC<br>GCGGCAGCGGTACCATGATCTACCGTGAGAATTTTAAGCGGAA<br>AAAGGAGAAGATTGAAATGAACACTGGGTTTAATGACTTCACT<br>AATTTGAGTTCCGTGACCAAGACGTTATGCAACCGGTTGATCC<br>CAACAGAAATTACCGCAAAGTACATTAAGGAGCATGGGGTAAT<br>TGAGGCGGACCAAGAACGGAACATGATGAGTCAAGAGCTGAAA<br>AATATCTTGAATGACTTTTACCGGAGTTTCCTGAACGAGAACC<br>TTGTGAAGGTGCACGAACTTGATTTCAAGCCGTTATTCACCGA<br>GATGAAAAAGTACCTCGAAACAAAAGATAACAAGGAAGCACTC<br>GAAAAGGCCCAGGACGACATGCGGAAGGCAATCCATGATATCT<br>TTGAAAGTGATGACCGCTACAAAAAAATGTTCAAGGCTGAGAT<br>CACGGCGTCGATTTTGCCTGAATTCATTCTTCATAACGGGGCA<br>TATTCAGCCGAAGAAAGGAGGAGAAAATGCAAGTAGTCAAGA<br>TGTTCAATGGCTTTATGACGTCTTTCTCAGCATTCTTTACGAA<br>TCGTGAGAATTGTTTCTCCAAAGAAAAAGATCAGCTCCTCCGA<br>TGTTACCGTATTGTTGATGACAACGCGAAAATCCATTTCGATA<br>ACATTCGTATTTATAAAAATATCGCCAACAAGTTCGATTATGA<br>AATTGAAATGATCGAGAAGATCGAAGAGGCGGCGGGGGGTGCC<br>GACATTCGTAATATCTTCTCGTACAACTTTGACCACTTTGCAT<br>TCAATCATTTCGTTAGTCAAGATGATATCTCATTCTACAATTA<br>TGTTGTTGGTGGTATTAACAAGTTTATGAACTTGTATTGTCAA<br>GCCACCAAAGAGAAATTATCGCCTTATAAACTGCGTCACCTTC<br>ACAAACGATCTGTGTATTGAAGAAAGCCTCTATGACGTGCC<br>AGCGAAGTTTAATTGTGATGAGGACGTATATGCAGCTGTCAAC<br>GATTTTCTTAATAACGTTCGGACGAAATCAGTAATTGAACGCT<br>TGCAAATGCTCGGCAAAAATGCAGACAGTTACGACCTGGATAA<br>AATTTATATCTCTAAAAAGCACTTCACCAATATCTCTCAAACT<br>TTATATCGCGACTTCTCTGTGATCAACACTGCCCTCACTATGT<br>CTTATATCGATACTCTTCCGGGTAAGGGGAAAACCAAGGAAAA<br>AAAGGCAGCATCGATGGCCAAAAACACCGAACTTATTTCGTTA<br>GGCGAAATTGATAAGTTGGTGGATAAATATAACCTCTGTCCAG<br>ATAAGGCAGCTTCGACCCTAGCCTCATTCGGTCTATTAGCGA<br>CATCGTCGCTGACTACAAGGCAAACCCTCTTACAATGAATAGT<br>GGGATTCCGTTGGCAGAGAACGAGACAGAAATCGCGGTGTTAA<br>AAGAGGCGATCGAGCCTTTTATGGATATCTTCCGGTGGTGTGC<br>TAAGTTTAAAACCGACGAGCCTGTCGATAAGGATACAGATTTC<br>TACACGGAGTTAGAAGACATTAACGATGAAATCCATAGTATTG<br>TCAGTCTTTATAACCGGACCCGGAATTATGTCACTAAAAAGCC<br>GTACAACACAGATAAGTTCGGTCTGTATTTTGGCACTTCGTCG<br>TTCGCATCGGGTTGGAGCGAGCAGAAGGAGTTTACTAACAACG<br>CAATTTTGTTAGCCAAGGATGACAAGTTTTACCTCGGCGTGTT<br>CAACGCAAAAAACAAGCCAGCAAATCGATTATCAAAGGGCAT<br>GACACAATCCAAGATGGTGATTATAAGAAAATGGTGTATTCAC<br>TGCTCACCGGGCCAAATAAGATGCTTCCTCACATGTTTATCTC<br>GAGCAGTAAAGCGGTTCCTGTTTACGGGCTCACTGACGAGCTT |

TABLE 4-continued

Sequences of exemplary engineered ABW nucleases

| Engineered Amino Acid Sequence | Engineered Nucleotide Sequence |
|---|---|
| IVVMEDLNSRFKEKRSKIERGV YQQFETSLIKTLNYLTFKDRKP LEAGGIANGYQLTYIPESLKNV GSQCGCILYVPAAYTSKIDPTT GFVTLFKFKDISSEKAKTDFIG RFDCIRYDAEKDLFAFEFDYDN FETYETCARTKWCAYTYGTRVK KTFRNRKFVSEVIIDITEEIKK TLAATDINWIDSHDIKQEIIDY ALSSHIFEMFKLTVQMRNSLCE SKDREYDKFVSPILNASGKFFD TDAADKSLPIEADANDAYGIAM KGLYNVLQVKNNWAEGEKFKFS RLSNEDWFNFMQKRAAAKRPAA TKKAGQAKKKKASGSGAGSPKK KRKVEDPKKKRKV (SEQ ID NO: 68) | CTCAGCGACTATAAGAAAGGTCGCCACCTTAAGACATCCAAGA ATTTCGACATTGATTACTGTCACAAACTTATCGATTACTTCAA ACATTGTCTGCTTTGTATACTGATTGGGATTGCTTCAACTTC AAATTCTCTGATACGGAGTCCTACAATGATATCGGCGAGTTCT ACAAAGAGGTTGCCGAGCAAGGCTACTACATGAACTGGACATA TATCGGGTCGGACGATATCGATTCGCTGCAGGAAAACGGCCAG CTCTATCTTTTTCAAATTTATAACAAAGATTTCAGCGAAAAGT CATTCGGTAAACCGTCTAAACATACGGCCATCCTGCGTAGCTT ATTCAGCGATGAAAACGTGGCCGACCCAGTCATTAAACTGTGT GGGGGGACCGAAGTTTTTTCCGGCCGAAGTCTATTAAGACAC CAGTAGTACATAAAAAAGGCAGCATCCTCGTATCCAAACCTA TAACGCACAAGAAATGGACGAGAATGGTAATATCATCACCGTG CGGAAGTGTGTTCCAGACGACGTCTATATGGAGCTCTACGCT ATTACAACAACTCTGGGACGCCTCTGTCCGCCGAAGCTTTGAA ATACAAGGATATTGTGGACCACCGCACGGCTCCGTACGACATT ATCAAGGACCGGCGTTACACCGAAGACGAATTTTTCATCAACA TGCCGGTGTCATTGAATTATAAAGCGGAAAACCGCCGTGTTAA TGTGAACGAAATGGCCTTAAAATACATCGCACAGACCAAGGAC ACCTACATCATTGGCATCGATCGGGGCGAACGTAATCTGTTGT ATGTGAGCGTTATCGATACTGACGGCAATATCGTTGACGAAA GAGTCTCAATATCATCAATAACGTGGATTATCAAGCCAAATTA AAGCAAGTGGAAATCATGCGTAAACTGGCCCCGTCAGAATTGGA AGCAGGGGGTAAAGATTGCAGACCTGAAAAAGGGCTACCTGTC ACAAGCGGTACATGAAGTCGCGGAACTTGTAATTAAATACAAC GGGATTGTTGTAATGGAGGACTTAAACTCCCGCTTCAAAGAGA AGCGTTCTAAAATTGAACGCGGCGTCTACCAACAGTTTGAGAC ATCATTAATCAAGACATTGAATTATTTGACGTTCAAAGATCGC AAACCGTTAGAAGCCGGGGGCATTGCGAATGGTTATCAATTAA CTTATATTCCGGAGTCTCTTAAAAATGTGGGCTCTCAGTGCGG CTGTATCTTGTATGTGCCAGCAGCCTACACCTCGAAGATCGAC CCTACCACTGGTTTCGTCACCTTGTTCAAATTCAAAGACATTT CGAGCGAGAAAGCTAAAACGGATTTTATTGGTCGGTTCGACTG CATCCGTTATGATGCAGAAAAGGACCTTTTCGCATTTGAATTC GATTATGACAACTTTGAGACTTATGAGACTTGTGCGCGTACCA AATGGTGTGCATATACATACGGGACTCGGGTGAAGAAAACTTT CCGGAATCGGAAATTCGTGTCAGAGGTGATCATCGACATCACT GAAGAGATCAAGAAGACCCTTGCAGCGACCGATATTAATTGAA TTGACAGTCACGACATCAAACAAGAGATCATCGACTATGCCCT TAGCAGCCATATTTTTGAAATGTTCAAATTAACGGTACAGATG CGTAACAGCCTTTGCGAGAGTAAAGATCGCGAGTACGACAAGT TCGTCTCACCTATTCTCAACGCGTCGGGCAATTTTTCGACAC CGATGCCGCTGATAAAAGTCTGCCTATTGAAGCTGATGCGAAC GATGCGTATGGTATTGCTATGAAAGGGTTGTATAATGTTTTAC AAGTCAAAAACAACTGGGCGGAGGGCGAGAAATTTAAGTTCTC CCGTTTAAGCAACGAAGATTGGTTCAACTTCATGCAAAAGCGG GCGGCCGCAAAAAGGCCGGCGGCCACGAAAAAGGCCGGCCAGG CAAAAAAGAAAAAGGCTAGCGGCAGCGGCGCCGGATCCCCAAA GAAGAAAAGGAAGGTTGAAGACCCCAAGAAAAAGAGGAAGGTG TGATAA (SEQ ID NO: 69) |
| ABW 7 | MGHHHHHHSSGLVPRGSLQMTM DYGNGQFERRAPLTKTITLRLK PIGETRETIREQKLLEQDAAFR KLVETVTPIVDDCIRKIADNAL CHFGTEYDFSCLGNAISKNDSK AIKKETEKVEKLLAKVLTENLP DGLRKVNDINSAAFIQDTLTSF VQDDADKRVLIQELKGKTVLMQ RFLTTRITALTVWLPDRVFENF NIFIENAEKMRILLDSPLNEKI MKFDPDAEQYASLEFYGQCLSQ KDIDSYNLIISGIYADDEVKNP GINEIVKEYNQQIRGDKDESPL PKLKKLHKQILMPVEKAFFVRV LSNDSDARSILEKILKDTEMLP SKITEAMKEADAGDIAVYGSRL HELSHVIYGDHGKLSQIIYDKE SKRISELMETLSPKERKESKKR LEGLEEHIRKSTYTFDELNRYA EKNVMAAYIAAVEESCAEIMRK EKDLRTLLSKEDVKIRGNRHNT LIVKNYFNAWTVFRNLIRILRR KSEAEIDSFYDVLDDSVEVLS LTYKGENLCRSYITKKIGSDLK PEIATYGSALRPNSRWWSPGEK | ATGGGCCACCATCATCATCATCATAGCAGCGGCCTGGTGCCGCG CGGCAGCCTGCAGATGACAATGGATTACGGTAACGGTCAATTTG AGCGGCGCGCCCCGCTCACCAAGACAATCACTCTCCGGTTGAAA CCGATCGGGAGACCCGTGAGACGATTCGCGAGCAAAAGCTCCT CGAACAAGATGCTGCATTCCGTAAACTTGTTGAAACTGTCACCC CTATCGTGGATGATTGTATCCGGAAAATTGCTGACAACGCTTTG TGTCATTTTGGCACGGAATATGATTTCTCCTGTTTAGGTAATGC CATCTCAAAAAATGACAGCAAAGCGATTAAGAAAGAGACGAAA AAGTAGAGAAGCTGTTGGCCAAGGTTCTGACAGAGAACTTGCCA GACGGTCTGCGTAAAGTCAACGATATTAACAGCGCGGCTTTTAT TCAGGACACACTGACATCATTCGTCCAGGACGATGCTGACAAAC GTGTGTTAATTCAAGAGTTAAAGGGCAAAACTGTTTAATGCAA CGCTTTTTAACAACCCGGATTACTGCATTGACTGTATGGCTCCC TGACCGGGTGTTTGAGAACTTCAACATTTTTATCGAAAATGCTG AAAAGATGCGCATCTTGCTCGACTCACCATTGATGAAAAGATC ATGAAGTTCGATCCGGATGCAGAACAATACGCGAGTTTGGAATT CTATGGTCAATGTCTGTCCGAAGGATATTGATTCGTACAACC TCATCATTTCCGGGATTTATGCCGATGATGAGGTCAAGAACCCA GGTATCAATGAAATTGTTAAGGAATACAACCAGCAAATTCGCGG GGATAAGGATGAGTCACCTTTACCTAAACTGAAAAAGTTGCATA AACAAATTTTGATGCCTGTCGAGAAGGCATTTTTCGTTCGGGTA CTCAGTAATGATTCTGATGCTCGTTCAATTTTAGAAAAAATCTT GAAGGATACTGAGATGTTGCCTTCTAAGATCATTGAAGCGATGA AAGAAGCAGACGCTGGGGACATCGCTGTATATGGTTCACGTTTG CACGAGTTAAGCCACGTAATCTATGGCGATCACGGGAAGCTCTC |

TABLE 4-continued

Sequences of exemplary engineered ABW nucleases

| Engineered Amino Acid Sequence | Engineered Nucleotide Sequence |
|---|---|
| FNVKFHTIVRRDGRLYYFILPK<br>GAKPVELEDMDGDIECLQMRKI<br>PNPTIFLPKLVFKDPEAFFRDN<br>PEADEFVFLSGMKAPVTITRET<br>YEAYRYKLYTVGKLRDGEVSEE<br>EYKRALLQVLTAYKEFLENRMI<br>YADLNFGFKDLEEYKDSSEFIK<br>QVETHNTFMCWAKVSSSQLDDL<br>VKSGNGLLFEIWSERLESYYKY<br>GNEKVLRGYEGVLLSILKDENL<br>VSMRTLLNSRPMLVYRPKESSK<br>PMVVHRDGSRVVDRFDKDGKYI<br>PPEVHDELYRFFNNLLIKEKLG<br>EKARKILDNKKVKVLESERV<br>KWSKFYDEQFAVTFSVKKNADC<br>LDTTKDLNAEVMEQYSESNRLI<br>LIRNTTDILYYLVLDKNGKVLK<br>QRSLNIINDGARDVDWKERFRQ<br>VTKDRNEGYNEWDYSRTSNDLK<br>EVYLNYALKEIAEAVIEYNAIL<br>IIEKMSNAFKDKYSFLDDVTFK<br>GFETKLLAKLSDLHFRGIKDGE<br>PCSFTNPLQLCQNDSNKILQDG<br>VIFMVPNSMTRSLDPDTGFIFA<br>INDHNIRTKKAKLNFLSKFDQL<br>KVSSEGCLIMKYSGDSLPTHNT<br>DNRVWNCCCNHPITNYDRETKK<br>VEFIEEPVEELSRVLEENGIET<br>DTELNKLNERENVPGKVVDAIY<br>SLVLNYLRGTVSGVAGQRAVYY<br>SPVTGKKYDISFIQAMNLNRKC<br>DYYRIGSKERGEWTDPVAQLIN<br>AAAKRPAATKKAGQAKKKKASG<br>SGAGSPKKKRKVEDPKKKRKV<br>(SEQ ID NO: 81) | TCAGATTATCTATGATAAGGAGTCGAAACGCATCAGCGAGCTCA<br>TGGAAACGTTATCGCCTAAGGAGCGCAAAGAGTCAAAGAAACGC<br>TTGGAGGGTCTGGAAGAACATATCCGGAAGTCGACATATACCTT<br>CGACGAGCTTAATCGTTATGCGGAAAAGAACGTCATGGCTGCCT<br>ACATCGCGGCCGTGGAGGAAAGCTGCGCCGAAATTATGCGTAAG<br>GAGAAGGACTTACGCACGCTTCTTAGTAAGGAGGATGTCAAGAT<br>TCGTGGTAATCGCCACAATACGTTAATTGTTAAGAACTACTTCA<br>ATGCCTGGACTGTCTTCCGGAATTTGATCCGCATCCTCCGGCGG<br>AAATCCGAGGCGGAGATCGACTCAGATTTCTATGACGTCTTGGA<br>TGACTCTGTGGAAGTTTTATCGCTCACATATAAAGGTGAAAACT<br>TGTGCCGGTCTTACATTACGAAGAAGATCGGGAGCGATTTAAAG<br>CCAGAGATTGCTACCTATGGTTCCGCCTTGCGCCCTAATTCACG<br>GTGGTGGTCACCGGGCGAGAAGTTTAACGTAAAGTTCCACACCA<br>TTGTTCGCCGGGACGGTCGCCTTTATTATTTCATCTTGCCGAAA<br>GGTGCCAAACCTGTCGAGCTCGAAGATATGGATGGGGACATCGA<br>ATGCTTGCAAATGCGCAAGATTCCGAATCCGACTATTTTCCTTC<br>CAAAATTGGTTTTCAAGGACCCAGAGGCCTTCTTCCGCGACAAT<br>CCAGAGGCAGATGAATTCGTTTTTCTTTCGGGTATGAAAGCTCC<br>AGTGACCATCACGCGTGAAACCTATGAGGCGTATCGCTACAAAC<br>TTTATACAGTTGGGAAGTTACGCGACGGTGAAGTGAGCGAAGAA<br>GAGTATAAACGTGCGTTGTTACAAGTATTGACCGCCTATAAGGA<br>ATTCTTAGAGAATCGGATGATCTACGCAGATCTGAACTTTGGCT<br>TTAAAGATCTCGAAGAATACAAAGACTCGTCAGAATTTATCAAA<br>CAAGTCGAAACTCACAACACTTTTATGTGCTGGGCTAAGGTCAG<br>TAGCAGTCAGCTCGACGACCTGGTCAAGAGCGGGAACGGGTTAC<br>TGTTCGAAATCTGGTCAGAACGGTTGGAGTCCTATTACAAATAT<br>GGCAACGAGAAGGTGCTGCGTGGGTACGAGGGCGTTCTTTTGAG<br>TATCCTTAAGGACGAGAACCTCGTGAGCATGCGGACGCTGCTTA<br>ATTCTCGGCCGATGCTCGTCTACCGCCCTAAAGAATCATCCAAG<br>CCGATGGTCGTTCACCGGGACGGTAGCCGCGTCGTTGATCGGTT<br>CGATAAGGATGGGAAGTATATTCCACCAGAGGTACACGACGAAT<br>TATACCGGTTCTTTAACAATTTGCTTATTAAGGAAAAGCTCGGC<br>GAGAAAGCGCGCAAAATTTTAGACAACAAAAAAGTAAAAGTAAA<br>GGTATTGGAATCTGAACGTGTAAAGTGGTCAAAGTTTTATGATG<br>AACAGTTTGCAGTTACATTCTCTGTTAAAAAGAATGCAGACTGT<br>CTGGATACCACGAAAGATCTCAATGCCGAAGTTATGGAGCAGTA<br>TTCCGAATCGAACCGGCTTATCCTGATCCGCAATACCACTGACA<br>TCTTGTATTATCTTGTACTTGATAAGAATGGGAAAGTGCTGAAA<br>CAACGCTCATTGAATATCATTAACGACGGGGCTCGCGACGTTGA<br>TTGGAAAGAGCGTTTTCGGCAGGTAACAAAAGATCGTAACGAAG<br>GCTATAACGAGTGGGACTACTCGCGGACTAGCAACGATTTGAAA<br>GAGGTCTATCTGAATTATGCATTGAAGGAGATTGCCGAAGCGGT<br>AATCGAATACAACGCAATTTTGATTATTGAAAAAATGTCGAATG<br>CCTTCAAGGATAAGTACTCCTTTTTGGATGATGTTACCTTCAAA<br>GGTTTTGAGACCAAACTTCTTGCGAAGCTCTCTGACTTGCATTT<br>CCGGGGTATTAAAGATGGGGAGCCATGTTCGTTTACGAACCCGT<br>TACAGTTATGTCAGAACGACTCAAACAAAATTTTACAAGACGGT<br>GTGATTTTCATGGTCCCTAACAGCATGACGCGCAGTCTGGACCC<br>TGACACTGGGTTCATTTTTGCGATTAACGATCACAACATCCGCA<br>CTAAGAAAGCGAAGTTAAACTTCCTTAGTAAATTCGATCAGCTG<br>AAAGTGTCATCAGAGGGCTGTTTAATCATGAAATATTCGGGGGA<br>CTCCCTTCCTACACACAACACAGATAATCGTGTATGGAACTGTT<br>GTTGCAATCACCCGATCACCAACTACGACCGCGAGACGAAAAAG<br>GTCGAATTCATCGAGGAGCCAGTGGAAGAGTTGAGTCGCGTCTT<br>AGAAGAGAATGGGATTGAGACAGATACGGAACTTAACAAGCTTA<br>ACGAGCGCGAGAATGTTCCGGGCAAGGTAGTAGATGCCATCTAT<br>TCTCTGGTGTTGAATTACTTGCGTGGTACCGTGTCCGGCGTTGC<br>AGGCCAACGGGCGGTCTACTATTCCCCTGTGACGGGGAAAAAT<br>ATGATATTTCGTTTATCCAAGCAATGAATCTGAATCGTAAGTGC<br>GATTACTACCGGATCGGGAGCAAAGAACGCGGCGAATGGACGGA<br>TTTTGTAGCGCAGTTAATTAACGCGGCCGCAAAAAGGCCGGCGG<br>CCACGAAAAAGGCCGGCCAGGCAAAAAAGAAAAAGGCTAGCGGC<br>AGCGGCGCCGGATCCCAAAGAAGAAAAGGAAGGTTGAAGACCC<br>CAAGAAAAAGAGGAAGGTGTGATAA (SEQ ID NO: 82) |
| ABW8 | MGHHHHHHSSGLVPRGSGTMCY<br>DLNNIKTKLREREVETMGNNMD<br>NSFEPFIGGNSVSKTLRNELRV<br>GSEYTGKHIKECAIIAEDAVKA<br>ENQYIVKEMMDDFYRDFINRKL<br>DALQGINWEQLFDIMKKAKLDK<br>SNKVSKELDKIQESTRKEIGKI<br>FSSDPIYKDMLKADMISKILPE<br>YIVDKYGDAASRIEAVKVFYGF<br>SGYFIDFWASRKNVFSDKNIAS | ATGGGCCACCATCATCATCATCATAGCAGCGGCCTGGTGCCGC<br>GCGGCAGCGGTACCATGTGCTACGACTTAAACAACATCAAGAC<br>AAAGTTACGTGAACGCGAAGTCGAAACTATGGGCAATAACATG<br>GATAATAGCTTCGAGCCTTTTATTGGCGGTAATAGTGTCTCTA<br>AAACACTTCGGAATGAGCTGCGTGTAGGTTCCGAATATACTGG<br>TAAACACATTAAAGAGTGCGCGATCATTGCAGAGGACGCCGTG<br>AAGGCGGAGAACCAGTACATCGTAAAAGAGATGATGGACGACT<br>TTTACCGTGACTTCATTAATCGCAAACTTGACGCCTTGCAGGG<br>TATTAATTGGGAGCAGCTTTTTGACATTATGAAGAAGGCGAAA<br>TTGGATAAGTCGAATAAAGTCAGCAAAGAGTTAGACAAGATTC |

TABLE 4-continued

Sequences of exemplary engineered ABW nucleases

| Engineered Amino Acid Sequence | Engineered Nucleotide Sequence |
|---|---|
| AIPHRIVNVNARIHLDNITAFN RIAEIAGDEVAGIAEDACAYLQ NMSLEDVFTGACYGEFICQKDI DRYNNICGVINQHMNQYCQNKK ISRSKFKMERLHKQILCRSESG FEIPIGFQTDGEVIDAINSFST ILEEKDILDRLRTLSQEVTGYD MERIYVSSKAFESVSKYIDHKW DVIASSMYNYFSGAVRGKDDKK DVKIQTEIKKIKSCSLLDLKKL VDMYYKMDGMCLEHEATEYVAG ITEILVDFNYKTFDMDDSVKMI QNEHMINEIKEYLDTYMSIYHW AKDFMIDELVDRDMEFYSELDE IYYDLSDIVPLYNKVRNYVTQK PYSQDKIKLNFGSPTLANGWSK SKEFDNNVVVLLRDEKIYLAIL NVGNKPSKDIMAGEDRRRSDTD YKKMNYYLLPGASKTLPHVFIS SNAWKKSHGIPDEIMYGYNQNK HLKSSPNFDLEFCRKLIDYYKE CIDSYPNYQIFNFKPAATETYN DISEFYKDVERQGYKIEWSYIS EDDINQMDRDGQIYLFQIYNKD FAPNSKGMQNLHTLYLKNIFSE ENLSDVVIKLNGEAELFFRKSS IQHKRGHKKGSVLVNKTYKTTE KTENGQGEIEVIESVPDQCYLE LVKYWSEGGVGQLSEEASKYKD KVSHYAATMDIVKDRRYTEDKF FIHMPITINFKADNRNNVNEKV LKFIAENDDLHVIGIDRGERNL LYVSVIDSRGRIVEQKSFNIVE NYESSKNVIRRHDYRGKLVNKE HYRNEARKSWKEIGKIKEIKEG YLSQVIHEISKLVLKYNAIIVM EDLNYGFKRGRFKVERQVYQKF ETMLINKLAYLVDKSRAVDEPG GLLKGYQLTYVPDNLGELGSQC GIIFYVPAAYTSKIDPVTGFVD VFDFKAYSNAEARLDFINKLDC IRYDAPRNKFEIAFDYGNFRTH HTTLAKTSWTIFIHGDRIKKER GSYGWKDEIIDIEARIRKLFED TDIEYADGHNLIGDINELESPI QKKFVGELFDIIRFTVQLRNSK SEKYDGTEKEYDKIISPVMDEE GVFFTTDSYIRADGTELPKDAD ANGAYCIALKGLYDVLAVKKYW KEGEKFDRKLLAITNYNWFDFI QNRRFAAAKRPAATKKAGQAKK KKASGSGAGSPKKKRKVEDPKK KRKV (SEQ ID NO: 94) | AAGAGTCTACGCGGAAAGAAATCGGGAAAATCTTCTCATCCGA TCCAATCTATAAAGACATGCTCAAAGCGGACATGATCAGCAAA ATTCTGCCAGAGTATATTGTCGACAAATACGGTGATGCAGCCT CGCGGATCGAAGCTGTAAAGGTGTTTTACGGCTTTTCGGGTTA TTTTATCGACTTCTGGGCATCGCGCAAGAACGTCTTCTCAGAT AAGAACATCGCGTCGGCCATTCCGCACCGGATTGTCAATGTGA ACGCTCGGATCCATCTGGACAACATCACGGCCTTCAACCGTAT CGCAGAAATTGCAGGGGATGAAGTCGCCGGCATTGCTGAAGAT GCTTGTGCTTACCTGCAGAATATGAGCTTAGAGGATGTATTCA CGGGGGCCTGCTACGGTGAGTTCATCTGTCAGAAGGATATTGA TCGTTACAATAACATTTGCGGTGTTATCAACCAGCACATGAAT CAATACTGCCAAAACAAAAAGATCTCACGCTCAAAATTTAAGA TGGAACGTCTGCACAAACAGATCTTTATGTCGCTCTGAGAGTGG TTTTGAGATCCCGATTGGGTTTCAAACCGACGGGAGGTAATC GATGCTATCAACTCCTTTTCTACGATTCTTGAAGAGAAAGATA TCTTGGATCGTCTGCGCACTTTGTCGCAGGAGGTAACAGGTTA TGACATGGAGCGTATCTATGTAAGTTCCAAGGCGTTTGAGTCT GTATCAAAGTACATCGATCACAAATGGGACGTAATTGCTTCTT CCATGTACAATTACTTTTCTGGGGCTGTTCGTGGGAAGGACGA CAAGAAAGATCTCAAGATTCAGACGGAAATTAAAAAGATTAAG TCATGTTCGTTATTGGACCTCAAAAAGCTGGTAGATATGTATT ATAAAATGGATGGGATGTGTTTAGAGCACGAAGCGACGGAGTA CGTGGCAGGTATTACGGAGATCCTGGTTGACTTTAACTATAAG ACCTTCGACATGGATGATTCCGTTAAGATGATTCAAAATGAGC ACATGATTAATGAAATTAAAGAATATTTAGATACCTATATGTC TATCTATCATTGGGCGAAGGACTTTATGATCGATGAGCTCGTA GATCGCGACATGGAATTCTACAGTGAGCTCGATGAAATCTATT ATGATTTGTCCGACATCGTACCACTGTATAATAAAGTCCGCAA CTACGTCACGCAAAAACCGTATTCCCAGGATAAAATCAAGTTA AACTTTGGCAGCCCAACCTTAGCAAACGGTTGGAGCAAGTCGA AAGAATTTGATAACAACGTTGTAGTATTGTTGCGTGACGAAAA GATTTATCTGGCCATCTTAAATGTGGGGAATAAACCGTCAAAG GATATCATGGCGGGCGAAGACCGTCGTCGCTCCGATACTGATT ACAAGAAATGAATTACTATCTGCTCCCTGGGCAAGCAAAAC CCTGCCACACGTTTTTATCTCTTCAAATGCATGGAAGAAATCC CACGGTATCCCTGACGAGATTATGTACGGCTATAACCAAATA AGCATTTAAAATCTTCGCCAAACTTCGACTTAGAGTTTTGTCG CAAGCTGATCGATTATTACAAAGAATGTATTGACAGCTATCCT AACTATCAGATCTTCAATTTCAAATTCGCCGCTACGGAAACTT ACAACGATATTTCGGAGTTCTACAAAGATGTTGAACGTCAGGG GTACAAGATTGAATGGTCGTACATTTCCGAGGACGATATTAAT CAGATGGATCGTGACGGCCAGATTTATCTTTTTCAAATCTACA ACAAGGATTTTGCCCCAAACTCTAAGGGCATGCAGAATTTACA TACACTCTATTTAAAAAATATTTTTTCAGAGGAAAACCTCTCT GATGTCGTCATTAAACTGAATGGCGAGGCTGAGCTCTTCTTCC GCAAGAGCTCGATCCAACATAAACGCGGTCATAAGAAGGGTAG TGTGTTGGTAAATAAGACCTATAAAACCACAGAAAAACTGAA AATGGTCAAGGCGAAATTGAAGTAATCGAGAGCGTGCCGGACC AGTGTTACCTGGAGCTTGTTAAGTACTGGTCAGAGGGTGGTGT AGGTCAGTTGTCAGAAGAGGCTTCCAAATACAAAGATAAAGTC AGCCACTACGCTGCAACAATGGATATTGTCAAGGACCGGCGT ACACGGAGGATAAGTTCTTTATTCACATGCCGATTACGATTAA TTTTAAAGCTGATAACCGGAACAATGTCAACGAGAAAGTGCTG AAGTTTATTGCAGAAAACGATGATCTCCACGTTATTGGTATTG ACCGTGGGGAACGTAATCTCCTGTACGTCTCAGTAATTGATTC ACGTGGGCGTATTGTTGAGCAGAAGTCGTTTAATATTGTTGAG AATTACGAGAGCAGTAAAAATGTGATCCGCCGCCATGATTATC GTGGGAAATTAGTAAATAAAGAGCACTATCGTAATGAGGCACG TAAGAGCTGGAAAGAAATCGGCAAAATCAAGGAGATCAAAGA GGTTATCTCAGTCAAGTTATCCATGAGATTAGTAAGTTGGTAT TAAAGTATAACGCCATCATCGTGATGGAAGATCTTAATTATGG CTTCAAACGCGGGCGGTTTAAAGTCGAGCGGCAGGTATACCAG AAGTTCGAGACCATGCTTATTAACAAATTAGCCTACTTAGTGG ACAAATCACGCGCGGTAGACGAACCGGGTGGGTTATTAAAAGG CTACCAGCTGACATACGTGCCAGATAACTTGGGTGAACTGGGG TCCCAGTGCGGGATCATTTTTTATGTGCCAGCAGCATACACTT CGAAAATCGATCCTGTTACGGGCTTTGTAGACGTGTTTGATTT TAAGGCATACTCCAATGCCGAAGCACGTTTAGATTTCATCAAT AAACTGGACTGCATCCGGTATGACGCGCCGCGTAACAAGTTTG AAATTGCTTTCGACTACGGTAACTTCCGGACTCATCATACAAC CCTTGCAAAGACTAGCTGGACTATTTTTATTCACGGCGACCGT ATTAAAAAGGAGCGCGGTTCTTACGGCTGGAAGGACGAAATTA TCGATATCGAGGCCCGTATTCGTAAGCTGTTTGAAGACACAGA CATCGAATACGCCGATGGTCACAATTTGATCGGTGACATTAAC GAGCTCGAGAGTCCAATTCAAAAGAAATTCGTTGGTGAGCTGT |

TABLE 4-continued

Sequences of exemplary engineered ABW nucleases

| | Engineered Amino Acid Sequence | Engineered Nucleotide Sequence |
|---|---|---|
| | | TCGACATTATCCGTTTCACTGTCCAACTGCGCAACAGCAAAAG<br>TGAGAAATATGACGGCACCGAAAAGGAGTATGACAAAATTATT<br>TCGCCGGTAATGGACGAGGAGGGGGTTTTCTTTACAACCGACA<br>GTTATATCCGCGCAGATGGTACTGAATTACCTAAAGATGCTGA<br>TGCTAACGGGGCCTATTGTATCGCGCTGAAGGGTCTTTACGAC<br>GTGCTCGCGGTAAAGAAATATTGGAAGGAGGGGGAGAAGTTCG<br>ATCGGAAGTTACTTGCCATCACCAATTACAACTGGTTTGATTT<br>CATTCAGAATCGTCGCTTCGCGGCCGCAAAAAGGCCGGCGGCC<br>ACGAAAAGGCCGGCCAGGCAAAAAGAAAAAGGCTAGCGGCA<br>GCGGCGCCGGATCCCCAAAGAAGAAAAGGAAGGTTGAAGACCC<br>CAAGAAAAGAGGAAGGTGTGATAA (SEQ ID NO: 95) |
| ABW9 | MGHHHHHHSSGLVPRGSGTMSD<br>RLDVLTNQYPLSKTLRFELKPV<br>GATADWIRKHNVIRYHNGKLVG<br>KDAIRFQNYKYLKKMLDEMHRL<br>FLQQALVLEPNSNQAQELTALL<br>RAIENNYCNNNDLLAGDYPSLS<br>TDKTIKISNGLSKLTTDLFDKK<br>FEDWAYQYKEDMPNFWRQDIAE<br>LEQKLQVSANAKDQKFYKGIIK<br>KLKNKIQKSELKAETHKGLYSP<br>TESLQLLEWLVRRGDIKLTYLE<br>IGKENEKLNELVPLVELKDIHR<br>NFNNFATYLSGFSKNRENVYST<br>KFDRRSGYKATSVIARTFEQNL<br>MFCLGNIAKWHKVTEFINQANN<br>YELLQEHGIDWNKQIAALEHKL<br>DVCLAEFFALNNFSQTLAQQGI<br>EKYNQVLAGIAEIAGQPKTQGL<br>NELINLARQKLSAKRSQLPTLQ<br>LLYKQILSKGDKPFIDDFKSDQ<br>ELIAELNEFVSSQIHGEHGAIK<br>LINHELESFINEARAAQQQIYV<br>PKDKLTELSLLLTGSWQAINQW<br>RYKLFDQKQLDKQQKQYSFSLA<br>QVERWLATEVEQQNFYQTEKER<br>QQHKDTQPANVTTSSDGHSILT<br>AFEQQVQTLLTNICVAAEKYRQ<br>LSDNLTAIDKQRESESSKGFEQ<br>IAVIKTLLDACNELNHFLARFT<br>VNKKDKLPEDRAEFWYEKLQAY<br>IDAFPIYELYNKVRNYLSKKPF<br>STEKVKINFDNSHFLSGWTADY<br>ERHSALLFKFNENYLLGVVNEN<br>LSSEEEEKLKLVGGEEHAKRFI<br>YDFQKIDNSNPPRVFIRSKGSS<br>FAPAVEKYQLPIGDIIDIYDQG<br>KFKTEHKKKNEAEFKDSLVRLI<br>DYFKLGFSRHDSYKHYPFKWKA<br>SHQYSDIAEFYAHTASFCYTLK<br>EENINFNVLRELSSAGKVYLFE<br>IYNKDFSKNKRGQGRDNLHTSY<br>WKLLFSAENLKDVVLKLNGQAE<br>IFYRPASLAETKAYTHKKGEVL<br>KHKAYSKVWEALDSPIGTRLSW<br>DDALKIPSITEKTNHNNQRVVQ<br>YNGQEIGRKAEFAIIKNRRYSV<br>DKFLFHCPITLNFKANGQDNIN<br>ARVNQFLANNKKINIIGIDRGE<br>KHLLYISVINQQGEVLHQESFN<br>TITNSYQTANGEKRQVVTDYHQ<br>KLDMSEDKRDKARKSWSTIENI<br>KELKAGYLSHVVHRLAQLIIEF<br>NAIVALEDLNHGFKRGRFKIEK<br>QVYQKFEKALIDKLSYLAFKDR<br>TSCLETGHYLNAFQLTSKFKGF<br>NNLGKQSGILFYVNADYTSTTD<br>PLTGYIKNVYKTYSSVKDSTEF<br>WQRFNSIRYIASENRFEFSYDL<br>ADLKQKSLESKTKQTPLAKTQW | ATGGGGCATCACCACCACCACCACTCGTCGGGTCTTGTTCCAC<br>GTGGTTCTGGTACCATGTCTGATCGCCTGGACGTGCTTACTAA<br>CCAATACCCATTATCGAAAACTTTGCGCTTCGAATTGAAGCCG<br>GTTGGAGCCACAGCTGACTGGATTCGCAAACACAACGTTATCC<br>GCTATCATAATGGTAAACTGGTTGGAAAGGATGCGATCCGTTT<br>TCAAAATTATAAGTATCTGAAGAAAATGCTTGATGAGATGCAT<br>CGCTTATTTCTTCAGCAAGCACTGGTGTTGGAGCCAAATAGCA<br>ACCAGGCGCAGGAGTTGACCGCACTGCTGCGTGCTATTGAGAG<br>TAATTATTGCAACAACAACGACCTGCTGGCGGGCGATTATCCC<br>AGCCTCTCTACCGATAAGACCATTAAAATCAGCAACGGCCTTA<br>GCAAGCTGACCACGGATCTGTTCGATAAGAAGTTCGAAGACTG<br>GGCATACCAATACAAGGAAGATATGCCCAATTTCTGGCGTCAA<br>GATATTGCGGAATTAGAGCAAAAGCTTCAGGTGAGTGCGAACG<br>CAAAAGATCAAAAGTTCTACAAAGGGATCATCAAGAAGCTGAA<br>GAATAAGATCCAGAAGTCTGAACTGAAAGCGGAAACGCACAAG<br>GGCTTATACTCACCTACGGAGTCACTGCAACTGCTGGAGTGGC<br>TGGTACGCGTGGCGATATTAAACTGACTTACTTAGAGATTGG<br>TAAAGAGAACGAGAAACTTAATGAACTGGTCCCGCTGGTCGAA<br>CTTAAGGACATTCATCGCAATTTCAATAATTTCGCCACATATC<br>TTTCTGGCTTCAGCAAGAATCGTGAGAATGTGTACTCAACCAA<br>ATTTGATCGTCGTTCGGGTTATAAAGCCACCAGTGTAATCGCA<br>CGCACGTTCGAACAGAATTTAATGTTCTGTCTTGGTAACATTG<br>CCAAGTGGCACAAGGTGACAGAATTCATCAACCAGGCGAACAA<br>TTACGAGCTCCTGCAGGAGCACGGCATCGATTGGAATAAGCAA<br>ATTGCCGCGCTGGAACACAAACTGGACGTGTGTCTCGCAGAGT<br>TCTTCGCGCTTAATAACTTCTCACAAACCCTTGCACAACAGGG<br>TATCGAAAAGTATAACCAGGTCTTGGCCGGCATCGCCGAGCTT<br>GCAGGCAACCCAAGACCCAGGGCCTGAACGAACTCATTAACC<br>TGGCCCGTCAGAAATTGTCTGCCAAACGCTCACAACTGCCTAC<br>GTTGCAACTCCTTTACAAACAAATCTTAAGCAAGGGTGATAAG<br>CCATTCATCGACGATTTTAAAAGCGACCAAGAGTTGATCGCCG<br>AATTAAATGAGTTTGTAAGCAGCCAGATTCACGGAGAGCATGG<br>TGCAATCAAATTAATTAATCACGAACTTGAAAGCTTTATCAAT<br>GAAGCCCGTGCAGCGCAGCAACAGATTTATGTGCCCAAGGACA<br>AGCTTACCGAATTAAGTCTTCTTAACGGGCAGTTGGCAAGC<br>TATTAATCAATGGCGTTACAAACTGTTCGACCAGAAACAGCTG<br>GATAAACAACAGAAACAATATTCATTTAGCCTGGCCCAGGTTG<br>AACGCTGGCTGCAACTGAGGTTGAGCAACAAAACTTCTACCA<br>AACCGAAAAGGAGCGCCAGCGACATAAAGATACGCAGCCGGCG<br>AACGTCACCACCAGCAGCGATGGACACAGCATTTTAACAGCAT<br>TTGAGCAACAGGTGCAGACCTTATTAACCAACATCTGTGTTGC<br>TGCCGAGAAATATCGCCAATTAAGTGATAATCTCACAGCCATC<br>GATAAACAACGCAGAAGCCAGTTAAGCACTGAGAAAGTCAAA<br>TCGCGGTGATTAAAACCTTGCTGGACGCGTGTAACGAGCTGAA<br>TCACTTTCTGGCACGCTTCACGGTCAACAAGAAGGACAAACTC<br>CCCGAAGATCGCGCAGAATTTTGGTATGAAAGTTACAAGCGT<br>ACATTGACGCGTTTCCGATCTACGAGCTGTATAATAAAGTGCG<br>TAATTACTTAAGCAAGAAGCCGTTTAGCACTGAGAAAGTCAAA<br>ATTAATTTTGACAATTCCCATTTCCTGTCGGGTTGGACGGCGG<br>ACTATGAGCGTCACAGCGCCTTATTATTCAAATTTAATGAAAA<br>TTACCTGCTGGGTGTAGTGAATGAGAACTTAAGCAGCGAGGAA<br>GAAGAAAAGCTGAAGCTCGTGGGCGGCGAAGAACATGCCAAGC<br>GCTTCATTTATGATTTTCAGAAAATCGACAACTCAAACCCACC<br>GCGCGTTTTCATTCGTAGCAAGGGGTCATCGTTCGCACCTGCG<br>GTCGAAAAGTATCAGTTACCGATTGGCGATATCATTGACATTT<br>ACGATCAGGGTAAATTTAAGACAGAACACAAGAAGAAGAATGA<br>GGCCGAGTTTAAAGACAGTCTGGTACGTTTGATCGATTATTTT<br>AAGCTGGGCTTCTCTCGCCATGACAGCTATAAGCACTACCCAT<br>TCAAGTGGAAAGCCAGTCATCAATATAGCGACATTGCGGAATT |

TABLE 4-continued

Sequences of exemplary engineered ABW nucleases

| Engineered Amino Acid Sequence | Engineered Nucleotide Sequence |
|---|---|
| TVSSHVTRSYYNQQTKQHELFE VTARIQQLLSKAEISYQHQNDL IPALASCQSKALHKELIWLFNS ILTMRVTDSSKPSATSENDFIL SPVAPYFDSRNLNKQLPENGDA NGAYNIARKGIMLLERIGDFVP EGNKKYPDLLIRNNDWQNFVQR PEMVNKQKKKLVKLKTEYSNGS LFNDLAFKAAAKRPAATKKAGQ AKKKKASGSGAGSPKKKRKVED PKKKRKV (SEQ ID NO: 107) | TTACGCTCATACCGCCTCATTTTGTTACACGCTTAAGGAAGAA AACATCAATTTTAACGTTCTGCGTGAGTTGTCGTCGGCGGGCA AAGTATATCTCTTCGAAATTTACAATAAGGATTTCTCAAAGAA CAAGCGCGGCCAAGGACGCGACAACTTGCATACCAGTTATTGG AAGTTGCTGTTCTCGGCTGAGAACCTGAAGGATGTTGTGCTGA AATTAAACGGCCAAGCGGAGATCTTTTACCGCCCAGCGTCTTT GGCCGAAACCAAGGCCTACACCCATAAGAAAGGGGAAGTACTG AAACATAAGGCTTATAGCAAAGTGTGGGAAGCCCTGGATTCTC CCATTGGCACCCGCCTGAGCTGGGACGATGCTTTAAAGATCCC GTCTATTACCGAGAAGACCAATCACAATAATCAGCGTGTTGTC CAGTACAACGGCCAAGAAATTGGCCGCAAAGCGGAGTTCGCTA TTATCAAGAACCGCCGTTATTCCGTCGATAAATTCCTCTTTCA CTGCCCGATTACACTCAACTTCAAGGCGAACGGCCAGGACAAC ATTAACGCACGCGTTAATCAATTCCTGGCAAATAACAAGAAGA TCAACATTATTGGAATTGACCGTGGTGAAAAGCATTTACTGTA TATCAGCGTGATTAATCAACAAGGCGAAGTCCTGCATCAGGAA AGCTTCAATACAATCACGAATTCATATCAGACCGCCAATGGCG AGAAACGCCAAGTAGTCACTGACTATCACCAGAAGTTGGACAT GAGCGAGGACAAACGCGATAAAGCACGTAAGAGCTGGAGTACA ATCGAAAATATCAAAGAGCTGAAGGCGGGGTATCTGAGCCACG TTGTACATCGCCTCGCGCAACTGATTATCGAATTTAATGCCAT TGTTGCGTTGGAAGATCTTAACCACGGGTTCAAACGCGGACGT TTTAAAATCGAAAAGCAAGTGTATCAGAAGTTCGAAAAGGCGC TGATCGACAAATTGAGCTACTTAGCGTTTAAGGATCGCACGTC GTGTCTGGAAACTGGACATTACTTGAATGCCTTTCAATTAACC TCAAAGTTCAAAGGCTTTAACAACCTTGGCAAGCAATCCGGGA TTTTGTTCTACGTTAACGCCGATTACACGAGCACCACGGATCC CTTAACAGGCTATATTAAGAACGTATACAAAACCTACTCCTCG GTGAAGGATTCGACCGAATTTTGGCAGCGCTTTAACTCTATCC GCTATATTGCGAGCGAGAACCGTTTTGAATTTAGCTACGACTT AGCGGACCTGAAACAGAAGTCGCTCGAGAGTAAAACCAAACAG ACCCCTCTCGCCAAGACCCAATGGACGGTCTCTAGCCACGTTA CCCGTTCCTATTACAACCAGCAGACGAAGCAACATGAGTTATT CGAAGTGACAGCGCGCATTCAGCAATTGCTTAGCAAAGCAGAA ATCAGCTATCAACATCAAAACGACTTGATCCCTGCGTTAGCAT CATGTCAAAGTAAGGCGTTACACAAGGAGTTGATTTGGCTGTT CAACAGCATCCTGACTATGCGCGTCACGGACTCAAGCAAACCG TCCGCGACCTCGGAGAATGATTTTATCCTGAGCCCGGTAGCGC CGTACTTCGACTCCCGCAATCTGAATAAGCAGCTGCCGGAAAA CGGCGACGCGAACGGCGCATACAATATCGCTCGTAAAGGTATC ATGCTTCTGGAACGTATCGGGGACTTCGTCCCGGAAGGTAACA AGAAGTACCCCGATTTACTGATCCGCAATAATGACTGGCAGAA TTTTGTACAACGCCCGGAGATGGTGAACAAGCAGAAGAAGAAA CTCGTGAAGTTGAAAACGGAATACTCTAATGGCAGCCTCTTCA ATGATTTGGCGTTTAAGGCCGCAGCTAAGCGCCCCGCCGCGAC TAAGAAAGCGGGTCAAGCGAAGAAGAAGAAAGCGTCGGGGTCG GGAGCGGGCAGTCCGAAGAAGAAGCGTAAAGTAGAGGATCCGA AGAAGAAACGCAAAGTATAATAA (SEQ ID NO: 108) |

In another exemplary method, the nine targeted type V CRISPR-associated protein Cas12a (referred to as ABW) nucleases were further engineered to create novel variants ABW1-ABW9 for each of the targeted nucleases and then compared to native amino acid sequences of three Cas12a (Cpf1) nucleases from different organisms. Exemplary results are provided in Tables 5-6 below:

Table 5 represents the percent identity between amino acid sequences of engineered ABW nucleases and native Cas12a nucleases. Percent identity between sequences was assessed by alignment and comparison in a BLAST, using a blastp algorithm. NCBI references are provided for each Cas12a sequence. As demonstrated below, arrows indicate decrease (↓) and increase (↑) in sequence similarity after this round of engineering.

| | Percent Identity Amino Acid Between Sequences | | |
|---|---|---|---|
| | AsCpf1 (WP_021736722.1) | FnCpf1 (WP_003040289.1) | EeCpf1 (WP_055225123.1) |
| ABW1 | 48.81 | 34.75 | ↑ 32.29 |
| ABW2 | 34.14 | 37.25 | ↓ 30.15 |
| ABW3 | ↓ 33.60 | ↓ 42.72 | 35.66 |
| ABW4 | ↓ 34.63 | 41.17 | 33.65 |
| ABW5 | ↓ 32.95 | ↓ 42.73 | ↓ 35.00 |
| ABW6 | 32.64 | 33.28 | 52.45 |
| ABW7 | ↑ 23.36 | 22.80 | ↑ 26.54 |
| ABW8 | 31.65 | 35.39 | 48.69 |
| ABW9 | 30.67 | 32.36 | ↑ 34.17 |

TABLE 6

Percent identity between amino acid sequences of engineered novel ABW nucleases and native Cas12a nucleases. Percent identity between sequences was assessed using alignment and pairwise comparison in CLC Main Workbench 7.9.1. NCBI references are provided for each Cas12a sequence.

| | Percent Identity Amino Acid Between Sequences | | | | | | | | | | |
|---|---|---|---|---|---|---|---|---|---|---|---|
| | AsCpf1 | FnCpf1 | EeCpf1 | ABW1 | ABW2 | ABW3 | ABW4 | ABW5 | ABW6 | ABW7 | ABW8 | ABW9 |
| AsCpf1 (WP_021736722.1) | 100.00 | | | | | | | | | | | |
| FnCpf1 (WP_003040289.1) | 29.15 | 100.00 | | | | | | | | | | |
| EeCpf1 (WP_055225123.1) | 29.04 | 31.22 | 100.00 | | | | | | | | | |
| ABW1 | 46.65 | 29.27 | 27.38 | 100.0 | | | | | | | | |
| ABW2 | 28.54 | 32.33 | 25.07 | 32.98 | 100.0 | | | | | | | |
| ABW3 | 27.72 | 39.56 | 29.02 | 31.86 | 36.65 | 100.0 | | | | | | |
| ABW4 | 27.55 | 37.89 | 27.10 | 33.42 | 37.38 | 48.89 | 100.0 | | | | | |
| ABW5 | 26.82 | 40.30 | 28.37 | 30.59 | 35.79 | 55.64 | 48.25 | 100.00 | | | | |
| ABW6 | 27.30 | 26.82 | 48.89 | 30.87 | 28.07 | 31.10 | 29.28 | 29.74 | 100.0 | | | |
| ABW7 | 16.12 | 16.04 | 16.53 | 20.68 | 20.36 | 20.11 | 19.91 | 19.22 | 20.23 | 100.0 | | |
| ABW8 | 26.71 | 28.37 | 45.97 | 31.51 | 29.06 | 32.37 | 30.90 | 32.57 | 46.02 | 20.03 | 100.0 | |
| ABW9 | 23.50 | 27.02 | 22.23 | 27.39 | 30.67 | 29.61 | 34.31 | 30.84 | 25.47 | 16.48 | 26.07 | 100.00 |

The nucleotide sequences of the engineered ABW1-ABW9 nucleases were also compared to nucleotide sequences of two engineered control nucleases: Cas12a (Cpf1) and MAD7 (positive control). Sequences of engineered AsCpf1 and FnCpf1 was obtained from Zetsche et al. (2015) Cell; 163(3):759-71, the disclosure of which is incorporated herein. The results are provided in Table 7 below:

Table 7 represents the percent identity between nucleotide sequences of engineered ABW nucleases and engineered Cas12a nucleases. Percent identity was assessed by alignment and pairwise comparison in CLC Main Workbench 7.9.1.

can be used in protein purification to allow binding to the chromatographic columns for purification, and 2) the N-terminal glycine allows further, site-specific, chemical modifications that permit advanced protein engineering. Further, the Gly-6xHis (SEQ ID NO: 152) was designed for easy removal, if desired, by digestion with Tobacco Etch Virus (TEV) protease. For these constructs, the Gly-6xHis tag (SEQ ID NO: 152) was positioned on the N-terminus. Gly-6xHis tags (SEQ ID NO: 152) are further described in Martos-Maldonado et al., *Nat Commun.* (2018) 17;9(1): 3307, the disclosure of which is incorporated herein by reference.

| | Percent Identity Between Nucleotide Sequences | | | | | | | | | | |
|---|---|---|---|---|---|---|---|---|---|---|---|
| | AsCpf1 | FnCpf1 | MAD7 | ABW1 | ABW2 | ABW3 | ABW4 | ABW5 | ABW6 | ABW7 | ABW8 | ABW9 |
| AsCpf1 | 100.00 | | | | | | | | | | | |
| FnCpf1 | 51.08 | 100.00 | | | | | | | | | | |
| Positive Control | 39.44 | 37.68 | 100.00 | | | | | | | | | |
| ABW1 | 43.19 | 51.02 | 36.66 | 100.00 | | | | | | | | |
| ABW2 | 40.44 | 37.72 | 34.55 | 40.49 | 100.00 | | | | | | | |
| ABW3 | 41.34 | 37.38 | 36.68 | 39.59 | 45.57 | 100.00 | | | | | | |
| ABW4 | 42.05 | 38.11 | 36.79 | 40.95 | 47.66 | 53.49 | 100.00 | | | | | |
| ABW5 | 41.37 | 36.96 | 36.69 | 39.12 | 45.57 | 57.06 | 52.96 | 100.00 | | | | |
| ABW6 | 41.39 | 39.04 | 47.21 | 40.64 | 38.35 | 37.95 | 39.45 | 38.27 | 100.00 | | | |
| ABW7 | 33.27 | 31.99 | 30.78 | 34.30 | 33.80 | 34.90 | 33.65 | 34.21 | 35.00 | 100.00 | | |
| ABW8 | 41.05 | 38.80 | 46.36 | 40.82 | 39.60 | 39.96 | 39.76 | 40.71 | 54.90 | 35.02 | 100.00 | |
| ABW9 | 35.17 | 32.86 | 32.64 | 34.65 | 34.58 | 36.13 | 37.96 | 35.55 | 35.22 | 28.41 | 36.77 | 100.00 |

Example 2

In some methods, codon optimization, as described in Example 1, can lower nucleotide sequence similarity in most cases; however, it does not change the amino acid sequence of the protein. Further engineering was applied to sequences to improve the activity of the nucleases outside their native context. The native sequences of nine type V CRISPR-associated protein Cas12a/Cpf1 (ABW) nucleases were engineered to include glycine, 6x Histidine (SEQ ID NO: 151), and 3x nuclear localization signal tags.

These Gly-6xHis tag (SEQ ID NO: 152) were applied for several reasons including: 1) a 6xHis tag (SEQ ID NO: 151)

The NLS (Nuclear Localization Signal) fragments were added to improve transport to the nucleus. NLS fragments used in these examples were successfully added to Cas9 constructs, as previously described.

Using the engineered ABW nuclease sequence, at least 10 variants were developed for each of the nine engineered ABW nucleases. The nucleotide sequence of each ABW engineered novel variant was compared to the corresponding ABW engineered nucleotide sequence. Exemplary sequence comparisons are provided in Tables 8-16 below. Note that the sequences provided in Tables 7-15 do not exhaust all possible sequences as only 10 variants were selected for each ABW nuclease.

Table 8 represents the percent identity between nucleotide sequences of engineered ABW 1 nuclease and engineered ABW1 nuclease variants 2-10. The percent identity between sequences illustrates resulted from alignment and pairwise comparison in CLC Main Workbench 7.9.1.

| Peercent Identity Between Nucleotide Sequences of ABW1 Engineered Variants | | | | | | | | | |
|---|---|---|---|---|---|---|---|---|---|
| | ABW1 (SEQ ID NO: 4) | Variant 2 (SEQ ID NO: 5) | Variant 3 (SEQ ID NO: 6) | Variant 4 (SEQ ID NO: 7) | Variant 5 (SEQ ID NO: 8) | Variant 6 (SEQ ID NO: 9) | Variant 7 (SEQ ID NO: 10) | Variant 8 (SEQ ID NO: 11) | Variant 9 (SEQ ID NO: 12) | Variant 10 (SEQ ID NO: 13) |
| variant #6 | 100.00 | | | | | | | | | |
| variant #10 | 78.94 | 100.00 | | | | | | | | |
| variant #3 | 78.99 | 78.84 | 100.00 | | | | | | | |
| ABW1 | 78.53 | 78.62 | 78.53 | 100.00 | | | | | | |
| variant #8 | 78.84 | 77.57 | 79.01 | 78.84 | 100.00 | | | | | |
| variant #9 | 79.23 | 78.50 | 78.77 | 78.94 | 78.65 | 100.00 | | | | |
| variant #5 | 78.57 | 78.11 | 77.72 | 78.28 | 78.57 | 78.84 | 100.00 | | | |
| variant #2 | 78.28 | 78.21 | 78.97 | 78.79 | 78.53 | 78.75 | 78.87 | 100.00 | | |
| variant #4 | 78.84 | 78.36 | 77.84 | 79.14 | 78.67 | 78.38 | 78.31 | 79.40 | 100.00 | |
| variant #7 | 78.28 | 78.36 | 79.09 | 79.11 | 78.06 | 79.04 | 78.48 | 78.31 | 78.16 | 100.00 |

Table 9 represents the percent identity between nucleotide sequences of engineered ABW2 nuclease and engineered ABW2 nuclease variants 2-10. Percent identity between sequences is illustrated from alignment and pairwise comparison in CLC Main Workbench 7.9.1.

| Percent Identity Between Nucleotide Sequences of ABW2 Engineered Variants | | | | | | | | | |
|---|---|---|---|---|---|---|---|---|---|
| | ABW2 (SEQ ID NO: 17) | Variant 2 (SEQ ID NO: 18) | Variant 3 (SEQ ID NO: 19) | Variant 4 (SEQ ID NO: 20) | Variant 5 (SEQ ID NO: 21) | Variant 6 (SEQ ID NO: 22) | Variant 7 (SEQ ID NO: 23) | Variant 8 (SEQ ID NO: 24) | Variant 9 (SEQ ID NO: 25) | Variant 10 (SEQ ID NO: 26) |
| variant #8 | 100.00 | | | | | | | | | |
| variant #9 | 79.84 | 100.00 | | | | | | | | |
| ABW2 | 79.23 | 77.97 | 100.00 | | | | | | | |
| variant #10 | 79.60 | 78.41 | 78.51 | 100.00 | | | | | | |
| variant #5 | 78.63 | 78.19 | 78.51 | 78.89 | 100.00 | | | | | |
| variant #3 | 78.94 | 78.24 | 78.04 | 78.26 | 79.04 | 100.00 | | | | |
| variant #4 | 78.92 | 78.17 | 79.14 | 78.85 | 78.92 | 78.99 | 100.00 | | | |
| variant #6 | 78.68 | 78.43 | 78.55 | 78.48 | 78.14 | 79.31 | 78.48 | 100.00 | | |
| variant #2 | 78.53 | 77.87 | 78.02 | 78.75 | 78.26 | 78.68 | 78.41 | 79.26 | 100.00 | |
| variant #7 | 78.34 | 78.07 | 78.85 | 78.31 | 78.85 | 78.63 | 78.85 | 79.18 | 77.90 | 100.00 |

Table 10 represents the percent identity between nucleotide sequences of engineered ABW3 nuclease and engineered ABW3 nuclease variants 2-10. Percent identity between sequences is illustrated from alignment and pairwise comparison in CLC Main Workbench 7.9.1.

| Percent Identity Between Nucleotide Sequences of ABW3 Engineered Variants | | | | | | | | | |
|---|---|---|---|---|---|---|---|---|---|
| | ABW3 (SEQ ID NO: 30) | Variant 2 (SEQ ID NO: 31) | Variant 3 (SEQ ID NO: 32) | Variant 4 (SEQ ID NO: 33) | Variant 5 (SEQ ID NO: 34) | Variant 6 (SEQ ID NO: 35) | Variant 7 (SEQ ID NO: 36) | Variant 8 (SEQ ID NO: 37) | Variant 9 (SEQ ID NO: 38) | Variant 10 (SEQ ID NO: 39) |
| variant #8 | 100.00 | | | | | | | | |
| variant #10 | 79.00 | 100.00 | | | | | | | |
| variant #6 | 77.73 | 79.20 | 100.00 | | | | | | |
| variant #4 | 78.31 | 78.06 | 78.54 | 100.00 | | | | | |
| variant #3 | 78.13 | 77.93 | 79.60 | 78.82 | 100.00 | | | | |
| ABW3 | 78.49 | 77.14 | 77.70 | 78.13 | 78.13 | 100.00 | | | |
| variant #7 | 79.48 | 78.61 | 78.59 | 78.39 | 78.29 | 79.05 | 100.00 | | |
| variant #2 | 78.61 | 78.44 | 78.31 | 79.25 | 78.08 | 78.44 | 78.06 | 100.00 | |
| variant #5 | 78.59 | 77.90 | 77.78 | 77.32 | 78.23 | 78.36 | 78.46 | 77.75 | 100.00 |
| variant #9 | 78.69 | 78.56 | 78.34 | 77.45 | 78.41 | 78.29 | 78.64 | 78.46 | 79.38 | 100.00 |

Table 11 represents the percent identity between nucleotide sequences of engineered ABW4 nuclease and engineered ABW4 nuclease variants 2-10. Percent identity between sequences is illustrated from alignment and pairwise comparison in CLC Main Workbench 7.9.1.

| Percent Identity Between Nucleotide Sequences of ABW4 Engineered Variants | | | | | | | | | |
|---|---|---|---|---|---|---|---|---|---|
| | ABW4 (SEQ ID NO: 43) | Variant 2 (SEQ ID NO: 44) | Variant 3 (SEQ ID NO: 45) | Variant 4 (SEQ ID NO: 46) | Variant 5 (SEQ ID NO: 47) | Variant 6 (SEQ ID NO: 48) | Variant 7 (SEQ ID NO: 49) | Variant 8 (SEQ ID NO: 50) | Variant 9 (SEQ ID NO: 51) | Variant 10 (SEQ ID NO: 52) |
| variant #2 | 100.00 | | | | | | | | |
| variant #6 | 79.57 | 100.00 | | | | | | | |
| variant #5 | 79.35 | 80.08 | 100.00 | | | | | | |
| variant #4 | 80.01 | 79.59 | 79.01 | 100.00 | | | | | |
| variant #9 | 79.74 | 79.08 | 79.59 | 78.49 | 100.00 | | | | |
| ABW4 | 79.03 | 78.74 | 78.86 | 78.93 | 78.91 | 100.00 | | | |
| variant #7 | 79.23 | 78.54 | 79.20 | 79.11 | 79.67 | 79.23 | 100.00 | | |
| variant #3 | 79.20 | 79.35 | 79.08 | 78.93 | 78.64 | 79.35 | 78.74 | 100.00 | |
| variant #10 | 78.98 | 79.18 | 79.55 | 79.57 | 79.40 | 78.98 | 78.59 | 78.91 | 100.00 |
| variant #8 | 79.37 | 78.79 | 79.33 | 78.89 | 78.89 | 79.25 | 78.57 | 78.62 | 78.98 | 100.00 |

Table 12 represents the percent identity between nucleotide sequences of engineered ABW5 nuclease and engineered ABW5 nuclease variants 2-10. Percent identity between sequences is illustrated from alignment and pairwise comparison in CLC Main Workbench 7.9.1.

| Percent Identity Between Nucleotide Sequences of ABW5 Engineered Variants | | | | | | | | | |
|---|---|---|---|---|---|---|---|---|---|
| ABW5 (SEQ ID NO: 56) | Variant 2 (SEQ ID NO: 57) | Variant 3 (SEQ ID NO: 58) | Variant 4 (SEQ ID NO: 59) | Variant 5 (SEQ ID NO: 60) | Variant 6 (SEQ ID NO: 61) | Variant 7 (SEQ ID NO: 62) | Variant 8 (SEQ ID NO: 63) | Variant 9 (SEQ ID NO: 64) | Variant 10 (SEQ ID NO: 65) |
| variant #3 | 100.00 | | | | | | | | |
| variant #5 | 79.43 | 100.00 | | | | | | | |
| variant #8 | 79.15 | 79.58 | 100.00 | | | | | | |
| variant #4 | 78.75 | 78.85 | 79.33 | 100.00 | | | | | |
| variant #6 | 78.72 | 79.36 | 79.26 | 79.03 | 100.00 | | | | |
| variant #10 | 79.23 | 78.85 | 79.48 | 79.41 | 79.79 | 100.00 | | | |
| variant #2 | 78.77 | 78.29 | 78.19 | 78.98 | 79.56 | 78.57 | 100.00 | | |
| ABW5 | 77.89 | 77.58 | 78.95 | 78.34 | 78.65 | 77.36 | 79.1 | 100.00 | |
| variant #7 | 79.18 | 77.71 | 78.88 | 78.9 | 78.55 | 78.29 | 79.13 | 78.95 | 100.00 |
| variant #9 | 78.93 | 78.44 | 78.42 | 78.34 | 79.41 | 79.13 | 78.57 | 78.88 | 79.38 | 100.00 |

Table 13 represents the percent identity between nucleotide sequences of engineered ABW6 nuclease and engineered ABW6 nuclease variants 2-10. Percent identity between sequences is illustrated from alignment and pairwise comparison in CLC Main Workbench 7.9.1.

| Percent Identity Between Nucleotide Sequences of ABW6 Engineered Variants | | | | | | | | | |
|---|---|---|---|---|---|---|---|---|---|
| ABW6 (SEQ ID NO: 69) | Variant 2 (SEQ ID NO: 70) | Variant 3 (SEQ ID NO: 71) | Variant 4 (SEQ ID NO: 72) | Variant 5 (SEQ ID NO: 73) | Variant 6 (SEQ ID NO: 74) | Variant 7 (SEQ ID NO: 75) | Variant 8 (SEQ ID NO: 76) | Variant 9 (SEQ ID NO: 77) | Variant 10 (SEQ ID NO: 78) |
| variant #5 | 100.00 | | | | | | | | |
| variant #2 | 79.88 | 100.00 | | | | | | | |
| variant #4 | 79.60 | 79.88 | 100.00 | | | | | | |
| ABW6 | 79.88 | 79.03 | 78.98 | 100.00 | | | | | |
| variant #6 | 79.35 | 79.13 | 79.38 | 78.50 | 100.00 | | | | |
| variant #10 | 79.28 | 79.00 | 78.50 | 79.03 | 79.85 | 100.00 | | | |
| variant #7 | 79.25 | 78.68 | 78.80 | 79.18 | 79.13 | 79.58 | 100.00 | | |
| variant #3 | 77.55 | 79.38 | 79.73 | 79.20 | 79.08 | 78.13 | 78.35 | 100.00 | |
| variant #8 | 78.65 | 78.53 | 79.20 | 77.95 | 77.88 | 78.10 | 78.43 | 78.78 | 100.00 |
| variant #9 | 78.88 | 79.28 | 79.50 | 79.00 | 79.83 | 78.70 | 78.48 | 78.78 | 79.20 | 100.00 |

Table 14 represents the percent identity between nucleotide sequences of engineered ABW7 nuclease and engineered ABW7 nuclease variants 2-10. Percent identity between sequences is illustrated from alignment and pairwise comparison in CLC Main Workbench 7.9.1.

| Percent Identity Between Nucleotide Sequences of ABW7 Engineered Variants | | | | | | | | | |
|---|---|---|---|---|---|---|---|---|---|
| | ABW7 (SEQ ID NO: 82) | Variant 2 (SEQ ID NO: 83) | Variant 3 (SEQ ID NO: 84) | Variant 4 (SEQ ID NO: 85) | Variant 5 (SEQ ID NO: 86) | Variant 6 (SEQ ID NO: 87) | Variant 7 (SEQ ID NO: 88) | Variant 8 (SEQ ID NO: 89) | Variant 9 (SEQ ID NO: 90) | Variant 10 (SEQ ID NO: 91) |
| variant #2 | 100.00 | | | | | | | | |
| variant #8 | 79.80 | 100.00 | | | | | | | |
| variant #7 | 78.01 | 78.70 | 100.00 | | | | | | |
| variant #4 | 78.34 | 77.68 | 78.6 | 100.00 | | | | | |
| variant #9 | 78.47 | 78.93 | 78.34 | 78.24 | 100.00 | | | | |
| variant #6 | 77.85 | 78.32 | 77.85 | 78.39 | 78.47 | 100.00 | | | |
| variant #5 | 78.91 | 78.11 | 78.16 | 79.34 | 78.65 | 78.52 | 100.00 | | |
| variant #3 | 78.32 | 77.80 | 78.03 | 78.75 | 77.75 | 78.14 | 78.68 | 100.00 | |
| variant #10 | 77.24 | 78.27 | 77.93 | 77.78 | 78.09 | 78.24 | 78.47 | 78.27 | 100.00 |
| ABW7 | 78.27 | 76.98 | 77.88 | 77.83 | 77.44 | 78.09 | 77.85 | 78.65 | 76.98 | 100.00 |

Table 15 represents the percent identity between nucleotide sequences of engineered ABW8 nuclease and engineered ABW8 nuclease variants 2-10. Percent identity between sequences is illustrated from alignment and pairwise comparison in CLC Main Workbench 7.9.1.

| Percent Identity Between Nucleotide Sequences of ABW8 Engineered Variants | | | | | | | | | |
|---|---|---|---|---|---|---|---|---|---|
| | ABW8 (SEQ ID NO: 95) | Variant 2 (SEQ ID NO: 96) | Variant 3 (SEQ ID NO: 97) | Variant 4 (SEQ ID NO: 98) | Variant 5 (SEQ ID NO: 99) | Variant 6 (SEQ ID NO: 100) | Variant 7 (SEQ ID NO: 101) | Variant 8 (SEQ ID NO: 102) | Variant 9 (SEQ ID NO: 103) | Variant 10 (SEQ ID NO: 104) |
| ABW8 | 100.00 | | | | | | | | |
| variant #6 | 79.64 | 100.00 | | | | | | | |
| variant #3 | 79.27 | 79.32 | 100.00 | | | | | | |
| variant #10 | 78.39 | 78.54 | 79.15 | 100.00 | | | | | |
| variant #8 | 78.52 | 79.66 | 79.73 | 78.91 | 100.00 | | | | |
| variant #9 | 78.83 | 79.64 | 79.37 | 79.46 | 79.59 | 100.00 | | | |
| variant #7 | 79.32 | 78.95 | 79.46 | 77.98 | 79.93 | 78.47 | 100.00 | | |
| variant #2 | 78.81 | 79.32 | 79.17 | 78.32 | 79.08 | 79.68 | 79.32 | 100.00 | |
| variant #4 | 79.03 | 79.56 | 78.91 | 78.20 | 79.15 | 79.34 | 79.64 | 80.02 | 100.00 |
| variant #5 | 78.73 | 79.42 | 78.59 | 78.86 | 79.76 | 79.98 | 79.15 | 78.81 | 78.35 | 100.00 |

Table 16 represents the percent identity between nucleotide sequences of engineered ABW9 nuclease and engineered ABW9 nuclease variants 2-10. Percent identity between sequences is illustrated from alignment and pairwise comparison in CLC Main Workbench 7.9.1.

Percent Identity Between Nucleotide Sequences of ABW9 Engineered Variants

| | ABW9 (SEQ ID NO: 108) | Variant 2 (SEQ ID NO: 109) | Variant 3 (SEQ ID NO: 110) | Variant 4 (SEQ ID NO: 111) | Variant 5 (SEQ ID NO: 112) | Variant 6 (SEQ ID NO: 113) | Variant 7 (SEQ ID NO: 114) | Variant 8 (SEQ ID NO: 115) | Variant 9 (SEQ ID NO: 116) | Variant 10 (SEQ ID NO: 117) |
|---|---|---|---|---|---|---|---|---|---|---|
| variant #3 | 100.00 | | | | | | | | | |
| variant #4 | 78.96 | 100.00 | | | | | | | | |
| variant #7 | 78.59 | 78.02 | 100.00 | | | | | | | |
| variant #9 | 78.50 | 78.02 | 78.56 | 100.00 | | | | | | |
| variant #5 | 77.21 | 78.32 | 77.14 | 77.67 | 100.00 | | | | | |
| variant #10 | 77.71 | 77.65 | 77.54 | 78.13 | 78.61 | 100.00 | | | | |
| variant #2 | 77.80 | 76.58 | 78.32 | 77.17 | 77.69 | 77.54 | 100.00 | | | |
| variant #8 | 77.10 | 78.37 | 77.28 | 78.13 | 78.26 | 77.69 | 77.91 | 100.00 | | |
| variant #6 | 77.28 | 77.78 | 77.14 | 77.04 | 77.62 | 77.69 | 77.76 | 77.08 | 100.00 | |
| ABW9 | 75.94 | 76.27 | 75.90 | 75.51 | 75.55 | 75.07 | 76.58 | 76.34 | 75.88 | 100.00 |

Example 3

In another exemplary method, it is understood that a CRISPR-Cas genome editing system requires at least 2 components: a guide RNA (gRNA) and CRISPR-associated (Cas) nuclease. Guide RNA is a specific RNA sequence that recognizes the targeted DNA region of interest and directs the Cas nuclease to this region for editing. gRNA is made up of two parts: crispr RNA (crRNA), a 17-20 nucleotide sequence complementary to the target DNA, and a tracr RNA, which serves as a binding scaffold for the Cas nuclease in order to facilitate editing. The crRNA part of the gRNA is customizable and this feature enables specificity in every CRISPR experiment. In one method, predicted crRNA sequence of the gRNA for nucleases ABW1-ABW9, MAD7 (positive control), and AsCas12a are provided in Table 17 below:

TABLE 17

Predicted crRNA Sequences

| | Organism of origin | predicted crRNA_sequence | Spacer length | CRNA length | SEQ ID NO: |
|---|---|---|---|---|---|
| ABW1 | Acidaminococcus massiliensis Marseille-P2828 | GUCUAAAAGACCAUAUGAAUUUCUACUUUCGUAGAUN NNNNNNNNNNNNNNNNNNNNNNNNNNNN | 28 | 36 | 129 |
| ABW2 | Sedimentisphaera cyanobacteriorum strain L21-RPul-D3 | GUCUAAAGGCCUUAUAAAAUUUCUACUGUCGUAGAUN NNNNNNNNNNNNNNNNNNNNNNNNNNN | 27 | 36 | 130 |
| ABW3 | Barnesiella sp. An22 | GUCUAUACAGACACUUUAAUUUCUACUAUUGUAGAUN NNNNNNNNNNNNNNNNNNNNNNNNNNN | 28 | 36 | 131 |
| ABW4 | Bacteroidetes bacterium HGW-Bacteroidetes-6 | GUCUGAAAGACAAGUAUAAUUUCUACUAUUGUAGAUN NNNNNNNNNNNNNNNNNNNNNNNNNNN | 27 | 36 | 132 |
| ABW5 | Parabacteroides distasonis strain 8-P5 | GGCUAUAAGCCUUGUAUAAUUUCUACUAUUGUAGAUN NNNNNNNNNNNNNNNNNNNNNNNNNNN | 27 | 36 | 133 |
| ABW6 | Collinsella tanakaei | GUUGAAACUGUAAGCGGAAUGUCUACUUGGGUAGAUN NNNNNNNNNNNNNNNNNNNNNNNNNNN | 27 | 36 | 134 |
| ABW7 | Lachnospiraceae bacterium MC2017 | GCAUGAGAACCAUGCAUUUCUAAGGUACUCCAAAACN NNNNNNNNNNNNNNNNNNNNNNNNNNN | 29 | 36 | 135 |

TABLE 17-continued

Predicted crRNA Sequences

| | Organism of origin | predicted crRNA_sequence | Spacer length | CRNA length | SEQ ID NO: |
|---|---|---|---|---|---|
| ABW8 | Coprococcus sp. AF16-5 | GUUGAGUAACCUUAAAUAAUUUCUACUGUUGUAGAUN NNNNNNNNNNNNNNNNNNNNNNNN | 26 | 36 | 136 |
| ABW9 | Catenovulum sp. CCB-QB4 | AUCUACAACAGUAGAAAUUUAAGCUAAGGCUUAGACN NNNNNNNNNNNNNNNNNNNNNNNNN | 27 | 36 | 137 |
| MAD7 | Eubacterium rectale | GUCAAAAGACCUUUUUAAUUUCUACUCUUGUAGAUNN NNNNNNNNNNNNNNNNNNN | 21 | 35 | 138 |
| AsCpf1 | Acidaminococcus sp. BV3L6 | UAAUUUCUACUCUUGUAGAUNNNNNNNNNNNNNNNNN NNNNNNN | 24 | 20 | 139 |

Example 4

In another exemplary method, cleavage efficiency of ABW nucleases was tested in vitro. As efficacy of in vitro cleavage efficiency is a predictor of in vivo cleavage, it is important prior to testing the ABW nucleases to determine which nucleases would be predicted to be the more effective prior to delivering to the nucleases to test in cells.

Figure 3:
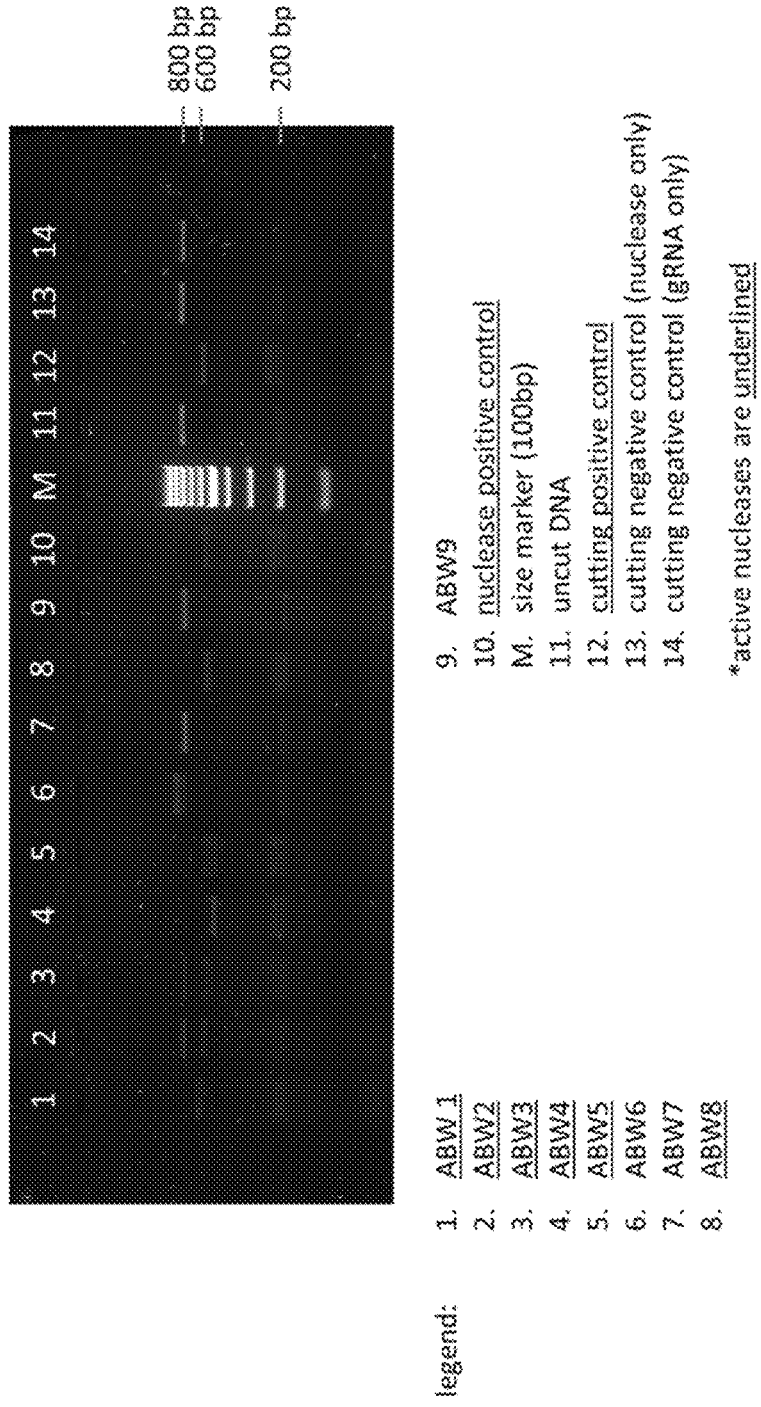
FIG. 3 is an exemplary image illustrating an in vitro cleavage assay to assess the efficiently of ABW nucleases and cognate gRNAs of some embodiments disclosed herein.
Figure 4:
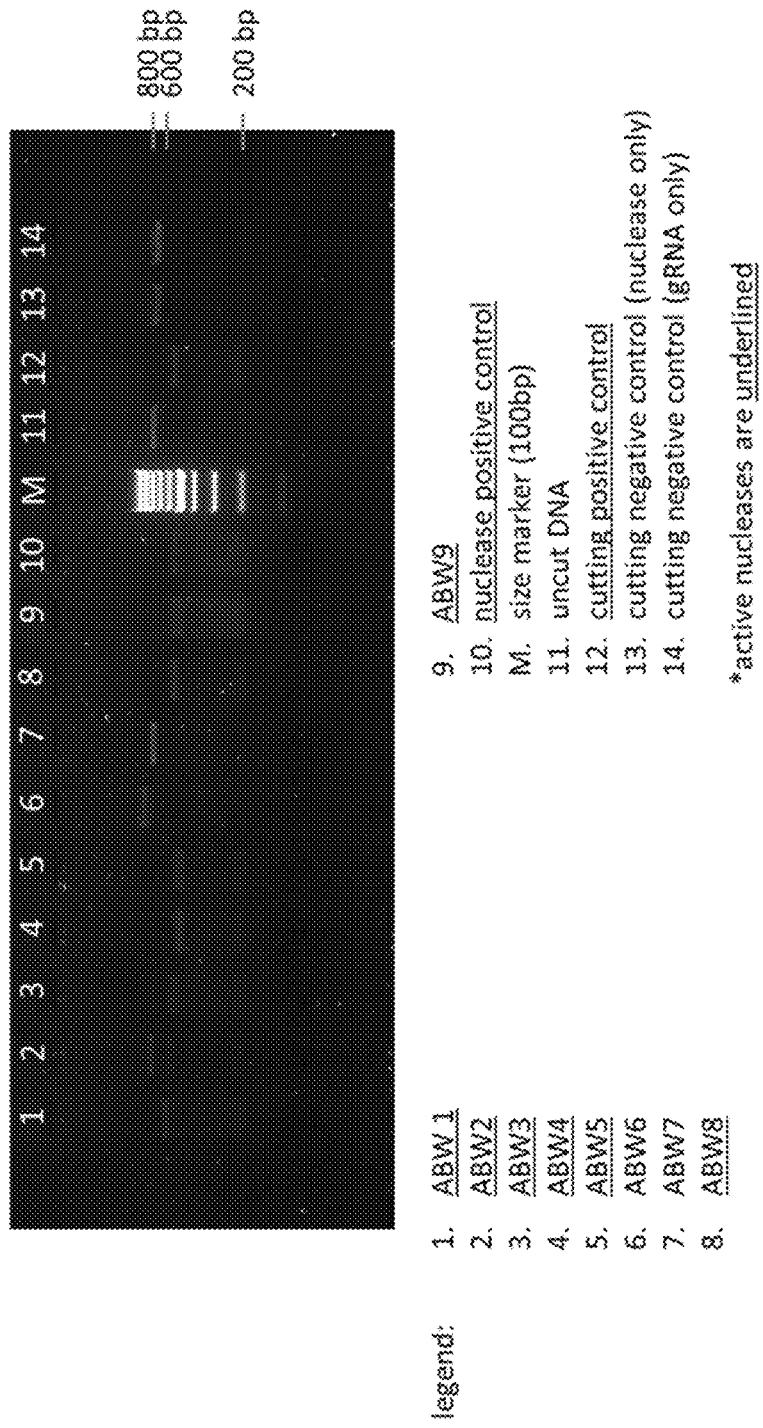
FIG. 4 is an exemplary image illustrating an in vitro cleavage assay to assess the efficiently of ABW nucleases and Cas12a gRNA of some embodiments disclosed herein.

In one exemplary method, to prepare partially cognate DNA substrates for the in vitro cleavage assay, DNMT1 target sequences and partially cognate target sequences were cloned to a plasmid, pRG2 plasmid. Before testing for in vitro DNA cleavage, the target plasmids were linearized and purified. An aliquot of linearized products was incubated with purified ABW1, ABW2, ABW3, ABW4, ABW5, ABW6, ABW7, ABW8, or ABW9 and 35 ng (165.3 nM) DNMT1 in combination with predicted-cognate gRNAs, Cas12a gRNA, or as referenced herein, "split" gRNA prepared using STAR. After incubation, products were loaded in 1.5% agarose gel for analysis. The sequences of gRNAs used the DNMT1 in vitro cleavage assays are provided in FIG. 2. Images of the 1.5% agarose gels illustrating DNMT1 cleavage are provided in FIGS. 3-5. Data illustrated in these figures is provided as an overview in Table 18 below.

These experiments indicate that ABW nucleases: ABW1, ABW2, ABW3, ABW4, ABW5, and ABW8 effectively cleaved the gRNAs tested. ABW9 cleaved only Cas12a gRNA whereas ABW6 and ABW7 failed to cleave any of the gRNAs tested.

CRISPR nucleases, in general, can differ in properties such as activity and specificity. Although ABW6 and ABW7 failed to demonstrate activity in the in vitro experiment, the nucleases behave differently under different conditions but retain genome editing properties in other settings.

TABLE 18

DNMT1 Amplicon in vitro Cleavage Assay Overview

| Nuclease (engineered and synthetized variant) | gRNAs | | |
|---|---|---|---|
| | predicted-cognate gRNA | Cas12a gRNA (SEQ ID NO: 127) | STAR gRNA (SEQ ID NO: 128) |
| ABW1 | ✓ | ✓ | ✓ |
| ABW2 | ✓ | ✓ | ✓ |
| ABW3 | ✓ | ✓ | ✓ |
| ABW4 | ✓ | ✓ | ✓ |
| ABW5 | ✓ | ✓ | ✓ |
| ABW6 | | | |

TABLE 18-continued

DNMT1 Amplicon in vitro Cleavage Assay Overview

| Nuclease (engineered and synthetized variant) | gRNAs | | |
|---|---|---|---|
| | predicted-cognate gRNA | Cas12a gRNA (SEQ ID NO: 127) | STAR gRNA (SEQ ID NO: 128) |
| ABW7 | | | |
| ABW8 | ✓ | ✓ | ✓ |
| ABW9 | | ✓ | |

In another exemplary method, the in vitro DNA cleavage assay was repeated using a time-course assay using a known nuclease as the active nuclease reference. The pRG2 plasmid having the DNMT1 target sequence was linearized and purified before testing. An aliquot of linearized products was incubated with a control gRNA (UAAUUUCUACUCUUGUAGAUCUGAUGGUC-CAUGUCUGUUA; SEQ ID NO: 149) and one of the following purified nucleases: Cas12a Ultra, LbaCas12a, control nuclease (MAD7), ABW1, ABW5, ABW8, M21, M44. The ratio of nuclease:gRNA:target DNA per incubation is provided in Table 19.

Table 19 represents the ratio of nuclease: gRNA: target DNA per assay incubation.

| Nuclease (Cas12a Ultra, LbaCas12a, MAD7, ABW1, ABW5, ABW8, M21, or M44) | gRNA (SEQ ID NO: 149) | target DNA (DNMT1) |
|---|---|---|
| 20 | 60 | 1 |
| 10 | 30 | 1 |
| 5 | 15 | 1 |
| 2.5 | 7.5 | 1 |
| 1.25 | 3.75 | 1 |
| 0.625 | 1.875 | 1 |

Figure 6A:
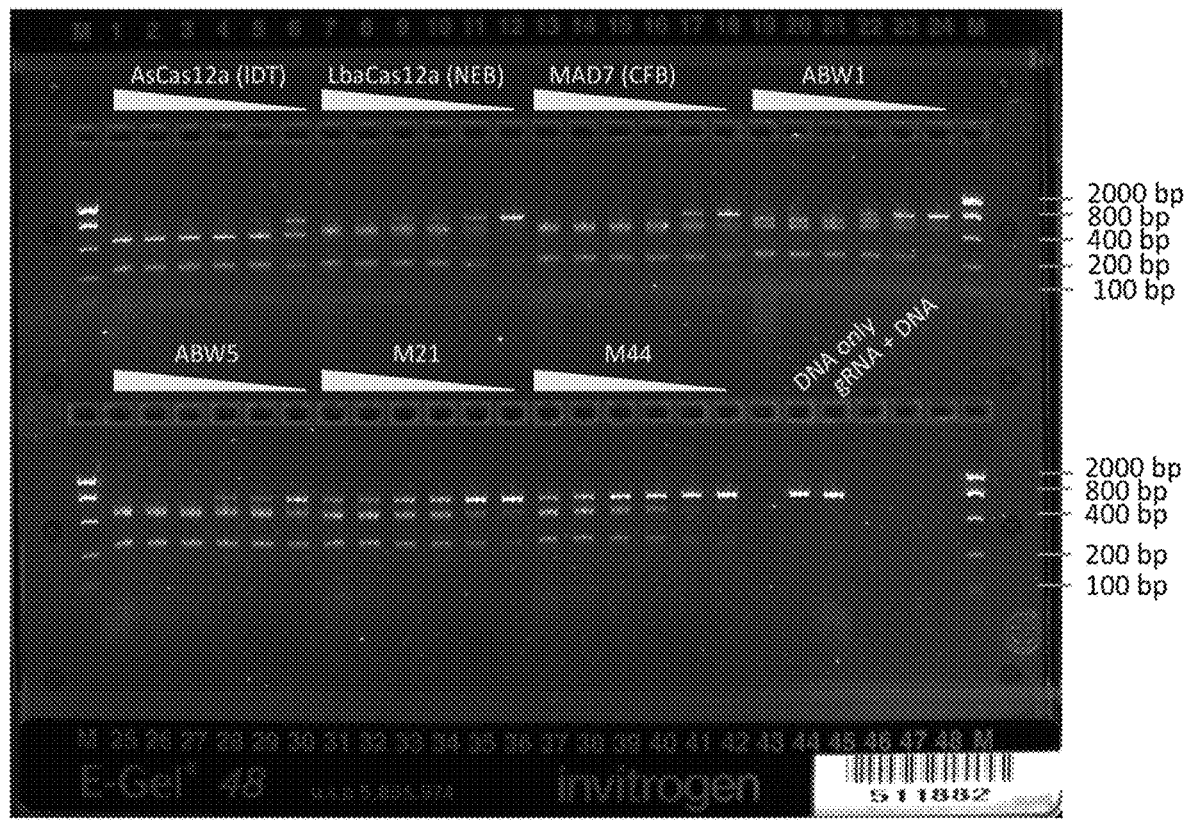
FIGS. 6A and 6B are exemplary images illustrating in vitro cleavage assays to assess the efficiently of Cas12a Ultra, LbaCas12a, MAD7, ABW1, ABW5, M21, M44 (FIG. 6A) or a Cas12a Ultra, LbaCas12a, MAD7, ABW1, ABW5, ABW8 (FIG. 6B) and Cas12a gRNA of some embodiments disclosed herein.
Figure 6B:
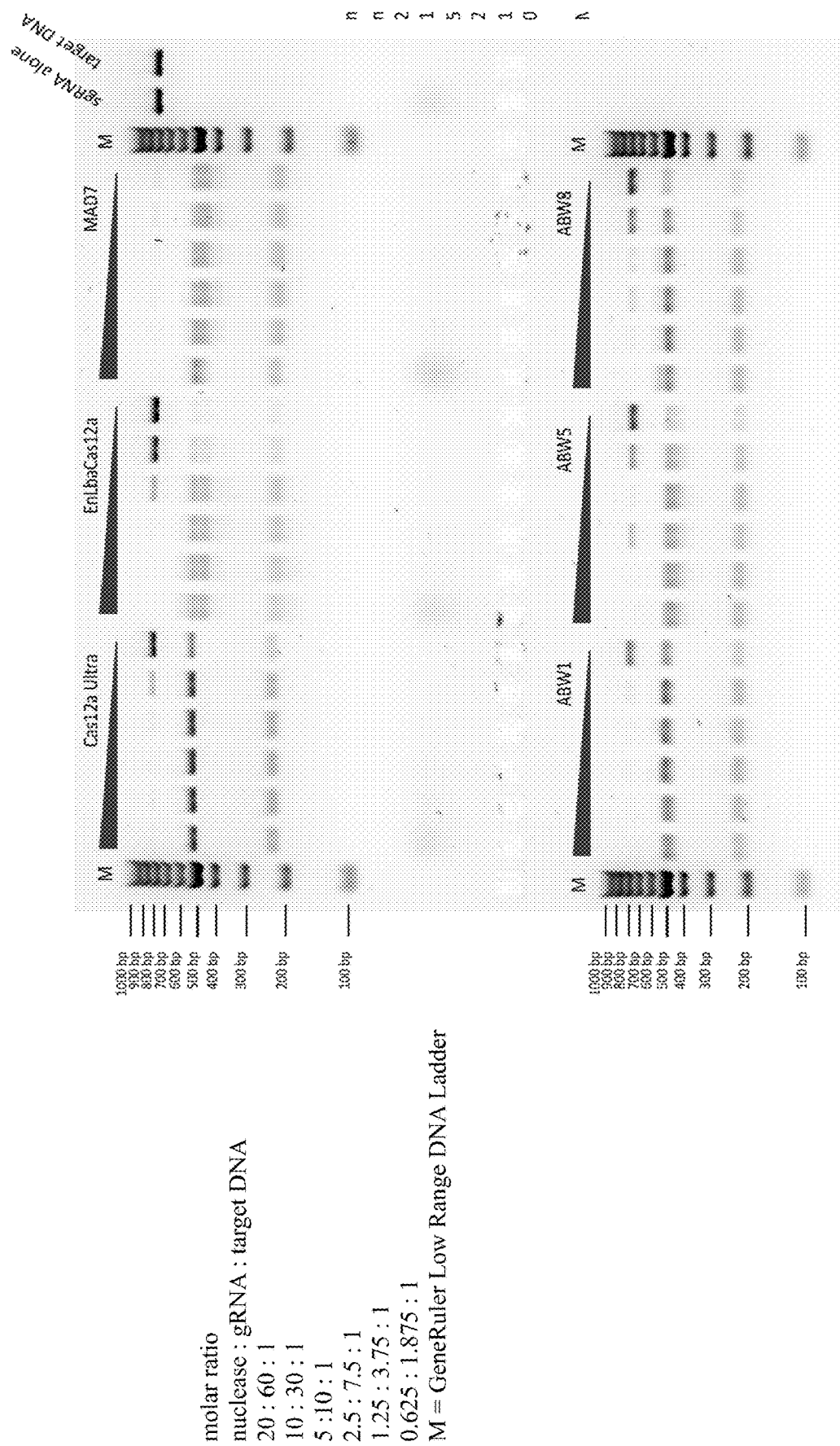

After incubation, products were loaded in 1.5% agarose gel for analysis and separation. Exemplary results are illustrated in FIGS. 6A and 6B.

Example 5

In another exemplary method, cleavage efficiency of ABW nucleases was tested in vivo in an exemplary eukaryotic cell population. Using these methods, the assay is based on the in vitro DNA cleavage assay. Jurkat cells, an acceptable immortalized line of human T lymphocyte cells, were cultivated under exemplary conditions in RPMI 1640 media with 10% Fetal Bovine Serum (FBS) and split regularly before being harvested for the transfection. Two target loci, DNMT1 and TRAC43, were chosen in genomic Jurkat's DNA as targets. Nucleases ABW1, 2, 3, 4, 5, 8, and control nuclease were diluted in the storage buffer (e.g. NaCl 300 mM, Na-phosphate 50 mM, EDTA 0.1 mM, DTT 1 mM, and glycerol 10%) to 20 mg/mL. Analogically, the gRNAs were diluted in the nuclease-free water to 100 μM. The RNA-protein complexes (RNPs) were prepared by mixing 1 μL nuclease solution and 1.5 μL gRNA solution. Complexes were formed in 96-well V-bottom plate during 10 minute incubations at room temperature.

Cells were counted and their viability was estimated in the NucleoCounter NC-200. Harvested cells were resuspended in the transfection buffer (SF from SF Cell Line 96-well Nucleofector Kit, Lonza) at 100×10$^5$ cells/mL concentration. 20 μL of that solution was added to the well with formed RNPs, mixed by pipetting, and transferred to 96-well Nucleocuvette plate (Lonza). Cells were electroporated. 80 μL of fresh RPMI 1640 media with 10% FBS were added to the Nucleocuvette plate immediately after the electroporation. The solution was mixed and 50 μL was transferred to the 96-well flat-bottom cultivation plate with 150 μL of fresh media. Cells were cultivated for 72 hours before being harvested for DNA extraction.

Figure 7A:
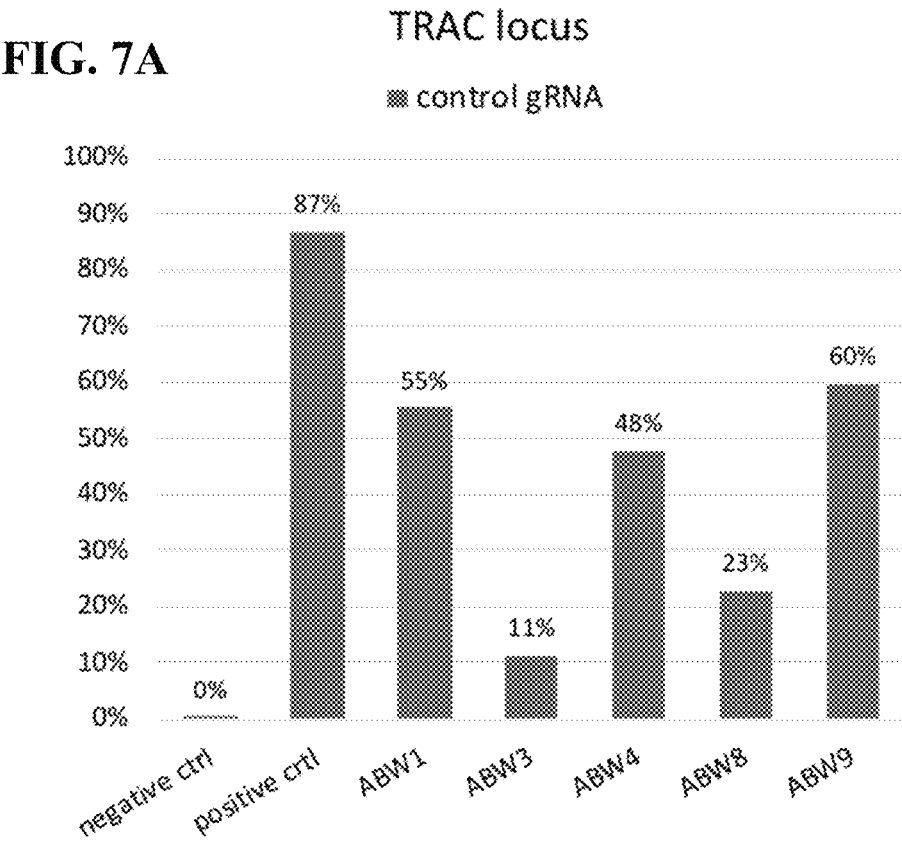
FIGS. 7A-7C are exemplary graphs illustrating Next Generation Sequencing (NGS) data of cleaved TRAC (FIG. 7A and FIG. 7B) and DNMT1 (FIG. 7C) target sequences resulting from an activity and editing efficiency test performed in Jurkat cells.
Figure 7B:
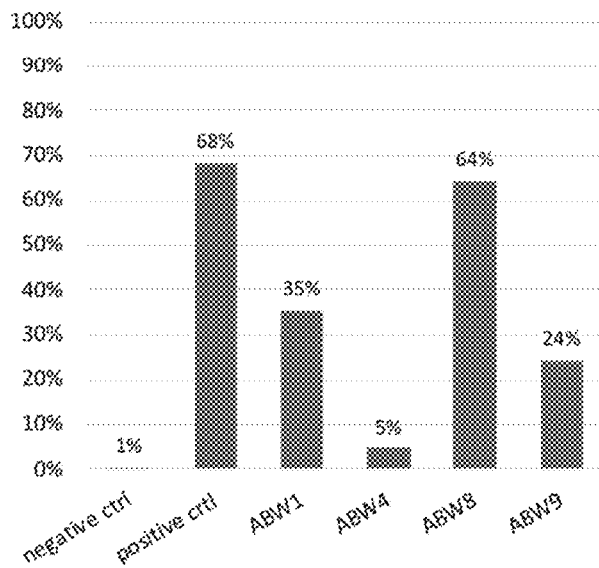
Figure 7C:
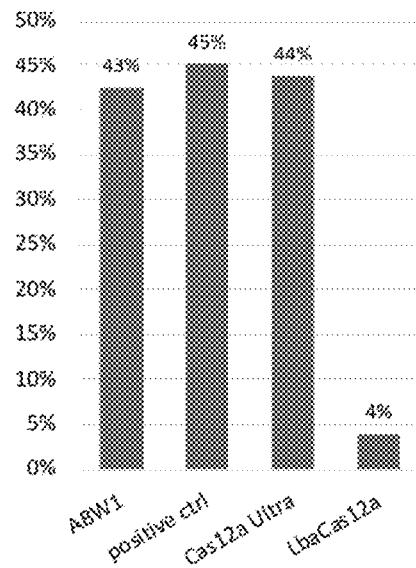
Figure 10:
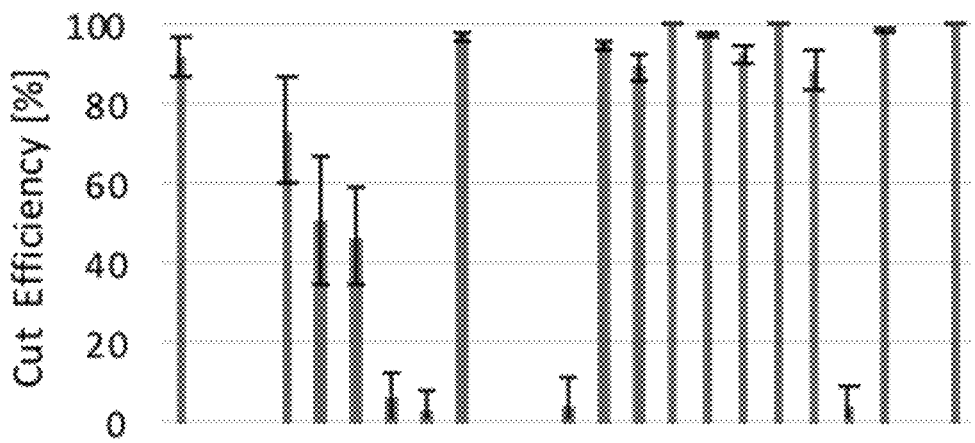
FIG. 10 is an exemplary graph illustrating a depletion assay to assess cutting efficiency of an ABW1 nucleic acid-guided nuclease of some embodiments disclosed herein.
Figure 11:
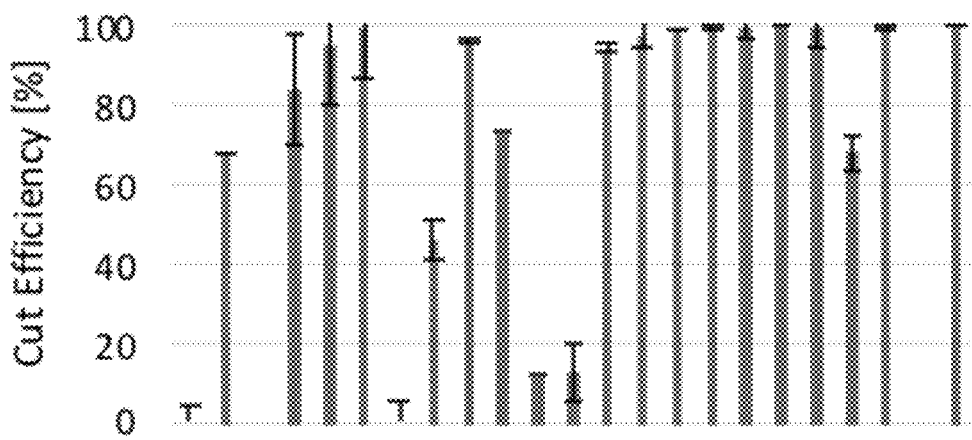
FIG. 11 is an exemplary graph illustrating a depletion assay to assess cutting efficiency of an ABW4 nucleic acid-guided nuclease of some embodiments disclosed herein.
Figure 12:
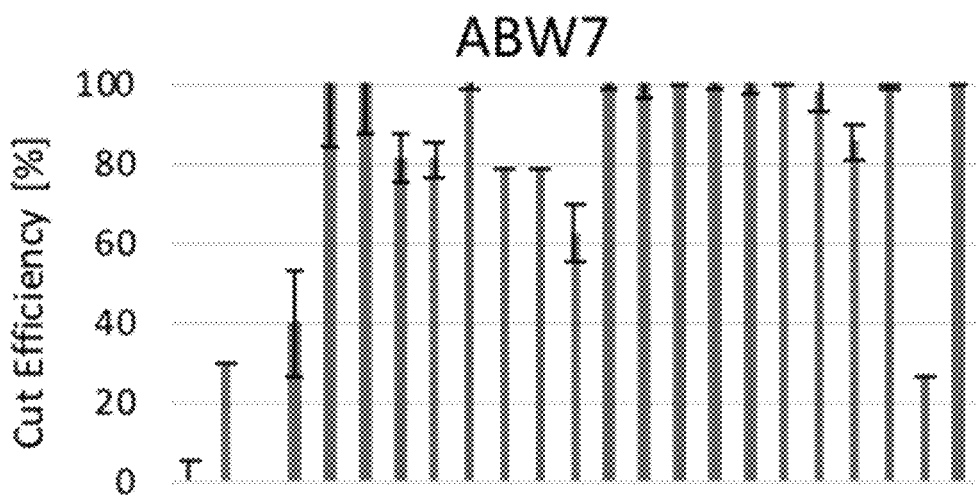
FIG. 12 is an exemplary graph illustrating a depletion assay to assess cutting efficiency of an ABW7 nucleic acid-guided nuclease of some embodiments disclosed herein.
Figure 13:
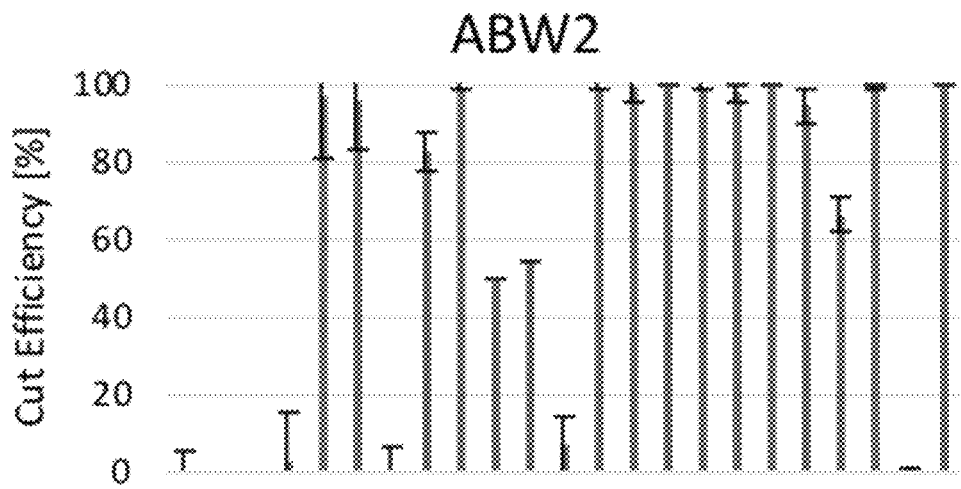
FIG. 13 is an exemplary graph illustrating a depletion assay to assess cutting efficiency of an ABW2 nucleic acid-guided nuclease of some embodiments disclosed herein.
Figure 14:
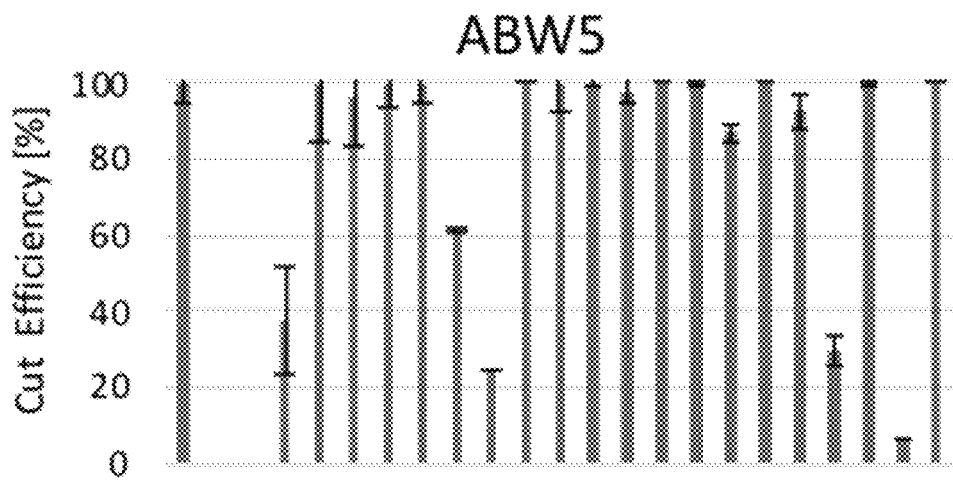
FIG. 14 is an exemplary graph illustrating a depletion assay to assess cutting efficiency of an ABW5 nucleic acid-guided nuclease of some embodiments disclosed herein.
Figure 15:
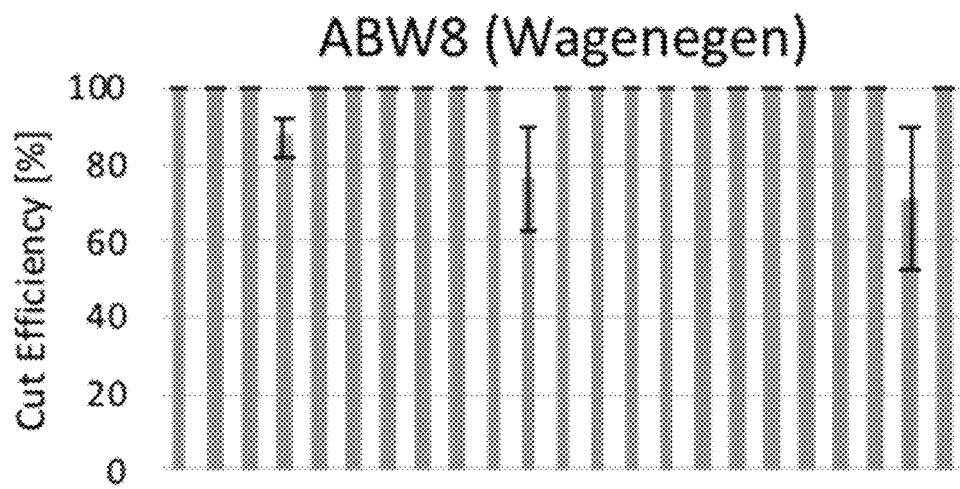
FIG. 15 is an exemplary graph illustrating a depletion assay to assess cutting efficiency of an ABW8 nucleic acid-guided nuclease of some embodiments disclosed herein.
Figure 16:
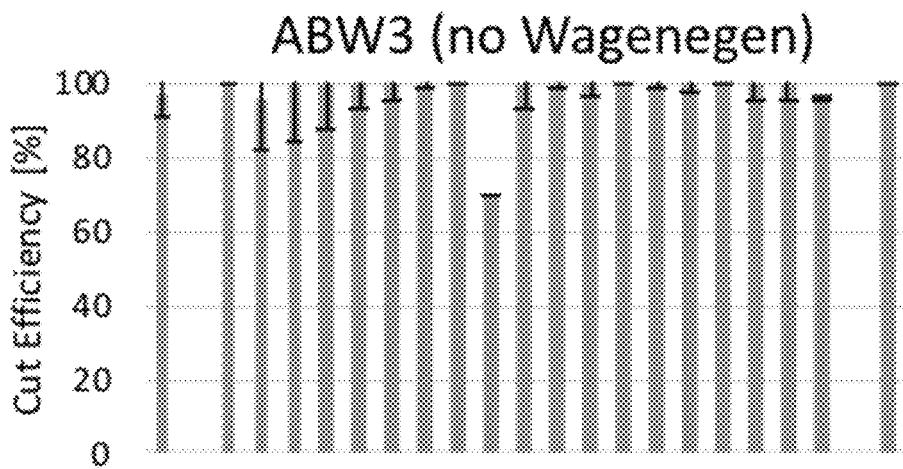
FIG. 16 is an exemplary graph illustrating a depletion assay to assess cutting efficiency of an ABW3 nucleic acid-guided nuclease of some embodiments disclosed herein.
Figure 17:
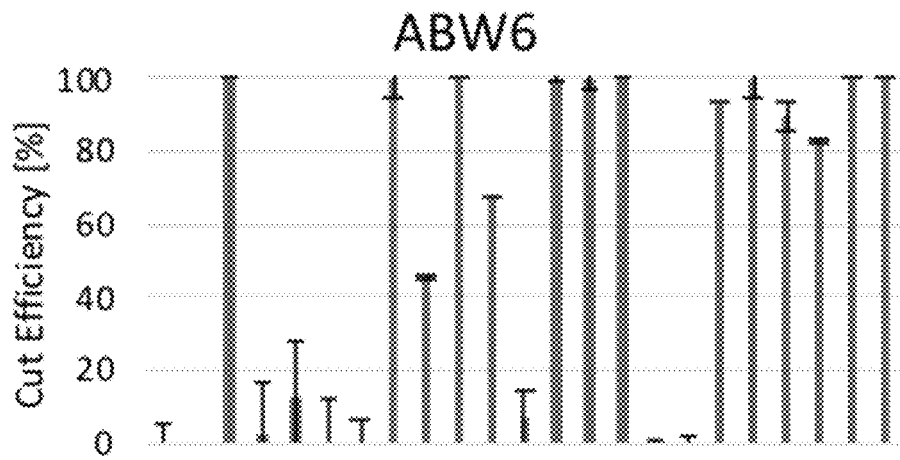
FIG. 17 is an exemplary graph illustrating a depletion assay to assess cutting efficiency of an ABW6 nucleic acid-guided nuclease of some embodiments disclosed herein.
Figure 18:
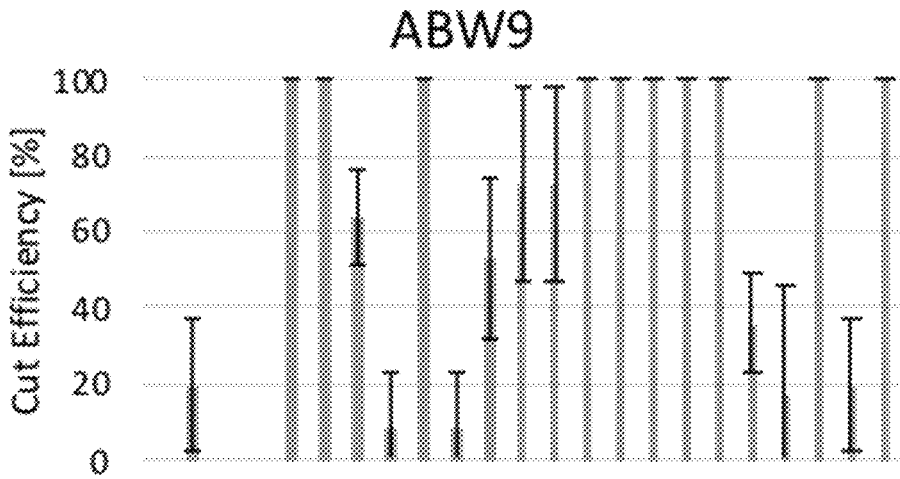
FIG. 18 is an exemplary graph illustrating a depletion assay to assess cutting efficiency of an ABW9 nucleic acid-guided nuclease of some embodiments disclosed herein.

Cells were harvested by centrifugation 1000×g for 10 minutes and washed with buffer (PBS). The supernatant was carefully removed, and the cell pellet was treated with 20 μL preheated QuickExtract DNA Extraction Solution (Lucigen). The plate was placed in the thermocycler (Biorad) and the temperature treatment (e.g. 15 minutes at 65° C., 15 minutes at 68° C., 10 minutes at 95° C., cold down to 4° C.) was applied. Cell debris was harvested by centrifugation, and the supernatant containing genomic DNA was collected. DNA fragments containing target sites were amplified in the PCR reaction and DNA was prepared for sequencing. The Next Generation Sequencing (NGS) data are presented in FIGS. 7A-7C.

Example 6

In another exemplary method, a T7 assay was performed on the genomic DNA from Jurkat cells. The T7 endonuclease catalyzes cleavage DNA mismatches and non-ß DNA structures like junctions and cruciform. When DNA cleavage occurs, random nucleotides are inserted or deleted, and a double-strand break is repaired. Thermal denaturation causes separation of strands and cooling down allows a DNA duplex to reassemble. If the edited strand reassembles with an unedited strand, a mismatch(s) appears. T7 endonuclease cleaves the mismatch, and DNA fragments can be visualized on the agarose gel in order to verify the process. In these examples, the targeted DNA was amplified in a PCR reaction. PCR products were purified and temperature treated (e.g. 10 min at 95° C., gradual cooling to 85° C.—5 cycles, -2°C per cycle, gradual cooling to 25° C.—200 cycles, -0.3°C per cycle) to create the heteroduplexes with mismatches. DNA was divided into two tubes, and one aliquot was treated with T7 endonuclease. Both DNA samples were analyzed on an agarose gel.

It was observed that using these exemplary conditions ABW1, ABW2, ABW3, ABW4, ABW5, and ABW8 demonstrated editing of the DNMT1 gene in Jurkat cells (FIG. 8), and ABW1, ABW2, ABW3, ABW4 and ABW8 demonstrated TRAC gene cleavage (FIG. 9).

Example 7

In another exemplary method, cleavage efficiency of ABW nucleases was tested in vitro. As efficacy of in vitro cleavage efficiency is a predictor of in vivo cleavage, it is important prior to testing the ART nucleases to determine which nucleases would be predicted to be the more effective prior to delivering to the nucleases to test in cells.

In some exemplary methods, cleavage efficiency of ABW nucleases was tested in vivo in *Escherichia coli* (*E. coli*). In these methods, the assay was based on in vivo depletion assay in *E. coli*. First, a glycerol stock of *E. coli* MG1655 harboring a plasmid that expresses the ART nuclease was removed from -80° C. freezer and take 20 μL cells into 2 of 4 mL LB (lysogeny broth) medium with 34 μg/mL chloramphenicol in 15 mL tubes. The cells were cultured at 30° ° C. and 200 rpm for overnight. Then, 4 mL overnight culture was put into 200 mL LB medium with 34 μg/mL chloramphenicol into 2 of 1 L flasks The cells were cultured at 30° C. and 200 rpm until OD600 reached 0.5-0.6. The flasks were put into a shaking water bath incubator at 42° C. and 200 rpm for 15 minutes. Then, the flasks were put in the ice with manually slow shaking and were kept in the ice for 15 minutes. After that, the cells were transferred from flasks to 50 mL tubes (4 tubes for 200 mL cells) and centrifuged at 8000 rpm and 4° C. for 5 minutes to remove supernatant. Then, 50 mL ice-cold 10% glycerol were added for 200 mL culture and the cells were resuspended. The resuspended cells were centrifuged at 8000 rpm and 4°C for 5 minutes to remove supernatant and 2 mL ice-cold 10% glycerol was added. Cells were resuspended with pipette gently and divided into 50 μL of the competent cells. The mixtures was then aliquoted into 72 chilled 0.1 cm electroporation cuvettes (Bio-rad).

The 24 gRNAs and one non-targeting control gRNA were diluted in the nuclease-free water to 25 ng/ul. gRNA_EC1 to gRNA_EC23 were targeted 18 target loci which are galK, lpd, accA, cynT, cynS, adhE, oppA, fabI, IdhA, pntA, pta, accD), pheA, accB, accC, arok, aroB, and aroK genes. 2 μL (50 ng) chilled plasmids were put into the electroporation cuvettes and the electroporation were done at 1800 V. Then, 950 μL LB medium were added into the cuvette and mixed, then the cells were taken out into a 96-deep well plate (Light labs). The 96-deep well plate with cells were put at 30° C. and 200 rpm for 2 hours.

Dilutions were made at 10/\0, 10/\1, and 10/\2 for the recovered cells after 2 hours of culture. Then, 10 μL of cells were put into 90 μL ddH$_2$O and mixed with pipette. After dilution, 8 μL of cells were taken from each dilution and placed by pipette onto a LB agar plate 34 μg/mL chloramphenicol and 100 μg/mL carbenicillin and allowed to dry without covers for several minutes. Then the covers were put back onto the plates and the plates were returned to culture at 30° C. for overnight. The next day, results were checked by counting the number of colonies.

Exemplary depletion assay outcomes using constructs disclosed herein, ABW1, ABW2, ABW3, ABW4, ABW5, ABW6, ABW7, ABW8, and ABW9 are provided in FIGS. 10-18 where the data depict percent cutting efficiency=1−(#of colonies plate with on-target gRNA/#of colonies on plate with non-target gRNA)*100%. In this example, ABW8 had the highest microbial activity of the nucleases tested followed by ABW3, then ABW7, then ABW9 compared to the remaining nucleases which showed some activity (i.e., ABW8>ABW3>ABW7>ABW9>ABW1, ABW2, ABW4, ABW5, and ABW6).

Example 8

In another exemplary method, ribonucleoproteins (RNPs) are produced by complexing of a single gRNA or STAR gRNA with nucleases disclosed herein (e.g., ABW nucleases but can be other nucleases). Single or STAR gRNAs are synthesized as described herein. Recombinant ABW are produced by expression of a E. coli codon optimized and 6Xhis-tagged (SEQ ID NO: 151) ABW nuclease in E. coli and purified by standard methods. Recombinant ABW nuclease is stored in a 25 mM Tris-HCl pH 7.4, 300 mM NaCl, 0.1 mM EDTA, 1 mM DTT, and 50% (v/v) glycerol buffer at −80° C. prior to use. Single gRNAs or STAR gRNAs are resuspended in IDTE (10 mM Tris. 0.1 mM EDTA) pH 7.5 buffer to produce a 100 µM stock and stored at −80° C. prior to use. Just before nucleoporation, recombinant ABW is diluted in a working buffer consisting of 20 mM HEPES and 150 mM KCl pH 7.5 and gRNAs are diluted to a final working concentration with IDTE pH 7.5 buffer (annealed first if STAR). Following dilutions of the ABW nuclease and gRNA, both are then mixed 1:1 by volume (2:1 gRNA to nuclease ratio) at 37°C for 10 minutes to form RNPs. Following complexing, RNPs are resuspended in the appropriate nucleoporation buffer and delivered via an optimized nucleoporator program and assessed.

The foregoing discussion of the disclosure has been presented for purposes of illustration and description. The foregoing is not intended to limit the disclosure to the form or forms disclosed herein. Although the description of the disclosure has included description of one or more embodiments and certain variations and modifications, other variations and modifications are within the scope of the disclosure, e.g., as can be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

SEQUENCE LISTING

```
Sequence total quantity: 152
SEQ ID NO: 1            moltype = AA  length = 1302
FEATURE                 Location/Qualifiers
REGION                  1..1302
                        note = Description of Artificial Sequence: Synthetic Native
                        Cas12a/Cpf1 [Acidaminococcus massiliensis] sequence
source                  1..1302
                        mol_type = protein
                        organism = synthetic construct
SEQUENCE: 1
MAAFDKFIHQ YQVSKTLRFA LIPQGKTLEN TKNNVLQEDD ERQKNYEKVK PILDRIYKVF  60
AEESLKDCSV DWNDLNACLD AYQKNPSADK RQKVKAAQDA LRDEIAGYFT GKQYANGKNK  120
NAVKEKEQAE LYKDIFSKKI FDGTVTNNKL PQVNLSAEET ELLGCFDKFT TYFVGFYQNR  180
ENVFSGEDIA TAIPHRIVQD NFPKFRENCR IYQDLIKNEP ALKPLLQQAA AAVMAQNPKG  240
IYQPRKSLDD IFVIPFYNHL LLQDDIDYFN QILGGISGAA GQKKIQGLNE TINLFMQQHP  300
QEADKLKKKK IRHRFIPLYK QILSDRTSFS FIPEAFSNSQ EALDGIETFK KSLKKNDTFG  360
ALERLIQNLA SLDLKYVYLS NKKVNEISQA LYGEWHCIQD VLKQDFSLES LIQINPQNSS  420
NGFLATLTDE GKKRISQCRN VLGNPLPVKL ADDQDKAQVK NQLDTLLAAV HYLEWFKADP  480
DLETDPNFTV PFEKIWEELV PLLSLYSKVR NFVTKKPYST AKFKLNFANP TLADGWDIHK  540
ESDNGALLFE KGGLYYLGIM NPKDKPNFKS YQGAEPYYQK MVYRFFPDCS KTIPKCSTQR  600
KDVKKYFEDH PQATSYQIHD SKKEKFRQDF FEIPREIYEL NNTTYGTGKS KYKKFQTQYY  660
QKTQDKSGYQ KALRKWIDFS KKFLQTYVST SIFDFKGLRP SKDYQDLGEF YKDVNSRCYR  720
VTFEKIRVQD IHEAVKNGQL YLFQLYNKDF SPKSHGLPNL HTLYWKAVFD PENLKDPIVK  780
LNGQAELFYR PKSNMQIIQH KTGEEIVNKK LKDGTPVPDD IYREISAYVQ GKCQGNLSPE  840
AEKWLPSVTI KKAAHDITKD RRFTEDKFFF HVPITLNYQS SGKPTAFNSQ VNDFLTEHPE  900
TNIIGIDRGE RNLIYAVVIT PDGKILEQKS FNVIHDFDYH ESLSQREKQR VAARQAWTAI  960
GRIKDLKEGY LSLVVHEIAQ MMIKYQAVVV LENLNTGFKR VRGGISEKAV YQQFEKMLIE  1020
KLNFLVFKDR AINQEGGVLK AYQLTDSFTS FAKLGNQSGF LFYIPSAYTS KIDPGTGFVD  1080
PFIWSHVTAS EENRNEFLKG FDSLKYDAQS SAFVLHFKMK SNKQFQKNNV EGFMPEWDIC  1140
FEKNEEKISL QGSKYTAGKR IIFDSKKKQY MECFPQNELM KALQDVGITW NTGNDIWQDV  1200
LKQASTDTGF RHRMINLIRS VLQMRSSNGA TGEDYINSPV MDLDGRFFDT RAGIRDLPLD  1260
ADANGAYHIA LKGRMVLERI RSQKNTAIKN TDWLYAIQEE RN                    1302

SEQ ID NO: 2            moltype = DNA  length = 3909
FEATURE                 Location/Qualifiers
misc_feature            1..3909
                        note = Description of Artificial Sequence: Synthetic Native
                        Cas12a/Cpf1 [Acidaminococcus massiliensis] sequence
source                  1..3909
                        mol_type = other DNA
                        organism = synthetic construct
SEQUENCE: 2
atggctgctt ttgataagtt tatccatcag tatcaggttt cgaagaccct gcgttttgct  60
ttgattcccc aggggaagac tcttgaaaac actaaaaata acgttttgca ggaggatgat  120
gaacgtcaga aaaattatga aaaggtcaaa ccgatcctgg accgtatcta taagtatttt  180
gcagaggaaa gcctaaaaga ttgttctgtg gattggaacg acctgaacgc ctgcctggat  240
gcctaccaga aaaatccttc cgctgataag cgtcaaaagg taaaagctgc ccaggatgca  300
ctccgggatg aaatcgctgg ctatttttacc gggaaacaat atgcgaatgg aaaaaataaa  360
```

```
aatgcggtga aggaaaaaga acaggccgaa ttgtacaaag atattttag caaaaaaatt   420
tttgatggaa ccgtaaccaa taataaattg ccccaagtaa atctttctgc agaggaaaca   480
gagcttctgg gctgctttga taaatttacc acttacttcg tcggttttta tcagaacaga   540
gagaatgttt tttcggggga agatattgca acggccattc cccatcggat cgtccaggac   600
aattttccaa aattccggga gaattgcaga atctaccagg acctcataaa aaatgaaccg   660
gcactgaaac ctttgctgca gcaggctgct gctgcagtga tggctcagaa ccccaaggga   720
atctatcagc caaggaaatc gttggatgat attttttgtga ttccattta taatcatctg   780
ttgttacaag atgatattga ttatttcaac cagatcttgg gaggcatcag cggtgctgca   840
ggacagaaaa aaatccaggg cctgaacgaa accatcaatc tattcatgca gcagcatccc   900
caggaagctg acaaattaaa gaagaagaag attcgccatc ggttcatccc tctttacaag   960
cagatttta  gcgatcgtac cagctttcg  tttatcccag aggcttttc  caattctcag  1020
gaagccctgg atgggataga aacctttaaa aaatccttga aaagaacga  tacctttggc  1080
gctttggagc ggctcatcca aaatcttgct tctttagacc tgaaatatgt ttatctttcc  1140
aataaaaaag tcaatgaaat atcccaggct ttgtatgggg aatggcattg tatccaggat  1200
gtgctgaagc aggattttc  cctgaatcg  cttatccaga taaatccgca aaattcttcc  1260
aatggattcc ttgccacttt gaccgatgaa ggcaaaaaaa gaatctccca gtgcaggaat  1320
gtccttggga atccgttgcc tgtcaaattg gcggatgacc aggataaagc acaggtcaag  1380
aatcagctgg atacgctgct ggctgctgtc cattatctgg aatggttcaa agcggatcct  1440
gacctggaaa ccgatccgaa ttttacggtt cctttttgaaa aaatctggga agagttggtt  1500
cctttgctga gcctttatag taaagtacgg aattttgtga ccaaaaagcc ttattctaca  1560
gcaaaattca agctgaattt tgccaacccc acattggccg atggctggga tatccataaa  1620
gaatcagata tggagccttt gttatttgaa aaaggaggtt tgtattatct ggggattatg  1680
aatcccaaag ataaacctaa tttaaatct  tatcaagggg ccgaaccata ctatcagaaa  1740
atggtttatc ggttctttcc ggactgttcc aagacaatac aaaatgttc  tacccagaga  1800
aaagatgtga aaaatatt  cgaagaccat ccccaagcca cttcctacca gattcatgat  1860
tcaaaaaagg acaaattcag acaagatttt ttcgagattc cccggaaat  ctatgaattg  1920
aacaatacta cgtatggtac ggggaaaagt aaatacaaga aattccagac ccagtattat  1980
cagaagaccc aagataaatc tggatatcaa aaagcccttc gcaaatggat cgattttcc   2040
aaaaaattt  tgcagacgta tgtaagtacc tcaattttg  atttcaaggg gctgcgtccc  2100
agcaaggact atcaagatt  ggggaattt  tataaggatg tcaacagcag atgctatcgg  2160
gtcactttg  aaaaaatcag ggtacaagat atccatgagg ctgtaaaaaa tggccagctg  2220
tatctgttcc agctgtacaa caaagacttt tcccccaaaa gccatggtct gcccaatctc  2280
catacccttt actggaaagc agtttttgac cccgaaaatt taaaggatcc gattgtgaaa  2340
ctcaatgggc aggctgaatt gttctatcgt cccaagagca acatgcagat tatccagcat  2400
aaaaccggtg aagagatcgt aaataagaaa ctgaaggatg ggacgccagt ccctgatgat  2460
atctatcggg aaatctctgc ttatgtacaa ggcaagtgcc agggaaattt atctccggaa  2520
gctgaaaaat ggctgccttc agtgaccatt aaaaaggctg cccatgatat taccaaggac  2580
agacggttta cggaagacaa attcttcttc catgttccca ttaccctgaa ctaccaaagc  2640
tcgggcaaac caactgcctt taattcccag gtcaatgatt tcttgacaga gcatccaaag  2700
accaatatca tcggtatcga tcggggagaa aggaacctga tttatgcggt agttataact  2760
cccgatggga aaatcctgga acaaaaatcc tttaatgtga tccatgactt cgattatcat  2820
gaaagcttga gccagagaga aaaacagcgg gtggcagccc gccaggcatg gaccgccatt  2880
ggtcggatca aagatctgaa agaggggtat ctgtctctgg tcgtccatga gattgcccag  2940
atgatgatca ataccaggc  tgtggttgta ctgaaaaatc tcaatacggg atttaaacgt  3000
gtccgtggag ggatttcaga aaaagccgtc tatcagcagt ttgaaaagat gctcatagaa  3060
aaactgaatt tccttgtgtt caaagatcgg gccataaatc aggaaggcgg ggtactgaaa  3120
gcgtatcagc tgacggacag cttccaccag tttgcaaaat tagggaataa aagtggattc  3180
ctgttctaca tccccttccgc ttatacatct aagatagatc caggcacggg cttttgtagat  3240
cctttcatct ggagccatgt tacagccagt gaggagaatc ggaatgaatt tctgaagggg  3300
ttcgacagtt tgaagtatga tgcccaatct agtgcttttg tcctgcattt caagatgaag  3360
agcaacaaac agttccaaaa gaacaatgtg gaaggattca tgcctgaatg ggatatctgc  3420
tttgagaaaa acgaagagaa aatcagtctg cagggaagca aatatactgc cggaaagcgg  3480
atcatttttcg attccaagaa aaaacagtat atggagtgtt ttccccaaaa tgaactgatg  3540
aaggccctgc aggatgttgg catcacttgg aatacgggga tgatatctg  caggatgtc   3600
cttaagcagg cgtcgactga tactgggttc cggcatcgca tgatcaatct gatccgctcc  3660
gtgctgcaga tgcgcagcag caatggagca accggcgaag attacatcaa ttcgcccgtc  3720
atggatttgg atgccgtttt cttcgatacc agggcgggta tccggatctc gccgctggac  3780
gcagacgcca atgggcata  ccatattgcc ttaaagggaa gaatggtcct ggagcggatc  3840
cgcagtcaaa aaaatacagc catcaaaaat acagattggc tgtatgccat tcaggaagaa  3900
agaaactga                                                          3909
```

SEQ ID NO: 3          moltype = AA   length = 1364
FEATURE               Location/Qualifiers
REGION                1..1364
                      note = Description of Artificial Sequence: Synthetic
                      polypeptide
source                1..1364
                      mol_type = protein
                      organism = synthetic construct
SEQUENCE: 3
MGHHHHHHSS GLVPRGSGTM AAFDKFIHQY QVSKTLRFAL IPQGKTLENT KNNVLQEDDE    60
RQKNYEKVKP ILDRIYKVFA EESLKDCSVD WNDLNACLDA YQKNPSADKR QKVKAAQDAL   120
RDEIAGYFTG KQYANGKNKN AVKEKEQAEL YKDIFSKKIF DGTVTNNKLP QVNLSAEETE   180
LLGCFDKFTT YFVGFYQNRE NVFSGEDIAT AIPHRIVQDN DGTVTNNKLP QVNLSAEETE   180
LLGCFDKFTT YFVGFYQNRE NVFSGEDIAT AIPHRIVQDN FPKFRENCRI YQDLIKNEPA   240
LKPLLQQAAA AVMAQNPKGI YQPRKSLDDI FVIPFYNHLL LQDDIDYFNQ ILGGISGAAG   300
QKKIQGLNET INLFMQQHPQ EADKLKKKKI RHRFIPLYKQ ILSDRTSFSF IPEAFSNSQE   360
ALDGIETFKK SLKKNDTFGA LERLIQNLAS LDLKYVYLSN KKVNEISQAL YGEWHCIQDV   420
LKQDFSLESL IQINPQNSSN GFLATLTDEG KKRISQCRNV LGNPLPVKLA DDQDKAQVKN   480
QLDTLLAAVH YLEWFKADPD LETDPNFTVP FEKIWEELVP LLSLYSKVRN FVTKKPYSTA   540

```
KFKLNFANPT LADGWDIHKE SDNGALLFEK GGLYYLGIMN PKDKPNFKSY QGAEPYYQKM     600
VYRFFPDCSK TIPKCSTQRK DVKKYFEDHP QATSYQIHDS KKEKFRQDFF EIPREIYELN     660
NTTYGTGKSK YKKFQTQYYQ KTQDKSGYQK ALRKWIDFSK KFLQTYVSTS IFDFKGLRPS     720
KDYQDLGEFY KDVNSRCYRV TFEKIRVQDI HEAVKNGQLY LFQLYNKDFS PKSHGLPNLH     780
TLYWKAVFDP ENLKDPIVKL NGQAELFYRP KSNMQIIQHK TGEEIVNKKL KDGTPVPDDI     840
YREISAYVQG KCQGNLSPEA EKWLPSVTIK KAAHDITKDR RFTEDKFFFH VPITLNYQSS     900
GKPTAFNSQV NDFLTEHPET NIIGIDRGER NLIYAVVITP DGKILEQKSF NVIHDFDYHE     960
SLSQREKQRV AARQAWTAIG RIKDLKEGYL SLVVHEIAQM MIKYQAVVVL ENLNTGFKRV    1020
RGGISEKAVY QQFEKMLIEK LNFLVFKDRA INQEGGVLKA YQLTDSFTSF AKLGNQSGFL    1080
FYIPSAYTSK IDPGTGFVDP FIWSHVTASE ENRNEFLKGF DSLKYDAQSS AFVLHFKMKS    1140
NKQFQKNNVE GFMPEWDICF EKNEEKISLQ GSKYTAGKRI IFDSKKKQYM ECFPQNELMK    1200
ALQDVGITWN TGNDIWQDVL KQASTDTGFR HRMINLIRSV LQMRSSNGAT GEDYINSPVM    1260
DLDGRFFDTR AGIRDLPLDA DANGAYHIAL KGRMVLERIR SQKNTAIKNT DWLYAIQEER    1320
NGAPKRPAAT KKAGQAKKKK ASGSGAGSPK KKRKVEDPKK KRKV                     1364

SEQ ID NO: 4             moltype = DNA   length = 4098
FEATURE                  Location/Qualifiers
misc_feature             1..4098
                         note = Description of Artificial Sequence: Synthetic
                         polynucleotide
source                   1..4098
                         mol_type = other DNA
                         organism = synthetic construct
SEQUENCE: 4
atgggccacc atcatcatca tcatagcagc ggcctggtgc cgcgcggcag cggtaccatg      60
gcggcgttcg ataagttcat ccatcaatat caagtaagca aaaccctccg ttttgcactt     120
attccgcagg ggaaaacctt ggagaataca aaaaataacg tactccagga agatgatgag     180
cgtcagaaaa attacgaaaa agtcaaacct atccttgatc gtatttataa ggtattcgct     240
gaggaaagcc tgaaagattg cagcgttgac tggaatgacc tcaatgcatg tctggatgct     300
taccaaaaaa atcctagcgc ggataagcgt cagaaggtga ggccgcgca ggacgcgttg      360
cgggacgaaa ttgccggtta ttttacaggg aaacaatacg cgaacgggaa gaacaaaaat     420
gccgttaagg agaaagagca ggcagaattg tataaggata tctttagcaa aaagatcttt     480
gatgggaccg taacgaacaa caaattgcca caggtcaacc tttcagccga gaaacagag     540
ttattaggct gttttgataa attcacaaca tatttcgtcg gcttttacca gaaccgtgag     600
aacgtattt caggggagga tattgctaca gctattccgc atccggatcgt ccaggataat     660
tttcctaaat tccgggaaaa ctgtcggatt tatcaggact taatcaaaaa tgaacctgcc     720
cttaaaccgc tgcttcagca agcagcggcc gcggtgatgg cccagaatcc aaaggggatc     780
tatcaaccac gtaagagtct ggacgatatt tttgtcattc cgtttataa ccatctcctc     840
ttacaggatg atattgatta tttcaatcaa atcttaggcg gcatttcggg ggcagcgatt     900
cagaaaaaaa tccagggttt aaatgaaaca attaatctgt ttatgcaaca gcacccacaa     960
gaagccgata agttaaagaa aaaaaagatt cgtcatcggt ttattccgct gtataaacaa    1020
attctctctg accgtacgtc tttctcgttc atccctgaag cttttttccaa ttctcaggaa    1080
gcgttagacg gcattgagac attcaaaaag tctcttaaga agaatgacac attcggcgcg    1140
ttggagcggc tgattcaaaa tcttgcttcc ctggacctga aatacgtgta tttatcgaac    1200
aagaaggtca atgagatttc gcaggcatta tacggcgaat ggcactgcat ccaagacgtc    1260
ctcaagcaag atttcagcct tgagagcctg atccagatca cccacaaaa ttctagcaat     1320
ggtttcctgg ccacacttac cgacgaaggc aagaaacgta tctcccaatg tcgtaacgta    1380
ctggggaatc ctcttccagt caagcttgcg gatgatcaag acaaagcgca agtcaaaaac    1440
caattggata cattactggc tgctgtacac tatctcgagt ggttcaaggc agatccagac    1500
ctggaaacag cccctaactt cactgttcct ttcgaaaaga tctgggagga attggttcct    1560
ttactttcac tgtactctaa agttcggaat tttgttacaa agaagccata ttctacagct    1620
aaatttaaac tgaactttgc taacccgaca ttagcggatg ggtgggatat tcacaaggaa    1680
agtgataacg gcgcgctcct gtttgaaaag ggtggtttgt attacttggg tatcatgaac    1740
cctaaagata agcctaattt taaatcctat cagggtgcag agccatacta tcagaagatg    1800
gtgtaccgtt ttttttcctga ctgttcgaag accatcccaa aatgcagcac ccaacgtaag    1860
gatgtaaaaa agtacttcga agaccaccct caagcgacct cataccagat ccacgactca    1920
aagaaagaga agtttcgtca ggatttttt gagatccctc gggagattta cgagcttaat    1980
aacaccacat acggcacagg taagtctaaa tataaaaat tccagaccca gtattaccag    2040
aagactcagg ataagtcagg ctatcagaaa gcacttcgca aatggattga cttttccaaa    2100
aagtttcttc aaacatacgt cagtacttcc attttttgatt tcaaaggtct ccgtccttcg    2160
aaggattatc aggacttagg cgagttctat aaagacgtta attcgcgttg ttaccgtgtg    2220
acgttcgaga aaattcgcgt acaggacatc cacgaagcag tcaaaaatgg caactgtat    2280
ctcttccaat tatataataa ggacttctca cctaaaagcc atgggttgcc taatcttcac    2340
actctctatt ggaaagccgt gttcgatcct gagaacttta aggaccctat cgtaaaactt    2400
aatggccaag ctgagttatt ctatcggccg aaatccaaca tgcaaatcat ccaacataag    2460
accggggagg agattgtgaa caaaaagctg aaggacggca cccgggtccc tgatgatatc    2520
taccgcgaaa tcagtgctta cgtccagggg aaatgtcaag caacttatc ccggaggca    2580
gagaagtggc tcccaagtgt cacaatcaag aaagccgccc atgatatcac aaagatcgt    2640
cgcttaccg aagataagtt ttttctttcat gtccctatta cactgaacta tcagagttca    2700
ggcaagccga cggcattcaa ctcgcaagta aacgattttct tgaccgagca ccctgagaca    2760
aatatcatcg gcattgatcg gggtgaacgt aactgattt atgccgttgt aatcactcca    2820
gatggcaaga ttctcgaaca gaaatctttt aacgtgatcc acgactttga ttatcatgaa    2880
tccctgtccc agcgggaaaa acagcgggta gcagcgcgtc aggcttggac agcgattggt    2940
cgcatcaagga atctcaagga aggttacctg tcgcttgtgg tgcacgaaat tgctcaaatg    3000
atgatcaaat accaagcagt cgtcgtatta gaaaacctca acgggcgct taagcgtgtg    3060
cgcggtggta tcagtgagaa ggccgtctac caacagttcg aaaaaatgtt gattgaaaaa    3120
ttgaacttcc tggtatttaa agatcgggca atcaatcagg aaggcgggt tctcaaagct    3180
taccagctga cagactcgtt tacgtctttt gcaaagttag gtaaccagtc cggtttcctg    3240
ttctacatcc cgtccgccta caccagcaaa atcgaccctg gtacgggctt cgtcgatcct    3300
```

```
tttatctggt ctcacgtgac cgcttctgag gaaaatcgga atgaatttt  aaagggcttt  3360
gatagcttga aatatgacgc ccaatcatcc gcctttgtac tgcatttcaa gatgaaatcc  3420
aataagcaat tcagaagaa caatgttgaa ggtttcatgc cggaatggga tatctgcttc   3480
gagaaaaacg aggaaaagat ttccttgcag ggtagtaagt atacagccgg taaacgcatt  3540
attttcgact ccaaaaagaa gcaatacatg gagtgcttcc cgcagaatga gctcatgaaa  3600
gcactgcagg acgtaggcat cacctggaac acgggcaacg atatctggca ggatgtcctt  3660
aaacaagcga gcacagatac agggtttcgt caccggatga tcaacctgat ccgttcagtg  3720
ctccagatgc ggtccagtaa tggtgcgacc ggggaggatt acatcaattc acctgtgatg  3780
gatctggacg gccgttttt  cgacactcgg gcggggatc  gtgatctgcc attggatgcc  3840
gacgccaacg gcgcatacca catcgcttta aaagggcgta tggtactcga acgcattcgc  3900
tcccaaaaga ataccgcgat taagaacact gactggttat acgcaatcca agaggaacgt  3960
aacgcgcgc  caaaaaggcc ggcggccacg aaaaaggccg gccaggcaaa aagaaaaag   4020
gctagcggca gcggcgccgg atccccaaag aagaaaagga aggttgaaga ccccaagaaa  4080
aagaggaagg tgtgataa                                                4098

SEQ ID NO: 5               moltype = DNA  length = 4098
FEATURE                    Location/Qualifiers
misc_feature               1..4098
                           note = Description of Artificial Sequence: Synthetic
                           polynucleotide
source                     1..4098
                           mol_type = other DNA
                           organism = synthetic construct
SEQUENCE: 5
atgggccacc atcatcatca tcatagcagc ggcctggtgc cgcgcggcag cggtaccatg  60
gcagctttcg ataagttcat ccaccagtac caggtttcta aaacactgcg tttttgcactg  120
attccacaag gcaagacgct ggaaaatacc aagaataatg tacttcagga ggacgatgag  180
cgccaaaaaa actacgaaaa ggtaaaaccg atcctcgacc gtatctataa ggttttcgcc  240
gaggagagtc tgaaggactg ttcagtggat tggaacgacc tgaatgcttg ccttgatgca  300
taccagagaa atccaagcgc agacaaacgg caaaaggtga aggctgccca ggatgcgctt  360
cgtgatgaga tcgctgggta tttcactggg aagcaatacg ctaacggtaa gaataagaac  420
gcggtgaagg aaaaaggagca agcagaactc tacaaagaca tctttagtaa gaaaatcttc  480
gacgggacgg ttacaaacaa caaactgcca caggtgaact tatccgccga agaaaccgaa  540
ttgtggggtt gttttgacaa atttactacg tacttcgttg ggtctatca  aaatcgtgaa  600
aatgttttct ctggcgagga cattgctaca gcgattccgc accgcatcgt tcaggataat  660
ttcccgaagt tccgggagaa ctgtcggatc taccaggatc ttattaaaaa cgagccagca  720
ctgaagccac ttttacagca agctgcagcg gcagttatgg cgcaaaaccc taagggatc   780
taccagccac gcaaaagctt ggatgatatt ttcgttatcc cattttacaa ccacctgtta  840
ctccaagatg acatcgatta cttcaatcag attttaggcg ggatctcagg tgcagcaggt  900
cagaagaaaa ttcagggctt aaacgagacc attaatctgt ttatgcaaca gcacccgcag  960
gaagccgaca agcttaaaaa aaaaaagatt cgccatcgct tcattccttt atacaagcaa  1020
atcttgagcg atcgcacctc tttctccttt atccctgaag cctttcaaa  ctctcaggag  1080
gcgttggacg ggatcgagac ctttaaaaaa agtttgaaaa agaatgacac cttcgggcgt  1140
cttgaacgtt taattcagaa cctcgcatcg ctggacttga agtatgttta tttgagtaat  1200
aaaaaagtaa acgagatctc tcaagctttg tacggcgagt ggcactgtat ccaagatgtt  1260
ttgaaacaag acttcagtct tgaaagcctt atccaaatta atccacaaaa ttcttccaac  1320
gggtttcttg cgactctgac cgacgagggt aagaagcgaa tcagccaatg ccgcaacgtt  1380
ctcggcaacc ctctcccgtgt aaaactggcc gacgatcaag acaaagcgca ggtcaaaaac  1440
cagttggaca ctttacttgc ggccgttcac tatttggagt ggttcaaggc cgacccagac  1500
ttggagactg acccctaattt cacagtccct tttgagaaga tttgggaaga actggttcct  1560
ctcttaagct tgtacagtaa ggttcgcaat ttcgttacca aaaaccata ctcgacagcg  1620
aagtttaagt taaattttgc aaacccgact ctcgccgacg gttgggacat ccataaggaa  1680
tccgataacg cgcgcttct  ctttgagaag ggtggcttgt attatttagg tatcatgaat  1740
cctaaggata agcctaactt caagtcgtac caaggcgcag aaccgtatta tcaaaaaatg  1800
gtatatcggt tcttcccaga ttgcagtaag accattccaa aatgctcaac ccagcgtaaa  1860
gatgtaaaaa aatactttga agaccatcct caggcgacct cttaccaaat tcacgactcg  1920
aagaaggaaa agttcggca  agacttcttt gaaattccgc gcgaaatcta tgagctgaac  1980
aataccacct acggtaccgg gaagagtaag tacaagaagt ttcaaaccca atattaccaa  2040
aaaacacaag acaagagcgg gtatcagaag gccttgcgta aatggattga cttttcaaaa  2100
aagttcctgc agacttacgt tagcaccagc atttttcgact ttaaaggctt gcgtccgtct  2160
aaaagactacc aagatttagg ggagttttat aaagatgtta actcacgttg ttaccgcgta  2220
actttcgaga agatccgggt tcaggacatc catgaagcgg ttaagaatgg ccaactctat  2280
ttattccaac tctacaacaa agatttttct ccaaaatcgc atgggttacc taaccttcac  2340
accctctact ggaaagctgt gtttgaccct gagaatctga agatcctat  cgtgaaactg  2400
aatgggcagg ccgaactctt ttaccgtccg aaatcgaaca tgcaaatcat tcaacacaag  2460
acgggcgagg agattgttaa taaaaagctt aaggacggta ctccggttcc agatgacatc  2520
taccgcgaga tctctgccta cgtacagggt aagtgccaag gtaacctgag tccagaagcg  2580
gaaaagtggt taccatctgt cacaatcaag aaagcagctc atgacattac taaggatcgg  2640
cggtttacgg aggataagtt tttttccat  gtaccgatca cactgaatta tcagagctca  2700
gggaagccga cggcgtttaa ttctcaagtc aatgattttc tcacggagca tccagaaacc  2760
aatattatcg ggatcgatcg gggggagcgg aacctcatct atgcggtagt tatcacgcct  2820
gatggtaaga ttctcgaaca aaaatctttt aacgtaatcc acgactttga ctatcacgag  2880
agtttatccc aacgcgagga gcagcgtgtt gcagcacgcc aagcttggac agcaattggt  2940
cgtattaaag acctgaagga gggtaccctc agccttgtgc tcatgagat cgcacagatg  3000
atgattaagt atcaagcggt agtggtgctc gaaaatttga atcgggcctt taacgggtta  3060
cggggtggga tctcggagaa ggccgtgtat cagcagtttg aaaagatgct catcgaaaag  3120
ctgaacttcc ttgttttcaa ggaccgtgcc attaatcaag aaggggcgt  ccttaaggca  3180
tatcagctga cagattcgtt cacctcattt gcgaaactgg ggaccagtc  cgggttttg   3240
ttttacatcc ctagcgctta tacgagtaaa attgaccctg gtactgggtt cgtggacccg  3300
```

```
tttatttggt cgcatgtaac ggcgtcggag gagaaccgta acgaatttct caaagggttc 3360
gatagtctca agtacgatgc ccaatcgtcg gccttcgttc tgcatttcaa aatgaagtcg 3420
aataaacagt tccaaaagaa caatgtggaa ggctttatgc cggaatggga catttgcttc 3480
gaaaagaacg aagaaaagat ttcgttacag ggcagcaagt ataccgctgg caaacgcatt 3540
atctttgact cgaaaaaaaa acagtacatg gaatgctttc ctcaaaacga actgatgaag 3600
gcgttgcaag acgtagggat cacatggaat actggtaatg atatttggca ggacgtactg 3660
aagcaggcct cgaccgatac cgggtttcgt caccgcatga ttaatttaat tcggagtgtt 3720
ttacagatgc ggtcttctaa cggcgcaact ggtgaggatt atattaacag cccagtcatg 3780
gacctcgacg gtcgtttttt cgacacacgg gcgggtattc gtgacctgcc gttagacgcc 3840
gatgctaatg gggcttacca cattgcgtta aaaggtcgca tggtccttga gcgtattcgc 3900
tcccagaaaa acactgcgat caagaacaca gactggctgt atgcgatcca ggaggagcgt 3960
aacggcgcgc caaaaaggcc ggcggccacg aaaaagccg gccaggcaaa aagaaaaag 4020
gctagcggca gcggcgccgg atccccaaag aagaaaagga aggttgaaga ccccaagaaa 4080
aagaggaagg tgtgataa                                              4098
```

SEQ ID NO: 6           moltype = DNA  length = 4098
FEATURE             Location/Qualifiers
misc_feature       1..4098
                     note = Description of Artificial Sequence: Synthetic
                     polynucleotide
source              1..4098
                     mol_type = other DNA
                     organism = synthetic construct

```
SEQUENCE: 6
atgggccacc atcatcatca tcatagcagc ggcctggtgc cgcgcggcag cggtaccatg   60
gcggccttcg ataagtttat tcatcagtac caagtgttacg agacgttacg cttcgcgctc  120
atcccacagg gtaaaaccct cgaaaacacg aagaacaacg tgctccaaga agatgatgag  180
cgtcaaaaaa attatgaaaa agtaaagcct attctggatc gcatttacaa agtgttcgct  240
gaagagtccc ttaaagactg cagcgtagac tggaacgatc tgaatgcatg cctggatgcc  300
taccaaaaga acccgtcagc tgacaaacgc caaaagtaa aagcagcaca ggatgcgttg  360
cgggatgaaa tcgcagggta cttcacaggt aaacagtatg ccaatggcaa aaacaagaat  420
gcggttaaag agaaggaaca agcggagtta taaggaca tctttccaa gaagattttt  480
gatgggacag tcacaaacaa caaattgccg caagtgaacc tgtcggcaga agaaacagaa  540
cttttgggtt gcttcgacaa attttaccacg tattttgtag gctctatca gaatcgggaa  600
aacgttttct cggggagaaga catcgcaaca gctatccctc atcgtatcgt tcaagacaat  660
tttccaaaat ttcgggagaa ttgtcgcatc tatcaagact taattaagaa tgaaccagcc  720
ttaaaaccat tgttacaaca ggcagcagct gctgtaatgg cccagaaccc gaagggcatt  780
tatcagcctc gtaagagcct tgatgacatt tttgttatcc cattctataa ccacttactg  840
ttgcaagatg atattgatta ttttaatcag attttaggg gtatttcggg tgcggctgtt  900
caaaagaaga tccagggtct taacgagacc attaatttgt ttatgcagca gcatccacag  960
gaggcagaca aactcaagaa aaaaaaaatt cgtcaccgct ttattccact ctacaagcaa  1020
atcttgtctg atcgtacctc gttctccttc attccgaag cattcagtaa ctctcaagag  1080
gcgttaagag gcatcgaaac ctttaaaaaa tctctcaaga agaacgatac attcggggca  1140
ctcgagcggt taattcagaa cttagcctcc ttggatttaa aatatgtgta cttgtccaat  1200
aagaaggtca atgaaattag tcaggctctg tacggtgagt ggcactgcat ccaggacgtg  1260
ttaaagcaag attttagtct ggaatcttta atccagatca cccacaaaa tagttcgaac  1320
gggttttag ccaccttac tgatgaaggc aaaaagccta tctcccagtg ccgtaagta  1380
ttgggcaacc cattgccggt taagctcgcg gatgatcaag ataaagcaca agtcaaaaat  1440
caacttgaca cgcttttggc ggccgtacat tacctcgaat ggttcaaggc ggaccctgat  1500
ttagagactg atcctaattt caccgttccg tttgaaaaaa tttgggaaga attagtcccg  1560
ctgctagct tatattctaa ggttcgtaat tttgtgacta aaaagccgta tagtactgca  1620
aagttcaaac tcaactttgc caatccaacc ttagcagatg ggtgggatat ccataaagaa  1680
agtgataacg gggctttgct ttttgaaaag ggcgggcttt attatctggg cattatgaat  1740
ccgaaggaca agcctaactt caagagctat cagggcgccg aaccgtatta tcagaagatg  1800
gtttatcggt tcttcccaga ctgcagtaag accattccaa agtgctccac tcaacggaaa  1860
gacgtgaaaa aatacttcga agaccacccg caagctactt cgtaccaaat ccatgacagt  1920
aaaaaagaaa aatttcggca agatttcttc gagattccgc gggagattta tgagcttaat  1980
aataccactt atggcaccgg gaaagtaag tacaaaaaat tccaaacgca atactatcaa  2040
aaaacccaag ataagagtgg gtaccagaaa gccctgcgta agtggattga cttttcgaag  2100
aaattcctgc agacttatgt gtccacaagt atcttgact ttaaaggctt acgtccatct  2160
aaagattacc aggatcttgg ggaatttac aaagatgtca atagtcgttg ctatcgtgtt  2220
acgttcgaga agatccgggt ccaggacatt cacgaagctg tcaaaaatgg caactgtac  2280
ttattccaac tttacaataa ggatttctct cctaaatcac atggcctccc aaacttacac  2340
acgctctact ggaaagcgtt cttcgaccca gagaatttga aggaccaat tgtaaaattg  2400
aacggccagg cggaattatt ttaccgtcct caagtcaaata tgcaaatcat ccaacacaag  2460
actggcgagg aaatcgtcaa caaaaaatta aagacggga cgcctgtgcc ggacgacatc  2520
taccggaaa tctcagcata cgtacagggc aagtgtcagg caacctctc gccggaagca  2580
gagaaatggc ttccaagcgt gaccatcaaa aaggcggctc acgatattac taaggatcgc  2640
cggttaccg aagacaaatt tttcttccat gtacctatca ccctgaacta tcaatcgtcc  2700
ggtaagccga cagcattcaa tagccaggtc aatgatttcc ttacagagca cccagaaacc  2760
aacatcattg gtattgaccg tgggagcgt aacctgatct acgcagtagt gattactccg  2820
gatggcaaaa ttcttgagca aaagagcttc aacgtcattc atgattttga ctatcacgag  2880
agcttgtcgc aacgtgaaaa gcagcgcgtg gcagcacggc aggcatggac cgcgatcggt  2940
cgtatcaagg atctcaaaga gggttactta tcgctcgtcg tccatgaaat tgcacaaatg  3000
atgatcaaat atcaagcggt cgttgttctc gagaatctca acacgggctt caagcgcgtg  3060
cgtggcggga tctccgagaa ggccgtatac cagcaattcg agaagatgtt gatcgaaaag  3120
cttaattttc ttgtctttaa ggaccgtgct atcaatcagg aaggtgggt gctcaaagcg  3180
tatcagttga cagatagttt cacaagtttc gctaaattag gtaatcagag cgggtttctc  3240
ttctatatcc cgagcgccta tacgtcgaag atcgaccgg gtacgggttt cgtggatccg  3300
```

```
ttcatttggt cacacgttac tgctagcgag gagaatcgga acgaattttt aaaagggttt    3360
gattcgttaa agtacgatgc tcagagctcc gcgttcgttc ttcatttcaa gatgaaatct    3420
aacaaacagt tccaaaaaaa caacgttgaa ggcttcatgc cagagtggga catctgcttc    3480
gaaaaaaacg aagaaaaaat ctccttacag ggttctaagt atacggcggg gaagcgcatt    3540
attttgact ccaagaaaaa gcagtatatg gaatgtttcc ctcagaatga actgatgaag    3600
gcactgcagg acgtaggtat tacatggaac actggcaacg acatttggca ggatgtcctg    3660
aaacaagcat ctacggacac tgggtttcgg caccggatga ttaacttaat tcgctccgtg    3720
ttgcaaatgc ggtcgtcaaa tggcgctacc ggcgaagact atattaacag tccagtcatg    3780
gacctggacg gtcgtttctt cgatacacgt gctggtattc gtgacctccc tcttgatgcc    3840
gatgccaatg gcgcatatca tattgctctt aaagggcgta tggttctgga gcgtattcgt    3900
tcgcaaaaga ataccgcaat taaaaatact gattggctgt atgctatcca agaggagcgc    3960
aacgcgcgc caaaaaggcc ggcggccacg aaaaaggccg gccaggcaaa aagaaaaag     4020
gctagcggca gcggcgccgg atccccaaag aagaaaagga aggttgaaga ccccaagaaa    4080
aagaggaagg tgtgataa                                                  4098
```

SEQ ID NO: 7        moltype = DNA  length = 4098
FEATURE          Location/Qualifiers
misc_feature      1..4098
                     note = Description of Artificial Sequence: Synthetic
                     polynucleotide
source           1..4098
                     mol_type = other DNA
                     organism = synthetic construct

SEQUENCE: 7

```
atgggccacc atcatcatca tcatagcagc ggcctggtgc cgcgcggcag cggtaccatg    60
gctgcgttcg ataagtttat ccaccaatac caggtaagta aaacactgcg tttcgcactt    120
attccgcagg gtaagacact tgaaaacaca aagaacaacg tgttacaaga ggacgacgaa    180
cgtcaaaaga actacgagaa agtaaagcct attctcgatc gtatctacaa ggttttcgct    240
gaggagtccc ttaaggactg ctcggtagat tggaacgact tgaatgcctg tttagacgcg    300
taccaaaaaa atccaagcgc agacaagcgg cagaaagtga aagcagctca ggacgcgttg    360
cgtgacgaaa tcgccggtta cttcaccggc aaacagtacg ccaatgggaa aaacaaaaac    420
gcggtaaagg agaaggagca agcagagtta taaggata ttttctccaa gaagatcttt      480
gatgggacag ttacaaataa caagctgcct caagttaatt tgagcgcgga agaaactgaa    540
ttattaggct gtttcgataa gttttacgacg tattttggta gtttctatca gaatcgcgag    600
aatgtgtttt ccggggagga cattgccact gcaattccac atcgtatcgt ccaggacaac    660
ttccctaaat tccgggagaa ctgtcgtatc taccaagatc ttattaaaaa cgaacctgct    720
ttgaaacctc ttcttcaaca agccgctgcg gcagtgatgg cccagaatcc gaaggggatc    780
tatcaacctc gtaagtcatt ggacgatatt ttcgtgattc cttttataa ccatcttctg     840
ctgcaggatg atattgacta cttcaaccaa attctggttg ggattagtgg ggccgctgtg    900
cagaaaaaaa tccaaggtct taacgaaacc attaacctgt tcatgcagca acatccgcag    960
gaagcagaca aacttaagaa gaaaaaaatc cgtcaccgtt tcatccctct ttataagcaa    1020
atccttagtg accgtactag cttctcattt atccagaaga cattctccaa tagccaagaa    1080
gcattgagcg gcatcgagac gttttaaaaa agcttaaaga aaaatgatac ctttggggcg    1140
ttagaacgtc ttattcaaaa tctcgcgtca ttggacctca agtatgttta tttgagcaat    1200
aaaaaggtta acgaaatttc caagcgctct atggcgaat ggcactgtat ccaagacgtc     1260
ttaaagcagg atttctcgct tgagagcctg atccaaatta atccgcaaaa ctcctccaat    1320
ggcttcttag ccactctgac ggatgaaggt aagaagcgta ttagccaatg tcgcaacgta    1380
ttggggaacc cgcttccagt taaattggct gacgatcaag acaaagctca ggtaaagaac    1440
caactcgaca ctttactggc cgcagttcat tacctcgagt ggttcaaagc tgatccagac    1500
cttgaaacag atcctaattt cacagtaccg ttcgagaaaa tttgggagga actggtccct    1560
ctgttatccc tttacagcaa agtgcgtaat ttcgtcacga agaagccata cagtactgcg    1620
aaattcaagc tgaactttgc caacccaacg ttggcagacg ggtgggatat ccataaagag    1680
tcagacaatg gggcgctttt attcgaaaag ggggggttat actatttagg gatcatgaac    1740
cctaaggata aacctaattt caagtcatac caaggtgcgg agccgtacta ccaaaaaatg    1800
gtctaccgct tcttttccaga ttgcagtaag acgattccta aatgtagcac ccaacgcaag    1860
gacgtaaaga agtactttga ggaccatcca caagctactt cgtatcagat ccatgactcg    1920
aaaaaggaaa aatttcggca agactttttt gagatccctc gcgagatcta cgagctgaat    1980
aacactacac acggtacggg taagagcaag tataagaagt tccaaaccca atattatcag    2040
aagacccaag ataagtcggg ctatcagaag gcgctgcgca agtggattga cttttccaag    2100
aaattcttac agacttatgt aagcacctct attttcgatt ttaaagggct gcgtccgagt    2160
aaagactatc aggacttggg cgaattctac aaagatgtca attctcggtg ttatcgtgta    2220
acgtttgaaa agatccgtgt acaggacatt catgaagcgg ttaagaacgg gcaactctat    2280
ctcttccagc tctataacaa ggacttctct ccgaagtcac atgggttgcc aaatcttcac    2340
acgctgtact ggaaagtcgt gtttgacccg gaaaacctca aagtcctat cgtcaagctc    2400
aacgggcaag ctgaattatt ttaccgccca aagagtaata tgcagatcat tcagcataaa    2460
actggtgaag agatcgtcaa taagaaattg aaggatggga cccggttcc agacgatatc    2520
taccgtgaaa ttagcgcata cgtgcaggt aagtgccagg gcaatttatc accggaagcc     2580
gaaaaatggc tgccttcagt cacaattaag aaagcagact acgacattac gaaggatcgg    2640
cgcttacag aggacaaatt cttctttcac gttccaatta cattaaatta ccagtcctcg     2700
ggcaagccaa cggcattcaa ctctcaggta aatgatttct taacggaaca cccggaaact    2760
aacatcatcg ggattgaccg tgggggaacgt aacctgatct atgcagttgt cattacccct    2820
gatggcaaaa ttttagaaca aaagagttt aatgtcatcc atgattttga ctaccatgag     2880
tctctctctc aacgcgaaaa acagcggggtg gcagcgcggc aggcgtggac agcaattggg    2940
cggatcaaag acctgaagga agggtactta agtctcgtgg tgcatgagat cgcgcaaatg    3000
atgattaagt atcaagccgt cgttgtgctc gaaaatttaa ataccggggtt taagcgggtt    3060
cggggtggta tttctgagaa agctgtgtat caacaattcg agaaaatgct cattgagaag    3120
ttgaacttct tggtttttaa agaccggggcc attaaccaag agggggggcgt cctcaaggct    3180
tatcaattga ctgactcttt tacatcgttc gccaaacttg gaatcaatc aggcttcttg     3240
ttctatatcc cttcagcgta tacctccaag atcgaccag gcactggttt cgtagaccct     3300
```

```
ttcatttgga gtcacgttac agcaagtgag gaaaatcgga atgaatttct taaagggttc   3360
gattcgctga aatacgatgc tcaatcgtct gccttcgtcc tgcactttaa gatgaagtct   3420
aataaacaat tccaaaaaaa taatgtggag ggttttatgc ctgaatggga tatttgtttc   3480
gagaaaaacg aggagaaaat ctctcttcaa ggtagtaaat atactgctgg taaacggatt   3540
attttcgact ccaaaaaaaa gcaatacatg gaatgcttcc cgcaaaacga gcttatgaaa   3600
gctctccagg atgtgggcat tacatggaac acagggaatg acatctggca ggacgtatta   3660
aaacaagctt ccacgcgatac tgggtttcgg caccggatga ttaatttgat tcgttctgtc   3720
cttcagatgc gcagcagtaa cggcgcaacc ggtgaagact acatcaactc cccagtaatg   3780
gacctggatg gtcgtttttt tgatacccgc gccggcattc gcgactttgcc actcgacgcg   3840
gatgcaaatg gcgcctacca catcgcctta aagggccgta tggtgcttga gcggatccgc   3900
agccaaaaga atacagccat caagaatact gattggctct acgctattca agaagaacgg   3960
aatggcgcgc caaaaaggcc ggcggccacg aaaaaggccg gccaggcaaa aagaaaaag   4020
gctagcggca gcggcgccgg atccccaaag aagaaaagga aggttgaaga ccccaagaaa   4080
aagaggaagg tgtgataa                                                 4098

SEQ ID NO: 8         moltype = DNA   length = 4098
FEATURE              Location/Qualifiers
misc_feature         1..4098
                     note = Description of Artificial Sequence: Synthetic
                     polynucleotide
source               1..4098
                     mol_type = other DNA
                     organism = synthetic construct
SEQUENCE: 8
atgggccacc atcatcatca tcatagcagc ggcctggtgc cgcgcggcag cggtaccatg   60
gcagcatttg ataagtttat tcatcagtac caagtcagta aaacgcttcg gttcgcactc   120
attccacaag gtaaaacact cgagaacact aaaaacaatg tgttacagga ggacgacgag   180
cggcaaaaga attacgaaaa agtgaagccg atcttagacc gcatctataa ggtattcgca   240
gaagaatcct tgaaagattg ctcggtcgac tggaatgacc tcaacgcttg tttagacgcc   300
taccaaaaaa acccttcagc ggacaaacgc caaaaagtga aggcagcaca agatgcgtta   360
cgggatgaga tcgcgggtta cttcacgggc aaacagtatg ccaatgggaa aaataaaaat   420
gcggttaagg aaaaagagca ggctgaattg tacaaagaca ttttcagtaa gaagatcttt   480
gatggcactg ttactaataa taagctccct caggtaaatt taagtgccga agaaaccgaa   540
ttgctcgggt gctttgataa gttcacaaca tacttcgtcg ggttttacca aaatcgtgag   600
aacgtcttta gtggcgagga tatcgctacc gcgatcccaa atcgcattgt tcaagataac   660
ttcccaaagt tccgggagaa ttgccgtatt taccaggact tgattaagaa cgaacctgcc   720
ctcaagccac tccttcagca ggcggctgca gcagttatgg cgcagaaccc taaaggtatt   780
taccagccac gtaagtcatt ggatgatatt ttcgtaatcc cttctacaa ccatctgctt   840
ttacaagatg acatcgatta cttaaccaa atcttagggg tatctctgg tgcggctgga   900
caaaaaaaga tccaagggct caatgaaact atcaacctgt tcatgcaaca acaccctcag   960
gaagctgata agtaaaaaa gaaaaaaatt cgccaccgct ttattccact gtacaagcag   1020
atcttgtcgg atcgtacaag tttttctttc atcccagaaa cattctcaaa cagccaggag   1080
gctctcgatg ggattgaaac attcaagaag tccttgaaga agaacgacac ttttggcgcc   1140
cttgagcgtt taatccaaaa tttagcaagc ctcgatttaa aatatgtata tttgtcaaat   1200
aaaaaggtca atgagatttc ccaagcactt tatggggagt ggcactgcat tcaagatgta   1260
ctgaaacagg atttctccct cgagagtctg atccagatta cccacagaa ctcgtctaat   1320
gggttttctcg caacacttac cgacgaaggg aaaaaacgca ttagtcaatg tcgcaatgtg   1380
ttaggcaatc cactgcctgt caaattggca gacgatcagg acaaggcaca agttaagaac   1440
caacttgata ctctcctcgc cgcggttcac tacttagaat ggttcaaggc tgatcctgac   1500
ttagaaactg acccgaattt cacggtgcca ttcgaaaaga tttgggagga gcttgtacca   1560
ctcttgtctt tatattcaaa agtacggaat ttcgttacta agaaaccata tagtaccgcc   1620
aagttcaagc ttaactttgc taacccaacg ctcgctgatg gttgggatat tcataaggaa   1680
agtgacaatg ggcattatt atttgagaaa ggcggtctct actacctcgg tatcatgaac   1740
ccgaaagata aaccaaactt taaagttat caaggcgcag agccttacta tcaaaaaatg   1800
gtgtaccggt ttttccggaa ttgttccaaa actatcccta aatgcagcac tcaacgtaag   1860
gatgtgaaga aatatttga ggaccaccct caggccactt cataccagat tcatgattcg   1920
aagaaagaga agttccgcca ggacttcttc gaaatcccac gtgaaatcta tgaacttaac   1980
aatacgacct acggcacggg gaagagtaag tacaaaaagt ttcagacaca atactaccag   2040
aagacccagg acaagtccgg gtatcaaaag gctcttcgca aatggattga tttctccaaa   2100
aaattcttgc aaacctacgt aagcacgagt attttcgact tcaaaggcct gcgtccgagt   2160
aaagactatc aagacctcgg cgaattctac aaggacgtaa attctcgctg ttaccgtgtc   2220
acattcgaaa aaattcgcgt gcaggatatc catgaggcag ttaagaacgg tcaactctat   2280
ctcttccagt tatacaacaa ggattttca ccaaagtccc acggtttacc aaacttacac   2340
actctctact ggaaggcagt gttcgatcca gaatcttca aagcccgat cgttaaactc   2400
aatgggcagg ccgaattatt ttatcgtcca aagtccaata tgcaaattat tcagcataaa   2460
acgggtgagg agattgtgaa caaaagtta aaggacggta caccggtacc agatgacatt   2520
tatcgcgaga tcagcgctta tgtacaaggg aaatgccagg gaatctgtc accagaggcg   2580
gagaagtggc tgcactctgt gacgatcaag aaagcagctc atgatattac taaagatcgt   2640
cgcttcacag aggacaagtt cttcttccat gtaccgatta tctgaacta ccaatcgtt   2700
gggaagccga ctgcctttaa tagtcaagta aacgactttt tgaccgaaca ccctgagaca   2760
aatattatcg gtattgatcg cggcgagcgt aacctcatct acgctgttgt tattaccccg   2820
gacggcaaga tcctcgaaca aaaatctttc aacgtaattc atgactttga ctaccacgaa   2880
tcgctgtctc agcgcgagaa gcagcgtgtc gctgctcgtc aggcgtggac ggctatcggg   2940
cgtattaagg acctgaagga ggttattta tctctcgatg tgcgagat cgctcaaatg   3000
atgatcaagt accaggcagt tgtagtttta gagaatctta acactgggtt taagcgcgtc   3060
cgcggcggga tcagcgaaaa agccgtttac cagcaatttg agaaaatgct catcgagaaa   3120
ttgaactttc tcgtctttaa ggaccgtgct attaaccaag aagggggcgt actcaaggct   3180
tatcagttga cagatagttt taccagtttc gccaaactcg gaatcagag cggctttta   3240
ttttacatcc caagcgcata tacaagcaaa atcgatcctg gacaggcctt tgttgacccg   3300
```

```
tttatctggt cccacgtaac cgcatcagaa gaaaaccgta atgaattctt gaagggtttt   3360
gatagcctta aatatgatgc acaaagcagc gcgttcgttc ttcatttcaa aatgaagtcg   3420
aataaacagt tccagaaaaa caacgttgaa gggttcatgc cggaatggga catttgtttc   3480
gaaaaaaacg aggaaaaaat ttctttgcaa ggttcgaaat ataccgctgg caaacggatc   3540
atctttgatt caaaaaaaaa gcagtacatg gaatgctttc cgcaaaatga gttgatgaag   3600
gcactgcagg acgtcggtat tacgtggaat acgggtaatg acatctggca agacgtcctc   3660
aagcaggcaa gtacggatac aggtttcgg catcggatga ttaatttaat ccggagtgtc   3720
cttcaaatgc ggagttctaa tggggccact ggcgaagact acattaatag tcctgttatg   3780
gacctcgacg gccggttctt tgacacgcgc gccggcattc gcgacctgcc acttgacgtt   3840
gatgcgaacg gggcatatca tattgcgctg aaagggcgta tggtattgga gcgtatccgg   3900
tcgcagaaaa ataccgcgat caagaatacc gactggcttt atgccatcca ggaagagcgg   3960
aatggcgcgc caaaaaggcc ggcggccacg aaaaaggccg gccaggcaaa aagaaaaag   4020
gctagcggca gcggcgccgg atccccaaag aagaaaagga aggttgaaga ccccaagaaa   4080
aagaggaagg tgtgataa                                                  4098
```

```
SEQ ID NO: 9           moltype = DNA  length = 4098
FEATURE                Location/Qualifiers
misc_feature           1..4098
                       note = Description of Artificial Sequence: Synthetic
                        polynucleotide
source                 1..4098
                       mol_type = other DNA
                       organism = synthetic construct
SEQUENCE: 9
atgggccacc atcatcatca tcatagcagc ggcctggtgc cgcgcggcag cggtaccatg   60
gctgccttcg ataaatttat tcaccaatat caggttagca aaacgctccg ctttgccctt   120
attccgcagg gtaagactct ggagaacacc aagaacaacg tcctgcaaga agacgacgaa   180
cgccaaaaaa actatgaaaa agttaagcct atccttgatc gcatctacaa agtattcgcc   240
gaagaaagcc ttaaggattg ttcggtggac tggaacgact tgaacgcatg cttggatgcc   300
taccaaaaaa acccgtcagc agacaaacgt cagaaagtaa cagcagctca agatgcgctt   360
cgtgacgaaa ttgccggtta ttttacgggc aaacaatacg caaacgggaa aaataagaac   420
gccgtgaaaa agaaagagca agcggagctc tacaaggata ttttctccaa aaagatcttc   480
gatggtaccg taaccaacaa caaattacct caagtcaact taagtgccga ggagaccgag   540
ttactgggtt gttttgacaa gttttactac tattttgttg ggttttacca gaatcgtgag   600
aacgtcttct ccggcaagaa tatcgctacg gcgatccctc atcgcattgt gcaggacaat   660
ttccctaagt tccgggaaaa ttgtcgcatc tatcaggatt tgatcaagaa tgagccagca   720
ctcaaaccgt tacttcagca ggccgcagct gctgtcatgg cgcaaaaccc gaagggatt   780
tatcagccgc gtaagtcctt agacgatatt ttcgttatcc cgttctataa ccatttattg   840
ctccaagatg atatcgacta cttttaatcaa atcttggggg gatcagtgg ggcagcaggc   900
cagaagaaga ttcagggctt aaacgagacg attaacctct tcatgcagca gcacccacag   960
gaggccgata agttaaaaaa gaagaaaatt cgtcatcgtt ttattcctct gtacaaacaa   1020
atttttgtctg atcgtacatc cttcagcttt attcctgagg cctttttccaa ctcacaagag   1080
gccccttgatg gtatcgagac gtttaagaaa tcgttaaaga aaaacgacac ttttggcgta   1140
ctcgagcgtt tgatccaaaa tctggcgagt ttggatctga agtatgttta tctttcgaac   1200
aaaaaagtta acgagatcag tcaagcatta tatggtgagt ggcactgtat tcaagacgtg   1260
ttgaaacagg atttcagctt agaatcatta attcaaatca atccgcagaa ctcctcgaat   1320
ggctttttag ccacgctcac tgacgagggt aagaagctta tctctcagtg ccgcaacgta   1380
ctgggtaacc cgctgccggt caaactcgca gatgaccagg ataaggctca agtaaagaat   1440
cagttagata cgttacttgc cgctgtacat tatttagagt ggtttaaggc agatccggat   1500
cttgaaaccg atccaaattt taccgtgcct tttgaaaaaa tttgggagga attagtcccg   1560
cttctttctc tctactctaa ggtgcgcaat ttgtcacga agaaaccgta tagcacagcg   1620
aagtttaagc tgaacttcgc gaaccctact cttgcgacg gctgggatat ccataaggag   1680
tccgataacg gcgccctcct ttttgaaaaa ggcgggttat attatttagg gatcatgaac   1740
ccaaaagata aaccgaattt taaatcttat caaggggcag aaccatacta tcaaaagatg   1800
gtctaccgtt tcttttcctga ctgctctaag accattccaa agtgctctac acaacggaaa   1860
gacgtcaaga agtattttga agatcaccct caggcgacat cctatcaaat ccacgatagc   1920
aaaaaaggaga agtttcgtca ggacttcttc gagatccctc gcgagattta cgagctgaac   1980
aacacgacct acggtaccgg caagtctaag tataaaaaat tccaaactca atactaccaa   2040
aaaactcaag ataagtcggg ctaccagaaa gcacttcgta agttgattga cttctcgaga   2100
aaattttttgc aaacatacgt ctcgacgagc atttttcgatt ttaagggctt acgcccgagt   2160
aaagattacc aggatctggg ggaatttttac aaggatgtaa acagtcggtg ctatcgtgtt   2220
actttcgaaa agattcgggt acaggacatt cacgaggctg taaagaatgg tcaattatac   2280
ctctttcaat tatataataa agatttctct cctaagtccc acggtttgcc taacttgcac   2340
acccttttatt ggaaagcggt gttcgaccca gagaatctca aggacccgat cgtaaagtt   2400
aatgggcagg cggagctgtt ttatcgccca aaaagtaata tgcagatcat tcagcataaa   2460
accggtgaag aaatcgtgaa caagaaattg aagacggca ctccggtccc agatgacatt   2520
taccgcgaga ttagtgcgta tgtacagggg aaatgtcaag gtaacctgag tcctgaagca   2580
gaaaaatggc ttccgtcggt gacaaagaag aaacgcggcg atgatcacaa aaaggaccgg   2640
cgcttactg aagataagtt tttcttccat gtgccaatca cgcttaacta tcaaagcagc   2700
ggcaaaccga cggcatttaa ctcgcaggta aatgacttct taacggaaca tcctgagact   2760
aacattattg gtatcgaccg cggggaacgt aacctgatct acgcagtggt aattactccg   2820
gatgggaaga tcctcgagca aaaaagcttc aatgttatcc acgatttcga ctaccacgaa   2880
tcactctcac aacgcgaaag gcagcgggtg gccgcgcgcc aggcatggac ggcaatcggc   2940
cggatcaagg acctgaagga aggctacctc agtttggtag tccatgaaat tgcgcaaatg   3000
atgatcaaat accaggccgt ggtcgtgttg gaaaatttaa ataccggctt caacgtgtc   3060
cggggtggta tttcagaaaa agcagtgtat caacagttcg aaaaaatgtt gatcgagaag   3120
ttgaactttt tagtgtttaa ggatcgtgcg attaatcaag aaggtggcgt gctgaaggcg   3180
tatcaattaa cagatagctt taccagcttc gctaaattag ggaatcagag tgggtttctc   3240
ttttacattc cttccgctta cacttcaaaa attgatcctg gtactgggtt tgtggatccg   3300
```

```
ttcatctggt ctcatgttac tgcatcagaa gagaatcgga atgagttttt aaagggcttt    3360
gattccctga agtacgacgc gcagagttct gcgtttgtac ttcatttcaa aatgaagagt    3420
aataaacaat tccagaagaa taacgtcgaa ggcttcatgc cagaatggga catctgtttc    3480
gaaaaaaatg aagagaagat tagcctgcaa gggtcaaaat acaccgctgg caaacgtatc    3540
attttgatt cgaaaaagaa acagtacatg gaatgtttcc ctcagaacga attgatgaag    3600
gccctgcaag acgttggcat tacctggaat acaggcaatg atatttggca ggatgtgttg    3660
aaacaggcca gcacagacac gggcttccgc caccggatga ttaatttgat ccggtcagtg    3720
ttgcaaatgc gttcgtcaaa cggtgcaacc ggggaagatt acatcaattc accagtaatg    3780
gacctggatg gccgttcttt cgacactcgc gccggcattc gcgatttgcc acttgacgtt    3840
gatgctaacg gggcatacca catcgctttg aaaggccgga tggttctgga gcggatccgt    3900
agccagaaga acactgcaat caagaatacc gactggctct atgccatcca agaggagcgc    3960
aatggcgcgc caaaaaggcc ggcggccacg aaaaaggccg gccaggcaaa aagaaaaag    4020
gctagcggca gcggcgccgg atccccaaag aagaaaagga aggttgaaga ccccaagaaa    4080
aagaggaagg tgtgataa                                                 4098

SEQ ID NO: 10           moltype = DNA   length = 4098
FEATURE                 Location/Qualifiers
misc_feature            1..4098
                        note = Description of Artificial Sequence: Synthetic
                        polynucleotide
source                  1..4098
                        mol_type = other DNA
                        organism = synthetic construct
SEQUENCE: 10
atgggccacc atcatcatca tcatagcagc ggcctggtgc cgcgcggcag cggtaccatg      60
gctgcgttcg ataagttcat ccatcagtat caagtgagca agaccctccg cttcgccctg     120
atccctcagg ggaagacttt ggagaatacg aaaaacaacg tcttgcagga agacgatgag     180
cgccagaaga attacgaaaa agtgaagccg atcttagatc gcatctataa agtctttgct     240
gaggagtctc tcaaagattg cagtgtcgac tggaatgacc tcaacgcctg cctggatgca     300
tatcaaaaaa atccttcagc cgacaagcgc cagaaggtta aagcggccca agacgcgttg     360
cgggatgaga tcgctggcta ctttacgggt aagcaatatg ctaacgggaa gaataagaat     420
gcagtaaagg aaaaggagca agcggagtta tacaaagata ttttctcgaa aaaaatcttt     480
gatggcaccg tgacgaataa taagctcccg caagttaatc tttctgcgga agaaacagaa     540
ttgctcgggt gtttcgacaa gttttacaac gtattttcg gttctatcca aaatcgcgag     600
aatgttttt cgggcgaaga tattgccaca gctattccac atcgcattgt gcaggataac     660
ttccctaagt ttcgggaaaa ctgtcggatc tatcaggatt taattaagaa tgagcctgcc     720
ctcaagcctc tgctccagca agcagccgca gcagtcatgg cacaaaatcc taaaggcatc     780
taccagccgc gtaagtctct ggatgatatt tttgtcattc ctttctacaa tcatctcctc     840
ttgcaggatg atattgacta ttttaatcag attctggatcg ggatctcggt tgcagcaggc     900
cagaagaaga ttcaggggct gaacgagacc attaatttgt tcatgcaaca gcacccgcaa     960
gaagcagaca aacttaaaaa aaaaaaaatc cgtcatcggt tcatcccatt atataaacag    1020
atcttatctg atcggacatc attcagtttc attcctgaag ctttctctaa tagtcaggaa    1080
gcactcgatg gcatcgagac tttcaagaag tcgcttaaga agaatgacac atttggcgtg    1140
ctggagcgcc tcattcaaaa tcttgcttca ttggatctga agtacgtata cttgtccaat    1200
aaaaaagtca atgaaattc gcaagcactt tacggcgaat ggcattgtat ccaagacgta    1260
ttaaagcaag atttctcgct tgagtcattg atccaaatta accctcaaaa ttcttcgaac    1320
ggttttttgg ctacgttgac tgacgagggg aaaaacgta tctcccagtg tcgtaacgtg    1380
ttaggtaacc cactgccggt caaactggcc gacgatcaag ataaagcgca agtcaagaat    1440
caacttgata cccttctcgc ggcagttcac tatttggagt ggtttaaagc agaccctgat    1500
ctcgaaactg atccgaattt cacggttcca ttcgaaagga tctgggagga actcgttcca    1560
cttctgagcc tctatagtaa agttcgtaat tttgtaacaa agaagccgta ttccaccgca    1620
aaattcaaac tcaacttcgc caatccaact ctcgcggatg ttgggacat tcataaggag    1680
tcagataacg gggcgctgtt gtttgagaaa ggtggtctct actatctggg gattatgaat    1740
ccgaaagaca agcctaattt taaatcgtat caaggcgctg agccttacta ccagaagatg    1800
gtctatcgtt tttttccgga ttgtagcaaa actatcccga agtgttccac gcaacgcaag    1860
gacgtcaaaa agtatttga ggatcatcca caggctacta gttaccaaat ccacgactct    1920
aagaaggaaa aattccgcca ggatttttc gagattcctc gggagatcta cgagctcaac    1980
aatacgacgt atgggactgg caagtccaag tataagaagt tccaaacaca gtattaccag    2040
aaaacgcagg ataaaagcgg gtaccaaag gcgcttcgga agtggatcga ttttctcgaag    2100
aagttcttac agacatacgt gtcgaccagc atcttcgact taagggctt gcgcccatca    2160
aaggattatc aggacctggg ggagtttat aaagatgtca atagtcggtg ttaccgtgtg    2220
acattcgaga aaatccgcgt gcaggatatt catgaagcag ttaaaacgg tcagctttac    2280
ctgtttcaac tttacaataa agacttttca ccgaagtcac atggccttcc aaacctgcat    2340
acattgtact ggaaggccgt atttgaccct gaaaatctca agatccaat tgtaaagtta    2400
aacggtcagg ccgaactctt ttatcgtccg aaatcaaata tgcaaatcat ccaacacaaa    2460
actggggagg aaatcgtcaa caaaaaatta aggacgggga ctccagtccc tgatgatatt    2520
tatcgtgaga tctctgcgta tgttcagggc aagtgtcaag gtaacctgtc tccggaggcc    2580
gagaagtggc tcccgagtgt gactatcaaa aaggcagacc acgatattac aaaagaccgt    2640
cgtttcaccg aagacaaatt cttttccac gtacctatta cattaaatta ccagattcg    2700
ggcaaaccaa cagcctttaa ttcgcaggta aatgattttt tgactgaaca ccctgaaact    2760
aacatcatcg gcattgaccg cggtgaacgg aatctcatct atgccgtggt gattactcca    2820
gatggtaaga tcttagaaca aaaatcgttt aacgtaattc acgattttga ttatcacgaa    2880
agcctcagcc aacgtgaaaa gcaacgggtc gcggcccgcc aagcctggac cgcgatcggg    2940
cgtattaaag accgtaagga ggggtattg tccccttgtc tcatgagat tgcccagatg    3000
atgatcaaat accaggccgt cgtcgttctg gagaatttaa acacaggctt taacgtgta    3060
cggggggga tttcagaaaa ggctgtttac caacaattcg agaaaatgct catcgagaag    3120
cttaatttcc ttgttttaa agaccgtgcg attaatcaag agggcggggt acttaaggcg    3180
taccaattga cggattcgtt cacttccttt gccaagttag ggaaccaatc ggggttttta    3240
ttctacattc cgtctgcata cacctccaaa attgaccctg tacagggtt cgtggacccg    3300
```

```
ttcatctggt cgcacgtcac agcgtctgaa gagaaccgga atgaattttt aaaagggttc   3360
gattctctta agtatgacgc tcaatccagc gcttttgtgc ttcactttaa gatgaaaagc   3420
aacaagcagt ttcaaaaaaa taacgttgag ggcttcatgc cggagtggga catttgcttt   3480
gagaagaatg aggagaaaat ctcattacag ggcagtaagt acacagcagg caagcggatc   3540
attttttgact caaagaaaaa gcagtacatg gaatgctttc ctcagaacga acttatgaaa   3600
gccctgcagg atgtcgggat cacgtggaat acaggcaacg atatctggca ggatgtcttg   3660
aagcaagcgt caaccgacac cggctttcgc catcgtatga tcaacttgat tcgcagtgtg   3720
ttacagatgc ggtcctccaa cggcgcgaca ggtgaggatt atatcaacag cccggtgatg   3780
gacctcgatg ggcggttctt tgacacgcgt gccggcattc gtgactttgcc tttggatgcc   3840
gacgcgaacg gtgcatatca tatcgcgctg aaaggccgca tggttctcga acgcatccgc   3900
agtcagaaga acactgcaat caagaatacg gactggcttt acgcaatcca agaggaacgt   3960
aatggcgcgc caaaaaggcc ggcggccacg aaaaaggccg gccaggcaaa aagaaaaag   4020
gctagcggca gcggcgccgg atccccaaag aagaaaagga aggttgaaga ccccaagaaa   4080
aagaggaagg tgtgataa                                                  4098
```

SEQ ID NO: 11         moltype = DNA  length = 4098
FEATURE            Location/Qualifiers
misc_feature       1..4098
                     note = Description of Artificial Sequence: Synthetic
                     polynucleotide
source              1..4098
                     mol_type = other DNA
                     organism = synthetic construct
SEQUENCE: 11

```
atgggccacc atcatcatca tcatagcagc ggcctggtgc cgcgcggcag cggtaccatg     60
gcggccttcg ataaattcat ccaccaatac caggtatcaa agactctgcg gtttgccttg    120
attcctcaag gtaaaactct cgagaatact aaaaacaatg tattacaaga agacgacgag    180
cgtcaaaaga actacgaaaa ggtcaaaccg attttggatc gcatctataa agtattcgca    240
gaagagagtt tgaaggattg tagcgttgac tggaacgatt taaacgcatg cctggatgct    300
taccagaaga atcctagcgc tgataaacgc cagaaagtga aagcagctca ggatcgcgtta   360
cgtgacgaaa ttgcgggcta tttcacgggg aaacagtacg ctaacgggaa aaatagaat    420
gccgtcaaag aaaaggaaca agcggagctc tataaggaca tctttagcaa gaaaattttt    480
gacggcactg taactaacaa taaattacct caagtgaacc tcagcgcgga ggagactgaa    540
ctcctggggt gtttcgataa atttactaca tatttcgtgg gcttttatca aaatcgtgag    600
aacgtcttct caggggaaga tattgccacg gcgatccctc tcaagacaat                660
ttccctaaat tccgggaaaa ttgtcgcatt tatcaagatc tcattaaaaa tgagccggct    720
ttaaaaccttt tgctccagca agctgccgca gcagtaatgg cgcagaaccc gaaaggcatt    780
taccagccgc gtaaatcttt agatgacatc tttgttatcc cttttctacaa tcaccttctc    840
ttacaggata acattgatta ttttaatcag atcttggggg gtgatttcagg ggcagcgggc    900
cagaagaaga tccagggcct gaatgaaact atcaatctgt tcatgcaaca gcatcctcag    960
gaagccgaca agcttaaaaa gaaaaagatc cgtcaccggt tcattccgtt gtacaagcag   1020
attctgtcag accgcacgag ttttttcctt tatcccagagg cgttcagcaa ctcgcaagaa   1080
gccctgcagg gtattgaaac ttttaaaaag agtctcaaga agaatgatac ttttggtgta   1140
ctcgagcgtt taattcaaaa cctcgcgtcg ttggatctca agtacgtgta cttatctaac   1200
aagaaagtaa acgaaatttc acaagcgctc tatggtgagt ggcattgtat tcaagatgtg   1260
ttaaagcaag atttctcgct tgaatccctt attcagatca cccacagaa ctccagtaat    1320
ggcttcctcg ccactctcac ggacgaaggc aaaaagcgca tttcgcagtg ccggaatgta   1380
ctggggaatc cgttgccagt gaaattagct gatgatcaag ataaagcaca ggtcaaaaac   1440
caattggaca ctctcctcgc tgcggttcac tatctcgaat ggttcaaagc agatccggat   1500
ctcgaaaccg acccgaactt tacagttcct ttcgagaaga tttgggaggca gctcgttcca   1560
ttactttccc tttacagtaa agtacgcaac ttcgtaacga aaaaaccta tagtactgcc   1620
aagttcaagt taaacttcgc gaatcctacg ttagctgacg ggtgggacat tcataaagag   1680
tctgataacg gggctctttt gttcgaaaaa ggtggtttgt attacttagg cattatgaac   1740
ccgaaggata agccgaactt caagagctac cagggcgccg agccttatta tcaaagatg    1800
gtttaccgct tcttcccgga ctgttcaaaa acgattccta aatgttctac ccaacgtaag   1860
gacgtcaaaa agtactttga agatcatcca caggcgactt cgtaccagat ccatgattca   1920
aaaaaagaga agtttcgcca ggatttttttt gaaattccac gggagatcta tgagcttaac   1980
aacacgacgt atggcaccgg gaagagtaaa tacaagaagt tccaaacaca atactatcaa   2040
aagacacaag ataaaagcgg gtaccagaag gcgttgcgta aatggatcga ctttagtaag   2100
aaattcctcc agacgtacgt ttccacgagc atttttgatt tcaaaggctt gcgcccgagc   2160
aaagattatc aagacttggg cgagttctac aaggatgtta acagtcgttg ctaccgggtc   2220
acttttgaaa aaatccgggt tcaagatatc catgaggccg ttaagaatgg gcagttgtat   2280
ttattccagt tatataataa agacttctct cctaagtcgc atggtctgcc aaacctgcat   2340
accttgtatt ggaaagcgat atttgatccg gagaattaa gaattcctat tgtaaaatta   2400
aacgggcagg cagagcttttt ctaccggccg aagtccaaca tgcaaattat tcagcataag   2460
accgggaag aaatcgtaaa taaaaactct aagacgggaa ctccagttcc ggacgacatt   2520
taccgggaaa tcagtgccta tgtgcaaggc aaatgtcagg gcaatcttag tccagaagcg   2580
gagaaatggc tgccgtcagt aaccatcaag aaggcagcgc acgatattac taaggatcgc   2640
cgttttactg aagataaatt tttctttcat gtaccaatca cactcaatta tcagagtagt   2700
ggtaaaccaa ccgcgttcaa cagtcaagta aatgacttcc tcactgagca ccctgagacc   2760
aacattatcg gtatcgatcg tggcgaacgc aatttaattt acgctgttgt catcacacca   2820
gatgggaaga ttttggaaca gaaaagtttt aacgttattc atgactttga ttaccatgag   2880
agcttatcgc aacgggagga caacgcgtg gctgcgcggc aggcttggac ggcaattggt   2940
cgcatcaagg atttgaagga agggtactta agctcgtgg tgcatgagat cgctcaaatg   3000
atgattaaat atcaggcagt cgttgttctg gagaacctta acactggttt caaacgtgta   3060
cgtggtggca ttagcgaaaa agctgtctac cagcaattcg aaaagatgtt aatcgaaag   3120
ttgaactttc tcgtctttaa ggatcgtgct attaaccagg agggcggcgt gctcaaagct   3180
taccaactca ctgattcgtt cactagtttc gcgaagctgg gtaatcaatc gggtttcctc   3240
ttctacattc cttctgcata taccagcaaa attgaccag gcacgggttt tgtagaccca   3300
```

```
tttatttggt cacacgtcac tgcttcggag gaaaaccgga atgaattctt aaagggcttt   3360
gattccttaa aatatgatgc ccaaagtagc gcgtttgtat tgcattttaa aatgaaatca   3420
aataaacaat ttcagaaaaa caatgtagag ggcttcatgc cggaatggga catctgcttt   3480
gaaaagaatg aagagaagat ctctctgcag ggtagcaagt atacggcagg gaaacgtatc   3540
attttttgact ccaaaaagaa gcaatacatg gaatgcttttc cgcaaaatga gttaatgaag   3600
gcattgcaag acgtggggat tacatggaac actgggaatg acatctggca ggacgttctc   3660
aaacaggctt ctactgatac cggttttcgc caccgtatga tcaatctgat tcggtctgtg   3720
ctccaaatgc gctcatccaa tggtgccaca ggcgaagatt atatcaactc tccagttatg   3780
gacctcgatg gtcggttttt tgatacgcgt gcaggcattc gcgattttgcc tctcgacgct   3840
gatgcaaacg gtgcgtacca tattgcgtta aagggggcgta tggtgctgga acggattcgt   3900
tcgcagaaaa acacggctat caagaacacg gactggctct atgctattca agaggaacgc   3960
aacggcgcgc caaaaaggcc ggcggccacg aaaaaggccg gccaggcaaa aagaaaaag   4020
gctagcggca gcggcgccgg atccccaaag aagaaaagga aggttgaaga ccccaagaaa   4080
aagaggaagg tgtgataa                                                 4098

SEQ ID NO: 12        moltype = DNA   length = 4098
FEATURE              Location/Qualifiers
misc_feature         1..4098
                     note = Description of Artificial Sequence: Synthetic
                     polynucleotide
source               1..4098
                     mol_type = other DNA
                     organism = synthetic construct
SEQUENCE: 12
atgggccacc atcatcatca tcatagcagc ggcctggtgc cgcgcggcag cggtaccatg   60
gcagccttcg acaaatttat tcaccagtat caagtctcca aaactctgcg ttttgcgttg   120
attccgcagg gtaaaacttt ggaaaacaca aaaaataacg tattacagga ggatgacgag   180
cgccagaaga attatgaaaa agtgaaacca attctggacc gtatctacaa agtattcgct   240
gaagagtcgt taaggactg ctcagttgat tggaatgacc tgaatgcttg tctggatgct   300
tatcagaaga atcctagcgc ggacaaacgc cagaaggtca aggctgcgca aggctgcactc   360
cgcgatgaga ttgcggggta cttcacgggc aagcagtacg caaatggcaa aaataagaac   420
gccgtgaagg aaaaagaaca ggctgaattg tacaaggata tcttctcgaa aaagatcttc   480
gacggcactg tgaccaataa taaattgcct caagtgaatc tgtcggctga agaaaccgaa   540
ttactcggtt gctttgataa gttttactacc tacttcgtgg gcttttatca aaaccgcgag   600
aacgtgttct ctggtgagga tattgcgaca gcgatcccac accgcatcgt ccaggacaac   660
ttcccgaagt tcggggaaaa ctgccgcatt tatcaggatt tgattaaaaa tgaacctgca   720
ctgaaacctc tcctgcaaca ggccgctgcg ccgtgatgg cgcagaaccc taaaggtatt   780
taccaaccgc gcaaatctct cgatgacatc ttcgtcatcc ctttctataa tcacctgctg   840
cttcaagatg acatcgatta ttttaatcag atcctcggtg gtatctcggg ggctgccggt   900
cagaagaaga ttcagggggtt gaatgaaaca atcaactgt ttatgcagca gcatccgcag   960
gaagcagata aacttaaaaa aaaaaaaatt cgtcatcgtt tcattcctct ttataagcaa   1020
atcctttccg atcgtacaag ttttagcttc atcccagagg cgttctctaa ctcgcaggaa   1080
gcactggatg ggatcgagac tttttaaaaaa tcgttgaaga aaaatgatac attcggggcg   1140
ctcgaacgct tgatccaaaa cttggcttct ctggacctta agtatgtata cctttccaat   1200
aaaaaagtaa acgagatctc ccaggcttta tacggcgaat ggcattgcat ccaagatgtc   1260
cttaaacaag actttagttt agaatcatta atccagatca acccgcaaaa ttcttccaat   1320
ggcttttttag ccacactcac ggacgaaggc aaaaagcgta ttagccaatg tcggaatgtg   1380
ctgggtaatc cactccctgt taagctggca gatgatcagg ataaggctca agtgaagaac   1440
cagctcgaca cattacttgc agctgtccat tatttagaat ggtttaaagc tgatccagat   1500
ttggaaacag acccgaactt cacggttcca tttgaaaaaa tctgggaaga gctcgtgcct   1560
ctgttatcgc tttattctaa agtccgcaat ttcgtcacga agaaaccta cagcacagca   1620
aaatttaaac tgaacttcgc caatcctaca ctcgcggatg ggtgggacat tcacaaagaa   1680
agtgataatg cgcgccttact gtttgaaaaa ggtggtcttt attacttgg cattatgaac   1740
ccgaaggaca aaccaaactt caagtcatat caaggcgctg aaccgtatta tcagaagatg   1800
gtctatcggt tcttttccgga ttgtagcaag actatcccaa agtgctccac gcaacggaag   1860
gacgttaaaa aatactttga ggaccaccca caagctacgt catatcaaat ccatgacagt   1920
aaaaaggaga agttccgtca ggatttttttc gagattccac gcgaaattta tgagctgaat   1980
aatacaactt acggcacagg taagagtaaa tacaaaaagt tcagacaca atattatcaa   2040
aagacgcagg ataagtccgg ttatcagaag gctctgcgga agtgatcga tttctcaaag   2100
aagttccttc aaacttacgt gtcgacctct attttcgatt ttaaaggctt gcgcccgtcg   2160
aaagactatc aagatcttgg cgagtttttat aaggacgtta acagccgctg ctaccgggta   2220
acttttgaga agattcgcgt ccaagacatc catgaggcag tcaaaatgg ccagttatac   2280
ttatttcaac tctacaacaa ggactttagc cctaagtctc atggtttgcc taacttacat   2340
accttatatt ggaaagtcgt tttcgatcca gagaattgaa gattccgat tgtgaagctc   2400
aatggccaag ctgagttatt ttatcgcccg aagtccaaca tgcaaattat tcagcacaaa   2460
accggcgaag agattgtcaa caagaaattg aaggacggta ctcctgtgcc tgatgacatc   2520
taccgcgaaa ttagcgcgta tgtgcagggc aaatgccagg gaacttatc tccggaggcg   2580
gagaaatggc tcccatcagt gaccattaag aaagtcgcgc acgacattac taaagatcgc   2640
cgttttactg aggataaatt tttcttttcat gttcctatca ctctccaatta ccaatcagc   2700
ggcaaaccta cggcgtttaa ttctcaggtt aacgattct taacagaaca cccagaaaca   2760
aacattatcg ggattgaccg cggtgaacgt aatcttatct atgcggtggt cattactccg   2820
gatggtaaaa tcctcgaaca gaaatcattt aatgttattc acgatttcga ttatcatgag   2880
tcacttagtc aacgggagaa acagcgtgtc gctgcccggc aggcttggac agcgattggc   2940
cgtatcaagg acctgaagga gggctattta tcattggtg tgcatgaaat tgcccaaatg   3000
atgatcaagt atcaggcggt cgtggtactg gagaatctga acaccggctt taagcgggta   3060
cgcggtggga tttcagagaa gcagtatac caacagtttg aaaaaatgct gattgagaaa   3120
ttgaattttc tggtcttcaa agatcgcgcg atcaaccaag agggggggtgt actcaaagca   3180
tatcagttga cggattcgtt cacctccttt gctaagcttg gaaccaatc ggggtttctg   3240
ttttacattc catctgccta cacgtcgaag atcgatccgg ggacaggctt tgtagatcca   3300
```

```
tttatttggt cacatgtgac tgctagcgaa gaaaatcgta atgaattcct caagggggttc  3360
gattcgctca agtacgatgc acagtcatct gcatttgtcc ttcattttaa gatgaaaagt  3420
aacaaacagt ttcagaagaa taatgtcgaa ggttttatgc cagaatggga tatctgcttc  3480
gagaagaacg aggaaaagat tagtctgcaa ggttcgaaat ataccgccgg gaaacgtatc  3540
attttcgatt ctaaaaaaaa acagtacatg gagtgctttc cgcaaaacga actcatgaag  3600
gccctccaag acgtaggcat cacgtggaac acaggcaatg atatctggca ggatgtcctg  3660
aaacaggcat caaccgatac cggcttccgc catcgcatga tcaacttaat ccgttccgta  3720
ttacagatgc gctcgtccaa tggggcaaca ggtgaggatt acattaatag ccctgtcatg  3780
gatctcgacg gccgtttctt tgatacacgc gccgggatcc gggatttacc gctcgacgca  3840
gacgcgaacg gggcatatca tatcgcttta aaggggcgca tggtccttga acggattcgt  3900
tcgcaaaaga atacggcaat taaaaatact gactggttgt atgcaatcca agaggaacgc  3960
aacgcgcgc caaaaaggcc ggcggccacg aaaaaggccg gccaggcaaa aagaaaaag  4020
gctagcggca gcggcgccgg atccccaaag aagaaaagga aggttgaaga ccccaagaaa  4080
aagaggaagg tgtgataa                                                 4098

SEQ ID NO: 13              moltype = DNA   length = 4098
FEATURE                    Location/Qualifiers
misc_feature               1..4098
                           note = Description of Artificial Sequence: Synthetic
                           polynucleotide
source                     1..4098
                           mol_type = other DNA
                           organism = synthetic construct
SEQUENCE: 13
atgggccacc atcatcatca tcatagcagc ggcctggtgc cgcgcggcag cggtaccatg  60
gctgcctttg acaaattcat tcatcaatat caggttcta aaacattgcg ttttgcactt  120
attccgcagg gcaagacgct cgagaatact aaaaataatg tgctccagga agatgacgag  180
cgtcagaaga actatgagaa ggtcaaacca attctggacc ggatttacaa agtattcgcg  240
gaggaatcac tgaaggactg cagtgttgac tggaatgacc tcaatgcttg cttagacgcg  300
tatcaaaaga acccgagcgc agataaacgg cagaaagtaa aggctgcgca ggacgctctg  360
cgggacgaaa tcgccggcta ctttacgggc aaacaatatg ccaacggcaa gaataagaac  420
gccgtcaaag agaaagagca ggctgagtta caaggaca tcttttccaa gaaaattttt  480
gacggtaccg taacgaacaa taaactgcct caggttaact tgtccgcgga agagaccgaa  540
cttctcggct gttttgataa gttttaccaca tatcgtcg gttttacca aaatcgcgag  600
aacgtcttca gcggcgaaga tattgcgacg gcaatccctc accgcatcgt tcaggacaac  660
ttccctaaat ttcgtgaaaa ctgccgcatc tatcaagact tgatcaaaaa cgaacctgcg  720
ttgaagccgc tcttgcaaca agcagccgcc gcagtcatgg cgcagaatcc gaagggtatc  780
taccaaccgc gtaaatcact ggacgatatt ttcgtgattc cattctacaa tcaccttctc  840
ttacaggacg acatcgacta cttcaatcaa atcttggtg ggatctctgg tgctgcaggt  900
caaaaaaaaa ttcaaggttt aaatgagacc atcaacctt tcatgcaaca catccacag  960
gaggcagata agctgaagaa aaagaagatt cgtcaccgct ttatcccgct ctacaaacag  1020
attttaagcg atcggacgag tttctcgttc atcccggagg cgttttcgaa ctcccaggaa  1080
gcgcttgacg gtatcgaaac gtttaagaaa tcattgaaaa aaatgacac gtttgggcgt  1140
ctggagcgcc ttatccagaa tctggcgtcc ttggatttga aatatgtgta cctcagtaac  1200
aagaaggtca acgaaatttc acaggctctt tacggtgagt ggcactgcat ccaagacgtt  1260
ctgaaacagg atttttcact ggaatcactg atccaaatta acccgcagaa tagttcaaat  1320
ggtttcttgg cgaccctttac cgatgaaggg aagaaacgga tttcacagtg ccgtaacgtg  1380
ctggggaacc ctttgcctgt taaattggca gatgatcaag ataaggcaca ggttaaaaat  1440
caacttgaca cattattggc ggctgtacac tacttagagt ggtttaaggc tgaccctgat  1500
ttagagacag acccaaattt cacggtgcca tttgaaaaga tctgggaaga gctcgtgccg  1560
ctcttaagtt tatactccaa ggtgcgcaac ttcgtcacga aaagccgta ttcgacggcg  1620
aagttcaagt taaacttcgc taatccgacc ctgcgcgatg ggtgggatat tcataaagag  1680
tcagataatg gcgcattgct cttcgagaaa gcggttttgt attatctggg gatcatgaac  1740
cctaaagaca aacctaattt taagtcgtac aaggggcgg aaccgtatta ccagaagatg  1800
gtttatcgtt tcttttccaga ctgcagtaaa acgattccaa agtgctctac tcagcgtaaa  1860
gacgtaaaga aatactttga ggaccacccg caggcgacca gttatcaaat tcacgacagt  1920
aagaaagaaa agtttcgcca ggattttttc gagattccgc gtgagattta tgaattgaac  1980
aataccacgt atggcaccgg caaatcgaaa tataagaaat tccaaactca atactaccag  2040
aagacccaag ataagtcagg ctaccaaaaa gccctccgta aatggattga tttttctaaa  2100
aagttttgc aaacctatgt tagcacatca atctttgact ttaagggggtt acgcccaagc  2160
aaggactatc aggacctcgg ggaattctat aaggacgtta attcgcggtg ttaccgggtt  2220
actttcgaga agattcgggt gcaagatatt cacgaggcag tcaaaatgg gcagctgtat  2280
ctgtttcaac tctataataa agatttcagc ccgaaaagcc atggtcttcc gaatcttcac  2340
acttctatact ggaaagcagt attcgacccg gaaaacttaa aggatccgat tgtgaagttg  2400
aacggtcaag cggaacttt ctatcgccca aaaagtaata tgcaaatcat ccagcataag  2460
accggtgagg atcgtcaa caagaagttg aaagatggga ctccggtgcc tgacgacatt  2520
taccgtgaga tttccgcata tgttcaaggt aagtgccaag gtaatttaag ccctgaagca  2580
gaaaaatggc tcccgtcggt cactattaag aaagctgtaa ctgatatcac taaagaccgt  2640
cgctttactg aagacaaatt ttttttccat gtgcctatta cgctgaatta ccaatcgtta  2700
gggaagccga cggcattcaa ctctcaggtt aacgactttc ttactgaaca cccagaaact  2760
aacatcatcg gtattgatcg tggcgaacgg aacctcattt atgccgtggt aattacgcct  2820
gacgggaaga ttctcgaaca aaagtctttc aacgttatcc acgactttga ctaccacgaa  2880
tcgttgagtc aacgtgaaaa acaacgtgtt gcggcgcgcc aggcatggac agctatcggg  2940
cgtatcaagg atctgaaaga gggttacctg tcgctggtcg tgcgagat tgcgcaaattg  3000
atgattaaat atcaagcagt ggtagtgctt gagaatctta acactggttt caaacgtgtg  3060
cgcggggga tttcggaaaa ggctgtttac cagcaatttg aaaagatgct cattgaaaag  3120
ttgaatttc tcgtctttaa agaccgtgcc atcaatcaag aaggtggcgt gcttaaagca  3180
taccagttaa ccgactcatt cacgtcattt gcaaaacttg gaaccagag tggcttcctt  3240
ttctacatcc cttcagcgta cacatcaaag attgaccag ggactggctt tgttgatcca  3300
```

-continued

```
tttatctgga gtcacgtcac cgcgagtgaa gagaaccgca atgaatttct caagggcttt    3360
gattcattaa aatacgatgc tcagagctca gcatttgtgt tgcacttcaa gatgaaatcg   3420
aataagcagt tccagaaaaa taatgtcgaa ggcttcatgc ctgaatggga tatctgtttc   3480
gagaaaaatg aagagaagat cagcttacag ggttctaaat acacggcagg taagcggatt   3540
atcttcgatt ctaagaagaa acagtacatg gaatgtttcc ctcaaaacga gctgatgaag   3600
gccttacaag atgtggggat cacctggaac accggtaacg atatttggca agacgtatta   3660
aaacaagcgt cgacagatac cggttttcgt caccgtatga ttaacctgat ccggagtgtg   3720
ttgcaaatgc gcagcagcaa tggcgcaacg ggcgaagatt acattaacag tccagtcatg   3780
gacctggacg gccggttctt cgacacgcgg gcagggcgta gggatctccc tctggatgct   3840
gatgctaacg gcgcctacca tattgcgctg aagggggcgta tggttttgga gcgtattcgt   3900
tctcagaaga acactgccat caaaaatacg gactggttat acgcgatcca ggaggagcgc   3960
aatggcgcgc caaaaaggcc ggcggccacg aaaaaggccg gccagcaaa aagaaaaag   4020
gctagcggca gcggcgccgg atccccaag aagaaaagga aggttgaaga ccccaagaaa   4080
aagaggaagg tgtgataa                                                  4098
```

```
SEQ ID NO: 14          moltype = AA  length = 1310
FEATURE                Location/Qualifiers
REGION                 1..1310
                       note = Description of Artificial Sequence: Synthetic
                       Cas12a/Cpf1 [Sedimentisphaera cyanobacteriorum] sequence
source                 1..1310
                       mol_type = protein
                       organism = synthetic construct
SEQUENCE: 14
MKEFTNQYSL TKTLRFELRP VGETAEKIED FKSGGLKQTV EKDRERTEAY KQLKEVIDSY    60
HRDFIEQAFA RQQTLSEEDF KQTYQLYKEA QKEKDGETLT KQYEHLRKKI AAMFSKATKE   120
WAVMGENNEL IGKNKESKLY QWLEKNYRAG RIEKEEFDHN AGLIEYFEKF STYFVGFDKN   180
RANMYSKEAK ATAISFRTIN ENMVKHFDNC QRLEKIKSKY PDLAEELKDF EEFFKPSYFI   240
NCMNQSGIDY YNISAIGGKD EKDQKANMKI NLFTQKNHLK GSDKPPFFAK LYKQILSDRE   300
KSVVIDEFEK DSELTEALKN VFSKDGLINE EFFTKLKSAL ENFMLPEYQG QLYIRNAFLT   360
KISANIWGSG SWGIIKDAVT QAAENNFTRK SDKEKYAKKD FYSIAELQQA IDEYIPTLEN   420
GVQNASLIEY FRKMNYKPRG SEEDAGLIEE INNNLRQAGI VLNQAELGSG KQREENIEKI   480
KNLLDSVLNL ERFLKPLYLE KEKMRPKAAN LNKDFCESFD PLYEKLKTFF KLYNKVRNYA   540
TKKPYSKDKF KINFDTATLL YGWSLDKETA NLSVIFRKRE KFYLGIINRY NSQIFNYKIA   600
GSESEKGLER KRSLQQKVLA EEGEDYFEKM VYHLLLGASK TIPKCSTQLK EVKAHFQKSS   660
EDYIIQSKSF AKSLTLTKEI FDLNNLRYNT ETGEISSELS DTYPKKFQKG YLTQTGDVSG   720
YKTALHKWID FCKEFLRCYR NTEIFTFHFK DTKEYESLDE FLKEVDSSGY EISFDKIKAS   780
YINEKVNAGE LYLFEIYNKD FSEYSKGKPN LHTIYWKSLF ETQNLLDKTA KLNGKAEIFF   840
RPRSIKHNDK IIHRAGETLK NKNPLNEKPS SRFDYDITKD RRFTKDKFFL HCPITLNFKQ   900
DKPVRFNEQV NLYLKDNPDV NIIGIDRGER HLLYYTLINQ NGEILQQGSL NRIGEEESRP   960
TDYHRLLDER EKQRQQARET WKAVEGIKDL KAGYLSRVVH KLAGLMVQNN AIVVLEDLNK  1020
GFKRGRFAVE KQVYQNFEKA LIQKLNYLVF KEVNSKDAPG HYLKAYQLTA PFISFEKLGT  1080
QSGFLFYVRA WNTSKIDPAT GFTDQIKPKY KNQKQAKDFM SSFDSVRYNR KENYFEFEAD  1140
FEKLAQKPKG RTRWTICSYG QERYSYSPKE RKFVKHNVTQ NLAELFNSEG ISFDSGQCFK  1200
DEILKVEDAS FFKSIIFNLR LLLKLRHTCK NAEIERDFII SPVKGNNSSF FDSRIAEQEN  1260
ITSIPQNADA NGAYNIALKG LMNLHNISKD GKAKLIKDED WIEFVQKRKF              1310
```

```
SEQ ID NO: 15          moltype = DNA  length = 3933
FEATURE                Location/Qualifiers
misc_feature           1..3933
                       note = Description of Artificial Sequence: Synthetic
                       Cas12a/Cpf1 [Sedimentisphaera cyanobacteriorum sequence
source                 1..3933
                       mol_type = other DNA
                       organism = synthetic construct
SEQUENCE: 15
atgaaggaat tcaccaatca gtattctctt accaaaacgc tccgatttga gcttcgtcct     60
gttggagaga cagcagaaaa aattgaagat ttcaaaagtg gagggctcaa gcagactgtt   120
gaaaaagacc gcgaaaggac agaggcttac aagcagctca agaagttat tgattcatac   180
cacagggatt tcatagaaca ggcctttgca aggcagcaaa cttttaagcga agagatttc   240
aagcaaactt atcagctcta taaggaagcc cagaaagaga agacggcga acattaact   300
aaacaatacg agcatctcag aaaaaaaatt gcagccatgt tcagcaaagc cactaaggaa   360
tgggctgtaa tggggggaaaa taacgaatta ataggcaaga acaaagaatc aaagctctat   420
caatggctcg aaaaaaatta cagggcaggc aggattgaga agaagaatt tgatcataat   480
gcagggctta tcgaatattt cgaaaaattt tctacatatt ttgttggctt tgataaaaac   540
agggcaaata tgtattccaa agaggctaag gctacagcca tctcttttcg caccataaac   600
gaaaatatgt ttaagcattt cgataactgc cagagattgg aaaaaataaa aagcaaatac   660
cctgatcttg ctgaagagct aaaggatttt gaagaattct tcaagccttc atatttcatt   720
aattcatga accagtccgg aattgattat tacaatatca gcgcaattgg cgggaaagac   780
gagaaggatc agaaggccaa tatgaaaatc aaccttttca cccagaaaaa ccatctcaag   840
ggctctgata gccccgttt tttcgccaag ctctacaagc agattctcag cgacagaaa   900
aagagctag ttatgatga attcgaaaaa gacagcgaac ttaccgaagc tctcaaaaat   960
gttttcagca agatggctt aatcaatgaa gaatttttca ctaaactaaa atcgctctc   1020
gaaaacttta tgctccccga atatcaggga cagctctaca tcaggaacg ttcctaca   1080
aaaatctcag cgaacatttg gggttcaggg agctgggta taatcaaaga tgccgttact   1140
caagcggcag aaaacaactt taccagaaaa agcgacaaag agaaatatgc aaaaggat   1200
ttttacagca tcgccgagct tcagcaggca atcgatgaat atatcccaac cctcgaaaac   1260
ggagttcaaa acgcctctct aattgaatat ttccgcaaaa tgaattacaa gcccagggc   1320
agcgaagaag atgcaggcct aatagaagaa ataaacaata atctacgtca ggcaggaata   1380
```

```
gttcttaacc aggcagaact gggcagcgga aagcagcgag aggaaaatat cgaaaagatc 1440
aaaaatctgc tcgattcggt tttaaatctg gagcgttttt tgaagcccct ctaccttgaa 1500
aaggagaaaa tgaggccgaa ggcagcgaat ttgaacaaag atttctgcga aagctttgac 1560
cctttatacg aaaaactgaa aacatttttc aaactctaca ataaggtgag aaattacgcc 1620
accaaaaagc catacagcaa agacaaattc aaaatcaatt tcgacacagc taccctgctt 1680
tacggctggt cactggataa ggaaacggct aatctttctg ttattttcag aaagcgggaa 1740
aaattctatc tcggaattat aaacaggtat aactctcaga ttttcaacta taaaatagca 1800
ggcagtgaaa gcgaaaaggg cttggaaaga aagcggagcc ttcagcaaaa ggtattggca 1860
gaagaaggcg aagattattt tgaaaaaatg gtttatcatt tattgctggg cgcttcaaag 1920
acaatcccga aatgctccac ccagcttaaa gaagttaaag ctcatttcca aaaaagcagc 1980
gaagactata ttatccaaag caaaagtttt gcaagtcgc ttactttaac aaaagaaatc 2040
tttgatttga acaatctaag atacaacaca gaaacaggcg aaatatcatc agaactttct 2100
gatacttacc cgaaaaagtt tcagaaaggg tatctcaccc agactggtga tgtttccggg 2160
tataaaaccg ctctgcataa gtggattgat ttttgcaaag aatttctcag atgctaccgc 2220
aataccgaaa tctttacttt ccatttcaag gacaccaagg aatatgaatc tcttgatgag 2280
ttcctcaaag aagttgattc cagcggttac gaaatcagtt tcgataagat aaaggcttca 2340
tacataaatg aaaaggttaa cgcaggcgag ctttatcttt tcgaaatata caacaaggat 2400
ttctctgaat acagcaaagg aaagcccaac tgcacacca tttattggaa aagcttttt 2460
gagacgcaga atcttctcga taaaacagct aagctcaacg ggaaggcaga gatattcttc 2520
cgcccccggt ctatcaaaca caacgataaa ataatacaca gggcaggcga aacgcttaaa 2580
aacaaaaatc cattaaatga aaagccctca agcagatttg attacgacat tacaaaagac 2640
agaagattta ctaaagacaa attttttcctt cactgcccga taacactgaa tttcaaacag 2700
gacaagcctg tccgtttcaa tgagcaggta aatctatatc ttaaggacaa ccccgatgta 2760
aacatcatcg gaatagacag gggcgagaga catcttctct actacacgct aataaatcag 2820
aacggcgaaa tcctccagca gggctcgctt aatagaatcg gggaagaaga aagccgcccg 2880
acagattatc atcgtctcct tgatgagcgg gaaaagcagc ggcagcaggc cagagaaaca 2940
tggaaagctg tggagggcat caaagacctc aaagccggct atctttcccg cgtggttcat 3000
aagcttgcag ggctgatggt gcagaataat gcaatagttg tgctgaaaga tttaaacaaa 3060
ggcttcaaac gagggcggtt tgctgtgaaa agcaggtgt atcagaattt cgaaaaagcc 3120
cttatccaaa agctgaacta cctttgtattc aagaggtca attcaaaaga cgccccccgg 3180
cattacctta aagcttatca gcttacagca ccttttatat gctttgaaaa gcttggtact 3240
cagagcggtt tcttttcta cgtgcgggcc tggaatacat caaaaataga ccctgcaaca 3300
ggttttacag accagattaa gcctaaatac aaaaatcaaa gcaggcgaa agattttatg 3360
agcagttttg attctgtaag gtacaaccgt aaggaaaact atttcgagtt tgaagcagac 3420
tttgagaaat tagcccaaaa gcccaaagga cgaacccgct ggacaatctg ctcctacgag 3480
caggaaagat actcttacag ccccaaagaa aggaaatttg taaaacacaa cgttactcag 3540
aatcttgcag agcttttcaa ttcagaaggc atctcttttg attcaggcca atgcttcaaa 3600
gatgaaatct tgaaagttga agacgcttca ttttttcaaat ctataatttt caatctgcgt 3660
ttgcttttga agctgcgcca cacctgcaaa aatgcagaaa tcgagagaga tttataatc 3720
tcgccggtga aagggaataa ttcaagtttc ttcgattcgc gaatagccga gcaggaaaac 3780
ataacatcta tcccgcaaaa cgcagatgca acgggggctt acaatattgc cctcaaaggc 3840
cttatgaatc ttcataatat cagcaaagac ggaaaagcaa aacttataaa agatgaggac 3900
tggatcgaat tcgttcagaa gaggaaattt tag                             3933

SEQ ID NO: 16        moltype = AA  length = 1372
FEATURE              Location/Qualifiers
REGION               1..1372
                     note = Description of Artificial Sequence: Synthetic
                     polypeptide
source               1..1372
                     mol_type = protein
                     organism = synthetic construct
SEQUENCE: 16
MGHHHHHHSS GLVPRGSGTM KEFTNQYSLT KTLRFELRPV GETAEKIEDF KSGGLKQTVE  60
KDRERTEAYK QLKEVIDSYH RDFIEQAFAR QQTLSEEDFK QTYQLYKEAQ KEKDGETLTK 120
QYEHLRKKIA AMFSKATKEW AVMGENNELI GKNKESKLYQ WLEKNYRAGR IEKEEFDHNA 180
GLIEYFEKFS TYFVGFDKNR ANMYSKEAKA TAISFRTINE NMVKHFDNCQ RLEKIKSKYP 240
DLAEEELKDFE EFFKPSYFIN CMNQSGIDYY NISAIGGKDE KDQKANMKIN LFTQKNHLKG 300
SDKPPFFAKL YKQILSDREK SVVIDEFEKD SELTEALKNV FSKDGLINEE FFTKLKSALE 360
NFMLPEYQGQ LYIRNAFLTK ISANIWGSGS WGIIKDAVTQ AAENNFTRKS DKEKYAKKDF 420
YSIAELQQAI DEYIPTLENG VQNASLIEYF RKMNYKPRGS EEDAGLIEEI NNNLRQAGIV 480
LNQAELGSGK QREENIEKIK NLLDSVLNLE RFLKPLYLEK EKMRPKAANL NKDFCESFDP 540
LYEKLKTFFK LYNKVRNYAT KKPYSKDKFK INFDTATLLY GWSLDKETAN LSVIFRKREK 600
FYLGIINRYN SQIFNYKIAG SESEKGLERK RSLQQKVLAE EGEDYFKMV YHLLLGASKT 660
IPKCSTQLKE VKAHFQKSSE DYIIQSKSFA KSLTLTKEIF DLNNLRYNTE TGEISSELSD 720
TYPKKFQKGY LTQTGDVSGY KTALHKWIDF CKEFLRCYRN TEIFTPFHFKD TKEYESLDEF 780
LKEVDSSGYE ISFDKIKASY INEKVNAGEL YLFEIYNKDF SEYSKGKPNL HTIYWKSLFE 840
TQNLLDKTAK LNGKAEIFFR PRSIKHNDKI IHRAGETLKN KNPLNEKPSS RPFDYDITKDR 900
RFTKDKFFLH CPITLNFKQD KPVRFNEQVN LYLKDNPDVN IIGIDRGERH LLYYTLINQN 960
GEILQQGSLN RIGEEESRPT DYHRLLDERE KQRQQARETW KAVEGIKDLK AGYLSRVVHK 1020
LAGLMVQNNA IVVLEDLNKG FKRGRFAVEK QVYQNFEKAL IQKLNYLVFK EVNSKDAPGH 1080
YLKAYQLTAP FISFEKLGTQ SGFLFYVRAW NTSKIDPATG FTDQIKPKYK NQKQAKDFMS 1140
SFDSVRYNRK ENYFEFEADF EKLAQKPKGR TRWTICSYGQ ERYSYSPKER KFVKHNVTQN 1200
LAELFNSEGI SFDSGQCFKD EILKVEDASF FKSIIFNLRL LLKLRHTCKN AEIERDFIIS 1260
PVKGNNSSFF DSRIAEQENI TSIPQNADAN GAYNIALKGL MNLHNISKDG KAKLIKDEDW 1320
IEFVQRKRKFA AAKRPAATKK AGQAKKKKAS GSGAGSPKKK RKVEDPKKKR KV       1372

SEQ ID NO: 17        moltype = DNA  length = 4122
FEATURE              Location/Qualifiers
```

| misc_feature | 1..4122 |
| | note = Description of Artificial Sequence: Synthetic polynucleotide |
| source | 1..4122 |
| | mol_type = other DNA |
| | organism = synthetic construct |

SEQUENCE: 17

```
atgggccacc atcatcatca tcatagcagc ggcctggtgc cgcgcggcag cggtaccatg    60
aaggagttta ccaaccaata ttccttaacc aagaccctgc ggttcgagtt gcggccagtc   120
ggcgaaacag cagaaaagat cgaagatttt aaatcgggcg ggctcaagca aacagtggaa   180
aaggatcgtg agcgtacaga agcgtataag cagttgaaag aggttattga ctcctatcat   240
cgtgacttca ttgagcaagc ttttgcgcgc cagcagacgc tgtccgagga ggattttaaa   300
caaacatatc aactgtacaa agaggccag aaagagaagg atgggaaac attaacaaag   360
cagtacgacg atttacggaa gaaaatcgca gctatgttca gcaaggctac gaaggaatgg   420
gccgttatgg gggagaataa cgaattgatc gggaaaaaca aagagtcaaa gttgtatcag   480
tggctggaga agaactaccg cgcaggtcgc atcgaaaaag aggaattcga ccataatgcg   540
ggcttaatcg aatacttcga gaattttcc acatatttcg taggttttga caaaaatcgt   600
gcgaatatgt attcaaagga ggcaaaggcg accgcaattt ccttccggac gattaatgag   660
aacatggtca agcattcga taattgccag cggctcgaga agattaaatc taaatatcct   720
gatttggccg aggagctgaa ggattttgag gagttttta aacctagcta tttcattaat   780
tgtatgaatc aatcgggtat cgactactac aatatcagcg cgatcggcgg taaggatgaa   840
aaggatcgaa aagcgaatat gaagatcaac cttttcacgc aaaaaaatca tttaaagggc   900
agtgataaac caccattttt tgctaagctc tacaagcaaa ttttgagtga ccggagaag   960
tccgtggtaa tcgacgagtt cgaaaaggac agcgaattga cagaggcact caaaaacgtg  1020
ttttccaagg acgtttgat caatgaggag ttttttacaa agttaaaaag tgcattagaa  1080
aattttatgt tgcctgaata tcaaggtcaa ctctacatca gtaacgcttt ccttacgaag  1140
atcagcgcaa acatttgggg ctctggttct tggggcatca tcaaggacgc agttaccag  1200
gctgcggaaa acaatttcac gcgtaagtct gacaaggaaa agtatgccaa gaaagacttc  1260
tattccattg ctgaactcca gcaggctatt gatgaataca ttcctactct ggagaacggg  1320
gttcaaaacg catcactcat cgagtacttt cgcaaaatga attacaaacc acgcggttct  1380
gaagaagacg caggcttgat cgaagaaatt aataacaacc tgcgtcaggc tgggatcgtc  1440
ctgaatcaag ccgagctggg gtctggtaag cagcgggaag agaatattga aaaattaag  1500
aacttattag attcggtttt gaatctcgaa cgtttcttaa agccactttta cttggagaaa  1560
gagaaaatgc gtccaaaagc tgctaacctg aataaggatt tttgtgagtc atttgatcca  1620
ctttacgaga aactgaaaac gttttttcaag ctctacaata aagtacgtaa ctacgcaaca  1680
aagaaaccat actcaaagga caatttaag atcaatttg ataccgctac gttattatat  1740
gggtggagtt tggataagga aaccgcgaat ctcagcgtca ttttccgtaa acgcgaaaaa  1800
ttctatttgg gtatcatcaa ccggtacaat agccagattt tcaattataa gattgcgggc  1860
agtgagacgg agaaagggtt agagcgtaag cggtcgctgc agcaaaaggt gcttgcagag  1920
gagggtgaag attattttga gaaatggta taccacctgc tgcttggcgc gtcgaaaact  1980
attccgaaat gctcgacaca gttgaaagaa gtaaaagcac actttcaaaa gtcatcagaa  2040
gattatatta tccaatccaa atcatttgca aagtcattaa cattaacaaa agagatcttt  2100
gacttaaata atctgcggta taacacagaa acggggcgaaa ttagttccga gcttttctgat  2160
acatatccga agaagttcca gaaggggtat ctcacacaaa caggcgacgt ttcgggttac  2220
aaaactgctc tgcataagtg gattgatttc tgcaaagagt tcttgcgttg ctatcgtaat  2280
acggagatct tcacgttcca tttcaaggac acgaaggagt acgagtcgtt agatgagttc  2340
ttgaaagaag tggatagttc aggttatgag atttcattcg ataagatcaa agcctcttat  2400
atcaacgaga aggttaatgc aggcgagctg tacttgttcg agatctataa taaagatttc  2460
tccgagtatt ccaaaggtaa gccaatctg cataccattt attggaaaag tctcttcgag  2520
actcaaaact tgctggataa aacagcgaaa ctcaacggca aggcagagat cttcttccgg  2580
ccacgttcga tcaaacacaa cgacaaaatc atccaccgtg cgggcgaaac acttaagaat  2640
aaaaaccgc tcaatgaaaa gcctagttcg cgtttcgatt acgatattac gaaagatcgt  2700
cgttttacga agacaaatt tttttacac tgccctatta cgttaaactt taagcaggac  2760
aagcctgttc gctttaatga acaagtcaac ttatacttaa agacaatcc agacgtgaat  2820
attatcggta tcgatcgtgg tgagcgtcac ttgctttatt acactttgat caatcagaat  2880
ggtgagatct tacagcaggg ttcacttaat cgcattggtg aggaagaatc tcggcctacg  2940
gactaccatc ggttactcga tgagcgtgaa aagcagcgtc aacaagcacg ggagacgtgg  3000
aaagcagtag aagggattaa ggacttaaa gctgggtatc tttcacgggt tgtacataaa  3060
cttgcaggtt taatggtaca aaacaacgca attgtcgttc tggaagatct taacaagggt  3120
tttaagcgcg tcgtttcgc tgttgagaaa caggtgtacc agaacttcga aaagcacttt  3180
attcaaaagc ttaactattt agtgttcaag gaggtcaact ctaaagacgc ccctggccac  3240
tatttgaagg catatcagct tacggcccct tcatctcgt tcgaaaaatt gggtactcag  3300
agcggtttcc tttttttatgt gcgcgcatgg aatacctcga gatcgaccc ggcgacgggt  3360
tttaccgacc aaatcaaacc aaagtataaa aaccaaaaac aggcagaaga cttcatgtca  3420
agcttcgact ctgtccggta caaccgcaag gaaaattatt ttgaattcga ggcggactttt  3480
gaaaaactgg cacagaaacc taaggggcgc acccgctgga cgatttgttc ctatggccag  3540
gaacggtact cttactcccc aaaagaacgg aagtttgtaa agcacaacgt tacacaaaat  3600
cttgctgagc ttttttaattc agagggtatc tcgttcgact ccgggcagtg tttcaaggat  3660
gagatcctga aggtcgagga tgccagtttc tttaagtcta ttattttcaa tcttcgcctc  3720
cttctcaagc ttcgtcacac ttgcaagaac gccgagatcg aacgtgattt catcatttct  3780
cctgtcaagg gaacaattc gtcctttttt gactccgta ttgccgaaca agaaaatatc  3840
accagcattc cacagaatgc tgatgcaaac ggtgcataca acatcgcgct gaagggcctg  3900
atgaacctcc ataatatctc taaggacggc aaggcaaat aattaaagga tgaagattgg  3960
atcgaatttg tccaaaaacg caagttcgcg ccgcacagtg aaggcagaaag  4020
gccggccagg caaaaaagaa aaaggctagc ggcagcggcg ccggatcccc aaagaagaaa  4080
aggaaggttg aagaccccaa gaaaaagagg aaggtgtgat aa                     4122
```

| SEQ ID NO: 18 | moltype = DNA   length = 4122 |
| FEATURE | Location/Qualifiers |

| misc_feature | 1..4122 |
| | note = Description of Artificial Sequence: Synthetic polynucleotide |
| source | 1..4122 |
| | mol_type = other DNA |
| | organism = synthetic construct |

SEQUENCE: 18

```
atgggccacc atcatcatca tcatagcagc ggcctggtgc cgcgcggcag cggtaccatg   60
aaagagttca cgaatcagta ttcgttaact aaaaccctcc gttttgaact ccgtccggtg  120
ggcgagacgg cggaaaaaat tgaggacttt aagtctgggg gtttaaagca aactgtggag  180
aaagaccgtg aacgtaccga ggcgtacaag cagcttaagg aggtgatcga cagttatcat  240
cgggatttta ttgagcaagc ctttgctcgt caacagactt tgtcagagga agattttaaa  300
caaacgtacc aactgtacaa agaggcccaa aagaaaaag acgggagac cttaacgaaa  360
caatatgaac atctgcgcaa aaaaattgca gcaatgtttt caaaggccac gaaggagtgg  420
gccgtcatgg gcgaaaacaa cgagttgatc ggtaagaaca aagaatcgaa attataccaa  480
tggcttgaga agaattaccg cgccggccgt atcgagaaag aagagtttga tcacaatgcc  540
ggtcttatcg aatatttcga gaagttcagt acctacttcg tgggtttcga caaaaaccgc  600
gcaaatatgt actcgaagga agccaaggcc accgcaatta gtttccgtac catcaatgag  660
aatatggtaa agcatttcga caattgtcag cgtcttgaga aaatcaagag taagtaccca  720
gatttagctg aagaattaaa ggattttgaa gagtttttta aaccgtcgta cttcatcaat  780
tgtatgaacc aatccggcat cgattactac aatatttctg ctattggggg taaggacgag  840
aaagaccaga aggcaaatat gaagatcaac ttattcacgc aaaagaacca cttgaaaggc  900
tcagacaagc ctccttttctt tgcgaaattg tacaagcaga tcttgagtga ccggagaaa  960
agtgtggtga ttgatgaatt cgagaaagat tcagaattga cggaggccct taaaaacgtg 1020
ttctctaaag acgggctcat caacgaagaa ttcttcacga aactcaagtc tgcacttgag 1080
aactttatgc tcccagagta ccaagggcaa ttatacatcg gaatgctttt cctcacgaaa 1140
atctcagcaa atatctgggg gagcgggagc tggggcatta tcaaagacgc tgttaccag 1200
gcggcggaga caactttac tcggaagtca gacaaggaaa aatatgcgaa gaaggatttc 1260
tacagtatcg ctgagttgca gcaggcaatc gacgaataca ttccaacgct ggagaatggt 1320
gttcagaacg caagccttat cgagtacttt cggaaaatga attataagcc ggcggggagt 1380
gaggaagatg ctggcttaat tgaagaaatc aacaacaatt tacgccaagc tggcatcgta 1440
ttgaaccagg ccgaactcgg cagcgggaag cagcgtgaag aaaacatcga aagatcaag 1500
aaccttctcg attcggtcct gaacctggag cgtttcctta gccgctttta cctcgagaaa 1560
gagaaaatgc gcccaaaggc tgcgaacttg aacaaagact tttgcgaatc atttgatcca 1620
ttatatgaga aattgaaaac gttttttcaaa ctttataata agtacgtaa ttacgctact 1680
aagaaaccgt actctaaaga taagttcaag atcaacttcg atacagccac gttgctttat 1740
ggctggtcgt tagataagga aacggccaac ctttcggtta tcttccgtaa acgcgagaaa 1800
ttctacctcg gcattattaa tcggtataac agccagatct tcaattataa gatcgccggg 1860
agcgaatcgg agaaggggtt agaacgtaaa cgcagcctcc aacagaaagt attggccgaa 1920
gaaggtgagg actacttcga aaagatggtt taccatctcc tccttggtgc aagcaaaacg 1980
atcccaaaat gcagtacaca acttaaagag gttaaagccc attttcaaaa atcttccgaa 2040
gattacatca ttcaaagcaa atcattcgct aagtcactga ccctcaccaa agagattttc 2100
gatttaaaca atcttcgcta caactactgaa acggggaaa tctcgtcaga acttctgat 2160
acttacccga aaaaatttca gaaaggttat ttgactcaga ctgccgacgt gtccggctat 2220
aaaactgcct tgcacaagtg gattgacttc tgtaaagaat tcttacgttg ctatcgcaac 2280
acagagattt ttaccttcca tttcaaggat actaaggaat atgaatcatt ggacgagttt 2340
cttaaagagg tcgattcctc tgggtatgag atttcattcg acaaaatcaa agcgtcgtac 2400
atcaacgaaa aagtgaatgc ggggaatta tatttattcg agatctacaa taaggacttt 2460
agcgagtata gcaaagggaa gcctaatctc catacgatct actggaaatc actgttcgaa 2520
acacaaaatc tcctcgacaa aacagcgaag ctcaacggca aggctgagat ctttttcgc 2580
ccgcgttcta tcaaacacaa tgacaaaatt atccaccgc ccggtgaaac cttaaaaaat 2640
aagaatccat taaatgagaa acctagctct cgtttcgact atgatattac gaaggaccgg 2700
cggttcacga aggacaagtt cttcttgcac tgtcctatta cattaaattt caagcaagat 2760
aagccagtcc ggttcaatga gcaagttaat ctttatctta agacaaccc tgacgtcaat 2820
atcattggta ttgaccgtgg tgaacggcac ttattgtatt ataccttaat caatcagaac 2880
ggggaaattc tgcaacaggg ctctttgaac cgtattggcg aagaggagtc acgcctacc 2940
gactaccacc gtctcttaga tgaacgcgaa aaacagcgtc agcaggcacg ggaaacttgg 3000
aaagctgtag aaggtattaa agacctcaag gccggttatc tttcacgcgt tgtacataaa 3060
cttgcaggcc tgatggtgca aaataacgct atcgtcgtct tggaggacct gaacaaaggt 3120
tttaagcggg ggcggtttgc tgtagaaaaa caggtgtatc aaaacttcga gaaggcattg 3180
atccaaaagc ttaactacct ggtgtttaaa gaggtaaact caaaggatgc tccaggtcat 3240
tatcttaaag cataccaatt aaccgcccct tttatttcat cgagaagct tgggactcaa 3300
agtggtttcc ttttttatgt gcgcgcttgg aacaccagta agatcgaccc tgcgaccggt 3360
ttcacagacc agattaagcc gaagtataaa atcagaagc agcaaaggga ttttatgagt 3420
agttttgatt ctgtgcgcta taatcggaaa gagaactact ttgaatttga ggcagacttc 3480
gaaaaacttg cacaaaagcc gaaggccgc actcggtgga ctatttgctc atatgggcag 3540
gagcggtata gctacagtcc aaaggaacgc aaattcgtca acataatgt tacgcaaaat 3600
cttgccgaac tcttttaactc agaaggcatt tcttttgaca gtggccagtg cttcaaagat 3660
gaaattttga aggtggagga tgcctctttc ttcaagagta ttattttta acttgcgtct 3720
ttattgaaat tacgtcacac atgcaaaaac gcagaaattg agcgcgattt tattatctct 3780
cctgttaagg gcaataattc atcgttttc gacagccgca ttgcgaaaca ggagaacatt 3840
acatcaattc ctcagaatgc cgacgccaac ggcgcctaca atattgcgct caaaggcttg 3900
atgaacctgc ataacatctc gaaggacggc aaagcgaagt aatcaagga tgaggattgg 3960
atcgaattcg ttcaaaaacg taaatttggc tgcgcaaaag gccggccgc cacgaaaaag 4020
gccgccagg caaaaagaa aaaggctagc ggcagcggcg ccggatcccc aaagaagaaa 4080
aggaaggttg aagaccccaa gaaaagagg aaggtgtgat aa                     4122
```

| SEQ ID NO: 19 | moltype = DNA length = 4122 |
| FEATURE | Location/Qualifiers |

| misc_feature | 1..4122<br>note = Description of Artificial Sequence: Synthetic polynucleotide |
|---|---|
| source | 1..4122<br>mol_type = other DNA<br>organism = synthetic construct |

SEQUENCE: 19

```
atgggccacc atcatcatca tcatagcagc ggcctggtgc cgcgcggcag cggtaccatg   60
aaaagagttca cgaaccagta ctccttgaca aagactttac gctttgaatt gcgtccagtc  120
ggtgagactg cagagaaaat tgaagacttt aagtctgggg ggttaaaaca gactgttgaa  180
aaggatcggg aacggaccga agcatacaaa cagctgaaag aggttatcga ttcataccac  240
cgggacttta ttgaacaggc tttcgctcgg caacaaacct tgtcagagga ggacttcaaa  300
caaacatacc aattgtacaa agaagcacaa aagaaaaggg acggcgaaac actcaccaag  360
cagtacgagc acttgcgtaa gaaaatcgca gctatgtttt cgaaagcgac aaaggagtgg  420
gctgtcatgg gcgagaacaa cgagcttatc ggtaaaaata agaatccaa actttatcaa  480
tggttggaaa agaactatcg cgcaggtcgc attgaaaagg aggagttcga ccacaacgca  540
gggttgattg agtatttcga aaagtttagt acctactttg tgggtttcga taagaatcgc  600
gccaatatgt actcaaaaga agctaaggcc acagccatct ccttccgtac catcaacgaa  660
aatatggtta acattttga taactgccaa cgtctggaaa agattaagag caaatacct   720
gatttagctg aggagctcaa ggactttgaa gaattcttta agccttcata ctttatcaac  780
tgcatgaacc aaagcgggat cgattactat aatatctccg cgatcggggg taaggacgaa  840
aaagatcaaa aagccaacat gaaaatcaat ctttttacg agaagaacca ccttaagggg  900
tcagacaaac ctccattctt cgctaaactg tataaacaaa tcttatccga tcgtgagaaa  960
tccgttgtta ttgacgaatt cgagaaggat agcgagctga cagaagcctt gaagaacgta 1020
tttagcaaag acgggctcat caacgaggag ttctttacga aacttaaatc ggcactgaa  1080
aactttatgc ttcctgagta tcaaggccag ttatatatca ggaatgcatt tctcactaag 1140
atctccgcta acatctgggg ttctgggtca tgggggatca ttaaggacgc tgttacacag 1200
gcagctgaga caattttac tcgtaaaagt gataaggaaa aatatgcgaa aaagattt    1260
tatagtatcg ccgagctcca acaggctatt gacgagtaca tcccgaccct ggaaaacggt 1320
gtacaaaatg catctctcat cgaatacttc cgtaagatga attacaaacc gcgtgggtct 1380
gaggaagacg ctgggctcat cgaagaaatt aataacaacc tccgtcaggc gggcatcgtg 1440
cttaatcaag cggagctggg cagtgggaag caacgggagg aaaacatcga aaaatcaag  1500
aatttgttgg actctgtact gaacctggaa cgcttcctca agccattata cctcgaaaag 1560
gaaaaaatgc gcccaaaagc ggcaaacctc aataaggatt tctgcgagtc cttcgatcct 1620
ctttacgaaa agctcaaaac ctttttaaa ctgcaataa agttcggaa ctatgcgacg  1680
aagaaaccat attcaaagga taagtttaag atcaactttg atactgcaac acttttatat 1740
ggctggtcgc tcgacaagga aacggccaat ctgtctgtaa tttttcgtaa acgcgagaag 1800
ttctatctcg gtatcattaa tcgttataac tcacaaatct tcaattacaa aatcgcaggc 1860
tcggaatcgg aaaaggggct tgaacgcaaa cgctccctgc aacagaaggt tctcgctgaa 1920
gaaggggagg actattttga agatggtc tatcatttgc tcttaggggc gtctaagaca  1980
attccgaaat gcagtaccca actgaagaa gtgaaggcgc atttccaaaa atcttcagag 2040
gattatatta tccaatcaaa atcttttgca aagtcactga ccccttaccaa agagatttt  2100
gaccttaata atttacggta taacacagaa actggtagga tttccagtga acttagtgac 2160
acttatccta aaaagttca gaagggttac ctgactcaga caggggatgt atcaggctat 2220
aagactgcac tgcataaatg gatcgatttt tgcaaggaat tcttgcgttg ttatcggaat 2280
acggaaattt ttacattcca tttcaaagac actaaagagt atgagtcgtt ggacgaattt  2340
ctgaaggga tggactcctc tgggtatgaa atttcttttg acaagattaa agcatcgtat 2400
attaatgaga aggtaaacgc aggggagctg tatctgtttg aaatttacaa caaagatttt 2460
tcggaatact caaaaggcaa accgaacctc catacaatct actggaagtc actttttgag 2520
acacaaaact tgctggataa aacagccaaa ttaaacggca agcggaaat cttctttcgg 2580
cctcgtacga ttaaacataa tgataaaatt atccaccgg caggcgaaac gttgaagaat 2640
aagaatcctc tcaatgaaaa gccatccagc cgctttgact acgatattac aaaggatcgg 2700
cgtttacga agataagtt ctttcttcac tgtccaatta ccttgaattt caaacaagac 2760
aagcctgtcc gctttaacga acaggttaac ttgtacctga aggacaatcc tgacgttaac 2820
attattggta tcgatcgtgg cgagcgccac ttattatatt ataccctcat caatcaaaac 2880
ggcgaaatct tgcagcaggg tagcttgaac cgtattgggg aagaagaaag tcgtcctaca 2940
gactaccatc ggctgctcga cgagcgggaa aagcaacgcc aacaggcgcg cgaaacttgg 3000
aaaagcggtgg agggcattaa ggacttgaag gccgggtatc ttagccgtgt ggttcataag 3060
ttagctggct tgatggtaca gaataacgcg attgtggtgt tagaggacct caacaaagg  3120
tttaagcgtg gccggttcgc cgtggagaaa caggtatate aaaactttga gaaggcatta 3180
attcaaaaac tgaactatct tgtctttaag gaggtcaaca gcaaggacgc accgggcat  3240
tatctgaaag catatcagct caccgcacca ttcatctcat tgagaagtt aggcactcag 3300
tcagggttcc tgttttatgt gcgcgcctgg aacacaagta agattgatcc ggccaccggt 3360
ttcactgatc aaatcaagcc aaagtataaa atcagaaac aggagatta ttttatgtct 3420
tcatttgact ccgtcggta taatcggaag gaaaattatt tgagtttga ggcggatttt  3480
gagaaacttg cgcaaaaacc aaaaggtcgt accggtgga cgatctgctc ctatggccaa 3540
gagcgctact cctacagccc gaaagaacgg aagttcgtga acacaacgt cactcagaat 3600
ttagctgagt tattcaactc ggagggtate agttttgact cggggcaatg ttttaaggac 3660
gaaattttga aggtcgaaga cgcttcttc tttaaaagca ttatttttcaa tttgcgcctc 3720
ctcttgaagt tgcgtcatac ctgtaaaat gctgagattg aacggacttt cattatctct 3780
ccggttaaag gtaataattc gtccttcttt gatagtcgca tcgctgaaca ggagaatatt 3840
acatctatcc cacagaacgc ggacgccaac ggggcctata atatcgccct gaaagggtta 3900
atgaatcttc taatatcag taaagacggg aaagctaagc ttatcaagga cgaggactgg 3960
attgagtttg tgcagaacg caagtttggc gcgcaaaaag gcgggaagcg cacgaaaaag 4020
gccggccagg caaaaagaa aaaggctagc ggcagcggcg ccggatcccc aaagaagaaa 4080
aggaaggttg aagaccccaa gaaaagagg aaggtgtgat aa                      4122
```

| SEQ ID NO: 20 | moltype = DNA length = 4122 |
|---|---|
| FEATURE | Location/Qualifiers |

| misc_feature | 1..4122 |
| | note = Description of Artificial Sequence: Synthetic polynucleotide |
| source | 1..4122 |
| | mol_type = other DNA |
| | organism = synthetic construct |

SEQUENCE: 20

```
atgggccacc atcatcatca tcatagcagc ggcctggtgc cgcgcggcag cggtaccatg   60
aaggaattta ctaaccaata cagtctcacc aaaaccttgc gttttgaact tcgcccagtc  120
ggcgagacag ctgagaaaat cgaggatttc aagtcggggg ggttaaaaca gactgtagaa  180
aaagaccgcg agcgcactga ggcctataag cagttgaagg aggttattga ttcgtaccat  240
cgggatttta tcgaacaggc gtttgcgcgg caacagacgt tgtctgagga gatttcaag   300
caaacgtacc agtatacaa agaagcccag aaagaaaagg acggcgagac gttgactaag  360
cagtatgaac atctgcggaa gaagatcgct gctatgttta gcaaggccac gaaagagtgg  420
gctgtaatgg gggagaataa cgagctgatc ggcaagaaca aggaatcgaa attgtaccag  480
tggcttgaaa agaattatcg ggcaggccgg atcgaaaagg aagaattcga tcataacgca  540
ggcttgattg aatactttga aaaattcagt acctattttg tggggttcga caaaaaccgt  600
gcaaatatgt atagcaagga ggcaaaggct acagctatct cgtttcgtac gattaatgaa  660
aacatggtaa agcacttcga taactgccag cgccttgaga aaattaagag caaatatcct  720
gatcttgccg aggagttgaa ggacttcgaa gaattcttta acctagcta ttttatcaac  780
tgtatgaatc aatcagggat tgattattat aatatttccg cgattggtgg caaagatgaa  840
aaggatcaga aagcaaatat gaaaattaat ctcttcactc aaaaaaatca cctcaaggg   900
tccgataagc cacctttttt cgcgaaactg tataaacaga ttttatcgga ccggaaaaaa  960
agcgttgtca ttgacgagtt cgaaaaagac tcagaattga ctgaggcact caagaatgtt 1020
ttctctaagg atgggctcat taacgaagag ttttcacga agttaaagtc tgcactcgag 1080
aacttcatgt taccagagta ccaagttcag tctctatatcc ggaacgcatt cttaaccaag 1140
atttcagcta atatctgggg ctccgggagc tggggcatca tcaaggacgc cgttacacag 1200
gctgctgaaa ataatttcac gcgtaagtca gataaagaaa agtatgctaa gaggacttt  1260
tactcaatcg cggaactcca gcaagcgatc gatgaataca ttccgacttt agagaacggg 1320
gtacaaacgg ctagcctcat cgaatatttc cggaagatga actacaagcg cgcggctct  1380
gaggaagatg ctgggctcat cgaagagatc aataataact tacgtcaggc tgggattgtt 1440
cttaatcaag cggagttagg ttcaggtaaa cagcgtgagg aaaatattga aaagattaaa 1500
aatttgttag actctgtcct caatcttgaa cgctttctga agccattata cttggaaaaa 1560
gaaaagatgc gtccgaaggc cgcaaatctg aacaaggact tctgcgagtc ctttgacccg 1620
ctttatgaga agctgaagac gtttttcaag ctttacaaca aggtgcgtaa ttacgccaca 1680
aaaaaaccgt actctaaaga caattcaag atcaatttcg acacggcgac tctgttatat 1740
ggttggtcct tagataaaga aactgctaac ttgtccgtaa tcttccggaa acgcgaaaaa 1800
ttttattag ggatcattaa tcgctacaac tcacagattt ttaattacaa aatcgcaggt 1860
agcgaaagtg aaaagggcct cgagcggaag cggtctctcc gcagaaagt gctggccgag 1920
gagggggaag actacttcga aaagatggtg tatcacttac ttctgggtgc aagtaagaca 1980
atcccgaaat gttcaacgca actgaaggaa gtaaagcgc actttcagaa atctagtgag 2040
gactatatca tccagagtaa atcttttgca aagtccctga ctcttactaa ggaaatcttt 2100
gatttgaaca atttgcgcta taatactgag acgggcggaa tttcgtccga ttgtgtccgaa 2160
acgtatccta aaaaatttca gaagggctac ttgacccaaa cggggggatgt tagcggttat 2220
aaaactgcgt tgcataaatg gatcgatttt tgcaaagagt tccttcgctg ctatcggaat 2280
accgagattt tcacttttca tttcaaagac acgaagagt acgaatctct ggacgaattc 2340
ttgaaagaag tagactcatc tggctatgaa atttcgtttg ataagattaa agcctcttac 2400
attaatgaga aggtaaacgc aggggaactg tacctctttg agatctacaa caaggatttc 2460
tccgaatatt ctaagggcaa accgaacctt catactattt attggaaatc tctcttcgaa 2520
acccaaaact tgctcgataa aacggcaaaa cttaacggca aggccgagat ttttttccgg 2580
ccacgttcga ttaagcataa cgacaagatc atttcaccggg cgggtgaaac gctcaagaac 2640
aagaacccat aaatgagaa accgtcatcg cggtttgact atgacatcac gaaggaccgt 2700
cgttttacga agacaaatt ctttctgcat tgcccaatta ccctcaattt caagcaggat 2760
aagccagtac gtttcaacga gcaagttaac ttatacttga agataaccc agacgtcaac 2820
atcattggca tcgatcgtgg cgagcgtcat ctgctctatt atactctgat caaccagaat 2880
ggcgaaatct tgcaacaggg cagcctgaat cggattggcg aagaagagtc gcgcccaacc 2940
gactatcatc ggcttcttga cgagcgggag aaacaacgcc aacaagcccg tgaaacatgg 3000
aaagcggtcg aaggtatcaa ggacttgaaa gctggttatc tgtcgcgcgt tgtacataag 3060
cttgccggtt tgatggtaca gaacaacgct attgtggtgc tggaggactt aaacaaaggc 3120
tttaagcgtg gtcggttcgc tgtggaaaag caagtcgac agaactttga gaaagcgctc 3180
atccaaaaat tgaactactt ggtgtttaaa gaggttaact cgaaggatgc tcctggtcat 3240
tatcttaaag cgtaccaatt aaccgcccct tttatttcct tcgaaaaact gggtactcag 3300
tctgggttcc ttttctacgt acgtgcctgg aatacatcaa agatcgaccc agccacgggt 3360
tttaccgacc aaattaaacc taagtataaa atcagaaac aaaagatttatgagt 3420
tcttttgaca gtgtccgcta taaccggaaa gagaactatt ttgagtttga agcggatttt 3480
gagaaattgg ctcaaaagcc taagggccgt actcgctgga caatctgcag ttatggccag 3540
gaacgctatt cttacagtcc aaaggagcgc aagtttgtaa agcacaacgt aacacagaac 3600
ttggctgaat tattcaattc tgaaggtatc agctttgatt cgggccaatg cttcaaagat 3660
gaaattctga agtcgaaga tgccagttt tttaagtcca ttatctttaa cctccggttg 3720
ctcttgaaac tgcgccacac ctgtaaaaac gccgaaatcg aacgcgattt cattatctct 3780
ccggtgaagg gcaataacag ttccttttttc gatagtcgga tcgcagaaca agaaaacatc 3840
acctctatcc cacaaaatgc tgacgcgaac ggtgcctaca atattgcatt gaaagggtta 3900
atgaatttgc ataacatttc gaaggatggc aaagcaaaat tgattaagga tgaagattgg 3960
atcgagttcg ttcaaaacg taagtccgcg gcgccaaaag cggcaaaaaa gcacgaaaaag 4020
gccggccagt caaaaaagaa aaaggctagc ggcagcggcg ccggatcccc aaagaagaaa 4080
aggaaggttg aagaccccaa gaaaagaagg aaggtgtgat aa                    4122
```

SEQ ID NO: 21    moltype = DNA   length = 4122
FEATURE          Location/Qualifiers

| | |
|---|---|
| misc_feature | 1..4122<br>note = Description of Artificial Sequence: Synthetic polynucleotide |
| source | 1..4122<br>mol_type = other DNA<br>organism = synthetic construct |

SEQUENCE: 21

```
atgggccacc atcatcatca tcatagcagc ggcctggtgc cgcgcggcag cggtaccatg   60
aaagaattca ccaaccagta ttcactcact aagacactgc gctttgaatt gcgtccggtt  120
ggcgaaaccg cggagaagat tgaagatttt aaatcgggtg gcttgaaaca aactgtagag  180
aaagaccggg aacgcaccga ggcctacaag caactgaaag aagtaattga ttcctatcat  240
cgcgacttca tcgagcaggc attcgctcgg caacaaactc tgtcggaaga agacttcaag  300
cagacttacc aattgtacaa ggaagcccaa aagaaaaag acggggaaac cttgacaaag  360
caatacgagc acctgcggaa aaaaatcgcc gcgatgttca gtaaagcaac aaaagaatgg  420
gccgtgatgg gggaaaacaa tgagttgatc ggtaagaaca aagaaagtaa actgtatcag  480
tggttagaga agaactatcg cgctggtcgc atcgagaagg aagagtttga tcacaatgcc  540
ggtttaatcg agtattttga aaagttttcc acttacttcg taggcttcga caagaaccgc  600
gccaacatgt atagcaagga ggcaaaggct acggcgatca gctttcggac gatcaacgag  660
aacatggtca agcacttcga taattgccaa cggttggaga aaattaagag caagtaccca  720
gatctcgcgg aagaattgaa agacttcgaa gaattcttca aaccatctta cttcatcaat  780
tgcatgaatc aatcaggcat tgactactat aacatctccg cgattggggg taaagacgaa  840
aaggaccaga aagccaatat gaaaatcaat cttttcacac aaaaaaacca ctgaaaggc  900
tcagacaagc caccgttctt tgcaaaactc tacaaacaaa tcttatctga tcgcgagaag  960
tccgtggtga tcgatgaatt cgaaaggat agtgaactta cggaagccct gaagaacgtc 1020
ttctctaaag acgtttaat caatgaagag ttttttacta agttgaagtc tgcgttagaa 1080
aacttcatgc ttccggaata tcagggtcag ttatatcatc ggaacgcgtt cttgaccaag 1140
atctctgcga atatttgggg gagtggctcg tggggcatta tcaaggatgc agttactcaa 1200
gcggcggaga ataatttcac ccgtaagagc gacaaagaga agtatgcgaa gaaggacttt 1260
tacagcattg cggaattgca gcaggcgatc gatgagtaca ttccaactct cgaaaacggc 1320
gtacagaacg cgagtttgat tgagtatttc cgcaagatga attataagcc tcggggttca 1380
gaggaggacg ctggtttgat cgaggaaatc aataacaatt tacgtcaggc cggcatcgtg 1440
ctgaaccagg cggagttagg cagtgggaag caacgggaag agaatattga gaagatcaaa 1500
aacctcttgg actctgttct taaccttgaa cgtttcctga aacctttgta cttggaaaaa 1560
gaaaaaatgc gtccgaaagc cgccaatttg aataaggatt tctgcgagtc gttcgacccg 1620
ttatatgaaa agctgaagac attcttcaaa ttatacaata aggtcgtaa ctacgccacc 1680
aagaagcctt acagcaaaga taatttaaa atcaatttcg atacggctac actgttgtat 1740
ggttggagtc tggacaagga acagcaaat ctcagtgtga tctttcggaa acgggagaaa 1800
ttctatcttg ggattattaa ccgctataat tctcaaatct ttaactacaa aatcgctggt 1860
tcagaatcag aaaagggtct tgaacgcaaa cgtagcttac agcaaaaagt cctcgcgaa 1920
gaggggagg attacttcga gaagatggtc taccaccttt tgctgggcgc atcaaaaacg 1980
attcctaaat gttctacgca gttgaaggag gtgaaggcac atttccaaaa gagttctgag 2040
gactacatta ttcaatccaa atcgtttgcc aaatctttaa ctctgaccaa ggaaatcttt 2100
gacttaaata atttacgctg taatactgaa actggcgaaa tttctagtga gctctccgaa 2160
acctatccga aaaaatttca gaaaggttac ttgactcaaa cgggcgatgt cagcgggtac 2220
aagacagcac ttcacaaatg gattgactt tgcaaggaat tccttcgttg ctatcgcaat 2280
acagaaattt tacattcca tttcaaagat actaaagagt atgaaagttt ggatgaattc 2340
ctgaagaaga tcgatagttc ggggtatgag atcagttttg acaagattaa ggcatcatac 2400
atcaatgaaa aggtgaatgc gggcgaatta tatctgttcg aaatctacaa caaagacttc 2460
tccgaatatt cgaaaggcaa accgaatctt cacactattt actggaagtc cttattcgaa 2520
acgcaaaacc ttctcgacaa gacagctaaa ttaaatggga agctgagat cttctttcgg 2580
ccacgtcga tcaaacataa cgacaaaatt attcaccgag ctggcgagac attaaagaat 2640
aaaaacccgc ttaatgaaaa gccttcctcg cggttcgatt acgacattac taagaccgc 2700
cgcttcacta aggacaagtt tttcttgcat tgtccgatta cattgaactt caaacaggac 2760
aagccagtgc ggtttaatga acaggttaac ctgtacctca aagataaccc tgacgtgaat 2820
atcattggga tcgatcgtgg tgaacgtcac ctcttatact atactctcat caaccagaac 2880
ggtgaaatct tacaacaggg ttcactcaac cgcattggcg aggaggagtc acgtccaaca 2940
gactatcacc ggctgctcga cgagcggaa aagcagcgcc aacaagcacg tgaaacttgg 3000
aaggcagtcg agggtattaa agatctgaaa gcaggttatt tatctcgtgt cgtacataaa 3060
ttggctggct tgatggtaca aaacaacgcc attgtagtct tggaggattt aaacaaaggt 3120
tttaagcgtg ggcggtttgc tgtagagaaa caggttacc agaacttcga aaaagctctc 3180
attcaaaaac ttaactacct cgtattcaaa gaggtcaact ccaaagacgc cccaggtcac 3240
tacctgaagg catatcaact gacggcccct tcattagct ttgaaaagtt gggtactcaa 3300
tctggctttc tcttttatgt tcgggcctgg aacacctcca aaatcgatcc ggcaactggc 3360
ttcacggacc aaattaagcc aaaatacaaa accaaaagc aagctcatgtca 3420
tcgtttgact cggttcggta caaccggaag gaaaactact tcgaatttga agcagattc 3480
gagaaattgg ctcagaagcc aaaaggccgg acgcgctgga ctatctgttc ttatggccag 3540
gagcggtact cttatagccc taaagagcgg aagtttgtta agcataatgt aacacaaaac 3600
ttggcagagc tcttcaattc ggaagggatc tccttcgata gcggcaatg cttcaaggat 3660
gagatttaa agttgaaga cgctagtttc ttcaagtcca tcattttaa ccttcggctg 3720
cttctcaaac ttcggcacac atgcaagaat gctgaaattg aacggacttt tattatttct 3780
ccggttaagg gcaataatag ctcattcttt gacagtcgga tcgcagaaca ggagaatatc 3840
acctctatcc ctcaaaatgc cgatgcaaat ggtgcataca atatcgccct taagggctt 3900
atgaacttac acaatattag taaagacggg aaggccaagc tcattaagga tgaggattgg 3960
atcagtttg tacaaaacg gaaattcggc ggcgcaaagc gccagaaaag cacgaaaaag 4020
gccggccagc caaaaaagaa aaaggctagc ggcagcggcg ccggatcccc aaagaagaaa 4080
aggaaggttg aagaccccaa gaaaagagg aaggtgtgat aa                     4122
```

| | |
|---|---|
| SEQ ID NO: 22 | moltype = DNA length = 4122 |
| FEATURE | Location/Qualifiers |

| misc_feature | 1..4122 |
| --- | --- |
| | note = Description of Artificial Sequence: Synthetic polynucleotide |
| source | 1..4122 |
| | mol_type = other DNA |
| | organism = synthetic construct |

SEQUENCE: 22

```
atgggccacc atcatcatca tcatagcagc ggcctggtgc cgcgcggcag cggtaccatg    60
aaagagttca cgaaccagta ctctttgact aagacacttc ggttcgaact ccggccggtg   120
ggtgaaaccg ctgagaagat cgaggatttt aagagtgggg ggttgaaaca aacagtagag   180
aaagaccgtg aacggaccga ggcctataag cagcttaagg aggttatcga ctcttaccac   240
cgtgatttta ttgaacaggc ttttgcccgc cagcaaacat tatcagagga ggattttaag   300
cagacctatc aactgtacaa agaagcccag aaggaaaaag atggcgagac gttaacaaag   360
cagtacgagc atttgcgtaa aaaaatcgca gccatgtttt caaaggccac aaaggaatgg   420
gctgtaatgg gcgaaaataa tgagttgatt ggtaaaaata aagagagtaa attgtatcaa   480
tggcttgaaa agaattatcg ggccggtcgg attgagaaag aggagtttga tcacaacgcg   540
gggttaattg agtattttga aaaattttcg acctactttg ttgggttcga caagaatcgc   600
gccaatatgt attcaaaaga ggcaaaggcc acggccatct cattccgcac tattaacgag   660
aacatggtga aacacttcga caactgtcaa cggttagaga agatcaagtc gaagtaccct   720
gatctcgccg aggagctcaa ggatttcgag gaattttttca accgtcctca cttcatcaat   780
tgtatgaatc aatctgggat cgattattac aacatttctg cgatcggcgg caaagacgaa   840
aaggatcaga aggcaaacat gaagattaat ctgtttaacg agaagaatca cttaaaaggg   900
agcgacaaac ctcctttttt cgcaaagctg tataagcaga tcctctcaga ccgcgaaaag   960
tcggtggtaa ttgacgaatt tgaaaaagat agtgagctca ctgaagctct caaaaatgtt  1020
ttttcaaagg atggttttgat taatgaggag ttcttcacca agctcaagtc agcgctggaa  1080
aatttcatgt tacctgagta ccaaggtcaa ctgtacattc gcaacgcctt tcttacgaaa  1140
atttccgcca acatctgggg tagcgggagc tggggtatta tcaaagacgc agttacgcaa  1200
gccgccgaga caactttac gcgcaagagt gacaaagaga agtatgccaa aaaggacttc  1260
tattccatcg cagaattaca gcaagctatt gacgagtaca tccctacact ggagaacggt  1320
gtccagaatg cctctctcat cgaatatttc cgcaaaatga actacaagcc acgcgggagc  1380
gaggaggatg ctgggctcat cgaagagatt aataacaact tacgccaagc aggtattgtt  1440
ctcaaccagg cggagctcgg ttcagggaaa cagcgggagg agaacatcga aaaaatcaag  1500
aatctcctcg actctgtctt gaacttggaa cgctttctga aaccactcta cttggagaaa  1560
gagaagatgc gtccgaaagc ggctaactta aataaagact tttgcgagag ttttgatcca  1620
ttgtacgaga agtttgaaaac atttttttaaa ctgtataaca aggtacgtaa ttatgctacg  1680
aagaagccgt actctaagga taagtttaag attaatttcg acacagcgac cctcttgtac  1740
ggttggtctt tagataaaga gaccgcgaac ctctcggtta tcttccggaa gcgtgaaaaa  1800
ttctaccttg ggatcatcaa tcgctacaac agtcaaatct tcaattacaa aatcgcaggc  1860
agcgaatccg agaaggggct ggagcgtaaa cggagttac aacagaaagt ccttgcagaa  1920
gaaggggaag attattttga gaaaatggtg taccaccttc ttttgggtgc gagtaagaca  1980
atcccgaaat gtagcacaca gcttaaggag gtgaaagcgc atttccagaa atcgtcggag  2040
gattacatca tccaatcaaa gtctttcgcc aaaagtctga cactcaccaa agaaattttt  2100
gacctcaata atctgcgtta caacaccgag acggggaata tcagttcaga actttcggat  2160
acgtacccga agaaattcca gaaaggttac ctgactcaaa caggggacgt ttctggttat  2220
aaaacagccc tccacaaatg gattgatttc tgtaaggaat tcttcgttg ttaccggaat  2280
accgaaatct ttacattcca ttttaaggac actaaggaat atgagagtct ggacgagttt  2340
ttaaaggaag tagattctag tggttatgag atttcttttcg ataagatcaa agcgtcctat  2400
attaatgaga aagtgaacgc cggcaattta tatctttttg agatctataa taaggatttt  2460
agtgaatatt cgaagggcaa acctaatctg catacaatct attggaaatc gttattcgaa  2520
acccagaatt tactggataa aactgccaaa ttaaatggca agcagagat ttttttccgc  2580
cctcgttcga ttaaacacaa cgacaaaatc atccaccgcc caggcgaaac cttaaaaaat  2640
aagaatccat taaatgaaaa gccttcctca cgcttcgact acgacatcac aaaggaccgt  2700
cgttttacta aggataagtt ttttctgcat tgtccaatta ccctgaattt caagcaagac  2760
aagccggttc gctttaatga acaggtgaat ttatatctta aggataaccc tgacgttaac  2820
attattggta ttgatcgtgg ggagcggcat ctgctgtatt acacactgat taatcagaac  2880
ggggaaattc ttcaacaagg ttctctgaac cgtatcggtg aagaggaatc ccggcctaca  2940
gactatcatc ggctgttaga cgaacgggaa aaacagcgtc agcaggcgcg ggagacttgg  3000
aaaagccgttg aagggattaa ggatttgaaa gccggctatt tgagtcgcgt cgtccacaaa  3060
ttagcagggc tgatggtaca gaacaatgcc atcgtagtgt tggaggatct taataagggg  3120
ttcaagcggg gtcgttttgc tgttgaaaag caggtgtacc agaatttcga gaaagctctt  3180
attcaaaaac ttaactatct ggttttcaaa gaagttaact ccaaggacgc accaggtcac  3240
tatcttaagg cgtaccagct tactgcgccg ttcatcagtt tcgagaagct cggcacgcag  3300
tcgggggttcc ttttttatgt gcgcgcttgg aacacctcca agatcgatcc tgctacaggt  3360
ttcacggatc agattaagcc gaaatacaag aaccaaaagc gacaaaaga tttcatgtca  3420
agcttcgact ctgttcgtta caatcggaag gagaactatt tcgagttcga agccgacttc  3480
gaaaaactgg cccaaaaacc gaaaggccgt acacgctgga caatttgttc ctacgggcaa  3540
gagcgttatt cgtactcacc aaaagagcgg aagttcgtta acacaatgt cacgcaaaat  3600
ttagccgaat tgttcaactc cgaaggtatc agcttcgact caggcagtg tttcaaggac  3660
gagattttga aagtcgagga cgcgtcgttt tttaaatcca ttattttaa tcttcgcctc  3720
ctgttgaagt tgcggcatac gtgcaaaaat gccgagatcg aacgggattt tatcatcagc  3780
ccggtaaagg caacaactc aagcttctt gactccggga tcgccgaaca agaaaatatt  3840
acttcgatcc ctcaaaacgc agacgcaaac ggtgcatata atatcgcctt gaaaggtttg  3900
atgaatcttc acaatatctc aaaggacggt aaggctaagt tgattaagga cgaagattgg  3960
atcgaatttg tacaaaaacg taaatttggc gccgccggga ggcatgttta cggcaaaaag  4020
gccgcccagg caaaaagaa aaaggctagc ggcagcggcg ccggatcccc aaagaagaaa  4080
aggaaggttg aagaccccaa gaaaaagagg aaggtgtgat aa                     4122
```

| SEQ ID NO: 23 | moltype = DNA length = 4122 |
| --- | --- |
| FEATURE | Location/Qualifiers |

| misc_feature | 1..4122 |
| --- | --- |
| | note = Description of Artificial Sequence: Synthetic polynucleotide |
| source | 1..4122 |
| | mol_type = other DNA |
| | organism = synthetic construct |

SEQUENCE: 23

```
atgggccacc atcatcatca tcatagcagc ggcctggtgc cgcgcggcag cggtaccatg   60
aaggagttta ccaatcaata ttcgttgaca aaaaccttac gttttgagtt acgtccagta  120
ggggagactg ccgaaaagat tgaggatttc aagagcgggg gtctgaagca aacggtggaa  180
aaagaccgtg aacgcactga agcttacaag cagcttaagg aggtgattga tagctaccat  240
cgggacttta ttgaacaggc cttcgcgcgt caacagactc tttcggaaga agattttaag  300
caaacgtacc agttatacaa agaggcccag aaagaaaagg acggggagac tctgaccaaa  360
cagtatgagc atcttcgcaa aaagatcgcg gctatgttct caaaggccac caaagagtgg  420
gcagttatgg gcgagaacaa tgagttgatc ggtaaaaata agaaagcaa gttatatcag  480
tggttagaaa aaaattaccg tgctggtcgc attgagaaag aggaattcga ccataatgcc  540
gggttaatcg agtacttcga gaagttctca acttacttcg tcgggtttga taaaaaccgc  600
gctaacatgt atagtaagga ggccaaggcc accgccattt ccttccggac catcaatgaa  660
aacatggtga agcatttcga caactgtcag cggttggaga aaatcaaaag caagtatcct  720
gatttggcgg aagagttgaa ggattttgaa gaattttta agccaagcta tttcatcaac  780
tgtatgaatc agtctgggat cgactattat aacatcagcg ccattggtgg gaaagacgaa  840
aaggaccaaa aggcgaatat gaagatcaat ctttttacc aaaaaaacca cctcaaggag  900
tctgacaagc ctccattctt tgcaaaactc tataaacaaa ttctctcgga ccggaaaaaa  960
tctgtagtga tcgatgaatt cgaaaaagat tccgagttga ccgaagcgct taagaatgtc 1020
ttttccaaag atggcttaat caatgaagag ttttttacta agttgaagtc cgcttttgaa 1080
aattttatgc tgcctgaata tcaagggcaa ttgtacttca gtaacgcttt cctgacaaaa 1140
atcagcgcga acatttgggg ttccgggtcc tgggggatta ttaaggatgc agtgacccaa 1200
gccgcagaga acaattttac acgcaagagt gataaggaaa aatatgctaa gaaagatttt 1260
tacagtatcg cggaattaca acaggctatc gatgaatata ttcctacctt agagaatggg 1320
gtacagaccg cctctcttat cgagtatttc cgcaaaatga actacaagcc tcgtggttca 1380
gaggaggatg ctggccttat cgaggagatt aataataatc tgcgtcaagc cggtatcgtg 1440
ctcaaccagg cggagctggg ctcgggtaag cagcgcgaag aaaatattga gaagattaag 1500
aatcttttgg actcggtgct gaacttggag cgttttctta accgcttta tctggaaaag 1560
gagaaaatgc ggcctaaagc ggcaaacctg aacaaagatt tctgtgagag ttttgaccca 1620
ctgtatgaga agctgaagac gttctttaag ctctacaaca aggtgcgcaa ttatgcgacc 1680
aagaaaccgt attcgaaaga taattcaaa attaattttg acacagccac gcttctctac 1740
gggtggtctt tggataagga cggccaac ttatcgtga tcttccgtaa acgggaaaaa 1800
ttctatcttg gtattatcaa tcggtacaac tcccaaattt ttaattataa gatcgcaggc 1860
agcagtctg aaaaaggcct ggagcgcaaa cgctctttac aacagaaggt ccttgcggag 1920
gagggcgagg actacttcga gaaaatggtt taccatctgc tgcttgggc atccaagacc 1980
atcccaaagt gttccaccca gcttaaggag gtcaaagctc acttccaaaa aagctcggaa 2040
gattacatta tccagagcaa atcgttcgcc aaatcattga cattgacaaa ggaaatcttc 2100
gaccttaata acctccggta taatactgaa actggtgaaa tttcttccga actcagcgac 2160
acataccga aaaagttcca aaggggtac ctgacccaga ctggcgacgt ctctggctac 2220
aaaacggcat acacaagtg gatcgatttc tgtaaagagt ttcttcgctg ttaccgcaac 2280
acagaaattt tcaccttcca tttcaaagac acaaggagt atgagtctct ggacgagttt 2340
ttaaaggaag tggacagcag cggctacgaa atctccttcg ataagatcaa ggctagttat 2400
attaatgaga aggtcaatgc aggtgagttg tacctgtttg aaatttataa caaagatttt 2460
tctgaatatt caaagggcaa accgaacctc cacacgattt attggaagtc gcttttcgag 2520
acgcagaatt tgttggacaa aactgctaag ttgaacggga agcagaaaat ttcttccgt 2580
ccgcgttcaa ttaagcacaa cgacaaaatt atccaccgag ccggtgaaac actcaagaat 2640
aagaacccgc ttaatgaaaa gccttcctct cgtttcgatt atgacattac taaagaccgg 2700
cggtttacga aggacaagtt ctttcttcac tgcccaatca cgctcaactt taagcaagat 2760
aagccggttc gtttcaatga acaagtcaac ttatacctga aggataatcc ggacgtgaac 2820
attattggga ttgatcgcgg ggagcgtcat ctcttatact atacattaat taaccaaac 2880
ggcgaaatct tgcagcaagg ttcgctgaat cgcatcgggg aagaagagtc tcgcccgact 2940
gattaccatc gtcttcttga cgagcgggag aaacaacggc agcaggcgcg cgaaacctgg 3000
aaggccgtcg aagggatcaa ggatttgaaa gctggctatc tgagtcgggt ggtgcacaaa 3060
cttgcaggtt tgatggtcca aaacaacgct atcggtgtc tcgaagacct taataagggg 3120
tttaaacgtg ggcggttcgc ggtagagaag caggtgtac agaacttcga aaaagcactg 3180
attcagaagt taaattacct ggtatttaaa gaggtgaatt ccaaggatgc cccaggtcat 3240
tacctgaagg cttaccaatt gacagcgccg ttcattcctt tcgagaaact cgggacgcag 3300
tcaggcttcc tcttctatgt acgcgcgtgg aacacgtcaa aaatcgaccc agctacaggg 3360
tttaccgacc aaattaaacc aaagtacaag aaccagaaac aagcaaaaga tttcatgtct 3420
tcctttgact ccgttcgtta caatcgcaag gaaaactatt tcgagttcga ggctgatttt 3480
gagaaactgg cccaaaaacc gaaaggtcgc actcgttgga cgatttgctc gtacggttcaa 3540
gagcgctata gctattcacc aaaggagcgg aagttcgtaa agcacaatgt gacgcagaat 3600
ttggccgagc ttttaactc ggagggtatc tctttcgata gtggtcaatg tttcaaggac 3660
gagatcttaa aggtcgaaga cgctagtttc ttcaagtcca tcatcttcaa tttacgtcta 3720
ctcctcaaat tgcgccatac gtgcaaaat gccgaaatcg agcgcgactt cattatttca 3780
cctgttaaag gaacaactc ctcttttctt gatagtcgga ttgctgaaca agaaaacatt 3840
acaagtattc cgcagaacgc cgatgcaaac ggggcgtata atatcgcctt aaaagggttg 3900
atgaacttac ataacattc gaaagacggg aaggctaaac ttattaagga cgaagactgg 3960
atcgagtttg tacagaaacg taagtcggc gcgcaaaagc cttgctgccc cacgaaaaag 4020
gccggccagg caaaaaagaa aaggctagc ggcagcggcg ccggatcccc aaagaagaaa 4080
aggaaggttg aagaccccaa gaaaaagagg aaggtgtgat aa                    4122
```

| SEQ ID NO: 24 | moltype = DNA length = 4122 |
| --- | --- |
| FEATURE | Location/Qualifiers |

| misc_feature | 1..4122 |
| | note = Description of Artificial Sequence: Synthetic polynucleotide |
| source | 1..4122 |
| | mol_type = other DNA |
| | organism = synthetic construct |

SEQUENCE: 24

```
atgggccacc atcatcatca tcatagcagc ggcctggtgc cgcgcggcag cggtaccatg    60
aaggagttta ctaatcaata cagcctcact aaaactctcc ggtttgagct ccggcctgta   120
ggcgagaccg cagaaaaaat cgaagatttc aagtctggcg ggctcaaaca gacggttgaa   180
aaagatcgcg agcgcactga ggcctacaaa cagttaaaag aggtgattga ctcctaccat   240
cgggatttta tcgagcaagc cttcgctcgg caacagactt tgtccgaaga ggattttaag   300
cagacgtacc agctctataa agaagcacaa aaggaaaagg atggtgagac cttgacaaaa   360
cagtacgaac atttacggaa gaagatcgcg gcgatgttta gcaaggccac taaggagtgg   420
gccgtaatgg gcgagaataa tgaacttatt gggaagaaca aagaaagtaa gctctaccaa   480
tggctcgaga aaaactatcg cgcaggtcgg attgaaaaag aggagtttga ccataatgcc   540
ggtttaatcg agtattttga gaattctcg acttactttg tgggtttcga taagaaccgt   600
gcgaacatgt actcaaagga agcaaaggct actgcaatct cgtttcggac aatcaatgaa   660
aacatggtaa acattttga caattgccaa cgcctcgaga agattaagtc caagtaccct   720
gatttggccg aggagcttaa agatttcgag gagttcttca aacctagcta ctttatcaac   780
tgtatgaatc aatcagggat tgattattat aacatctccg ccattggtgg taaagacgag   840
aaagaccaga aggctaatat gaaaatcaat ctgtttacgc aagaaccaa tcttaaggagt   900
tccgataaac caccttttctt cgccaaatta tataagcaaa tcttaagcga tcgtgagaaa   960
tcagtagtca tcgatgagtt cgagaaggac agtgagctga ccgaggcgct caaaaacgtg  1020
ttctccaagg atgggttaat caatgaggag tttttttacca agctcaagtc tgcgttggaa  1080
aattttatgc tcccggagta tcaaggccag ttatacatcc gtaacgcgtt tttaaccaag  1140
atctcggcta acatttgggg ttctggtagc tggggtatta tcaaggatgc ggtgacacag  1200
gctgcggaaa ataattttac acgtaagagt gacaaagaaa aatatgcgaa aaaggatttt  1260
tactcaattg ctgagctgca acaagctatt gatgaataca ttcctactct tgagaacggc  1320
gtgcagaacg cgtctttaat tgagtatttc cgcaaaatga actataaacc gctggctca   1380
gaagaggacg caggcttaat tgaagaaatc aataataact tgcgccaagc gggcattgtt  1440
cttaatcaag ccgagcttgg cagcgggaag cagcgtgagg agaacattga gaaaatcaaa  1500
aatttgctgg atagtgtatt gaatttggaa cgctttctga gccgctgta tttggagaaa  1560
gaaaaaatgc gtccaaaggc tgcgaacctg aataaggatt tttgcgagag cttttgacccg  1620
ctctacgaga agcttaaaac gttcttcaag ctgtataaca aggtacggaa ttacgcaact  1680
aaaaaaacctt atagcaaaga caagttcaag atcaactttg acactgccac attactctat  1740
ggttggagtc ttgataagga aactgcaaac ttgtctgtca ttttttcgtaa acgcgagaag  1800
ttttatctgg gcatcattaa ccggtacaac tcacaaatct ttaactacaa gatcgccggc  1860
agcgaatcgg aaaaaggtct ggagcgtaaa ccagtcttc acagaaaagt gttggccgaa  1920
gagggcgagg attacttcga gaaatggtg taccatcttt tattaggcgc cagcaagacg  1980
attccgaaat gtagtacgca actcaaagag gtaaaggccc actttcaaaa atcgagtgag  2040
gactacatca ttcaatccaa gagtttgcgc aagagcttga cattaacaaa ggaaatcttt  2100
gacctgaata acttgcgcta caataccgag actggcagga tttccagtga gctgtcggaa  2160
acatatccga aaaaattcca gaaggggtat ctgacgcaaa cggggacgt ctcagggtat  2220
aagaccgccc tccacaagtg gattgatttt gcaaggagt ccttgcgttg ttaccgtaac  2280
acagaaattt tcacatttca ctttaaagat actaaggaat acgagtccct ggatgagttt  2340
ttgaaagaag tagatagttc cgggtatgaa atctcatttg ataagattaa ggcatcatat  2400
attaatgaga aagttaacgc cggcgagttg tatttatttg aaatttacaa taaggacttt  2460
agtgagtata gcaaggggaa acctaattta catcgatttt attggaaaag tttgtttgaa  2520
acccaaaacc tcctggataa gaccgccaag ttgaacggca aggcggaaat tttctttcgt  2580
ccacgtagca ttaaacataa tgacaaaatc attcaccgtg cgggcgagac cttgaaaaac  2640
aaaaatccat tgaatgaaaa acctagctcc cgcttcgact acgacattac taaagaccgg  2700
cggttcacaa aagataagtt tttcttacat tgccctatca cattaaattt taagcaggac  2760
aagccggtcc gtttcaacga gcaagttaac ttgtacctta agacaatcc ggatgtaaac  2820
atcattggta tcgatcgcgg cgaacgccac actgtctact acaccctcat taatcagaac  2880
ggtgagatcc tccaacaggg gtctctgaat cgcattgggg aggaggaatc acggccgact  2940
gactaccacc ggctcttaga cgaacgggaa aaacaacgtc agcaggcgcg ggagacatgg  3000
aaagccgtag agggtatcaa ggatcttaag gcaggctatc ttagccgggt tgtacataaa  3060
ttggctggtc tgatggtcca aaacaacgct atcgttgtac ttgaagatct taacaaaggg  3120
ttcaagcgcg gccgtttcgc cgtagaaaaa caagtatacc aaaacttcga gaaggcactt  3180
attcaaaagc tgaactattt agttttcaag gaggtcaact cgaaagacgc accaggtcat  3240
tatcttaagg cctatcaact caccgcgcca tttattcgt tcgagaagct gggcacgcag  3300
agtgggtttt tgtttatgt gcgtgcgtgg aatacgtcga aatcgatcc ggcgacaggc  3360
ttcaccgatc aaattaagcc gaaatacaaa atcagaaac aagcgaaaca ctttatgtca  3420
tcctttgatt cagtccggta caatcggaaa gagaactatt ttgaatttga gcgggacttc  3480
gagaaactcg cacaaaagcc aaagggccgc acgcggtgga ccatttgcag ctatggtcaa  3540
gagcgctata gttacagtcc gaaggaacgg aagttcgtca acacaacgt cacgcagaac  3600
ttagcggaac tcttcaattc tgaagggatc tcgtttgact cggggcaatg ttttaaggat  3660
gagatcctca aagttgagga tgcgagcttc ttcaagagta ttatttttcaa tttacgttta  3720
cttcttaagc tgcgtcacac atgcaaaaat gcagaaattg agcgtgactt catcatttca  3780
cctgttaaag caacaactc cagttttttt gactctcgta ttgccgagca agaaacatt   3840
acctcaatcc ctcaaaacgc ggacgctaat ggcgcgtaca acatcgcatt aaagggcctt  3900
atgaatcttc ataacatttc taaggatggg aaggcgaaac ttatcaagga tgaagattgg  3960
attgagtttg tacaaaagcg taagttcggc tgcgcaaagg cgcggccggc cacgaaaaag  4020
gccggccagg caaaaaagaa aaaggctagc ggcagcggcg ccggatcccc aaagaagaaa  4080
aggaaggttg aagaccccaa gaaaaagagg aaggtgtgat aa                     4122
```

SEQ ID NO: 25   moltype = DNA   length = 4122
FEATURE         Location/Qualifiers

| | |
|---|---|
| misc_feature | 1..4122<br>note = Description of Artificial Sequence: Synthetic polynucleotide |
| source | 1..4122<br>mol_type = other DNA<br>organism = synthetic construct |

SEQUENCE: 25

```
atgggccacc atcatcatca tcatagcagc ggcctggtgc cgcgcggcag cggtaccatg   60
aaagaattca cgaaccagta cagcctcacg aaaactctgc gcttcgaact tcgtccagta  120
ggtgagactg ccgaaaaaat tgaggacttt aagtcaggtg ggctcaaaca aacagtagag  180
aaagaccgtg agcgcactga ggcttacaaa caactcaagg aagtaattga ctcgtaccac  240
cgcgatttca ttgagcaggc ctttgcccgt cagcaaactc tgtctgagga ggattttaag  300
caaacctacc aattgtataa agaagcgcag aaagagaaaa tggtgaaac gctgaccaag  360
cagtacgagc atttacggaa aaagatcgcg gctatgttct caaaggctac gaaggagtgg  420
gccgtgatgg gggaaaacaa cgaactcatc ggcaaaaaca aggagtcaaa gctttatcag  480
tggttagaga agaactaccg ggcgggtcgt atcgaaaaag aggaatttga ccacaacgca  540
gggcttatcg agtactttga gaattttca acgtatttcg ttggtttcga taagaatcgt  600
gcgaacatgt atagcaagga agccaaagca accgctattt cgttccggac tatcaatgaa  660
aatatggtaa agcattttga caactgccaa cgtcttgaaa agatcaaatc gaagtacccg  720
gatttggcgg aggagttgaa agacttcgag gaattcttca agccgtccta ctttatcaac  780
tgcatgaatc aatcaggcat tgactactat aacatctccg cgattggggg caaagacgag  840
aaggaccaaa aggcgaactaa gaagattaac ctgtttacac aaaaagaatca tttaaagggt  900
tcagacaagc caccttttctt tgctaagttaa tacaagcaaa ttttgagtga ccgtgaaaaa  960
tcggtagtga tcgatgagtt cgagaaagac tccgagctca ccgaggctct taaaaacgtc 1020
ttctcgaaag atggcttaat taacgaggaa ttcttcacca aattaaaatc tgcgctggaa 1080
aactttatgc tcccagaata ccaaggtcag ttatacatcc ggaatgcttt cttgactaag 1140
attagtgcga atatttgggg ttcgggttcc tgggggatta tcaaagatgc tgttacgcaa 1200
gcagctgaaa ataactttac ccgcaaaagt gataaagaaa aatacgcgaa aaagatttc 1260
tactccatcg cagaactcca gcaagcaatt gatgaataca tcccgaccct ggagaatggc 1320
gtacagatag cgagtcttat tgagtacttc cggaagatga actataagcc gcgggctca 1380
gaggaagatg ctggtctgat cgaggaaatc aataacaact gcggcaggc agggattgtt 1440
ttaaaccaag ctgaattagg tagcggcaaa cagcgtgagg agaatatcga gaaatcaaa 1500
aatttattag attccgttct caacctggaa cgttttttaa agcattgta tctcgagaag 1560
gagaagatgc gcccaaaggc ggcgaatctg aataaagatt tctgcgagag cttcgatcct 1620
ctctacgaga aactcaagac attctttaaa ttgtataaca aggtccggaa ttatgcaacc 1680
aaaaagccat attccaaaga taagttcaaa attaatttcg acaccgctac tttgttgtac 1740
gggtggagcc ttgacaaaga gaccgcgaat ctttctgtta tcttccgcaa acgggaaaag 1800
ttctatctgg gtatcatcaa ccgttacaac tcgcaaattt tcaattacaa aatcgccggg 1860
agtgaatctg aaaaaggctc tggagcgcaag cgttctcttc aacagaaagt tttagcggag 1920
gaaggcgaag attattttga aaaaatggtg taccacttac tcctgggtgc atcaaaaacg 1980
atccctaaat gcagtactca attaaggag gttaaggccc acttttcagaa gagtagcgaa 2040
gattacatta ttcaatctaa atcgttcgcc aagtctttga cacttactaa ggagatcttc 2100
gatcttaaca acctccgcta taacacggag actggcgaga tcagcagcga gctgagtgac 2160
acgtacccta aaaaattcca aaaggggtac ttgacacaaa cggggggatgt gtccggttca 2220
aaaacggctc tccacaaatg gattgacttc tgcaaggagt tcttgcggtg ctatcgcaat 2280
acggagatct tcacgttcca ctttaaggac acaaaggagt acgagagcct cgatgagttc 2340
ctgaaagaga tggactcttc gggtgtatgaa attagctcac acaaaattaa ggcctcgtac 2400
atcaatgaga aggtaaatgc cggcgaactg tatcttttg aaatctataa caaggatttc 2460
agtgagtatt ccaaggggaa accgaatctg catacgatct actggaagag tctttttgaa 2520
acccagaacc ttcttgataa gaccgcaaag ttaaacggca agccgaaaat cttctttcgc 2580
ccgcgctcaa ttaagcacaa tgacaagatt attcatcgtc ctggtgaaac attgaagaat 2640
aagaatccat tgaacgagaa gccatcgtct cggttcgatt atgacatcac caaggatcgc 2700
cgctttacga aagacaagtt ttttctccat tgtcctatca cgctgaattt caagcaggat 2760
aagcctgttc gcttcaatga gcaggtaaac ctgtatctta aggacaaccc tgatgttaat 2820
attatcggga ttgatcgcgg ggaacggcac ctgctctatt ataccttaat caatcaaaac 2880
ggggagattc ttcagcaggg gtcgttgaat cgtatcggcg aagaggaaag ccgcccgacg 2940
gactaccacc gcctcttaga cgagcgtgaa aagcagcgtc aacaggcccg cgagacctgg 3000
aaagccgtag agggtatcaa agacttaaag gcagggtatt tgtcacgtgt tgtgcataag 3060
ctcgcgggtc ttatggtgca gaataatgcc attgttgtgt tagaagatct taacaaggc 3120
tttaaacgcg gcggggttcgc tgtggagaag caagtatatc agaactttga gaagctttg 3180
attcagaaat tgaactatct tgtatttaag gaggttaatt cgaaggacgc gcctgggcac 3240
tatcttaaag catatcagct gactgcacct tttatcagct tcgagaagtt agggaccaaa 3300
agcggctttc tgttttacgt ccgcgcttgg aatacctcaa aaattgaccc tgctacaggt 3360
tttacggatc agatcaagcc aaagtacaag aatcagaagc gggcaaagga cttatgtca 3420
tctttcgaca gtgtccgcta taaccgtaaa gaaaactatt tcgagttcga agcagacttc 3480
gaaaagttgg cccagaaacc aaaggggcgc actcgttgga caatctgctc ttacgggcag 3540
gaacggtatt cttatagtcc gaaggagcgg aagtttgtca agcacaacgt cacgcagaac 3600
ctcgcagagc tgtttaacag cgaagggatt tcgtttgact cgggccagtg cttcaaagac 3660
gagatcctta aagttgagga cgctagcttc ttcaaatcga ttatcttcaa cttgcgtttg 3720
ttgcttaagt tgcgtcatac gtgcaagaat gcagagattg agcgtgattt catcatctcc 3780
ccggttaaag caacaacag ctccttcttt gactcacgta tcgccgagca agagaacatc 3840
acgtcgattc ctcagaacgc ggacgcaaat ggtgcgtaca acattgcgct taagggtctc 3900
atgaaccttc ataacatctc taaagatggt aaggcgaaac ttattaagga cgaagactgg 3960
atcgaatttg tgcaaaagcg taagtccggc gcgcaaaag ccgtgcaaaag 4020
gccggccagt caaaaagaa aaaggctagc ggcagcggcg ccggatcccc aaagaagaaa 4080
aggaaggttg aagaccccaa gaaaaagagg aaggtgtgat aa                       4122
```

| | |
|---|---|
| SEQ ID NO: 26 | moltype = DNA   length = 4122 |
| FEATURE | Location/Qualifiers |

| misc_feature | 1..4122 |
| | note = Description of Artificial Sequence: Synthetic polynucleotide |
| source | 1..4122 |
| | mol_type = other DNA |
| | organism = synthetic construct |

SEQUENCE: 26

```
atgggccacc atcatcatca tcatagcagc ggcctggtgc cgcgcggcag cggtaccatg   60
aaagaattca ctaatcagta ctccctcact aagacactgc gcttcgagct ccggccagta  120
ggtgaaaccg cggagaaaat cgaggatttc aaaagcggcg gcctcaaaca gacggtcgaa  180
aaagaccgtg aacgcaccga ggcctacaag caacttaagg aagtgattga cagttaccat  240
cgggatttta tcgaacaggc attcgcacgg caacagacgc tgtccgagga ggacttcaag  300
caaacctacc agctgtataa agaagcgcag aaagagaagg acggtgagac cttgaccaag  360
caatacgagc atctgcgcaa gaagattgcg caatgttct caaaagcaac taaggagtgg  420
gccgttatgg gcgaaaataa cgagctcatt gggaaaaaca aagaatccaa attatatcaa  480
tggttggaga aaaactatcg cgcaggccgg attgaaaaag aagaatttga tcacaacgct  540
ggtcttattg aatattttga aaaattctcc acttatttcg taggctttga caagaaccgg  600
gcgaacatgt actccaagga ggcaaaggct acggccatct cgtttcgcac cattaacgaa  660
aatatggtca acatttcga taactgccag cgtctcgaaa aaatcaagtc gaaatacca  720
gacttagcag aagaactgaa ggatttcgag gagtttttca aaccaagtta ttttatcaac  780
tgcatgaacc aaagcgggat tgattattac aacatctcag cgatcggggg caaggatgaa  840
aaagatcaaa aagccaatat gaagatcaac ttgtttactc aaaaaaatca cctgaaaggt  900
tccgataaac ctccgttctt tgctaagctc tataagcaga tcttaagcga tcgtgaaaag  960
agcgtcgtaa tcgatgagtt tgaaaaggat tcggaattaa cggaagcgct gaaaaatgtt 1020
ttttcaaagg acggcctcat caatgaagaa ttctttacaa aattaaaatc ggcgttggaa 1080
aacttcatgt taccagaata tcaaggccag ctttatattc ggaatgcgtt cctgacgaag 1140
atcagtgcga atatttgggg cagcgggtcg tggggatca tcaaggatgc agttacgcaa 1200
gcagccgaga acaatttcac tcggaaaagt gataaagaga agtacgcgaa gaaagatttt 1260
tatagcatcg ctgagctgca gcaagcgatt gacgaataca tcccgacgtt agaaaacggg 1320
gttcagaatg cctcactcat tgaatatttc cgtaagatga attacaaacc acgcggcagt 1380
gaagaggacg cggggctgat tgaagaaatt aacaataatt tgcgccaagc gggtatcgtc 1440
cttaatcaag cagaacttgg gtctggtaag cagcgtgaag aaaacattga gaagatcaag 1500
aatcttctgg attcagtttt gaaccttgaa cgtttttttga aaccactta tctggagaag 1560
gaaaagatgc gtccgaaagc ggcgaacctc aacaaagact tctgcgagtc gttcgacccg 1620
ctctacgaga aattgaagac cttcttcaag ttgtacaata aggtccgtaa ttacgcgact 1680
aaaaaaccgt attccaaaga taatttaag atcaactttg acaccgcgac cctcctgtat 1740
ggctggagtc tggataagga gaccgcgaac ctttctgtca ttttccgtaa gcgtgaaaaa 1800
ttctacctcg ggatcatcaa tcggtataat tcgcagattt caattacaa gattgcaggg 1860
tctgaaagcg aaaagggcct ggaacgtaag cgttctttgc gcaaaaagt cttagccgag 1920
gaagggagg actactttga aaagatggtg taccacccttt tattaggtgc atctaaaact 1980
attccgaaat gtagcactca gttaaaagag gttaaagctc acttttcaaaa aagtagtgaa 2040
gactatatca ttcaatccaa gtccttttgcg aagtcattga ctttaacgaa ggaaatcttc 2100
gatctcaata accttcggta caataccgaa accggcgaaa tctccagcga gcttagcgat 2160
acatatccga aaaaatttca aaaaggctat ctcacccaaa ctggcgatgt gtccggttac 2220
aagactgcat tgcacaagtg gatcgacttt tgtaaggaat tccttcggtg ttatcggaac 2280
accgagatct ttacgttcca cttcaaagat acaaaggaat atgaatcgct tgacgaattc 2340
ttaaaagaag tagattcaag cggctacgag atcagctttg ataagattaa ggccagctac 2400
atcaatgaaa aagtcaacgc aggggaatta tacctgttcg aaatttacaa taaggacttt 2460
tccgagtatt ccaaggggaa gccgaatctg catacgatct attggaaatc cctgtttgag 2520
acccagaacc tgttagacaa aacagcgaag ctgaatggta aggcggaaat tttttttcgg 2580
cctcgtagta ttaaacacaa cgataaaatc attcatcgtt ctggcgagac tctgaaaaat 2640
aaaaaccgt taaacgaaaa gcctagctct cgttttgact acgatatcac aaaggaccgc 2700
cgctttacta agacaaatt cttcctccac tgcccgatta ccttaaactt taagcaggac 2760
aagcctgtgc gttttaacga acaagtaaat ctctacctga agataatcc ggacgtaaac 2820
atcattggca tcgatcgcgg cgagcgccat ttgctttatt acacgctgat taatcagaac 2880
ggggagatct tgcaacaggg gtcacttaat cggatcggcg aggaagaatc ccgtccaaca 2940
gactaccacc ggctgcttga cgaacgggaa aaacagcgtc agcaggcccg tgagacttgg 3000
aaagcggtcg agggtatcaa ggccttaag gccggttact tgagccgggt cgtacataag 3060
cttgcaggcc tcatggtcca gaataatgca atcgtggtac tcgaggacct gaataaaggt 3120
tttaagcgcg gcgcggttcg cgttgagaaa caagtctatc aaaacttcga aaaagccctt 3180
attcaaaaat tgaattattt agtattcaaa gaggtcaact ccaaggatgc accggggcac 3240
tatcttaaag cctatcagtt aaccgcgcct tcatttcct ttgaaaaact ggggactcag 3300
agcggttct tattttacgt acgtgcgtgg aatacaagca gattgatcc tgcgaccggg 3360
ttcacggacc aaatcaagcc taaatacaaa atcaaaagc aagcaaaaga tttcatgtcg 3420
agtttcgatt ccgtacgta taatcggaag gagaattact tcgagttcga agctgacttt 3480
gaaaagcttg cacaaaagcc gaaaggccgt acccgctgga ctatctgttc gtatgggcag 3540
gagcggtata gctacagtcc taaggaacgg aaatttgtaa agcataacgt gacgcaaaat 3600
ttagcagagt tgttcaattc ggaaggcatc tcctttgatt ctggtcagtg cttcaaggat 3660
gagatcttga aggtgggagga tgctagtttc ttcaagacga tcatctttaa tctgcgtctg 3720
ttgctcaaat tacgccatac gtgcaaaat gctgaaatcg agcgtgactt tattatttca 3780
ccggtgaagg gtaacaacag tagttttttt gattcacgta tcgccgaaca ggagaacatc 3840
acgtcaatcc cacaaaacgc ggacgcgaac ggggcttaca atatcgcgct taaggggctg 3900
atgaacttgc ataacatctc caaggatggt aaggcaaagt tgatcaaaga cgaagactgg 3960
atcagtttg ttcaaaaacg caattcggc gcgcaaaaga gcgcaaaaag 4020
gccggccagt caaaaaagaa aaaggctagc ggcagcggcg ccggatcccc aaagaagaaa 4080
aggaaggttg aagaccccaa gaaaaagagg aaggtgtgat aa                     4122
```

| SEQ ID NO: 27 | moltype = AA length = 1250 |
| FEATURE | Location/Qualifiers |

```
REGION                    1..1250
                          note = Description of Artificial Sequence: Synthetic
                          Cas12a/Cpf1 [Barnesiella sp. An22] sequence
source                    1..1250
                          mol_type = protein
                          organism = synthetic construct
SEQUENCE: 27
MKTLSDFTNL FPLSKTLRFK LIPIGNTLKN IEASGILDED RHRAESYVKV KAIIDEYHKA    60
FIDRVLSDTC LQTESIGKHN SLEEFFFYYQ IGAKSEQQKK TFKKIQDALR KQIADSLTKD   120
KHFSRIDKKE LIQEDLIQFV RDGEDAAEKT SLISEFQNFT VYFTGFHENR QNMYSPDEKS   180
TAIAYRLINE NLPKFVDNMK VFDRIAASEL ASCFDELYHN FEEYLQVERL HDIFSLDYFN   240
LLLTQKHIDV YNALIGGKAT ETGEKIKGLN EYINLYNQRH KQEKLPKFKM LFKQILTDRE   300
AISWLPRQFD DNSQLLSAIE QCYNHLSTYT LKDGSLKYLL ENLHTYDTEK IFIRNDSLLT   360
EISQRHYGSW SILPEAIKRH LERANPQKRR ETYEAYQSRI EKAFKAYPGF SIAFLNGCLT   420
ETGKESPSIE SYFESLGAVE TETSQQENWF ARIANAYTDF REMQNRLHAT DVPLAQDAEA   480
VARIKKLLDA LKGLQLFIKP LLDTGEEAEK DERFYGDFTE FWNELDTITP LYNMVRNYLT   540
RKPYSEEKIK LNFQNPTLLN GWDLNKEVDN TSVILRRNGN YYLAIMHRNH RRVFSQYPGT   600
ERGDCYEKME YKLLPGANKM LPKVFFSKSR IDEFNPSEEL LARYQQGTHK KGENFNLHDC   660
HALIDFFKDS IEKHEEWRNF HFKFSDTSSY TDMSGFYREI ETQGYKLSFV PVACEYIDEL   720
VRDGKIFLFQ IYNKDFSTYS KGKPNMHTLY WEMLFDERNL MNVVYKLNGQ AEIFFRKASL   780
SARHPEHPAG LPIKKKQAPT EESCFPYDLI KNKRYTVDQF QFHVPITINF KATGTSNINP   840
SVTDYIRTAD DLHIIGIDRG ERHLLYLVVI DSQGRICEQF SLNEIVTQYQ GHQYRTDYHA   900
LLQKKEDERQ KARQSWQSIE NIKELKEGYL SQVVHKVSEL MIKYKAIVVL EDLNAGFKRS   960
RQKVEKQVYQ KFEKMLIDKL NYLVFKTAEA DQPGGLLHAY QLTNKFESFK KMGKQSGFLF  1020
YIPAWNTSKI DPTTGFVNLF DTRYENVDKS RAFFGKFDSI RYRADKGTFE WTFDYNNFHK  1080
KAEGTRSSWC LSSHGNRVRT FRNPAKNNQW DNEEIDLTQA FRDLFEAWGI EITSNLKEAI  1140
CNQSEKKFFS ELFELFKLMI QLRNSVTGTN IDYMVSPVEN HYGTFFDSRT CDSSLPANAD  1200
ANGAYNIARK GLMLARRIQA TPENDPISLT LSNKEWLRFA QGLDETTTYE             1250

SEQ ID NO: 28             moltype = DNA  length = 3753
FEATURE                   Location/Qualifiers
misc_feature              1..3753
                          note = Description of Artificial Sequence: Synthetic
                          Cas12a/Cpf1 [Barnesiella sp. An22] sequence
source                    1..3753
                          mol_type = other DNA
                          organism = synthetic construct
SEQUENCE: 28
atgaaaacat tatctgattt tacaaattta ttccctctct caaaaacgct acggttcaaa    60
ctgataccca taggtaacac cttgaagaac atcgaagcca gcgggatact cgacgaagac   120
cggcaccggg ccgaaagcta cgtaaaagta aagccatca tcgacgaata ccacaaagca   180
tttatcgacc gcgttctctc cgacacctgc ttgcaaaccg aaagcatagg gaaacacaac   240
tcgctgaag agttttttt ctactatcaa atcggggcaa agagcgagca acagaagaaa   300
actttcaaaa aaatacagga cgctctcgcg aaacagattg ccgacagtct caccaaagac   360
aaacattttt cccgcatcga taaaaaagag ttgatacagg aagaccttat ccaattcgtc   420
cgggacgggg aagacgctgc cgagaaaacg agtctgattt ctgaatttca aaactttacc   480
gtctacttta ccgggttcca cgagaaccgc caaaacatgt attcgccgga cgagaaatct   540
acggctatcg cctatcggtt aatcaacgag aaccttccca aattcgtcga acatgaaa    600
gtgttcgacc ggattgcagc cagcgaattg gcctcttgtt tcgacgaact gtaccacaat   660
ttcgaagaat acctgcaagt agagcggctc acgatatct tctccctcga ctatttcaat   720
ctgttactca cccaaaaaca tatcgacgta taaacgact taatcggagg aaaagccacc   780
gaaaccggcg aaaaaatcaa aggcctcaac gagtatatca acctgtacaa tcagcgacac   840
aaacaagaaa agctgcccaa attcaagatg cttttcaagc agatattgac cgatcgcgag   900
gccatatcgt ggctcccccg gcaattcgac gacaacagcc aactgctctc ggctatcgag   960
caatgctaca atcacctctc gacctatacc ctgaaagatg ggctctgaa atatctgctc  1020
gaaaacctgc ataccacga caccgaaaaa atctttattc gcaacgactc gcttctgacc  1080
gaaatatcgc aacggcacta tggcagctgg agcatactgc ccgaagccat caagcgccac  1140
ctcgaaagag ccaatcctca aaagcggcgc gaaacatacg aagcatacca aagccgcatc  1200
gaaaaagcct tcaaagctta tcccggcttc tcgattgcct ttctgaacgg ttgtctgacc  1260
gaaaccggca aagaatcgcc ctcgatcgaa agttattcgg agagcctggg ggctgtcgag  1320
accgaaacct cgcagcaaga aaactggttt gcccgcatag ccaatgccta taccgatttc  1380
cgggagatgc agaatcgcct ccatgcaaca gatgtccccc tggcccaaga tgccgaagcc  1440
gtggcacgca tcaagaaact actcgatgcg ctcaaagggc tgcaactgtt tatcaagcct  1500
ctgctcgaca cgggcgaaga ggccgaaaaa gacgaacgct tctatggcga tttcaccgaa  1560
ttttggaacg aactcgacac cattactccc ttgtacaaca tggtgcgtaa ctaccttacc  1620
cgcaaaccct actcgaaga aaaatcaaa ctcaactttc agaatcccac actgctcaac  1680
ggctgggatc tgaacaagga ggtcgacaac acctcggtta tcctgcggcg taacggccgg  1740
tactacctgg ccatcatgca ccggaatcac cgtcgggtct ctgccggagc ccaacaaatg  1800
gaacgaggcg actgctatga aaagatggag tataaactac tgcccggagc caacaaaatg  1860
ctgcccaaag ttttcttctc caaatcgcga atcgacgaat tcaatcccag cgaagaacta  1920
ttggcccgtt accaacaagg cactcacaag aaaggcgaga atttcaacct gcacgactgc  1980
catgccctca tcgatttctt caagactcg atcgagaagc acgaggagtg cgcaatttc  2040
catttcaaat tctccgacac ctcctcttat accgacatga gcggcttcta ccgcgaaatc  2100
gaaaccaag gttacaaact tcattcgta cccgtacgtg cgaatacat cgaactgtcg  2160
gtgcgcgacg gtaaaatatt tctgttccag atatacaaca aagtttctc gacatacagc  2220
aaagggaagc caacatgca cacgttgtac tgggaaatgc tcttcgacga acgtaacctg  2280
atgaatgttg tctacaaact caacgggcaa gccgaaatat tcttccgcaa agccagcctc  2340
tcggcccggc atcccgagca cccggccgga ttacccatca gaaaaaaca agccccccaca  2400
gaagagagtt gtttcccta cgacctaatc aaaaacaaac ggtatacggt cgaccaattt  2460
```

```
cagtttcatg ttcccatcac aatcaatttc aaagcaaccg gcacctccaa catcaaccce  2520
tcggtaaccg actatatacg cacagccgac gacctgcaca tcatcgggat agaccgcggg  2580
gaacggcatc tgctctacct cgtggtaatc gacagccaag ggcgcatttg cgaacaattc  2640
tccctgaacg agattgtcac tcaatatcag ggacatcaat atagaaccga ctatcatgcc  2700
ctgctgcaaa agaaagaaga tgaacgacaa aaggcccgac aaagctggca aagcatcgaa  2760
aacatcaagg agctcaaaga agggtatttg agccaggtcg ttcacaaggt ctcggaactg  2820
atgataaaat acaaggccat cgtggttctc gaagacttga atgccggctt caaacgcagc  2880
cgacagaagg tagaaaaaca agtctaccaa aaatttgaaa agatgttgat tgacaagctc  2940
aactatctgg tattcaaaac agccgaagcc gaccaaccgg gcggactgct tcatgcctat  3000
caactgacca acaaattcga aagtttcaaa aaaatgggaa aacaaagcgg cttcctcttc  3060
tatatcccgg cctggaacac cagcaagata gacccgacaa ccggttttgt caatctgttt  3120
gataccegct atgaaaacgt agacaagagc cgggccttct cggcaaatt cgactcgatt  3180
cgttaccgcg ccgacaaagg gacttttgag tggacattcg actacaacaa tttccataaa  3240
aaggccgagg gaactcgctc atcgtggtgc ctgagctctc aagcggacaa tgtgcgaaca  3300
ttccggaacc ccgccaaaaa caaccaatgg gacaacgaag agattgacct cacccaagct  3360
ttccgagacc ttttcgaagc gtggggcatc gagataacct ccaacttgaa agaagctatc  3420
tgcaaccagt cggagaaaaa gttcttctcc gaactgttcg aactcttcaa gctgatgatt  3480
cagttgcgaa atagcgtgac aggcaccaac atcgactaca tggtgtcgcc cgtagaaaac  3540
cattacggga cattttcga cagccgcacc tgcgacagct ccctgccggc caatgccgat  3600
gccaacgggg catacaacat cgccgcaaaa gggctcatgc ttgcccgacg catacaagcg  3660
actcccgaaa acgaccccat atccctaacc ctctccaaca aagaatggct gcggtttgca  3720
caaggcttgg acgaaacgac gacctatgaa tga                                3753
```

SEQ ID NO: 29          moltype = AA  length = 1312
FEATURE                 Location/Qualifiers
REGION                  1..1312
                        note = Description of Artificial Sequence: Synthetic
                        polypeptide
source                  1..1312
                        mol_type = protein
                        organism = synthetic construct

```
SEQUENCE: 29
MGHHHHHHSS GLVPRGSLQM KTLSDFTNLF PLSKTLRFKL IPIGNTLKNI EASGILDEDR   60
HRAESYVKVK AIIDEYHKAF IDRVLSDTCL QTESIGKHNS LEEFFFYYQI GAKSEQQKKT  120
FKKIQDALRK QIADSLTKDK HFSRIDKKEL IQEDLIQFVR DGEDAAEKTS LISEFQNFTV  180
YFTGFHENRQ NMYSPDEKST AIAYRLINEN LPKFVDNMKV FDRIAASELA SCFDELYHNF  240
EEYLQVERLH DIFSLDYFNL LLTQKHIDVY NALIGGKATE TGEKIKGLNE YINLYNQRHK  300
QEKLPKFKML FKQILTDREA ISWLPRQFDD NSQLLSAIEQ CYNHLSTYTL KDGSLKYLLE  360
NLHTYDTEKI FIRNDSLLTE ISQRHYGSWS ILPEAIKRHL ERANPQKRRE TYEAYQSRIE  420
KAFKAYPGFS IAFLNGCLTE TGKESPSIES YFESLGAVET ETSQQENWFA RIANAYTDFR  480
EMQNRLHATD VPLAQDAEAV ARIKKLLDAL KGLQLFIKPL LDTGEEAEKD ERFYGDFTEF  540
WNELDTITPL YNMVRNYLTR KPYSEEKIKL NFQNPTLLNG WDLNKEVDNT SVILRRNGRY  600
YLAIMHRNHR RVFSQYPGTE RGDCYEKMEY KLLPGANKML PKVFFSKSRI DEFNPSEELL  660
ARYQQGTHKK GENFNLHDCH ALIDFFKDSI EKHEEWRNPH FKFSDTSSYT DMSGFYREIE  720
TQGYKLSFVP VACEYIDELV RDGKIFLFQI YNKDFSTYSK GKPNMHTLYW EMLFDERNLM  780
NVVYKLNGQA EIFFRKASLS ARHPEHPAGL PIKKKQAPTE ESCFPYDLIK NKRYTVDQFQ  840
FHVPITINFK ATGTSNINPS VTDYIRTADD LHIIGDRGE RHLLYLVVID SQGRICEQFS  900
LNEIVTQYQG HQYRTDYHAL LQKKEDERQK ARQSWQSIEN IKELKEGYLS QVVHKVSELM  960
IKYKAIVVLE DLNAGFKRSR QKVEKQVYQK FEKMLIDKLN YLVFKTAEAD QPGGLLHAYQ 1020
LTNKFESFKK MGKQSGFLFY IPAWNTSKID PTTGFVNLFD TRYENVDKSR AFFGKFDSIR 1080
YRADKGTFEW TFDYNNFHKK AEGTRSSWCL SSHGNRVRTF RNPAKNNQWD NEEIDLTQAF 1140
RDLFEAWGIE ITSNLKEAIC NQSEKKFFSE LFELFKLMIQ LRNSVTGTNI DYMVSPVENH 1200
YGTFFDSRTC DSSLPANADA NGAYNIARKG LMLARRIQAT PENDPISLTL SNKEWLRFAQ 1260
GLDETTTYEA AAKRPAATKK AGQAKKKKAS GSGAGSPKKK RKVEDPKKKR KV         1312
```

SEQ ID NO: 30          moltype = DNA  length = 3942
FEATURE                 Location/Qualifiers
misc_feature        1..3942
                        note = Description of Artificial Sequence: Synthetic
                        polynucleotide
source                  1..3942
                        mol_type = other DNA
                        organism = synthetic construct

```
SEQUENCE: 30
atgggccacc atcatcatca tcatagcagc ggcctggtgc cgcgcggcag cctgcagatg   60
aagaccttgt ctgattttac caatctgttc ccttttatcta agactctccg tttcaagctg  120
attccaatcg gcaacacgct caagaacatt gaagctagtg gcatccttga cgaggatcgc  180
caccgcgcgg agtcctatgt caaggtcaag gccatcatcg acgaatatca taagctttcc  240
atcgatcggg tcctgtcgga tacttgcctc cagacggaat ctatcggcaa acacaacagt  300
ctcgaggaat tcttttttcta ctaccaaatt ggtgcaaaaa gtgaacagca gaaaaagacg  360
tttaaaaaga ttcaagacgc cttgcgcaaa caaatcgcag atagcctcac caaggacaaa  420
catttttcac ggattgataa aaaagaattg atccaagagg atttgatcca gtttgtgcgc  480
gatgggagg atgccgctga aaagacgtct ctgatttccg aatttcaaaa tttcacagtt  540
tattttaccg ggtttcatga gaatcgccag aacatgtaca gcccggacga gaagtccaca  600
gccatcgcat atcgcttaat taacgagaat ctcccaaaat tcgtagacaa catgaaagtt  660
tttgaccgta tcgcggcgtc cgaattggca tcgtgtttcg acgaattata ccacaacttc  720
gaggaatacc tccaagtgga gcggttacat gatatcttta gtttggacta tttcaatctg  780
cttctcacgc agaaacatat cgacgtctat aatgctctga tcggtgggaa ggcaaccgaa  840
accgggggaa agatcaaggg cttaaatgaa tacatcaatc tctacaatca acgtcacaag  900
```

```
caggaaaaac tgccaaaatt caagatgtta ttcaagcaaa ttcttaccga ccgtgaggca    960
atcagctggt tgccacgcca atttgacgat aatagtcagt tactctcagc cattgaacag   1020
tgttataacc acctttcgac ctacacactc aaggatgggt cactcaaata cctgttagaa   1080
aacctgcata catacgatac tgaaaagatc ttcatccgca atgacagttt acttacgaa    1140
atctcccaac ggcattacgg ttcgtggtcg attttaccag aagctatcaa acgtcatctc   1200
gagcgcgcga acccgcaaaa acggcgcgaa acatacgagg cctatcaatc tcgcattgag   1260
aaggcccttta aggcatatcc gggtgttttca attgctttcc tcaatgggtg tttaacagag   1320
acaggtaagg agtcgccatc catcgaaagc tattttgaaa gtctgggtgc tgtcgaaaca   1380
gagacctctc agcaggaaaa ctggtttgcc cgcatcgcaa acgcttatac ggactttcgt   1440
gaaatgcaaa atcggctgca cgccactgac gtgccgttgg ctcaagacgc tgaggcagtg   1500
gcccggatca agaagctgtt agatgcactg aaaggcctgc aattattcat taagcctctt   1560
ttggatactg gcgaagaagc agagaaagat gaacggttct atgggacttt accgaattc    1620
tggaacgagt tagacactat cacgccattg tacaatatgg tacggaacta tctcacgcgt   1680
aagccttata gtgaagaaaa aatcaagctc aatttccaga atccgacatt actgaacggt   1740
tgggatttga acaaagaggt agataataca tctgtcatcc tccgccggaa tggtcgttat   1800
tatcttgcca tcatgcaccg caaccaccgg cgtgtatttt cacagtatcc aggcacagaa   1860
cgtggcgatt gttatgagaa aatggaatat aaactgcttc cgggcgccaa caagatgctc   1920
ccaaaagtct tcttctctaa atcacgcatc gatgaattca acctagcga agaattatta    1980
gcacgttacc agcaaggtac ccacaagaag ggtgagaatt taatttaca cgactgccat    2040
gccttgattg attttttaa agactctatt gagaaacatg aagaatggcg taactttcat    2100
tttaaattta gtgatacgtc cagttacacc gacatgagcg gcttttatcg tgaaatcgaa   2160
acacaggggtt acaagttgtc attttgtgcca gtggcgttgta aatacatcga tgagttggta   2220
cgtgatggca aaatcttttt gttccagatc tataataagg acttttcgac ctactctaag   2280
ggcaagccaa atatgcacac tctttattgg gaaatgcttt tcgacgagcg gaacctgatg   2340
aacgtggtgt ataaactcaa tggccaagca gagatctttt ttcgtaaagc atcactgagc   2400
gcacgtcacc ctgagcaccc ggcagggttg ccaattaaaa aaaaacaggc cccgacggga   2460
gaatcttgtt tcccatatga tctcattaag aataagcggt atacagttga ccagtttcag   2520
tttcacgtgc caattactat taattttaaa gcaactggga cttcaaatat caacccgtcg   2580
gtcactgatt atattcgtac ggccgatgac ctccatatca ttggcattga tcgcggtgag   2640
cgccatttac tttatttagt ggtgattgac tcacaagggc gcatctgtga acagttttcc   2700
ttaaacgaga tcgtaacgca ataccaaggt caccagtacc gtacagatta tcatgctctc   2760
ttgcagaaaa aagaggatga acggcaaaaa gctcgccagt cttggcaatc gatcgaaaac   2820
atcaaggaat taaagagggg gtatctgagc caagtagtgc acaaggtttc tgaactgatg   2880
atcaaatata agcaattgt ggtgttgaaa gatttaaatg ctgggttcaa gcggagtcgg   2940
cagaaggttg aaaagcaagt gtatcaaaaa tttgagaaga tgctgatcga caaacttaac   3000
tatcttgtgt tcaagaccgc agaagctgac caacctggcg gcctcctgca cgcataccaa   3060
ttaacaaata aatttgagtc attcaagaaa atggggaagc aaagtggctt cctcttctac   3120
attcctgcat ggaacacgtc taaaatcgac ccgaccacgg gctttgtcaa cctttttgat   3180
acccggtatg agaacgtaga caaatcccgt gccttcttcg gcaaattcga tagcatccgc   3240
taccgtgcgg acaagggcac gttcgagtgg acgttcgatt ataataactt tcacaaaaag   3300
gccgaaggta cgcggtcgag ctggtgtttg tcttctcatg gtaaccgggt ccgtactttc   3360
cgcaatcctg cgaaaaacaa ccaatgggac aacgaagaga tcgacttaac acaagcgttc   3420
cgcgatctgt ttgaagcttg ggggatcgaa atcacttcga acttaaaaga ggccattttgc   3480
aaccagtctg agaagaaatt ctttttctgag cttttcgaac tgttcaaact tatgatccag   3540
ctgcggaact cagtgacagg cacgaatatc gactatatgg tgagcccagt cgagaatcac   3600
tacggcacgt tcttcgattc gcgcacatgc gattcgtctc tgccggctaa cgctgacgct   3660
aatggtgctt ataatattgc ccgtaagggg ttaatgctgg ctcgccgcat tcaggctacc   3720
cctgagaatg atccgatctc cttaacattg agcaacaaag agtggttacg ctttgcacag   3780
gggctcgatg agacaacaac ctacgaggcg ccgcaaaaa ggccggcggc cacgaaaaag   3840
gccgccagg caaaaagaa aaaggctagc ggcagcggcg ccggatcccc aaagaagaaa   3900
aggaaggttg aagaccccaa gaaaagagg aaggtgtgat aa                      3942
```

SEQ ID NO: 31              moltype = DNA   length = 3942
FEATURE                    Location/Qualifiers
misc_feature               1..3942
                           note = Description of Artificial Sequence: Synthetic
                           polynucleotide
source                     1..3942
                           mol_type = other DNA
                           organism = synthetic construct
SEQUENCE: 31

```
atgggccacc atcatcatca tcatagcagc ggcctggtgc cgcgcggcag cggtaccatg     60
aagactctga gtgacttcac gaacttgttt ccgctcagca agacattacg ttttaaatta    120
attccaattg ggaacaccct gaaaaacatt gaagcgtccg gcattttgga cgaggatcgc    180
caccgcgctg aatcctacgt caaagttaaa gcaatcatcg acgagtatca taagcatttt    240
atcgaccggg tgctctcaga cacatgctta caaacagagt ccattggcaa gcataattcg    300
ttagaggaat tcttcttcta ttatcaaatc ggcgcaaaaa gcgaacagca gaagaagaca    360
ttcaagaaga tccaagacgc tttgcgcaag caaattgctg attcacttac taaagataag    420
cacttcagcc gtattgacaa gaaggaattg atccaagaag atttaatcca atttgtgcgg    480
gacggggagg atgcggcgga gaagacctct ttaattttctg agttccaaaa ctttactgtc    540
tattttacag ggttccatga aaccggcag aacatgtaca gtccggacga gaagtctacc    600
gcgatcgcct accggttgat taatgaaaac ctgcctaagt tgtcgacaa tatgaaagta    660
tttgatcgga ttgcagcgtc ggaacttgcg tcatgtttcg atgaattgta ccataacttc    720
gaagaaatat tgcaagttga acggctccat gacatcttct ccctcgatta ttttaattta    780
ctgctgacgc agaagcatat cgatgtatat aacgctttga tcgggggaa ggccaccgaa    840
acaggtgaaa aaattaaagg cctgaacgaa tatatcaatt tgtataatca gcggcacaag    900
caggagaagt tacctaaatt taagatgctt tttaagcaaa tcctcacgga ccgggaagca    960
atttcctggt taccgcggca attcgatgac aacagccaac tccttccgc aattgagcag    1020
tgttataatc acctgagtac atatactctg aaagatgggt cattgaagta tttattggaa    1080
```

```
aatttacaca cgtacgatac agaaaagatc ttcatccgta acgacagcct cctgacggag 1140
attagtcagc gccattacgg ttcatggtcg atcttgcctg aagctattaa gcggcacctg 1200
gagcgtgcca acccacaaaa gcggcgtgaa acctatgaag catatcaatc gcgtattgag 1260
aaggctttca aggcgtatcc tggcttttcg atcgcttttt tgaacggttg cctcacagaa 1320
acgggtaagg aaagccctag cattgaatca tattttgagt cattggggcc agtcgaaaca 1380
gaaacttctc agcaagaaaa ctggttcgca cggattgcaa acgcatatac cgacttccgt 1440
gaaatgcaaa atcgcttaca tgccaccgat gtgccattgg ctcaggacgc ggaggcagta 1500
gctcgcatta agaaactctt agacgccctg aaggggctgc aattatttat caaacctctg 1560
ttggatacag gtgaggaagc ggagaaggac gaacgtttct acggggattt tacagaattt 1620
tggaatgaac tggataccat tactccgctt tacaacatgg tccgtaatta tctcacgcgg 1680
aagccttata gtgaggaaaa gattaaattg aactttcaga atccgaccct acttaatggt 1740
tgggacttaa acaagaagt agataatacg agcgtcatcc tgcggcgcaa cggtcgctat 1800
tatctggcca ttatgcaccg taatcatcgt cgggttttt cacagtatcc gggtacggaa 1860
cgcggggatt gttatgaaaa aatggagtat aaactcctcc ctggcgctaa taaaatgttg 1920
ccgaaggtat tttttccaa atcccggatc gacgaattta acccgagtga ggagctgctc 1980
gcccgctacc agcaaggcac tcataagaaa ggggagaact ttaatttaca cgactgccat 2040
gcgctcattg actttttcaa agactcaatc gaaaagcatg aggagtggcg caacttccat 2100
tttaagttta gtgacacatc ttcgtacact gacatgacgg ggttttaccg ggagattgaa 2160
actcaaggtt acaaattgtc tttcgtgcca gtcgcgtgcg aatatatcga tgagcttgtt 2220
cgcgatggta aaattttttt attccagatt tataataagg acttctctac ctatagcaag 2280
ggtaagccga atatgcacac actttactgg gaaatgctct cgacgagcg caatcttatg 2340
aacgtagttt ataaattgaa cggccaagcc gagattttct ttcggaaagc gtcgttaagt 2400
gcccggcacc cagagcatcc agctgggctt ccgatcaaga agaaacaggc gccgacagag 2460
gagtcttgct ttccgtatga tttaatcaaa aacaagcggt ataccgtaga tcaatttcag 2520
ttccacgttc ctattactat caactttaaa gccacaggta cttctaacat caacccgtct 2580
gtcacagact atattcgcac cgcggacgat ttgcatatca ttggcattga tcgtggcgga 2640
cggcatttgt tatatctcgt tgtgatcgat agtcaaggtc ggatctgtga gcagttttca 2700
ctcaatgaaa ttgtgaccca gtatcaaggt caccagtatc ggacagatta ccatgccctt 2760
cttcagaaaa aagaggacga gcgccaaaaa gcgcgccagt cgtggcagag cattgaaaac 2820
atcaaagaat tgaaggaagg ctaccttagc caggtcgtac ataaggtctc agagttaagg 2880
atcaagtata aagccatcgt ggtgcttgaa gatttaaacg ccggttttaa gcgctcccgt 2940
caaaaggttg agaaacaagt gtaccagaaa ttcgaaaaga tgctgatcga taaacttaat 3000
tatcttgtat ttaagactgc agaagcggat cagccagggg gcctccttca cgcataccaa 3060
ttgacgaaca agttcgagtc cttcaaaaag atgggcaaac agtcgggttt cctttttctac 3120
atccctgcat ggaatacaag taagattgat cctacgacgg gcttcgtaaa tttgtttgac 3180
acacggtatg aaaatgtaga taaatcccgc gcgttcttcg gcaagtttga cagcattcgc 3240
tatcgcgccg ataaggggac atttgagtgg acgtttgatt acaacaactt ccataagaaa 3300
gcagagggga cgcgcagctc ctggtgctta tcaagccacg gtaatcgggt ccgcacgttt 3360
cggaaccctg ccaagaacaa tcaatgggat aacgaggaaa ttgatttaac ccaagctttc 3420
cgcgacttgt tcgaggcctg gggcatcgaa attacatcaa atttgaagga ggcaatctgt 3480
aaccaatccg agaaaaaatt cttcagcgag ctccttcgaac tctttaaact catgatccag 3540
ctgcgcaata gtgtaactgg gacaaacatc gactacatg tgtcaccggt agaaaaccat 3600
tacgggacct tcttttgactc tcgcacgtgc gatagctcat taccagcaaa cgccgatgcc 3660
aacggggcgt ataatattgc ccgcaagggg ctgatgctgg cacgtcgtat tcaagcgacg 3720
ccggaaaatg atccaatctc ccttactttg tctaacaaag agtggctgcg tttcgcccag 3780
ggcttagacg agaccacaac atatgagggc gcgccaaaaa ggccggcggc cacgaaaaag 3840
gccggccagg caaaaaagaa aaaggctagc ggcagcggcg ccgggatcccc aaagaagaaa 3900
aggaaggttg aagaccccaa gaaaaagagg aaggtgtgat aa 3942

SEQ ID NO: 32      moltype = DNA    length = 3942
FEATURE            Location/Qualifiers
misc_feature       1..3942
                   note = Description of Artificial Sequence: Synthetic
                   polynucleotide
source             1..3942
                   mol_type = other DNA
                   organism = synthetic construct
SEQUENCE: 32
atgggccacc atcatcatca tcatagcagc ggcctggtgc cgcgcggcag cggtaccatg  60
aaaaccttgt cagatttcac gaacctcttc ccactttcaa agaccctgcg cttcaagctc 120
attccgattg gtaatacttt aaagaatatt gaagcatccg gtatcttaga cgaggatcgt 180
catcgcgcag aatcatacgt gaaggttaag gcaatcattg acgaatatca aaggctttc 240
attgaccgcg ttttaagcga tacctgcctc cagactgaaa gtattgggaa acataactct 300
ttagaggaat tcttcttta ttaccagatc ggggccaagt ctgaacaaca gaaaagaca 360
tttaagaaga tccaagatgc ccttcgtaaa caaattgctg attcgctcac gaaagataaa 420
cactttccc gcatcgacaa gaaggaactt atccaggaag acctgatcca gttcgtacgg 480
gatggcgagg atgcggccga aaaacgagt ttgatctcag agtttcagaa ttttacagtc 540
tatttcactg gttttcacga aaatcgccaa aacatgtact ccccgacga gaagagcacg 600
gcaattgcct accgtttgat taacgagaac ttgccaaagt ttgttgataa catgaaggtc 660
tttgatcgca tcgctgctag cgaactcgcc tcctgctttg atgaactgta tcacaatttt 720
gaggagtatc tccaggtgga gcgcttacac gatatcttct ctctggatta tttcaatctc 780
ttgctgacac agaagcacat tgacgttat aacgcactta tcggcgggaa ggcaaccgag 840
accggggaga aaattaaagg tctcaatgag tatattaact tatacaatca acgcacaaa 900
caagaaaaat tgcctaaatt caaaaatgttg ttcaaacaaa ttttaactga tcgggaagca 960
attagttggc tcccgcgtca atttgacgac aattccccaac tccttcggc aattgaacaa 1020
tgctataatc atctttccac atataccttg aaagacggca gcctgaaata cttgctggaa 1080
aatttacata cctatgacac tgaaaaaatt ttcatccgta atgattcatt gctgacagaa 1140
atctctcagc gtcattacgg gtcctggtcc atttaccgg aagccattaa cgccacctt 1200
gaacgggcga acccacagaa acggcgggaa acatacgaag catatcaaag ccggatcgag 1260
```

```
aaagctttca aggcttatcc tggtttcagc atcgcgtttc ttaatggctg cttaaccgaa   1320
actgggaagg aatccccatc aatcgagagt tactttgaga gtcttggcgc ggttgagaca   1380
gagacttcac aacaggagaa ttggtttgcc cgtatcgcaa atgcttatac cgatttccgc   1440
gaaatgcaaa atcgcttaca cgctacagat gtaccgttag cgcaagacgc ggaggctgta   1500
gcgcgtatta aaaagttgct cgatgccctc aaagggttac aattatttat caagcctctt   1560
ttggacactg gcgaagaagc ggaaaaggat gaacgctttt atggcgattt cacggaattc   1620
tggaatgaat tggataccat cacacctttg tataacatgg tgcgtaacta ccttacacgt   1680
aaaccgtaca gtgaggagaa aattaagttg aattttcaga accctaccct gttgaatggc   1740
tgggatctca ataaggaggt tgataacacg agtgtgatcc ttcgtcgtaa cggccggtat   1800
tacttggcga ttatgcaccg taatcatcgt cgtgttttct ctcaataccc aggcactgag   1860
cgtggggact gctatgaaaa gatggaatat aaactgctcc ctggtgccaa taaaatgttg   1920
ccgaaagttt ttttctcaaa atcacggatc gatgagttca accctagcga ggagttgctc   1980
gcacgctacc aacagggtac acacaaaaaa ggtgaaaact ttaacttgca cgattgccat   2040
gctctgattg acttttcaa agacagcatt gagaagcatg aggagtggcg taatttccat   2100
tttaagttct ctgatacatc aagttacact gacatgtcgg gcttctaccg ggaaatcgaa   2160
acccaagggt acaagcttag cttcgtccct gtagcgtgcg aatacattga tgagttggtg   2220
cgggatggga agatcttttt gttccagatc tataataagg attttttcgac atactccaaa   2280
gggaagccta atatgcatac attgtattgg gaaatgcttt tcgatgagcg caatttgatg   2340
aacgtggtat acaagctcaa cggccaagct gagatcttct ttcgcaaggc ctctcttagt   2400
gcccgccacc ctgagcatcc agcgggctta ccgatcaaaa aaaagcaagc gcctactgaa   2460
gagtcctgtt ttccatatga tctcattaaa aataaacgct acaccgtcga ccaattccag   2520
tttcatgtac cgatcaccat taactttaag gcaacgggta catctaacat aatccatcg   2580
gtaactgact acatccggac ggcagatgat ctgcatatta ttgggattga ccgtggggag   2640
cgccacttgt tatacctggt tgttattgac agccagggtc gtatctgcga acaattttca   2700
ctcaacgaaa ttgttaccca gtaccagggc caccaatatc ggaccgatta tcatgcgctt   2760
ttgcaaaaaa aggaggacga gcgtcaaaaa gcgcggcagt cctggcagag tattgaaaac   2820
atcaaggaac tgaaggaagg gtacttgtcg caggtggtac ataaggtaag tgaattgatg   2880
attaaataca aggcgatcgt cgtcctggag gacttgaatg caggtttcaa gcgttcacgg   2940
caaaaagtgg aaaaacaagt gtatcagaag ttcgaaaaga tgttgatcga caagcttaat   3000
tacttggtct ttaaaacagc tgaagctgat cagccgggtg gtcttcttca cgcatatcag   3060
ctcactaata aatttgagtc tttcaaaaag atggggaagc aatcgggttt cttattttat   3120
attcctgcgt ggaacacatc caaaatcgat ccaaccacgg ggtttgtaaa cttatttgac   3180
acgcggtacg aaaatgttga caaatcgcgc gccttttttg gcaagttcga ttcgattcgc   3240
tatcgtgcgg ataaaggtac tttcgaatgg acttttgatt ataataattt tcataaaaaa   3300
gccgaaggga cgcgctcgtc ctggtgtctt tcctcccatg gcaacccggg acggaccttc   3360
cggaacccgg ctaagaataa tcaatgggac aacgaagaaa ttgacctcac gcaagcgttc   3420
cgggatctgt tcgaggcttg ggggatcgaa attacgagca atctcaagga agcgatctgt   3480
aatcaatcgg agaaaaaatt cttagtgag ttattcgagt tgttcccctg aatgattcaa   3540
ctgcgcaatt ccgtgaccgg cactaatatt gactatatgg tgtccctgt ggaaaatcat   3600
tatggcactt ttttcgactc ccggacttgc gattcctccc tccctgctaa cgcagacgcg   3660
aatgggcat ataatattgc acgtaagggg ttgatgctgg cgcggcggat ccaggctact   3720
ccagaaaatg atccgatctc tctcacccctt tcgaataaag aatggttgcg tttcgcacaa   3780
gggctggatg agaccactac ttacgagggc gcgccaaaa ggccggcgcg cacgaaaaag   3840
gccggcagg caaaaagaa aaaggctagc ggcagcggcg ccggatcccc aaagaagaaa   3900
aggaaggttg aagaccccaa gaaaaagagg aaggtgtgat aa                     3942

SEQ ID NO: 33        moltype = DNA   length = 3942
FEATURE              Location/Qualifiers
misc_feature         1..3942
                     note = Description of Artificial Sequence: Synthetic
                     polynucleotide
source               1..3942
                     mol_type = other DNA
                     organism = synthetic construct
SEQUENCE: 33
atgggccacc atcatcatca tcatagcagc ggcctggtgc cgcgcggcag cggtaccatg    60
aaaactttat ccgacttcac taacttattc ccactctcca aaacgttacg gtttaaactt   120
atccctatcg gtaatacgtt gaagaatatt gaggccagcg ggatcctcga tgaagaccgg   180
catcgcgcag aatcctatgt gaaagttaaa gctattatca acgagtatca taaggcattt   240
attgaccgtg tgctttcgga cacatgcctc cagactgaat cgattgggaa acataactca   300
ttggaggaat ttttcttcta ttatcaaatc ggtgcaaagt cggaacaaca aaagaagact   360
ttcaaaaaaa tccaagatgc tctccgtaaa caaattgctg actcgttgac gaaggataaa   420
catttcagcc gtattgataa gaaagagctt attcaagagg atttgattca attcgttcgc   480
gacggtgagg acgctgcaga gaagaccagc ttgatctcga aatttcagaa cttcacagtc   540
tatttcacag gttttcatga aaaccgtcag aacatgtata gcccggacga gaagtctact   600
gcaatcgcgt accgtttgat taatgagaat ctgcctaagt tcgtagataa catgaaggtc   660
tttgatcgta tcgccgccag tgaattggct agctgctttg atgagttata ccacaacttc   720
gaggaatact tgcaagtcga gcgtttgcac gacatcttct cattggacta ctttaatttc   780
ctgttgacac aaaaacacat cgacgtgtat aatgctctga tcggtgggaa agcgacagag   840
actggggaga aaattaaagg tttgaacgaa tacatcaatc tctacaacca gcggcataaa   900
caagaaaaac tgccaaagtt caaaatgttg tttaaacaga tcctcaccga ccgtgaggct   960
attagttggc ttccgcggca gtttgatgat aacagtcagc tccttagcgc catcgagcag  1020
tgctataacc accttctac gtacaccctta aaggacggca gcctgaaata cctcctcgag  1080
aatttgcaca cgtacgacac ggaaaagatt ttcattcgta atgattcctt actgaccgag  1140
atttcccaca ggcattacgg ctcatggagt attctccctg aagctattaa gcgtcacctt  1200
gaacgcgcta acccacaaaa acgtcgggaa acatacgagg cttatcaaag ccggattgaa  1260
aaggccttca agcgtatccc gggtttctcg attgcttttc tgaacggttg tctcacggaa  1320
acggggaaag aaagtcctag catcgagagc tatttcgaat ctttgggggc ggtcgagacg  1380
gagacatcac agcaggaaaa ttggtttgct cggattgcaa acgcatacac cgatttccgc  1440
```

```
gagatgcaga accgcttaca tgctacagac gtgccgctgg ctcaagacgc agaggcggtt    1500
gctcggatca aaaaacttct ggacgcgttg aaggggctcc agttatttat taaaccgctc    1560
ttagatactg tgtgaggaagc ggagaaggat gaacgctttt atggtgattt cacgaatttt    1620
tggaacgagt tagatacgat cactccgctc tataatatgg ttcggaacta tctgacgcgg    1680
aagccgtaca gcgaagaaaa aattaaattg aactttcaga atccaacatt acttaatggc    1740
tgggatttaa ataaggaggt agataacaca agcgtcatct tacgtcgcaa cggtcgttac    1800
tatttggcaa tcatgcaccg caatcatcgg cgggtgttct cgcagtatcc agggaccgaa    1860
cgtggtgact gctatgagaa aatggagtat aaacttttac caggcgccaa caagatgctg    1920
cctaaagtat tcttctccaa atcccgtatt gacgagttca atccgtccga ggaactcttg    1980
gcacgttacc aacaaggcac tcataaaaag ggcgagaact ttaacctgca tgattgccat    2040
gctctcattg atttttttaa agattcgatt gagaaacacg aggaatggcg taatttccac    2100
tttaagttct ccgatactag cagttacacc gatatgagcg gcttttaccg cgagatcgaa    2160
actcaggggt acaagcttag cttcgtcccg gtcgcctgcg agtatatcga cgaacttgtc    2220
cgcgacggta aaatttttttt gttccagatc tacaacaagg acttttccac ctatagcaag    2280
ggtaaaccta atatgcatac cttatactgg gagatgcttt tcgacgagcg gaacttgatg    2340
aacgttgtct ataaacttaa cgggcaggca gagatctttt tccgcaaagc gagcttaagc    2400
gcccggcacc ctgagcatcc tgcagggttg cctattaaga agaagcaggc accaaccgag    2460
gaaagttgct ttccatatga tctgatcaag aacaagcgtt atacagtaga ccaattccag    2520
tttcatgtac cgatcactat taactttaag gccactggga catcaaacat caatccgagt    2580
gtgactgact acatccggac agcagacgac ttgcacatta ttggtattga tcgcggtgag    2640
cgccaccttc tttaccttgt agtcattgac tcgcaaggtc gcatttgcga acagttttca    2700
cttaatgaga tcgtcacgca gtaccagggt caccagtacg cacggatta ccatgcgctt    2760
cttcagaaaa aggaagacga acggcagaaa gcgcgccaat cctggcaatc tattgaaaat    2820
attaaagaac tcaaagaggg gtatctctct caggtggtgc ataaggtctc ggaattgatg    2880
atcaaataca aggccattgt cgtgctggag gacctcaacg ctggtttcaa gcgttcgcgt    2940
caaaaggttg agaagcaggt gtaccaaaaa tttgaaaaag tgttgatcga taagttgaat    3000
tatcttgttt tcaagactgc cgaagctgat caacctgggg ggcttctgca tgcgtatcag    3060
ttgacaaata agttcgagtc cttttaagaaa atgggcaaac agagtggctt cctcttctat    3120
atccctgcat ggaacacgag taaaatcgat cctaccactg gcttcgttaa cttatttgat    3180
acacgctacg aaaacgtcga caagagtcgg gccttcttttg ggaaatttga ttctattcgg    3240
tatcgtgcag ataagggcac ttttgagtgg acgtttgact acaataactt tcataagaag    3300
gcagagggga ctcggagttc ctggtgttta agctcacatg gaaccgtgt tcgtacatttt    3360
cggaacccgg ccaagaataa ccaatgggat aatgaggaga ttgacttaac tcaggcgttt    3420
cgtgatttgt tcgaagcctg ggggattgag atcacaagta acctgaagga ggcaatttgt    3480
aatcagacg aaaagaaatt ttttttcggaa ctctttgaac tcttcaagtt aatgattcag    3540
ttgcgcaact ccgtaaccgg taccaatatc gattacatgg tttcaccggt agaaaatcac    3600
tatgggacgt tctttgatag tcggacttgc gacagtagtc ttccagcgaa cgccgatgcc    3660
aacggcgctt acaatatcgc ccggaagggg cttatgctcg cccgccgtat ccaagcaact    3720
cctgagaacg atcctatctc tcttacactc tctaacaagg aatggcttcg gttcgcacag    3780
gggttagatg agaccaccac atatgagggc gcgccaaaaa ggccggcggc cacgaaaaag    3840
gccggccagg caaaaaagaa aaaggctagc ggcagcggcg ccggatcccc aaagaagaaa    3900
aggaaggttg aagaccccaa gaaaagagg aaggtgtgat aa                        3942
```

SEQ ID NO: 34          moltype = DNA   length = 3942
FEATURE                Location/Qualifiers
misc_feature           1..3942
                       note = Description of Artificial Sequence: Synthetic
                        polynucleotide
source                 1..3942
                       mol_type = other DNA
                       organism = synthetic construct
SEQUENCE: 34

```
atgggccacc atcatcatca tcatagcagc ggcctggtgc cgcgcggcag cggtaccatg    60
aaaaccccttt ctgattttac aaatctcttc ccgcttagta agacgcttcg ttttaaatta    120
atccctattg gcaatacgtt gaagaacatc gaagcaagtg ggatccttga tgaggaccgg    180
catcgtgccg aaagctatgt taaggtaaag gccattatcg atgaatacca caaggcgttc    240
atcgatcgtg tattatctga cacgtgtttta caaactgaga gtattggcaa acacaacagt    300
ctggaggagt ttttttttta ctatcaaatt ggggcaaagt cagaacagca aaaaaagact    360
tttaagaaga ttcaggacgc cttgcgcaag cagattgctg actctctgac gaaagataaa    420
cacttttccc ggattgataa gaaggaactt attcaagagg atcttattca atttgtgcgt    480
gacggtgagg acgcggcaga gaaaacgagc cttatctcag aattccaaaa tttcacagtg    540
tatttcacag gcttccatga gaaccggcag aatatgtatt cacctgatga aaagtctaca    600
gccatcgcgt atcggcttat caatgagaat cttccgaaat ttgttgacaa catgaaagta    660
ttcgatcgca tcgcggctag tgaattagca agttgcttttg ccacaattcc ccacaattcc    720
gaagaatacc tccaagtaga gcggttacat gatatcttct cccttgatta ctttaatctg    780
ttacttactc aaaagcacat cgatgtctat aatgcgttga tcggggtaa agccaccgaa    840
accggtgaga aaattaaggg gctcaatgaa tacattaatt tgtataatca cgccataag    900
caggaaaaat taccgaaatt taagatgctc tttaaacaaa ttcttaccga tcgtgaggct    960
atcagctggc tgccgcggca gttgatgat aactcacagt tactctccgc tattgaacaa    1020
tgctacaacc acttgtccac ttacacgctg aaggatggta gtttgaaata ttattggaa    1080
aattttgcaca cttatgatac agaaaagatt tttattcgca acgactcatt gttaactgaa    1140
atttcgcaac gccactatgg ttcatggagt atttttacctg aggcaatcaa acgccatttg    1200
gaacgcgcga atccgcagaa acggcgggaa acatacgagg cttatcagtc tcgtattgag    1260
aaggctttta aagcatatcc tggtttttcc atcgcctttt tgaatggtgt cctcaccgaa    1320
acaggtaaag agagtccttc catcgaatct tatttcgagt ctctcggcgc tgtagaaact    1380
gagacatcac aacaagagaa ctggttcgcc ggatcgcca atgcttatac agatttccgg    1440
gagatgcaaa atcgtcttca tgccactgat gtaccgttgg cccaggacgc agaagcgta    1500
gcgcgtatta aaaagttatt ggacgcatta aaaggtcttc agctttttcat taagccactc    1560
ctggatactg tgaagaggc cgagaaggat gagcggtttt atgggggattt cacagagttc    1620
```

```
tggaacgagc tggatacgat tacaccattg tacaatatgg ttcgtaatta ccctcactcgc    1680
aaaccatact ctgaggagaa aatcaagctc aattttcaaa acccgacttt gctcaatggc    1740
tgggacttaa acaaagaggt ggacaatact tctgtgattc tccggcgcaa cggccgctac    1800
tatttggcga tcatgcaccg caaccatcgc cgggtgttta gtcaatcccc gggtacggaa    1860
cgtggcgatt gttatgagaa aatggagtat aagctgctac ctggcgcgaa taagatgtta    1920
ccaaaagtat ttttttctaa gtcccgcatt gatgaattca acccgtccga ggaactcttg    1980
gcacggtatc aacagggtac gcacaaaaag ggcgaaaatt tcaatttgca tgattgtcac    2040
gccttgattg acttttttaa agactctatt gaaaaacatg aggagtggcg caactttcat    2100
tttaagttta gtgatacttc gtcctataca gatatgagtg ggttttatcg ggaaatcgag    2160
acccaaggct ataaactgtc gtttgtgcct gtggcctgca aatcattga tgagttagtc    2220
cgcgacggta agatctttct ctttcaaatc tacaacaaag attttcctac atatagcaaa    2280
ggtaagccaa acatgcacac actttattgg gaaatgcttt tgacgaacg caatttgatg    2340
aatgtggttt ataaattgaa tgggcaggcg gagattttct ttcgcaaagc gtccctgtca    2400
gcacggcacc cggagcaccc tgcgggtctt ccaatcaaga aaaagcaggc cccgactgaa    2460
gagtcatgtt ttccgtatga tttaattaaa aataaacgct atacggttga tcagttccag    2520
tttcatgttc caatcaccat taacttcaaa gctacaggga ctagcaacat taatccttct    2580
gttacggatt atattcgcac ggcggacgat ctccatatca ttgggatcga ccgtggggaa    2640
cgtcacctcc tttacctcgt tgtcattgac agtcagggtc gcatttgcg gcagttctct    2700
ctcaatgaga ttgttactca gtaccaaggt catcaatacc ggacagatta ccatgcactc    2760
ctccaaaaga aagaggacga gcgccagaag gcacgtcaga gctggcagag cattgagaac    2820
attaaggagc ttaaggaggg ctacttgtct caggtagtcc ataaggtgag tgagttaatg    2880
attaagtata aggcaatcgt tgtcttggaa gatctgaacg ctggcttcaa gcggtctcgc    2940
cagaaggtag agaaacaagt atcagaaa tttgaaaaga tgctcatcga taaattgaac    3000
tatctcgttt tcaaaaccgc cgaggctgat cagccaggcg gctgttgca cgcatatcaa    3060
ctcacgaata aatttgagtc gttcaaaaag atgggtaaaa aaagcgggtt tctgttttat    3120
atcccggcgt ggaacacttc gaagatcgat ccaactacgg gtttttgtaa ttttattcgat    3180
acacgttacg aaaacgtaga caatcacgt gctttcttg gcaaattcga tagcattcgt    3240
taccgtgcgg acaaaggtac attcgagtgg acttttcgact ataataattt ccacaaaaaa    3300
gcagagggga cccgctccag ttggtgctta tctagccatg ggaaccgtgt tcgtacattt    3360
cgcaatcctg caaagaataa tcagtgggat aacgaagag ttgatctcac tcaggcattt    3420
cgcgatttat ttgaggcctg gggtatcgag atcacctcaa atcttaagga agcgatttgc    3480
aatcagtcag aaaagaaatt tttttcagag ctgtttgagt tattcaaact catgatccaa    3540
ttgcggaaca gcgtcacagg cacgaatatt gattatatgg ttagcccggt ggaaaatcat    3600
tacggtactt tcttcgatag ccgtacttgt gactcctcgc tccctgcaa tgctgacgct    3660
aatggcgctt ataacatcgc acgtaaaggg ctgatgctgc cacgtcggat tcaggccacg    3720
cctgagaacg atccaatcag cctgacgttg tctaataagg agtggctccg ttttgctcaa    3780
ggtttagatg agacaactac ttacgaaggc gcgccaaaaa ggccggcggc cacgaaaaag    3840
gccggccagg caaaaagaa aaaggctagc ggcagcggcg ccggatcccc aagaagaaa    3900
aggaaggttg aagaccccaa gaaaagagg aaggtgtgat aa    3942
```

SEQ ID NO: 35             moltype = DNA    length = 3942
FEATURE                   Location/Qualifiers
misc_feature              1..3942
                          note = Description of Artificial Sequence: Synthetic
                          polynucleotide
source                    1..3942
                          mol_type = other DNA
                          organism = synthetic construct
SEQUENCE: 35

```
atgggccacc atcatcatca tcatagcagc ggcctggtgc cgcgcggcag cggtaccatg      60
aagacacttt cggacttcac caacttattc cctctttcga agacactccg tttcaagttg     120
attccgattg ggaataccct gaagaacatt gaagcttcgg gtatcctcga tgaagaccgt     180
catcgcgcag aatcctacgt taaagttaag gcaatcatcg acgaatacca taagctttc     240
atcgatcgcg tgttaagcga cacatgtctg caaaccgaga gtattggcaa gcataattcg     300
ctcgaggaat tcttcttcta ctatcagatt ggtgcgaaca gcagcaaca aaaaaagact     360
tttaagaaga ttcaggatgc tttacggaag caaattgcgg acagcctgac gaaagataaa     420
catttagtc gtatcgataa gaaggagctg attcaggaag atcttattca gttcgtccgt     480
gacggtgagg atgcagcgga aaagacatcc ttaattagcg agtttcagaa ttttactgta     540
tactttacag gtttccatga aaaccggcaa aacatgtaca gcccggacga aaaatccacg     600
gccatcgctt accgtctcat taatgaaaac ctgccgaaat tcgtcgacaa catgaaggtg     660
tttgatcgca ttgctgcctc tgaattagcc tcctgctttg atgaacttta tcacaacttc     720
gaagagtatc tgcaagtaga gcgcttacac gatatttttt cttggacta cttcaatttg     780
ctgttgacac aaaagcatat cgatgtgtac aatgcactga tcgggggtaa ggcgacggag     840
acgggtgaaga agattaaagg gctcaacgaa tatataacc tctacaacca acggcatagg     900
caggagaagc ttccgaagtt taagatgctc tttaagcaga ttctgactga ccgcgagcc     960
attagctggc tcccacgcca atttgacgat aactcgcaac tcttatctgc aatcgagcag    1020
tgctacaacc atttaagtac atacactttg aaagacggct ccctgaaata tctgttagaa    1080
aatcttcaca cttacgcac agagaaagtt ccattcgta atgatagtct gttaacgag    1140
attagccaac gtcactatgg ctcatggagt attttaccgg aggctattaa acgtcattta    1200
gagcgcgcta atccgcagaa acgtcgtgag acctacgagg catacccgag ccgcatcgag    1260
aaggctttta agcttatccc tgggttttca attgcatttc tcaatggggtg cttaacggag    1320
acaggtaaag agtcgcctcc catcgagtcc tatttcgagt cgctcggtgc ggtcgaaaca    1380
gaaactagcc aacaggaaaa ttggtttgct cgcatcgcta atgcttatac tgattttcgc    1440
gagatgcaga accggttaca tgcgaccgac gtaccactgg cccaggatgc cgaggccgta    1500
gcacggatca agaagctcct tgatgccttg aaagggttac agctgtttat taaacctctt    1560
ttggatacag gcgaggaggc cgagaaggac gagcgtttct atggtgactt caccgaattt    1620
tggaacgagt tagacaccat cactccgttg tacaacatgg tccgtaacta cttgacacgc    1680
aaaccatact ctgaggaaaa gattaagttg aattttcaga acccaacttt gttaaatggg    1740
tgggacttga ataaggaggt cgataacaca agcgtgattc tgcggcgcaa tggccggtat    1800
```

```
tatttagcta tcatgcaccg taatcatcgc cgcgttttct cacagtatcc gggtacagag 1860
cgggggact gctatgaaaa gatggagtat aaactgctcc ctgggcgaa caaaatgctg 1920
ccaaaagtgt tcttctcaaa aagtcgtatc gatgagttta atccaagtga ggagcttctc 1980
gctcgctacc agcaaggcac tcataaaaaa ggtgagaact tcaatctcca cgattgtcat 2040
gctttaatcg atttttcaa ggacagtatt gaaaaacatg aggaatggcg taatttcat 2100
tttaaatttt cggatacctc cagttacaca gacatgtcgg gtttctatcg tgaaattgag 2160
actcaggtt acaaactgag ttttgtcccg gtggcatgtg aatatatcga tgaactggta 2220
cgcgatggga agatctttct gttccagatc tacaataagg atttcagcac ttattcgaag 2280
gggaagccta acatgcatac actttactgg gaaatgttat ttgacgaacg taatctgatg 2340
aatgtcgtat acaaactgaa cgggcaggct gagatctttt ttcgcaaagc ctcactttct 2400
gcacgccatc cggagcaccc agctggttta cctatcaaaa agaagcaggc tcctactgag 2460
gaaagctgtt tcccttatga cttgattaaa aacaaacgct acaccgtgga tcaatttcag 2520
ttccacgtgc ctattacgat caactttaag gcaacgggta cgagcaatat caatccgagt 2580
gtgaccgact atatccgtac tgcagatgac ttacatatca ttgggatcga ccgggggtgag 2640
cgtcacctgc tgtacttagt agtaattgac tctcaaggtc ggatttgcga acagttttct 2700
ctcaatgaaa tcgttacgca atatcagggt caccaatacc gtaccgatta tcacgcgctg 2760
ttacaaaaaa aggaagacga acggcaaaag gcccggcaga gctggcagtc tatcgagaat 2820
atcaaggaac ttaaagaggg ctatcttagc caggtcgtac ataaagtatc agagttgatg 2880
atcaaatata aggcgatcgt tgtactcgag gacctcaacg caggtttcaa acgctcccgt 2940
cagaaagtag agaagcaagt atatcaaaag tttgaaaaaa tgttaatcga taagcttaat 3000
tatttggttt ttaaaacggc tgaagcagat caacctgggg gtttgttaca tgcctatcag 3060
ctcaccaaca agtttgaatc gttcaaaaaa atggggaaac agtcgggctt tctctttat 3120
atccctgcat ggaatacgtc gaagatcgac ccaacaacgg gtttcgtgaa tctcttcgat 3180
acccgctacg agaacgtcga caagtcgcgc gcattttttg gcaagttcga ttcgattcgg 3240
tatcgtgcgg ataaggggac tttcgagtgg acttttgact ataacaactt ccataagaag 3300
gctgagggta cgcgttcatc ctggtgtctt tccagccagg ggaatcgtgt acgtacattc 3360
cgcaaccctg cgaaaaataa tcaatgggat aacgaagaaa tcgatttgac gcaagctttc 3420
cgggatctgt tcgaagcatg gggcattgaa atcacgtcga acttaaaaga ggcgatctgc 3480
aaccagtccg agaagaagtt cttctccgag ttgtttgagc tgttcaagct catgatccaa 3540
ttacgcaata gcgttactgg gacgaatatc gattatatgt tatcgcctgt agaaaaccac 3600
tacggcacgt tctttgactc acgcacatgt gattcttcgc tgcctgcgaa cgcagatgcc 3660
aacggtgcat acaatattgc gcggaagggc cttatgttgg cgcgccgtat ccaagctaca 3720
ccagagaatg atccaatctc ccttacccttt agtaataaag aatggttgcg ttttgcgcag 3780
ggtctggatg agacaaccac gtatgagggc gcgccaaaaa ggccggcggc cacgaaaaag 3840
gccggccagg caaaaagaa aaaggctagc ggcagcggcg ccgatccccc aaagaagaaa 3900
aggaaggttg aagaccccca gaaaagagg aaggtgtgat aa 3942

SEQ ID NO: 36        moltype = DNA  length = 3942
FEATURE              Location/Qualifiers
misc_feature         1..3942
                     note = Description of Artificial Sequence: Synthetic
                     polynucleotide
source               1..3942
                     mol_type = other DNA
                     organism = synthetic construct
SEQUENCE: 36
atgggccacc atcatcatca tcatagcagc ggcctggtgc cgcgcggcag cggtaccatg 60
aagacacttt ctgatttcac taacttattc cctctctcaa aaaccttgcg ttttaaactt 120
atcccgattg ggaacacgct caaaaacatt gaggctagtg gtattttaga tgaggaccgc 180
catcgcgccg agagttatgt caaagttaag gccatcatcg atgagtacca caaggcattc 240
attgaccggg tgctgtcaga tacgtgcctc cagacggaaa gcatcggtaa gcataactcc 300
cttgaggagt tctttttta ttatcaaatt ggggcgaaaa gcgaacaaca gaaaaagacg 360
ttcaaaaaga tccaagacgc cctccggaaa caaattgccg actcattaac taagacaag 420
cactttagtc ggatcgacaa aaaagagctt attcaagaag atcttatcca atttgtgcgc 480
gacgggaag acgcagccga gaaaacctcc cttatttcgg agttccagaa cttcactgta 540
tactttacag ggttccatga aaatcgccag aacatgtact ctccagacga aaagagtact 600
gctatcgcgt atcggcttat taacgaaaat cttcctaagt ttgttgacaa catgaaggtt 660
tttgaccgta ttgctgcatc tgagtttagcg agttgcttcg acgagctgta tcacaacttc 720
gaagaatatc tccaggtgga acgtctgcac gacattttca cagtttgatta tttttaatttg 780
ttattaaccc agaagcacat tgacgtttat aatgcgctca tcggcgggaa agcaacagag 840
accggcgaga agattaaggg cttgaacgaa tacattaatc tctataacca gcgccacaaa 900
caggaaaaac ttccaaagtt caagatgtta ttcaagcaga tcctgacgga tcgtgaggct 960
atctcctggc tgccacgcca atttgatgac aactcgcagt tgttatccgc gatcgaacag 1020
tgctataatc atttaagtac atacactctg aaggacgct ccctcaaata tcttttgaag 1080
aatcttcata cctacgacac ggagaaaatt tttattcgca acgactcttt gttgacggaa 1140
atttcccagc gtcattacgg cagttggagt atccgccgg aagcgattaa gccatctt 1200
gagcgggcaa atcctcagaa gcggcggaa acatacgagg cctaccagag tcgcattgaa 1260
aaggcgttta aggcatatcc tggcttttct atcgcgtttt taaatggttg cctgactgag 1320
acaggtaaag agagtccttc tattgagtcc tacttcgaat cattggggc tgtggagacg 1380
gaaactagtc agcaggagaa ttggtttgcg cgcattgcca atgcctatac tgattttcgg 1440
gagatgcaga accgtctgca cgccaccgat gtcccgttag cccaagatgc tgaagcggtc 1500
gcacgtatca aaaagctctt ggatgccctg aaaggtctcc aattatttat taagcctttg 1560
ctcgatactg gtgaagaagc agaaaagat gaacgttttt atgcgatttt acagaatttt 1620
gagagcgagc tggaataccat tactccttta taataatgcg tacgaaatta cttgacccgt 1680
aagccgtaca gtgaggagaa aattaagctg aattttcaaa acccaacact gttaaatggc 1740
tgggatctga acaagaagt ggataacaca agtgtcatcc tccgccgtaa tggtcgctac 1800
tatctggcta tcatgcaccg taaccatcgc gcgttttttt cccaataccc ggggacggag 1860
cgtgggact gttacgagaa aatggagtat aagctcttgc caggcgctaa taaaatgttg 1920
ccaaaagtgt ttttcagcaa gagccgcatt gatgaattta atccgtcgga agaactgctc 1980
```

```
gcccgctatc agcagggtac ccacaagaag ggtgaaaatt ttaatttgca cgattgccac    2040
gctttgattg atttctttaa agactcgatt gagaaacatg aggagtggcg caacttccac    2100
ttcaaattca gtgacacgag tagctatacc gatatgtctg gtttctatcg cgaaattgaa    2160
acccaggggtt acaaattgtc atttgttcct gtggcttgcg aatacatcga cgagttggtt    2220
cgggatggga aaatcttctt attccagatc tataataaag acttctcaac ttacagtaaa    2280
ggtaaaccta atatgcacac tctgtactgg gagatgctct ttgatgagcg caatcttatg    2340
aacgtggtat acaagcttaa cggtcaagct gaaatctttt tccgcaaggc aagtctgagc    2400
gcgcgccatc cggagcatcc agccggcctt cctattaaaa agaagcaggc ccctactgag    2460
gagtcatgtt tcccttacga cctcatcaag aataagcgct acacggtcga tcaattccag    2520
ttccatgttc ctattacaat caattttaag gccactggga cctcgaatat caatccaagc    2580
gtaacagatt atatccggac gcggacgat ctgcatatta tcggtatcga tcgggggag     2640
cgccatttgc tgtaccttgt ggtaatcgat tcccaaggtc ggatttgtga acagtttagc    2700
ctcaacgaga ttgtaacaca gtatcaaggt caccagtacc gtacagacta ccatgctctc    2760
cttcagaaaa aagaagatga gcgccaagaa gcccgtcagt cttggcaatc catcgaaaac    2820
attaaggaac tgaaagaggg ctatctgtct caggtagtgc acaaagtttc ggaactgatg    2880
atcaaataca aggcgattgt agtactgaaa gacctcaacg cgggcttcaa acgcagccgg    2940
cagaaggttg agaagcaagt ttaccagaaa tttgagaaga tgctcattga taaacttaat    3000
tacttggtgt tcaagactgc tgaagccgat cagcctggcg gcttgctgca cgcgtatcag    3060
cttaccaaca aattcgaatc cttaaaaag atggggaaac aatcagggtt cttattttat    3120
atcccggcgt ggaacacgtc taagatcgac ccaaccacag gttttgtcaa cctgtttgat    3180
acacggtacg agaacgttga caaatcgcgt gccttttcg gcaagttcga ctcaattcgc    3240
taccgcgcag acaaagggac attcgagtgg acgttcgatt acaataattt tcacaaaaaa    3300
gctgaaggca cccgctcgag ctggtgttta tcctctcacg ggaaccgtgt gcgcacgttc    3360
cgtaacccag ctaaaaacaa ccagtgggac aatgaagaga tcgattgac acaggccttt    3420
cgtgatctgt tgaagcatg gggtatcgag atcacgtcga atctcaaaga ggccatttgt    3480
aatcaatccg aaaaaaagtt cttcagtgaa ctcttcgatt tgtttaagtt aatgattcag    3540
ctccgcaata gtgtcacagg cactaatatt gattacatgg tctcacctgt tgagaaccac    3600
tacgggacgt ttttcgattc tcggacatgc gactcttcac tccctgctaa cgccgacgcc    3660
aatggtgcat ataatattgc ccgcaaaggg ttgatgttag cacgtcggat tcaagcaact    3720
ccagaaaacg atccgatctc ccttacactt agcaacaaag agtggttgcg cttcgcgcaa    3780
gggttagacg aaacaacgac ctatgagggc gcgccaaaaa ggccggcggc cacgaaaaag    3840
gccggccagg caaaaaagaa aaaggctagc ggcagcggcg ccggatcccc aagaagaaa    3900
aggaaggttg aagaccccaa gaaaaagagg aaggtgtgat aa                      3942
```

```
SEQ ID NO: 37           moltype = DNA   length = 3942
FEATURE                 Location/Qualifiers
misc_feature            1..3942
                        note = Description of Artificial Sequence: Synthetic
                        polynucleotide
source                  1..3942
                        mol_type = other DNA
                        organism = synthetic construct
SEQUENCE: 37
atgggccacc atcatcatca tcatagcagc ggcctggtgc cgcgcggcag cggtaccatg     60
aaaacacttt cagactttac caatcttttc ccgctgtcaa aaacgctccg gtttaagtta    120
attccaattg gcaacactct caaaaacatt gaggctagcg ggattcttga tgaggatcgg    180
catcgcgcgg agagctatgt taaggtaaaa gcaatcatcg acgagtatca caaggcgttt    240
attgaccgtg tactgagtga cacgtgcttg caaacagaaa gcattggcaa gcacaattct    300
ttggaggaat ttttttcta ctatcaaatc ggtgccaaga gcgaacagca aaaaaagact    360
tttaaaaaga tccaagacgc actgcgcaag caaatcgctg actccctcac gaaagataaa    420
cactttagtc gtatcgataa aaaagagttg atccaggaag atctgattca attcgtactg    480
gacggtgaag atgctgcaga aaaaacgtct ctcatttccg aattccagaa ctttactgtt    540
tacttcacgg ggttcatga aatcgtcag aacatgtatt ctccagatga aaatccacc      600
gctatcgctt atcgtttgat caacgagaat ctcccaaaat tgttgataa tatgaaggtt    660
tttgatcgta tcgctgcgag cgaacttgcc tcatgcttcg acgagttata ccataatttc    720
gaggagtact tacaagtgga acgcttgcac gatatcttct cgcttgacta tttcaattta    780
ttgctcaccc agaaacacat cgacgtctac aatgctctca tcggggtaa agcgaccgag    840
actggggaga agattaaagg tttgaacgag tatatcaacc tgtacaacca acggcataaa    900
caggagaaac tcccaaaatt taagatgtta ttcaaacaaa tcctcaccga ccgcgaagcg    960
atttcctggc ttccacgtca gttcgatgac aactcgcaac tgttgtccgc aattgaacaa   1020
tgttacaacc atttgtcaac gtacacgtta aaggacgggt cgcttaagta cttactggaa   1080
aatttgcaca cttacgatac ggagaaaatc ttcatccgga atgattcgct tcttactgag   1140
atttcgcagc gtcactatgg ttcttggtca atcctgccgg aagcaatcaa acgccatctt   1200
gagcgtgcaa atcctcagaa gcgtcgcgag acttatgagg cctaccaatc acggatcgaa   1260
aaggctttca aggcgtatcc tggcttctct attgcatttt taaatgggtg tctgactgag   1320
acgggcaagg aaagcccatc gatcgagtca tactttgagt cattgggggc tgtggaaact   1380
gaaacttcac agcaagaaaa ctggtttgcg cgcatcgcga acgcttacac cgattttcgt   1440
gaaatgcaaa accggctcca cgcaacggat gtacctcttg cgcaagacgc ggaagcagta   1500
gctcggatta agaagctttt ggacgcttta aagggtccaa aattgttcat caaaccactg   1560
ttggataccg gggaagaagc tgagaaagat gagcggttct atggtgattt caccgagttt   1620
tggaacgagc ttgacacgat tacgcctctc tataatatgg tccggaacta cttaacgcgt   1680
aagccgtact cagaggagaa gattaaactt aacttccaga atccaacgtt attgaatggg   1740
tgggatctga ataggaagt ggataacact tccgttatct tacgccgcaa tggcggtac     1800
tacctgcca ttatgcatcg gaatcaccgt cgtgttttct cccagtaccc gggtacagag    1860
cggggtgact gctatgagaa aatgaatat aaactcttac cggggcaaa taaaatgctc     1920
ccaaaggtgt tttttcgaa gtcccgcatc gatgagttca atccgtcgga agaacttttg    1980
gctcgctatc agcagggtac ccataagaag ggtgaaaatt ttaatctgca tgattgtcac   2040
gcattaattg acttttttaa ggattccatc gaaaagcatg aagagtggcg caacttcac    2100
tttaagttct ctgataccctc ttcttatacc gacatgtcgg gcttctatcg ggagattgag   2160
```

-continued

```
actcaaggtt ataaattatc attcgtccct gtagcatgcg aatacatcga cgagttggtt  2220
cgggatggga agatctttct ctttcagatt tataacaagg atttctcgac ctacagtaag  2280
ggcaagccta atatgcatac actttattgg gagatgttgt tcgacgaacg caatttgatg  2340
aacgtagtct ataagctgaa tgggcaggcc gagattttt tccgtaaagc ctctctgtca  2400
gcccggcacc cagagcatcc ggctggcctc ccgattaaaa aaaagcaggc gcctacagaa  2460
gagagctgtt ttccgtacga cctcattaag aacaagcggt atacggtaga tcagttccag  2520
ttccatgtcc caattacaat caacttcaaa gcgactggga catcaaatat taatccatca  2580
gtcactgact atatccggac cgctgatgat cttcacatta tcggcatcga tcgcgggaa  2640
cggcaccttc tgtacctggt agtaatcgac tctcaagggc ggatctgcga acagttcagt  2700
ctcaacgaga tcgtgacgca atatcaaggc caccagtacc gcacagacta ccatgctctc  2760
cttcagaaaa aagaggatga gcgccagaaa gcccgtcagt cttggcagtc aattgaaaat  2820
attaaggaat taaggaagg ctacctttct caagtagtgc ataagttag tgagcttatg  2880
attaaatata aggctatcgt agtgttagag gatttgaatg caggctttaa gcgctcgcgc  2940
caaaaagttg aaaaacaggt gtatcaaaaa ttcgaaaaaa tgcttattga taagctcaat  3000
tatctggtgt ttaagaccgc agaggcagat caaccgggtg ggctgctgca cgcatatcag  3060
ttgactaata aattcgagtc atttaagaaa atggggaaac aatccgggtt tttgttctat  3120
atcccagcat ggaatacttc aaagattgac ccgacaacag gctttgtcaa tctctttgac  3180
acccgctacg aaaacgtaga caagtcacgc gctttcttcg ggaagttcga tagtatccgc  3240
taccgcgccg acaaagggac ctttgagtgg acttttgact ataataactt ccataaaaag  3300
gcagaaggga cacggagttc atggtgtttg tcttctcacg gcaaccgggt acgcacgttc  3360
cggaaccctg ctaagaacaa ccaatgggac aatgaagaaa ttgacctcac gcaagcgttc  3420
cgcgacctct ttgaagcgtg gggtattgaa atcacttcta atcttaagga agcgatttgc  3480
aaccagagtg agaagaagtt ttttctgaa ttatttgagc ttttttaagct gatgattcag  3540
cttcgcaata gtgtgacagg tacaaatatc gattatatgg tatcacctgt cgaaaaccac  3600
tacggcacat ttttcgactc tcggacatgc gactcctccc tcccgccaa tgcggatgcg  3660
aatggcgctt acaacattgc tcggaagggt ctgatgcttg cccgtcggat tcaagctacg  3720
ccggagaatg atcctatcag tttaactctc tccaacaagg aatggcttcg cttcgctcag  3780
gggctcgacg aaaccacaac atacgaaggc gcgccaaaaa ggccggcggc cacgaaaaag  3840
gccgccagg caaaaagaa aaaggctagc ggcagcggcg ccggatcccc aaagaagaaa  3900
aggaaggttg aagaccccaa gaaaagagg aaggtgtgat aa  3942
```

| | | |
|---|---|---|
| SEQ ID NO: 38 | moltype = DNA length = 3942 | |
| FEATURE | Location/Qualifiers | |
| misc_feature | 1..3942 | |
| | note = Description of Artificial Sequence: Synthetic polynucleotide | |
| source | 1..3942 | |
| | mol_type = other DNA | |
| | organism = synthetic construct | |

SEQUENCE: 38

```
atgggccacc atcatcatca tcatagcagc ggcctggtgc cgcgcggcag cggtaccatg  60
aaaactctgt cagatttcac aaatcttttc cctctctcga aaacactgcg cttcaaactc  120
atcccaattg gtaacacctt aaagaacatc gaggctgtta gcgaagaccgc gcaaagaccgc  180
catcgcgcgg agagttacgt aaaagtgaag gctatcatcg atgaatacca taaggcgttc  240
attgaccggg tgctgtccga tacgtgcttg cagaccgaaa gcattggcaa acacaacagc  300
ttggaagagt tcttcttta ttatcaaatc ggtgctaaat cagagcagca gaagaaaact  360
tttaagagaa tccaggacgc cttgcggaag caaattgcta actctcttac caaagataag  420
cattttagtc gtatcgataa aaagaactg attcaggagg atttaatcca attcgttcgt  480
gacggcgagg acgccgcgga aaaaacgtca ttgatttccg agtttcagaa tttttacagtg  540
tattttaccg gtttccatga gaaccgtcag aatatgtatt cccctgatga gaaatcgaca  600
gccattgctt atcggcttat caacgaaaat ctgccaaaat ttgtagacaa catgaaagtg  660
tttgatcgga ttgctgcgag cgagctcgct tcatgtttcg acgagttgta tcacaacttc  720
gaggagtatt tgcaagtcga acggcttcat gacatctttt cgttagacta tttcaatctt  780
cttctcacgc agaaacatat cgatgtctac aatgctctga ttggtggtaa ggccacggaa  840
accggcgaaa aaattaaagg gctcaatgag tacatcaacc tttacaatca gcgccacaag  900
caagagaaac tgcctaagtt taaatgctt ttcaagcaga ttcttacaga tcgcgaagcc  960
atcagctggc tccctcgtca gtttgatgat aattcacaat tactgtcggc tattgaacaa  1020
tgttacaacc atctcagcac gtatacacctg aaggatggct cattgaagta cttattgaa  1080
aatttgcaca cgtacgatac ggagaaaat ttcattcgta acgattcatt gttaacgag  1140
atttcgcagc gccactatgg gtcttggtcg attttgccag aagccatcaa gcgccacctc  1200
gagcgtgcta acccgcagaa gcgtcgtgaa acttacgagg cataccagtc gcgtatcgag  1260
aaaagcattca aggcctaccc tggttttttct atcgctttct tgaatgggtg cttaacagag  1320
acgggcaaag agtctccttc catcgaatcg tattttgagt cgttgggggc tgtagaaact  1380
gaaaccagtc aacaagagaa ctggttcgcg cggatcgaaa atgcgtatac tgactttcgt  1440
gagatgcaga accgtttgca tgccacagat gtgccgctgg cgcaggatgc tgaagccgta  1500
gcacgtatta aaaattact tgatgctttg aaagggctcc aacttttcat caaaccactg  1560
ttggacaccg tgaggaggc agaaaagac gaacgtttct atgggattt cacggaattc  1620
tggaacgaac tcgacaccat cactccgtta tacaacatgg tgcgtaatta tttaaccgg  1680
aagccatata gcgaagagaa aatttaagctc aactttcaaa acccacgct gttaaacggt  1740
tgggatctga acaagaggt ggacaacact tcagtgattt tacgccggaa cggtcgttat  1800
tacttggcta tcatgcaccg taaccatcgc cgcgtattct ctcagtaccc agggacagag  1860
cgtgggat gctacgagaa aatggagtac aagctccttc caggggccaa taaaatgctc  1920
cctaaagtgt tcttctcgaa atcccgtatt gatgagttca atcctagcga ggagcttctc  1980
gcccgctatc agcagggcac acataagaag ggtgaaaact ttaaccttca cgactgccac  2040
gccttgattg attttcttta agactctatc gagaaacacg aagaatggcg taactttcat  2100
tttaagttct ccgacaccag cagttatacc gatatgtctg gttttatcg cgagatcgaa  2160
acccaagggt ataaactgtc ctttgtacct gttgcttgcg agtatatcga tgaattagtc  2220
cgggacggta agatttttcct ttttcaaatt tacaacaaag attttctac atactccaag  2280
ggcaagccaa acatgcacac tctctattgg gagatgctgt tcgatgaacg taatctcatg  2340
```

```
aatgtcgttt acaaactcaa cggccaggca gagatttttt tccgtaaagc ctcactttcc  2400
gctcgccacc cggaacaccc agcgggcctg ccgatcaaaa aaaaacaagc ccaacggag   2460
gagagttgct tcccgtacga cctgatcaag aacaaacgtt atacggtgga ccagttccaa  2520
tttcatgtgc cgattaccat taatttcaag gctaccggaa cctccaacat taatccgtct  2580
gtaacggact atattcggac cgccgacgat ctgcatatca ttgggatcga tcggggcgaa  2640
cgtcacttac tttatctcgt cgttattgac agccaggggc gcatctgtga gcaattctcc  2700
cttaacgaaa tcgttactca gtatcagggc catcagtatc gcaccgatta tcacgctctc  2760
ctgcaaaaaa aagaagacga acgtcaaaaa gcacgtcagt cttggcaaag tatcgagaac  2820
attaaggagc tgaaagaggg ctacctgagt caagtggtac ataaggtgtc cgaattaagtg 2880
attaaataca aagcaattgt ggtcctggaa gacctgaatg ccggcttcaa gcgctctcgc  2940
caaaaagttg aaaaacaagt ttaccaaaaa ttcgaaaaaa tgttgattga caagttaaat  3000
tacttagtct tcaagacggc tgaggctgat cagcctggtg gtctccttca cgcctaccaa  3060
ctcacgaaca agttcgagtc cttttaaaaag atgggcaagc agtcgggctt cctcttctac  3120
atccctgctt ggaataccag caagattgat ccaactacag gttcgtcaa cccttttcgac  3180
acacggtatg aaaatgtaga taaatcgcgt gcgttcttcg ggaaattcga ttcaatccgt  3240
tatcgggctg acaaaggcac gttcgaatgg acgttcgact acaataactt tcacaaaaaa  3300
gctgagggga cacgttcctc ctggtgcctg agcagccatg gtaaccgggt acggacttttt 3360
cgtaatcctg ccaaaaataa tcagtgggat aatgaggaga tcgacttaac ccaggccttc  3420
cgcgatctct ttgaggcctg gggtattgaa atcactagca accttaagga agccatctgc  3480
aaccaaagtg agaagaaatt cttttctgaa cttttcgaat tgtttaaact catgatccaa  3540
ttgcgtaaca gtgttacagg tactaacatt gattacatgg tgtcaccagt agagaaccat  3600
tacggtacat tttttgactc gcggacatgt gactcatctt tacctgcgaa cgcggacgct  3660
aacggggcat acaacattgc ccgcaaaggg ctgatgttag cccgccggat ccaagcgact  3720
ccagagaacc acccgatttc gcttaccctc tctaacaaag aatggcttcg gtttgcccag  3780
ggtcttgacg aaactacaac ttatgaaggc gcgccaaaaa ggccggcggc cacgaaaaag  3840
gccggccagg caaaaaagaa aaaggctagc ggcagcggcg ccggatcccc aaagaagaaa  3900
aggaaggttg aagaccccaa gaaaaagagg aaggtgtgat aa                     3942

SEQ ID NO: 39          moltype = DNA    length = 3942
FEATURE                Location/Qualifiers
misc_feature           1..3942
                       note = Description of Artificial Sequence: Synthetic
                       polynucleotide
source                 1..3942
                       mol_type = other DNA
                       organism = synthetic construct
SEQUENCE: 39
atgggccacc atcatcatca tcatagcagc ggcctggtgc cgcgcggcag cggtaccatg  60
aaaaccttat ccgatttcac caacttgttt ccgttatcta agactctccg gtttaagtta  120
atccctattg ggaacactct caaaaatatc gaggcgtcgg gtattttaga tgaggaccgg  180
caccgtgctg aaagctacgt taaagttaag gcaatcattg acgagtatca caaggctttc  240
attgatcgcg tcttgtcaga tacctgcctg caaaccgaat caatcggcaa gcacaacagc  300
ttggaagagt tcttttttta ctatcaaatt ggtgcaaaga gcgagcaaca gaaaaagacc  360
ttcaaaaaga ttcaggatgc gttacgcaag cagatcgctg acagtctcac taaagacaaa  420
catttcagtc gcattgataa aaaagaactg atccaagaag acttaattca gtttgtccgt  480
gatggtgaag atgctgcaga gaaaacttca cttatctccg agtttcaaaa cttcacagtg  540
tatttcaccg gcttccacga gaatcgccag aaatatgtact caccggacga gaaaagtaca  600
gccattgcat atcgccttat caacgaaaac ttgcctaaat ttgtcgataa tatgaaggtt  660
ttcgatgcca ttgcagcctc ggagttagca tcatgctttg atgagcttta tcacaacttc  720
gaggaatact tgcaagtcga acgcttgcac gatatcttca gccttgatta tttttaacctt  780
ctcctgaccc aaaagcatat tgatgtctac aatgcattaa tcggtgggaa agctactgag  840
accggcgaaa agattaaagg tttgaatgag tacattaatc tttacaacca gcgccataag  900
caggaaaagc tcccaaagtt taagatgctg ttcaaacaaa tcctcactga ccgcgaagca  960
atctcgtggc tgccgcgcca gttcgacgac aactcgcagc tcctttcagc aatcgagcaa  1020
tgctataacc atctcagtac gtataccttg aaagacggct ccttgaaata tttgttagaa  1080
aatctccata catatgacac agagaagatc tttatccgta acgattcgtt actcacggag  1140
atcagccagc gtcactacgg ttcctggtcc attctgccgg aagcaatcaa acggcacctg  1200
gagcgtgcca atccgcagaa acgccgtgaa acgtacgagg cttatcagag ccgtattgaa  1260
aaagcgttta aagcctaccc aggcttctct atcgcattct tgaatggttg tttgacggaa  1320
actggcaaag aatcgccttc gattgaaagt tacttcgaga tgtcggtgc ggtggagacg  1380
gagacgagtc aacaggagaa ctggttcgct cgtatcgcga acgcttacac cgacttccgg  1440
gagatgcaaa atcgccttca cgcaaccgac gttccactcg gcaagatgc tgaagcggtt  1500
gcgcgtatca aaaaactcct tgatgcctta aaaggcttac aattatttat taagcccttta  1560
ctggatactg ggaggaggc ggaaaaggac gagcggttct atggtgattt tactgaattt  1620
tggaacgaac tcgacacgat tactccatta tacaatatgg tccgtaacta ccttactcgc  1680
aagccttact ccgaggaaaa aattaaattg aacttccaga acccaacgct gcttaatggt  1740
tgggatttaa ataaggaggt cgataacact tcggttatct tacggcgcaa tggccgctat  1800
tatctggcca ttatgcaccg gaaccatcgc cgggtgttct cgcagtgtcc gggcacagag  1860
cgtggcgatt gttatgaaaa gatggagtat aaacttctcc cgggtgctaa taaatgcctg  1920
ccgaaagtat tcttcagcaa gtctcgcatc gacgagttta atccatccga ggagcttctt  1980
gctcggtacc aacaagggac gcataagaaa gcgagaatt tcaacttaca tgattgtcat  2040
gcattgatcg actttttcaa ggactctatc gaaaaacacg aggaatggcg caactttcat  2100
ttcaaattct ccgacaccag ttcttatacc gatatgtcgg ggtttaccg ggagattgag  2160
acgcaaggt ataaactttc gttcgtccca gtggcctgcg agtatattga cgagttggtt  2220
cgcgatggca agattttcct tttcaaatc tataataagg attttctcaac ttatagtaag  2280
gggaagccta acatgcatac gctctattgg gagatgttat tcgacgaacg taatttaatg  2340
aacgtcgtat ataacttaa cgggcaagcc gagatctttt ccgtaaagc gagtctttca  2400
gcccgccatc cagagcaccc tgcaggttta ccgattaaga agaagcaggc tcctacagag  2460
gaatcgtgtt ttccgtatga tcttattaaa aataaacgct atacggtcga tcagtttcaa  2520
```

-continued

```
tttcatgttc caattacgat caacttcaag gccacgggta cctccaatat taatccgtcc 2580
gtgacagatt atattcgcac cgccgatgat ctccacatca ttgggattga ccgtggggag 2640
cgccacttgc tctatctcgt cgttatcgat tcgcagggcc gtatctgcga gcagttcagc 2700
ttgaacgaaa tcgtaacaca atatcagggt catcaatatc gtactgatta ccacgcgctc 2760
ttgcaaaaga aagaggtga gcgtcaaaag gcccgtcagt cctggcaatc tatcgagaat 2820
attaaagaat tgaaagaagg gtacctctcg caagtggttc ataaggtttc agaactcatg 2880
attaaataca aggctatcgt cgtccttgag gacctgaacg ctggttttaa gcgtagccgt 2940
cagaaggtcg aaaagcaggt gtatcaaaaa ttcgaaaaga tgcttatcga caaattgaat 3000
tacttggtct tcaaaactgc cgaggcagac caaccagggg gcctgttgca cgcgtaccaa 3060
ctcacgaaca agtttgaaag ttttaagaag atgggcaaac aatcagggtt tctcttctat 3120
atcccagcct ggaataccto taagattgac ccgacgactg gtttcgttaa cctttttcgat 3180
acccgctacg aaaatgttga taaatcgcgc gcgttctttg gtaagtttga ctcgattcgc 3240
taccgggctg ataaaggcac tttcgaatgg acctttgatt acaataactt ccataaaaa 3300
gcagaaggta cccgtagttc gtggtgtttg tcttctcacg gtaatcgtgt tcggactttt 3360
cggaacccgg caaagaacaa ccagtgggat aacgaagaaa ttgatttaac gcaagcatt 3420
cgggatctct tcgaggcatg gggtattgag attacatcca atttgaagga agctatttgt 3480
aaccaatccg agaagaaatt tttctcggaa ctgttcgaac tctttaaatt gatgatccag 3540
ttgcgtaatt cagtaacagg gaccaacatc gattacatgg tatctccggt cgagaatcac 3600
tatgggacct tttttgattc tcgcacatgt gattccagcc tgccagcgaa cgctgacgca 3660
aatgcgcttt ataacattgc acgcaaaggc cttatgttag ctcggcgtat tcaagccact 3720
ccagagaatg acccaatctc tctgactttaa gtaacaagg aatggcttcg gttcgcccag 3780
ggtttggatg agaccacaac gtatgaaggc gcgccaaaac gcgccggcc cacgaaaaag 3840
gccggccagg caaaaaagaa aaaggctagc ggcagcggcg ccggatcccc aaagaagaaa 3900
aggaaggttg aagaccccaa gaaaaagagg aaggtgtgat aa 3942
```

SEQ ID NO: 40         moltype = AA    length = 1300
FEATURE                Location/Qualifiers
REGION                 1..1300
                         note = Description of Artificial Sequence: Synthetic
                         Cas12a/Cpf1 [Bacteroidetes bacterium HGW-Bacteroidetes-6]
                         sequence
source                 1..1300
                         mol_type = protein
                         organism = synthetic construct
SEQUENCE: 40

```
MKNMESFINL YPVSKTLRFE LKPIGKTLET FSRWIEELKE KEAIELKETG NLLAQDEHRA  60
ESYKKVKKIL DEYHKWFITE SLQNTKLNGL DVFYHNYMLP KKEDHEKKAF ASCQDNLRKQ 120
IVNAFRQETG LFNKLSGKEL FKDSKEEVAL LKAIVPYFDN KTLENIGVKS NEGALLLIEE 180
FKDFTTYFGG FHENRKNMYS DEAKSTAVAF RLIHENLPRF IDNKKVFEEK IMNSELKDKF 240
PEILKELEQI LQVNEIEEMF QLDYFNDTLI QNGIDVYNHL IGGYAEEGKK KIQGLNEHIN 300
LYNQIQKEKN KRIPRLKPLY KQILSDRETA SFVIEAFEND GELLESLEKS YRLLQQEVFT 360
PEGKEGLANL LAAIAESETH KIFLKNDLGL TEISQQIYES WSLIEEAWNK QYDNKQKKVT 420
ETETYVDNRK KAFKSIKSFS IAEVEEWVKA LGNEKHKGKS VATYFKSLGK TDEKVSLIEQ 480
VENNYNIIKD LLNTPYPPSK DLAQQKDDVE KIKNYLDSLK ALQRFIKPLL GSGEESDKDA 540
HFYGEFTAFW DVLDKVTPLY NKVRNYMTKK PYSTEKFKLN FENSYFLNGW AQDYETKAGL 600
IFLKDGNYFL AINNKKLDEK EKKQLKTNYE KNPAKRIILD FQKPDNKNIP RLFIRSKGDN 660
FAPAVEKYNL PISDVIDIYD EGKFKTEYRK INEPEYLKSL HKLIDYFKLG FSKHESYKHY 720
SFSWKKTHEY ENIAQFYHDV EVSCYQVLDE NINWDSLMEY VEQNKLYLFQ IYNKDFSPNS 780
KGTPNMHTLY WKMLFNPDNL KDVVYKLNGQ AEVFYRKASI KKENKIVHKA NDPIDNKNEL 840
NKKKQNTFEY DIVKDKRYTV DKFQFHVPIT LNFKAEGLNN LNSKVNEYIK ECDDLHIIGI 900
DRGERHLLYL SLIDMKGNIV KQFSLNEIVN EHKGNTYRTN YHNLLDKREK EREKERESWK 960
TIETIKELKE GYISQVVHKI TQLMIEYNAI VVLEDLNFGF KRGRFKVEKQ VYQKFEKMLI 1020
DKLNYLVDKK KEANESGGTL KAYQLTDSYA DFMKYKKKQC GFLFYVPAWN TSKIDPTTGF 1080
VNLFDTHYVN VSKAQEFFSK FKSIRYNAAN NYFEFEVTDY FSFSGKAEGT KQNWIICTHG 1140
TRIINFRNPE KNSQWDNKEV VITDEFKKLF EKHGIDYKNS SDLKGQIASQ SEKAFFHNEK 1200
KDTKDPDGLL QLFKLALQMR NSFIKSEEDY LVSPVMNDEG EFFDSRKAQP NQPENADANG 1260
AYNIAMKGKW VVKQIRESED LDKLKLAISN KEWLNFAQRS                       1300
```

SEQ ID NO: 41         moltype = DNA    length = 3903
FEATURE                Location/Qualifiers
misc_feature           1..3903
                         note = Description of Artificial Sequence: Synthetic
                         Cas12a/Cpf1 [Bacteroidetes bacterium HGW-Bacteroidetes-6]
                         sequence
source                 1..3903
                         mol_type = other DNA
                         organism = synthetic construct
SEQUENCE: 41

```
atgaaaaaca tggaatcttt tatcaacctg tatccggtgt cgaaaacttt gcggtttgaa  60
ttgaaaccga ttgggaaaac ccttgaaact ttttcgagat ggattgaaga actgaaagaa 120
aaagaagcta ttgaactaaa agaaacagga aacctattgg ctcaagatga acacagggca 180
gaaagctata aaaaagtaaa aaaaatcctg gacgaatacc acagtggtt tattacagaa 240
tcgcttcaga ataccaaact aaacgggttg gatgtatttt atcacaatta catgctccca 300
aagaaagaag atcatgaaaa gaaggctttt gcaagttgtc agagaaacag 360
atagtcaatg cattcaggca gaaacaggt tgttaata agctgtctgg aaaagagtta 420
tttaaggata gtaaagaaga gtcgcgctt ctaaaggcaa ttgtgcccta tttgataac 480
aaaaccttg agaacatagg agtcaaatca atgaaggcg cctgttact aattgaagaa 540
tttaaagact tcacaaccta tttcggtggc tttcacgaaa accgaaaaaa catgtattcc 600
gatgaagcca aagcacagc tgttgctttt cgtttgatac acgaaaacct tccgcgtttt 660
```

```
attgacaata agaaggtttt cgaagaaaaa attatgaatt ctgaattgaa agataagttc    720
ccggaaattt tgaaagaact tgaacaaatt cttcaagtaa atgagataga agaaatgttt    780
cagttggatt acttcaatga tacattgatt caaaacggaa ttgatgtata taaccatctg    840
attggagggt atgcagaaga gggcaagaaa aaaattcagg gattaaatga acacatcaac    900
ctgtacaacc agattcagaa agaaaaaaac aaaagaatac ccaggctaaa gccccttttac   960
aaacaaatat tgagcgacag ggaaacggca tcttttgtca ttgaggcgtt tgagaacgac   1020
ggcgaattgt tggaaagcct tgaaaaaagc taccgcttac tacaacagga agtattcacc   1080
cctgaaggga agagggctt ggcaaatctg cttgctgcca ttgctgaatc tgaaacccat   1140
aaaattttc taaaaaacga tttgggactt accgaaatat cgcaacaaat ctatgagagt   1200
tggtcgctaa tcgaagaggc atggaacaaa cagtacgaca acaaacaaaa gaaggtaacg   1260
gaaacggaaa cttatgttga taaccgaaaa aaagctttca aatctattaa aagttttcc   1320
attgctgagg ttgaagaatg ggtaaagca ttgggcaatg aaaagcataa aggcaaatca   1380
gtggccacat atttcaaaag tctgggcaaa accgatgaaa aagtatcgtt gattgaacaa   1440
gtagaaaaca attacaatat catcaaagat ttgctgaata cgccttaccc gccatcaaaa   1500
gatttggcac agcaaaaaga tgatgtggag aaaattaaaa attacctaga tagcctaaaa   1560
gccttgcaac ggtttataaa accacttctg ggttcaggcg aagaatccga taagatgca   1620
catttttatg gtgagtttac agcttttgg gatgttctgg acaaagttac accgctttac   1680
aacaaggtaa ggaattacat gaccaaaaag ccctattcta ccgaaaagtt taactaaat   1740
tttgaaaaca gttatttcct taacggatgg gcacaagatt atgagactaa agcaggcctt   1800
atttttctaa aagacggtaa ttattctta gcaataaaa ataaaaaact cgatgaaaaa   1860
gagaaaaaac aattaaaaac aaactacgag aagaatcctg caaaaagaat aatactggat   1920
ttccaaaaac ctgataataa gaatattccc aggttattta ttagatcaaa aggcgataac   1980
tttgctcctg ctgttgaaaa atacaatctt ccaatatctg acgtaattga catttacgat   2040
gaaggaaagt ttaaaactga atatcgaaaa atcaatgaac cagagtattt aaaatcgctt   2100
cataaactaa ttgattattt caaattagga tttagtaaac atgaatccta taaacattat   2160
agtttttcct ggaaaaagac acatgaatat gaaaatattg cacgtttta tcatgatgta   2220
gaagtttcat gttatcaagt gctagatgaa aatatcaatt gggattcatt aatgaaatac   2280
gtagagcaaa acaaactcta tctcttccaa atctacaaca aagattctc cccaaacagc   2340
aagggcactc gaacatgca taccttgtac tggaaaatgc ttttcaatcc tgataattta   2400
aaagatgttg tttataaact caacgggcaa gccgaagtgt ttttaccgaa agccagtatc   2460
aaaaaggaaa ataagatcgt acataaagcc aatgaccca ttgacaataa aaacgaactc   2520
aacaaaaaga aacaaaacac ttttgaatat gacattgtta aggacaaacg ctataccgtt   2580
gacaaattcc agtttcatgt acccataact ctcaatttca aggctgaagg cctcaacaac   2640
ctcaattcaa aagtaaatga atacataaaa gagtgtgaca atttgcacat catcggtatc   2700
gatcgaggcg aacggcattt attgtacctg agtttgattg acatgaaggg aaatatcgtg   2760
aagcaattt cattgaacga aatcgtaaac gaacacaaag gcaatactta ccgcaccaat   2820
taccataatc tgttggacaa acgggaaaaa gaaagagaaa aagaaagaga gagctggaaa   2880
accatcgaaa ccatcaaaga acttaaggaa ggctatattt cgcaggtcgt ccacaaaatc   2940
acccaactga tgattgagta caatgccatt gtagtactcg aagatttgaa ttttggttt   3000
aaacgcggaa ggttcaaagt agaaaagcag gtatatcaga aattcgaaaa gatgttgatt   3060
gataaattga actatctggt tgacaaaaag aaagaggcca acgaatcagg aggtacatta   3120
aaagcgtatc aactaaccga ctcttatgca gactttatga aatataagaa aaaacagtgt   3180
ggtttcttgt tttacgtacc tgcctggaac accagcaaga ttgacccaac tacaggattt   3240
gtaaacctgt ttgacacccc ctatgtaaac gtttcaaaag cgcaggagtt tttcagcaag   3300
tttaaatcta tacgctacaa tgcggcaaat aattattttg agtttgaagt aacagattat   3360
ttctcattta gcggcaaagc agaaggaaca aaacaaaact ggataattg tacacacgga   3420
acaagaatta tcaatttccg aaatcccgaa aaaaacgctc aatgggataa taaagaagtg   3480
gtaattacag atgaattcaa aaaactattg gagaaacatg gaattgatta taaaaattca   3540
agcgacttaa aaggtcaaat cgcatcacaa agtgaaaaag cattttttca caatgaaaaa   3600
aaagacacaa aagacccgga tggcctgcta caattgttca aactagctct gcaaatgcgc   3660
aatagttta tcaaatcaga agaagattat ttggtttctc cggtaatgaca cgatgaagga   3720
gaattcttcg acagcagaaa ggcacagccc aaccacccg aaaatgccga tgccaatggt   3780
gcatacaata ttgcaatgaa aggcaaatgg gtagttaaac aaataaggga aagtgaagat   3840
ctggacaagc tgaaactggc aatcagcaac aaagaatggt tgaattttgc tcaaaggagc   3900
taa                                                                 3903

SEQ ID NO: 42              moltype = AA   length = 1362
FEATURE                    Location/Qualifiers
REGION                     1..1362
                           note = Description of Artificial Sequence: Synthetic
                           polypeptide
source                     1..1362
                           mol_type = protein
                           organism = synthetic construct
SEQUENCE: 42
MGHHHHHHSS GLVPRGSGTM KNMESFINLY PVSKTLRFEL KPIGKTLETF SRWIEELKEK    60
EAIELKETGN LLAQDEHRAE SYKKVKKILD EYHKWFITES LQNTKLNGLD VFYHNYMLPK   120
KEDHEKKAFA SCQDNLRKQI VNAFRQETGL FNKLSGKELF DSKEEVALL KAIVPYFDNK   180
TLENIGVKSN EGALLLIEEF KDFTTYFGGF HENRKNMYSD EAKSTAVAFR LIHENLPRFI   240
DNKKVFEEKI MNSELKDKFP EILKELEQIL QVNEIEEMFQ LDYFNDTLIQ NGIDVYNHLI   300
GGYAEEGKKK IQGLNEHINL YNQIQKEKNK RIPRLKPLYK QILSDRETAS FVIEAFENDG   360
ELLESLEKSY RLLQQEVFTP EGKEGLANLL AAIAESETHK IFLKNDLGLT EISQQIYESW   420
SLIEEAWNKQ YDNKQKKVTE TETYVDNRKK AFKSIKSFSI AEVEEWVKAL GNEKHKGKSV   480
ATYFKSLGKT DEKVSLIEQV ENNYNIIKDL LNTPYPPSKD LAQQKDDVEK IKNYLDSLKA   540
LQRFIKPLLG SGEESDKDAH FYGEFTAFWD VLDKVTPLYN KVRNYMTKKP YSTEKFKLNF   600
ENSYFLNGWA QDYETKAGLI FLKDGNYFLA INNKKLDEKE KKQLKTNYEK NPAKRIILDF   660
QKPDNKNIPR LFIRSKGDNF APAVEKYNLP ISDVIDIYDE GKFKTEYRKI NEPEYLKSLH   720
KLIDYFKLGF SKHESYKHYS FSWKKTHEYE NIAQFYHDVE VSCYQVLDEN INWDSLMEYV   780
EQNKLYLFQI YNKDFSPNSK GTPNMHTLYW KMLFNPDNLK DVVYKLNGQA EVFYRKASIK   840
```

```
KENKIVHKAN DPIDNKNELN KKKQNTFEYD IVKDKRYTVD KFQFHVPITL NFKAEGLNNL   900
NSKVNEYIKE CDDLHIIGID RGERHLLYLS LIDMKGNIVK QFSLNEIVNE HKGNTYRTNY   960
HNLLDKREKE REKERESWKT IETIKELKEG YISQVVHKIT QLMIEYNAIV VLEDLNFGFK  1020
RGRFKVEKQV YQKFEKMLID KLNYLVDKKK EANESGGTLK AYQLTDSYAD FMKYKKKQCG  1080
FLFYVPAWNT SKIDPTTGFV NLFDTHYVNV SKAQEFFSKF KSIRYNAANN YPEFEVTDYF  1140
SFSGKAEGTK QNWIICTHGT RIINFRNPEK NSQWDNKEVV ITDEFKKLFE KHGIDYKNSS  1200
DLKGQIASQS EKAFFHNEKK DTKDPDGLLQ LFKLALQMRN SFIKSEEDYL VSPVMNDEGE  1260
FFDSRKAQPN QPENADANGA YNIAMKGKWV VKQIRESEDL DKLKLAISNK EWLNFAQRSA  1320
AAKRPAATKK AGQAKKKKAS GSGAGSPKKK RKVEDPKKKR KV                    1362

SEQ ID NO: 43           moltype = DNA   length = 4092
FEATURE                 Location/Qualifiers
misc_feature            1..4092
                        note = Description of Artificial Sequence: Synthetic
                        polynucleotide
source                  1..4092
                        mol_type = other DNA
                        organism = synthetic construct
SEQUENCE: 43
atgggccacc atcatcatca tcatagcagc ggcctggtgc cgcgcggcag cggtaccatg   60
aagaacatgg agtctttat taatttatat ccggtttcga aaactttacg ttttgagtta  120
aagcctattg gcaaaaacact cgaaactttc tcccgctcga tcgaagagtt gaaagagaaa  180
gaggctattg agctgaaaga actggcaac ctgttggcgc aggatgagca tcgggccgag  240
tcttataaga aggtcaaaaa aattcttgac gaatatcata aatggttcat cactgaaagc  300
ctccagaaca caaagtaaa tgggttggac gtttttatc ataactatat gctcccgaag  360
aaagaggacc atgagaagaa agcttttgct tcgtgtcaaa ataatctccg taagcaaatt  420
gtaaacgcgt tcgtcaaga aaccggttta tttaacaaac tgtcaggcaa agaactgttt  480
aaagattcga aggaagaggt tgcactgttg aaagccattg taccgtattt cgataacaag  540
actctgaaa acattggtgt taagagtaat gaagggctc tccttttaat tgaagagttc  600
aaggattta ccacgtattt cggtggcttc catgagaatc gcaaaaatat gtatagcgac  660
gaagcaaaat caacagcggt tgccttcgt cttattcacg aaatttgcc gcgcttcatt  720
gacaataaga aggtcttcga agagaaaatc atgaatagtg aattaaagga taaatttcca  780
gagattttga aggagctgga acagattctg caagtcaacg agattgaaga gatgtttcag  840
ctcgactatt ttaacgacac attgatccag aatggcatcg atgtctataa ccatttgatc  900
ggcggctacg ccgaggaagg caagaaaaa attcaagggc ttaacgagca tattaacctc  960
tataaccaga tccagaagga gaagaataag cgtatcccgc ggctgaaacc actctataag 1020
caaattttga gtgatcgcga aaccgcctca tttgttatcg aggcgtttga aacgatggc 1080
gagttattag aatcattgga gaagtcatat cgcttactgc agcaggaggt ctttacgcct 1140
gaaggtaaa aagtctggc gaattactc gcagcaatcg ctgaaagcga gacacacaag 1200
atctttctga agaacgactt gggtctcacc gagatctctc aacaaaatta tgaatcatgg 1260
tcgctgattg aagaggcatg gaataaacaa tatgacaaca aacagaagaa agttacggag 1320
acagagacat atgtggacaa tcggaaaaag gctttcaagt ccatcaagag ctttagcatc 1380
gcagaggttg aggaatgggt gaaagcactt gggaatgaca aacacaaggg caaaagcgtg 1440
gcaacctatt ttaaaagtct cgggaagact gacgaaaaag ttagcctat tgaacaggta 1500
gagaacaatt ataatatcat caaggacctt ttgaacacac cgtatcctcc ttcgaaggac 1560
ttggcccagc aaaaagatga cgttgaaaaa atcaaaaatt atttggactc tctgaaggcc 1620
ctccagcgt tcattaagcc attgttgggt agcggggagg aatccgataa agatgcgcac 1680
ttttatggtg agtttaccgc tttctgggat gtgctcgaca aagtaacccc actctacaat 1740
aaagtccgca actatatgac taagaaacct tatagcacag agaaatttaa gctgaatttt 1800
gaaaatagtt acttttgaa tggttgggca caggactacg agacaaaagc ggggcttatc 1860
ttcttgaagg acggcaatta cttccttgcc atcaataata agaaattaga tgaaaaggag 1920
aaaaaacagc tcaagactaa ttatgagaag atcctgcga agcgtatcat cttagacttt 1980
cagaagccag acaataagaa cattcctcgc ttgttcattc gcagtaaagg cgacaatttc 2040
gctcctgcag tagaaaagta taatcttccg atctctgacg ttattgacat ctatgacgag 2100
gggaagttta agactgagta tcgcaaaatt aacgagccgg aatatctca atctctccat 2160
aagctgattg actacttcaa acttgggttc tccaagcatg aatcctaca gcattattct 2220
ttttcatgga agaaacaca tgagtatgag aacatcgcc agtttaccca cgacgtggag 2280
gtctcttgct atcaggtgct cgacgaaaat attaactggg attccctcat ggagtatgta 2340
gaacagaaca aattgtactt gttccagatt taaacacag acttctcccc aaactcgaaa 2400
ggcactccga atatgcacac tttgtactgg aagatgttgt taatccgga taatcttaag 2460
gacgtggtct ataagctgaa cggtcaggct gaagtattct accggaaggc gagtattaag 2520
aaagaaaaca agattgtcca aaggcgaac gaccctattg acaataaaaa cgagttgaat 2580
aagaaaaagc aaaatacatt tgaatacgac atcgtcaaa ataaacgta tacagtggat 2640
aagtttcaat tccatgttcc tatcacgctc aactttaaag ctgaaggcct gaataacttg 2700
aatagcaaag ttaacgaata catcaaagag tgtgacgacc ttcacattat tggcatcgac 2760
cggggtgaac ggcaccctctt gtatctgagc ctcatcgata tgaaaggtaa cattgtaaag 2820
caatttagtc ttaacgagat cgttaatgag cacaagggga acacgtaccg cacgaactat 2880
cataacctct tggacaaacg tgaaaaggaa cgtgaaaaga gcgcgagtc atggaaaacc 2940
attgagacca tcaaagagct gaaagaaggc tatattagtc aagtagtaca taaatcact 3000
cagttaatga tcgaatataa tgcgatcgtt gtactcgaag acctgaattt cggcttcaaa 3060
cgcggccggt tcaaggtgga aagcaagtg tatcaaaaat ttgagaagat gttaattgat 3120
aaactgaact acttggtcga taagaagaag aagccaatg agagtggcgg gacactcaaa 3180
gcctaccagc ttacgatag ttacgctgac ttcatgaagt acaagaaaaa gcaatgcggc 3240
ttcctgttcg aatccccggc ctggaacact tccaaaatcg atcctactac tggttcgtg 3300
aatctgttg acacacatta tgtcaatgtt agtaaggccc aggaatttt ctcgaaattc 3360
aagtcaattc gctacaacgc ggccaacaac tatttcgagt ttgaagtaac agattatttt 3420
tccttcagtg gtaaagctga gggcaccaag cagaattgga tcatttgcac ccatggcacc 3480
cgcattatca ttttcgtaa cccggaaaaa aattcgcagt gggataataa ggaagtagtg 3540
atcacagatg aattcaagaa actgtttgag aagcacggca ttgactacaa aaatagttcc 3600
```

```
gacctcaagg ggcagatcgc ctctcaatcg gagaaggcgt ttttttcataa cgaaaaaaaa   3660
gatacaaagg acccagatgg ccttctgcag cttttttaaac tggcgctgca gatgcggaac   3720
tctttcatta agagcgaaga ggactactta gtatctcctg tgatgaacga cgaaggtgaa   3780
ttctttgact cgcgcaaagc ccagcctaat cagccagaga acgctgatgc taatggggcg   3840
tacaatattg caatgaaagg gaaatgggtt gttaagcaaa tccgcgaatc ggaggacctc   3900
gacaagctga aactggcaat ctcaaataaa gaatggttga acttcgccca gcgctccgcg   3960
gccgcaaaaa ggccggcggc cacgaaaaag gccggccagg caaaaaagaa aaaggctagc   4020
ggcagcggcg ccggatcccc aaagaagaaa aggaaggttg aagaccccaa gaaaagagg    4080
aaggtgtgat aa                                                       4092

SEQ ID NO: 44         moltype = DNA   length = 4092
FEATURE               Location/Qualifiers
misc_feature          1..4092
                      note = Description of Artificial Sequence: Synthetic
                      polynucleotide
source                1..4092
                      mol_type = other DNA
                      organism = synthetic construct
SEQUENCE: 44
atgggccacc atcatcatca tcatagcagc ggcctggtgc cgcgcggcag cggtaccatg   60
aaaaatatgg aatcgtttat taacctttac cctgtttcaa agacattacg gttcgagctc   120
aagccgatcg gcaaaacctt agagactttc tcccggttgga tcgaagagct caaagaaaaa   180
gaggcaatcg agcttaaaga aaccgggaac ttattagcac aagatgaaca tcgcgcagag   240
tcctataaga aagtgaagaa aattctcgac gagtatcata aatggtttat taccgaaagc   300
cttcagaata ccaaattgaa tggtttggat gttttctacc ataactacat gctccctaag   360
aaagaagatc acgagaaaaa agcctttgcc tcctgccaag acaatttacg caagcaaatc   420
gtcaacgctt tccgtcagga gactgggttg ttcaacaaat tgtcaggaa ggaactgttt    480
aaggactcga agaagaagt tgcgttgttg aaagcaatcg tgccgtattt tgacaataag    540
acgcttgaga acatcggcgt gaagtccaat gagggggctc tccttcttat tgaggaattt   600
aaggactttta ccacatattt cggcggcttt catgaaaacc gtaagaacat gtactcggat   660
gaagctaaat caactgcagt agcctttcgt cttattcacg agaacctccc acggttcatc   720
gataacaaga aagtattcga ggaaaagatc atgaacagtg agttgaagga taatttccg    780
gaaatcctga aggaactgga acaaatcctg caggtgaacg agattgaaga aatgtttcag   840
ctcgactatt ttaatgatac acttatccaa aatggtatttc acgttacaa ccatctcatc    900
ggcgggtatg ctgaggaggg taagaagaaa atccagggct tgaatgagca tatcaattta   960
tataatcaga tccaaaagga gaagaataaa cgtatcccgc gccttaagcc gttatataag   1020
caaattctgt ctgaccggga aacagcgtca ttcgtaatcg aagctttcga gaacgatggg   1080
gagttgctcg aatctctgga aaaatcgtac cgtctcttac aacaagaggt gttcacacct   1140
gaggggaagg aagggctcgc gaacttgctg gccgccattg cagagtcgga aactcacaag   1200
atctttctca agaacgactt gggcttaaca gagatctcac agcagattta cgagtcctgg   1260
agcttgatcg aagaagcttg gaacaaacag tacgataaca gcagaaaaa agtgactgag   1320
acggagcgt atgttgacaa tcgcaaaaag gcattcaaaa gcatcaagag ttttagtatc   1380
gctgaagttg aagaatgggt aaaagcgctt gggaatgaga agcacaaagg gaaatcgatt   1440
gcaacatact ttaagtctttt agggaagact gatgagaagg tgagcctcat gaacaagtg    1500
gagaataatt ataacattat taaagatctc ctcaacactc cgtaccctcc ttccaaagac   1560
ctcgcgcagc agaaggatga cgtagagaag atcaagaact acctcgattc tctgaaggcc   1620
ttacagcgtt ttatcaaacc gctcctgggc tcaggtgagg aaagtgacaa ggacgctcac   1680
ttctatggcg agttcaccgc cttctgggac gttcttgata aggtgacgcc tctgtacaat   1740
aaagtacgta actacatgac taaaaaaccg tattccacgg aaaagtttaa acttaatttc   1800
gagaatagtt atttcctgaa cgggtgggcg caagactatg aaacgaaggc aggtttaatc   1860
ttccttaagg atggtaacta cttcttagct attaacaaca aaaagctgaa tgaaaaggag   1920
aagaagcagt tgaaaactaa ctatgagaag aacccagcca agcggattat tcttgattt    1980
caaaagccag ataacaagaa cattcctcgt ttatttatcc gtagcaaagg tgacaatttc   2040
gcgccagctg tagaaaagta caatctgcca atcagtgatg tcattgacat ttatgacgaa   2100
gggaaattta agaccgaata ccggaagatc aacgagcctg aatatctgaa atctcttcac   2160
aaactcatcg attacttcaa attgggcttc agcaaacacg agtcatacaa acattactca   2220
ttttcatgga aaaagacaca cgagtatgaa aatattgccc aattctatca tgatgtagaa   2280
gtgagttgtt accaagttct tgacgaaaat atcaactggg acagtttgat ggagtatgtc   2340
gaacagaaca agctgtacct ctttcaaatc tataataaag acttctcacc aaactccaaa   2400
ggcacaccaa acatgcacac gttatattgg aaaatgctct ttaaccctga taacctcaag   2460
gacgtcgtat ataaactcaa tggtcaggcc gaggtgttct accgtaaagc ttcaattaaa   2520
aaagaaaaca aaatcgttca taagcaaac gatccaatcg acaacaaaaa cgagctcaac   2580
aaaaaaaaac agaacacatt tgagtacgat atcgtcaagg ataagcgtta tactgtcgac   2640
aaatttcaat ttcacgttcc gatcaccttg aacttcaaag ccgaaggcct taacaatctg   2700
aattctaagg ttaatgagta catcaaagaa tgcgatgatc tgcacatcat tggcattgat   2760
cgtggtgagc gccaccttgt tgtatctgagt ctcattgata tgaaaggtaa cattgtgaaa   2820
cagttcagtc ttaatgaaat cgttaacgaa cacaagggta atacttaccg gacgaattat   2880
cacaacctcc ttgacaagcg cgagaaggag gcgcgaaaag aacgcgagag ctggaaaact   2940
atcgaaacta tcaaggagct taaagaaggt tacatttcac aggttgtaca caaattacg    3000
cagctcatga tcgaatacaa cgcaatcgtc gtacttgaag acttaaactt cgggtttaag   3060
cgggggcggt ttaaagtaga aaagcaagtg taccaaaaat tcgaaaagat gctgatcgac   3120
aaattgaatt atctcgtaga taaaaagaag gaagcgaatg agtctggtgg actttaaaa    3180
gcttaccaac tcactgattc ttatgcagac tttatgaaat acaaaaaaaa gcagtgcggc   3240
tttctttttt acgtgcctgc atggaataca tcctactac gggttttgtt                3300
aatctgtttg acacgcatta cgttaatgtg tccaaggccc aggagttctt ttcaaagttc   3360
aagtccatcc ggtacaacgc cgcgaacaac tactttgagt tcgaggttac ggactacttc   3420
agcttttcgg gcaaagcgga aggcactaaa cagaactgga tcatctgtac ccacgggact   3480
cggatcatca actttcgtaa cccagaaaaa aatcccagt gggacaacaa ggaggtcgta   3540
attccgacg agttcaaaaa acttttttgaa aaacacggta ttgattataa aaactcgtct   3600
```

```
gatctcaaag gccaaattgc cagtcagtcg gagaaagcgt ttttcacaa tgaaaaaaag    3660
gataccaaag acccgacgg cttgttacag ctgtttaaac tggcactcca gatgcggaat    3720
tcgttcatca agagtgagga ggactacttg gtttcgccag tcatgaacga tgaaggcgag    3780
tttttgact cccgcaaggc gcaaccaaac caacctgaaa atgccgacgc caatggtgcc    3840
tataacattg cgatgaaggg gaagtgggtc gtgaagcaga ttcgggaatc cgaagactta    3900
gacaagctga aattggccat cagtaataag gagtggctta acttcgcaca acgtctggc    3960
gcgccaaaaa ggccggcggc cacgaaaaag gccggccagg caaaaaagaa aaaggctagc    4020
ggcagcggcg ccggatcccc aaagaagaaa aggaaggttg aagaccccaa gaaaagagg    4080
aaggtgtgat aa                                                        4092

SEQ ID NO: 45          moltype = DNA   length = 4092
FEATURE                Location/Qualifiers
misc_feature           1..4092
                       note = Description of Artificial Sequence: Synthetic
                       polynucleotide
source                 1..4092
                       mol_type = other DNA
                       organism = synthetic construct
SEQUENCE: 45
atgggccacc atcatcatca tcatagcagc ggcctggtgc cgcgcggcag cggtaccatg      60
aaaaacatgg agagcttcat caacttatat ccggtctcca aaacgttgcg ctttgaactc     120
aaaccaattg ggaagacctt ggaaaccttt tcgcgctgga ttgaagaact taaagaaaaa     180
gaggccatcg aattaaaaga gaccgggaac ttgctggccc aagacgaaca tcgcgcagag     240
tcgtacaaga aagtgaagaa aattctggac gaataccata agtggtttat cacagaatcc     300
ttacagaata cgaagctgaa cggttggat gtgttctacc ataattatat gttgccgaag     360
aaagaagatc acgaaaaaaa agcattcgct agttgtcaaa acaatctgcg caaacaaatt     420
gtgaacgcgt tcggcaaga aactggtctg tttaacaagc tctccggcaa ggagctgttt     480
aaggattcca aggaggaggt agcacttctg aaggcaatcg tgccatactt tgataacaag     540
acgttggaaa acattggggt aaaaagcaat gaaggtgctt tgttgctgat cgaggaattt     600
aaggatttca cgacctactt cggtggcttt catgagaacc gtaaaaacat gtatagcgac     660
gaggctaagt ccacagccgt cgcattccgt cttatccacg agaaccttcc acggttcatc     720
gacaataaga aggtatttga ggaaaaaatc atgaacagtg agctcaagga caagtttcct     780
gaaattctca aggaattaga acagatcctg caggtgaatg aaatcgaaga gatgttccaa     840
ttagattatt ttaatgatac cctgatccag aatggtattg acgtttataa tcatttgatt     900
ggcgggtacg cggaagaagg caagaagaaa attcaaggcc ttaatgaaca tattaatttg     960
tataaccaga tccaaaagga gaagaataag cgcatcccac gtttgaagcc actgtacaaa    1020
caaattttgt ctgatcgcga aacggcaagt tttgtaatcg aagcttttga aaatgatggg    1080
gaactccttg aatcgttaga aaagtccat cgtcttctcc agcaagaagt cttcactcca    1140
gaaggcaagg aggtctggc aaatttactt gcagccatcg cggagagcga aaccataag    1200
atcttcctca aaaacgattt ggggttaaca gagatcagtc aacaaattta cgaatcctgg    1260
tccctgattg aggaggcgtg gaacaaacag tacgataata aacaaagaa ggttacagaa    1320
acagagacat acgtggacaa tcgcaaaaag gcgtttaaat cgatcaagag tttctccatc    1380
gcggaggtcg aagagtgggt gaaagctctg ggaaacgaaa agcataaggg caagtccgta    1440
gcgacatatt ttaaatcact gggcaaaacc gatgagaagg tgtcacttat tgagcaagtg    1500
gagaacaatt ataatatcat caaggacctt ttaaacaccc cttacccacc ttcgaaggat    1560
ctggctcaac aaaaggatga cgttgagaaa atcaaaaact acctggattc tttaaaagca    1620
ttgcagcgtt ttatcaagcc attattaggt agcggcaaga agtcagacaa ggatgcacat    1680
ttctatgggg aatttaccgc attctggaac gtattggaca aagtaactcc gttatataat    1740
aaagttcgga attatatgac gaaaaagccg tatagcacag aaaagtttaa gctgaatttt    1800
gagaattctt acttccttaa tgggtgggcg caagattatg aaactaaagc cggtctgatc    1860
ttcttgaagg acggcaacta ttttttggct attaataata agaaattaga cgaaaaggaa    1920
aaaaaacaat taaaaccaa ctacgagaag aacccggcga agcgtattat tctcgacttc    1980
caaaagccag ataataagaa cattcctcgc ttatttatcc gttcgaaagg gataatttt     2040
gctccagccg tcgaaaagta caacttgccg atttcagatg tgatcgatat ctacgatgag    2100
ggcaagttca agaccgaata ccgtaaaatt aacgaaccgg atacctgaga gagccttcat    2160
aagttgatcg actacttcaa attagggttc tctaaaacag agtcctataa gcactattcc    2220
tttagttgga aaaaaaccca cgaatatgaa aacatcgcac agtttaccca cgatgtggag    2280
gttagctgtt accaagtttt ggacgagaac atcaactggg attccctgat ggagtatgtc    2340
gagcaaaata gctgtacct cttccagatc tacaataagg acttagtcc taacagtaaa    2400
gggacccccaa acatgcacac cttatattgg aagatgctct ttaaccctga caatttaaag    2460
gacgtcgtgt ataagctgaa tgggcaagcc gaagtttttt atcggaaggc gagtatcaaa    2520
aaggaaaata aaatcgtaca caaagctaac gaccctattg caataaaaaa cgaacttaac    2580
aaaaaaaagc aaaacacttt tgaatacgat atcgttaaag ataaacgtta tagtggat    2640
aaattttcag tccccacgttcc gatcacactc aacttcaagg ctgagggctt gaataacctg    2700
aatagtaagg tcaatgaata catcaaagaa tgtgatgatc tccatattat tggcattgac    2760
cgtggtgagc ggcatctgct ttatttatca ctgattgata tgaagggcaa tattgtaaag    2820
caatttagtc ttaacgagat tgtaaacgaa cataaaggta acacttaccg gactaattac    2880
cataattat tggacaagcg ggaaaaagaa cgggaaggag aactggaaaact    2940
atcgaaacaa ttaaggagct caaagagggg tatatcagcc aagttgtcca caaatcacc    3000
cagctgatga ttgagtataa tgcgattgta gtactggagg acctgaattt ggttttaag    3060
cgcggtcgtt ttaaagtgga gaacaagtg tatcaaaagt ttgagaagat gctcatcgac    3120
aagctcaatt acctggtaga taaaagaaa gaggcgaacag agtcaggtgg tacgctgaaa    3180
gcctaccagt tgacagacag ttacgcgac ttcatgaagt acaaaaaaaa acagtgcggc    3240
ttttattttt atgttcctgc gtggaataca agcaagatcg atccgcaac ggggttcgtg    3300
aacttatttg atactcatta tgtaaacgtc agtaaagccc aagaattctt ttccaagttt    3360
aagtctatcc gctataacgc agcaaacaat tactttgaat ttgaggttac ggattacttt    3420
agttttagcg gtaaggcaga ggggacaaaa caaaactgga tcatttgcac acacggggaca    3480
cggatcatta acttccgcaa tccggaaaag aactcgcaat gggacaataa agaagtcgta    3540
attactgacg agttcaaaaa actcttcgaa aaacacggta tcgattacaa aaattccagt    3600
```

```
gatttaaagg ggcaaattgc ttcgcaatcg gagaaggcgt tcttccataa tgaaaagaag  3660
gacacgaagg acccagatgg gctgttgcag ctttttaaat tggccctcca aatgcgcaat  3720
agttttatca aatcagagga agattattta gtctcaccag ttatgaatga cgagggtgag  3780
tttttcgact cacgcaaggc acaaccaaat cagccggaaa acgcggacgc aaatgggget  3840
tacaatatcg ctatgaaggg taaatgggtt gtaaaacaga tccgcgagtc ggaggatttg  3900
gacaaactta aattggccat ctcaaataaa gagtggctta acttcgctca acggtctggc  3960
gcgccaaaaa ggccggcggc cacgaaaaag gccggccagg caaaaaagaa aaaggctagc  4020
ggcagcggcg ccggatcccc aaagaagaaa aggaaggttg aagaccccaa gaaaagagg   4080
aaggtgtgat aa                                                      4092
```

```
SEQ ID NO: 46           moltype = DNA   length = 4092
FEATURE                 Location/Qualifiers
misc_feature            1..4092
                        note = Description of Artificial Sequence: Synthetic
                        polynucleotide
source                  1..4092
                        mol_type = other DNA
                        organism = synthetic construct
SEQUENCE: 46
atgggccacc atcatcatca tcatagcagc ggcctggtgc cgcgcggcag cggtaccatg   60
aagaatatgg agtcgtttat caacttatac ccggtttcaa aaactttgcg ttttgagctc  120
aaaccaatcg ggaaaacctt ggaaacattt tcacgttgga tcgaggaatt gaaggagaag  180
gaggctatcg aattgaaaga aacgggcaat cttcttgccc aggacgaaca ccgtgccgaa  240
tcctacaaaa aagtaaagaa gattctcgat gaataccaca agtggtttat cacggaaagc  300
ctccaaaaca caaaacttaa tggcctcgac gtattctatc acaattatat gctcccgaag  360
aaagaggacc atgaaaagaa agcatttgca agttgccagg ataatcttcg gaaacaaatt  420
gttaacgcat ttcgtcagga gaccgggctt tttaacaaat tatcaggaa agagctcttt   480
aaggactcta aggaagaggt cgctctgttg aaagcaattg tgccatattt tgataacaag  540
acgttggaga acattggtgt caagtctaac gaaggggcat gttgctcat tgaggaattc   600
aaagacttca ctacttactt cggcggcttc cacgaaaatc ggaaaaatat gtattccgat  660
gaggcgaaat ctactgccgt agcattccgg ttgatccatg agaatctccc acgcttcatt  720
gacaataaga agtatttga ggagaaaatt atgaattcag agcttaaaga taaattccca  780
gagattctca agaactgga gcagattttg caagtcaatg aaatcgagga aatgttccag  840
ctcgattatt tcaacgatac tctcatccaa aatgggattg atgtctacaa ccatctcatc  900
ggtggctatg cggaagaagg gaagaagaaa atccagggtt taaacgagca catcaatctg  960
tacaatcaaa ttcaaaagga aaagaacaaa cggattccac gcctcaagcc gttatacaag 1020
caaatcctct ctgatcgtga aaccgcttca ttcgtaatcg aggcgtttga gaacgatggc 1080
gaacttctgg agtccctcga aaagtcctac cgtttgttgc aacaagaggt tttcacgcca 1140
gagggcaagg agggcctcgc aaacttttg gcggcgttg cagaatctga gacacacaa   1200
atcttcttga agaatgactt agggctgacg gagatcagtc aacagattta cgaatcctgg 1260
agcttaatcg aagaggcctg gaacaaacaa tacgacaata gcaaaagaa ggtaacggaa  1320
acggagacat atgtcgataa ccgtaaaaaa gcattcaaaa gcattaaaag cttcagcatt 1380
gcagaggtcg aagaatgggt caaggcgtta ggcaacgaga aacacaaggg taaatccgtt 1440
gcaacttact tcaaaagttt ggggaagacc gacgagaagg tttccctcat tgagcaagtg 1500
gagaataatt acaatatcat caagatctc ctgaacaccc cttatccgcc ttctaaggat  1560
ctggcacaac agaaggatga tgttgagaaa attaagaatt acttagatag tttgaaggcc 1620
ttacagcgtt tcattaaacc tcttcttggg tccggtgaag agagcgataa agacgctcat 1680
ttctatggtg aatttacggc cttttgggat gtcttagaca aagtcacacc gctgtataat 1740
aaagtgcgta actatatgac taaaaagccg tatagtacgg agaagtttaa gctgaacttc 1800
gagaattctt acttttgaa tgggtgggcc caggattacg aaactaaagc agggctgatt  1860
ttcctgaagg atgggaatta ttttttagcg attaacaata agaagctgga cgagaaggaa 1920
aagaagcagt tgaagaccaa ctatgaaaag aacccggcga acgatcattt tagacttt   1980
cagaaaccgg ataataaaaa cattccacgt cttttcattc gctccaaagg ggacaatttc 2040
gccccggccg tagagaaata caatcttccg atcagcgacg ttatcgatat ctacgacgag 2100
ggtaagttta aaactgagta ccggaagatc aacgagccgg aatacctgga gagtttacat 2160
aaattaattg actacttcaa gcttggcttt agtaagcacg agagttacaa cgactattct 2220
ttttcatgga aaaaaactca cgagtacgag aacattgccc aattaccat gacgttgaa   2280
gtatcatgtt atcaggtact ggacgagaat attaattggg acagcttaat ggagtatgtt 2340
gagcagaata aactttattt attccagatc tataacaaag atttctcgcc gaattcaaaa 2400
ggtaccccga atatgcatac cttatactgg aagatgctct ttaatcctga caacttaaaa 2460
gatgtggtt acaagctcaa cggccaggct gaagtcttct accggaaggc ttccatcaaa 2520
aaagagaata agatcgtaca taagctaac gatccaatcg acaataaaaa cgaactcaac  2580
aagaaaaaac aaaatacgtt tgagtatgac attgtaaagg ataaacgtta cactgtggac 2640
aagttccagt ttcatgtacc tattactta aacttcacga cagggcct caacaattta    2700
aattcgaagg ttaacgaata catcaaggag tgtgacgatc ttcatattat cgggattgat 2760
cgtggtgaac ggcacttact gtatttgtca ctcattgata tgaaaggcaa catcgtcaaa 2820
cagttctcgc tcaacgaaat cgtaaatgag cataagggta atacatatcg gactaactat 2880
cataatttac ttgataaacg ggaaaaggaa gcgcgaaaag aacgcgagag ctggaaaact 2940
atcgaaacca tcaaggagct caaagagggc tatatttcac aggtcgtaca taaaatcact 3000
cagttgatga tcgagtacaa cgcgatcgtt gtgttggagg attttaaattt tgggtttaaa 3060
cgtggtcgtt ttaaggtcga aaagcaagtg tatcaaaagt tcgaaaagat gctgattgac 3120
aaattaaatt atctggtgga caagaagaaa gaggcaaatg aatcaggtgg acattgaag   3180
gcataccaac tcacgcgattc ttatgctgac ttcatgaagt ataagaaaaa gcagtgcggg 3240
tttttattct atgttccagc ctgaaacact tcaaagatcg atccgacgac aggctttgta 3300
aacctcttcg atacgcacta cgtgaatgtc agcaaggcac aagagttttt cagcaaattc 3360
aagtcgattc gctacaacgc ggcaaacaat tattttgaat ttgaagttac tgactatttt 3420
tcattttcag ggaaggcgga aggtacgaaa caaaactgga ttatttgcac ccacggcact 3480
cggattatta ttttcggaa cccggaaaaa aactcacagt gggacaacaa agaggtcgta 3540
atcactgatg agttcaagaa actctttgag aaacacggga ttgactacaa gaacagttct 3600
```

```
gatttgaagg gccagatcgc atcacagtct gaaaaggcgt tttttcataa tgagaaaaag 3660
gacacaaagg atccggacgg cctcttacag ctctttaaac tggccttgca aatgcgcaac 3720
tcatttatta agtcaggagga ggattatttg gtttcaccag tcatgaacga cgaagggag 3780
ttcttcgatt cgcggaaggc ccagccgaac caaccgaaa atgctgatgc aaatggtgcc 3840
tataacattg cgatgaaggg gaagtgggtc gtcaaacaga tccgcgaatc agaagacttg 3900
gataagttga aactcgccat ctcgaacaag gagtggctta acttcgcgca gcgtagtggc 3960
gcgccaaaaa ggccggcggc cacgaaaaag gccggccagg caaaaaagaa aaaggctagc 4020
ggcagcggcg ccggatcccc aaagaagaaa aggaaggttg aagaccccaa gaaaagagg 4080
aaggtgtgat aa                                                     4092
```

| SEQ ID NO: 47 | moltype = DNA  length = 4092 |
|---|---|
| FEATURE | Location/Qualifiers |
| misc_feature | 1..4092 |
| | note = Description of Artificial Sequence: Synthetic polynucleotide |
| source | 1..4092 |
| | mol_type = other DNA |
| | organism = synthetic construct |

SEQUENCE: 47
```
atgggccacc atcatcatca tcatagcagc ggcctggtgc cgcgcggcag cggtaccatg 60
aagaatatgg agagcttcat taacttgtac cctgtatcta agacgttgcg ttttgagctt 120
aagccgattg gcaagacgct ggagaccttc tcccggtgga ttgaggagtt gaaagaaaaa 180
gaagcgatcg aattgaagga gacaggcaat ctttttagcgc aagatgagca ccgcgctgag 240
tcctataaga aggtaaagaa aattctggac gaatatcaca aatggttcat taccgaaagc 300
cttcagaaca ctaagttgaa cgggcttgac gtcttttatc acaactacat gctgccgaaa 360
aaagaagacc atgaaaagaa ggcgtttgca tcgtgtcagg acaacttacg gaaacaaatc 420
gtgaatgcct ttcgccagga gacaggctta tttaataagc tctccggtaa ggaactgttt 480
aaagactcaa agaggaagt cgcattgttg aaagccattg tcccgtactt cgataataaa 540
actctggaga atattgggt caagagcaac gagggtgctc ttctgttaat cgaagagttc 600
aaagatttca ccacttactt tggtgggttt cacgaaaatc ggaaaaatat gtattcagac 660
gaggcgaaat cgacggccgt cgcctttcgt ctgatccatg aaaatttgcc acggttcatt 720
gacaataaga aggttttga ggaaaagatc atgaatagcg aattaaaaga caaattcccg 780
gaaatcctta agagctcga gcaaatcctt caagtgaacg agatcgaaga atgttccag 840
ctcgactact caatgatac actgatccag aatggcattg acgtatacaa tcacctgatc 900
ggtgggtatg cagaagaagg taaaaaaaa atccaggtt taaatgagca tattaatctt 960
tacaaccaaa tccaaaagga aaagaacaaa cggatcccac gcttaaagcc gttgtacaag 1020
caaattctct ctgatcgcga gactgcaagc ttcgtaatcg aagctttcga gaacgacggt 1080
gaacttctcg aatcgctgga aaaatcatat cggcttctcc agcaggaggt gtttacgcca 1140
gagggtaaag agggtcttgc gaatttgctt gctgccattg cggaatccga gacgcataaa 1200
atttttctca aaatgacttt gggccttacg gaaatctcgc aacaaatcta cgaaagctgg 1260
tcacttatcg aggaggcctg gaacaaacaa tacgacaata aacagaaaaa ggtaacggag 1320
actgagacct atgttgataa tcggaaaaa gcttttaaat caattaaatc tttctctatc 1380
gcggaggtgg aagaatgggt taaagcgttg ggtaacgaga aacacaaagg gaagagtgta 1440
gcgacatatt tcaagagtct cggcaagacg gacgagaaag tttctctgat cgagcaagta 1500
gagaacaact ataatattat caaggatttg ttgaacacgc catacccgcc gagtaaggac 1560
cttgccagc aaaaggacga tgtggagaaa attaagaatt acttggattc gctgaaggca 1620
ctccaacggt tcattaaacc acttttaggt tcaggtgaag agagcgacaa ggacgcacat 1680
ttctacggcg agtttacggc attctgggac gtcttggaca aagtgacccc attatacaac 1740
aaagtccgta attacatgac aaaaaagcca tattcgacgg aaaagtttaa gctgaacttc 1800
gaaaactctt acttcctcaa cggctgggct caggattatg aaaccaaagc tggcctgatc 1860
ttcctcaaag acggcaatta cttcctggcg attaataata agaaactga tgagaaagag 1920
aagaagcagc tcaaaacgaa ctatgaaaag aatccagcta agcgcatcat tcttgacttt 1980
caaaaacctg acaacaagaa tattcctcgt ctgtttatcc gctccaaggg tgacaatttc 2040
gccccagcag ttgagaagta taatcttcca attagcgatg tcattgacat ctatgatgag 2100
ggcaaattca aaacagagta ccggaaaatt aatgagcctg agtacttaaa gtctctccac 2160
aagcttatcg attattttaa gctgggcttt tcgaagcatg agtcctataa gcattactca 2220
ttttcctgga agaaaacgca tgagtacgag aatattgcac agttttatca cgatgtggca 2280
gtgtcttgtt atcaagtttt agatgagaac atcaactggg actctcttat ggagtatgtg 2340
gagcagaata agctgtattt gttccaaatt tataacaagg acttctctcc gaactccaag 2400
gggaccccta acatgcatac ccttttactgg aaaatgctgt ttaaccctga taacctgaag 2460
gatgtcgtct ataagctgaa cggccaagct gaggttttt atcgcaaggc gtctatcaag 2520
aaggaaaata aaattgtgca aaggctaac gatccgatcg acaacaaaaa tgagcttaac 2580
aagaagaagc aaaacacttt tgaatacgat atcgttaaag ataagcggta caccgtggac 2640
aaattccagt tcacgtccc tattaccctg aatttcaggggtt aaataactta 2700
aacagtaaag taaatgaata cattaaggaa tgtgatgacc tgcatatcat cgggattgac 2760
cgggggggagc ggcacctgct ctatttaagc ttgattgata tgaagggcaa cattgtgaaa 2820
caattctcgc tgaatgaaat tgtcaacgaa cataagggga acactatcg tacgaattat 2880
cataacctcc ttgacaaacg ggaaaaagaa gcgcaaaagg agcgtgaatc ttggaaaact 2940
atcgagacta ttaaggagtt aaaggagggg tacatttcgc aagtggtaca taaaattaca 3000
cagctgatga ttgagtacaa cgctattgtc gttttagagg attttgaattt tggctttaaa 3060
cggggtcgct ttaaggtaga aaagcaagtc taccagaagt tcgaaaagat gttgattgat 3120
aagctcaatt atttggtgga taagaagaag gaggctaatg aaagcggggg gacgcttaaa 3180
gcctatcagc ttacagattc ctatgcggac tttatgaagt acaaaaaaaa acagtgtggt 3240
tttctcttt atgtacctgc ttggaacacg atcctacaac tgcggttttt 3300
aatctgttcg atactcacta tgttaacgtg tccaaggccc aggagttctt ctcaaagttc 3360
aaaagcatcc ggtacaacgc agcaaataac tattttgagt cgaagtgac cgattatttt 3420
tcatttcag gtaaggcgga gggcactaaa caaaactgga ttatctgcac gcacggtact 3480
cgcatcatta atttccggaa cccagaaaaa actcccagt gggacaacaa agaagtggtc 3540
attcggacg aattcaagaa gttattcgag aagcatggga tcgattataa aaactcaagc 3600
```

```
gacctgaagg gccagattgc ctcacagtca gagaaagctt tcttccacaa cgaaaaaaag 3660
gataccaagg atccagacgg cctcttacaa cttttttaaac tggctctgca aatgcggaac 3720
agtttcatta agtcagagga agactatttg gtctccccgg taatgaatga tgagggtgag 3780
ttttttgact cccgcaaagc tcaacctaat cagcctgaga acgcagatgc gaacggcgct 3840
tataatatcg cgatgaaagg caaatgggtt gtcaaacaaa ttcgtgagag cgaagactta 3900
gacaagctta agttggctat tagtaataaa gaatggttga atttcgcaca acgttccggc 3960
gcgccaaaaa ggccggcggc cacgaaaaag gccggccagg caaaaaagaa aaaggctagc 4020
ggcagcggcg ccggatcccc aaagaagaaa aggaaggttg aagaccccaa gaaaagagg 4080
aaggtgtgat aa                                                   4092
```

| SEQ ID NO: 48 | moltype = DNA length = 4092 |
|---|---|
| FEATURE | Location/Qualifiers |
| misc_feature | 1..4092 |
| | note = Description of Artificial Sequence: Synthetic polynucleotide |
| source | 1..4092 |
| | mol_type = other DNA |
| | organism = synthetic construct |

SEQUENCE: 48

```
atgggccacc atcatcatca tcatagcagc ggcctggtgc cgcgcggcag cggtaccatg   60
aaaaacatga agtcgttcat taacctgtac ccagtcagta agacattgcg gtttgagctt  120
aagccgattg gtaagactct cgagacattc tcccgctgga tcgaggaatt gaaagaaaaa  180
gaggcgatcg agcttaagga aacgggcaat cttctggccc aagatgaaca tcgggcggaa  240
tcctataaga aagtcaaaaa aatccttgac gagtatcaca aatggtttat tacgagtcc   300
ttacagaaca ctaagctcaa cggggttagac gtgttctatc acaactatat gctcccgaag  360
aaagaagatc atgaaaagaa agcctttgca tcgtgtcagg ataatttacg gaaacagatc  420
gttaacgcct tcgtcagga gaccggtctc tttaataaac tctcgggtaa ggaattattt   480
aaggactcga aggaagaagt tgctttattg aaggcgattg ttccatactt cgataacaag  540
actctggaga acattggggt caaatcgaac gagggtgctc ttttacttat tgaggagttt  600
aaggatttca cgacatattt cggggggtttt cacgagaatc gtaagaatat gtattctgat  660
gaagcgaagt caactgcggt tgcattccgt ttgattcatg agaatctccc acgtttcatt  720
gataacaaaa aggtcttcga agaaaaaatc atgaattcag aacttaagga taagttccca  780
gagattctga aggaactcga acaaattctt caggtgaacg aaattgagga atgtttcaa   840
cttgactatt tcaatgatac cctttatccag aatgggatcg atgttttacaa ccatttaatt  900
ggtgggtatg cagaggaggg taagaaaaaa atccagggtc ttaacgagca tattaatctg  960
tacaatcaaa ttcaaaaaga aaaaacaaa cgcatcccac gcctgaaacc tctctacaaa 1020
caaatcctct ctgatcggga aaccgcctct ttcgttatcg aagcctttga aacgacggt  1080
gagttgctcg agagcttgga gaaatcctac cggttgttgc aacaggaagt atttactcca  1140
gaaggcaagg aagtctcgc taatctcctg gcagctatcg ccgagagtga gacacacaa  1200
attttttttaa agaacgatct ggggctgacg gaaattagtc agcagatcta tgagtcgtgg  1260
agtcttattg aggaagcttg gaacaaacaa tatgataaca acaaaaaa ggtaactgaa   1320
acagagacat atgtcgataa ccgcaaaaag gcttttaaat cgatcaaatc tttctcaatc  1380
gctgaagtcg aagaatgggt taaggctttg ggcaacgaaa aacacaaggg gaaatcagta  1440
gccacgtact ttaagagctt aggtaagacc gacgagaagg tctcgttaat tgagcaggtt  1500
gagaacaatt acaacattat taaagacttg ttaaatacac cgtacccacc aagtaaagac  1560
ctcgctcagc aaaaggatga cgttgagaag atcaaaaact acctggactc acttaaggca  1620
cttcagcggt ttatcaaacc tcttctgggg tcgggggagg aatctgacaa agacgcgcat  1680
ttctacggcg agttcacggc atttttgggac gttttagaca aggtaacgcc tcttacaat   1740
aaagtacgca attacatgac gaaaaagccg tatagcacag aaaaatttaa actgaacttt  1800
gagaactcat atttccttaa tgggtgggcg caagattacg agacaaaggc cggcctgatc  1860
ttcctgaaag acggtaatta ctttttagct attaacaata aaaagctcga cgaaaaggag  1920
aagaagcagc ttaaaaccaa ttatgaaaaa acccctgcta agcgtatcat tttgactttt  1980
cagaagccag acaacaagaa atatccctcgc ctcttttatcc gcagcaaagg cgataatttt  2040
gcgccagctg tggaaaagta taatcttccg atttccgacg tgatcgacat ttatgatgaa  2100
ggcaagttta aaactgaata tcggaagatt aacgaacctg aatatcttaa gtcgttacat  2160
aagctcatcg actatttcaa gttaggtttt tcgaagcatg agagttacaa acactattcc  2220
tttagttgga gaagaccca cgaatatgag aatatcgctc aattctatca tgatgtggag  2280
gtctcttgct accaagtact cgatgagaac atcaattggg actccttaat ggagtatgta  2340
gaacagaata agctgtatct cttttcagatt tacaacaagg acttttcccc gaactgagaa  2400
ggtacaccaa atatgcacac actgtattgg aagatgctgt ttaacccgga taatctcaaa  2460
gatgttgtct acaaactcaa cggccaagct gaagtttttt atcgtaaagc ttcaattaaa  2520
aaggagaata aaattgtgca caaagcgaac gatcctattg acaacaagaa tgagttgaac  2580
aaaaagaagc agaacacttt cgagtacgat attgttaaag ataagcgtta tactgttgac  2640
aagttttcgt tccatgttcc gattacttta aattttaacg ctgaagggct gaacaattta  2700
aatagcaagg taaatgaata catcaaagaa tgtgacgatt tacacatcat cgggatcgat  2760
cgtggtgaac gccatttgct ttatttgtca ttgatcgata tgaagggaa cattgttaaa  2820
caattttcgt tgaacgagat cgtgaacgaa cataaaggaa acacataccg gacgaactac  2880
cataattttat tggataagcg cgaaaaggag cgcgaaaaag agcgtgaaag ctggaaaacg  2940
atcgaacgaa ttaaggaact caaggagggg tatattctc aagtagtcca caaaattaca   3000
caattgatga ttgaatacaa tgccattgtc gtccttgagg attttgaactt ggcttttaag  3060
cgcggtcgtt tcaaggtcga gaagcaagtg taccagaagt tgagaaaat gttgattgat  3120
aagttaaaatt atttggtgga taaaaaaaaa gaagccaacg aatccggcgg gactctgaaa  3180
gcatatcaac tgacagacag ctacgcagac tttatgaaat ataaaagaa acaatgcggg  3240
tttctcttct atgtcccggc ctgaaacact agtaagattg acccaactac tggtttcgta  3300
aaccttttcg ataccccacta tgtcaatgtg agcaaggcgc aggaattttt ctctaaattc  3360
aaatctattc ggtacaatgc agccaacaat tatttcgaat tcgaggttac agattacttc  3420
tcattcagtg gtaaggccga gggtacaaaa caaaactgga tcatctgcac acacgggaca  3480
cggattatta acttccgtaa cccagagaag aattctcaat gggacaacaa agaggtggtg  3540
attaccgacg aatttaaaaa gttattcgaa aagcatggta tcgactacaa aaacagtagc  3600
```

```
gacttaaaag gccagattgc cagtcagagc gaaaaagcat ttttccacaa tgaaaaaaag    3660
gacacaaagg atcctgatgg gctcctccaa ctgttcaaac tggcccttca gatgcggaat    3720
tcctttatta agagcgaaga agattatctt gtttcgccgg tcatgaacga cgagggtgaa    3780
tttttcgact cgcgcaaggc ccaaccgaac caaccgaaaa atgcggacgc caacggcgca    3840
tacaacattg caatgaaggg taaatgggtc gtgaaacaaa tccgggaatc tgaagactta    3900
gataagctga agctggccat ctcaaataag gaatggctca actttgccca gcggtcaggc    3960
gcgccaaaaa ggccggcggc cacgaaaaag gccggccagg caaaaaagaa aaaggctagc    4020
ggcagcggcg ccggatcccc aaagaagaaa aggaaggttg aagaccccaa gaaaagagg     4080
aaggtgtgat aa                                                        4092

SEQ ID NO: 49          moltype = DNA   length = 4092
FEATURE                Location/Qualifiers
misc_feature           1..4092
                       note = Description of Artificial Sequence: Synthetic
                       polynucleotide
source                 1..4092
                       mol_type = other DNA
                       organism = synthetic construct
SEQUENCE: 49
atgggccacc atcatcatca tcatagcagc ggcctggtgc cgcgcggcag cggtaccatg     60
aaaaacatgg agagtttcat taatctgtat ccagtgtcaa aaactttgcg gttcgagttg    120
aagccgatcg gcaagacctt ggagacattt tctcgctcga tcgaggaact taaagaaaaa    180
gaggctatcg aattaaagga cgggtaatt tgcttgcgc aggatgaaca ccgggcggaa     240
agttacaaaa aggtaaaaaa aattctcgac gaatatcata aatggtttat cactgagtca    300
ttacaaaaca caaaattaaa tggtttggac gttttctatc ataattatat gcttccgaaa    360
aaggaagacc acgagaaaaa ggcgtttgcc tcgtgccaga aatttgcg caagcaaatt     420
gtaaatgctt tccgtcaaga gaccggggttg ttcaacaaac tgtcggggaa agagctgttt    480
aaggattcga agaggaagt tgcgctgctc aaggctattg taccatactt cgataacaaa    540
accctcgaaa acatcggcgt caaatcaaat gaaggcgcat tactcctcat cgaggaattt    600
aaagacttta ccacctactt cggtgggttc catgaaaatc ggaagaatat gtattctgat    660
gaagcgaaat caactgctgt tgcatttcgg ctcatccacg aaaatttacc acggttcatc    720
gacaataaga agtctttga ggagaagatc atgaacagcg agctcaagga taaattccca    780
gagatcttga aggaattaga acaaatcttg caggttaatg agatcgaaga gatgtttcag    840
ctggactact tcaatgatac tctgatccag aatggtattg atgtatacaa ccaccttatt    900
ggggggtacg ccgaagaagg caaaaaaaaa attcaagggt tgaatgagca catcaacctg    960
tacaatcaga tccagaagga aaaaaataag cgtattccac gcctcaaacc tctctacaag   1020
caaatcctct ctgatcgtga cacagcctca ttcgtgatcg aggcgttcga gaatgatggc   1080
gaacttctgg aatccctgga gaaatcttac cgcttgctgc agcaggaagt tttcacgcct   1140
gaaggtaagg aagggttggc gaacctgctg gctgcaattg ccgagagcga gacgcacaag   1200
atcttttttga agaacgacct ggggcttaca gaaatttccc aacaaatcta tgagagttgg   1260
tcactgattg aagaggcctg gaacaaacag tacgataaca acaaaaaaa agttacggaa    1320
acggaaactt atgtggacaa ccgtaagaag gcttcaagt cgattaagtc cttctccatt    1380
gccgaagttg aggaatgggt gaaagctctc gggaacgaga aacataaagg taaaagtgtg   1440
gcaacgtact tcaaatcgct gggtaaaacc gatgaaaagg taagccttat tgagcaagta   1500
gagaataact acaatattat caaggatctc ttaaatacgc cataccctcc atccaaggat   1560
cttgcccagc aaaaggatga tgtagaaaaa attaaaaatt atttggattc cctgaaggcg   1620
ttgcagcgtt tcatcaagcc tcttcttggc tcgggtgaag aagcgataa agatgcccac   1680
ttctatgggg agtttaccgc gttctggac gttttagata aagtcactcc tttgtacaac    1740
aaggtgcgga actatatgac caagaaaccg tactctactg agaaatttaa actcaatttc    1800
gagaactcct atttccttaa tgggtgggca caggattatg agaccaaggc ggggctcatt   1860
ttcttaaagg atggcaacta cttttctggcc attaataaca aaaactgca cgagaaagaa   1920
aagaaacagc tcaagactaa ttatgagaag aacccagcga acggattat tttagatttt    1980
cagaagcctg acaacaaaaa tatcccacgt ctgttcatcc gttctaaggg cgacaatttt   2040
gccccagccg ttgagaagta taacttacct atttcagacg tgattgacat ttacgatgag   2100
ggtaaattca aaaactgaata ccgtaaaatc aatgaaccgg agtacttaaa aagtctgcat   2160
aagttgattg actatttaa gttaggttc agtaaacacg agtcatacag cactacagc    2220
ttctcttgga gaaaacaca cgagtacgag aacatcgcac agttctatca tgacgttgag   2280
gtcagttgct accaagtact cgacgagaac atcaattggg atagtttgat ggagtatgtg   2340
gaacaaaaca agctttatct cttccaaatc tacaataagg attttagcgc aaatagcaag   2400
ggcaccccga acatgcatac cttatactgg aaaatgttat ttaatccaga caatcttaaa   2460
gatgttgtct acaaattgaa cgggcaagcc gaggtcttct accgcaaagc ttcgatcaag   2520
aaagaaaaca aaatcgttca caagcaaac gacccgatcg acaacaagaa tgaattaaac   2580
aagaaaaagc agaacacttt cgagtatgat atcgttaaag ataagcggta acggtggac    2640
aagtttcagt tccacgtccc tatcaccttg aactttaagg cggaaggggct caataacctg   2700
aacagcaaag tcaatgaata cattaaagag tgcgatgatc ttcatattat tggcatcgat   2760
cgtgggagc ggcattgct ctatctgtcg ctgattgata tgaaggtaa tatgtgtcaaa    2820
caattctcct tgaatgagat tgtaaacgag cataagggta cacgtaccg tactaattac    2880
cacaatctgc ttgacaaacg ggaaaaggag cgggagaagg aacgcgaatc gtggaagaca   2940
attgagacta ttaaggagtt aaaggagggt tatatcagtc aagtagttca taagatcaca   3000
caactgatga ttgaatataa tgccatcgtt gttttggaag atctcaactt cgggttcaaa   3060
cgtgccgtt taaagttga gaagcaggta taccagaaat cgaaaaat gttgattgac      3120
aagttgaact atcttgtaga caaaaaaaa gaggccaacg agagtggtgg tactcttaag   3180
gcttatcagc tcactgattc atatgctgac ttcatgaagt ataagaaaaa acagtgtggg   3240
ttcctgttct acgttgccgg atggaatact agtaaaattg atccataac cggctttgta   3300
aacctgtttg acacacatta cgttaatgtg tcgaaagctc aggagttctt ctcgaagttc   3360
aaaagcattc gctataatgc ggccaacaat tatttcgagt tcgaggtcac tgactatttc   3420
tcttttccg gcaaagcgga aggtactaaa caaaactgga tcatttgtac ccatggtact   3480
cgcattatca acttccgcaa tccggaaaaa actcccagt gggacaataa agaggtcgta   3540
atcactgacg agttcaaaaa acttttttgaa aagcatggta ttgactataa gaatagtagc   3600
```

```
gacctgaaag gccagatcgc atcgcagagt gagaaagcat tcttccacaa tgaaaagaaa  3660
gatactaaag atcctgatgg tcttctccag ttatttaagt tagcgctcca gatgcgtaat  3720
tcctttatca agagtgagga ggactacttg gtgtctccgg taatgaatga tgaaggtgag  3780
tttttcgatt cccggaaagc ccagccaaat cagccagaga acgcagatgc taatggggcg  3840
tacaacattg ccatgaaggg gaagtgggta gtcaaacaga tccgggagtc tgaggatctt  3900
gataagctga aattggcaat ctcgaataag gaatggttga attttgctca gcgctctggc  3960
gcgccaaaaa ggccggcggc cacgaaaaag gccggccagg caaaaaagaa aaaggctagc  4020
ggcagcggcg ccggatcccc aaagaagaaa aggaaggttg aagacccgaa gaaaagagg   4080
aaggtgtgat aa                                                      4092

SEQ ID NO: 50         moltype = DNA   length = 4092
FEATURE               Location/Qualifiers
misc_feature          1..4092
                      note = Description of Artificial Sequence: Synthetic
                      polynucleotide
source                1..4092
                      mol_type = other DNA
                      organism = synthetic construct
SEQUENCE: 50
atgggccacc atcatcatca tcatagcagc ggcctggtgc cgcgcggcag cggtaccatg   60
aagaatatgg agtcctttat caatctgtac cctgtgtcga aaacacttcg tttcgaattg  120
aaaccaatcg ggaagaccct ggaaacgttc agtcgttgga ttgaagaact caaagaaaag  180
gaagcaattg aactgaagga aacagggaac cttttagcac aggatgagca tcgcgccgag  240
tcgtacaaga aagttaaaaa aattcttgac gaataccaca agtggttcat cactgagtct  300
ctccagaata cgaaacttaa cggtcttgac gtatttacc acaattatat gttgcctaag  360
aaggaagacc atgagaaaaa agcgttcgcc tcctgtcaga gaacttgcg taaacagatc  420
gtgaacgcct tcggcaaga gacaggtctc ttcaacaagc tcagcggtaa agaactcttc  480
aaggactcca agaggagt agctctcctt aaagcaattg tgccttactt cgacaataag  540
acgttggaga atatcggcgt aaagtccaac gaaggcgcat tgcttttgat tgaagagttc  600
aaggactta cgacttattt cgggggggttt cacgagaacc ggaaaaacat gtactccgac  660
gaagcgaaat cgacagctgt ggcttttcgt ctcatccacg aaaacttacc gcgctttatt  720
gataatataga agtattcga ggagaagatt atgaattcgg agcttaagga caagttccct  780
gaaatcttga aagagcttga gcagatcctg caggtaaatg aaattgagga atgtttcag   840
ttggattatt tcaacgatac tcttatccag aacggcactc acgttttaca ccatctcatc  900
gggggcctacg ctgaagaggg caagaagaag atcaaggtt taaacgagca cattaacttg  960
tataaccaaa tccagaaaga aaagaataaa cggatcccgc gtttgaaacc attgtacaag  1020
cagatccttgt ctgaccggga gaccgcgtct tttgttatcg aggcatttga aaacgatggg  1080
gagctcctcg aaagcttgga gaaatcgtat cgcttatac aacaggaggt ttttacccca  1140
gaaggcaaag aagttttagc gaaccttctg gcagcaatcg ctgagagtga aacccacaaa  1200
atttttccga gaacgacct tgggttgacc gagatttcac agcaaatcta tgaatcctgg  1260
tcgctgattg aagaggcctg gaataagcaa tacgataaca agcagaaaaa ggtaacagag  1320
actgaaacct acgttgataa ccggaaaaaa gccttcaaaa gcattaagtc ttttctcaatt  1380
gcggaggtag aggagtgggt caaagcttta gggaatgaaa aacacaaggg gaaatccgtt  1440
gcaacatatt tcaaatcact tggtaaaacg gacgaaaagg tctctctgat tgagcaggtc  1500
gagaataact acaacatcat taaagatttg ctgaataccc catatccgcc gtcgaaagac  1560
ctcgcccagc agaaggacga cgtagagaag atcaaaaatt atctcgatag cttaaaagca  1620
ctcaaacgtt tcattaagcc tttgttgggt tccggcgcac atcagataa agacgcgcac  1680
ttttatggtg aattcactgc tttctggac gtgcttgata aggtgaccc ttgtataat   1740
aaggttcgta attatatgac caagaaaccg tattctacgg aaaaatttaa gttgaatttc  1800
gagaacagtt attttcttaa cggttgggca caagactatg agaccaaagc gggtcttatc  1860
ttcctgaagg acggtaacta cttcttagct attaacaaca aaaacttga cgaaaaggaa  1920
aagaaacagt taaagacgaa ttatgaaaaa aatccagcca aacgcatcat tcttgacttc  1980
cagaaaccgg acaacaagaa cattccacgc ttgttcatcc gttcgaaagg tgataacttt  2040
gccccggcag ttgagaagta aacctgcct atcagcgatg tcatcgacat ttacgacgag  2100
ggtaagttca agacagaata ccggaaaatt aatgagcgga atgtatctgaa gtcccttcac  2160
aagttgatcg actactttaa gctgggtttc tccaagcatg agtcttacaa acactattc   2220
ttttcgtgga agaagactca tgagtatgag aatatcgcgc agttctatca cgacgttgag  2280
gttagttgct accaggttct cgatgaaaac atcaactggg attctctcat ggaatatgta  2340
gaacagaaca agttatattt attcagatt tacaacaaag acttttcccc tacctctaaa  2400
ggcaccccaa atatgcatac gctttactgg aaaatgcttt ttaacccaga taacctgaaa  2460
gacgtcgtgt acaaactgaa cggtcaggct gaggtgttct accggaaagc atctattaaa  2520
aaggagaaca agatcgtcca aaggcgaac gatccgatcg ataataagaa tgagcttaat  2580
aaaaagaagc aaaacacctt tgagtacgac atcgtaaaag acaagcgcta cggtggac   2640
aaattccagt ttcatgtccc aattactttg aatttaagtg cggagggcgt taacaatctc  2700
aattccaaag tcaacgaata catcaaagag tgtgacgact gcacatcat cggcattgat  2760
cggggcgaac gccatcttt gtatcttca tgattgata tgaaggtaa tatcgttaaa  2820
caattctcac tcaacgaaat tgttaatgaa cataagggta atacatatcg taccaattat  2880
cacaacccttt tagacaaacg cgaaaagcaa cgtgagaagg aacgcgagag ctggaaaacc  2940
attgaaacta tcaaggagtt aaagaaaggc tacatttctc aggtggtaca caaaattacg  3000
cagctgatga ttgagtacaa cgccatcgtg gtgctggagg atctcaacatt tggcttcaag  3060
cggggccggt tcaaagtgga aaaacaggtt atcaaaaat ttgagaaaat gttaatcgat  3120
aagctgaact atctggtaga taagaagaaa gaggccaacg aaagtggcgg tacacttaag  3180
gcctatcagt tgacagattc atacgcgaat tttatgaagt acaaaaagaa acagtgcggt  3240
ttcttattct acgtacctgc gtggaacaca caaagatcga ggcgaagatc gatcatcgta  3300
aacctttttg ataccactaa cgtaaatgtc tctaaagccc aggaattctt ctctaaattt  3360
aaatcaatcc gctacaatgc cgcaaacaac tattttgagt cgaggtaac cgattacttc  3420
tccttttcag gcaaagcaga aggcacaaag cagaattgga ttatttgcac acatgggaca  3480
cgtattatca atttccgtaa tcctgagaaa acagtcaatg ggataataa ggaggtggta  3540
atcaccgacg aatttaagaa attgtttgag aaacatggta tcgattataa aaacagttct  3600
```

```
gatttaaaag ggcagattgc ctctcagtcg gaaaaggctt tcttccataa cgagaagaag  3660
gacaccaagg atccggatgg gctgctgcaa cttttttaagt tagcattgca gatgcggaat  3720
agttttatta agagtgaaga agactacctt gtatcgccgg tcatgaatga cgaggggag   3780
tttttttgatt cgcgcaaagc ccagccaaac cagcctgaaa atgccgatgc taacgggct   3840
tataacattg cgatgaaggg gaagtgggtt gttaaacaga tccgggaaag cgaagacttg  3900
gacaagttga aattagctat ttccaataaa gaatggctta acttcgccca gcgcagcggc  3960
gcgccaaaaa ggccggcggc cacgaaaaag gccggccagg caaaaaagaa aaaggctagc  4020
ggcagcggcg ccggatcccc aaagaagaaa aggaaggttg aagaccccaa gaaaagagg   4080
aaggtgtgat aa                                                      4092

SEQ ID NO: 51          moltype = DNA    length = 4092
FEATURE                Location/Qualifiers
misc_feature           1..4092
                       note = Description of Artificial Sequence: Synthetic
                       polynucleotide
source                 1..4092
                       mol_type = other DNA
                       organism = synthetic construct
SEQUENCE: 51
atgggccacc atcatcatca tcatagcagc ggcctggtgc cgcgcggcag cggtaccatg   60
aaaaacatgg agagcttcat caacttgtac ccggtttcaa aaacacttcg ttttgaattg  120
aaacctatcg ggaaaacatt ggaaaccttc tctcggtgga ttgaggaact taaagaaaaa  180
gaggcgatcg aactgaagga gacagggaat ctcctcgcgc aagacgagca ccgggcagaa  240
tcgtataaaa aggtaaagaa aatccttgac gaatatcaca aatggtttat cactgagtcg  300
ttacaaaaca caaagcttaa cggccttgat gttttctatc ataactatat gttgccaaag  360
aaggaagacc acgaaaaaaa ggcttttgcc tcctgtcagg ataacaatcc taagcaaatc  420
gtcaacgcat tccgtcagga gactggtttg ttcaacaaac tttccggtaa ggagctcttt  480
aaagacagca aggaagaggt cgcgcttttg aaagcgattg ttccttactt tgacaataaa  540
acgttggaaa acatcggcgt caaatctaat gagggtgctt tacttctcat cgaagagttc  600
aaagacttca cccacctactt tgggggttt catgagaacc gtaagaacat gtattcgaat  660
gaggcgaagt ccacggcagt ggcattccgc ctcattcatg aaaacctccc acgtttcatc  720
gacaacaaaa aagtgtttga ggaaaagatc atgaacagcg aacttaaaga taaattccca  780
gaaatcttga aggagcttga acagatcttg caggtgaacg aaattgaaga gatgttccag  840
cttgattatt tcaacgacac cctgattcag aatggtatcg acgtttataa tcacctcatt  900
ggggggttatg cggaggaagg gaaaaagaag atccaaggcc tcaacgaaca catcaactta  960
tacaatcaaa tccaaaagga gaagaacaaa cggatcccac gtttgaagcc tctttataag 1020
cagattctgt ctgaccgtga aacagcctca tttgtcatcg aagcctttga gaacgatggg 1080
gagctgttgg agagcctcga aaagtcgtat cggcttctcc agcaggaggt ttttaccccg 1140
gagggtaaag aggggctggc caatctgctt gctgctattg ccgagacgga gacgcacaag 1200
attttttctca aaaatgacct tggtctcaca gaaatttctc agcagattta cgaatcttgg 1260
agtctgatcg aagaagcttg gaataaacag tacgacaaca acaaaaaaaa ggtgactgaa 1320
acggagactt atgtagacaa tcgcaaaaag gcctttaagt ccattaaaatc ttttttcgatt 1380
gcggaagtgg aagagtgggt caaagccctc ggcaacgaga aacacaagggg taagagtgtt 1440
gccacctatt ttaaaagtct gggcaagact gacgaaaagg ttagtcttat cgaacaggtc 1500
gaaaacaatt acaacatcat caaggatctc tcaatacac cttaccctcc gtctaaagac 1560
ctggcacaac aaaaagacga cgttgagaag atcaaaaatt acttggactc gctcaaggcc 1620
ctccaacggt ttatcaagcc acttttaggt tctggcgaag agtgacaa agatgcccac 1680
ttctatgggg aattcactgc ttttttgggat gtcctcgaca aggtaactcc attgtacaac 1740
aaagtacgga attatatgac caagaagcct tattccaccg aaaatttaa gctcaatttt 1800
gagaatagtt atttccttaa tggctgggca caagactacg agacgaaggc aggcctgatt 1860
tttttgaaag acgggaacta cttcttagcc atcaacaata aaagcttga cgaaaaggaa 1920
aaaaaacaac ttaagacgaa attatgagaaa aacccagcaa aacgattat tttagatttc 1980
cagaagccag acaacaagaa cattccgcgc ttatttatcc ggtcaaaagg ggacaatttc 2040
gctccagctg tggagaaata taacttacca atcagcgacg tcattgacat ttacgatgag 2100
ggtaagttca aaaccgagta ccggaaaatc aacgaaccag agtatcttaa gtctctgcac 2160
aagctgatcg actattttaa acttgggtt tcaaagcacg aatcgtacaa acattacagc 2220
ttctcttgga gaagactca tgagtacgaa aacatcgctc aatttatca tgatgtggag 2280
gtgtcatgct accaagtcct tgatgagaat attaattggg attcacttat ggagtacgta 2340
gagcagaata agctctatct ttttcaaatc taacataaag atttctcccc aaactcgaaa 2400
ggtaccccga acatgcatac cctttactgg aagatgttat ttaaccctga caatctgaag 2460
gacgtagttt acaaattgaa tggccaggcg gaagtgttct accgcaaggc gtctattaag 2520
aaggagaata aaattgtcca caaagcaaat gatccgattg acaataagaa cgaattaaat 2580
aagaagaagc agaatacttt cgagtatgac atcgtaaaag ataagcggta taccgtcgac 2640
aagtttcaat tccatgtgcc aatcacgtta aatttcaaag cagagggctt gaataatctc 2700
aactcaaagg taaacgaata catcaaagaa tgcgacgacc ttcacatcat gggattgat   2760
cgcggcgagc gtcacctcct ctacctcagt ctcattgaca tgaagggaa tatcgttaag  2820
cagttcagtc tcaatgagat tgttaacgag cacaaaggga atacttaccg cacgaattac  2880
cacaaatttgc ttgacaagcg ggagaaagaa cgtgaaaaag agcgcgaatc ttggaaaacc  2940
atcgaaacta tcaaggaatt aaaggaaggg tacatctccc aggttgtaca taagatcacg  3000
caattgatga tcgaatataa tgcgattgtg tgttggaag acttgaattt tggttttaag  3060
cgtggccgtt ttaaggtaga gaaacaggtg tatcaaaagt cgagaaaat gcttattgat  3120
aaaattgaact atctcgtgga caagaaaag gaagctaatg aatcaggtgg gacgttgaag  3180
gcataccaac ttcagattc ttatgccgac tttatgaaat acaagaaaaa gcagtgcggt  3240
tttctctttt atgtcccggc atggaatacc tctaagatcg acccttaccac ggggttttgtt  3300
aacttgttcg atactcacta cgtcaacgta tccaaggctc aagaattctt ctccaaattc  3360
aagagcattc gctataacgc ggccaataat tactttgagt cgaggtaac cgactacttc  3420
agcttctccg gcaaagctga gggtacgaag cagaactgga ttatctgtac ccatgggaca  3480
cggatcatca atttttcgtaa tcctgaaaaa acagccagt gggacaacaa agaagtagtt  3540
atcactgatg aatttaaaaa gttgtttgaa agcacggga tcgattacaa aaattcatca  3600
```

```
gaccttaaag ggcagattgc cagccaaagc gaaaaggcat tctttcataa cgagaaaaag   3660
gacacaaagg atccagatgg cttactgcag ttgttcaaac ttgcactgca gatgcggaac   3720
tccttcatta aatcagagga ggattacctg gtatcacctg taatgaacga cgaaggcgaa   3780
tttttcgact ctcgtaaagc tcaacctaat caaccagaga acgccgatgc caacggcgca   3840
tataacattg cgatgaaggg caaatgggta gtgaagcaaa tccgtgagtc cgaggattta   3900
gataaactca aattggcaat tagtaacaag gaatggctga actttgcaca acggagtggc   3960
gcgccaaaaa ggccggcggc cacgaaaaag gccggccagg caaaaaagaa aaaggctagc   4020
ggcagcggcg ccggatcccc aaagaagaaa aggaaggttg aagaccccaa gaaaagagg    4080
aaggtgtgat aa                                                       4092
```

| | | |
|---|---|---|
| SEQ ID NO: 52 | moltype = DNA length = 4092 | |
| FEATURE | Location/Qualifiers | |
| misc_feature | 1..4092 | |
| | note = Description of Artificial Sequence: Synthetic polynucleotide | |
| source | 1..4092 | |
| | mol_type = other DNA | |
| | organism = synthetic construct | |

SEQUENCE: 52

```
atgggccacc atcatcatca tcatagcagc ggcctggtgc cgcgcggcag cggtaccatg    60
aaaaacatgg agtcgttcat caatttatat cctgtttcaa agacactgcg ttttgaattg   120
aaacctatcg gcaaaacgct tgagaccttc agtcggtgga ttggaact caaagaaaag    180
gaggccatcg aactgaagga aacgggcaac cttttagctc aggatgagca ccggcagag   240
tcttataaaa aggtgaaaaa atccttgac gaatatcata aatggttcat tacagaatct    300
ctgcaaaaca ccaagcttaa cggcctcgac gttttttacc ataattatat gcttcctaag   360
aaggaggatc atgagaagaa agccttcgca tcttgtcaag ataaccttcg gaagcaaatt   420
gtgaacgcgt tccgtcagga aactggctta tttaataagc tgtcaggtaa agaactcttt   480
aaggacagta aggaagaagt tgcactcttg aaggccattg taccttactt tgataacaaa   540
acgctcgaaa atattggcgt aaaatcgaat gagggtgcct tgttattaat tgaagagttt   600
aaagacttta caacatattt tgggggtttt cacgaaaacc gtaaaaacat gtattccgat   660
gaagcgaaat cgactgccgt ggcttttcgc ttgattcacg agaattaccc acgctttatt   720
gataataaga aagttttcga ggagaaaatt atgaatagtg aactcaagga taagtttcca   780
gagattttaa aagagctcga acaaatctta caggtgaacg agatcgaaga aatgttccag   840
ttagactatt ttaacgatac tttaattcag aatgggatac acgtttataa ccacctgatc   900
ggtgggtatg ctgaagaagg caagaaaaaa atccagggc tgaatgaaca cattaatcct   960
tataaccaaa ttcagaaaga aaaaaataag cggatcccgc gcctcaaacc attatacaag  1020
cagatccttt cagatcgcga gacagcatca tttgtgattg aagcattcga aaacgacggg  1080
gaactgttag agtcgctgga agagttctac cggttgctcc aacaagaagt attcaccccg  1140
gagggcaaag aaggtcttgc caacctcctg gccgctatcg cggagtcaga aacgcacaaa  1200
attttttaa aaaatgactt agggttaacg gagatttctc agcagatcta cgaaagctgg  1260
tcacttattg aagaagcttg gaataagcaa tacgacaata gcaaaaaaa ggttacggag   1320
acggagacgt atgttgataa tcgtaagaag gcctttaaat cgattaagtc attttcaatt  1380
gccgaggtag aggaatgggt aaaggcactc ggcaatgaga aactaaaagg taagagcgta  1440
gcaacctatt ttaaatcctt gggcaaaacg gacgagaaag tgtcgttaat cgagcaggtg  1500
gagaacaact ataatattat taaggatctt ctgaatacccc gtatccgcc atctaaagat  1560
cttgcacagc agaaagacga cgtagaaaag atcaagaact acttggatag tctgaaggcc  1620
ttacaacggt ttattaaacc tttgctcggc tcaggcgaac agatcgcgac agatgcgcac  1680
ttttacggtg agtttactgc cttttgggat gtattggaca aggtaacccc tctttataac  1740
aaggtccgca attacatgac caaaaagccg tattcaacag agaaatttaa actgaatttc  1800
gaaaacagtt atttttaaa tggttgggcg caagattatg aaaccaaggc cggtcttatc  1860
tttctgaaag acggcaacta ttttctcgct attaacaaca agaagctgga tgagaaggaa  1920
aagaagcaat taaaaactaa ctacgagaag aacccagcga agcgcatcat tcttgatttt  1980
cagaagcctg acaataagaa catccctcgg ttgttcatcc ggtcaaaggg tgacaatttc  2040
gcccctgcag tgaaaagta caacttacct atctcggacg tcatcgacat ctacgacgaa  2100
ggcaagttca agacggagta ccgcaagatt aatgaacctg aatacttaaa atccttacat  2160
aaactcattg attatttcaa attggggttt tcgaagcatg agtcttacaa acactactcg  2220
ttctcttgga aaaaaactca cgaatacgaa aatatcgccc agtttatca tgacgtcgaa  2280
gtaagttgct atcaagtcct ggatgagaat attaattggg atagttaat ggagtacgtt  2340
gaacaaaata aactgtattt gttccagatt tataacaaag atttttctcc gaacagtaag  2400
ggtactccga acatgcacac actgtactgg aagatgctct ttaaccctga caacttgaag  2460
gatgtggtct acaagctcaa tgggcaagct gaagtgtttt atcgcaaggc atcaattaaa  2520
aaagaaaata agatcgtcca aaagccaat gacccaattg acaataaaaa cgaactcaac  2580
aagaaaaaac agaatacttt tgagtatgat attgtgaagg caaacgcta cacagtggat  2640
aagttccaat ttcatgtacc tatcacactc aactttaaag cagagggtct taataatctg  2700
aacagcaaag tgaatgagta cattaaggaa tgtgatgatt tacacatcat gggatcgac  2760
cgtggtgagc gtcatcttct ttacttgtcc ttgattgata tgaagggaa cattgtgaag  2820
caattctcat taaacgagat tgtcaacgag cacaagggga acacgtatcg cacaaattat  2880
cacaacctgc ttgacaaacg tgaaaaggaa cgcgaaaagg aacgtgaaag ttggaaaacc  2940
atcgaaacca ttaaggaact gaaggagggt tatatcagtc aggtggtgca caaaatcaa  3000
cagctgatga tcgagtacaa tgcgattgtt gtcctggaag acttaaattt cgggttaag  3060
cgcgggcgtt tcaaggttga gaagcaggtc tatcagaagt tcgagaagat gctgattgac  3120
aaacttaatt atctcgttga taagaaaag gaagctaacg agtccggtgg acattgaaa   3180
gcgtatcaat taacagatag ttacgcggac tttatgaaat ataaaaaaa acagtgtggc  3240
tttttgttt atgttcgagc ctggaacacg tcaaaaaatcg acccgacaac cgggtttgtt  3300
aacttatttg acactcacta cgtaaacgtc agcaaggctc aagaattctt ttctaaattt  3360
aagtccattc ggtacaatgc agccaataat tatttcgagt tcgaagtcac agattacttc  3420
agcttcagcg gcaaagcgga agggactaag caaaactgga tcatttgcac gcacgggacg  3480
cggattatta attttcgtaa tccggagaag aattcccaat gggataataa ggaggtcgtc  3540
attacagacg agttcaagaa gctctttgag aaacatggta ttgattacaa aaactcatcc  3600
```

```
gatcttaaag ggcaaatcgc ttctcaatca gagaaggcgt ttttccacaa tgagaaaaag   3660
gacacgaagg acccagatgg cttactgcaa ttgttcaagc tcgcactgca aatgcgaaac   3720
tcctttatta agtcggaaga ggattacctg gtctcgccag tgatgaacga tgaaggtgag   3780
ttctttgata gccgtaaggc tcagccaaat cagccagaaa acgctgatgc gaatggtgcg   3840
tataacatcg ctatgaaagg caagtgggta gtaaaacaaa ttcgcgagtc agaagatttg   3900
gataagctca agcttgcgat ttccaataag gagtggctga atttcgctca acgtagcggc   3960
gcgccaaaaa ggccggcggc cacgaaaaag gccggccagg caaaaaagaa aaaggctagc   4020
ggcagcggcg ccggatcccc aaagaagaaa aggaaggttg aagaccccaa gaaaaagagg   4080
aaggtgtgat aa                                                      4092

SEQ ID NO: 53            moltype = AA   length = 1252
FEATURE                  Location/Qualifiers
REGION                   1..1252
                         note = Description of Artificial Sequence: Synthetic
                         Cas12a/Cpf1 [Parabacteroides distasonis] sequence
source                   1..1252
                         mol_type = protein
                         organism = synthetic construct
SEQUENCE: 53
MKNILEQFVG LYPLSKTLRF ELKPLGKTLE HIEKKGLIAQ DEQRAEEYKL VKDIIDRYHK   60
AFIHMCLKHF KLKMYSEQGY DSLEEYRKLA SISKRNEKEE QQFDKVKENL RKQIVDAFKN   120
GGSYDDLFKK ELIQKHLPRF IEGEEEKRIV DNFNKFTTYF TGFHENRKNM YSDEKESTAI   180
AYRLIHENLP LFLDNMKSFA KIAESEVAAR FTEIETAYRT YLNVEHISEL FTLDYFSTVL   240
TQEQIEVYNN IIGGRVDDDN VKIQGLNEYV NLYNQQQKDR SKRLPLLKSL YKMILSDRIA   300
ISWLPEEFKS DKEMIEAINN MHDDLKDILA GDNEDSLKSL LQHIGQYDLS KIYIANNPGL   360
TDISQQMFGC YDVFTNGIKQ ELRNSITPSK KEKADNEIER ERINKMFKSE KSFSIAYLNS   420
LPHPKTDAPQ KNVEDYFALL GTCNQNDEQP INLFAQIEMA RLVASDILAG RHVNLNQSEN   480
DIKLIKDLLD AYKALQHFVK PLLGSGDEAE KDNEFDARLR AAWNALDIVT PLYNKVRNWL   540
TRKPYSTEKI KLNFENAQLL GGWDQNKEPD CTSVLLRKDG MYYLAIMDKK ANHAFDCDCL   600
PSDGACFEKI DYKLLPGANK MLPKVFFSKS RIKEFSPSES IIAAYKKGTH KKGPNFSLSD   660
CHRLIDFFKA SIDKHEDWSK FRFRFSDTKT YEDISGFYRE VEQQGYMLGF RKVSEAFVNK   720
LVDEGKLYLF HIWNKDFSKH SKGTPNLHTI YWKMLFDEKN LTDVIYKLNG QAEVFYRKKS   780
LDLNKTTTHK AHAPITNKNT QNAKKGSVFD YDIIKNRRYT VDKFQFHVPI TLNFKATGRN   840
YINEHTQEAI RNNGIEHIIG IDRGERHLLY LSLIDLKGNI VKQMTLNDIV NEYNGRTYAT   900
NYKDLLATRE GERTDARRNW QKIENIKEIK EGYLSQVVHI LSKMMVDYKA IVVLEDLNTG   960
FMRNRQKIER QVYEKFEKML IDKLNCYVDK QKDADETGGA LHPLQLTNKF ESFRKLGKQS   1020
GWLFYIPAWN TSKIDPVTGF VNMLDTRYEN ADKARCFFSK FDSIRYNADK DWFEFAMDYS   1080
KFTDKAKDTY TWWTLCSYGT RIKTFRNPAK NNLWDNEEVV LTDEFKKVFA AAGIDVHENL   1140
KEAICALTDK KYLEPLMRLM TLLVQMRNSA TNSETDYLLS PVADESGMFY DSREGKETLP   1200
KDADANGAYN IARKGLWTIR RIQATNCEEK VNLVLSNREW LQFAQQKPYL ND           1252

SEQ ID NO: 54            moltype = DNA   length = 3759
FEATURE                  Location/Qualifiers
misc_feature             1..3759
                         note = Description of Artificial Sequence: Synthetic
                         Cas12a/Cpf1 [Parabacteroides distasonis] sequence
source                   1..3759
                         mol_type = other DNA
                         organism = synthetic construct
SEQUENCE: 54
atgaaaaata tattggaaca attcgtagga ttatatcctt tgagtaagac actgcggttt   60
gaactaaaac ccttgggcaa gacattagag catatcgaga aaaaaggtct tattgcgcaa   120
gacgagcaaa gagcggaaga gtacaaactt gtcaaggata ttatcgaccg ttatcataag   180
gcatttatto atatgtgtct aaaacatttc aaattgaaaa tgtattcaga acaaggttat   240
gactctttag aagaatatag gaaactggcc tctatctcca aacgtaatga aaaagaagaa   300
caacagtttg ataaagtaaa ggaaaactta cgcaaacaaa ttgtcgatgc tttcaagaat   360
ggtggctcgt atgatgattt gtttaagaaa gaactaatac agaagcatct gcctagattt   420
atagagggag aagaagagaa acgaatagtt gataacttca taaatttac cacatacttc   480
accggttttc atgaaaaccg gaagaacatg tattcggatg agaaggaatc aacagccatt   540
gcctatcggt taatacatga gaatcttccc ttgtttttgg acaatatgaa atcgtttgcc   600
aaaatagcag agagtgaagt agctgcccgg tttactgaaa tagaaacggc ataccgcaca   660
tatctcaatg tggaacacat cagtgaactg tttacgcttg actatttttc tactgtgctt   720
acacaagaac agatagaagt ttataacaat atcattggtg gccgtgtgga tgatgacaat   780
gtcaagatac aagggcttaa cgagtatgtg aaccttttca accaacagca aaaagaccgt   840
agtaaacgac tgcctttatt aaagtcactc tataagatga ttcttagtga tcgtatagct   900
atttcgtggc taccagaaga gtttaagagt gacaaggaga tgattgaggc cattaataat   960
atgcatgatg acttgaaaga cattcttgcc ggtgacaatg aggattcatt gaaatcatta   1020
ctacagcaca tcggacaata tgaccttttct aaaatttata ttgccaacaa tccagggctt   1080
acggatattt cacaacagat gttcggatgc tatgatgttt tcacaaatgg aatcaaacaa   1140
gaactccgca actctatcac tcccagtaaa aaggaaaaag ccgacaatga atatatgag   1200
gaaagaataa acaaaatgtt caagtcggaa aagagtttca gcatagcgta tctaaacagc   1260
ttgccacatc ccaaaacaga tgctccccaa agaatgtgg aagattattt tgccctgctt   1320
ggcacttgta accagaatga cgagcaaccg ataaacctat ttgcacaaat agaaatggct   1380
cgtcttgtca catcggatat tcttgctggc cgacatgtca acctcaacca atcaagaaac   1440
gatatcaagc taataaaaga tttgcttgat gcctataagg cattgcagca ttttgtcaag   1500
cccttgttag gcagcggcga tgaggccgaa aagacaatga gtttgatgcc cgtctcgct   1560
gcggcttgga atgcgctgga tattgtaacc ccttttatata acaaggtgcg caattggctg   1620
actcgcaagc cgtatagcac agaaaagata aaattgaatt ttgaaaatgc gcagttgctg   1680
ggaggttggg atcagaacaa agaaccagac tgcacttctg tattgttgcg taaagatggt   1740
```

```
atgtattatc ttgccatcat ggataaaaaa gccaatcatg cgttcgattg tgattgtctg   1800
ccttcggatg gcgcttgttt tgaaaaaatt gactacaaac tattgcccgg agcgaacaag   1860
atgcttccaa aggtattctt ctcaaagtca cgcataaaag aattctcccc ttccgaaagc   1920
atcatcgcag cctataaaaa aggcacccat aaaaaaggtc cgaatttcag tctgtcagac   1980
tgtcatcgac tgatcgactt cttcaaggca tctattgaca agcacgaaga ctggagcaaa   2040
ttccggttca gattctccga tacgaaaact tacgaagaca tcagtggatt ttatcgtgag   2100
gtagagcaac aaggatatat gcttggcttt agaaaggtct ctgaagcatt tgtcaacaaa   2160
ctggtcgacg aaggtaaact ttatctgttc catatatgga acaaggattt ctcgaaacat   2220
agcaagggga cgcctaatct gcatacgata tactggagca tgctgttcga cgagaaaaac   2280
ctaactgatg taatatataa actgaatggc caagcagaag tattctatcg taagaagagt   2340
ctcgaccttta caagaccac gacacataag gcacacgcgc ccattacgaa caagaataca   2400
cagaatgcca agaaaggcag cgttttcgat tacgacatca taaagaaccg tcgttatacg   2460
gttgacaagt tccagtttca tgtgcctata accctcaact ttaaggcaac cggacggaat   2520
tatcaacg agcatacgca ggaagccata cgaaacaacg gtattgagca tattatcggc   2580
attgaccgtg gtgaaagaca tctgctctat ctgtcactaa tcgatttgaa agggaatatc   2640
gtaaagcaaa tgcactgaa cgacattgtc aatgagtata acggacgcac ctatgccacg   2700
aattacaaag acctccttgc cacacgagag ggagaacgca cagatgcacg ccgcaactgg   2760
cagaaaatag agaacataaa agagattaag gaaggttatc tcagtcaagt tgtccatatt   2820
ctctccaaga tgatggtgga ctaaaagca atcgtagtgc ttgaagattt gaatacggga   2880
ttcatgcgca accgtcagaa aatagaacgg caagtgtatg aaaaattcga aaagatgctt   2940
atcgacaaac tgaactgcta tgtagacaag cagaaggatg ccgatgaaac gggaggcgca   3000
ttgcatccgc tccaactcac caacaaattt gaaagcttcc gcaaactcgg taaacagagc   3060
ggctggctgt tctatattcc cgcatggaac accagtaaga tagaccctgt caccggtttc   3120
gtgaacatgc tcgataccag gtatgagaat gcagacaagg caagatgttt tttctcgaaa   3180
ttcgattcta tccgatataa cgctgataag gattggtttg aatttgccat ggactacagc   3240
aaatttaccg acaaggcaaa ggatacgtac acttggtgga cactttgttc ctacggaaca   3300
cgaatcaaga ccttccgcaa cccgccaag aacaatctgt gggataatga ggaagttgtt   3360
ctgaccgatg aatttaagaa agttttgca gctgccggca tagatgttca cgaaaacctg   3420
aaagaagcca tttgtgcatt aaccgacaag aaatatcttg agccgttgat gcgcttaatg   3480
accctattag tacaaatgcg caacagtgcc accaactgga aggagatta tctgctctga   3540
ccagtagccg atgaaagcgg aatgttctat gacagtcggg aaggcaagga acgctgccc   3600
aaggatgctg atgccaatgg tgcgtacaac attcccgaa aaggcttgtg gactatccgt   3660
cggatacagg cgacaaactg tgaggagaaa gtaaatcttg tcctatctaa cagagaatgg   3720
ctgcagtttg cccaacaaaa accttatctg aatgactga                         3759

SEQ ID NO: 55           moltype = AA  length = 1314
FEATURE                 Location/Qualifiers
REGION                  1..1314
                        note = Description of Artificial Sequence: Synthetic
                        polypeptide
source                  1..1314
                        mol_type = protein
                        organism = synthetic construct
SEQUENCE: 55
MGHHHHHHSS GLVPRGSGTM KNILEQFVGL YPLSKTLRFE LKPLGKTLEH IEKKGLIAQD    60
EQRAEEYKLV KDIIDRYHKA FIHMCLKHFK LKMYSEQGYD SLEEYRKLAS ISKRNEKEEQ   120
QFDKVKENLR KQIVDAFKNG GSYDDLFKKE LIQKHLPRFI EGEEEKRIVD NFNKFTTYFT   180
GFHENRKNMY SDEKESTAIA YRLIHENLPL FLDNMKSFAK IAESEVAARF TEIETAYRTY   240
LNVEHISELF TLDYFSTVLT QEQIEVYNNI IGGRVDDDNV KIQGLNEYVN LYNQQQKDRS   300
KRLPLLKSLY KMILSDRIAI SWLPEEFKSD KEMIEAINNM HDDLKDILAG DNEDSLKSLL   360
QHIGQYDLSK IYIANNPGLT DISQQMFGCY DVFTNGIKQE LRNSITPSKK EKADNEIYEE   420
RINKMFKSEK SFSIAYLNSL PHPKTDAPQK NVEDYFALLG TCNQNDEQPI NLFAQIEMAR   480
LVASDILAGR HVNLNQSEND IKLIKDLLDA YKALQHFVKP LLGSGDEAEK DNEFDARLRA   540
AWNALDIVTP LYNKVRNWLT RKPYSTEKIK LNFENAQLLG GWDQNKEPDC TSVLLRKDGM   600
YYLAIMDKKA NHAFDCDCLP SDGACFEKID YKLLPGANKM LPKVFFSKSR IKEFSPSESI   660
IAAYKKGTHK KGPNFSLSDC HRLIDFFKAS IDKHEDWSKF RFRFSDTKTY EDISGFYREV   720
EQQGYMLGFR KVSEAFVNKL VDEGKLYLPH IWNKDFSKHS KGTPNLHTIY WKMLFDEKNL   780
TDVIYKLNGQ AEVFYRKKSL DLNKTTTHKA HAPITNKNTQ NAKKGSVFDY DIIKNRRYTV   840
DKFQFHVPIT LNFKATGRNY INEHTQEAIR NNGIEHHIGI DRGERHLLYL SLIDLKGNIV   900
KQMTLNDIVN EYNGRTYATN YKDLLATREG ERTDARRNWQ KIENIKEIKE GYLSQVVHIL   960
SKMMVDYKAI VVLEDLNTGF MRNRQKIERQ VYEKFEKMLI DKLNCYVDKQ KDADETGGAL  1020
HPLQLTNKFE SFRKLGKQSG WLFYIPAWNT SKIDPVTGFV NMLDTRYENA DKARCFFSKF  1080
DSIRYNADKD WFEFAMDYSK FTDKAKDTYT WWTLCSYGTR IKTFRNPAKN NLWDNEEVVL  1140
TDEFKKVFAA AGIDVHENLK EAICALTDKK YLEPLMRLMT LLVQMRNSAT NSETDYLLSP  1200
VADESGMFYD SREGKETLPK DADANGAYNI ARKGLWTIRR IQATNCEEKV NLVLSNREWL  1260
QFAQQKPYLN DAAAKRPAAT KKAGQAKKKK ASGSGAGSPK KKRKVEDPKK KRKV         1314

SEQ ID NO: 56           moltype = DNA  length = 3948
FEATURE                 Location/Qualifiers
misc_feature            1..3948
                        note = Description of Artificial Sequence: Synthetic
                        polynucleotide
source                  1..3948
                        mol_type = other DNA
                        organism = synthetic construct
SEQUENCE: 56
atgggccacc atcatcatca tcatagcagc ggcctggtgc cgcgcggcag cggtaccatg    60
aagaacatct tagagcagtt tgtcggctta tatccgttgt ctaaaacact tcggtttgag   120
cttaaacctt tgggtaagac cttggaacat attgagaaaa aaggcttgat tgcccaagac   180
```

```
gaacagcggg cggaggagta caaattggtt aaagatatta ttgatcgcta ccacaaggct    240
tttattcata tgtgcttaaa acatttttaag ctcaagatgt acagtgaaca agggtatgat   300
agcttggagg agtaccgcaa gcttgcgtca atttccaaac gcaacgagaa agaggagcag    360
caatttgaca aagtcaagga aaatcttcgt aagcaaattg tcgacgcgtt taaaaatggc    420
gggagttatg atgatctgtt taagaaagaa ttgatccaga aacacctccc acgtttttatt   480
gagggtgaag aagaaaaacg tatcgttgac aacttcaaca agttcacgac ctattttact    540
ggttttcatg aaaatcgcaa gaatatgtat agtgacgaaa aggaatcgac ggctattgct    600
tatcgtctca ttcacgaaaa cttgccattg ttttttggata acatgaagag cttcgctaag   660
atcgccgaat cggaagtggc tgctcgtttt accgaaatcg aaaccgctta ccggacatac    720
ttgaacgtag aacacattag tgaactgttc accctcgact attttagcac ggttttgacg    780
caagaacaaa tcgaagtata taataacatt atcggcgggc gcgtcgacga cgacaacgta    840
aagatccaag ggttgaatga gtacgtaaat ttatataatc agcagcagaa ggaccggtct    900
aagcgcttac cgcttcttaa gtccctctac aaaatgatct tatccgatcg tattgcaatt    960
tcgtggttac ctgaggagtt caaatccgat aaggagatga ttgaagcaat taacaacatg   1020
catgacgacc tgaaggacat tctggcaggc gacaacgaag actcgcttaa gtccttactg   1080
cagcatattg gccaatacga tctctcgaaa atctacattg cgaacaatcc gggcctgaca   1140
gatatctcac aacaaatgtt cgggtgttat gacgtcttta ctaatgggat caagcaggag   1200
ctccggaaca gtattacccc ttcaaaaaag gagaaagccg ataacgaaat ctacgaggag   1260
cggattaaca aaatgtttaa aagtgagaag agtttctcaa ttgcctacct gaattcgttg   1320
ccgcacccaa agacggatgc gcctcaaaaa aatgttgagg attattttgc tctcctgggg   1380
acttgcaatc aaaacgatga acagccgatt aatttgtttg cccaaattga gatggcacgc   1440
ttagtcgcct ctgatattct cgcaggccgc cacgttaatc tgaaccaatc tgagaatgat   1500
atcaagttaa tcaaggatct gttagatgct tacaaggctc tgcagcattt cgtcaaacca   1560
ctccttggct cgggtgacga ggctgagaaa gataacgagt tcgatgcacg cctccgtgcg   1620
gcttggaatg cgttggacat tgttacacca ctctataaca aggttcggaa ctggctgacc   1680
cgcaaaccat attctacaga aaaaatcaag cttaatttcg aaacgcccca acttctgggg   1740
ggttgggatc agaacaaaga accggattgc acatcagtcc tccttcggaa ggatgggatg   1800
tactatttag cgatcatgga taaaaaggcg aatcacgcct ttgactgtga ctgcttaccg   1860
tctgacgggg cctgtttcga gaaaattgac tacaagctgc tcccgggcgc gaataaaatg   1920
ttgccgaaag tttttttttc taaaagccgc atcaaagaat tttccccttc ggaatcgatc   1980
atcgctgctt ataaaaaggg gactcataaa aaagggccga atttcagtct ctctgattgt   2040
catcgcttga ttgactttttt taaggctagc attgataagc acgaagattg gtcaaaattt   2100
cgttttcgct tctcagatac caaaacgtat gaagacatca gtggtttcta ccgtgaagta   2160
gaacagcaag gctatatgct gggttttcgt aaagtctctg aggcctttgt gaataaactc   2220
gttgatgaag gtaagttata cttattccat atctgaacaa aagactttag taagcactcc   2280
aaaggtacac ctaatctcca cactatttat tggaaaatgc tcttcgatga gaaaaatctc   2340
actgacgtca tctacaaact gaatgggcag gctgaagtat tctaccgtaa aaaaagtctg   2400
gatcttaata agacaactac tcacaaggca catgccccaa tcaccaataa aaatacccaa   2460
aacgcaaaga agggtagtgt tttcgattac gatatcatca aaaatcgtcg ctacacagtg   2520
gacaaattcc agttccacgt ccctatcacc ttaaattttta aggcaacagg tcgtaattac   2580
attaatgagc acactcaaga ggcaatccgt aataatggca tcgaacatat cattggcatc   2640
gaccgtgggg agcgtcactt gctttacttg tcgctcattg atctgaaggg taatatcgtc   2700
aagcagatga cccttaatga tatttgtcaat gaatataatg gtcggactta tgcgacgaac   2760
tacaaggact tgctggcaac acgggagggt gagcgtacgg acgctcggcg caactggcag   2820
aagattgaaa atattaaaga aatcaaggaa ggttacctta gccaggtggt gcacatcttg   2880
agtaaaatga tggtcgacta caaggctatc gttgttctgg aagacttgaa tacaggcttc   2940
atgcggaatc gtcaaaaaat cgaactgcaa gtatatgaga agttcgaaaa aatgttaatt   3000
gacaagctga actgctatgt tgacaaacaa aaggatgctg acgagacggg cggtgccctc   3060
cacccgctgc agctgacaaa caaatttgag tcgtttcgta agttaggtaa gcagagtggt   3120
tggcttttttt acatcccagc atggaacact tcgaaaatcg acccagttac tgggttcgtg   3180
aacatgttag acacgcgcta cgagaacgcc gataaggcgg ggtgtttctt ctcgaaattc   3240
gattccatcc ggtataacgc tgacaaagat tggtttgagt ttgctatgga ttacagtaag   3300
ttcactgata aagcgaaaga tacttacacg tggtggactc tgtgttccta tgggacgcgt   3360
attaaaactt ttcgtaatcc ggctaagaat aatttgtggg ataatgagga ggttgtcctt   3420
actgatgagt tcaagaaagt tttcgcagcg gcaggtattg atgtccatga gaaccttaag   3480
gaagcgatct gtgctctgac agataaaaag tatcttgaac cactcatgcg tctcatgacc   3540
ctgctcgttc aaatgcggaa ctctgctact aactccgaaa cagactattt actttcacca   3600
gttgctgacg agtcagggat gttctatgac tcccgcgaag gaaggaaac actgccaaaa    3660
gatgcggacg ccaacggtgc atataacatt gcccgtaagg gcctctggac catccggcgg    3720
attcaagcca ccaactgtga ggagaaagtt aacttagtcc tcagtaatcg tgaatggttg    3780
cagtttgccc agcagaaacc atatctgaat gatgcggccg caaaaaggcc ggcggccacg    3840
aaaaaggccg gccaggcaaa aagaaaaag gctagcggca gcggcgccgg atccccaaag    3900
aagaaaagga aggttgaaga ccccaagaaa aagaggaagg tgtgataa              3948
```

SEQ ID NO: 57        moltype = DNA  length = 3948
FEATURE               Location/Qualifiers
misc_feature       1..3948
                       note = Description of Artificial Sequence: Synthetic
                       polynucleotide
source                 1..3948
                       mol_type = other DNA
                       organism = synthetic construct
SEQUENCE: 57

```
atgggccacc atcatcatca tcatagcagc ggcctggtgc cgcgcggcag cggtaccatg     60
aagaatatcc tcgaacaatt tgtcggtctt tatccactta gcaagactct gcgcttcgaa    120
ctgaagccaa ttgggaagac attgaacatt atcgagaaaa aggggctcat tgcccaagac    180
gaacaacgcg ccgaagagta taactggtaa aggacattac tcgatcgcta ccataaggca    240
ttcatccaca tgtgcttgaa acattttaaa ttaaagatgt attccgaaca gggtacgat    300
agtttagaag aatatcggaa actggcctcc atcagcaaac gcaacgagaa ggaggaacaa    360
```

-continued

```
cagttcgata aggtcaagga aaatttgcgg aagcaaattg tcgatgcgtt caagaatggc    420
ggctcgtatg acgatttgtt taaaaaagaa ttaatccaaa aacacttacc acgtttcatt    480
gagggggagg aagaaaagcg gatcgtggac aattttaaca aattcaccac ttatttcacc    540
ggttttcatg aaaatcgcaa aatatgtac tctgatgaaa aggaatcgac ggcaatcgcc    600
tatcgtctga ttcacgaaaa cttaccatta ttcctgacaa atatgaaaag tttcgcgaaa    660
atcgcagagt cggaagtggc ggcgcggttt acagaaatcg aaactgcgta tcgcacgtat    720
ttaaacgtag aacacattag tgagcggtttt acattagact acttctccac tgtactgaca    780
caggaacaaa tcgaggtcta taacaacatc attggcggcc cgtcgacga cgataatgtc    840
aagattcagg gtctcaatga atatgttaac ttatataacc aacaacaaaa agaccggtcg    900
aaacggctgc cactcttaaa aagtctgtat aaaatgattt taagcgaccg cattgcgatt    960
tcgtggttgc ctgaagagtt taagtcggac aaagagatga ttgaggctat taacaacatg   1020
catgatgatc tgaaggatat cttagccggc gacaatgagg actcactcaa aagtctgctt   1080
cagcacattg gtcaatatga cttgtccaaa atttatattcg ctaataatcc gggccttaca   1140
gacatctcgc agcaaatgtt tgggtgctat gacgtattca caaatggtat caagcaggag   1200
ttgcgtaact cgatcacgcc ttccaagaag gaaaaagcag ataacgaaat ttatgaggag   1260
cggattaata agatgttcaa gtcggagaag agcttctcaa ttgcatatct gaactcgttg   1320
ccgcatccga aaactgatgc cccacagaag aatgtagagg actactttgc cctgctcggc   1380
acatgtaatc aaaacgacga acaaccaatc aatttattcg cccagattga gatgcgcgc    1440
ttggtggcgt ccgacattct cgcgggccgc catgtaaatc ttaatcagtc ggaaaacgac   1500
attaagctta ttaaggacct gctcgatgcc tacaaagctt tacgcacttt cgttaaacca   1560
ctgttgggtt cgggtgatga agctgagaag gataatgaat ttgatgcccg cctccgcgcg   1620
gcctggaacg cactcgacat tgtaacacct ctttacaata aagtacggaa ttggcttacg   1680
cgtaaacctt attcgacgga gaagattaag ctcaactttg aaaatgctca gcttttaggt   1740
ggctgggacc agaacaaaga gccagattgc acgtctgtac ttctccgcaa agatggcatg   1800
tattatctcg ccattatgga caaaaaggct aatcatgcgt ttgattgcga ttgtttacct   1860
tcggatggtg cttgctttga aaaaattgat tacaaactcc tgccagggcc aaacaaaatg   1920
ctcccaaaag tgttctttag taaatcccgt atcaaggagt tttcgccttc cgagagcatc   1980
attgccgctt acaaaaaagg tacccacaaa aaggtccaa actttctct ttcggactgc     2040
caccgtctca tcgatttctt taaagcttca attgacaaac atgaggattg gtctaagttc   2100
cgttttcggt tctcggatac caaaacctac gaggatatct caggcttcta ccgggaggtt   2160
gaacagcagg ggtatatgct gggctttcgg aaggttagtg aagcttttgt aaataagctt   2220
gtagatgagg gtaaactcta tctcttccat atctggaaca aagatttctc gaagcattcc   2280
aaagggaccc caaacttgca tactatctat tggaaaatgc ttttcgatga aaagaacttg   2340
acggacgtta tttacaagct caacgggcaa gctgaagtct tctaccggaa aaaatctctc   2400
gacttaaaca agacgacgac tcacaaggcc cacgcaccta ttacgaacaa gaatactcaa   2460
aacgcgaaga aaggctccgt atttgattac gacatcatta aaaaccggcg gtatactgtc   2520
gataagtttc agtttcatgt gccaatcacc ttgaatttca aggcgacggg tcgtaactac   2580
atcaatgagc atactcaaga agctattcgt aacaatggca ttgaacatat tatttgggatc   2640
gaccgcgggg agcgtcacct gttgtatttg tcgctgatcg atctgaaagg gaatatcgtc   2700
aagcagatga ccttgaatga catcgtcaat gaatataacg ggcgcaccta cgctactaac   2760
tacaaagacc ttctggcaac gcgcgagggc gaacgcacgg atgctcgccg caactggcag   2820
aaaattgaga acatcaagga aatcaaggag ggttacttaa gccaggtagt tcatattctc   2880
tcaaagatga tggtagatta caaggcgatc gtggtgtttgg aagacttaaa tacaggcctc   2940
atgcgtaatc gccaaaaaat cgaacgggcaa gtatacgaga aatttgagaa atgttgatc    3000
gataaactca attgttacgt cgataaacaa aagacgcgg acgaacgggg cggggcttta   3060
cacccacttc agcttaccaa taaatttgaa agttttcgta aactggggaa gcagagtggc   3120
tggttattct atatcccggc atggaacaca tcgaaaattg accggtcgc gggtttttgtt   3180
aatatgctgg atacccgcta cgagaacgcc gacaaagccc ggtgttttttt ctctaagttc   3240
gactccattc gctacaatgc agacaaagat tggtttgagt tcgctatgga ttactcgaaa   3300
tttacagaca aagccaaaga cacttatacc tggtggacac tctgtagtta cgggacccgc   3360
atcaaaactt ttcggaatcc ggccaagaac aacctctgga ataatgagga ggtggtactc   3420
accgatgagt ttaaaaaggt ctttgcggca gcgggtatcg atgtccatga aaacttgaaa   3480
gaagccatct cgcgccttga ctgataaaaaa tacctcgaac cactgatgcg tttaatgacg   3540
ttacttgttc agatgcgcaa ttcggcaaca aactcggaga ctgactactt gttgtcccct   3600
gtggccggca agtcaggtat gttttatgat tcacgtgaag ggaaggaaac cttaccgaaa   3660
gatgcggacg ccaacggtgc ttataacatt gcccgcaagg gcttgtggac catccgtcgc   3720
atccaggcca cgaattgcga ggagaaagtc aaccttgtgt tgtcaaaccg ggaatggtta   3780
cagtttgcgc aacaaaagcc ttatctcaac gatggcgcgc caaaaggcc ggcggccacg    3840
aaaaaggccg gccaggcaaa aagaaaaag gctagcggca gcggcgccgg atccccaaag   3900
aagaaaagga aggttgaaga cccccaagaaa aagaggaagg tgtgataaa                3948
```

SEQ ID NO: 58        moltype = DNA  length = 3948
FEATURE               Location/Qualifiers
misc_feature       1..3948
                       note = Description of Artificial Sequence: Synthetic
                       polynucleotide
source                 1..3948
                       mol_type = other DNA
                       organism = synthetic construct
SEQUENCE: 58

```
atgggccacc atcatcatca tcatagcagc ggcctggtgc cgcgcggcag cggtaccatg     60
aaaaacattt tagaacaatt tgttggttta tatccgcttt ccaagacgct ccggttcgag    120
ttaaagccgt tgggcaagac actggagcat attgagaaga agggtttgat tgcgcaggat    180
gagcaacgcg cggaggaata taactggta aaagacatta tcgatcgcta ccataaagca    240
ttcattcaca tgtgcctgaa acatttaaa ttgaaaatgt acagcgagca agggtatgac    300
agtcttgagg agtatcgtaa gctggcatcg atttcaaagt gtaacgagaa agaagagcaa    360
cagtttgaca aggttaagga gaacttacgt aaacaaatcg tagatgcgtt taagaacggg    420
ggttcgtacg atgacttgtt caaaaaagaa ttaatccaga agcacttgcc gcgcttcatt    480
gagggcgagg aagagaaacg catcgtggac aacttcaata aatttacaac ttacttcacc    540
```

```
ggcttccacg aaaaccgtaa gaatatgtat tcagacgaaa aggaaagtac tgccattgcc  600
tatcggctga tccacgaaaa ccttccactc ttcttggata atatgaaatc ttttgcgaaa  660
atcgcggaga gcgaggtcgc cgcccgcttc accgaaatcg agacagccta ccggacgtac  720
ctcaacgtag agcatatctc cgagttattc acattggatt acttctcgac cgtacttacc  780
caagaacaaa tcgaagttta caacaacatc atcggtgcc gcgtcgacga tgataacgta  840
aagatccagg gccttaacga gtatgtcaac ctgtacaatc agcagcagaa agatcgcagc  900
aagcgcctgc cattattgaa atcgctttat aagatgattc tgagtgaccg catcgcaatc  960
tcctggcttc ctgaggagtt caagtcagat aaagagatga tcgaggcaat caacaacatg 1020
cacgatgatt tgaaggacat tcttgctggt gataatggaa actcgttgaa atcgctctta 1080
caacatattg gtcaatacga tttaagcaag atttacattg ctaacaatcc aggtctgaca 1140
gatatcagcc agcagatgtt tggctgctac gatgttttca ccaatggcat taagcaagag 1200
ctccggaaca gcattactcc ttccaagaaa gagaaggcgg acaatgaaat ttacgaggag 1260
cgtattaata agatgttcaa gtcggagaag tcgttcagca ttgcgtacct taattcgtta 1320
ccacacccaa aaactgacgc gcctcaaaaa aacgtgaaag actatttcgc actgctcggc 1380
acttgtaacc aaaacgatga gcaaccatt aatctgttcg ctcagattga gatggctcgt 1440
ctcgtagcgt ccgatattct cgcgggccgt catgtcaatc tgaaccaatc cgagaatgac 1500
attaaattga tcaaggactt actggacgcg tataaggcgc tgcagcactt tgtgaagcct 1560
ttgttaggtt cgggcgatga ggcagaaaag gataacgagt ttgatgcccg tctccgggcc 1620
gcatggaatg cgttagacat cgtgactcct ctgtacaata aggttcgtaa ctggttgacg 1680
cggaagcctt attccacgga gaagatcaaa ttgaactttg aaaatgcaca gttgcttggg 1740
gggtgggacc agaataagga gcctgattgt acttctgttt tattacgtaa ggatggtatg 1800
tactacttag caattatgga taagaaagca aatcatgcgt tcattgcga ttgtctccct 1860
tccgatgggg cttgcttcga aaagatcgac tacaaacttc tcccgggcgc gaataagatg 1920
ttgcctaaag ttttctttc taagagccgc atcaaagaat ttagtccaag cgagagcatc 1980
atcgctgctt acaagaaagg tacgcataaa aaaggtccta acttctcctt atcggattgc 2040
catcgtctca tcgacttctt caaggcctct attgacaaac atgaagactg gtctaagttt 2100
cgttttcgtt tctcagacac taagacatac gaagacattt ccggttttta tcgcgaggtg 2160
gagcaacagg ggtatatgtt aggttttcgc aaggtaagtg aggcatttgt gaacaagctt 2220
gtggacgagg gtaagttata tttatttcac atttggaaca aggacttctc aaagcacagc 2280
aagggacgc ctaatctgca taccatctac tggaaaatgc tgttcgacga aaagaatctc 2340
acggacgtga tctacaagtt gaacggccag gcgaggtgt tctatcgcaa aaagagttta 2400
gatttgaaca agactaccac tcacaaggcg catgcccaa ttacaaacaa gaacacccaa 2460
aacgcaaaaa agggctctgt gttcgactac gatattatta gaaccggcg ttataccgtt 2520
gacaagttcc aattccacgt gcctatcact ttaaacttca aggctactgg ccgtaactat 2580
atcaatgagc atacacagga ggcaatccgg aataatggta tcgagcacat cattggtatt 2640
gatcgcgggg agcgccactt attataccTT tccCttatCG acttaaaggg gaacattgtt 2700
aagcagatga cattaaatga tatcgtaaac gagtataatg gccggactta tgctacgaat 2760
tacaaagacc tcctggccac acgggaaggc gaacgcaccg atgcccgccg caactggcaa 2820
aaaatcgaga atattaagga gattaaagag ggctacttgt cccaggtcgt ccacatccgt 2880
tcgaaaatga tggtcgacta caaagctatc gtcgtcttag aagacttgaa cacaggttttt 2940
atgcgtaacc gtcagaaaat cgaacggcaa gtttatgaga aattcgaaaa aatgttgatt 3000
gacaagtaa attgctatgt tgacaagcag aaggacgcgg atgaaacagg ggggcatta 3060
catccattgc agttgaccaa caaattcgag tcgttccgta acctcggcaa acagtctggt 3120
tggctcttct acattcctgc ctggaataca tcgaaaattg acccggtgac gggctttgta 3180
aacatgttgg atacacggta tgagaacgcg acaaggccc gctgtttctt ttctaaattt 3240
gactcgatcc ggtacaatgc agacaaagac tggttcgagt tcgctatgga ttattcaaaa 3300
tttactgaca aggctaagga cacctatacg tggtggacga tctgctctta tggcactcgg 3360
attaagacgt tccgcaatcc tgcaaaaaac aatttatggg acaatgaaga agtagtactt 3420
accgatgagt tcaagaaagt ttttgcagcc gctggcatcg atgtacacga aaatcttaag 3480
gaggccatct gtgccttaac agataagaag tatttagaac cattaatgcg cttaatgaca 3540
ctccttgtgc agatgcgcaa cagtgcgacc aacagcgaaa ccgattactt actgtctccg 3600
gttgctgatg agtcaggcat gttttacgac tcccggagg ggaaagagac ccttcctaaa 3660
gacgccgatg caaacggcgc ctataatatc gcacgcaagg gcttatggac tattcgccgt 3720
attcaggcaa cgaactgcga agaaaaggtt aacttagtgt taagtaaccg tgagtggctc 3780
caattcgcgc agcagaagcc ttacttaaat gatggcgcgc caaaaaggcc ggcggccacg 3840
aaaaaggccg gccaggcaaa aagaaaaag gctagcgcgg gcggcgccgg atccccaaag 3900
aagaaaagga aggttgaaga ccccaagaaa aagaggaagg tgtgataa              3948
```

SEQ ID NO: 59       moltype = DNA length = 3948
FEATURE              Location/Qualifiers
misc_feature       1..3948
                    note = Description of Artificial Sequence: Synthetic
                    polynucleotide
source              1..3948
                    mol_type = other DNA
                    organism = synthetic construct
SEQUENCE: 59
```
atgggccacc atcatcatca tcatagcagc ggcctggtgc cgcgcggcag cggtaccatg   60
aaaaacattc ttgagcaatt cgttggtctt tatccgttat ccaaaaccct gcgctttgaa  120
ttaaaccctt taggtaaaac actgcagcac atcgagaaaa aagggcttat cgcacaggac  180
gagcaacgcg cagaagaata caagctcgtg aaggacatca ttgaccgcta ccacaaggct  240
ttcatccaca tgtgcttaaa acattttaaa ttaaaaatgt acagtgagca ggggtatgat  300
tcgctggaag agtatcggaa gctggcatct atcagcaaac gtaacgaaaa ggaggagcaa  360
cagttcgaca aagtcaaaga gaatctccgg aaacagattg ttgacgcttt caaaaatggc  420
gggagctacg acgacttgtt taagaaggaa ctgattcaga agcacttacc gcgcttcatc  480
gagggtgaag aggagaagcg gatcgtagat aacttcaaca gttcaccac ctatttcacg  540
ggctttcatg aaaaccggaa gaacatgtat agtgacgaaa agaatcgac agctatcgct  600
taccgtctta tccacgagaa cctccctctc tttctggata atatgaagtc gttcgcgaag  660
attgcggaat ccgaggtagc ggcccgtttc acggaaattg agactgctta ccggacttat  720
```

```
ttgaatgtag agcacatttc ggagttattt acacttgact atttctccac cgtgctgaca   780
caggaacaga ttgaagttta caataacatc attggtggcc gcgttgacga tgataatgtt   840
aagattcagg gcttaaacga atacgtgaac ctctataacc aacaacagaa agatcgtagt   900
aaacggctgc cattgttaaa gtccctctac aaaatgattc tcagcgatcg catcgcaatc   960
tcatgcgtgc ctgaagagtt caagagtgat aaggagatga tcgaggctat taataacatg  1020
catgacgatt tgaaagacat tcttgcaggc gataatgagg acagtttaaa gagcttgtta  1080
caacatattg gtcagtacga tttgtccaaa atttacattg caaacaatcc tgggttaact  1140
gatatctccc agcagatgtt tgggtgctac gatgtattta cgaacgggat taagcaagag  1200
ttgcgcaata gtatcactcc gagcaaaaaa gagaaggcag acaatgagat ttatgaagag  1260
cgtatcaata aaatgtttaa gtccgaaaag tcattttcaa tcgcctatct caatagtctc  1320
ccgcatccaa agacagatgc cccacagaag aacgtggaag attatttcgc gcttctgggt  1380
acctgcaatc agaatgatga gcagccgatt aatcttttcg ctcaaattga aatggcccgc  1440
ctggtggcat cggatatcct tgctggccgg catgtaaatc ttaaccaaag cgaaaacgat  1500
attaaactga ttaaggactt attagatgct taaaggcac ttcagcactt cgtcaaacca  1560
ttacttggga gtgggggatga ggctgaaaag gataatgaat tcgacgctcg gttacgtgcg  1620
gcgtggaacg ccttggatat tgttactcca ctttataaca aagtacgtaa ttggctgacg  1680
cgcaagccgt atagtacgga gaagattaaa ctgaattttg aaaatgcgca gttactgggg  1740
ggctgggatc aaaacaaaga accggattgc acgagcgttc tgcttcgtaa agatgggatg  1800
tattacctgg ccatcatgga taagaaagca aatcacgctt ttgattgtga ctgtttaccg  1860
tcggacggtg catgtttcga aaaaattgac tataaattac tgccgggtgc gaacaagatg  1920
ctgcctaagg tcttttttctc gaagtcccgc atcaaagagt tctcccccttc ggagagtatc  1980
atcgctgcct ataaaaaggg tactcataag aaggggccta attttagtct ctcagattgc  2040
caccgcttaa ttgacttctt caaggccagt attgacaaac atgaggattg gtctaaattt  2100
cgcttccggt tcagtgatac gaaaacgtat gaagatatta gcgggtttta tcgcgaggtc  2160
gaacagcagg ggtacatgct gggtttccgg aaggtgtcag aggcctttgt taacaagtta  2220
gttgatgaag gcaaactttta tttatttcat atctggaata aagatttctc gaagcattcg  2280
aaagggacac caaatctgca tactatctac tggaagatgc tgtttgatga gaaaaacctt  2340
acagacgtga tttataagct gaatgggcaa gcagaggtct tttaccgtaa aaagtctctg  2400
gatctcaaca agaccacaac acacaaagct cacgcgccaa ttacgaataa gaacacgcaa  2460
aatgcagaaa aaggctctgt gtttgactac gacattatca aaaatcgtcg ctacaccgtt  2520
gacaaatttc aatttcacgt gccaattacc ctcaacttca aggcgacggg gcgaattac   2580
atcaacgaac acacccaaga agctatccgg aataatggta ttgagcacat catcgggatt  2640
gatcgggggg aacgccactt gctttatctt tctttgattg atctcaaagg taacatcgtc  2700
aaacagatga cgcttaatga tatcgtaaat gagtacaacg ggcgtacata cgcgactaat  2760
tataaagatc ttttggctac ccgcgaaggg gaacgtacgg atgcgcgccg caactggcaa  2820
aaaatcgaaa atattaagga gattaaggag ggctatctgt cgcaggtagt acacatcctg  2880
tcgaaaatga tggtcgatta caaagctatt gtcgttcttg aggatttaaa taccggtttc  2940
atgcggaatc ggcaaaaaat tgaacgcag gtgtacgaga aattcgaaaa aatgctcatt  3000
gataaattga actgctacgt tgataaacaa aaagacgcgg atgagacggg cggtgctctc  3060
cacccattgc aactgacaaa caagtttgag agctttcgta aattaggcaa gcaaagtggt  3120
tggctgttct atatcccagc atggaatacc agcaagattg acccagtcac agggtttgtt  3180
aacatgctgg atactcgtta tgagaacgca gacaaagcgc gttgcttctt cagcaagttc  3240
gatagtattc ggtacaatgc agacaaggac tggttcgaat ttgcaatgga ctactccaaa  3300
tttacagaca aggccaagga cacatacact tggtggactc tctgctcgta cggcactcgt  3360
atcaagacat ttcgcaaccc ggcgaagaat aacctgtggg acaacgaaga ggttgtcctg  3420
acggacgagt ttaagaaggt gttcgcagcc gcggggatcg atgtccatga aaacttaaag  3480
gaagctttt gcgcacttac ggataaaaaa tatctgcagc cactttatgc ggttaatgact  3540
ctcctcgttc aaatgcgcaa tagcgctacc aacagtgaga cagactactt attatccct   3600
gtggcggacg agtcaggcat gttttatgac tctcgggaag ggaaggagac gctcccgaag  3660
gacgccgatg ctaatggcgc gtacaacatt gcccgtaagg gtttatggac catccgtcgc  3720
atccaagcaa ccaactgcga agaaaaagta aatcttgttc tgtcgaaccg cgagtggttt  3780
caattcgccc aacagaaacc ttacttgaat gacggcgcgc caaaaaggcc ggcggccacg  3840
aaaaaggccg gccaggcaaa aaagaaaaag gctagcggca gcggcgccgg atccccaaag  3900
aagaaaaggga aggttgaaga cccccaagaaa aagaggaagg tgtgataa            3948
```

```
SEQ ID NO: 60          moltype = DNA   length = 3948
FEATURE                Location/Qualifiers
misc_feature           1..3948
                       note = Description of Artificial Sequence: Synthetic
                       polynucleotide
source                 1..3948
                       mol_type = other DNA
                       organism = synthetic construct
SEQUENCE: 60
atgggccacc atcatcatca tcatagcagc ggcctggtgc cgcgcggcag cggtaccatg    60
aagaacattt tagaacaatt cgtcggcctg tatcctttgt caaaaacctt gcgcttcgag   120
ttgaagccac tgggcaaaac tttagagcat atcgagaaaa agggtcttat tgcccaggac   180
gaacaacgcg cggaagagta taagcttgtc aaggatatca tcgatcgtta tcataaagcg   240
tttattcata tgtgcttgaa gcattttaag ctcaaaatgt actcggagca aggttatgac   300
tcccttgagg agtaccggaa gttagctagc atcagtaagc ggaacgaaaa ggaagagcaa   360
caatttgaca aagtaaaaga gaatttgcgc aagcaaatcg tcgatgcgtt taaaaatggt   420
ggtagctacg atgacttatt taaaaaagag ctgatccaaa acacctcccc acgttttatt   480
gagggggaag aggaaaagcg tattgttgat aatttcaata aatttacaac gtattttacg   540
ggttttcacg aaaatgtcaa aaacatgtac tccgacgaga aggagtccac agcgatcgcc   600
tatcggctta tccacgagaa tttaccgctt tttcttgata acatgaaatc attcgccaag   660
attgctgagt ccgaggtggc agcccgcttt accgaaatcg agacggcata ccgcacttat   720
cttaacgttg aacatatctc cgaactttttt acactggact acttctcgac cgtgctgaca   780
caggaacaga tcgaggtgta taataatatt atcgggggcc gggtggacga tgataatgta   840
aaaattcagg ggctcaacga atacgtgaat ttatataacc aacagcaaaa ggaccgcagc   900
```

```
aaacgtctgc ctttacttaa gtcacttat aagatgatct tgagtgaccg gattgctatc    960
tcctggttgc cggaggaatt caaatctgat aaagagatga ttgaagctat taataacatg   1020
catgacgacc ttaaagacat cctcgccggt gacaatgagg atagtttaaa atcattgctg   1080
caacacattg gcaatatga tttgtccaaa atctatatcg cgaacaatcc gggccttact   1140
gacatttcac aacagatgtt cgggtgttac gacgttttta cgaacggtat taagcaagag   1200
ttacgtaatt caatcactcc atccaagaaa gaaaaggctg acaacgagat ctatgaagaa   1260
cggatcaata agatgtttaa atcggaaaaa tcatttagta ttgcgtacct gaatagcctc   1320
ccgcacccga agactgacgc cccgcaaaaa aacgtagaag actacttcgc cttgttgggg   1380
acctgcaatc aaaatgacga gcaaccaatc aacctctttg ctcaaatcga gatgcgcgg   1440
cttgtggcgt cggatattct tgcaggccgt cacgtaaact tgaatcaatc tgagaatgac   1500
attaagctca ttaaagattt actcgacgcg tataaggcgc tccaacattt tgtgaaaccg   1560
cttcttggtt cggggacga ggcggaaaag gataacgaat tgatgcgcg tcttcgggcg   1620
gcatggaacg cgctggatat cgtgacgcca ctttacaata aagtacgtaa ttggttaaca   1680
cgtaaaccgt attccacgga aaaaattaag ttaaatttg aaaacgcaca gttgctgggg   1740
gggtgggacc aaaataagga gccagattgt acatcagttc tgctccgcaa agatggtatg   1800
tactacctcg ctatcatgga taaaaaagcc aatcacgcct tgactgtga ctgcctgcct   1860
tccgacgggg catgtttcga gaaaatcgac tacaagctct tacctggtgc gaacaagatg   1920
ttaccaaaag tattctttc caagtcgcgc attaaggaat tctcaccgtc cgaaagcatt   1980
atcgcggcat acaagaaagg cacacataaa aaggcccaa actttagttt atccgactgt   2040
caccggctta tcgatttctt caaagcatcc atcgataagc acgaggattg gtcgaaattc   2100
cggttccgtt tctctgatac gaagacgtac gaggacatta gtggttttta tcgcgaagta   2160
gagcagcagg ggtacatgtt aggggttcgc aaagtgtctg aagcatttgt taataaattg   2220
gtcgacgagg gcaaattata cctgtttcac atttggaaca aagatttctc caagcacagc   2280
aagggtactc cgaatttaca tacaatctat tggaaaatgc tgtttgacga aaaaaacttg   2340
actgatgtta tctacaagtt gaatggccag gccgaggtgt tttaccgcaa gaaaagctta   2400
gatcttaata aaacaacaac acacaaggcg catgccactta ttacgaataa aaatacgtag   2460
aatgcgaaga aggggagcgt gttcgattat gacattatta aaaatcggcg gtatactgtg   2520
gacaagtttc aattccacgt ccctatcact cttaactta aggccaccgg ccggaattac   2580
atcaatgaac acacgcagga agcaattcgt aataacggta ttgagcacat catcgggatt   2640
gatcgtggcg agcgtcatct tttatacctg tccttgattg acttaaaggg caacatcgtt   2700
aaacagatga ccttaaatga tatcgtcaac gagtataacg ggcgtacgta cgctacgaat   2760
tataaggact tgctcgctac gcgggagggc gaacgcacgg atgcacgccg gaactggcag   2820
aagatcgaga acattaagga gattaaagaa gggtatttga gtcaggttgt gcatatctta   2880
tctaagatga tggttgacta caaagcgatt gttgtattag aagatttgaa tacagggttt   2940
atgcgcaacc gtcagaagat cgagcgccag gtatacgaaa agttcgaaaa gatgttaatc   3000
gacaaactga actgttacgt agataaacaa aaagatgccg acgaaactgg ggggcgtta   3060
cacccgcttc aattaactaa taagttcgag tccttccgta agttgggcaa acaatccggt   3120
tggctcttct atatcccagc ctggaacacc agtaagattg accggtaac gggctttgtg   3180
aatatgttgg ataccccgta cgaaaatgct gataaagcgc ggtgcttctt ttctaaattc   3240
gattctattc gttacaatgc cgataaggat tggttcgaat cgctatgga ttattcgaaa   3300
ttcaccgaca aggcaaaaga tacgtacacc tggtggacct tatgttcata cgggactcgg   3360
attaagacat tccgcaaccc tgccaagaat aacctttggg ataatgaaga agtagtgttg   3420
acagatgagt ttaaaaaagt attcgctgcg gcagggatcg atgtccatga aaacttaaag   3480
gaagctatct gtgcattaac ggacaaaaag taccttgagc cgctgatgcg gttgatgaca   3540
ctcctggtcc aaatgcggaa ttcagccacc aacagtgaaa ccgattactt gctgccccca   3600
gtagctgatg aaagtgggat gttctatgat tcgcggagg gtaaagaaac gcttccgaag   3660
gacgccgacg ccaacggcgc ctataatatt gctcggaagg gtctgtggac tattcgtcgt   3720
atccaggcaa caaactgcga ggagaaggtc aacttagtgc tttcaaaccg tgagtggctg   3780
cagttcgccc agcagaagcc gtatttgaac gacggcgcgc caaaaaggcc ggcggccacg   3840
aaaaaggccg ccaggcaaa aagaaaaag gctagcggca gcggcgccgg atccccaaag   3900
aagaaaagga aggttgaaga ccccaagaaa aagaggaagg tgtgataa              3948
```

```
SEQ ID NO: 61           moltype = DNA   length = 3948
FEATURE                 Location/Qualifiers
misc_feature            1..3948
                        note = Description of Artificial Sequence: Synthetic
                        polynucleotide
source                  1..3948
                        mol_type = other DNA
                        organism = synthetic construct
SEQUENCE: 61
atgggccacc atcatcatca tcatagcagc ggcctggtgc cgcgcggcag cggtaccatg     60
aaaaatatct tggaacaatt tgtgggcctt taccctctgt ccaagaccct ccgctttgaa    120
cttaagcctt taggtaagac tcttgaacat attgagaaa aaggtctcat cgcacaagac    180
gagcagcgtg cggaggagta taaattagtc aaggacatca tcgatcgtta ccataaggcg    240
tttattcaca tgtgtctgaa gcactttaag ctcaaaatgt acagtgagca gggttacgat    300
tccttggagg agtaccgtaa gttagcttca attagtaagc gtaacgagaa agaggagcaa    360
cagttcgata aagtaaagga aaatttacgt aagcagtcg ttgatgcttt caagaatggc    420
ggcagctacg atgacttgtt caagaaagag ttaattcaaa agcatttgcc gcgcttcatt    480
gaggggaag aagaaaaacg gattgttgac aacttcaaca agttcaccac atacttcact    540
gggttccacg agaaccgtaa aaacatgtat tccgacgaga aggaaagtac cgcgattgca    600
tatcgtttaa tccacgaaaa tttaccgctt ttttggata tatgaaatc attcgccaag    660
attgctgagt cggaagttgc agctcgtttt accgagatg aaacggcata tcgcacttac    720
ctgaacgtag aacacattag cgagcttttc actttagct atttcagtac tgttttaact    780
caggagcaaa tcgaggtcta caataacatc attggtggcc gtgtcgatga tgataatgtc    840
aaaaattcag gctcaacga gtatgttaac ctttacaacc aacaacaaaa ggaccggagc    900
aagcggctcc cattactgaa atcgctctat aaaatgatcc ttagtgatcg tattgcgatc    960
tcctggcttc cggaggaatt caaaagcgat aaggaaatga ttgaagccat taacaatatg    1020
catgacgact tgaaggatat tcttgcaggc gacaatgagg acagtctgaa gtctctcctt    1080
```

```
cagcatattg gtcagtatga cttgtccaag atctatatcg caaacaatcc tggtttgacc   1140
gatatcagtc aacagatgtt tggttgctac gacgtattca cgaatgggat taaacaagag   1200
ttacgtaatt ccattacacc aagcaaaaaa gaaaaagccg acaatgaaat ctatgaagag   1260
cggattaata agatgtttaa aagtgaaaag tctttctcta tcgcatacct caactctttg   1320
cctcatccaa agactgatgc cccgcaaaag aacgtggagg attactttgc cttgttgggc   1380
acttgcaacc agaacgacga gcaacctatc aacttgttcg cgcagattga gatggcgcgc   1440
ctcgtggcat ctgacatcct tgcagggcgt catgttaatt tgaaccaaag tgaaaatgat   1500
atcaagttga ttaaagactt gctcgacgcc tataaggcgt tgcaacactt cgttaagccg   1560
ctcctgggga gtggcgatga ggccgaaaaa gataacgaat ttgatgcacg gctgcgtgcg   1620
gcctggaacg ccttggacat tgtgacaccg ttgtataata agttcggaa ttggctgact   1680
cggaagccat acagtacgga aaaaatcaag cttaatttcg agaacgccca gttactgggt   1740
ggctgggacc agaataagga accagactgt acttccgtac tcctgcgtaa ggatgggatg   1800
tattatctgg ctattatgga taagaaagct aatcacgctt tcgactgcga ttgcttacca   1860
agcgatggtg cctgctttga aaaaattgat tacaaactcc tgccgggcgc caacaagatg   1920
ttaccaaaag tctttttttc aaaatcgcgg attaaggagt tttccccgtc tgagtccatt   1980
atcgcggcat acaaaaaagg gacacacaaa aagggtccga atttttccct ttccgattgc   2040
catcgcctga tcgacttttt taaagcctcc attgacaagc acgaggattg gagcaaattc   2100
cgctttcgtt tcagcgatac gaaaacctac gaagacatct ccggctttta tcgcgaagtg   2160
gagcagcagg ggtacatgtt aggtttccgt aaagtatcgg aagcttttgt taataaactc   2220
gtcgacgaag gtaaattata cctgttccat atttggaaca aagacttctc caagcactcc   2280
aagggcacac caaacctcca cacgatctat ggaagatgt atttgatga aaagaatttg   2340
accgatgtca tttataaact taacggtcag gccgaggttt tctaccggaa gaagtctctc   2400
gacctcaata agacgacgac ccataaggca cacgctccaa tcactaataa aaacacgcag   2460
aacgcaaaga agggctcggt cttcgactac gatattatta agaatcgtcg gtataccgtc   2520
gataaatttc aattccatgt gcctattact ttgaatttta agcgacggg gcggaactac   2580
atcaatgcaa atacgcagga ggctattcgc aataatgata tcgaacatat cattggcatt   2640
gatcgggggg agcgccacct gctgtacctg tcactgattg atcttaaagg taacattgtg   2700
aagcagatga cattgaatga catcgtgaac gagtataacg tcggaccta tgctacaaac   2760
tataaagatc ttctggccac ccgtgagggt gagcggacag acgcacggcg caactggcag   2820
aagatgaaa acattaaaga aattaaagag ggctacctttc ctcaagttgt acacatcctt   2880
agcaagatga tggtggatta taggcgatc gtggtgttgg aggaccttaa tacgggttc   2940
atgcggaatc ggcagaagat cgaacggcag gtatatgaaa agtttgaaaa aatgcttatt   3000
gacaaattaa attgttatgt tgataagcaa aaggacgcgg atgaaacggg tggggcgctg   3060
catccgctgc aactgacaaa taaattcgaa tctttccgta aacttggtaa acaatcgggc   3120
tggttattct acattccggc gtggaacaca agcaaaattg acccggtaac gggttttgta   3180
aatatgctcg atacgcgcta cgagaatgca gataaagcac ggtgtttctt cagcaagttc   3240
gacagcatcc ggtataatgc cgacaaagac tggttcgagt ttgcgatgga ctattctaaa   3300
tttaccgaca aagcaaagga cacttatacg tggtggacat tatgctcata tgggaccgc   3360
atcaaaactt ttcgtaatcc tgccaagaat aacttgtggg acaatgagga agtcgtgctt   3420
acggacgagt tcaagaaggt atttgcggcc gccggcattg atgtgcatga aaatttaaaa   3480
gaggcaatct gcgcacttac tgataaaaag tacttagagc cgctgatgcg tcttatgaca   3540
ttacttgtgc agatgcgtaa tagtgccacc aattcagaaa ctgattacct gttatcgcct   3600
gtggcagacg aatctgggat gttctatgat tcccgggaag gtaaggagac gttgccaaaa   3660
gacgcggacg cgaacggggc gtataatatt gctcggaagg ggctctggac aatccggcgg   3720
attcaagcga ccaattgcga agagaaggtt aatctcgtgt tgtcgaaccg ggagtggctt   3780
caatttgcac aacagaagcc gtatctgaac gacgcgcgc caaaaggcc ggcggccacg   3840
aaaaaggccg gccaggcaaa aaagaaaaag gctagcggca gcggcgccgg atccccaaag   3900
aagaaaagga aggttgaaga ccccaagaaa aagaggaagg tgtgataa               3948
```

SEQ ID NO: 62          moltype = DNA   length = 3948
FEATURE                Location/Qualifiers
misc_feature           1..3948
                       note = Description of Artificial Sequence: Synthetic
                       polynucleotide
source                 1..3948
                       mol_type = other DNA
                       organism = synthetic construct
SEQUENCE: 62

```
atgggccacc atcatcatca tcatagcagc ggcctggtgc cgcgcggcag cggtaccatg     60
aagaacatcc tggaacaatt tgttggtctc tacccactct ctaagacttt acgcttcgaa    120
ctgaaaccgt tagggaagac cttggaacat attgaaaaaa aagggctcat cgcacaggat    180
gaacaacgtg cggaggaata caaattagtt aaggatatca tcgaccgtta ccataaagcc    240
ttcatccata tgtgcttaaa acatttcaaa ctgaaaatgt atagcgagca agggtacgac    300
tcgctggagg agtaccgcaa attggcatcg atctctaaac gcaatgaaaa agaagagcaa    360
cagtttgata aagttaagga aaacctccgg aagcagattg ttgatgcctt taagaacggt    420
ggttcatacg atgatctctt caagaaagag ttaatccaga aacacctgcc acgttttatt    480
gagggggagg aggagaagcg tatcgtggat aatttcaata aattcaccac ctatttcact    540
gggtttcatg agaaccgcaa aaatatgtac tccgacgaaa aggaatctac cgccatcgct    600
tatcgtctca ttcatgagaa tctcccatta ttcctcgaca acatgaaatc gttcgcgaaa    660
atcgccgaaa gcgaagtagc cgctcgcttc acagagattg aaactgccta ccgtacttac    720
cttaatgtcg aacacatttc agaattattc acgttagatt acttttccac ggtcctcacg    780
caggaacaaa tcgaggtata caacaatatc atcgggggggc gtgttgatga cgacaatgtg    840
aagatccagg gcttaaacga gtacgtgaac ctttataacc agcagcagaa ggatcggagc    900
aagcgtttgc cattgctcaa atccctgtac aaaattgatc tctctgatcg catcgctatc    960
tcgtggttac cagaggaatt taagtcggat aaggagatga ttgaagccat caacaacatg   1020
catgatgact tgaaggatat ccttgctggg gataatgaag actcactcaa gtccctcctg   1080
caacacattg gccagtatga tttgagtaaa atctacatcg cgaacaatcc aggccttact   1140
gatatttcac aacaaatgtt cggctgctac gatgtgttca caaatggcat caaacaggaa   1200
cttcggaact ctatcactcc atcaaagaag gaaaaggctg acaacgaaat ctacgaagag   1260
```

```
cggattaaca agatgttcaa gtcagagaag agtttctcaa tcgcttacct caattctttg 1320
cctcacccaa agaccgacgc ccctcagaag aatgtcgaag attatttcgc tctccttggc 1380
acatgtaatc agaatgatga gcagccgatt aactatttg cgcaaattga gatggcacgg 1440
ttggtagcta gcgatatcct cgcaggtcgc acgtaaatt tgaatcagag tgaaaatgac 1500
atcaaactta tcaaagactt gttggatgcg tacaaggcgc ttcaacattt cgtgaagcca 1560
cttctggggt caggtgacga agcggagaag gacaatgaat tcgatgcgcg gctgcgggca 1620
gcctggaatg ccttggatat cgttacgccg ctctataaca aggtacgaa ctggttgacg 1680
cgtaaaccat actcgacgga aaaatcaag ttgaactttg agaatgccca gttactcggt 1740
gggtgggacc aaaataaaga gccagactgc actagcgtac tcctgcgcaa ggatggcagg 1800
tactacttag caatcatgga taagaaagca aaccatgcct tcgattgtga ctgtctccct 1860
tccgacggtg catgctttga gaagatcgat tataagttac tccctggcgc gaataagatg 1920
ttgcctaaag ttttcttctc caaatcgcgc atcaaggagt ttagcccttc ggagagtatc 1980
attgcagctt ataaaaaggg tactcacaaa aagggtccaa acttctccct tagcgattgt 2040
catcgtttga ttgacttctt taaagcatcg attgataagc acgaggactg gtccaaattc 2100
cggtttcgct tttctgatac gaaaacttat gaggatatct caggttttcta tcgtgaggtc 2160
gagcagcaag ggtacatgct cgggttccgg aaggtgtccg aggcatttgt gaataagtta 2220
gtggacgagg gtaaacttta tctttttcac atttggaaca aggacttcag taagcattca 2280
aaagggaccc ctaacttaca taccatttat tggaaaatgt tgtttgacga gaaaaatctg 2340
accgacgtta tttacaaatt gaacgggcag gcagaggtgt tctaccgcaa gaagtcactt 2400
gatctgaaca aaaccaccac ccacaaagct cacgcgccaa ttacaaacaa aaacacacag 2460
aatgccaaaa aaggttcggt gttcgattat gatattatta aaaaccggcg ctataccgtc 2520
gataagttcc agtttcacgt gcctattacg cttaacttca aggctaccgg gcgtaactac 2580
attaacgaac atactcaaga ggcgatccgg aataatggga ttgaacatat cattgggatc 2640
gatcgcggtg aacgccattt gctctattta agcctcattg atttaaaagg gaatattgta 2700
aagcagatga cccttaacga tattgtgaat gaatataacg gcggacata tgcgaccaat 2760
tataaagacc tgctcgcaac acgtgagggg gagcgtaccg acgcgcgccg gaattggcag 2820
aaaatcgaga acattaagga aatcaaagag ggctactgt cacaagtcgt tcatatcttg 2880
tcaaaaatga tggtagacta taaggcaatc gtggtacttg aggatttaaa cactgggttt 2940
atgcgcaatc gtcaaaagat tgaacgccaa gtctatgaga agtttgagaa aatgctgatc 3000
gataaactta actgctatgt cgacaagcag aaggacgcag atgagactgg tggcgcactt 3060
cacccgttac agctgactaa taaatttgag agctttcgta aactcgggaa acagagcggc 3120
tggttgttct atatccctgc ttggaacaca tcgaaaatcg atcctgtgac agggttcgtc 3180
aatatgctcg ataccgtta tgagaacgct gataaagctc gttgttttt cagtaaattt 3240
gacagcattc gctataacgc tgacaaagac tggttcgagt ttgcgatgga ctactcaaaa 3300
ttcacggata aggccaaaga tacctatact tggtggactt tatgttcata cggtacacgc 3360
atcaagactt tcggaaccc ggcaaaaaac aacctttggg acaatgagga ggtcgtactt 3420
actgacgaat tcaagaaggt atttgcagcc gcgggcatcg acgtccatga gaatcttaag 3480
gaggcaatct gcgcactcac agacaaaaaa tatttggaac ctctcatgcg tctgatgacg 3540
cttctggtgc aaatgcggaa ttcagccaca aactctgaga cggactacct tctctccccg 3600
gtcgcggacg aatcggggat gttctacgac tcacgggagg gtaaggagac tcttcctaaa 3660
gacgcggatg ccaacggtgc atataacatc gctcggaaag gcctttggac catccgtcgc 3720
attcaggcta cgaattgcga ggaaaaggta atcttgtac tctctaatcg ggagtggctc 3780
cagttcgctc agcaaaaacc atacctcaac gacggcgcc caaaaaggcc ggcggccacg 3840
aaaaaggccg gccaggcaaa aagaaaaag gctagcggca gcggcgccgg atccccaaag 3900
aagaaaagga aggttgaaga ccccaagaaa aagaggaagg tgtgataa 3948
```

SEQ ID NO: 63           moltype = DNA   length = 3948
FEATURE                 Location/Qualifiers
misc_feature          1..3948
                        note = Description of Artificial Sequence: Synthetic
                        polynucleotide
source                  1..3948
                        mol_type = other DNA
                        organism = synthetic construct
SEQUENCE: 63

```
atgggccacc atcatcatca tcatagcagc ggcctggtgc cgcgcggcag cggtaccatg 60
aagaatattt tagaacagtt tgttggtctt tatccgctgt caaaaacact ccgcttcgaa 120
ctgaagcctt taggtaaaac gctggagcac attgagaaga aggggcttat cgcccaagat 180
gaacaacgcg cggaggagta taaactcgtc aaagtatct ttgatcgcta ccacaaggct 240
ttcattcaca tgtgtttgaa acatttaaa ctgaaaatgt acagcgaaca gggttacgac 300
tcgcttgaag aataccgcaa attagcatct atttcaaaac gtaatgagaa agaagagcag 360
caattcgata aagttaaaga gaatttcgcg aagcaaattg tgacgctttt taaaaatggc 420
ggttcctacg atgatttgtt caagaaagaa ctcattcaaa aacacttgcc tcggttcatc 480
gagggggaag aggagaaacg tattgtagac aactttaata aatttaaac gtactttacc 540
ggcttccacg agaatcggaa gaatatgtat agcgatgaaa aggaatctac ggctatcgca 600
taccgtctga tccacgagaa cttaccgctt tccttgaca acatgaaatc atttgccaaa 660
attgccgaga gtgaagtcgc tgcacggttc actgaaattg agactgcata ccgcacctac 720
cttaatgtgg agcacattag tgagttgttt actcttgact actttcgac cgtcttgacc 780
caagaacaaa tcgaagtta caataatatc atcggggcc gtgtggacga tgataccggt 840
aaaattcagg tcttaacga gtacgtgaat ctctacaacc agcaacaaaaa ggaccgcagc 900
aagcgcttac ctctccttaa gtcattatat aagatgatct tgtccgaccg catcgcaatc 960
tcttggctgc ctgaggagtt caaatccgat aaagagatga tcgaagcgat caataacatg 1020
cacgcgatc tcaaagacat tttagccggc gacaacgagg actctctcaa atcccttctg 1080
cagcacattg gccagtatga tctctcaaag atttacattg ccaacaaccc tggcttaacg 1140
gatatttccc aacaaatgtt cggctgctac gatgtattca caaatggcat caaacaagaa 1200
ttacgtaatt ccatcacccc ttctaagaag gagaaggcgg acaacgagat ctacgaagag 1260
cgcattaata aaatgtttaa agcgaaaag tcattctcca ttgcttacct taactcttta 1320
ccacatccaa aaacagatgc accgcagaaa aatgtggagg actatttgc gctgttgggt 1380
acatgtaatc agaatgacga acaacctatc aacctgtttg ctcagatcga gatggccgt 1440
```

```
ctcgtggcta gcgatatctt ggcgggccgt cacgtcaacc tgaaccaatc ggagaatgat  1500
attaagttga ttaaggatct tctcgatgcc tacaagctc ttcaacactt cgtgaagccg  1560
ttactgggga gcggggatga agcggaaaaa gataatgagt ttgatgctcg gttgcgtgcg  1620
gcttggaacg cactcgacat cgtaaccca ctgtataaca aggtccgaa ttggttaact  1680
cggaagccat actcaacaga aaaaattaaa ttgaattcg gaacgctca gctgttgggc  1740
ggctgggacc aaaataaaga acctgactgc actagtgtac ttctgcggaa agacgggatg  1800
tactatttgg cgattatgga caaaaaagca aaccatgctt ttgattgcga ttgtttgcca  1860
tctgatggtc cgtgcttcga aaagatcgac tacaaattgt tgccggggc gaacaaaatg  1920
ctccctaagg tgttcttctc taagtctcgg atcaaggagt ttagtccttc agaatctatc  1980
attgcggcat acaaaaaagg gactcataag aaaggcccaa actttctct cagtgattgt  2040
catcggctta tcgactttt caaagcttct atcgacaaac acgaagactg gtccaaattc  2100
cgttttcgtt tcagtgacac aaagacctac gaagacattt ccggttttta tcgggaagta  2160
gaacaacaag gttacatgct tgggtttcgt aaagtatcgg aagccttgt taacaaactg  2220
gtggacgaag gcaagttgta cttatttcat atttggaaca aagatttcag taaacattcg  2280
aagggcactc caaatctgca taccatttat tggaaaatgc ttttcgacga gaagaacctc  2340
actgatgtca tttataagct gaacgggcag gcagaagtat tttatcggaa aaagtcttta  2400
gacctcaaca agaccacgac acacaaagct catgctccaa ttactaataa aaacacgcag  2460
aacgccaaaa aaggtagcgt gtttgactac gatattatca aaaccggcg ttacaccgta  2520
gataaattcc aatttcacgt cccaatcaca ttaaactta aagccacggg tcggaattac  2580
attaatgaac atactcagga ggcgatccgt aacaacggta tcgaacacat cattggcatc  2640
gaccgggggg agcgtcacct tctttacttg tctctcatcg atctcaaggg caatattgtc  2700
aagcagatga cactgaacga tatcgtaaac gagtacaacg gtcgtacgta tgccaccaac  2760
tataaggatt tgctggcgac ccgcgagggt gaacgtaccg atgcgcgccg gaattggcaa  2820
aagattgaaa acatcaagga gattaaggaa ggctacctga gtcaggtagt acacatcctt  2880
tctaagatga tggtcgatta caaagccatt gtcgttcttg aagatctgaa cacggggttt  2940
atgcgcaacc gtcagaaaat tgagcgccag gttatgaaa agttcgagaa gatgttgatc  3000
gataagctta actgttacgt agacaaacag aaagatgcgg acgagactgg cggcgcgttg  3060
caccctctgc agcttacgaa taaattcgaa agtttccgca agctgggtaa acagtccggt  3120
tggctttttt atattcctgc ttggaatacg tctaagatcg atcctgtgac tgggttcgtt  3180
aacatgctgg atactcgcta tgaaaatgct gataaagccc gttgtttctt cagcaaattt  3240
gactccatcc gctacaacgc tgataaagat tggtttgagt ttgctatgga ctatagtaag  3300
ttcacagata aagcgaagga tacgtatacc tggtggactt tatgttccta cgggacgcgc  3360
attaaaacct ttcgcaaccc agctaagaat aatctgtggg ataacgagga ggtagtgctg  3420
accgacgagt tcaaaaaagt atttgcagcg gcagggatcg atgtccatga gaacctgaaa  3480
gaggcaatct gcgcgttaac agataagaaa tatctgcagc cgcttatgcg cttgatgact  3540
ctgttagttc aaatgcgcaa tagtgcaacc aatagcgaga ccgattacct gctctccct  3600
gttgccgatg aatcaggtat gttctatgat tcgcgtgagg gtaaagaaac gcttcctaag  3660
gatgcagacg ctaatggcgc ctacaatatt gcccgtaagg gcttgtggac tatccgtcgg  3720
attcaagcta cgaactgtga agaaaaggtc aatctgatac tttcaaaccg tgaatgctt  3780
cagttcgccc agcaaaagcc ttacctgaat gacggcgcgc caaaaaggcc ggcggccacg  3840
aaaaaggccg gccaggcaaa aaagaaaaag gctagcggca gcggcgccgg atccccaaag  3900
aagaaaagga aggttgaaga ccccaagaaa agaggaagg tgtgataaa             3948

SEQ ID NO: 64         moltype = DNA   length = 3948
FEATURE               Location/Qualifiers
misc_feature          1..3948
                      note = Description of Artificial Sequence: Synthetic
                      polynucleotide
source                1..3948
                      mol_type = other DNA
                      organism = synthetic construct
SEQUENCE: 64
atgggccacc atcatcatca tcatagcagc ggcctggtgc cgcgcggcag cggtaccatg   60
aaaaatatct tagagcaatt cgtcgggctc tatccgctct ctaagacact gcgcttcgag  120
cttaaaccgc ttggcaagac gctcgaacac attgagaaaa aggggttgat tgctcaggac  180
gagcaacggg cggaagaata taagttggtc aaggacatca tcgaccgcta tcataaagcg  240
tttatccata tgtgtcttaa acacttcaaa ctcaaaatgt attcagaaca gggctatgac  300
agtcttgagg agtaccgcaa gctggcttct attagcaagc gcaatgagaa agaggagcaa  360
cagtttgaca aggtgaagga aaacctgcgt aagcaaatcg ttgacgcctt taagaatggt  420
ggcagctatg atgatttatt taagaaggaa ctcattcaaa agcacctgcc acggttcatc  480
gaaggggaag aagagaaacg tattgttgac aacttcaata aatttacaac ctatttcacg  540
ggttttcacg agaaccgtaa aaacatgtac agcgacgaga agaaagtac agctatcgca  600
tatcggctga ttcacgagaa tttaccactt tttctggaca atatgaagtc atttgccaaa  660
atcgcagaat cagaggtagc ggcgcggttc accgaaattg aaacggccta tcggacgtac  720
ttgaacgttg aacatatctc cgagctcttc actctcgact atttctctac agtgttaact  780
caagaacaaa tcgaggtata caacaacatt ttggcgggc gtagatga tgacaatgtc  840
aaaattcagg gcttgaatga gtacgttaac ttatataatc aacagcagaa agaccgttct  900
aaacggcttc cattattaaa gagcctctac aaaatgatgc ttagtgaccg gatcgcgatc  960
agttggttac ctgaggaatt caaaagtgac aaggaaatga tcgaagccat taacaacatg  1020
catgatgatt taaagatat tttggccggt gacaacgagg acagcttaaa atcactctta  1080
caaacacatcg gccagtatga tctctctaaa atttatattg ccaataaccc aggcttaact  1140
gacatttctc aacaaatgtt tggttgttac gacgtcttca ccaatggtat caaacaggaa  1200
ttgcgtaaca gtatcacgcc tagtaagaaa gaaaagccg ataacgaaat ttacgaagaa  1260
cggatcaaca agatgtttaa atcagaaaag agcttttcct taaattcgtta  1320
ccgcatccta agactgacgc ccctcagaag aacgtagaag attatttcgc actgttggc  1380
acgtgtaatc agaatgatga gcaacctatc aacttttcg cacaaatcga gatggcgcgt  1440
ctggttgcat ctgatattct tgcgggccgg catgttaacc tgaatcagag cgagaatgat  1500
atcaaactca tcaaagacct gctcgatgcc tacaagctc tccaacactt tgtcaaacct  1560
ttgctcggtt cgggtgatga agcagaaaag gacaatgaat tcgacgcacg tcttcgtgcc  1620
```

```
gcctggaacg ctctggatat tgtgaccccg ctgtacaaca aggtgcgcaa ctggttgaca 1680
cgtaagccgt actccacgga aaaaatcaaa ttgaattttg agaatgcgca acttctgggc 1740
gggtgggatc agaacaaaga gccagactgt acaagcgtcc tccttcggaa ggatggcatg 1800
tactatttgg ctatcatgga taagaaagcg aatcacgcat ttgattgtga ttgcttgcca 1860
tccgacgggg cgtgctttga gaaaatcgac tataagcttt tgccaggtgc caataaaatg 1920
ctccctaaag ttttcttctc taagtctcgc atcaaggagt ttagcccgtc tgaatctatc 1980
attgcggcgt acaaaaaggg cacccacaag aaagggccga acttctcact ttcggattgc 2040
caccgcctta tcgatttttt caaagcgtcg attgataagc atgaggactg gagtaaattt 2100
cggtttcggt tttccgacac aaaaacttat gaagatatct cggggttta tcgtgaggta 2160
gagcaacaag gttatatgct tggtttccgc aaagtttccg aagcctttgt gaacaagctg 2220
gttgacgagg gcaaactcta tttattccac atctggaaca aggactttag taagcacagt 2280
aagggcacgc caaacctcca cactatctac tggaaaatgt tatttgacga gaagaatctc 2340
accgatgtga tttacaaact caatgggcag gcggaagtgt tttatcgcaa aaaatcgttg 2400
gatttaaaca agacgaccac gcataaagca catgccccaa tcacgaacaa aaacacacaa 2460
aatgccaaga agggttccgt gtttgattat gatatcatca agaatcgtcg ttatacagtt 2520
gacaaattcc agttccacgt gccaattact cttaacttta aggcgacagg cgcaattac 2580
attaatgagc atacgcaaga ggccattcgt aataatggga tcgagcacat catcgggatc 2640
gaccgggcgg agcgccacct gttgtacctc tccttaatcg atctgaaggg taatatcgtg 2700
aaacaaatga cgttaaacga catcgtcaat gaatataatg gtcgcacgta cgcgacaaac 2760
tacaaagacc tccttgcaac tcgtgaaggc gaacgcacag acgctcgccg gaactggcag 2820
aaaattgaga atatcaaaga aattaaagag gggtatttaa gccaggtcgt acatatcctt 2880
tcgaaaatga tggtgactga caaggctatc gtagttcttg aggacctcaa cacgggctg 2940
atgcgtaatc gtcagaagat cgagcgccca gtgtatgaaa aatttgagaa aatgctgatc 3000
gacaaattga attgttatgt tgacaaacaa aaggacgccg acgaacaggg ggcgcgttg 3060
catccttac aactcacgaa taaatttgag tcgttccgca aactgggcaa acagtctggg 3120
tggctttttt atattccagc gtggaatacg tcgaaaatcg accctgtcac aggtttcgtc 3180
aatatgttag acactcggta tgaacgct gacaaggcac gttgttttt cagcaaattt 3240
gattccattc ggtataacgc cgataaagat tggttcgagt ttgcaatgga ttactcaaag 3300
tttaccgaca aagctaagga cacgtatact tggtggacgt tatgctccta cggtacgcgt 3360
attaagactt ttcgtaatcc ggcaaagaac aacctttggg acaacgaaga agtagtgctc 3420
accgatgaat tcaaaaaggt gttttgcagct gctggtattg atgtgcatga gaatcttaag 3480
gaggccattt gcgctctgac tgacaagaaa taccttgagc cactcatgcg tctcatgact 3540
cttcttgtac aaatgcgcaa ctcagcaacg aactctgaga cggattactt actcagcccg 3600
gtggccgatg agagcgggat gttctacgac tcccgggaag gcaaggagac tttaccaaag 3660
gacgctgatc ccaatggcgc gtataatatc gctcggaagg ggttatggac gattcggcgg 3720
attcaagcga caattgtga agagaaagtt aatctggttt taagtaatcg tgaatggctg 3780
caatttgcac aacaaaagcc gtatcttaac gatggcgcgc caaaaaggcc ggcggccacg 3840
aaaaaggccg gccaggcaaa aagaaaaag gctagcggca gcgcggcgg atccccaaag 3900
aagaaaagga aggttgaaga ccccaagaaa aagaggaagg tgtgataa 3948
```

```
SEQ ID NO: 65          moltype = DNA   length = 3948
FEATURE                Location/Qualifiers
misc_feature           1..3948
                       note = Description of Artificial Sequence: Synthetic
                         polynucleotide
source                 1..3948
                       mol_type = other DNA
                       organism = synthetic construct
SEQUENCE: 65
atgggccacc atcatcatca tcatagcagc ggcctggtgc cgcgcggcag cggtaccatg 60
aagaatattc ttgagcagtt tgttggcctc taccacttg ctaaaacct gcgtttcgag 120
ttaaagccct tggggaaaac tctcgaacac atcgagaaga agggcctcat cgcccaagat 180
gagcaacgtg ccgaggaata caagttggtt aaagacatta tcgaccggta tcacaaggcc 240
ttcatccata tgtgtctgaa gcatttcaaa ttgaagatgt actccgagca gggttatgac 300
agtcttgaag agtatcgtaa actggcttcg attagcaaac tagtgaaaa agaggagcaa 360
cagttcgata aggtgaaaga gaacctgcgc aagcaaattg tggacgcttt taagaatggt 420
ggttcctacg atgattgtt taaaaaagaa ttaattcaga acatcttcc tcgtttcatc 480
gagggggagg aggagaagcg gattgtagat aatttaca aatttactac ctacttcaca 540
gggttccatg agaaccgtaa gaacatgtac tcagacgaaa aagagtccaa agctatcgcc 600
taccgcttga ttcacgaaaa tcttccgctc ttccttgaca acatgaaatc ttttgctaaa 660
atcgctgaat cagaagtagc ggcacgtttc acagaaattg aaacggcata tcgcacatac 720
cttaacgtcg aacatatttc cgagttgttc accctcgact atttctctac agtcttaacc 780
caagagcaaa tcgaggttta caacaatatt ttggtggcc gtgttgatga tgacaacgtt 840
aaaatccagg ggttgaatga atatgtcaac ctctcaaacc aacaacagaa ggatcgttca 900
aaacgcctgc ctttactcaa atctctttat aaaatgatc tgagcgatc catcgcgatc 960
agctggcttc ctgaagaatt caagtctgat aagaaatga tcgaagctat caataatatg 1020
cacgacgatt taaagacat cttagcaggt gacaatgagg actccctcaa atcgttactg 1080
caacacatcg ggcaatatga cttgtcaaaa atctcactca caaataatcc aggcttaaca 1140
gacattagcc agcagatgtt tgggtgttat gacgttttca ccaacgggat caaacaagag 1200
ctgcgtaaca gtattacccc atcgaagaag gaaaaggctg acaatgagat ctacgaagag 1260
cgcatcaata agatgtttaa gagtgagaaa tcgtttttcta tcgcatatct caacagcctg 1320
cctcacccta aaccgacgc accgaaaaag aacgtggagg attactttgc gctgcttggg 1380
acgtgcaatc agaatgatga acagccgatt aatttgttcg cccaaattga gatggcccgg 1440
ttagtcgcat cagacattct ggccgggcgt catgtcaacc aaaagtgagaatgac 1500
attaaactga tcaaggactt actcgatgcg tataaagcac tgcagcactt cgttaagccg 1560
ctgcttggct ccggggacga agcagaaaaa gataatgagt ttgatgcgcg ctccgcgcg 1620
gcatggaatg cactggacat cgtcactccg ttgtacaaca aggtacgtaa ttggctgacg 1680
cgcaagccgt attcgacaga aaaaatcaaa ctgaactttg agaacgcaca attactcggc 1740
ggttgggacc agaacaaaga gcctgactgt acatcggtcc tcctgcggaa agacggtatg 1800
```

```
tattaccttg ccattatgga caagaaagcc aaccacgcat tcgactgcga ctgcttgccg   1860
agcgacggtg cttgtttcga aaagatcgac tataagcttt taccaggggc taacaagatg   1920
ttacctaaag ttttttttctc caagtcacgg atcaaggagt tttcgccttc ggaatcaatt   1980
attgctgcgt acaagaaggg gacccataag aaaggtccga acttcagcct gtcggactgt   2040
catcggctta tcgacttctt taaggcgtct atcgacaagc acgaagactg gtccaagttt   2100
cgcttccgct tcagtgacac taagacttat gaggacattt cgggctttta ccgcgaagtg   2160
gagcagcagg ggtatatgct cggttttcgc aaagtttccg aagccttcgt caataagctg   2220
gtagacgaag ggaagctcta tttgtttcat atctggaaca aagacttctc taaacattcc   2280
aagggcacgc caaacttaca taccatctac tggaagatgc tttttgacga aaaaaatctt   2340
acggatgtga tttataagct caatggtcaa gctgaagtct tctatcgtaa aaagtcgctg   2400
gatctgaata agacgacaac acacaaggct cacgcccga tcacgaacaa gaatacacaa   2460
aacgcaaaga aagggtccgt gtttgactac gacattatca gaatcgccg gtacacagtc   2520
gataagttcc aattccacgt accgattact ctcaatttca aagcgactgg tcgcaactac   2580
atcaacgagc atacccagga ggccattcgc aacaatggca ttgagcacat tatcggtatt   2640
gaccgcgggg aacgccattt attataccctt tcactcatcg atcttaaagg caacattgtt   2700
aagcagatga cccttaatga cattgttaat gagtataatg tcggactta tgctacaaac   2760
tacaaagact tgttggcgac tcgcgaaggg gagcgtactg atgcccgtcg taactggcaa   2820
aaaattgaaa atattaaaga aattaaggaa ggctatctct cccaagtagt ccatatcctc   2880
tcaaagatga tggtcgacta caaagccatt gtggttttag aagatctcaa cacgggcttc   2940
atgcgtaatc gccaaaagat cgagcgtcag gtatacgaga agtcgagaa atgcttatt   3000
gataagctta attgctacgt agataaacaa aaggatgccg acgagactgg tggggcgctt   3060
catccgctcc aattgacgaa taagtttgag tcttttccgta agttagggaa gcagtcaggg   3120
tggttatttt acatcccggc ctggaacacg agcaaaattg acccggttac ggggtttgta   3180
aatatgctgg acacgcgtta tgagaatgcg gataaagtc gctgcttctt cagcaaattt   3240
gactcgattc gctacaatgc ggataaagat tggttcgaat ttgcaatgga ttacagtaaa   3300
tttacagaca aggccaagga tacctacact tggtggactc tttgcagcta cggcacagtg   3360
attaagacct ttcgtaatcc agctaagaat aatctttggg ataacgagga agtcgtcctg   3420
acggatgagt tcaagaaagt attgcgggcc gccggtatcg acgtgcacga gaacttgaag   3480
gaagccatct gtgcactcac tgataaaaaa taccttgaac ctttaatgcg cttaatgaca   3540
ttattggtcc agatgcggaa tagcgcgacc aattcggaaa cagactacct cctctcgacc   3600
gtagcagacg aatctggtat gttctacgat tctcgcgagg gcaaagaaac tttgccaaag   3660
gacgccgatg cgaacggggc ctataatatc gcccgtaaag gtctgtggac atccgtcgg   3720
atccaggcga caaattgcga ggaaaaggtc aatttggtgt tgtcgaaccg cgagtggctt   3780
cagttcgcac agcaaaaacc gtatctgaat gacggcgcgc caaaaaggcc ggcggccacg   3840
aaaaaggccg gccaggcaaa aaagaaaaag gctagcggca gcggcgccgg atccccaaag   3900
aagaaaagga aggttgaaga ccccaagaaa aagaggaagg tgtgataa              3948

SEQ ID NO: 66           moltype = AA  length = 1271
FEATURE                 Location/Qualifiers
REGION                  1..1271
                        note = Description of Artificial Sequence: Synthetic
                        Cas12a/Cpf1 [Collinsella tanakaei] sequence
source                  1..1271
                        mol_type = protein
                        organism = synthetic construct
SEQUENCE: 66
MIYRENFKRK KEKIEMNTGF NDFTNLSSVT KTLCNRLIPT EITAKYIKEH GVIEADQERN    60
MMSQELKNIL NDFYRSFLNE NLVKVHELDF KPLFTEMKKY LETKDNKEAL EKAQDDMRKA   120
IHDIFESDDR YKKMFKAEIT ASILPEFILH NGAYSAEEKE EKMQVVKMFN GFMTSFSAFF   180
TNRENCFSKE KISSSACYRI VDDNAKIHFD NIRIYKNIAN KFDYEIEMIE KIEEAAGGAD   240
IRNIFSYNFD HFAFNHFVSQ DDISFYNYVV GGINKFMNLY CQATKEKLSP YKLRHLHKQI   300
LCIEESLYDV PAKFNCDEDV YAAVNDFLNN VRTKSVIERL QMLGKNADSY DLDKIYISKK   360
HFTNISQTLY RDFSVINTAL TMSYIDTLPG KGKTKEKKAA SMAKNTELIS LGEIDKLVDK   420
YNLCPDKAAS TRSLIRSISD IVADYKANPL TMNSGIPLAE NETEIAVLKE AIEPFMDIFR   480
WCAKFKTDEP VDKDTDFYTE LEDINDEIHS IVSLYNRTRN YVTKKPYNTD KPGLYFGTSS   540
FASGWSESKE FTNNAILLAK DDKFYLGVFN AKNKPAKSII KGHDTIQDGD YKKMVYSLLT   600
GPNKMLPHMF ISSSKAVPVY GLTDELLSDY KKGRHLKTSK NFDIDYCHKL IDYFKHCLAL   660
YTDWDCFNFK FSDTESYNDI GEFYKEVAEQ GYYMNWTYIG SDDIDSLQEN GQLYLFQIYN   720
KDFSEKSFGK PSKHTAILRS LFSDENVADP VIKLCGGTEV FFRPKSIKTP VVHKKGSILV   780
SKTYNAQEMD ENGNIITVRK CVPDDVYMEL YGYYNNSGTP LSAEALKYKD IVDHRTAPYD   840
IIKDRRYTED EFFINMPVSL NYKAENRRVN VNEMALKYIA QTKDTYIIGI DRGERNLLYV   900
SVIDTDGNIV EQKSLNIINN VDYQAKLKQV EIMRKLARQN WKQGVKIADL KKGYLSQAVH   960
EVAELVIKYN GIVVMEDLNS RFKEKRSKIE RGVYQQFETS LIKTLNYLTF KDRKPLEAGG  1020
IANGYQLTYI PESLKNVGSQ CGCILYVPAA YTSKIDPTTG FVTLFKFKDI SSEKAKTDFI  1080
GRFDCIRYDA EKDLFAFEFD YDNFETYETC ARTKWCAYTY GTRVKKTFRN RKFVSEVIID  1140
ITEEIKKTLA ATDINWIDSH DIKQEIIDYA LSSHIFEMFK LTVQMRNSLC ESKDREYDKF  1200
VSPILNASGK FFDTDAADKS LPIEADANDA YGIAMKGLYN VLQVKNNWAE GEKFKFSRLS  1260
NEDWFNFMQK R                                                      1271

SEQ ID NO: 67           moltype = DNA  length = 3816
FEATURE                 Location/Qualifiers
misc_feature            1..3816
                        note = Description of Artificial Sequence: Synthetic
                        Cas12a/Cpf1 [Collinsella tanakaei] sequence
source                  1..3816
                        mol_type = other DNA
                        organism = synthetic construct
SEQUENCE: 67
atgatataca gagagaattt taagcgaaaa aaggagaaaa ttgagatgaa tacaggtttt    60
```

```
aacgatttta caaatctttc atctgtcaca aaaacattgt gcaacagact gattccaaca    120
gaaattacgg caaatatat aaaagaaacac ggcgttattg aagctgatca ggaaagaaat    180
atgatgagtc aggagcttaa gaatatttta acgactttt acagaagctt cttaaatgag    240
aaccttgtaa aagttcatga acttgacttt aagccgctct ttacagaaat gaaaaagtat    300
ctggagacaa aggataataa ggaagctctt gaaaaagcac aggatgatat gagaaaagcc    360
atccatgaca ttttgagag cgatgacaga tacaaaaaga tgttcaaggc agaaattacc    420
gcttccatcc tgccagagtt tatcctgcac aacggagcct actccgctga ggaaaaagag    480
gagaaaatgc aggttgtcaa gatgttcaac ggcttcatga catcattttc agcattcttt    540
acgaacaggg agaactgctt ttcaaaggaa aagatttcat catctgcatg ctacagaatt    600
gttgatgaca atgcaaaaat ccattttgac aacatccgca tatacaaaaa cattgcaaac    660
aaatttgatt acgagattga aatgattgag aagattgagg aagctgctgg tggagctgat    720
attagaaata tcttttcgta taacttcgat cattttgcct tcaatcattt tgtgtcacag    780
gatgatattt ctttctacaa ctatgtcgta ggtggaatta ataaattcat gaacctctac    840
tgtcaggcga caaaggaaaa attaagccca tacaagttaa gacatcttca caagcagata    900
ctctgcatcg aagaatcact gtatgatgta cctgcaaaat tcaattgcga tgaagatgta    960
tatgctgccg ttaatgattt tcttaacaat gtcagaacca aatctgttat tgaaagactg   1020
cagatgctcg gtaagaatgc tgatagctat gaccttgata agatatacat ttcaaagaag   1080
cactttacaa atatatccca gacactgtac agggatttca gtgtaatcaa tactgctctt   1140
accatgagtt acattgacac tctcccgggc aaaggcaaga ccaagagaaa aaggctgca    1200
tccatggcta aaaacactga attaataagc cttggtgaaa ttgataaact tgttgataag   1260
tataacttat gtccggacaa agctgcaagc acaaggtcgc ttataagaag catttcagat   1320
attgtcgctg attacaaagc aaatccgtta actatgaatt ccggcattcc gctcgcagaa   1380
aatgagactg aaatcgctgt tcttaaggaa gcaattgaac cgtttatgga catctttcgc   1440
tggtgtgcaa agttcaagac agatgagcct gttgacaagg atacggatt ttacacagaa    1500
cttgaggata taaacgatga gatccattct attgtatcct tatacaaccg tacaagaaat   1560
tacgtaacca agaaaccgta caacacagac aagttcggat tgtattttgg cacgtcttca   1620
tttgcatcag gttggagtga aagcaaggaa ttcaccaaca atgccattct tcttgcaaaa   1680
gatgacaaat tttatcttgg agtgttcaat gccaaaaaca aacctgcaaa aagtattatc   1740
aaaggacatg atacgataca ggacggtgat tacaagaaaa tggtctactc tcttttaacc   1800
ggacctaacc agataagatgc tgcc tcacatgttt ataagctgca gcaaggctgt accggtttac  1860
ggactgacag atgagctgct ttctgattac aagaaaggca gacatcttaa gacgtcaaaa   1920
aactttgaca tagactactg tcacaaactg attgattact ttaagcactg tctcgcactg   1980
tatactgact gggactgctt taatttttaag ttctcagata ccgaaagtta caatgacatt   2040
ggtgagttct acaaggaagt tgccgaacag ggatattaca tgaactggac atacattgga   2100
agtgatgata ttgacagtct gcaggaaaat ggccagctgt atctgtttca gatatacaat   2160
aaagacttt cagaaaagag cttcggaaaa ccaagtaagc acactgctat tctacgcagt    2220
ttattcagtg atgaaaatgt tgcagatcct gttatcaagt atgcggcgg cacggaagta    2280
ttcttcaggc caaagagcat aaaaactcct gtcgttcaca agaaaggttc cattcttgtc   2340
agtaaaacct acaacgcaca ggaaatggat gaaaatgaaa acattattac cgtcagaaaa   2400
tgcgtgcctg atgatgttta catggagctt tacggctact caacaattc aggaacacct    2460
cttttcagcag aggcgcttaa gtacaaggat attgtagacc accgcactgc cccttatgac   2520
atcataaaag accgcagata tacagaggat gagttctttta tcaacatgcc ggtgtcacta   2580
aactacaagg cggaaaacag acgtgtaaat gtaaacgaaa tggctcttaa gtatattgct   2640
cagacaaagg acacttacat cattggaatt gaccgtgggg agagaaattt gctgtatgta   2700
tcagtaattg atactgacgg aaacattgtt gagcagaaat ccttaacat cattaacaat    2760
gtggactatc aggcaaagct caagcaggtt gaaatcatga gaaaactggc aaggcagaac   2820
tggaaacagg gtgtaaaaat agctgactta aagaaaggct atttgtcaca ggcagttcat   2880
gaagttgccg agcttgtaat aaaatacaat ggtattgttg tcatggaaga cttaaacagc   2940
aggtttaagg aaaagcgttc aaagattgag cgcggggttt accagcagtt tgagacaagc   3000
ctcattaaga ctctcaacta tctgacattc aaggacagaa aacctctgga gcaggcggaa   3060
attgccaatg gttatcagct tacatacatt ccggaaagcc ttaaaaatgt cggaagccag   3120
tgtggatgca ttctctatgt gccagccgca tatacgtcaa aaattgatcc gacaacagga   3180
tttgtaaacct tattcaagtt caaggatata tcgtctgaaa aagccaagac ggactttatt   3240
ggcagatttg actgcatcag atatgatgcc gagaaagatt gtttgcatt tgagtttgat    3300
tacgataact ttgagacata cgagacctgt gcaagaacaa aatggtgtgc atatacttac   3360
ggcacaagag ttaaaaaac attccgcaac agaaagttcg ttagtgaagt cattattgac   3420
ataacgagag aaatcaagaa aactcttgct gccacagaca taaactggat agataagtcat   3480
gacatcaaac aggaaattat tgactatgca ctctcctctc acatatttga gatgttcaaa   3540
ctcacagtac agatgagaaa cagcttatgc gaatcaaaag acagggaata tgacaagttt   3600
gtgtcaccga tattaaacgc ttcaggaaag ttctttgaca cggatgctgc tgacaagtca   3660
cttcctatcg aagcagatgc taacgatgca tatggcattg caatgaaagg cctatacaat   3720
gtgcttcagg tgaagaacaa ttgggccgag ggcgagaaat tcaaatttag cagactcagc   3780
aatgaagact ggttcaattt catgcagaaa aggtag                              3816

SEQ ID NO: 68         moltype = AA   length = 1333
FEATURE               Location/Qualifiers
REGION                1..1333
                     note = Description of Artificial Sequence: Synthetic
                     polypeptide
source               1..1333
                     mol_type = protein
                     organism = synthetic construct
SEQUENCE: 68
MGHHHHHHSS GLVPRGSGTM IYRENFKRKK EKIEMNTGFN DFTNLSSVTK TLCNRLIPTE    60
ITAKYIKEHG VIEADQERNM MSQELKNILN DFYRSFLNEN LVKVHELDFK PLFTEMKKYL   120
ETKDNKEALE KAQDDMRKAI HDIFESDDRY KKMFKAEITA SILPEFILHN GAYSAEEKEE   180
KMQVVKMFNG FMTSFSAFFT NRENCFSKEK ISSSACYRIV DDNAKIHFDN IRIYKNIANK   240
FDYEIEMIEK IEEAAGGADI RNIFSYNFDH FAFNHFVSQD DISFYNYVVG GINKFMNLYC   300
QATKEKLSPY KLRHLHKQIL CIEESLYDVP AKFNCDEDVY AAVNDFLNNV RTKSVIERLQ   360
```

```
MLGKNADSYD LDKIYISKKH FTNISQTLYR DFSVINTALT MSYIDTLPGK GKTKEKKAAS  420
MAKNTELISL GEIDKLVDKY NLCPDKAAST RSLIRSISDI VADYKANPLT MNSGIPLAEN  480
ETEIAVLKEA IEPFMDIFRW CAKFKTDEPV DKDTDFYTEL EDINDEIHSI VSLYNRTRNY  540
VTKKPYNTDK FGLYFGTSSF ASGWSESKEF TNNAILLAKD DKFYLGVFNA KNKPAKSIIK  600
GHDTIQDGDY KKMVYSLLTG PNKMLPHMFI SSSKAVPVYG LTDELLSDYK KGRHLKTSKN  660
FDIDYCHKLI DYFKHCLALY TDWDCFNFKF SDTESYNDIG EFYKEVAEQG YYMNWTYIGS  720
DDDIDSLQENG QLYLFQIYNK DFSEKSFGKP SKHTAILRSL FSDENVADPV IKLCGGTEVF  780
FRPKSIKTPV VHKKGSILVS KTYNAQEMDE NGNIITVRKC VPDDVYMELY GYYNNSGTPL  840
SAEALKYKDI VDHRTAPYDI IKDRRYTEDE FFINMPVSLN YKAENRRVNV NEMALKYIAQ  900
TKDTYIIGID RGERNLLYVS VIDTDGNIVE QKSLNIINNV DYQAKLKQVE IMRKLARQNW  960
KQGVKIADLK KGYLSQAVHE VAELVIKYNG IVVMEDLNSR FKEKRSKIER GVYQQFETSL 1020
IKTLNYLTFK DRKPLEAGGI ANGYQLTYIP ESLKNVGSQC GCILYVPAAY TSKIDPTTGF 1080
VTLFKFKDIS SEKAKTDFIG RFDCIRYDAE KDLFAFEFDY DNFETYETCA RTKWCAYTYG 1140
TRVKKTFRNR KFVSEVIIDI TEEIKKTLAA TDINWIDSHD IKQEIIDYAL SSHIFEMFKL 1200
TVQMRNSLCE SKDREYDKFV SPILNASGKF FDTDAADKSL PIEADANDAY GIAMKGLYNV 1260
LQVKNNWAEG EKFKFSRLSN EDWFNFMQKR AAAKRPAATK KAGQAKKKKA SGSGAGSPKK 1320
KRKVEDPKKK RKV                                                   1333

SEQ ID NO: 69           moltype = DNA   length = 4005
FEATURE                 Location/Qualifiers
misc_feature            1..4005
                        note = Description of Artificial Sequence: Synthetic
                         polynucleotide
source                  1..4005
                        mol_type = other DNA
                        organism = synthetic construct
SEQUENCE: 69
atgggccacc atcatcatca tcatagcagc ggcctggtgc cgcgcggcag cgtaccatg    60
atctaccgtg agaattttaa gcggaaaaag gagaagattg aaatgaacac tgggtttaat  120
gacttcacta atttgagttc cgtgaccaag acgttatgca ccgtttgat cccaacagaa   180
attaccgcaa agtacattaa ggagcatggg gtaattgagg cggaccaaga acggaacatg  240
atgagtcaag agctgaaaaa tatcttgaat gacttttacc ggagtttcct gaacgagaac  300
cttgtgaagt gcacgaact tgatttcaag ccgttattca ccgagatgaa aaagtacctc   360
gaaacaaaag ataacaagga agcactcgaa aaggcccaag acgcactgcg gaaggcaatc  420
catgatatct ttgaaagtga tgaccgctac aaaaaaatgt tcaaggctga gatcacggcg  480
tcgattttgc ctgaattcat tcttcataac ggggcatatt cagccgaaga aaaggaggag  540
aaaatgcaag tagtcaagat gttcaatggc tttatgacgt cttttctcag cattctttacg 600
aatcgtgaga attgtttctc caagaaaaag atcagctcct ccgcatgtta ccgtattgtt  660
gatgacaacg cgaaatcca tttcgataac attcgtattt ataaaaaatat cgccaacaag  720
ttcgattatg aaattgaaat gatcgagaag atcgaagagg cggcgggggg tgccgacatt  780
cgtaatatct tctcgtacaa ctttgaccac tttgcattca atcatttcgt tagtcaagat  840
gatatctcat tctacaatta tgttgttggt ggtattaaca agtttatgaa cttgtattgt  900
caagccacca aagagaaatt atcgcctat aaactgcgta accttcaaa acagattctg    960
tgtattgagg aaagcctcta tgacgtgcca gcgaagttta attgtgatga ggacgtatat 1020
gcagctgtca acgattttct taataacgtt cggacgaaat cagtaattga acgcttgcaa 1080
atgctcggca aaaatgcaga cagttacgac ctggataaaa tttatatctc taaaaagcac 1140
ttcaccaata tctctcaaac tttatatcgc gacttctctg tgatcaacac tgccctcact 1200
atgtcttata tcgatactct tccgggtaag gggaaaacca aggaaaaaaa ggcagcatcg 1260
atggccaaaa acaccgaact tatttcgtta ggcgaaattg ataagttggg ggataaaatat 1320
aacctctgtc cagataaggc agctagcact cgtagcctca ttcggtctat tagcgacatc 1380
gtcgctgact acaaggcaaa ccctcttaca atgaatagtg ggattccgtt ggcagagaac 1440
gagacagaaa tcgcggtgtt aaaagaggcg atcgagcctt ttatggatat cttccggtgg 1500
tgtgctaagt ttaaaaccga cgagcctgtc gataaggata cagatttcta cacggagtta 1560
gaagacatta cgatgaaat ccatagtatt gtcagtcttt ataaccggac ccggaattat  1620
gtcactaaaa agccgtacaa cacagataag ttcggtctgt attttggcac ttcgtcgttc 1680
gcatcgggtt ggagcgagag caaagagttt actaacgacg caattttgtt agccaaggat 1740
gacaagtttt acctcggcgt gttcaacgca aaaaacaagc cagcaaaatc gattatcaaa 1800
gggcatgaca caatccaaga tggtgattat aagaaaatgg tgtattcact gctcaccggg 1860
ccaaataaga tgcttcctca catgtttatc tcgagcagta agcggttcc tgtttacggg 1920
ctcactgacg agcttctcag cgactataag aaaggtcgcc accttaagca atccaagaat 1980
ttcgacattg attactgtca caaacttatc gattacttca acattgtct cgctttgtat  2040
actgattggg attgcttcaa cttcaaattc tctgatacgg agtcctacaa tgatatcggc 2100
gagttctaca agaggttgc cgagcaaggc tactacatga actggacata tatcgggtcg 2160
gacgatatcg attcgctgca ggaaaacggg cagctctatc tttttcaaat ttataacaaa 2220
gatttcagcg aaaagtcatt cggtaaaccg tctaaacata cggccatcct gcgtagctta 2280
ttcagcgatg aaaacgtggc cgacccagtc attaaactgt gtggggggac cgaagttttt 2340
ttccggccga agtctattaa gacaccagta gtacataaaa aaggcagcat cctcgtatcc 2400
aaaacctata acgcacaaga aatggacgag aatggtaata tcatcaccgt gcggaagtgt 2460
gttccagacg acgtctatat ggagctctac ggctattaca acaactctgg gacgcctcca 2520
tccgccgaag ctttgaaata caaggatatt gtggaccacc gcacggctcc gtacgacatt 2580
atcaaggacc ggcgttacac cgaagacgaa tttttcatca acatgccggt gtcattgaat 2640
tataaagcgg aaaccgccg tgttaatgtg aacgaaatgg ccttaaaata catcgcacag 2700
accaaggaca cctacatcat tggcatcgat cgggggcgaac gtaatctgtt gtatgtgagc 2760
gttatcgata ctgacggcaa tatcgttgag caaaagagtc taatatcat caataacgtg 2820
gattatcaag ccaaattaaa gcaagtggaa atcatgcgta aactggcccg tcagaattgg 2880
aagcaggggg taaagattgc agacctgaaa aagggctacc tgtcacaagc ggtacatgaa 2940
gtcgcgaac ttgtaattaa atacaacggg attgttgtaa tggaggactt aaactcccgc 3000
ttcaaagaga gcgttctaa aattgaacgc ggcgtctacc aacagtttga gacatcatta 3060
atcaagacat tgaattattt gacgttcaaa gatcgcaaac cgttagaagc cggggcatt 3120
```

```
gcgaatggtt atcaattaac ttatattccg gagtctctta aaaatgtggg ctctcagtgc   3180
ggctgtatct tgtatgtgcc agcagcctac acctcgaaga tcgacccta cactggtttc    3240
gtcaccttgt tcaaattcaa agacatttcg agcgagaaag ctaaaacgga ttttattggt   3300
cggttcgact gcatccgtta tgatgcagaa aaggaccttt tcgcatttga attcgattat   3360
gacaactttg agacttatga gacttgtgcg cgtaccaaca ggtgtgcata tacatacggg   3420
actcgggtga agaaaacttt ccggaatcga aaattcgtgt cagaggtgat catcgacatc   3480
actgaagaga tcaagaagac ccttgcagcg accgatatta attggattga cagtcacgac   3540
atcaaacaag agatcatcga ctatgccctt agcagccata ttttgaaat gttcaaatta    3600
acggtacaga tgcgtaacag cctttgcgag agtaaagatc gcgagtacga caagttcgtc   3660
tcacctattc tcaacgcgtc gggcaaattt ttcgacaccg atgccgctga taaagtctg    3720
cctattgaag ctgatgcgaa cgatgcgtat ggtattgcta tgaaagggtt gtataatgtt   3780
ttacaagtca aaaacaactg gcggagggca gagaaattta agttctcccg tttaagcaac   3840
gaagattggt tcaacttcat gcaaaagcgg gcggccgcaa aaggccggc ggccacgaaa    3900
aaggccggcc aggcaaaaaa gaaaaaggct agcggcagcg gcgccggatc cccaaagaag   3960
aaaaggaagg ttgaagaccc caagaaaaag aggaaggtgt gataa                   4005

SEQ ID NO: 70           moltype = DNA   length = 4005
FEATURE                 Location/Qualifiers
misc_feature            1..4005
                        note = Description of Artificial Sequence: Synthetic
                        polynucleotide
source                  1..4005
                        mol_type = other DNA
                        organism = synthetic construct
SEQUENCE: 70
atgggccacc atcatcatca tcatagcagc ggcctggtgc cgcgcggcag cggtaccatg     60
atctatcggg agaactttaa acgtaagaag gagaagatcg aaatgaacac cggttttaac    120
gatttcacca acctgtcttc agtaacaaaa accctgtgta accgtttgat ccctacggaa    180
atcactgcta aatacattaa agaacacggc gtcatcgagg cagaccagga acgcaatatg    240
atgtcgcaag agctcaagaa tatcttaaac gattttacc gttcattcct taacgagaac    300
ttagtcaaag tccatgaatt agattttaaa ccgttattta ctgagatgaa gaaatacctt    360
gaaacgaagg ataataagga ggccctcgaa aaagcccagg acgatatgcg caaagcgatt    420
catgacatct ttgaatccga cgatcgttat aagaagatgt tcaaagcgga gatcactgct    480
tctattttac ctgagttcat tttacataac ggcgcttata gtgcagagga gaaggaggaa    540
aagatgcaag tggtcaagat gtttaatggc ttcatgactt cgttctcggc gttctttact    600
aatcgtgaaa actgcttcag taaggaaaag atctcgtcct cggcctgcta tcgcattgtg    660
gacgacaatg ctaaaatcca tttcgacaat attcggattt ataagaatat tgcgaacaag    720
tttgattacg agatcgagat gattgaaaag atcgaggaag cggctggtgg cgccgacatc    780
cgtaacattt tcagttacaa ctttgatcat tttgcctta atcacttcgt gtctcaggat    840
gacatctcat tctacaatta tgttgtcggt ggcatcaata aatttatgaa cctgtattgt    900
caagccacca aggagaaatt atcaccgtat aaattacgcc atcttcataa gcaaattctg    960
tgtatcgagg agtcattata cgatgtaccg gctaaattca actgtgatga ggacgtttat   1020
gctgccgtga atgacttctt aaataatgtg cgcaccaaga gcgtaattga acgcctgcag   1080
atgctgggga aaaatgccga cagttacgac ctcgacaaaa tctatattag taagaagcat   1140
tttactaata tcagccaaac cttataccgc gatttctccg ttatcaacac ggcgttgact   1200
atgtcataca tcgatacgct tccggggaag gggaagacca aggagaagaa ggcggctagt   1260
atggccaaga atactgagct tatttccttg ggggaaattg ataagctggt ggacaagtac   1320
aacctttgcc ctgacaaagc agctagtacg cggagtctga tccgctcgat tcggatatt    1380
gttgctgatt acaaggccaa ccctttgact atgaatagtg gcatcccgct tgctgagaat   1440
gaaacagaga ttgccgtttt gaaggaagcc atcgagccat ttatgacat cttccgctgg    1500
tgtgctaagt tcaagactga cgagccggta gataaagata ctgatttta tacagattta   1560
gaagacatca atgacgagat ccattccatc gtcagcctct acaaccgtac gcgcaactac   1620
gtcactaaaa aaccttacaa cacagacaaa ttcgggttat actttggtac ctcctcattt   1680
gctagtggct ggtcggaatc caaggagttc accaataatg ccatcttatt agccaaagat   1740
gataagtttt aacctggggt ctttaatgcg aaaaacagca gcgaaaag tattatcaag     1800
gggcacgaca cgattcagga cggcgactac aaaaagatgg tctattcact gttaaccggc   1860
ccaaacaaaa tgctgccaca tatgtttatc agcagtagta agccgttcc tgtgtatggt    1920
ttaactgatg agcttctctc agactataaa aagggcggc acctgaaaac gtcaaaaaac    1980
tttgacatcg attactgtca taaactgatc gactactta agcactgtt agcactttat    2040
actgattggg attgttttaa tttcaaattt tcagatacag agtcgtacaa cgatattggc   2100
gaattctata agaagtggc agaacaaggc tactacatga actggacata catccggttcg   2160
gatgacatcg acagccttca ggaaaatggc cagttatacc tcttccaaat ttacaataaa   2220
gacttctccg aaaaagagttt tgggaagccg tccaaacata cagctatcct gcggagcttg   2280
ttttcggatg agaacgttgg cgatccggtt atcaaattat gcggggtac agaggtattc    2340
ttccgcccta atcgattaa gacacctgta gtccataaga agggcagtat ccttgtttcc    2400
aaaacttaca tgcccagga tggatgaa aatggtaaca ttattaccgt tcgcaagtgt      2460
gtgccgatg atgtctatat ggagctgtat ggttactata caattcgggg cacaccactc    2520
agtgcagagg cacttaaata caaagacatt gtggaccatc gtactgcgcc atacgatatt   2580
atcaaggatc ggcggtatac ggaggacgaa ttttttatca acatgccagt ctccttgaat   2640
tacaaggcgg agaatcggcg tgtcaatgtt aacgaaatgg cactgaagta tatcgctcag   2700
acaaaggata cgtatatcat tggtatcgat cgtggtgagc ggaatcttct ctatgttcc    2760
gtgatcgaca ctgatgggaa tatcgtcgag cagaagtcac ttaacattat taacaacgtc   2820
gactaccaag cgaagctgaa gcaagttgaa atcatgcgta aattagcccg gcaaaattgg   2880
aagcaggggg taaagatcgc agacttgaag aagggtatc tcagccaggc agtccacgaa    2940
gtggcagaat tagtgattaa atacaatggc attgtagtta tggaagatct caacagccgg   3000
ttcaaggaaa agcgttccaa gatcgagcgc ggggtttacc agcagttcga cgtccctt     3060
atcaagacgt tgaattactt aactttcaag gaccggaaac ttttagaagc cggggggatt   3120
gcaaatggct atcagctgac ctatatccgg gagtcgctta aaaacgtagg ttcacagtgt   3180
ggttgtattt tgtacgtacc tgctgcatac actagcaaga ttgatcctac taccgggtt    3240
```

```
gtcaccctgt ttaaatttaa ggatatttct tctgagaagg ctaagactga tttcatcggt    3300
cgctttgact gtatccgtta cgacgcggaa aaagaccttt tcgcctttga gttcgattat    3360
gacaacttcg aaacgtatga aacttgcgcc cgtacaaaat ggtgcgcgta tacctacggt    3420
actcgtgtaa agaaaacatt ccggaatcgg aagtttgtca gtgaggtgat catcgacatt    3480
accgaagaaa tcaagaaaac gttagcagcc acagacatca actggattga cagccacgat    3540
attaagcagg agatcattga ttacgcactg tcttcccaca ttttttgagat gtttaaactt    3600
actgtgcaga tgcgcaattc tctttgtgaa agtaaagatc gcgagtatga caaattcgtt    3660
tcgccaattt taaacgcgtc aggcaaattt ttcgacaccg acgcagccga caagtcttta    3720
cctattgaag cggacgcgaa cgatgcatac ggtattgcac tgaagggcct ttacaacgta    3780
ctgcaggtta agaataactg ggccgagggt gagaagttca aattctcccg ccttttccaat    3840
gaagactggt ttaacttcat gcagaagcgc ggcgcgccaa aaaggccggc ggccacgaaa    3900
aaggccggcc aggcaaaaaa gaaaaaggct agccggcagcg cgccggatc cccaaagaag    3960
aaaaggaagg ttgaagaccc caagaaaaag aggaaggtgt gataa                    4005
```

SEQ ID NO: 71                moltype = DNA  length = 4005
FEATURE                    Location/Qualifiers
misc_feature           1..4005
                            note = Description of Artificial Sequence: Synthetic
                            polynucleotide
source                     1..4005
                            mol_type = other DNA
                            organism = synthetic construct
SEQUENCE: 71

```
atgggccacc atcatcatca tcatagcagc ggcctggtgc cgcgcggcag cggtaccatg      60
atctatcgcg aaaattttaa gcggaagaag gaaaagatcg aaatgaatac cgggttcaac     120
gatttcacta acctgtcaag cgttactaaa acactgtcga atcgtttaat cccgactgaa     180
atcacagcta agtatatcaa agagcatggg gtaatcgagg ctgaccagga acgtaatatg     240
atgagccagg agctgaaaaa cattctcaac gactttttatc gttcatttct caacgagaat     300
ctcgtcaaag tacatgaatt ggacttcaaa ccgttgttca cggaaatgaa gaaatacctc     360
gagacaaagg ataataagga agcccttgaa aaagcacaag acgacatgcg gaaagccatc     420
catgatatct ttgagtcgga tgaccgttat aagaagatgt tcaaagcaga gattacagcc     480
tctatccttc cagagtttat cttgcacaac ggcgcgtact ccgctgagga aaagaagag      540
aagatgcagg tagtcaagat gttcaatggg ttcatgacta gctttagcgc cttttttcacg     600
aaccgggaaa actgtttttc caaagaaaaa atttcgtcat cgacatgca ccggatcgtg     660
gatgacaacg caaagattca cttcgataac atccgtatct acaaaaacat tgcgaacaca     720
ttcgactacg agatcgagat gatcgagaaa attgaagaag cagccggtgg ggcagatatc     780
cggaatattt tctcatacaa ctttgaccac ttcgcattca atcattttgt ttcacaagat     840
gacatctcat tctataatta tgtggttggg gggatcaata aatttatgaa cctttactgt     900
caagccacaa aagagaagtt atcaccatac aaactgcgg acctccacaa acagattctt     960
tgtattgagg agtctttgta cgatgtgcca gcaaagttca attgcgatga ggacgtttac    1020
gcagcggtaa acgacttcct taataacgtt cgtacgaaga gcgtgatcga gcgcttacag    1080
atgctgggga agaatgcaga ttcttacgat ctggataaga tctatatctc taaaaaacac    1140
tttacgaaca tctcacagac actctatcgg gacttcagtg tgatcaatac cgctttgacc    1200
atgtcgtata ttgataccct cccgggaaaa gggaagacta aggagaagaa agccgcgagc    1260
atggccaaaa acacagaact tatctcactc ggtgagatcg ataagctggt ggacaaatac    1320
aatctctgtc ctgacaaagc cgcaagtacc cgctcactta ttcgcagtat cagtgatatt    1380
gtggcggatt ataaggccaa cccacttact atgaacaacg gcatcccgct agcagaaaac    1440
gagacgaaa tcgcagtcct caaggaagcc attgagccgt ttatggatat tttccggtgg    1500
tgcgctaagt tcaaaactga cgagccagtg ataaagata ctgatttcta caccgagttg    1560
gaggacatta acgatgaaat tcactctatt gtctccctct acaatcggac acgtaactat    1620
gtcaccaaaa aacatataa tactgacaag ttttggcctgt acttcggtac ttcaagtttt    1680
gcgtcaggct ggagtgaaag taagaatttt actaataacg caatcttatt agccaaagat    1740
gacaagtttt accttggtgt atttaatgct aaaaataaac cggctaagag cattatcaaa    1800
gggcatgata ccattcagga cggtgactat aaaaaaatgg tttactcgct cttaacgggg    1860
ccaaataaaa tgctgccaca tatgttcatt agtagttcta aagccgtccc ggtgtatgg   1920
ctcacggatg agcttcttag tgactataag aagggtcggc acctcaaaac aagcaaaaac    1980
ttcgatatcg actattgtca aagcttatt gattacttta acattgctt ggcattatat    2040
accgactggg attgcttcaa cttcaaattc tccgataccg aatcgtacaa cgatatcggc    2100
gaattctaca aagaggtggc ggaacaaggt tattatatga agggaccta tatcggtagc    2160
gatgacattg attcgttca agagaattgg cagctttact tgtttcagat ctacaataaa    2220
gactttagtg agaagtcttt tggcaagccg agtaaacata cggcgatttt acggtcgctc    2280
ttctcggatg agaatgtggc ggatccagtt attaagctgt gcgtgggac ggaggtgtt    2340
tttcgtccga atcgattaa gactccgta gtacataaaa agggtagtat tttagtctcc    2400
aaaacctaca acgctcaaga gatgacgaa aacggcaaca tcattaccgt tcggaaagtg    2460
gttcctgatg acgtctacat ggagctctat ggttactaca ataattcggg tactccgtta    2520
agtgcggagg cactgaagta caaggatatt gtggatcacc ggacggcacc ttatgacatc    2580
attaaagatc ggcggtacac cgaagatgaa ttcttcatca atatgccggt gtctttgaac    2640
tataaggccg aaaaccgtcg cgttaacgtc aacgaaatgg cgctgaaata tatcgctcag    2700
actaaagata cctacattat cggtattgat cgtggcgagc gcaacttact gtacgtaagt    2760
gtaatcgata cagatggcaa tattgtgaaa cagaaatccc tgaatattat caataacgtc    2820
gactaccaag caaattaaa acaggtcgag attatgcgga agttagctcg gcagaactgg    2880
aaacagggcg tgaaaattgc cgaccttaaa agggcatt tgtctcaggc tgtacacgaa    2940
gtagcagagt tggtgatcaa gtaaacggt attgttgtta tggaggactt aaacagtcgg    3000
tttaaggaga aacggtacaa aattgaacgt ggcgtgcc aacgtttga aacatcattg    3060
attaaaacct taaattatct cactttcaag gaccggaaac tcttgaagc gggtggtatt    3120
gcaaatggct atcagctgac ttacatcccg gaatctctta aaaacgtagg ttcacagtgt    3180
ggctgtatct tgtacgtgcc agctgcttat acctcaaaaa tcgacctac cactggcttt    3240
gtcaccctt tcaaatttaa agatatttca tctgaaaag ctaagaccga cttcattggc    3300
cgtttcgact gtatccgtta tgatgccgag aaggacctct ttgcttttga gttcgactac    3360
```

```
gacaatttcg agacttatga gacttgtgct cgcacgaaat ggtgcgctta tacctacggg    3420
acccgggtga aaaaaacttt tcgcaatcgg aaattcgtat ccgaagttat tatcgatatc    3480
acagaagaga tcaagaagac tctcgcagct actgacatta attggattga tagtcacgac    3540
atcaaacagg agattattga ttacgcactg tcttctcaca tcttcgagat gttcaagtta    3600
accgtccaaa tgcgcaactc tctttgtgaa tcgaaggatc gtgaatacga taagtttgtc    3660
tcgccgattt taaatgcgtc tggtaaattt ttcgacacag atgcagctga caaatctctc    3720
ccaattgagg cagacgctaa tgacgcctat ggtatcgcca tgaaaggctt atataacgta    3780
ctgcaggtaa agaataactg ggcagagggt gagaagttta aattctcacg tttatctaat    3840
gaggattggt tcaactttat gcaaaaacgg ggcgcgccaa aaaggccggc ggccacgaaa    3900
aaggccggcc aggcaaaaaa gaaaaaggct agcggcacgg gcgccggatc cccaaagaag    3960
aaaaggaagg ttgaagaccc caagaaaaag aggaaggtgt gataa                    4005

SEQ ID NO: 72          moltype = DNA  length = 4005
FEATURE                Location/Qualifiers
misc_feature           1..4005
                       note = Description of Artificial Sequence: Synthetic
                       polynucleotide
source                 1..4005
                       mol_type = other DNA
                       organism = synthetic construct
SEQUENCE: 72
atgggccacc atcatcatca tcatagcagc ggcctggtgc cgcgcggcag cggtaccatg    60
atttatcggg agaattttaa gcgcaaaaaa gagaagatcg agatgaacac cgggtttaac    120
gatttcacta acttgtcatc ggtcacgaaa actctgtgta accgcctgat tccaaccgaa    180
atcactgcta agtacatcaa ggagcacggg gtaatcgagg ccgatcagga gcgcaatatg    240
atgagtcaag aattaaagaa cattttgaat gatttctacc ggtcatttct caacgagaac    300
ctggttaagg tccatgaact ggacttcaag ccattgttta cagaaatgaa gaagtacctg    360
gaaactaagg ataataaaga ggccttggag aaggctcagg acgatatgcg taaagcgatt    420
cacgatattt ttgagtcgga cgaccgctat aagaaaatgt tcaaggccga gatcaccgcg    480
agcatcctgc cggaattcat cttacacaac ggcgcctata gcgccgagga aaaagaagaa    540
aaaatgcagg tggtaaagat gttcaatggg ttcatgacca gcttttcagc gttttttacg    600
aatcgcgaaa attgcttttc caagagaag atttcctctt cagcatgcta ccgcattgtc    660
gatgataatg ctaaaattca ttttgacaat atccggatct acaagaatat cgctaacaag    720
ttcgattatg aaatcgagat gattgagaaa attgaggaag cagcgggcgg ggccgacatc    780
cggaatattt tttcatataa cttcgatcat tttgctttta atcacttcgt gtcacaagat    840
gatatttcct tctacaacta cgtggtcggt ggtatcaaca aattcatgaa tctttactgt    900
caagcaacca agaaaaaact cagcccttat aaacttcgtc acctccacaa gcagattctt    960
tgtatcgagg agtcctata cgatgttcca gccaaattta attgcgatga ggacgtctac    1020
gcggcagtta atgatttcct gaataatgtg cgtacaaagt ctgtgattga gcgtttacaa    1080
atgttaggta aaaatgcgga cagctatgat cttgataaga tctacattag taagaaacat    1140
tttactaata ttagccaaac gctctatcgc gacttcagcg tgattaacac agcgctgacc    1200
atgtcatata tcgatacgct tcctgggaag gggaaaacaa aagaaaagaa agcggcgagt    1260
atggctaaga atactgaact gatctctctt ggcgaaattg ataaattagt cgataaatac    1320
aacttatgtc cagataaagc agcatcaacg cgttcactga tccgtagcat ttcagatatc    1380
gtggctgatt acaaggcaaa cccattgact atgaattccg gcatcccgct ggcagagaat    1440
gagacggaga ttgcagtgct gaaggaggct attgagcctt ttatggacat ttttcgttgg    1500
tgtgcgaaat ttaaaaccga tgagccggtt gataaggaca cagattttcta caccgaatta    1560
gaggatatca atgatgaaat tcattctatc gtaagccttt ataaccgtac acgtaactac    1620
gtgaccaaga aaccttacaa cacagacaag ttcggcctct atttcgggac gagctcgttt    1680
gcatccggct ggtctgaatc taaggaattc acaaataatg caattttgtt ggcgaaggat    1740
gataaattct accttggtgt tttcaatgct aaaaacaaac cggctaaaag cattatcaag    1800
ggtcatgata caattcaaga cggcgactac aaaaaaatgg tgtattcgct gttaacgggc    1860
cctaacaaaa tgcttcctca tatgttcatt agttccagta aggcagtacc ggtctacggc    1920
ctcaccgatg agttgctttc ggattacaag aaaggtcgcc accttaagac gtccaaaaat    1980
ttcgacattg actattgtca caagtaatc gattatttca aacattgttt ggcgttgtac    2040
actgactggg attgtttcaa cttcaaattc tctgatactg agtcttacaa tgacatcggg    2100
gaattctaca agaagtagc tgaacaggc tactatatga attggactta catcgggagt    2160
gacgatatcg acagccttca agaaacggc caattgtatt tattccagat ttacaacaag    2220
gacttcagcg agaaaagttt cggtaaacct agtaaacata cggctatcct tcggagtcgc    2280
ttttcagatg aaaacgtggc agacccagtt attaagctgt gtggtggcac cggaggtgttc    2340
ttccgcccta agtcaattaa aaccccagta gtgcataaaa aagggtcaat tcttgtgtcg    2400
aagacatata acgcacagga aatggacgag aacggcaaca tcatcacagt acggaaatgc    2460
gtacctgatg acgtttatat ggagctgtac ggctattaca ataacagcgg caccccgctc    2520
tcggcggaag ctctgaagta caaagacatc gtggatcacc ggccgcc atacgatatc    2580
atcaaagatc gccgttacac ggaggacgag ttcttcatca acatgcctgt tagtttaaat    2640
tataaagccg aaaaccggcg tgtaaacgta aacgagatgg cacttaaata tattgcccag    2700
actaaggaca cctatattat cggcatcgac cgtggcgaac ggaatttgct ttacgtctcc    2760
gtaatcgaca cagacggcaa tattgtcgag caaaatcac tgaacattat caataacgtt    2820
gattaccagg cgaaattgaa acaagttgag attatgcgta agttagctcg gcaaaattgg    2880
aagcaaggtg taaagattgc cgatctgaag aagggttatc tgtcccaggc agtccacgag    2940
gtcgccgagc tggtcatcaa gtataacggg attgtggtga tggaagacct gaatagtcgc    3000
tttaaagaga agcggtccaa aattgagcgc ggtgtgtatc aacaattcga gacgtcgttg    3060
attaagcgct gaattacttt gacgttcaaa gatcgtaaac cattgagagc aggggggcatc    3120
gccaacggct atcaattgac atacattcct gagtccctta aaaacgtggg gtccaatgc    3180
ggttgtatcc tttacgtacc tgcagcgtat acaagcaaaa ttgacccta cacaggtttc    3240
gtcactttat tcaatttaaa ggatatccgt tcggagaaag ctaaaactga ttttatcggt    3300
cgctttgact gtatccgtta cgatgccgag aaggacctgt tcgcctttga attcgactac    3360
gataacttcg agacctacga gacctgcgcc cggaccaat ggtgtgccta cacttatggg    3420
actcgcgtca agaagacgtt ccgtaaccgc aaatttgtaa gcgaagttat catcgacatc    3480
```

```
actgaagaaa tcaaaaaaac tctggcggcg accgacatca actgattga tagccatgac   3540
attaagcaag aaattattga ttatgctttg tcctcgcata ttttttgaaat gttcaagtta   3600
acagtccaga tgcggaactc actgtgcgaa agcaaggatc gggagtatga caagttcgta   3660
tcaccgattc tcaatgcttc tggtaagttt tttgacacgg acgctgcaga taaatcgctc   3720
ccaattgaag ctgatgcgaa cgatgcctac ggtattgcta tgaaagggtt gtacaacgtg   3780
cttcaagtta agaacaattg ggcagaaggc gagaagttca aatttccccg gctcagtaat   3840
gaggactggt tcaacttcat gcaaaaacgc ggcgcgccaa aaaggccggc ggccacgaaa   3900
aaggccggcc aggcaaaaaa gaaaaaggct agcggcagcg cgccggatc cccaaagaag   3960
aaaaggaagg ttgaagaccc caagaaaaag aggaaggtgt gataa                   4005

SEQ ID NO: 73           moltype = DNA  length = 4005
FEATURE                 Location/Qualifiers
misc_feature            1..4005
                        note = Description of Artificial Sequence: Synthetic
                         polynucleotide
source                  1..4005
                        mol_type = other DNA
                        organism = synthetic construct
SEQUENCE: 73
atgggccacc atcatcatca tcatagcagc ggcctggtgc cgcgcggcag cggtaccatg   60
atctatcggg aaaacttcaa gcggaaaaaa gaaagatcg aatgaatac tggttttaat    120
gacttcacca accttagttc tgtaacgaag acgctctgta accgtctgat tccaactgaa   180
atcactgcta agtacattaa agaacatggc gttattgagg cagaccaaga acggaatatg   240
atgtcacaag agctcaagaa tatccttaac gactttatc gcagtttcct caatgagaac   300
cttgtcaagg tgcatgaact tgattttaag ccgttgttta cagaaatgaa aaaatatctg   360
gaaactaaag ataataaaga agcactggag aaagacatgg atgacatgcg caaagccatc   420
cacgacatct ttgagtctga cgatcgttat aagaagatgt tcaaggccga aattacagcg   480
tcgattctgc cagaatttat tcttcataac ggggcttact ctgccgaaga aaggaggag    540
aaaatgcagg tagtgaagat gttcaacggc tttatgacga gctttagtgc attctttacg   600
aacgggaga actgcttctc caaggaaaaa atttcctcta gcgcttgcta tcgcattgta   660
gacgataatg cgaagatcca tttcgataac atccgcatct ataaaaatat tgccaataag   720
ttcgattatg aaattgaat gattgaaaag attgaagagg ccgcaggcgg tgctgacatc   780
cgcaacattt tttcatataa ttttgaccac tttgcttca accacttcgt atcgcaagac   840
gacattttctt tttacaatta tgttgtcggc gggattaaca agttatgaa cctgtattgt   900
caggcgacta aggagaaact ctcaccatat aaattgcggc accttcataa acaaatcctc   960
tgtatcgagg agtcccttta tgacgttccg gctaagttta attgtgacga ggacgtctat   1020
gcagcagtaa acgacttttt aaacaatgtt cgtaccaaat ctgtaattga acggcttcaa   1080
atgctcggta aaaatgccga ttcttatgat ttagacaaaa tttatattag caaaaagcat   1140
tttaccaaca tctcccaaac tctctatcgt gatttctccg tcattaacac agcattgacg   1200
atgtcataca tcgacactct ccctggtaag ggcaaaacca aggagaaaaa ggctgcaagt   1260
atggcaaaaa acaccgagct tatcagtttg ggcgaaatcg ataaattggt cgataagtac   1320
aacttatgcc cagataaagc cgccagcaca cggagcctga tccgttccat ctccgacatc   1380
gtagcggact ataaagcaaa cccttaacg atgaactgac gtattccgtt ggcagaaaat   1440
gagactgaga ttgccgtgtt gaaggaggcc atcgagccat tcatggacat ttttcgctgg   1500
tgcgcaaagt tcaaaaccga tgagccagtt gataaagata ctgattttta caccgagctg   1560
gaagacatta atgacgagat tcactctatc gtgagcttat ataaccggac tcggaattat   1620
gtaactaaaa aaccttacaa tacagacaag tttgggttat atttttgggac gtcctcattc   1680
gctagtggct ggtcggaatc taaggagttt actaacaatg cgattctctt agctaaagat   1740
gataaatttt acttaggcgt cttttaatgct aagaacaaac cggcaaaatc catcattaag   1800
gggcacgaca ccattcaaga cggcgactac aaaaagatgg tctacagtct gttgaccggg   1860
cctaataaga tgcttccaca catgttcatc tcatcatcca aagccgtcc agtgtatgcg   1920
ttgaccgacg aactcctgtc ggattataaa aaaggtcgtc atcttaagac ttcaaaaaac   1980
ttcgatatcg actactgcca caattgatt gattacttca acattgttt agccttgtac    2040
acggattggg actgctttaa ttttaagttc tccgatacag agagctataa cgacatcggt   2100
gaattctata aggaggtcgc agaacaaggt tattatatga actggactta tatcggttcg   2160
gacgatatcg actctctcca ggaaaatggc caactttacc tttttccaaat ttacaacaag   2220
gacttttccg aaaaatcttt cggcaagcca tcaaagcata cggcaatcct tcgcagtttg   2280
ttctctgatg agaatgttgc cgacccggtc atcaagttgt gtggtggtac tgaggttttc   2340
ttccggccaa agtcgattaa gactccagtc gtccacaaaa aaggcagtat tctggtcagc   2400
aaaacctata atgctcaaga aatggacgag aatggcaaca tcatcacagt gcgtaaatgc   2460
gtccctgatg atgtatacat ggaattgtat ggttattaca ataactctgg tacgcctttg   2520
tcagcggagg ccttgaaata caaggacatc gtggaccacc gtactgcccc ttacgatatt   2580
attaaagatc ggcgttacac ggaggacgaa ttttttcatca atatgccagt tcactgaac   2640
tacaaagccg agaaccggcg ggttaacgtg aacgagatga cactgaagta tatcgctcag   2700
acaaaagaca cttatattat cggtattgat cgcggcgagc gtaatcttct ttatgtgtct   2760
gtgatcgata ctgatgggaa tattgtggag cagaagagcc tcaacatcat caacaacgtt   2820
gattatcagg caaaattaaa gcaagtgaaa tcatgcgta aattggcgcg gcaaaattgg   2880
aagcaaggtg taaagatcgc ggacttaaag aaagttacc tctctcaggc tgtccacgag   2940
gtcgcgaac ttgtaatcaa atacaacggg atcgtcgtta tggaggactt aaattcccgt   3000
tttaaagaaa gcggagtaa aatcgagcgc ggcgtttatc agcaatttga gacatcattg   3060
attaaaacgc tcaactacct tacttttaaa gaccgtaagc cgttagaggc gggtgggatt   3120
gccaatggct atcaattaac gtatattccg gagtccttga aaaatgtggg gtctcagtgc   3180
ggttgtatcc tctatgtacc tgccgcttat acgagcaaga tcgacccgac gacaggcttt   3240
gttacattgt tcaaattcaa agatatctcg tcagagaaag caaaaactga ttttatcggg   3300
cggttcgatt gcatccggta cgacgcagag aaggacttgt tcgctttcga attcgactat   3360
gacaattttg aaacctacga gacctgcgcg cggacaaagt ggtgtgccta tacctatggc   3420
acccgcgtca gaaaacgttt tcgtaaccgt aaatttgtaa gtgaggtgat tatcgacatt   3480
accgaggaaa ttaaaaaaac tctcgcgcc acggatatca attggatcga ctctcatgac   3540
atcaaacagg aaatcattga ttacgcattg agcagtcata tctttgaaat gtttaagttg   3600
```

```
actgttcaga tgcgcaattc tttatgcgaa agtaaggacc gggagtacga caaatttgta  3660
tcaccgattc ttaatgcttc cgggaaattc ttcgatacag acgccgcgga caagtcatta  3720
cctatcgaag ccgacgcgaa cgacgcgtat gggattgcta tgaaaggttt gtacaatgtt  3780
ttacaagtga aaaataattg ggcggaaggt gaaaagttca agtttagtcg gctctcaaat  3840
gaagattggt tcaatttcat gcaaaaacgc ggcgcgcaaa aaaggccggc ggccacgaaa  3900
aaggccggcc aggcaaaaaa gaaaaaggct agcggcagcg gcgccggatc cccaaagaag  3960
aaaaggaagg ttgaagaccc caagaaaaag aggaaggtgt gataa                 4005
```

| | | |
|---|---|---|
| SEQ ID NO: 74 | moltype = DNA  length = 4005 | |
| FEATURE | Location/Qualifiers | |
| misc_feature | 1..4005 | |
| | note = Description of Artificial Sequence: Synthetic polynucleotide | |
| source | 1..4005 | |
| | mol_type = other DNA | |
| | organism = synthetic construct | |

SEQUENCE: 74

```
atgggccacc atcatcatca tcatagcagc ggcctggtgc cgcgcggcag cggtaccatg  60
atttatcgcg aaaacttcaa acgcaaaaaa gaaaaaattg aaatgaatac cggcttcaat  120
gatttcacta atttgagctc cgttacaaaa accctgtgta atcgtttgat cccgacggaa  180
atcacagcaa aatacattaa ggagcatggg gttattgagg ccgaccagga gcggaatatg  240
atgtcccaga agctgaagaa cattcttaac gatttctaac gtctcttttt gaatgagaac  300
ttagtgaaag tacatgagtt ggatttcaag ccacttttca cagaaatgaa aaagtatctt  360
gagacgaagg ataacaaaga agcactcgaa aaagcgcagg atgtatatgcg taaagcaatt  420
catgatatct tcgaaagtga tgaccgctat aagaaaatgt tcaaggcgga aatcaccgca  480
tctatcttgc cggagtttat cttacacaat ggggcgtatt cggccgaaga gaaggaagaa  540
aaaatgcagg ttgttaagat gttcaatggc ttcatgacga gcttttctgc gttctttaca  600
aaccgtgaga actgtttcag taagaaaaag atttcgtctt cagcctgtta tcggatcgta  660
gatgacaatg ctaaaattca ctttgacaac attcgcatct ataagaacat cgcaaacaag  720
tttgactatg agatcgagat gattgaagag ccgcaggggg tgcggacatc  780
cgcaatattt tttcgtataa ctttgatcac tttgcttttta atcactttgt ttcgcaggac  840
gatatttcgt tttacaatta tgttgtaggg ggcatcaaca aattcatgaa cctgtactgc  900
caagctacca agaaaaaact ttctccatat aaattacggc acttacacaa acagatcctg  960
tgcattgaag agtctttata tgatgtccca gcaaaattca attgtgatga agatgtctat 1020
gccgcagtca acgatttcct caacaacgta cggactaagt ctgtgatcga gcgtttacag 1080
atgcttggca aaaacgctga ctcatatgac ttggataaaa tttacatttc taagaaacat 1140
ttcaccaata tctctcagac actgtatcgc gatttcagtg tcattaacac tgcacttact 1200
atgtcataca ttgacacact gccggggaag gggaaacga aggaaaaaaa agccgcctc 1260
atggcaaaga acacggaact catctcgctg ggggagatcg caaaactcgt tgataagtac 1320
aacttatgcc cagataaagc agctagtaca cgcagcttga ttcgtagcat ttccgacatt 1380
gtggcagatt acaaggcgaa tccttttgact atgaattctg gtatcccttt agccgagaat 1440
gagacagaaa ttgctgtcct caaggaagcg atcgagccat tcatggatat ttttcggtgg 1500
tgcgcaaaat tcaaaaccga cgagccagtc gacaaggaca cagattttta tactgagctt 1560
gaagacatca atgacgagat ccactcaatt gtgagcttat acaaccgcac gcgtaattac 1620
gtgaccaaga aaccatacaa cacagataaa tttgggttat acttcggtac atcgtcattt 1680
gcatccggtt ggagtgagag taaagagttt acaaacaatg ctatcctgct cgccaaggat 1740
gataagttct acttgggtgt tttcaacgcc aaaaataagc cggccaaaag tatcatcaag 1800
ggtcacgaca caattcagga tggtgattac aagaagatgg tatattccct gctgaccggg 1860
ccgaacaaaa tgcttcctca tatgttcatt tccagctcga aggcagttcc tgtatatggg 1920
ttgacagatg aactcctctc tgactataag aaaggtcgtc atctcaagac ctctaagaac 1980
tttgacattg actactgtca taagttgatc gattatttca aacactgctt ggccttttat 2040
acggactggg actgctttaa ttttaaaattc agtgatacag aatcctacaa cgacattggc 2100
gaattctata aggaggtagc cgaacagggt tattacatga actggacgta tattggttct 2160
gatgatattg attcgcttca ggagaatggc cagttgtatt tattccagat ttacaataaa 2220
gacttctcag agaaaagttt tggcaaaccg agcaagcatc ctgctatttt acggtcgtta 2280
ttctcagatg aaaacgtggc tgaccctgta attaagctct gcggggtac cgaggtgttc 2340
ttccgcccaa aaagcatcaa gacgccagtc gtacataaga aggggagcat cttagtatcg 2400
aagacttaca atgcgcagga gatggacgaa atggcaaca tcatcaccgt ccggaaatgc 2460
gtgccagacg atgtgtacat ggagttatac ggttactaca caattcgggg gacccctctc 2520
tcagcagaag cgttaaagta caaagatatt gttgaccatc ggaccgccgc atatgatatc 2580
attaaagacc gccggtacac ggaagatgaa ttttttatta acatgccagt gtcctcaat 2640
tataaagcag aaaatcggcg cgtaaacgtg aacgaaatgg ccttgaagta cattgcccaa 2700
acgaaagaca cttatatttat cgggatcgat cgggggggagc gtaatttgtt atacgtgagc 2760
gtcatcgaca cggacggcaa tatcgttgag caaaaaagtc ttaatatcat taacaacgtg 2820
gactatcagg cgaaacttaa gcaagtagaa attatgcgga aactggcacg gcagaattga 2880
aagcaaggtg tgaagatcgc cgacttgaag aagggttacc tttcgcaggc cgttcatgag 2940
gtcgcagagt tagtgatcaa atataaccggt atcgtgtaa tggaagatct taatagtcgc 3000
tttaaggaaa agcggtccaa aattgagcgc ggcgtctatc agcagtttga gacatcactc 3060
atcaaaaccc tcaattacct cacattcaaa gatcgcaagc gttagaggc cggcggtatc 3120
gctaatggct accagctgac ctacatcccg gaatcattga agaatgtggg ttctcaatgc 3180
ggctgcattc tttacgtacc agctgcatac acttcaaaga ttgaccctac cacgggcttt 3240
gtcacattgt ttaaatttaa ggatatcagt agtgagaaag cgaaaactga ctttatcggt 3300
cgttttgatt gcatccgcta tgatgctgag aaagacttat tgcatttga gtttgactat 3360
gacaattttg aaacctacga aacgtgtgcc gcactaagtg gtgtgcctaa cacgtacggc 3420
acacgggtta aaaaaacttt tcgcaaccgt aagtttgtca gtgaggtgat tattgatatc 3480
actgaagaaa ttaaaaaaaac gcttgccgcc acggacatca actggattga ctcacacgat 3540
atcaaacaag aaatcatcga ctatgctctt cgtctcata tctttgagat gtttaagctg 3600
accgttcaaa tgcggaattc actgtgtgag tcgaaagatc gtgagtatga aagttcgtc  3660
tctccaatct taaatgcttc gggtaaaattc tttgacaccg acgccgcgga taagtctctc  3720
```

```
cctatcgaag ccgacgcgaa tgacgcttat ggcattgcaa tgaaagggct ctataacgtg   3780
cttcaggtaa aaaataattg ggctgaaggg gaaaagttta agttctctcg cttatcaaat   3840
gaggattggt ttaactttat gcaaaaacgt ggcgcgccaa aaaggccggc ggccacgaaa   3900
aaggccggcc aggcaaaaaa gaaaaaggct agcggcagcg gcgccggatc cccaaagaag   3960
aaaaggaagg ttgaagaccc caagaaaaag aggaaggtgt gataa                  4005

SEQ ID NO: 75           moltype = DNA   length = 4005
FEATURE                 Location/Qualifiers
misc_feature            1..4005
                        note = Description of Artificial Sequence: Synthetic
                        polynucleotide
source                  1..4005
                        mol_type = other DNA
                        organism = synthetic construct
SEQUENCE: 75
atgggccacc atcatcatca tcatagcagc ggcctggtgc cgcgcggcag cggtaccatg    60
atttaccgtg aaaatttcaa gcgtaaaaag gaaaaaatcg aaatgaacac gggctttaac   120
gatttcacaa atctgagtag cgtgactaaa acattgtgta accgcttaat tcctacagag   180
attaccgcca agtatattaa ggagcacggc gtgattgagg ctgatcaaga gcgtaatatg   240
atgtcccagg aacttaagaa tatcctgaac gatttttatc gttcctttct gaatgaaaac   300
ctcgtcaaag tccatgagtt agatttttaaa cctcttttca cagaaatgaa aaaatacctg   360
gagacaaaag ataacaagga ggcgctgaaa aaggcacaga atgatatgcg taaggcgatt   420
catgatattt tcgagagtga cgatcgctat aaaaagatgt tcaaagcgga aattacagcc   480
tcaattcttc cggagtttat cttacacaat ggcgccatt ctgcagaaga aaaggaagaa    540
aagatgcaag tagtcaagat gttcaacggc ttcatgactt cctttagcgc ctttttttaca   600
aaccgcgaga attgcttctc aaaggaaaag atcagttcgt ccgcatgtta tcgcatcgtt   660
gacgacaacg ccaaaatcca ctttgataac atccgcattt ataaaaacat tgctaacaag   720
ttcgattatg agattgaaat gatcgaaaaa atcgaagagg cagctggggg tgccgacatt   780
cgcaatatct tcagctacaa cttcgatcac tttgcattta accacttcgt ctcccaggac   840
gacatctcgt tctacaacta tgtagttggc ggcatcaata aattcatgaa cctctactgt   900
caagctacga agaaaaaact ttcccttat aaactccgtc acttacataa acaaatctta    960
tgcattgagg aatctttgta tgatgtgcca gctaagttca attgcgatga ggacgtctac  1020
gcagcagtga atgactttt aaacaacgtc cgcaccaagt cggttattga acgcctccaa   1080
atgcttggta aaaatgcaga cagctatgat ttagataaga tttttacatctc aaagaaacat  1140
ttcactaata tcagccaaac actctaccgg gactttcgg taatcaacac cgctctcacc   1200
atgagttata tcgatacatt gccaggcaag ggtaagacaa aggaaaaaaa ggctgcgtcc   1260
atggcgaaaa atactgaact gatttcattg gcgagatcg ataagttagt ggacaagtat    1320
aatttatgcc ctgataaagc agcatccacc cggtcgctca tccgtagtat tagcgacatc   1380
gtcgcggact ataaggcaaa ccctcttact atgaattcgg ggattccact tgccgagaac   1440
gagactgaaa tcgcggtgct gaaggaggcg attgaacctt tcatggatat ctttcgttgg   1500
tgcgctaagt tcaagacaga tgagcctgtg gacaaggata cggatttta cacagagtta   1560
gaggacatca acgatgaaat tcactcgatc gtctctcttt ataatcggac acgtaactat   1620
gtaacgaaaa agccatacaa cacggataaa ttcggggttgt actttggtac aagctctttc   1680
gcaagtgggt ggagtgagtc aaaggagttc acgaataatg ccatcttgct cgcgaaagac   1740
gataagtttt acctgggggt ttttaatgct aagaacaagc tgctaagtc tattattaag   1800
ggtcatgaca ctattcaaga cggggattac aagaagatgt ctactccct tcttacaggg   1860
ccaaacaaga tgctcccaca tatgttcatt tcttcgtcca aagcggtacc ggtctacggc  1920
ctgacgacg aactgctgtc agattataaa aagggtcgtc acctgaagac gagtaagaat   1980
ttcgatattg attattgtca taagttaatc gattattttta agcactgcct cgcccttttac   2040
acagactggg attgctttaa ctttaaattt tctgacacag aatcctacaa tgacatcggt   2100
gaattttaca aagaggttgc cgaacagggg tattacatga attggactta tatcgggtcg   2160
gacgacattg attcgctcca ggagaacggc cagcttatt tgttccaaat ttacaacaag   2220
gacttcagcg aaaagtcttt tggtaagccg tcgaaacaca ctgcaattct tcgttcactg   2280
ttcagtgatg aaaacgttgc cgatccagta attaagcttt gtggtggcac tgaggtgttc   2340
tttcggccga agtcaatcaa gacaccagtc gtccacaaga agggctcgat tctggtctct   2400
aaaacatata acgcacaaga aatggatgaa aatgggaata ttatcaccgt gcgtaaatgt   2460
gttcctgacg acgtttacat ggaactttat gggtactata caactctggg gactccgttg   2520
agtgctgagg cgctgaagta taggacatc gttgatcacc ggacggcccc gtatgatatc   2580
atcaaagatc ggcgttacac tgaggcgtga tttttttatta acatgccagt gtctctcaac   2640
tataaagccg agaaccggcg ggttaatgtg aatgaaatgg ccttaaaata catcgcccag   2700
accaaggaca catatatcat cggcatcgac cgcggtgaac gtaatctcct ctatgtatca   2760
gtgattgata cggacggcaa cattgttgag cagaaatcgt taaacatcat taataacgtg   2820
gattaccaag caaagcttaa gcaagtagag atcatgcgga agctggcacg ccaaaattgg   2880
aagcaagggg tcaagatcgc ggatctgaag aaaggctacc tttcccaagc agtccacgag   2940
gtggcggaat tagtgatcaa gtacaatggg attgtcgtta tggaagatct taatagccgc   3000
ttcaaggaga agcgtagtaa aatcgagcgt ggcgtctatc agcagttcga aacctctctc   3060
attaagactc tgaattacct tactttcaaa gaccgtaagc cacttgaagc cggcggcatc   3120
gcaaacgggt accaacttac ttacatcccg gagtcattaa agaatgtggg ctctcaatgt   3180
ggttgtattt tgtacgtacc tgcagcatat acgagcaaga tcgatccgac aaccggtttg   3240
gtgaccctgt ttaagttcaa ggatatttcc agcgagaagg caaaaacaga cttcatcggg   3300
cgctttgatt gtatccggta cgcacgccag aaagatctgt ttgcctttga gttcgactat   3360
gataactttg agcctacga gacgtgtcgc cgtacgaaat ggtgcgcgta cacgtacggg   3420
acacgcgtca aaaaaacatt ccgcaatcgg aaattcgtct ctgaggtgat catcgatatt   3480
accgaggaaa ttaaaaaaac attggtgatc atcccgatga ttcccatgat   3540
attaaacagg agatcatcga ctacgctctg tcgagccata ttttcgaaat gttttaaattg   3600
accgtgcaga tgcgtaattc cctctgcgag agcaaggatc gcgaatacga taagttcgta   3660
tctcctattc tgaatgccag cgggaaattt ttgacactg atgcggctga taaatcgtta   3720
cctatcgagg cggacgccaa cgacgcctac gggattgcaa tgagggcct ttacaacgta   3780
ctgcaagtga aaaacaattg ggcggaaggc gaaaaattta aattttcccg cttgtcgaac   3840
```

```
gaggattggt tcaattttat gcaaaaacgg ggcgcgccaa aaaggccggc ggccacgaaa    3900
aaggccggcc aggcaaaaaa gaaaaaggct agcggcagcg gcgccggatc cccaagaag    3960
aaaaggaagg ttgaagaccc caagaaaaag aggaaggtgt gataa                    4005
```

SEQ ID NO: 76          moltype = DNA  length = 4005
FEATURE              Location/Qualifiers
misc_feature       1..4005
                     note = Description of Artificial Sequence: Synthetic
                     polynucleotide
source               1..4005
                     mol_type = other DNA
                     organism = synthetic construct

```
SEQUENCE: 76
atgggccacc atcatcatca tcatagcagc ggcctggtgc cgcgcggcag cggtaccatg     60
atctatcggg agaattttaa gcgcaagaag gaaaaaattg agatgaatac ggggtttaac    120
gatttcacta atctctcatc agttaccaag acccttttgca accgtttaat tccgactgaa    180
atcaccgcca agtatattaa agaacatggc gtaatcgaag ctgaccagga gcgtaacatg    240
atgagtcagg aacttaaaaa cattttaaat gactttttac ggagcttttt aaacgaaaat    300
ttggtaaagg tacacgagct cgactttaaa cctctttttta ccgaaatgaa aaaatacctg    360
gaaaccaagg acaacaagga agcactcgag aaggcacaag atgatatgcg taaagcgatt    420
catgatattt ttgagtccga cgatcggtac aaaaaaatgt tcaaagccga aattacggcc    480
agcattcttc cagagtttat tcttcataac ggggcttact cggcagaaga gaaagaagag    540
aagatgcaag tggttaaaat gttcaatggg ttcatgacat catttagtgc cttctttact    600
aatcggaga actgttttag taaggaaaaa atctcatcca gtgcctgtta tcggattgtt    660
gacgacaacg caaagatcca ctttgataat atccggatct acaagaatat tgctaataag    720
ttcgactatg aaattgaaat gatcgagaaa attgaggagg cggcggggtgg ggccgatatt    780
cgtaatatct ttagttacaa ttttgaccat tttgccttca atcactttgt ctctcaggac    840
gatatttctt tctataacta tgtagtcggg ggcattaaca aatttatgaa cctgtactgc    900
caagccacta agaaaagct gagtccatat aagttacggc atcttcataa gcagatctta    960
tgcattgagg agtccctgta tgatgtaccg gccaaattca attgtgacga ggatgtctat   1020
gctgctgtca acgatttctt gaacaatgta cggacgaaaa gcgtaatcga gcggctccaa   1080
atgcttggta aaaacgccga ttcctacgat ctcgacaaga tctacatttc caagaagcac   1140
ttcacaaata tcagtcaaac gctttatcgc gatttcagtg taatcaacac tgcccttact   1200
atgtcttaca ttgatccct tccaggcaag gggaagacaa aggagaagaa ggcagcatct   1260
atggcaaaga atacagagtt gatctccactc gggggaaatcg ataagttagt agataagtat   1320
aatctctgtc ctgataaagc ggcatcaacc cgctcactca ttcgttccat ctctgatatt   1380
gtagcggact acaaggcaaa cccctttgact atgaactcag gcattccact ggctgaaaac   1440
gagactgaga tcgccgtact caaggaggca attgaacctt tatggatat ttttcgctgg   1500
tgtgccaaat ttaagacaga cgaacctgtg gacaaagata cggactttta tacagaactc   1560
gaggatatca acgatgaaat ccactccatt gttagccttt acaatcgtac gcgtaattac   1620
gtgacgaaga agccttataa tactgacaag ttcggccttt atttcggtac gtcctcgttt   1680
gcgtcggggtt ggtccgagtc gaaagaattt actaacaacg ccatcttatt agccaaggac   1740
gataaattct atctcggggt gtttaatgca aaaaacaaac ctgcaaagtc cattatcaaa   1800
ggccacgata ctatccaaga cggtgactat aagaaaatgg tctatagctt attaactggg   1860
cctaacaaaa tgctcccgca catgttcatc tcctcgagta agcagttcc tgtgtatggg   1920
ttaacgatg aactcttgag tgactacaaa aaggccgtc atttaaaaac ttcgaagaac   1980
tttgacatcg actattgtca caagcttatc gattattta agcattgctt agcgctgtac   2040
acagattggg attgtttcaa ctttaagttt tcagacaccg agtcctacaa cgatatcggc   2100
gagttctaca agaagtggc ggagcaaggc tactatatga attggacata cattggttcc   2160
gatgatatcg actcattaca agagaacggt caactgtatc ttttccagat ctacaataag   2220
gacttctcgg agaagagttt tgggaagcct tcaaaacata cagcgattct tcggagtctc   2280
tttttctgacg aaaacgtcgc ggatccagta attaaattgt gtggcggcac cgaagtcttt   2340
tttcgcccta atccatcaa gacgcctgta gtgcacaaaa agggtagcat cctggtgtcg   2400
aaaacctata acgcacaaga gatggacgag aacgggaata tcattacagt acggaaatgt   2460
gtaccagacg acgtctatat ggagttgtat ggttattaca caataagtgg gactccactg   2520
tcagccgagg ctctgaaata taagagatc gtggatcacc gcacggcacc atacgatatt   2580
attaaagatc gtcgttacac agaggacgaa ttctttatta atgccggt atctctcaat   2640
tacaaagcag agaatcgtcg tgtcaatgtc aacgaaatgg cgctgaagta tattgcccag   2700
actaaggaca cttacattat cggcattgat cggggggggaac ggaatctctc atacgttagc   2760
gtaattgaca ccgacggtaa cattgttgaa caaaagagct tgaacattat caacaacgta   2820
gactaccagg ctaagctcaa acaagtcgaa attatgcgga aattggcccg ccagaactgg   2880
aagcaggggg tgaaaattgc tgaccttaaa aagggtact atcgcaggc tgtccatgaa   2940
gttgctgagc tggtgattaa gtacaacggt attgtggtaa tggaagacct caattcccgt   3000
ttcaaggaga agcgcagtaa gattgaacgg ggtgttttatc aacaattcga aacttcactt   3060
attaaaacat tgaactatct tacgtttaag gaccgtaagc ctttggaggc tggcggcatc   3120
gccaatggtt accaacttac atatatccca gaaagcttaa agaatgtcgg gagtcaatgt   3180
ggttgtatcc tctatgtgcc agcggcatat acaagcaaga ttgacccgac tacaggtttc   3240
gtgacactct tcaaattcaa ggatatctct tcagaggaaag cgaaaacaga tttcatcggg   3300
cgtttcgatt gcatccgcta tgatgcggag aaagacctgt tcgcattcga gttcgactac   3360
gataattttg aaacgtatga gacttgtgct cggactaaat ggtgcgccta tacgtatggg   3420
acgcgtgtga agaaaacatt tcgtaaccgt aagtttgttt cggaagttat tattgacatt   3480
actgaggaga ttaaaagac attggccgcg actgatatca actggatcga ttctcacgac   3540
atcaaacaag aaatcattga ttacgccctg tcatcacaca tttttgagat gttcaagctt   3600
acagtgcaga tgcggaacc tctgtgaa agcaaggacc gtgaatacga caaattgta   3660
tcgccgatct tgaatgcatc cggtaaattc tttgataccg acgcagcaga caaaagtttg   3720
ccaatcgagg ctgatgcgaa tgatgcttac ggtattgcaa tgaagggggtt gtacaatgtt   3780
cttcaagtga aaaataactg ggctgagggg gagaaattta gtttcccg cctttcgaat   3840
gaagactggt tcaatttcat gcagaaacgg ggcgcgccaa aaggccggc ggccacgaaa   3900
aaggccggcc aggcaaaaaa gaaaaaggct agcggcagcg gcgccggatc cccaagaag   3960
```
aaaaggaagg ttgaagaccc caagaaaaag aggaaggtgt gataa 4005

| SEQ ID NO: 77 | moltype = DNA length = 4005 |
|---|---|
| FEATURE | Location/Qualifiers |
| misc_feature | 1..4005 |
| | note = Description of Artificial Sequence: Synthetic polynucleotide |
| source | 1..4005 |
| | mol_type = other DNA |
| | organism = synthetic construct |

SEQUENCE: 77

| | | | | | |
|---|---|---|---|---|---|
| atgggccacc | atcatcatca | tcatagcagc | ggcctggtgc | cgcgcggcag | cggtaccatg | 60 |
| atttatcgtg | agaactttaa | acggaagaaa | gaaaaaattg | agatgaatac | aggtttcaat | 120 |
| gatttcacga | acctctcatc | ggtcacgaag | accctgtcga | atcgtctgat | tcctaccgaa | 180 |
| atcacagcta | agtacattaa | agagcacggg | gtcatcgagg | ctgatcagga | gcgtaacatg | 240 |
| atgtcccagg | agttgaaaaa | tatcttgaac | gactttacc | ggtcgtttct | taacgaaaac | 300 |
| ttagttaaag | ttcacgaact | ggatttcaaa | ccgctcttca | cagaaatgaa | aaagtatttg | 360 |
| gaaacgaagg | acaacaagga | agcgttagaa | aaagcgcaag | atgacatgcg | taaagcgatt | 420 |
| catgacatct | ttgaatcgga | tgaccgctat | aagaagatgt | tcaaggctga | gattacggcg | 480 |
| tccattctcc | ctgagtttat | tcttcataat | ggtgcctact | cggctgaaga | gaagaggag | 540 |
| aagatgcaag | ttgttaaaat | gttcaatggt | tttatgactt | cattttcggc | gttttcacc | 600 |
| aatcgcgaaa | attgttttag | caaagagaaa | atttccagtt | ccgcatgtta | tcgtattgtt | 660 |
| gacgataatg | caaagattca | cttcgacaac | attcgcatct | acaagaatat | tgctaacaaa | 720 |
| tttgactacg | aaattgagat | gatcgaaaaa | atcgaggagg | cggccggggg | ggcagatatc | 780 |
| cgtaatattt | tttcgtataa | tttcgatcat | tttgccttca | atcatttcgt | ttcgcaggat | 840 |
| gatatctctt | tttacaatta | tgttgttggg | ggtatcaata | agttcatgaa | tctttactgc | 900 |
| caagcgacaa | aagagaagct | gtcaccgtat | aaactccgcc | atttacacaa | gcaaattctt | 960 |
| tgtatcgaag | aatcactcta | cgacgtcccg | gcaaaattta | attgcgacga | ggacgtttat | 1020 |
| gccgccgtta | acgatttctt | aaataacgtc | cgtacgaagt | ccgttattga | gcgtctgcag | 1080 |
| atgttgggta | aaaacgctga | ttcatacgac | cttgacaaga | tctacatttc | gaagaagcat | 1140 |
| tttactaata | tcagtcagac | tctctatcgt | gattttagtg | tgatcaatac | cgccctgacg | 1200 |
| atgtcttaca | tcgacactct | ccctggcaag | gggaaaacga | aggaaaagaa | agccgcatcg | 1260 |
| atggcaaaga | atacgaatt | aatttcatta | ggcgagatcg | acaagctcgt | ggataaatac | 1320 |
| aacctctgcc | cggacaaagc | tgccagcacc | cgctctctca | tccgctcaat | ctcggacatt | 1380 |
| gtggccgatt | acaaggctaa | tccttgacg | atgaacagtg | ggatcccact | ggcagagaat | 1440 |
| gagacagaaa | tcgccgtact | gaaggaagct | atcgaaccat | tcatggatat | cttccgttgg | 1500 |
| tgtgctaaat | tcaaaacgga | tgagccggta | gacaaagata | cggactttta | caccgaactt | 1560 |
| gaggatatca | atgacgagat | tcatagtatt | gtcagtctgt | ataatcgtac | tcggaattat | 1620 |
| gtcacgaaga | aaccttacaa | caccgataaa | ttcggtttgt | acttcggtac | ctcctcattc | 1680 |
| gcgtccggtt | ggtcggaatc | gaaagagttt | actaacaacg | ccattttact | cgccaaggat | 1740 |
| gacaagtttt | atttaggcgt | gtttaatgcg | aaaaacaagc | cagctaagtc | aatcattaaa | 1800 |
| ggtcatgata | ccatccaaga | cggggactat | aagaagatg | tatattcgtt | attgactggc | 1860 |
| ccaaacaaga | tgcttccaca | tatgttcatt | tcttcatcga | aagcagttcc | tgtgtatggg | 1920 |
| ctgaccgacg | aattgttatc | cgattataag | aaaggtcgcc | atctgaaaac | atcgaaaaat | 1980 |
| ttcgacattg | attactgtca | caaattgatc | gattatttca | agcattgctt | ggcattatat | 2040 |
| actgactggg | actgctttaa | ctttaagttt | tctgacaccg | aatcgtataa | cgacattggt | 2100 |
| gagttctaca | aggaagtagc | agaacagggg | tattatatga | actggactta | tatcgggtct | 2160 |
| gatgatattg | attcactcca | ggagaacggg | caacttatc | tgttccagat | ttacaacaaa | 2220 |
| gatttcagcg | aaaaaagttt | cggtaagcca | tcgaaacaca | cagccattct | ccggtcatta | 2280 |
| ttcagcgacg | aaaatgttgc | ggacccggtt | atcaaactgt | gtggcggtac | ggaggtattc | 2340 |
| ttccggccaa | aaagtatcaa | aacccctgtt | gttcataaaa | aagggagtat | ccttgtatcc | 2400 |
| aaaacgtata | acgctcagga | aatggacgag | aatggtaaca | ttatcactgt | ccgtaagtgt | 2460 |
| gtgcctgacg | acgtatatat | ggagctttac | gggtattata | ataattctgg | tacaccgtta | 2520 |
| tctgccgaag | ctctgaagta | caaggacatt | gtagatcatc | gcacagcccc | atacgacatc | 2580 |
| atcaaagatc | gccgctacac | ggaggacggt | tttttcatta | atatgcctgt | cagcttaaat | 2640 |
| tacaaagccg | agaaccgccg | tgtaaatgta | aatgagatgc | ccttaaaata | tattgctcaa | 2700 |
| acgaaggaca | cttacattat | tgggatcgat | cggggtgaac | gtaatttact | ctatgtttca | 2760 |
| gttatcgata | cagacggcaa | tatcgtagag | caaaaatcgc | tgaacatcat | caacaacgtc | 2820 |
| gattaccaag | ccaaacttaa | gcaagttgaa | atcatgcgga | agttggcacg | tcaaaactgg | 2880 |
| aaacagggg | tgaaaattgc | ggatttaaaa | aagggtatc | tctcccaagc | agtacacgag | 2940 |
| gttgccgaac | ttgtgatcaa | atataacggc | attgtagtaa | tggaagacct | taactcccgc | 3000 |
| ttcaaggaaa | aacgctctaa | aattgaacgt | ggcgtctatc | agcagttcga | gacatcactc | 3060 |
| atcaagacct | tgaattatct | gacatttaaa | gaccggaaac | cacttgaggc | tggcgggatc | 3120 |
| gccaatggct | atcaattaac | atacattcct | gagtcactta | aaatgtgagg | tagccagtgc | 3180 |
| ggttgcatcc | tgtacgtccc | agccgcgtat | acatccaaaa | ttgatccaac | tacaggcttc | 3240 |
| gttacgctct | tcaattcaa | ggatattagc | agcgagaaag | caaaaacaga | ttttattggt | 3300 |
| cgctttgact | gtattcgcta | cgacgcagag | aaagacctct | ttgcttttga | gtttgactac | 3360 |
| gacaattttg | aaacgtacga | gacttgcgca | cgcactaagt | ggtgtgctta | cacctatggc | 3420 |
| acccgcgtca | agaagacgtt | tcggaaccgg | aaatttgtta | gtgaggtcat | tatcgatatt | 3480 |
| acggaagaga | tcaagaagac | ccttgctgct | acggacatca | attggatcga | ctcgcatgac | 3540 |
| atcaagcaag | aaatcattga | ttatgccctt | tcctcgcaca | ttttcgaaat | gttcaaactt | 3600 |
| acggtgcaaa | tgcgtaattc | gctttgtgag | tccaaagatc | gtgaatacga | taaatttgtc | 3660 |
| tctccgatcc | ttaatgccag | cggtaagttc | tttgataccg | atgcagcaga | caagtccttg | 3720 |
| cctattgagg | ccgatgcaaa | tgaatgcgtat | ggattgtca | tgaaaggcct | ctataacgtg | 3780 |
| ttgcaagtta | gaacaactg | ggctgaggt | gagaagttca | aattcagtcg | tctgtccaac | 3840 |
| gaagactggt | ttaactttat | gcagaaacgc | ggcgcgccaa | aaaggccggc | ggccacgaaa | 3900 |
| aaggccggcc | aggcaaaaaa | gaaaaaggct | agcggcagcg | cgccggatc | cccaaagaag | 3960 |
| aaaaggaagg | ttgaagaccc | caagaaaaag | aggaaggtgt | gataa | | 4005 |

| SEQ ID NO: 78 | moltype = DNA length = 4005 |
|---|---|
| FEATURE | Location/Qualifiers |
| misc_feature | 1..4005 |
| | note = Description of Artificial Sequence: Synthetic polynucleotide |
| source | 1..4005 |
| | mol_type = other DNA |
| | organism = synthetic construct |

SEQUENCE: 78

```
atgggccacc atcatcatca tcatagcagc ggcctggtgc cgcgcggcag cggtaccatg    60
atttatcgcg agaactttaa gcggaagaaa gagaagattg aaatgaacac cggtttcaat   120
gatttcacaa atttgagttc agtcaccaaa acgctctgta accgtcttat tcctacagaa   180
attaccgcta agtacattaa ggagcacggt gtaatcgaag cggatcagga gcggaacatg   240
atgtcgcaag aacttaagaa catccttaat gacttttacc gcagcttcct taatgagaac   300
cttgttaagg tacacgagct cgacttcaaa ccattgttta cggaaatgaa gaagtatctc   360
gagacaaagg acaacaaaga ggctcttgaa aaagcccagg acgatatgcg taaggcaatt   420
catgacattt tcgagtctga tgatcggtat aaaaaaatgt ttaaagctga atcaccgcg    480
tcaatcctcc cagagttcat tttacacaac ggcgcttatt cagccgagga gaaagaggaa   540
aaaatgcagg tagtaaaaat gtttaatggt tttatgacta gttttttccgc gttcttcaca   600
aatcgggaaa attgtttcag caaagagaag atttcgagca gcgcgtgcta ccggattgtt   660
gatgacaatg ccaaaatcca tttcgacaac atccgcattt ataagaatat tgctaacaaa   720
tttgattatg agatcgaaat gatcgaaaag attgaagaag ccgccggtgg tgctgatatt   780
cgtaatattt tttcatacaa cttcgatcac tttgctttta atcattttgt ctcgcaaagc   840
gatatctcgt tctataatta cgtagtaggc gggattaaca agttcatgaa tctgtactgt   900
caggcaacca aggagaaact gagcccgtat aagttcgcc atttgcacaa acagatctta   960
tgtatcgaag aatcactcta tgacgtgcca gcgaaattta attgtgatga agacgtgtat  1020
gccgctgtca acgacttctt gaataatgtt cggactaaaa gtgtaattga gcgcctccga  1080
atgttaggga agaatgccga cagctacgac ttggataaaa tctatatctc gaaaaagcat  1140
tttactaata tctcccaaac actttatcgc gacttttcag taatcaacac cgctctcacc  1200
atgtcgtaca ttgacacgtt gcctggcaag gcaaaacta aagagaagaa agctgcgtct  1260
atggcgaaga ataccgaatt aatctccttg ggggaaatcg ataagctggt agacaagtat  1320
aatctgtgtc cggataaggc agcaagcacc cggagcctta ttcggagtat ttcggatatc  1380
gtagcagatt acaaagctaa tccattaact atgaatagcg gtattccgtt ggcagaaaac  1440
gagacagaaa tcgccgtatt gaaggaggcc atcgagccat ttatggacat tttccgctgg  1500
tgcgcgaaat ttaaaacgga tgaacctgtc gataaggaca ctgatttcta tacggagctg  1560
gaggacatca atgacgaaat ccacagcatc gtgtctttat ataatcgtac acgcaattac  1620
gtaacaaaga agccgtataa cacagacaag tttgggttgt acttcggtac gtcatctttt  1680
gctagcggct ggagtgagag caaggaattc acaaataatg caattctcct tgctaaagac  1740
gacaagttct atttaggtgt tttcaacgcg aaaaataaac cggcgaagtc tatcatcaag  1800
ggccacgaca ccatccagga cggtgactac aagaagatgg tgtacagctt gcttactggg  1860
ccgaacaaaa tgctccctca catgtttatc tcaagctcga aagcagtccc ggtctatggt  1920
cttactgacg agttattatc ggattataaa aagggcgcc acttgaaaac atctaagaac  1980
tttgatattg attactgcca taaattaatt gactacttca aacactgtct cgccctctca  2040
actgactggg attgctttaa ttttaaattt tctgataccg agtcgtacaa tgacatcggc  2100
gaattctaca agaagtagc ggagcaaggg tactatatga attggactta cattgggtct  2160
gatgacattg attctttaca ggagaatggt cagctctacc tctttcaaat ctacaataaa  2220
gattttctg aaaaaagctt cgggaaacca agcaaacaca ccgcaattt acgtagtctc  2280
ttttcggatg aaaacgtggc agatccggtc atcaagcttt gtggtgggac ggaggttttt  2340
ttccgtccta gtcgatcaa gactccggtg gtgcataaaa aagggtcaat tctggtcagc  2400
aaaacgtaca acgctcagga aatggacgag aacggtaata ttatcacagt tcggaaatgc  2460
gttcctgtca acgtttatat ggagctctat gggtattata ataattctgg gacgcctctg  2520
tcggccgaag cgttaaagta taagacatt gtcgatcatc gtactgcccc gtatgatatt  2580
atcaaggacc gccggtatac cgaggacgaa ttttttatta acatgcctgt ctcattgaac  2640
tataaagctg aaaaccggcg cgtaaacgtc aatgagatgg cgttaaaata cattgcccag  2700
acgaaagata cttatatcat cggcatcgac cggggcgagc gtaatctget gtatgtgtcg  2760
gttattgata cggacggcaa catcgttgaa cagaagtcct tgaatatcat taataatgtg  2820
gactatcaag caaagctgaa acaagtagaa attatgcgga aacttgcgcg ccaaaactgg  2880
aagcaaggtc tcaagattgc agatctgaag aaagggtatc tgagtcaggc cgtccatgag  2940
gttgcggaac ttgtaatcaa gtacaatggc attgtggtga tggaagactt aaatagccgg  3000
tttaaggaga agcgttctaa aatcgagcgg ggtgtctatc agcaattcga gacttccctt  3060
atcaagaccc tcaactacct cacattcaag gaccgcaagc ctctggaggc cggcggtatt  3120
gcaaacgggt accaacttac ttacatccca gagtcattaa aaaatgtcgg ttcacagtgc  3180
gggtgcattc tgtatgtccc ggcagcgtac acgagtaaaa tcgatcctac cacgggcttc  3240
gtgacattgt ttaagttcaa agatatctct tcggaaaaag cgaaaacgga cttcatgcgg  3300
cggtttgact gtattcgtta cgacgcagaa aaagatctct tcgcgtttga attcgactat  3360
gataactttg acttacgaa acatgcgcg cgcaccaagt ggtgtgcgta acgtacggc  3420
acacgtgtca aaaaaacctt ccgtaaccgt aaattcgttt cggaggtgat tattgatatt  3480
accgaagaga tcaaaaaaac tctccagcgc acagcatta ttggatcga ctcacatgac  3540
attaaacaga gatcattga ctacgccctc agctcacaca tctttgagat gtttaagctt  3600
acggtgcaaa tgcgtaattc tctttgtgaa tcgaaagacc gggaatacga taagttcgta  3660
tctccgattc ttaatgcttc aggtaaattc ttcgacaccg atgcggcgga taaaagttta  3720
cctatcgagg cggacgctaa tgacgcctat gggatcgcca tgaaggtct ctacaacgtc  3780
ttacaggtca aaaataattg ggccgagggg agaaatttaa aattttctcg cttgtcgaat  3840
gaggactggt ttaacttcat gcagaaacgt ggcgcgcaa aaaggccggc ggccacgaaa  3900
aaggccggcc aggcaaaaaa gaaaaggct agccgcagcg gcgccggatc cccaaagaag  3960
aaaaggaagg ttgaagaccc caagaaaaag aggaaggtgt gataa                 4005
```

| SEQ ID NO: 79 | moltype = AA length = 1235 |
|---|---|
| FEATURE | Location/Qualifiers |

| | | | | |
|---|---|---|---|---|
| REGION | | 1..1235 | | |
| | | note = Description of Artificial Sequence: Synthetic | | |
| | | Cas12a/Cpf1 [Lachnospiraceae bacterium MC2017] sequence | | |
| source | | 1..1235 | | |
| | | mol_type = protein | | |
| | | organism = synthetic construct | | |

SEQUENCE: 79

```
MTMDYGNGQF ERRAPLTKTI TLRLKPIGET RETIREQKLL EQDAAFRKLV ETVTPIVDDC   60
IRKIADNALC HFGTEYDFSC LGNAISKNDS KAIKKETEKV EKLLAKVLTE NLPDGLRKVN  120
DINSAAFIQD TLTSFVQDDA DKRVLIQELK GKTVLMQRFL TTRITALTVW LPDRVFENFN  180
IFIENAEKMR ILLDSPLNEK IMKFDPDAEQ YASLEFYGQC LSQKDIDSYN LIISGIYADD  240
EVKNPGINEI VKEYNQQIRG DKDESPLPKL KKLHKQILMP VEKAFFVRVL SNDSDARSIL  300
EKILKDTEML PSKIIEAMKE ADAGDIAVYG SRLHELSHVI YGDHGKLSQI IYDKESKRIS  360
ELMETLSPKE RKESKKRLEG LEEHIRKSTY TFDELNRYAE KNVMAAYIAA VEESCAEIMR  420
KEKDLRTLLS KEDVKIRGNR HNTLIVKNYF NAWTVFRNLI RILRRKSEAE IDSDFYDVLD  480
DSVEVLSLTY KGENLCRSYI TKKIGSDLKP EIATYGSALR PNSRWWSPGE KFNVKFHTIV  540
RRDGRLYYFI LPKGAKPVEL EDMDGDIECL QMRKIPNPTI FLPKLVFKDP EAFFRDNPEA  600
DEFVFLSGMK APVTITRETY EAYRYKLYTV GKLRDGEVSE EEYKRALLQV LTAYKEFLEN  660
RMIYADLNFG FKDLEEYKDS SEFIKQVETH NTFMCWAKVS SSQLDDLVKS GNGLLFEIWS  720
ERLESYYKYG NEKVLRGYEG VLLSILKDEN LVSMRTLLNS RPMLVYRPKE SSKPMVVHRD  780
GSRVVDRFDK DGKYIPPEVH DELYRFFNNL LIKEKLGEKA RKILDNKKVK VKVLESERVK  840
WSKFYDEQFA VTFSVKKNAD CLDTTKDLNA EVMEQYSESN KLILIRNTTD ILYYLVLDKN  900
GKVLKQRSLN IINDGARDVD WKERFRQVTK DRNEGYNEWD YSRTSNDLKE VYLNYALKEI  960
AEAVIEYNAI LIIEKMSNAF KDKYSFLDDV TFKGFETKLL AKLSDLHFRG IKDGEPCSFT 1020
NPLQLCQNDS NKILQDGVIF MVPNSMTRSL DPDTGFIFAI NDHNIRTKKA KLNFLSKFDQ 1080
LKVSSEGCLI MKYSGDSLPT HNTDNRVWNC CCNHPITNYD RETKKVEFIE EPVEELSRVL 1140
EENGIETDTE LNKLNERENV PGKVVDAIYS LVLNYLRGTV SGVAGQRAVY YSPVTGKKYD 1200
ISFIQAMNLN RKCDYYRIGS KERGEWTDFV AQLIN                           1235
```

| | | | | |
|---|---|---|---|---|
| SEQ ID NO: 80 | | moltype = DNA  length = 3708 | | |
| FEATURE | | Location/Qualifiers | | |
| misc_feature | | 1..3708 | | |
| | | note = Description of Artificial Sequence: Synthetic | | |
| | | Cas12a/Cpf1 [Lachnospiraceae bacterium MC2017] sequence | | |
| source | | 1..3708 | | |
| | | mol_type = other DNA | | |
| | | organism = synthetic construct | | |

SEQUENCE: 80

```
atgactatgg attatgggaa tggtcagttt gagcggaggg cgccactgac taaaacaatc   60
acattaaggc taaaaccaat cggggagaca agagaaacca tacgtgagca gaagctcctt  120
gaacaggatg cagcttttag aaagctcgtc gaaacagtaa cccctatagt ggatgattgt  180
atccgaaaga ttgcagacaa tgcactttgt cattttggta cagaatatga ttttcgtgtc  240
ttaggtaatg cgatttcgaa aaatgattca aaagcgataa aaaaagaaac agaaaaagtt  300
gagaagttac tagcaaaagt attaaccgag aatcttccgg atggtcttcg taaagttaat  360
gacataaatt ctgcggcgtt tattcaggat acgttgacat cgtttgttca ggatgatgca  420
gataaaaggg ttcttattca ggagttgaaa ggcaaaactg tcctcatgca gagattttta  480
acgactcgga taactgctct tacggtatgg ctgccggatc gggttttga gaattttaac  540
attttcattg agaatgcaga gaaaatgcgt attttgttag attctccatt aaacgaaaag  600
atcatgaagt cgatcctga tgcagaacag tatgcatcgt tggagtttta tggacagtgc  660
ctttcacaaa aggatataga cagctacaat cttatcattt caggaattta tgctgacgat  720
gaggtaaaga atccgggaat taacgagata gttaaagagt ataatcagca gataagaggt  780
gacaaggacg agtcacccct acctaagctc aagaaactcc ataaacagat actcatgccg  840
gttgaaaagg cattctttgt cagggtactg agtaatgatt ctgacgcaag aagtattctt  900
gagaagatac tcaaggatac agaaatgctg ccatcgaaga ttatagaagc catgaaagag  960
gctgatgcgg gggatattgc agtatatgga agtcggttac gtagctttc tcatgttatt 1020
tacggggatc atggtaaact ctcgcagatt atttatgata agagtcaaa gcgtatctct 1080
gaattgatgg aaacttttaag tccaaaagag agaaaagaaa gcaaaagag actgaagg 1140
cttgaagagc atattcgtaa aagtacgtac acttttgacg aattaaatag atatgcagaa 1200
aagaatgtta tggctgcata tattgctgct gtggaagaat catgcgcgga aatcatgagg 1260
aaggaaaaga atcttcgcac actgcttagt aaagaagatg taaagataag aggaaatcga 1320
cacaatacac ttatcgtcaa gaactatttt aacgcatgga cggtatttag aaatttgatc 1380
cgaattttgc gccgaaagag cgaagcagag atagatagtg attttatga tgttttggat 1440
gattcagttg aagttctgag tcttacatac aaaggtgaga acctttgcag gagctatatt 1500
acaaaaaaaa tcggatcaga tttaaaaccg gagatagcga catatggatc ggcattgcgt 1560
cctaattccc ggtggtggag tcctggtgag aagtttaatg tcaagtttca cacgatcgtc 1620
agaagagacg gaagactgta ttattttatt ttaccaaagg gcgcgaagcc tgtagagttg 1680
gaggacatgg atggtgatat tgagtgtctt cagatgcgta agattccaaa tccgacaatc 1740
ttcctcccga aactcgtgtt taaggatcct gaagcttttt tccgggataa tccagaggcg 1800
gatgagtttg tttttttatc gggaatgaag gctccggtta ctatcacgcg agaaacatat 1860
gaggcatata gatataagct atacactgtt ggcaagttaa gggacggaga ggtaagcgaa 1920
gaggagtaca aagggctct tttacaagtg ttgaccgcat ataaggagtt cctagagaac 1980
aggatgatat atgcagatct taatttttga tttaaggatt tagaagaata taaagattca 2040
tccgaattca ttaaacaggt tgaaacgcat aatactttca tgtgttggc aaaggttagc 2100
agttctcagc ttgatgatct tgtgaaatca ggaaatggat tattatttga aatctgggag 2160
gagagactgg aaagttatta caaatacggc aatgaaaagg ttctgagagg atatgaggga 2220
gtgcttcttt caattctaaa agatgagaat cttgtcagca tgaggacact tctcaatagc 2280
cgcccaatgc ttgtttatag accgaaggaa tcgtcgaagc catggtcgt ccacagggac 2340
ggttcaagag ttgtagatcg cttcgataag gatgagaagt atatcccgcc tgaggttcac 2400
gatgaattgt accgcttttt taataattg ctcataaaag aaaaacttgg ggaaaaagca 2460
```

-continued

```
cggaagatct tagataataa aaaggtgaaa gttaaggttc ttgagtcaga gcgtgtgaaa    2520
tggtcgaagt tttacgatga gcaatttgct gttacgtttt cggttaagaa gaatgctgat    2580
tgcctagata ctactaaaga tctgaatgca gaggttatgg aacagtacag cgaaagtaac    2640
cgacttatcc tgatccggaa cacaacagat attcttatt atcttgtttt ggataaaaat    2700
gggaaagtat taaagcagag aagtcttaac attattaacg atggtgcaag agacgttgac    2760
tggaaggaga gatttaggca ggtaacaaag gatcggaatg aaggttataa cgaatgggac    2820
tattcacgaa cgtcaaatga cctgaaagag gtttatctaa actatgcctt gaaagagata    2880
gcggaagctg tcattgaata taatgcgatc cttatcatcg agaagatgag caatgctttc    2940
aaggataaat attcttttct tgatgacgtg acatttaagg ggttcgaaac aaagctgctt    3000
gcaaagttat ccgatctgca tttcagggga atcaaggatg gggagccgtg ttctttcaca    3060
aacccttttgc aactctgtca gaacgattca aacaagatat tgcaggatgg tgtcattttt    3120
atggttccga attcaatgac acgttctctt gatcctgata cgggattcat ttttgcaatc    3180
aacgatcaca acatccgtac caaaaaggca aagcttaatt tcctttctaa atttgatcag    3240
ctaaaggttt cgtctgaggg ttgtcttata atgaagtata gcggagattc tttaccaact    3300
cataatacag ataatagagt gtggaattgc tgctgcaatc atccaattac caactacgat    3360
cgtgaaacaa aaaagtcga atttatcgaa gagcctgtcg aagagctttc aagggtttta    3420
gaggagaatg gaattgagac ggatactgag ttaaataagc tgaatgaaag ggaaaatgtt    3480
ccgggaaaag tcgttgacgc aatttattcg cttgtactta attatcttcg aggaactgtt    3540
agtggagttg cgggacaacg tgcggtgtac tattcaccag taacaggaaa gaaatatgac    3600
atatctttta tacaggcgat gaatcttaat cgtaaatgtg attactacag aatcggctca    3660
aaggaaagag gcgaatggac tgatttgta gctcagttga ttaattga                 3708
```

SEQ ID NO: 81      moltype = AA   length = 1297
FEATURE            Location/Qualifiers
REGION             1..1297
                   note = Description of Artificial Sequence: Synthetic
                    polypeptide
source             1..1297
                   mol_type = protein
                   organism = synthetic construct
SEQUENCE: 81
MGHHHHHHSS GLVPRGSLQM TMDYGNGQFE RRAPLTKTIT LRLKPIGETR ETIREQKLLE    60
QDAAFRKLVE TVTPIVDDCI RKIADNALCH FGTEYDFSCL GNAISKNDSK AIKKETEKVE    120
KLLAKVLTEN LPDGLRKVND INSAAFIQDT LTSFVQDDAD KRVLIQELKG KTVLMQRFLT    180
TRITALTVWL PDRVFENFNI FIENAEKMRI LLDSPLNEKI MKFDPDAEQY ASLEFYGQCL    240
SQKDIDSYNL IISGIYADDE VKNPGINEIV KEYNQQIRGD KDESPLPKLK KLHKQILMPV    300
EKAFFVRVLS NDSDARSILE KILKDTEMLP SKIIEAMKEA DAGDIAVYGS RLHELSHVIY    360
GDHGKLSQII YDKESKRISE LMETLSPKER KESKKRLEGL KEHIRKSTYT FDELNRYAEK    420
NVMAAYIAAV EESCAEIMRK EKDLRTLLSK EDVKIRGNRH NTLIVKNYFN AWTVFRNLIR    480
ILRRKSEAEI DSDFYDVLDD SVEVLSLTYK GENLCRSYIT KKIGSDLKPE IATYGSALRP    540
NSRWWSPGEK FNVKFHTIVR RDGRLYYFIL PKGAKPVELE DMDGDIECLQ MRKIPNPTIF    600
LPKLVFKDPE AFFRDNPEAD EFVFLSGMKA PVTITRETYE AYRYKLYTVG KLRDGEVSEE    660
EYKRALLQVL TAYKEFLENR MIYADLNFGF KDLEEYKDSS EFIKQVETHN TFMCWAKVSS    720
SQLDDLVKSG NGLLFEIWSE RLESYYKYGN EKVLRGYEGV LLSILKDENL VSMRTLLNSR    780
PMLVYRPKES SKPMVVHRDG SRVVDRFDKD GKYIPPEVHD ELYRFFNNLL IKEKLGEKAR    840
KILDNKKVKV KVLESERVKW SKFYDEQFAV TFSVKKNADC LDTTKDLNAE VMEQYSESNR    900
LILIRNTTDI LYYLVLDKNG KVLKQRSLNI INDGARDVDW KERFRQVTKD RNEGYNEWDY    960
SRTSNDLKEV YLNYALKEIA EAVIEYNAIL IIEKMSNAFK DKYSFLDDVT FKGFETKLLA    1020
KLSDLHFRGI KDGEPCSFTN PLQLCQNDSN KILQDGVIFM VPNSMTRSLD PDTGFIFAIN    1080
DHNIRTKKAK LNFLSKFDQL KVSSEGCLIM KYSGDSLPTH NTDNRVWNCC CNHPITNYDR    1140
ETKKVEFIEE PVEELSRVLE ENGIETDTEL NKLNERENVP GKVVDAIYSL VLNYLRGTVS    1200
GVAGQRAVYY SPVTGKKYDI SFIQAMNLNR KCDYYRIGSK ERGEWTDFVA QLINAAAKRP    1260
AATKKAGQAK KKKASGSGAG SPKKKRKVED PKKKRKV                            1297

SEQ ID NO: 82      moltype = DNA   length = 3897
FEATURE            Location/Qualifiers
misc_feature       1..3897
                   note = Description of Artificial Sequence: Synthetic
                    polynucleotide
source             1..3897
                   mol_type = other DNA
                   organism = synthetic construct
SEQUENCE: 82
atgggccacc atcatcatca tcatagcagc ggcctggtgc cgcgcggcag cctgcagatg     60
acaatggatt acgtaacgg tcaatttgag cggcgcgccc cgctcaccaa gacaatcact    120
ctccggttga aaccgatcgg ggagacccgt gagacgattc gcgagcaaaa gctcctcgaa    180
caagatgctg cattccgtaa acttgttgaa actgtcaccc ctatcgtgga tgattgtatc    240
cggaaaattg ctgacaacgc tttgtgtcat tttggcacgg aatatgattt ctcctgttta    300
ggtaatgcca tctcaaaaa tgacagcaaa gcgattaaga aagagaccga aaaagtagag    360
aagctgttgg ccaaggttct gacagagaac ttgccagacg gtctgcgtaa agtcaacgat    420
attaacagcg cggcttttat tcaggacaca ctgacatcat tcgtccagga cgatgctgac    480
aaacgtgtgt taattcaaga gttaaagggc aaaactgtgt taatgcaacg ctttttaaca    540
acccggatta ctgcattgac tgtatggctc cctgaccggg tgtttgagaa cttcaacatt    600
tttatcgaaa atgctgaaaa gatgcgcatc ttgctgact caccattgaa tgaaaagatc    660
atgaagttcg atccggatgc tgaacaatac gcgagtttgg aattctatgg tcaatgtctg    720
tcccagaagg atattgattc gtacaacctc atcatttccg ggatttatgc cgatgatgag    780
gtcaagaacc caggtatcaa tgaaattgtt aaggaataca accagcaaat tcgcggggat    840
aaggatgagt caccttacc taaactgaaa aagttgcata acaaatttt gatgcctgtc    900
gagaaggcat ttttcgttcg ggtactcagt aatgattctg atgctcgttc aatttagaa    960
```

```
aaaatcttga aggatactga gatgttgcct tctaagatca ttgaagcgat gaaagaagca   1020
gacgctgggg acatcgctgt atatggttca cgtttgcacg agttaagcca cgtaatctat   1080
ggcgatcacg ggaagctctc tcagattatc tatgataagg agtcgaaacg catcagcgag   1140
ctcatggaaa cgttatcgcc taaggagcgc aaagagtcaa agaaacgctt ggagggtctg   1200
gaagaacata tccggaagtc gacatatacc ttcgacgagc ttaatcgtta tgccgaaaag   1260
aacgtcatgg ctgcctacat cgcggccgtg gaggaaagct gcgccgaaat tatgcgtaag   1320
gagaaggact tacgcacgct tcttagtaag gaggatgtca agattcgtgg taatcgccac   1380
aatacgttaa ttgttaagaa ctacttcaat gcctggactg tcttccggaa tttgatccgc   1440
atcctccggc ggaaatccga ggcggagatc gactcagatt tctatgacgt cttggatgat   1500
tctgtggaag ttttatcgct cacatataaa ggtgaaaact tgtgccggtc ttacattacg   1560
aagaagatcg ggagcgattt aaagccagag attgctacct atggttccgc cttgcgccct   1620
aattcacggt ggtggtcacc gggcgagaag tttaacgtaa agtccacac cattgttcgc   1680
cgggacggtc gcctttatta tttcatcttg ccgaaaggtg ccaaacctgt cgagctcgaa   1740
gatatggatg gggacatcga atgcttgcaa atgcgcaaga ttccgaatcc gactattttc   1800
cttccaaaat tggttttcaa ggacccagag gccttcttcc gcgacaatcc agaggcagat   1860
gaattcgttt ttcttcgg tatgaaagct ccagtgacca tcacgcgtga aacctatgag   1920
gcgtatcgct acaaacttta tacagttggg aagttacgcg acggtgaagt gagcgaagaa   1980
gagtataaac gtgcgttgtt acaagtattg accgcctata gggaattctt agagaatcgg   2040
atgatctacg cagatctgaa cttttggcttt aaagatctcg aagaatacaa agactcgtca   2100
gaatttatca aacaagtcga aactcacaac acttttatgt gctgggctaa ggtcagtagc   2160
agtcagctcg acgacctggt caagagcggg aacgggttac tgttcgaaat ctggtcagaa   2220
cggttggagt cctattacaa atatggcaac gagaaggtgc tgcgtgggta cgagggcgtt   2280
cttttgagta tccttaagga cgagaacctc gtgagcatgc ggacgctgct taattctcgg   2340
ccgatgctcg tctaccgccc taaagaatca tccaagccga tggtcgttca ccgggacggt   2400
agccgcgtcg ttgatcggtt cgataaggat gggaagtata ttccaccaga ggtacacgac   2460
gaattatacc ggttctttaa caatttgctt attaaggaaa actcggcga gaaagcgcg   2520
aaaattttag acaacaaaaa agtaaaagta aaggtattgg aatctgaacg tgtaaagtcg   2580
tcaaagtttt atgatgaaca gtttgcagtt acattctctg ttaaaaagaa tgcagactgt   2640
ctggatacca cgaaagatct caatgccgaa gttatggagc agtattccga atcgaaccgg   2700
cttatcctga tccgcaatac cactgacatc ttgtattatc ttgtacttga taagaatggg   2760
aaagtgctga aacaacgctc attgaatatc attaacgacg gggctcgcga cgttgattgg   2820
aaagagcgtt tcggcaggt aacaaaagat cgtaacgaag ctataacga gtgggactac   2880
tcgcggacta gcaacgattt gaagagggtc tatctgaatt atgcattgaa ggagattgcc   2940
gaagcggtaa tcgaatacaa cgcaattttg attattgaaa aaatgtcgaa tgccttcaag   3000
gataagtact ccttttttgga tgatgttacc ttcaaaggtt ttgaaccaa acttcttgcg   3060
aagctctctg acttgcattt ccggggtatt aaagatgggg agcatgttc gtttacgaac   3120
ccgttacagt tatgtcagaa cgactcaaac aaaattttac aagacggtgt gattttcatg   3180
gtccctaaca gcatgacgcg cagtctggac cctgacactg ggttcatttt tgcgattaac   3240
gatcacacca tccgcactaa gaaagcgaag ttaaacttcc ttagtaaatt cgatcagctg   3300
aaagtgtcat cagagggctg tttaatcatg aaatattcgg gggactccct tcctacacac   3360
aacacagata atcgtgtatg gaactgttgt tgcaatcacc cgatcaccaa ctacgaccgc   3420
gagacgaaaa aggtcgaatt catcgaggag ccagtggaag agttgagtcg cgtcttagaa   3480
gagaatggga ttgagacaga tacggaactt aacaagctta acgagcgcga gaatgttccg   3540
ggcaaggtag tagatgccat ctattctctg gtgttgaatt acttgcgtgg taccgtgtcc   3600
ggcgttgcag gccaacgggc ggtctactat tcccctgtga cggggaaaaa atatgatatt   3660
tcgtttatcc aagcaatgaa tctgaatcgt aagtgcgatt actaccggat cgggagcaaa   3720
gaacgcgcg aatgacgtta ttttgtagcg cagttaatta acgccgcc aaaaaggccg   3780
gcggccacga aaaaggccgg ccaggcaaaa aagaaaaagg ctagcggcag cggcgccgga   3840
tccccaaaga agaaaaggaa ggttgaagac cccaagaaaa agaggaaggt gtgataa      3897

SEQ ID NO: 83           moltype = DNA   length = 3897
FEATURE                 Location/Qualifiers
misc_feature            1..3897
                        note = Description of Artificial Sequence: Synthetic
                        polynucleotide
source                  1..3897
                        mol_type = other DNA
                        organism = synthetic construct
SEQUENCE: 83
atgggccacc atcatcatca tcatagcagc ggcctggtgc cgcgcggcag cggtaccatg    60
acgatggact acgggaacgg ccagttcgaa cgcgggcac ctttaacaaa actatcact   120
ttacgcctca agccgatcgg ggaaacgcgg gagactattc gtgagcaaaa actcctggaa   180
caggatgcag ccttccgcaa actcgtcgaa accgtgaccc caatcgtgga tgattgtatt   240
cggaaaatcg ctgataacgc cctttgtcac ttcggtactg aatatgattt tagttgtctt   300
ggtaatgcca tttccaagaa tgattccaag gctattaaaa aggaaacgga aaggtagaa   360
aagctgctcg cgaaggtctt aactgaaat ctccctgatg gcttcgtaa ggtcaatgac   420
attaattcgg cggcatttat tcaagatact ctgactagtt tcgtacagga tgatgccgat   480
aaacgggtct taattcagga attaaagggg aagacagtac tgatgcagcg gtttttaacc   540
acccgtatta ctgccctgac ggtttggctc ccggatgcg tgttcgaaaa cttcaatatt   600
tttatcgaga atgcggaaaa gatgcgtatc ttgctggact cgcctttaaa cgaaaaaatc   660
atgaagttcg atccagatgc tgagcagtac gcatcgttgg aatctctatgg tcaatgcctg   720
agtcaaaagg atattgattc ctacaatta atcatcctg gcatttacgc ggacgacgag   780
gttaaaaatc ctgggattaa cgaattgtc aaggagtaca atcaacagat ccgtggggac   840
aaagatgagt ccccgttgcc aaaacttaaa aagcttcata gcaaattcta catgccggtg   900
gaaaaagcct tttcgtgcg gtcctcagc aacgactcag atgccgcag tattctcgag   960
aagatcttaa aagacacaga atgttgccg tctaagatta tcgaagcgat gaaagaagct  1020
gatgctggtg acatcgccgt atatggctct cggctgcatg agctctctca cgttatctac  1080
ggggaccatg gcaagctctc gcagatcatt tatgataaag agagcaagcg catcagtgaa  1140
cttatggaaa ctttaagtcc aaaggagcgg aaagaatcta aaaaacggct cgaaggcctt  1200
```

```
gaagagcata tccgcaagtc cacttacacc tttgatgagt tgaaccgtta cgcagagaaa   1260
aatgtcatgg cggcgtatat cgcggcagtt gaggaatcgt gtgccgaaat tatgcggaag   1320
gagaaagatc tccgtacact cttgagtaag gaagacgtga aaatccgtgg taatcgtcat   1380
aacacactta ttgttaaaaa ctatttcaac gcctggacag tgttccgcaa cttaatccgc   1440
attttacgtc gcaaatcaga ggcggagatc gactcagact tctatgacgt gcttgatgat   1500
agcgttgaag tattgtccct gacctataag ggggagaatt tatgtcgctc gtacatcacg   1560
aaaaagattg gctccgattt aaaaccggag atcgcaacct atggcagcgc gctccggcca   1620
aactctcggt ggtggagccc aggcgaaaag tttaatgtaa aattccatac aattgtgcgg   1680
cgcgacggcc gtctctatta ctttatttta ccgaagggcg caaaacctgt agaattggag   1740
gacatggatg gcgacatcga gtgtctccaa atgcgcaaaa tcccgaatcc aacgatcttc   1800
ttaccaaaat tagtcttcaa agatcctgaa gccttcttcc gtgacaaccc agaggctgat   1860
gaattcgttt ttttgtcagg catgaaagcc ccggtcacta ttacacgtga aacttacgag   1920
gcctatcgct acaagttata tacagtgggc aaattacgtg atggtgaggt gtctgaagag   1980
gagtataaac gtgctctcct tcaggtctta actgcttata aagagttctt agagaaccgg   2040
atgatttatg cggacctcaa ttttggcttt aaagacttag aggaatataa agactcctca   2100
gagttcatta agcaagtcga aacccacaat acgtttatgt gctgggcgaa agtaagtagc   2160
agtcaattgg acgatctggt taagtcaggt aacggtctgc tttttgaaat ttggtctgaa   2220
cgtctggagt cctactacaa gtatgggaat gaaaaagttt tacgtgggta tgagggcgtt   2280
ctgctctcga ttctcaagga tgagaatctc gtatctatgc gcactttgct gaactcacgt   2340
ccgatgctcg tctatcgccc gaaagaaagt tccaagccga tggttgtaca ccgtgatggg   2400
tctcgggtgg tggatcggtt cgataaggat gggaagtaca tcccgcctga ggtccatgat   2460
gagctctacc gtttctttaa taatcttctc atcaaggaga aacttggcga aaaggcccgt   2520
aaaatcttag ataacaaaaa agtcaaggtc aaggtgttgg agtccgagcg tgtcaaatgg   2580
tctaagttct atgacgaaca gttcgctgta acttttttcgg tcaaaaaaaa tgccgactgt   2640
cttgacacta cgaaggattt gaacgccgag gtaatgaaac aatactccga aagtaatcgt   2700
ctcattctca tccggaacac aactgatatc tctattacc tggttcttga caaaaatgat   2760
aaggttctga agcagcggag cttgaacatt attaacgacg gtgcgcgtga tgtcgattga   2820
aaagagcgtt tccgtcaagt gaccaaagac cggaacgaag ggtacaatga atgggactat   2880
agtcgtacta gcaacgacct gaaggaggta tacttgaatt acgcgctgaa ggaaatcgcg   2940
gaggctgtaa ttgagtataa cgcgatcctc attattgaga aaatgtccaa tgcctttaag   3000
gacaaatatt ctttcttaga cgatgtaact ttcaaggggt tcgaaactaa gctcttagcc   3060
aagctgagcg atctccactt tcggggcatt aaggatggcg aaccatgctc ttttaccaat   3120
ccgctccagt tatgccagaa tgattctaat aaaattctgc aagacggggt gattttcatg   3180
gtgcctaaca gtatgacccg ttcattggat ccggatactg gttttatttt cgcaatcaat   3240
gatcataata tccgcactaa aaaagcaaag ttgaactttc tctccaaatt cgaccaactg   3300
aaggtctcat ctgaagggtg tttaatcatg aagtacagcg gggatagcct cccgaccat    3360
aacaccgata accgggtttg gaactgttgt tgcaatcacc ctattactaa ttacgaccgt   3420
gagacaaaga aagtcgagtt tatcgaagag cctgtagagg agttgtctcg cgtgcttgag   3480
gagaatggga tcgaaacaga caccgaactc aacaaattga acgaacggga aaatgtgccg   3540
gggaaagttg tagatgcaat ctactctctt gttttgaact acttacgtgg gaccgtgtcc   3600
ggggttgccg gcaacgggc cgtctattat tcgccggtga cagggaagaa gtatgacatc   3660
agtttcatcc aggccatgaa tttaaatcgg aaatgcgatt attatcggat cgggagcaaa   3720
gaacgggtg aatggacgga tttcgtggca caacttatta acgggcgcgcc aaaaaggccg    3780
gcggccacga aaaaggccgg ccaggcaaaa aagaaaaagg ctagcggcag cggcgccgga   3840
tccccaaaga agaaaaggaa ggttgaagac cccaagaaaa agaggaaggt gtgataa       3897
```

| | |
|---|---|
| SEQ ID NO: 84 | moltype = DNA   length = 3897 |
| FEATURE | Location/Qualifiers |
| misc_feature | 1..3897 |
| | note = Description of Artificial Sequence: Synthetic polynucleotide |
| source | 1..3897 |
| | mol_type = other DNA |
| | organism = synthetic construct |

SEQUENCE: 84
```
atgggccacc atcatcatca tcatagcagc ggcctggtgc cgcgcggcag cggtaccatg     60
actatggact acgcaatgg ccagttcgaa cgtcgcgctc cgttaaccaa gaccattact    120
ctccggctga agccaatcgg tgagacacg gagaccattc gggaacagaa gttattggag    180
caagatgccg catttcgcaa actcgttgag actgtgacca ctattgtaga cgattgcatt    240
cggaagattg cagacaatgc gctgtgtcat tttggcactg aatatgattt tagttgcttg    300
ggtaacgcga ttagtaagaa tgattctaaa gcaatcaaaa aggagacaga aaaggtagaa    360
aaactgctcg ccaaagtttt gacggagaac ctccgacg ggctccggaa ggtaaatgat    420
atcaactctg cagcattcat ccaagacacc cttacgtctt tcgttcaaga tgacgctgac   480
aaacgggttc tcatccagga gttaaaaggg aaaactgtct taatgcagcg tttttctcact   540
actcgtatca ctgcgctgac tgtatggttg cctgaccggg tgtttgaaaa cttcaacatt   600
ttcattgaga acgcggaaaa gatgcgtatt ctgcttgatt cgccactcaa cgagaagatc   660
atgaagttcg acccggatgc tgaacagtat gcctctttag agttctatgg cagtgccttt   720
tcgcaaaaag atattgattc atacaactta attatctcgg gcatttacgc agacgatgag   780
gttaaaaacc cggggatcaa tgaaattgtt aaggaatata accagcagat ccgtggggat   840
aaagatgagt caccgttacc gaaattgaaa aagctgcaca agcaaatcct catgccagtc   900
gagaaagcct tcttcgtacg ggtccttagc aatgattcag atgcacgctc aatcctggaa   960
aaaattctga agacactga tgctgcca agtaaaatca ttgaagctat gaagaagcc     1020
gacgcaggtg atatcgccgt gtacggcagt cggcttcatg aattgtctca tgtgatctac   1080
ggcgatcatg gtaagcttc gcaaattatc tatgcaagg agtctaaggg gatttcggaa   1140
ctcatggaga ctttatctcc gaagaacgg aaggagtcga aaaaacggct ggagggtctt   1200
gaagaacaca ttcgcaaag tacgtacacg ttcgatgagt taaatcgtta tgcagaaaaa   1260
aacgtaatgg ccgcgtacat cgcggcagta gaggagtctt gcgcggaaat tatgcgtaaa   1320
gaaaaggact acggacgct cctctcgaag gaagatgtaa aaattcgtgg gaatcgccac   1380
aatacgctta ttgtaaaaaa ctactttaat gcgtggaccg tcttccgcaa tctgatccgg   1440
```

```
atccttcggc ggaagtcgga ggccgaaatc gatagcgatt tctacgacgt attagacgat  1500
tctgtggaag ttctcagctt gacctacaaa ggcgagaacc tgtgtcgttc ttatattact  1560
aaaaaaatcg ggtctgatct taaacctgag attgcaacgt atggctccgc attacgccca  1620
aactctcggt ggtggtcacc aggcgaaaaa tttaacgtga agtttcatac tattgtccgg  1680
cgcgacggtc gtctttacta tttatcctg ccgaaaggag cgaagcctgt cgagttagag  1740
gacatggatg gtgatatcga gtgtctgcaa atgcgcaaga ttccgaatcc gaccattttc  1800
ctccctaaac ttgtgtttaa ggacccggaa gctttttcc gggataaccc agaggcggat  1860
gagttcgttt tccttagcgg catgaaggca ccagttacga tcacacgtga aacgtatgaa  1920
gcataccgct acaaactgta tacagttggt aaattacgcg acggggaagt cagtgaggaa  1980
gaatacaaac gtgctttact ccaggtatta accgcgtata aggagttttt ggagaaccgg  2040
atgatctatg ccgatcttaa ttttgggttc aaggacttgg aagaatataa ggactcctct  2100
gaattcatca agcaggttga aacccataac acattcatgt gctgggccaa ggtaagttca  2160
agccagttgg atgacctggt aaaatccggt aacggtcttc tgtttgaaat ctggtcagag  2220
cggttggaaa gctattataa atatggcaac gagaaggttc ttcgtggcta cgagggcgtt  2280
ttactgtcga tcttgaaaga tgagaacctg gtaagtatgc gtaccctttt gaattcacgt  2340
cctatgcttg tgtaccggcc aaaggagagt agtaaaccta tggttgtcca ccgcgacggg  2400
tcacgtgtcg tagaccgctt cgacaaggac gggaaataca tcccgcctga agtgcatgac  2460
gagctgtatc gcttcttcaa caatctgtta atcaaagaga agctcggtga agggcgcgt  2520
aagatcttgg acaacaaaaa agtgaaagtc aaagtactgg aatcggagcg cgttaaatgg  2580
tccaagttct atgacgagca attgcgcgta acatttagcg ttaagaaaaa cgccgattgc  2640
ttggatacaa cgaaggatct taatgctgag gtgatggagc aatacagcga aagcaatcgc  2700
ttaatccta ttcggaatac tactgatatt ctttactacc ttgtattgga caaaaatggt  2760
aaggttctga acaacgttcc ctgaacatc attaacgatg gtgctcggga tgttgactga  2820
aaagaacgct tccgccaggt cacaaaagac cgcaacgagg gttataatga gtgggactat  2880
tctcgtacct ctaatgatct aaagaggtg tacttgaatt atgcgttaaa agaaatcgcc  2940
gaggctgtga ttgagtataa tgccatttta attatcgaaa aaatgtcaaa tgccttcaaa  3000
gataaataca gcttcctgga cgatgtcaca tttaaagggt tcgaaactaa actgcttgcg  3060
aagttatcgg atctccattt ccggggcatt aaagacgggg agccgtgtag ctttacgaac  3120
ccactccaat tatgtcagaa cgactcaaac aagattttac aagatggggt aatttttatg  3180
gttcctaata gtatgacccg tagcctcgac ccagatactg gtttcatttt cgctatcaac  3240
gaccacaaca tccgtacgaa aaaagcaaaa cttaacttcc tttcgaagtt cgatcagttg  3300
aaggtctcgt cggaaggttg cctgatcatg aagtattctg gggacagtct tccaacacac  3360
aacaccgata atcgggtatg gaactgctgc tgtaatcacc caatcacaaa ctacgatcgc  3420
gaaaccaaaa aggttgagtt tattgaagag ccagtggagg aattgtctcg cgtattagaa  3480
gagaacggga tcgaaactga taccgagctt aacaaactga acgagcggga gaacgtacct  3540
gggaaagtcg ttgacgcaat ctatagcttg gtcttaaatt atttgcgtgg cacagtctcc  3600
ggtgtagccg gccaacgcgc tgtatattac agcccagtga cggggaagaa gtacgatatt  3660
tcattcattc aagcgatgaa tcttaatcgc aagtgtgact attaccggat tgggtcgaaa  3720
gagcgggcg aatgaccga cttcgttgct caattaatca atggcgcgcc aaaaaggccg  3780
gcggccacga aaaaggccgg ccaggcaaaa aagaaaaagg ctagcggcag cggcgccgga  3840
tccccaaaga agaaaaggaa ggttgaagac cccaagaaaa agaggaaggt gtgataa     3897

SEQ ID NO: 85         moltype = DNA  length = 3897
FEATURE               Location/Qualifiers
misc_feature          1..3897
                      note = Description of Artificial Sequence: Synthetic
                      polynucleotide
source                1..3897
                      mol_type = other DNA
                      organism = synthetic construct
SEQUENCE: 85
atgggccacc atcatcatca tcatagcagc ggcctggtgc cgcgcggcag cggtaccatg  60
accatggact acggcaatgg gcaattcgaa cggcgggcac cgctcaccaa gactattaca  120
cttcgcttaa aacctatcgg cgaaacccgc gagacgattc gtgagcagaa actgctcgag  180
caggatgctg cattccggaa attggtggag acggtcactg ctatcgtgga cgattgcatc  240
cgcaagatcg ccgataatgc tctgtgtcac ttcgggaccg aatacgactt ttcatgcctg  300
ggtaacgcta tttccaaaaa tgattctaag gccatcaaga agaaactga gaaagtggag  360
aagctgcttg caaaggtcct cactgaaaat cttccggatg gcctgcgtaa ggtgaacgat  420
atcaactctg ctgcgtttat ccaagatacc ctgacatcct tcgtcagga cgatgcagat  480
aagcgggtat taatccagga gcttaaaggg aaaaactgtac tgatgcagcg tttcttaaca  540
acacggatca ccgctctgac ggtctggctc cctgatcgtg ttttgagaa ctttaatatc  600
tttatcgaga atgcggagaa gatgcgtatt ccccttgact ctccgcttaa tgagaagatc  660
atgaaatttg atccggacgc ggaacaatac gcgtctcttg aattctacgg gcagtgctta  720
tcgcaaaaag acattgactc ctacaattta atcattagtg gtattttatgc tgacgatgaa  780
gttaagaatc caggcattaa cgaaatcgtt aaagagtaca atcagcagat ccgtggcgat  840
aaggatgaaa gcccgcttcc gaattgaaa aaactgcata gcaaatcct catgccagta  900
gagaaagctt tcttgtccg tgttctgtca atgattctg atgcccgttc gatcttgaa  960
aaatcctta aggatacaga gatgctgcct agtaagatta ttgaagccat gaaagaggca  1020
gatgctggcg atatcgtgt ctatgctct cgtctccatg aactcagtca cgttatttac  1080
ggggaccatg gtaagctctc gcagatcatt tatgacaaag agtcaaaacg catttccgag  1140
ttgatggaga ctttgtcccc aaaggagcgg aaggagagca aaaagcgtct cgaggggttg  1200
gaggagcata ttcgtaagag tacgtatacg tttgatgagc ttaatcgcta tgcagaaaag  1260
aatgttatgg cggcgtatat cgccgctgtt gaggaatctt tgtctgagat catgcgcaag  1320
gaaaagagtt tacggacttt gctgtccaag gaagatgtaa aattcgcgg caatcgcaca  1380
aacacattaa tcgtcaagaa ctatttcaat gcatggacgg ttttttcgca acttattcgt  1440
attctccgtc gcaaatctga ggccgaaatc gactctgatt tttacgatgt cctcgacgat  1500
tcagttgaag ttctgtccct tacttacaaa ggcgaaaact tatgtcgcag ttatatcaca  1560
aaaaaaatcg gctccgatct gaaaccggaa attgccacat atggttccgc cctgcggccg  1620
aactcacggt ggtggtcgcc tggggaaaag ttcaatgtaa agttccacac tatcgtccgc  1680
```

```
cgggacggcc gtctctacta ttttatcctg cctaaaggtg caaaaccggt tgaactcgaa   1740
gatatggacg gtgatattga atgtttacaa atgcgtaaga tcccaaatcc aacgatcttc   1800
cttcctaaat tggtgttcaa ggatcctgag gccttctttc gcgacaatcc ggaggcggac   1860
gaatttgtat ttctgtcggg gatgaaagcg ccagtaacga tcactcgtga aacgtatgag   1920
gcctatcgct acaagttgta tacggtaggc aagcttcgc atggtgaggt atcagaaagg    1980
gagtataaac gtgcgttgtt gcaggtctta acggcttata aggaatttct ggagaatcgt   2040
atgatttacg ctgatctcaa cttttggtttc aaggatctgg aggagtataa agactcttcg   2100
gaattcatca acaagtggaa aactcacaat acgttcatgt gttgggccaa ggtgtcgtcg   2160
tcccagcttg acgacctggt caagtctggc aatggtttgt tgttcgaaat ctggtcggaa   2220
cgtcttgaaa gttactacaa gtatgcgaac gaaaaggtct tgcgtggtta cgaaggtgtc   2280
ttactcagca tcctgaagga cgaaaatctg gtatcgatgc gcacactctt gaattcacgc   2340
ccgatgttag tgtaccgtcc taaggagtca tctaaaccta tggtcgtcca ccgcgatggt   2400
agccgtgttg tagaccgctt cgacaaagac ggcaaatata ttccaccgga agtgcacgac   2460
gaactctatc gcttcttcaa taatttgttg atcaaagaaa aattggtga gaaggcccgt    2520
aagattctcg ataacaaaaa ggtaaaagtc aaagtcttgg agagtgaacg cgttaaatgg   2580
tcaaaatttt atgacgaaca gttcgctgta accttctccg ttaaaaagaa cgccgattgc   2640
ctcgacacga ctaaggatct caacgctgag gttatggaac agtactcgga atctaatcgt   2700
cttatcctga ttcgtaacac aaccgatatc ttatactacc ttgttttgga caagaatggt   2760
aaagttctga agcaacgtag tttaaacatc atcaatgatg gggcacggga cgttgattgg   2820
aaagagcgtt ttcgtcaggt cacgaaagat cgtaatgagg ggtataatga gtgggactac   2880
tcgcgtacga gtaacgatct caagaagtc tacttaaatt acgcgcttaa agagatcgcg    2940
gaggcggtta ttgagtaaa cgccatcctg atcattgaga aatgtcaaa tgcttttaaa     3000
gacaaataca gtttccttga tgacgtcacc tttaaaggtt ttgagaccaa attgcttgca   3060
aaattgagtg atcttcattt ccgggggatt aaggatggtg aaccatgtag tttcactaac   3120
ccgctgcaat tatgtcaaaa cgatagtaac aagatcctgc aagacggcgt gatcttcatg   3180
gtaccgaact ctatgacccg gtcgctccga cctgatactg gctttatttt cgctatcaat   3240
gatcacaaca ttcgcactaa aaaggccaaa ttaaactttt tgtccaagtt tgatcaatta   3300
aaggtctcca gcgaagggtg ccttatcatg aagtatagcg gtgacagtct ccctacgcac   3360
aataccgaca atcgggtatg gaattgctgc tgtaaccacc cgattactaa ctatgaccgt   3420
gagaccaaaa aagtcgaatt catcgaagaa ccagtcgagg aattgtctcg ggttttggaa   3480
gagaacggta ttgagaccga caccgaattg aacaaactta acgaacgcga aaacgtccct   3540
ggcaaggtag tggatgccat ctactccctc gtattaaatt acttacgggg tacagtctct   3600
ggtgtcgctg gccaacgcgc tgtctactat agtccggtaa cgggcaaaaa gtatgatatc   3660
tcgttcattc aggccatgaa tctgaatcgt aaatgcgaat attatcgtat tgggagcaag   3720
gaacgcgggg aatggactga cttcgtcgca caactgatca acggcgcgcc aaaaaggccg   3780
gcggccacga aaaaggccgg ccaggcaaaa aagaaaaagg ctagcggcag cggcgccgga   3840
tccccaaaga agaaaaggaa ggttgaagac cccaagaaaa agaggaaggt gtgataa      3897

SEQ ID NO: 86          moltype = DNA   length = 3897
FEATURE                Location/Qualifiers
misc_feature           1..3897
                       note = Description of Artificial Sequence: Synthetic
                       polynucleotide
source                 1..3897
                       mol_type = other DNA
                       organism = synthetic construct
SEQUENCE: 86
atgggccacc atcatcatca tcatagcagc ggcctggtgc cgcgcggcag cggtaccatg    60
accatggact acggcaatgg gcaattcgag cggcgcgccc cattgacgaa accattacc    120
ctccgtctca aaccaattgg cgaaactcgc gaaacaatcc gtgagcagaa acttctggag   180
caagacgctg ctttccggaa gttagtggaa acagtcacac cgatcgttga cgattcgatt   240
cgcaagatcg ctgacaatgc cctttgccac tttggtaccg agtatgattt ctcatgcctt   300
ggcaacgcca ttagcaaaaa tgactccaaa gcaatcaaga aagagaccga gaaagttgag   360
aaactgttag cgaaggttct caccgagaat cttcctgacg tcttcgtaa agtcaacgat    420
atcaacagcg ctgcctttcat ccaggatacg ttaacttctt tcgttcagga tgatgcagac  480
aagcgggtgt tgattcaaga actgaaaggc aagaccgttc tgatgcaacg cttcctcacc   540
actcgtatca cggctttgac cgtgtggctc ccggatcgcg tatttgagaa cttcaacatc   600
ttcatcgaga acgccgagaa aatgcgtatc ctgttagata tccgctgaa cgagaaaatt   660
atgaagtttg accctgacgc ggaacaatat gcctcgctgg aattctacgg gcagtgtttg   720
agccaaaagg atatcgactc ctacaacttg atcatcagtg gtattacgc tgatgacgag    780
gtcaagaacc caggtatcaa cgaaatcgtt aaagagtaca atcaacaaat tcgggggat    840
aaggatgaga gtccgctccc taagcttaaa agttgcata acaaatcct tatgccggtc     900
gaaaaagctt ttttcgtacg ggttttaagt aatgatagtg acgctcgctc aatttttagg   960
aaaatcttaa aggacaccga gatgttgcca tcaaaaatca taagccat gaaagaggcg     1020
gacgcaggcg atatcgcagt atatggctcc cgtttacacg aactctcgca cgttatctac   1080
ggcgaccacg gcaaactcag tcagattatc tacgacaagg aatcaaaacg gatttctgag   1140
ctgatgagga ctctttctcc taagagcgcg aaagaatcta agaaacgcct cgagggcttg   1200
gaagagcata ttcgcaagtc cacctatacg tttgagagc ttaaccgtta cgccgaaaag   1260
aacgtgatgg ccgcgtatat tgctgcggtc gaggaaagct gcgcagaaat catgcgtaag   1320
gagaaggatt tgcggactct cctctcgaag gaagatgtca aaatccgcgg taaccgccac   1380
aacacactga tcgtcaaaaa ctattttaac gcttggacag tttttcgcaa cctgatccgt   1440
atcttacgtc gtaaatctga agctgagatt gactcagatt tctatgacgt cttggacgat   1500
agcgttgaag tcctctcatt aacctataag ggcgaaaatc tttgtcgtag ttacattacc   1560
aagaagattg gtccgatttt gaagccgaaa attgcaacgt atggttctgc gctgcggcca   1620
aattcgcggt ggtggtctcc tggcgagaag tttaatgtaa gttccatac tattgtacgg   1680
cgtgatggcc ggctgtacta ctttattttt ccgaagggg caagccagt gaactcgaa     1740
gatatggacg gcgacattga atgtttacag atgcgtaaaa ttcctaaccc gacaattttc   1800
cttcaaagt tagtctttaa agatcctgaa gccttttcc gtgataaccc agaggcggac    1860
gaatttgtct tttatccgg catgaaggcc ccagtaacga ttacgcggga aacgtacgag    1920
```

```
gcttatcgtt ataagctcta cactgtaggt aaattacggg atggtgaggt atctgaagag  1980
gagtacaagc gtgcattact tcaggtttta acgcgtaca aggagtttct cgaaaaccgg  2040
atgatctacg ccgatcttaa ttttgggttc aaggacttgg aagagtataa agattctagc  2100
gagtttatta acaggtaga gacccataat acattcatgt gctgggccaa agtttcgtca  2160
agtcaattag acgacctcgt aaagtccggg aacggtctct tatttgaaat ttggtcggaa  2220
cgtcttgagt cttactataa gtatggcaat gagaaagtac tccggggcta tgagggtgtt  2280
ctgttaagta ttctcaaaga cgagaattta gtatctatgc ggactttact taactcccgc  2340
ccgatgcttg tttatcgtcc taaggagagc agtaagccta tggtggtaca ccgtgatggt  2400
tctcgggtgg ttgaccgttt tgacaaagat ggcaaatata ttccgccaga ggtacatgat  2460
gagctttacc gcttttttaa caatctcctc atcaaagaga aattaggcga gaaagctcgt  2520
aaaatcctcg acaacaaaaa ggttaaagtc aaagtcttgg agtccgagcg cgtgaaatgg  2580
tccaagtttt acgacgagca gttcgctgtg acctttagcg tcaagaagaa tgccgattgc  2640
ctcgatacca ccaaggatct gaacgcgag gtgatgaaac aatactccga gagcaaccgc  2700
ctcatcttaa ttcgtaacac tactgatatc tctactacc tggtcttaga caagaatggt  2760
aaggtcctga aacagcgtag cttaaacatc attaacgatg gggcccggga cgtcgactgg  2820
aaggagcgtt tccgccaggt taccaaggat cgcaacgaag gttacaatga gtgggattac  2880
tcacgcactt cgaacgactt aaaagaggta taccttaatt atgctcttaa ggaaattgct  2940
gaagcggtca tcgagtataa cgcaattctt atcatcgaaa agatgtctaa tgccttaaa  3000
gacaaatata gcttcttgga tgacgtcaca tttaagggct ttgagacaaa acttctcgcg  3060
aagcttagcg acctgcattt tcgggggatt aaggacggcg agccgtgttc attcaccaat  3120
ccgctgcaat tgtgtcagaa cgattcaaac aaaattctcc aggatgggt tatttttatg  3180
gtacctaata gtatgacacg tagcttggac cctgacactg gctttatctt cgctattaac  3240
gaccataaca tccgcacgaa gaaggctaaa ttaaacttcc tctctaaatt tgaccagtta  3300
aaggtctcct cagagggctg tttaatcatg aagtattccg gtgacagtct tccgacccac  3360
aatactgata accgtgtgtg gaactgttgt tgtaatcacc ctatcaccaa ctacgaccgg  3420
gagacgaaga aagttgaatt tattgacgaa ccagtagaag aattgctcg cgtattagag  3480
gagaacggga ttgaaactga cacagagctc aacaagctga atgagcggga gaacgttccg  3540
ggcaaagtag ttgatgctat ctatagtttg gtactcaatt atctgcgcgg tacagtgtcc  3600
ggtgtggccg gccagcgtgc agtgtattac tccccagtta cgggtaagaa gtatgacatt  3660
tctttattc aggctatgaa ccttaatcgg aaatgtgact actaccggat cgggagcaag  3720
gaacgggggg agtggacgga tttcgtcgcc cagctgatca acgacgcgcc aaaaaggccg  3780
gcggccacga aaaaggccgg ccaggcaaaa aagaaaaagg ctagcggcag cggcgccgga  3840
tccccaaaga agaaaaggaa ggttgaagac cccaagaaaa agaggaaggt gtgataa      3897
```

SEQ ID NO: 87   moltype = DNA   length = 3897
FEATURE     Location/Qualifiers
misc_feature    1..3897
        note = Description of Artificial Sequence: Synthetic
        polynucleotide
source      1..3897
        mol_type = other DNA
        organism = synthetic construct
SEQUENCE: 87

```
atgggccacc atcatcatca tcatagcagc ggcctggtgc cgcgcggcag cggtaccatg   60
acaatggact atgggaacgg ccagtttgag cgccgggcac ctctcactaa acaattact  120
ctgcgcttaa aaccaatcgg ggaaacacgg gaaacaattg tgagcaaaa actcctcgaa  180
caggatgctg cgtttcgtaa gctggtcgag accgtaacac ctatcgtaga cgattgtatt  240
cggaaaattg cagacaatgc tctgtgtcac ttcgggaccg aatatgattt ttcgtgcctg  300
gggaacgcaa tctccaaaaa cgattccaag gcgatcaaga aggaaacgga gaaagtcgag  360
aaattactgg ctaaagttct tacagagaac ctccagatg gttgcgcaa ggtgaacgat  420
attaacagtg cggcattcat ccaagacaca ctgcatctt ttgtccagga tcgcgctgat  480
aaacgcgttc tgattcaaga attgaaaggg aagactgtct tgatgcaacg ctttttgacg  540
actcgcatca cagcacttac agtgtggctt cctgaccgtg ttttcgaaaa ttttaacatc  600
tttatcgaaa atgcggaaaa aatgcgtatc ttgttggaca gtcctctgaa tgagaagatt  660
atgaaatttg atcctgacgc ggaacagtat gcctcactgg aatttacgcg gcaatgtctg  720
tcccaaaagg atattgattc gtacaatctt attatctctg ggatctacgc cgacgatgaa  780
gtgaagaacc cgggtatcaa tgaaattgta aagaataca atcagcagat ccgcggggat  840
aaggatgagt ctccgctccc gaaattaaaa agcttcaca agcaaatcct tatgccagta  900
gaaaaagcat ttttcgtccg ggtgttgtca aatgatagcg acgcccggag cattcttgag  960
aaaatcttaa aagatacgga gatgttacct tcgaaaatca tcgaagcaat gaaagaggca 1020
gacgctggcg acatcgcagt atacggcagc cggttacatg agctctcgca cgtgatttat 1080
ggggatcacg gtaagctcag tcagatcatc tatgacaaag aatcaaaacg gatctctgag 1140
ttaatggaaa cgctttcccc taaggaacgc aaagagagca aaaagcgttt ggagggcctg 1200
gaagagcata ttcggaagtc gacctacacc tttgacgaag tcaaccgtta tgccgagaa  1260
aacgtcatgc cagcatatat cgctgccgtt gaagaatcat cgccgagat tatgcgtaag 1320
gagaaggatc tgcgtacgct gttaagtaaa gaagacgtaa aaattcgtgg gaaccgtcat 1380
aatacgctca ttgtgaaaaa ctatttaat gcatggactg tctttcggaa tctcatccgc 1440
attctgcgtc gcaaatcgga agcagaaatc gatagtgatt tttacgatgt gctggatgac 1500
tccgtggaag ttctcagttt gacgtacaaa ggcgagaact tgtgccgctc ctacattaca 1560
aagaaaattg gctccgatct caagccgaaa atcgccactt atggttcggc tctgcgtcct 1620
aattcgcggt ggtggagtcc tggcgaaaaa tttaatgtaa aatttcacac cattgtccgg 1680
cgggacggcc ggtatactac tttatccctt ccgaagggcg ccaagccagt tgagttagaa 1740
gatatggacg gtgacattga atgcctgcaa atgcggaaaa tcccgaatcc tacatcttc  1800
ctgccaaaac tggtgttcaa agatccagag gccttttgc ggaggcggat 1860
gagttcgtgt ttctcagtgg tatgaaagcc ccagttacta tcacgcggga gacgtacgaa 1920
gcgtaccggt ataaactcta tacggtgggg aaattgcggg acggcaagt ttcagaaga  1980
gaatacaaac gcgcccttct tcaagtactt acggcatata aagagttctt ggagaaccgc 2040
atgatttacg ccgatctgaa cttcgggttt aaagacctgg aggagtacaa ggatagcagt 2100
gagttcatca acaagttga aactcacaat accttcatgt gctgggcgaa agtcagctcg 2160
```

```
agccagcttg acgatctcgt caaaagtggc aacgggttat tatttgaaat ctggtcagag    2220
cggttggagt cgtattacaa gtacggcaac gagaaagtgc ttcgcggtta cgaggggta    2280
ctcctgtcga tcctcaaaga cgagaatttg gtctccatgc gtactcttct gaactctcgt   2340
ccgatgctgt tctaccgtcc aaaggaatct agtaagccaa tggtagtcca tcgtgacggg   2400
tcacgcgtcg tagatcggtt tgacaaagat ggtaaatata ttcctcctga agtccacgat   2460
gagctgtatc gtttcttcaa taacctcctg atcaaggaga agttagggga aaaagcacgc   2520
aaaatcttag acaataaaaa agtgaaagtg aaggtcctcg agtcggagcg ggttaaatgg   2580
agtaagtttt atgacgagca gttcgcagta acgttcagcg tcaagaagaa cgccgattgt   2640
ctcgatacta ctaaggatct gaatgccgag gtgatgacaa agtacagtga gtcgaatcgt   2700
cttatttaaa ttcgtaacac gaccgacatc ctgtattatt tggtcttgga taagaacggc   2760
aaggtattaa agcaacgttc actcaacatt atcaatgatg gggctcgcga cgtggactgg   2820
aaggaacggt tccgtcaagt aactaaggat cgcaatgagg ggtacaacga gtgggactat   2880
tctcggacct cgaacgacct gaaagaggtt taccttaact acgcccctcaa agagattgcg   2940
gaggcggtaa ttgaatacaa cgcgatcctc attattgaga agatgagcaa cgcattaaa   3000
gacaagtata gtttcttgga cgacgttacc ttcaaaggct ttgagacgaa gctcctggcg   3060
aagcttagtg acctgcattt tcggggtatt aaggacgggg aaccatgtag cttcactaac   3120
cctctgcaac tctgtcagaa tgatagcaac aaaatttac aggatggtgt gattttttatg   3180
gtacctaata gcatgacgcg ttcccttgac ccagatacag gcttttatctt tgcaatcaat   3240
gatcataaca tccgcacgaa aaaggcgaaa cttaactttc tgtcaaaatt cgaccagctc   3300
aaagttagta gtgaggggtg cttgatcatg aaatatagtg gcgattccct gcctacacat   3360
aatacagaca accgggtctg gaactgctgc tgcaaccatc cgatcacaaa ctatgatcgc   3420
gaaacaaaga aggtcgaatt tatcgaggaa cctgtagagg aattatctcg ggtcttaagg   3480
gagaatggga tcgaaacaga caccgagttg aataagctta acgagcgtga aaatgtgcca   3540
ggcaaagtgg ttgatgccat ctattccctt gtgttgaact atttacgggg gacagtgtca   3600
ggtgtggcgt gtcagcgcgc tgtgtattac tctccagtca ccgggaagaa atatgacatt   3660
agcttcattc aagcgatgaa cctcaatcgc aagtgcgact attatcgcat tggtagtaaa   3720
gaacgtggcg agtggactga cttcgttgct cagttaatta atggcgcgcc aaaaaggccg   3780
gcggccacga aaaaggccgg ccaggcaaaa aagaaaaagg ctagcggcag cggcgccgga   3840
tccccaaaga agaaaaggaa ggttgaagac cccaagaaaa agaggaaggt gtgataa     3897

SEQ ID NO: 88        moltype = DNA   length = 3897
FEATURE              Location/Qualifiers
misc_feature         1..3897
                     note = Description of Artificial Sequence: Synthetic
                     polynucleotide
source               1..3897
                     mol_type = other DNA
                     organism = synthetic construct
SEQUENCE: 88
atgggccacc atcatcatca tcatagcagc ggcctggtgc cgcgcggcag cggtaccatg     60
accatggact acggcaacgg ccagttcgaa cggcgtgcac cgttgactaa aactatcaca    120
cttcggttga agccgatcgg tgagacgcgg gaaacgatcc gcgaacaaaa gctgctcgag    180
caagacgcgg catttcgcaa gcttgtggag acagttaccc cgattgtgga cgactgtatt    240
cgtaaaattg ctgataatgc gttatgtcac tttgggacag agtatgactt ctcctgcctg    300
gggaatgcta tctcaaagaa tgattccaaa gctatcaaga aagaaacgga gaaagttgaa    360
aaattgctgg ccaaagtgtt gacggagaac ctgcctgatg gtttacgcaa agttaatgat    420
atcaactccg cagcatttat tcaagatacc ctgacatcgt ttgtgcaaga tgatgccgac    480
aagcgcgttc tgattcagga acttaagggc aagacggtac tgatgcagcg tttcctcacc    540
acacggatca cagccttgac tgtgtggctt cctgatcgcg ttttcgagaa cttcaatatc    600
ttcattgaga atgcggagaa gatgcgcatc ctgctcgaca gcccgctcaa tgaaaagatc    660
atgaaattga acccagacgc ggagcagtat gcatcactgg agttttatgg ccaatgtctc    720
agtcaaaaag acatcgattc gtataatctg atcatttcag gtattaccgc ggacgacgaa    780
gtcaaaaacc ctggcattaa cgagatcgtc aaggaataca atcagcaaat tcgtggggat    840
aaagatgaat cgccttttac taagctcaag aaattacata acaaattctt catgccagta    900
gaaaaggcct ttttcgtgcg cgtactgagt aatgactccg atgctcgttc catccttgag    960
aaaattctga aagacaccga aatgctgccg agcaagatca ttgaggctat gaaagaggca   1020
gatgcgggtg atattgccgt ctacggctcg cgtttgcatg agttatcgca cgtgatctat   1080
ggggaccacg ggaaattgtc ccaaattatt tacgacaagg aatctaaacg gatctccgaa   1140
ttaatggaaa cacttttcccc aaaagagcgt aaagaaagca aaaacggtt ggagggctg   1200
gaggaacaca ttcgcaagag tacgtatacg ttcgacgagc tcaatcgtta tgcggagaag   1260
aacgttatgg ctgcttacat cgcagccgta gaggaatcat gtgcagaaat catgcgtaaa   1320
gaaaaagatc tgcgcacgct tttaagcaaa gaggatgtta aaattcgcgg caaccgtcac   1380
aatactctga ttgtcaaaaa ttatttttaac gcttggactg tatttcgtaa tcttatccgt   1440
atcctgcgtc gcaaatctga ggccgaaatt gatagcgact tctatgacgt gctggatgac   1500
agtgtagaag ttttatcact cacttataag ggcgaaaacc tttgccggag ctatatcacc   1560
aaaaagatcg ggagtgacct taagccagaa atcgcgacgt acggctcagc tctgcgtccg   1620
aacagccgct ggtggtcacc gggggagaaa ttcaatgtga aattccacac aattgtgcgt   1680
cgggacggcc ggttgtatta ctttatcctg ccgaagggtg caaaaccggt tgaactcgaa   1740
gacatgggta gtgacattga gtgcttgcag atgcgtaaaa tcccaaaccc tacgattttt   1800
cttccgaagt tagtgttcaa ggaccctgaa gccttcttcc gtgataaccc agaggcggac   1860
gaattcgtct tcctgtctgg gatgaaagcc cggtaacga ttacgcgtga acttatgag    1920
gcttatcgct ataagtttata cactgtaggt aaattgcgcg atggcgaagt tcggaagag    1980
gaatataaac gtgctttatt gcaggtgtta acagcttata aagagttcct cgagaaccgg   2040
atgatttatg ctgatcttaa cttcggtttt aaagacttgg aaggataca agacagctgg   2100
gaatttatta gcaagttgga aacccacaat acgttcatgt gttgggctaa ggttagtagc   2160
tcacagctgg acgatctggt caaatcgggc aacggcttac tctttgaaat ctggtcggag   2220
cggttagaaa gctattataa atacggcaat gagaaggttc tgcgcgggta tgagggcgtc   2280
ctcttatcca tttctcaaaga tgagaatttg tgtgtcaatgc ggaccttatt gaactctcgg   2340
cctatgttgg tttatcggcc taaagaatcc agcaagccta tggtagttca ccgggatggg   2400
```

```
tcacgtgttg tagaccggtt cgacaaggac ggtaaatata ttcctcctga agtccacgac  2460
gaactgtacc gttttttttaa taatcttctt atcaaagaaa agcttggtga aaggcccgt   2520
aaaattttag ataataagaa ggttaaggtg aaagttctgg agtctgagcg ggtaaagtgg   2580
tccaaattct acgatgaaca gttcgccgtt acattctcgg ttaagaaaaa tgcggattgt   2640
ttagacacga ctaaggattt gaacgctgaa gttatgagac agtactcaag gtctaatcga   2700
ttaattctga tccgcaacac cactgatatc ttatactacc ttgttctgga caagaatggg   2760
aaggttctca aacaacgctc tctcaacatc attaacgacg cgcgcgtga cgtagactgg    2820
aaagagcgtt ttcgtcaagt gaccaaagac cgcaacgagg gctataatga atgggactat   2880
tcacgcacat ctaatgacct taaggaggtg tatctgaatt acgcactgaa ggaaatcgag   2940
gaggcagtaa ttgagtacaa tgcaatcctt attatcgaaa aaatgagcaa cgcttttaag   3000
gacaagtatt catttctgga tgacgtcacg tttaaggggt ttgaaacgaa actcctggca   3060
aaaactgtcag acctgcattt ccgcggtatt aaagatggcg agccgtgcag tttcacaaac  3120
ccgttacaat tgtgtcagaa cgactcgaat aagattcttc aagtgggggt aattttcatg   3180
gtgccgaatt cgatgacccg gagcttggac cctgacacag gtttatctt tgcaattaac    3240
gatcataaca ttcggacaaa aaaggcaaag ttaaatttcc ttagtaaatt tgaccagctc    3300
aaagtaagtt cggaaggctg cttgattatg aagtattcag gggactcatt acctacgcat   3360
aacaccgata accgtgtttg gaattgctgc tgtaatcatc caatcacgaa ctacgatcgg   3420
gagacaaaaa aagtgaatt tattgaagaa ccagttgaag gtctccgcg tgtactcgag    3480
gaaaacggca ttgagaccga caccgaactg aataagctca atgaacgcga gaatgtccca   3540
gggaaggtag tcgacgccat ttactcatta gtacttaact atttacgggg tacggtctca   3600
ggcgttgctg gccagcgggc agtatattac tctccagtga ccgggaagaa atacgatatt   3660
tcatttattc aagccatgaa cttgaatcgt aaatgcgaact actatcggat cgggtctaag  3720
gagcgcggcg aatggacgga cttcgtcgca caacttatta tggcgcgcc aaaaaggccg    3780
gcggccacga aaaaggccgg ccaggcaaaa agaaaaagg ctagcggcag cggcgccgga    3840
tccccaaaga agaaaaggaa ggttgaagac cccaagaaaa agaggaaggt gtgataa     3897

SEQ ID NO: 89         moltype = DNA   length = 3897
FEATURE               Location/Qualifiers
misc_feature          1..3897
                      note = Description of Artificial Sequence: Synthetic
                      polynucleotide
source                1..3897
                      mol_type = other DNA
                      organism = synthetic construct
SEQUENCE: 89
atgggccacc atcatcatca tcatagcagc ggcctggtgc cgcgcggcag cggtaccatg   60
acaatggact atgggaatgg tcagtttgag cgtcgggccc cattgacaaa gacgatcacg  120
ctccgtttga aaccgatcgg tgaaacgcgc gagaccatcc gggagcaaaa attgttggaa  180
caagacgcag cgttccgtaa gttggttgag accgtgacgc caatcgttga tgactgcatt  240
cgtaaaatcg ctgataatgc cttgtgtcac ttcggcaccg agtacgattt cagttgtctc  300
ggtaatgcga tcagcaagaa cgattcgaaa gccatcaaaa aggagactga aaggtagag   360
aaattattgg ccaaagtact tactgagaat ttacctgatg gcctccgtaa agttaacgac  420
attaatagcg ctgccttcat tcaggataca ttaaccagtt tcgtccagga cgacgccgat  480
aagcgcgtgc ttattcagga gcttaaaggt aagacggtat tgatgcaacg tttccttacg  540
acacgtatca ccgcgttgac ggtgtggtta ccagatcgcg tcttcgagaa ttttaatatt  600
tttattgaaa acgccgaaaa aatgcgtatc ctcttggaca gcccacttaa cgaaaagatt  660
atgaaatttg accctgatgc gaacagtac gcatcgctgg agttctacgg tcaatgtctt   720
agccagaagg acatcgattc atacaatctt attatctctg gcatttacgc tgacgacgaa  780
gtaaagaacc ctggtattaa tgagattgta aaggagtata accagcaaat ccggggggac  840
aaagatgaat ctccactccc aaagctcaaa aagcttcata agcagattct catgccggtt  900
gagaaagcat ttttttgtgcg tgtcttgagt aatgattcaa atgctcgtag tatttttagg  960
aagattctta aggatactga gatgctccca tcaaaaatta ttgaggcgat gaaagaagcg  1020
gatgctgggg atattgcagt gtatgggtcc cggctccatg agttatctca tgtcatttac  1080
ggtgaccacg gtaagctgtc ccaaattatc tacgataagg aaagcaagcg tatctcagaa  1140
ttaatggaaa ccctctcgcc taaggagcgc aaggagtcca aaaagcggct tgaagggctt  1200
gaggaacaca ttcggaagtc cacttacact tttgacgagc ttaatcgtta tgctgagaaa  1260
aatgtgatgg ctgcgtacat cgcagcagtg gaggaatcct gtgccgaaat catgcgcaaa  1320
gagaaagatc tgcgcaccct gcttagcaaa gaagatgtta agatccgggg taatcgccat  1380
aacaccctta ttgtaaagaa ctacttcaat gcatgacaag tcttccgcaa tcttatccgg  1440
atcctccgtc gtaagtcaga ggccgaaatc gactcagact tctatgatgt gctccgatgat  1500
agcgtggaag tattcactat gacttacaag ggggagaatc tgtgtcgctc ttatatcaca  1560
aagaagatcg ggtctgacct caaaccagaa atcgccactt atgggagtgc cctccggcct  1620
aactcgcgtt ggtggtcccc aggggaaaag ttcaacgtga aatttcatac gattgtgcgg  1680
cgcgacgccg gtctttatta ttttattttg cctaaggggtg caaaacctgt ggaattggaa  1740
gatatggatg gtgatattga atgccttcag atgcggaaaa ttcctaaccc tacaatcttt  1800
ctcccaaagc ttgtgtttaa agatccggag gccttttttc gtgacaatcc tgaggccgac  1860
gaattcgtgt tcctgtcagg tatgaaagcc ctgtgacaa tcacccggga aacctatgaa  1920
gcgtatcgct ataaacttta caccgtcggc aagctgcgtg acggcgaggt ttcagaggaa  1980
gagtacaaac gggcttctgt gcaggtgctc acggcttaca agagttttt agagaaccgc  2040
atgatttatg ctgatctcaa cttcgggttt aaagatttgg aggaatataa ggatagtagc  2100
gagttcatca gcaagtggaa aacgcataac acgttcatgt gctgggcaaa ggttagtagc  2160
tctcagttgg acgatctggt taagtcaggc aatggcctgt tattcgaaat ttggtccgaa  2220
cgtctggagt catactacaa gtacggtaac gagaaagtat tacgtggcta tgaaggtgta  2280
ttactctcta tcttaaaaga cgaaaccttg tttttcgatgc acttttgtt aaatagccgg  2340
ccgatgcttg tgtatcgccc gaaggagagt agcaaaccta tggtagtcca ccgcgatggt  2400
tcacgggtgg tcgatcgttt cgacaaggat gggaagtaca ttcaccctga ggtccatgat  2460
gagctttatc gcttctttaa taacttgctg atcaaagaaa agcttggtga aaagcacgg   2520
aagatccttg acaacaaaaa agttaaagta aaggtgctcg agtccgagcg tgtaaagtgg  2580
agcaagtttt acgatgaaca atttgccgtg actttctccg ttaagaaaaa cgcagattgt  2640
```

```
cttgacacta cgaaagacct caatgctgag gtaatggagc agtactcaga atcgaatcgt   2700
ttaatcctta ttcgcaatac cacggatatt ctgtattatc ttgttctgga caagaatggt   2760
aaagtgttaa aacagcgcag cttgaacatc attaacgatg gggcccggga cgtcgattgg   2820
aaggagcgct tccggcaagt gactaaagac cgcaatgaag ggtataatga gtgggactat   2880
tcgcggactt cgaatgatct taaggaggtt tatttgaact atgctcttaa ggagatcgca   2940
gaggccgtga tcgagtataa cgcaatcctt attattgaga agatgtccaa cgcttttaag   3000
gacaaatact cctttctcga tgacgtaacc tttaaggggg ttgaaacaaa gctcttagcg   3060
aagttgtcag accttcactt tcggggcatt aaagacggtg agccttgcag ttttactaat   3120
ccactccaat tatgtcaaaa cgactctaat aaaattttac aggacggtgt tattttcatg   3180
gtgccaaact ctatgacgcg cagcttagac ccagataccg gttttatctt cgcaattaat   3240
gatcacaata tccgcacaaa gaaagcgaaa ctgaattttc tctcaaaatt cgatcagctg   3300
aaggtctcgt ccgaggggtg ccttatcatg aaatacagcg tgactctctc gcctactcat   3360
aacacagaca atcgggtttg gaattgttgc tgtaatcatc cgatcactaa ttacgatcgt   3420
gagactaaaa aagtggaatt tatcgaagaa cctgtggagg agctgtctcg tgtacttgaa   3480
gagaacggca ttgagactga cacagagctg aataagttaa atgagcgtga aaacgttcct   3540
ggcaaagttg ttgatgctat ctacagcttg gtattaaact acctccgggg caccgttagt   3600
ggtgttgctg ggcagcgtgc agtttattac agccctgtta ccggcaagaa atacgacatt   3660
tccttatcc aagcgatgaa cctcaaccgg aaatgcgatt attatcggat tggtagcaaa   3720
gaacgtggtg aatggaccga tttcgtcgcg cagttgatta atggcgcgcc aaaaaggccg   3780
gcggccacga aaaaggccgg ccaggcaaaa agaaaaagg ctagcggcag cggcgccgga   3840
tccccaaaga agaaaaggaa ggttgaagac cccaagaaaa agaggaaggt gtgataaa     3897

SEQ ID NO: 90          moltype = DNA  length = 3897
FEATURE                Location/Qualifiers
misc_feature           1..3897
                       note = Description of Artificial Sequence: Synthetic
                       polynucleotide
source                 1..3897
                       mol_type = other DNA
                       organism = synthetic construct
SEQUENCE: 90
atgggccacc atcatcatca tcatagcagc ggcctggtgc cgcgcggcag cggtaccatg     60
actatggact acgggaatgg ccaatttgaa cgtcgggccc cactgacgaa acaatcacg    120
ctccgcctga agcctattgg tgagacccgg gaaacgattc gtgagcagaa gttattagag    180
caagatgccg cgttccgtaa gctggtcgag actgtgaccc ctattgttga cgactgtatc    240
cggaaaattg cagataacgc actttgtcac ttcgggacgg aatacgattt ctcctgcttg    300
ggtaacgcga tcagcaagaa tgattcgaaa gcaattaaga aggagacgga gaaggtggag    360
aaactcttgg caaaggtact tacagagaac ttacctgatg gtttacgtaa agtaaatgat    420
atcaattctg cggcgttcat tcaagatacg ttaacctcct tcgttcaaga tgatgcagat    480
aaacgtgtct tgatccagga gctgaaaggt aaaaccgtgc tgatgcaacg cttttttaacg    540
actcggatta ctgccttgac cgtctggctt ccggaccgcg tgttcgaaaa cttttaatatt    600
ttcatcgaga atgccgaaaa gatgcgtatt ttacttgaca gtcctctgaa tgagaagatc    660
atgaaattcg atccggatgc ggaacagtac gcgtcacttg aattttacgg ccagtgcctg    720
agtcagaaag acattgatag ctacaatctc attatcagtg gtatttacgc tgacgacgaa    780
gttaagaatc caggcattaa tgagattgta aaggagtaca accagcaaat ccgcggggac    840
aaagacgagt ctccttttacc aaaactgaag aagctccaca gcaaatcct gatgccagta    900
gaaaaagcat tcttcgttcg ggtcttgtct aacgactccg acgcgcggag catcctcgag    960
aagatcttaa aagatacgga aatgcttcca agtaaaatta tcgaggcaat gaaagaggca   1020
gacgctgggg atatcgctgt atacgggagc cgtttgcacg agcttagtca tgtgattac    1080
ggcgatcacg ggaaattaag tcaaattatc tacgacaaag aaagtaaacg gatctccgaa   1140
ttgatggaaa ctctgagccc aaaggagcgt aaggagtcca aaaacgtct tgaaggcttg   1200
gaagaacaca ttcgtaagtc gacttataca ttcgatgaac tgaatcgtta tgcggagaaa   1260
aacgtcatgc tgcttacat tgctgcagta gaagagtcct cgctgaaat tatgcgtaaa   1320
gagaaggacc tgcggacgtt actctcaaag gaagacgtca agattcgggg caaccgccat   1380
aacacgtca ttgtcaagaa ttattttaat gcatgacga tgttccggaa tctcatccgt   1440
attttgcggc ggaaatctga agctgagatt gactcggatt tctacgatgt actggacgat   1500
agcgttgaag tattgtcgct tacgtataag ggtgaaaacc tctgccgcag ttatatcacc   1560
aagaaaattg gcagcgatct taagccgaaa attgctacgt acggttcagc gctgcgtccg   1620
aactcacgtt ggtggagtcc aggtgagaaa tttaatgtga aattcacac gattgtccgt   1680
cgtgatgggc gcttatacta tttcattctg ccgaaagggg caaaaccagt agagctcgag   1740
gacatgacgc gcgatatcga gtgtttacaa atgcggaaaa ttcctaaccc gacgatcttc   1800
ctgcctaaac tcgtgttcaa ggacccgaag catcttttcg ggataatcc ggaggcggac   1860
gagtttgttt tcttatcggg gatgaaggct ccagtcacaa tcactcggga gacgtacgaa   1920
gcgtatcggt acaaacttta cacggtaggt aaattacgcg acggggaggt ttccgaagag   1980
gaatacaagc gcgccctgct ccaggttta acggcttaca aggagttcct cgagaatcgt   2040
atgatttacg cggatcttaa ctttgggtta aagatctgg aagaatataa agacagtagc   2100
gaatttatta acaggtcga gacccataat acattcatgt gttgggcaaa agtatccagt   2160
agtcaattag atgatttggt caagtcaggg aacggctgt tgtttgagat ttggtccgag   2220
cgcttagagt cactactacaa gtacgggaat gaaaagtac tcgtgggta cgagggcgta   2280
cttctgtcga ttttaaagga cgaaaatctc gtctcgatgc gcaccctgtt aaactctcgt   2340
ccaatgcttg tttaccgccc gaaagagagt tcaaaaccaa tggtagtgca tcgtgatggc   2400
tcccgggttg tggaccggtt tgacaaggac ggcaaatata tcccacctga agtacacgat   2460
gagctctatc ggttctttaa catttgcttt atcaaggaaa aactcgggga gaaggcacgg   2520
aagttcttgg ataataagaa agtgaaagta aaagttcttg aaagtgaacg tgtcaagtgg   2580
agcaaattct acgacgaaca attcgctgtc acctttcgg tgaaaaaaaa tgccgactgt   2640
ctcgacacaa cgaaggacct gaatgctgag gttatgaac aatactcaga gtcgaatcgg   2700
ctgatcttga tccggaacac cacagacatt ctctattacc tcgtgttaga taaaaatggc   2760
aaagtcctca aacagcggag tttgaatatt attaatgatg gggcacgcga tgtggactgg   2820
aaagaacgct tccggcaggt gacgaaggat cggaacgaag gctacaatga gtgggactac   2880
```

```
tcgcggacga gtaatgacct gaaagaagta tatttgaact atgctctgaa agaaatcgct    2940
gaggcggtca ttgagtataa tgcgattttg attattgaaa agatgtctaa cgcttttaaa    3000
gataagtatt cattcttaga tgatgtgact ttcaagggtt tcgaaacgaa acttttagcg    3060
aagcttagcg acttacactt ccgggggcatt aaagatgggg aaccatgttc cttcactaat   3120
cctctgcaac tctgccaaaa cgactctaac aaaattttgc aggacggtgt aatcttatg    3180
gtcccaaaact caatgactcg gagcttggat ccagataccg gctttatctt tgccattaac   3240
gatcataata tccggaccaa aaaggctaaa cttaattttc tttctaagtt tgaccagctt    3300
aaggtctcgt cggaagggtg tctgattatg aaatattcgg gtgacagttt gccgacccat    3360
aacaccgata atcgtgtgtg gaattgttgt tgcaatcatc caattactaa ctacgaccgg    3420
gaaacaaaga aggtagaatt tattgaagaa ccggttgagg agttgtcccg tgtgctcgag    3480
gagaacggta tcgagaccga tactgaactg aataaattga atgaacgtga aaatgtgccg    3540
ggcaaggtgg ttgatgctat ttatagcttg gtgctcaatt accttcgtgg taccgtgtca    3600
ggcgttgctg gccaacgggc tgtatactac tcgccggtga ctgggaaaaa atatgatatc    3660
tccttatcc aagctatgaa tttgaatcgt aaatgcgatt attatcggat tgggagtaag    3720
gagcgtggtg aatggaccga cttcgtggct cagttgatca atgcgcgcc aaaaaggccg    3780
gcggccacga aaaggccgg ccaggcaaaa aagaaaaagg ctagcggcag cggcgccgga    3840
tccccaaaga agaaaaggaa ggttgaagac cccaagaaaa agaggaaggt gtgataaa     3897

SEQ ID NO: 91          moltype = DNA   length = 3897
FEATURE                Location/Qualifiers
misc_feature           1..3897
                       note = Description of Artificial Sequence: Synthetic
                        polynucleotide
source                 1..3897
                       mol_type = other DNA
                       organism = synthetic construct
SEQUENCE: 91
atgggccacc atcatcatca tcatagcagc ggcctggtgc cgcgcggcag cgtaccatg     60
acaatggact atgggaatgg gcagttcgag cgccgcgcgc cacttaccaa gaccatcact    120
ctccggctta aaccaattgg cgagacccgc gaaactattc gggagcaaaa actcttagag    180
caggacgcgg cctttcgtaa actcgttgag acagttacgc cgatcgtgga tgactgtatc    240
cgcaaaatcg cagataacgc tttgtgtcac ttcggcactg agtatgactt cagttgtctg    300
gggaatgcca ttagtaaaaa tgactcaaag gctatcaaga agaaacaga aaaggttgag    360
aaactgcttg ccaaggtcct cacggagaac ttacctgatg ggctccggaa ggttaatgat    420
attaatagtg cggcgtttat tcaagacacg ctcacaagct tcgtccaaga tgatgcagac    480
aaacgggtgc tgattcagga gctgaaaggt aaaactgttt tgatgcagcg tttcctgacg    540
acccgcatca ccgcgttaac tgtttggctg ccagaccggg ttttcgaaaa ctttaacatt    600
ttcattgaaa atgcggaaaa aatgcgcatt ctgctcgaca gtccattgaa tgaaagatc    660
atgaaattcg atccggatgc tgagcaatat gcatcgcatt aattttacgg gcaatgcctt    720
agccagaaag atattgactc ctataaattg atcatctctg gtatctacgc agatgacgaa    780
gttaaaaacc ctggtatcaa cgagattgtc aaagagtata accaacagat ccggggcgac    840
aaagatgaga gtccacttcc taagttgaag aaactccaca agcagatcct gatgccagtt    900
gagaaggcct ttttcgtgcg ggtcctttct aacgacgcg atgcccgctc tatcttggag    960
aaaattttaa aggacacaga aatgttacct agcaaaatta tcgaggcgat gaaggaggcg    1020
gatgcgggtg acatcgcggt ttatggcagt cgcttacatg agttgtctca tgtaatctac    1080
ggcgatcatg ggaaattatc ccagatcatt tatgacaagg aatctaagcg tatctcagaa    1140
ttgatggaaa ccctttctcc gaaggaacgc aaggaatcca agaaacggct tgagggtctg    1200
gaagaacata tccgtaaatc tacatatacg ttcgacgagt taaaccgcta cgcggaaaag    1260
aatgtgatgg cagcatacat tgccgcggtc gaggagtcgt gtgcggaaat tatgcgtaag    1320
gaaaaagacc tgcgcacatt attgagcaaa gaagacgtca agatccgcgg caaccgccac    1380
aacaccctta ttgtcaaaaa ctactttaat gcatggatcg ttttccgcaa ccttatccgg    1440
attctgcgtc gcaagagcga agcagaaatc gattctgatt tctatgacgt tctggatgac    1500
tcggtcgagg tcttgtcctt gacgtacaag ggtgaaaatt tatgccggtc ctacatcact    1560
aagaaaatcg gttcggattt gaagccggag atcgccacgt acggttccgc gctccggcct    1620
aactcacgtt ggtggtcccc aggtgagaaa tttaacgtta agtttcatac aattgttcgc    1680
cgtgacggcc ggctgtatta ctttattctc ccaaaaggcg cgaagcctgt cgaattagaa    1740
gacatggatg gggacattga atgtttacag atgcgcaaaa tcccgaatcc tactatttt    1800
cttcctaagc ttgtattcaa agatccggaa gcattcttcc gggacaaccc agaagctgac    1860
gaatttgtat tcctcagtgg gatgaaggcc ccggtaacaa ttactcggga aacctatgaa    1920
gcataccgtt ataagttata tacggtgggc aagctccggg acggggaggt atcagaagaa    1980
gaatacaagc gggcgctcct ccaggttctc acagcctaca aggaatttct tgagaaccgt    2040
atgatctacg cagacttgaa ttttggtttc aaggatctgg aggagtacaa agacagctcg    2100
gagtttatca aacaggtgga gactcataac acttttatgt gttgggccaa agtatcatca    2160
agtcaacttg atgatctcgt taaatcaggt aatggcctct tgttcgaaat ctggagcgag    2220
cgtttagagt cctattataa gtatggcaac gagaaagtac tgcggggcta tgaaggcgta    2280
ctcttatcca tcttaaaaga cgagaactta gtctcaatgc gcacgcttct caattcgcgt    2340
cctatgcttg tttaccggcc aaaggagtct tcaaaaccga tggtggtaca ccgggatggg    2400
tcacgcgttg tagaccgttt tgacaaggac ggtaagtata tcccgccaga ggtgcatgac    2460
gagctttatc gctttttaa caatcttta attaaggaga aactcgggga gaagcacgc    2520
aaaatcctgg acaataaaaa agtcaaagtc aaagtccttg agtcagaacg tgtgaaatgg    2580
tcaaagttct acgacgagca gttcgctgtt acattctctg taaaaaaaaa cgctgattgc    2640
ttagatacca ccaaagacct taatgccgaa gtgatggagc agtatagtga gtcgaaccgg    2700
cttattctca ttcgtaacac cacagatatc ttatactatc tggtactcga caagaacggc    2760
aaggtgttaa aacagcgttc actgaacatc attaatggga gtgcacgcga tggtgactgg    2820
aaagagcgtt tcccgcaggt tactaaggac cgtaatgagg gttacaacga gtgggactat    2880
tcccggacgt ctaacgacct caaggaagtc tatcttaatt atgctctcaa agagattgct    2940
gaggccgtca tcgaatacaa cgcaattctc atcattgaaa aaatgtctaa cgcttttcaa    3000
gataagtatt cattcctcga tgatgtcacc tttaaggggt tcgaaacgaa attattggct    3060
aaactgagtg aacctgcactt ccgtggcatt aaagatggcg aaccatgctc gttcaccaac    3120
```

-continued

```
cctttacaac tgtgccaaaa cgatagcaat aaaatcctcc aagacggtgt tattttcatg 3180
gtgccaaata gtatgacccg gtcgttggac ccggacacgg gttttatttt tgccatcaat 3240
gaccataaca tccgcaccaa gaaagccaaa cttaacttcc tgtctaaatt tgaccagctg 3300
aaggtctcaa gcgaaggttg tctgatcatg aaatattccg gtgattccct gccgacgcac 3360
aatactgaca atcgcgtgtg gaattgctgt tgcaaccatc caatcacgaa ttatgaccgt 3420
gagactaaaa aggtagagtt tattgaggag ccggtggaag aactctcgcg ggtcctggaa 3480
gaaaatggca tcgaaactga caccgaactt aataagctca acgaacggga aaacgttccg 3540
ggcaaagttg tggacgctat ttattccttg gtcttaaatt atttgcgcgg tactgtcagt 3600
ggcgtagcgg ccagcgtgc agtttactac agcccggtta ccggcaaaaa gtacgacatc 3660
tcgttcattc aagccatgaa tctgaaccgg aaatgtgatt actaccgcat tggctccaaa 3720
gaacgcggcg agtggactga ttttgttgcg cagctcatca atggcgcgcc aaaaaggccg 3780
gcggccacga aaaaggccgg ccaggcaaaa aagaaaaagg ctagcggcag cggcgccgga 3840
tccccaaaga agaaaaggaa ggttgaagac cccaagaaaa agaggaaggt gtgataa    3897
```

| SEQ ID NO: 92 | moltype = AA length = 1306 |
|---|---|
| FEATURE | Location/Qualifiers |
| REGION | 1..1306 |
| | note = Description of Artificial Sequence: Synthetic Cas12a/Cpf1 [Coprococcus sp. AF16-5] sequence |
| source | 1..1306 |
| | mol_type = protein |
| | organism = synthetic construct |

SEQUENCE: 92

```
MCYDLNNIKT KLREREVETM GNNMDNSFEP FIGGNSVSKT LRNELRVGSE YTGKHIKECA   60
IIAEDAVKAE NQYIVKEMMD DFYRDFINRK LDALQGINWE QLFDIMKKAK LDKSNKVSKE  120
LDKIQESTRK EIGKIFSSDP IYKDMLKADM ISKILPEYIV DKYGDAASRI EAVKVFYGFS  180
GYFIDFWASR KNVFSDKNIA SAIPHRIVNV NARIHLDNIT AFNRIAEIAG DEVAGIAEDA  240
CAYLQNMSLE DVFTGACYGE FICQKDIDRY NNICGVINQH MNQYCQNKKI SRSKFKMERL  300
HKQILCRSES GFEIPIGFQT DGEVIDAINS FSTILEEKDI LDRLRTLSQE VTGYDMERIY  360
VSSKAFESVS KYIDHKWDVI ASSMYNYFSG AVRGKDDKKD VKIQTEIKKI KSCSLLDLKK  420
LVDMYYKMDG MCLEHEATEY VAGITEILVD FNYKTFDMDD SVKMIQNEHM INEIKEYLDT  480
YMSIYHWAKD FMIDELVDRD MEFYSELDEI YYDLSDIVPL YNKVRNYVTQ KPYSQDKIKL  540
NFGSPTLANG WSKSKEFDNN VVVLLRDEKI YLAILNVGNK PSKDIMAGED RRRSDTDYKK  600
MNYYLLPGAS KTLPHVFISS NAWKKSHGIP DEIMYGYNQN KHLKSSPNFD LEFCRKLIDY  660
YKECIDSYPN YQIFNFKFAA TETYNDISEF YKDVERQGYK IEWSYISEDD INQMDRDGQI  720
YLFQIYNKDF APNSKGMQNL HTLYLKNIFS EENLSDVVIK LNGEAELFFR KSSIQHKRGH  780
KKGSVLVNKT YKTTEKTENG QGEIEVIESV PDQCYLELVK YWSEGGVGQL SEEASKYKDK  840
VSHYAATMDI VKDRRYTEDK FFIHMPITIN FKADNRNNVN EKVLKFIAEN DDLHVIGIDR  900
GERNLLYVSV IDSRGRIVEQ KSFNIVENYE SSKNVIRRHD YRGKLVNKEH YRNEARKSWK  960
EIGKIKEIKE GYLSQVIHEI SKLVLKYNAI IVMEDLNYGF KRGRFKVERQ VYQKFETMLI 1020
NKLAYLVDKS RAVDEPGGLL KGYQLTYVPD NLGELGSQCG IIFYVPAAYT SKIDPVTGFV 1080
DVFDFKAYSN AEARLDFINK LDCIRYDAPR NKFEIAFDYG NFRTHHTTLA KTSWTIFIHG 1140
DRIKKERGSY GWKDEIIDIE ARIRKLFEDT DIEYADGHNL IGDINELESP IQKKFVGELF 1200
DIIRFTVQLR NSKSEKYDGT EKEYDKIISP VMDEEGVFFT TDSYIRADGT ELPKDADANG 1260
AYCIALKGLY DVLAVKKYWK EGEKFDRKLL AITNYNWFDF IQNRRF                1306
```

| SEQ ID NO: 93 | moltype = DNA length = 3921 |
|---|---|
| FEATURE | Location/Qualifiers |
| misc_feature | 1..3921 |
| | note = Description of Artificial Sequence: Synthetic Cas12a/Cpf1 [Coprococcus sp. AF16-5] sequence |
| source | 1..3921 |
| | mol_type = other DNA |
| | organism = synthetic construct |

SEQUENCE: 93

```
atgtgttatg atctgaataa cataaaaaca aaattacgcg aaagagaggt agaaactatg   60
ggcaataata tggataattc gtttgaacca ttcattggag gcaactcagt gagtaaaact  120
ttacgcaatg aacttagagt ggggaagtgag tacaccggga acatataaa agagtgtgca  180
atcatcgcag aagatgcggt taaggccgaa aaccagtata tcgtaaagga aatgatggac  240
gattttttacc gtgatttcat taatcgaaag ctagatgctt tacagggat aaattggaa   300
caactattcg atataatgaa gaaggctaag ctggataaga gtaataaggt ttcaaaggaa  360
ttggataaaa tacaggagtc taccccgtaaa gaaataggga agatcttctc ttcggatcct  420
atatacaagg atatgctaaa agcagatatg ataagtaaga tcttgccaga gtatattgtt  480
gataaaatatg gcgatgcagc ttcgagaata gaggctgtaa aagtgtttta tggattttcg  540
ggttatttta ttgactttg ggccagtcga aaaaacgttt tttctgacaa gaatattgca  600
tcagcaattc ctcacaggat tgtcaatgtt aatgctagaa ttcacctaga taatataact  660
gcttttaatc gaattgcaga gattgctggt gatgaggtag caggaattgc ggaagatgct  720
tgtgcttact tgcagaatat gtcactggag gatgtattca caggacgttg ttacggtgag  780
tttatatgtc agaaggatat tgatcggtat aacaatatat gtggcgtcat caatcaacat  840
atgaatcaat attgccagaa caaaaagata tccagatcaa agttcaaaat ggagagatta  900
cacaaacaga ttttgtgtcg atcggaatcg gggttcgaga ttcccattgg gttccagact  960
gatgggagg ttatagatgc gatcaattct tttagtacta ttctcgaaga aaaagatatt 1020
ttggatcgac ttagaacttt aagtcaggag gttacggat atggatatgga agaaatatat 1080
gtatcctcta aagcttttga aagcgtatct aaatacatag ggatgtgtt                1140
gcctcaagca tgtataatta ttttctgcg gctgttcgcg gtaaagatga caaaaagat  1200
gtaaagatac aaacagaaat taaaaaaata aagagttgta gtttgcttga ttgaagaaa  1260
cttgtggata tgtattataa aatggatgga atgtgtcgtg gaacatgaggc aacagagta  1320
gttgcaggaa taacagagat attagttgat tttaattata aaacctttga catggatat  1380
tcagtcaaga tgattcagaa tgagcatatg ataaatgaga taaggagta tcttgatact 1440
```

```
tacatgagta tctatcattg ggccaaggat tttatgattg acgagttggt tgatagggat    1500
atggagttct attcggagct tgatgagata tattacgatt tgtctgatat agtacctctt    1560
tataataaag tgaggaatta cgttacgcag aaaccatata gtcaggataa gataaagcta    1620
aatttcggct ccccaactct tgcaaatgga tggtcaaagt cgaaggagtt tgacaacaat    1680
gtcgttgttc tcttgcgcga tgaaaagata tacctggcaa ttttaaatgt tggcaataaa    1740
ccttcaaaag atattatggc aggagaggac aggcgtagaa gtgatacaga ctataagaag    1800
atgaattatt atctgctccc aggagcaagt aagacattgc cacatgtatt cattagctca    1860
aacgcttgga aaaaatcgca tggaatacca gatgaaataa tgtatggata taaccagaat    1920
aaacatctaa aatcatcgcc gaattttgat ttggagtttc gtcgtaaact gattgactat    1980
tataaagaat gcattgattc ctatccaaac taccagatct ttaattttaa atttgctgct    2040
acagaaacct acaatgatat atcagagttt tacaaggatg tagagagaca gggatataag    2100
atagaatggt cctatattag cgaagatgat attaaccaga tggaccgaga tggtcagata    2160
tatttatttc agatatacaa taaagacttc gctccgaata gtaagggaat gcagaatcaa    2220
catacactat atctgaagaa tatattcagt gaggagaatc ttagtgacgt tgtcataaag    2280
ctcaatggtg aggccgaatt gttcttccga aagtcaagta ttcagcataa aagaggtcat    2340
aagaagggct cggtactagt caataaaaca tacaaacaa cagaaaaaac tgagaatggt    2400
caaggtgaaa ttgaggtcat tgagtctgtg cctgatcaat gttacctaga actggtaaag    2460
tattgtcag agggtggtgt aggacagctc tcggaggaag cctccaagta taaggataaa    2520
gtatcacact acgcagccac catggatata gttaaggatc gtagatatac agaagataag    2580
tttttattc atatgcctat tacgatcaat ttcaaagctg ataacaggaa taacgtgaat    2640
gaaaagtct taaattcat agcagaaaat gatgatcttc atgtgatcgg aatagatagg    2700
ggagagagaa atcttctata tgtatcggtg attgatagta gggcagaat tgttgagcag    2760
aagtcattta atatagttga aaattacgaa tcatctaaaa atgtaattag acgacatgat    2820
tacaggggta aacttgtgaa taaggaacac tatagaaatg aagctagaaa gagttggaag    2880
gaaataggaa agataaagga gataaagag ggttatctgt cacaggttat ccatgagata    2940
tcgaaactcg tattgaagta taatgctatc atagttatgg aggatctgaa ttatggatt    3000
aagagaggtc gtttcaaagt tgaacgtcag gtttaccaga agtttgagac tatgttgata    3060
aataagctgg catatttggt agataagagc cgtgcagtag atgaacctgg aggattgctc    3120
aagggttatc agctcactta tgtacctgat aatttgggcg agctgggcag ccagtgtggc    3180
attatctttt atgttccggc agcgtatacg tcaaagatag acccgtgac gggatttgtg    3240
gatgtgtttg acttcaaggc ttattccaat gctgaagcca gacttgactt tatcaataag    3300
cttgattgta taaggtatga tgcacctagg aataagtttg agattgcatt tgattatggc    3360
aattttagga ctcaccatac aactcttgca aaaactagct ggactatatt tattcatggt    3420
gatcgaatca aaaaggaacg tggactcttat ggctggaaaa acgagattat agatattgaa    3480
gcaagaataa ggaaactgtt tgaagatacg gatatagaat atgcagatgc tcataacttg    3540
attggggata tcaatgagtt ggaatctcct atacagaaaa agtttgtagg tgaattgttt    3600
gatattatta gatttacagt tcagcttcgt aacagtaagt ctgaaagta tgatgggaca    3660
gaaaaagagt atgatataaat catatctccg gttatggatg aagaaggagt attcttcact    3720
actgatagtt atattcgtgc agatggaaca gagcttccta gatgctga tgcaaatgga    3780
gcgtattgca ttgctctaaa gggcttatat gatgtgttgg cagtaaagaa atactcgaag    3840
gaaggcgaga agttcgatag gaaactgtta gcaatcacta attacaattg gtttgatttt    3900
atacagaaca gaaggttcta g                                             3921

SEQ ID NO: 94           moltype = AA  length = 1368
FEATURE                 Location/Qualifiers
REGION                  1..1368
                        note = Description of Artificial Sequence: Synthetic
                         polypeptide
source                  1..1368
                        mol_type = protein
                        organism = synthetic construct
SEQUENCE: 94
MGHHHHHHSS GLVPRGSGTM CYDLNNIKTK LREREVETMG NNMDNSFEPF IGGNSVSKTL     60
RNELRVGSEY TGKHIKECAI IAEDAVKAEN QYIVKEMMDD FYRDFINRKL DALQGINWEQ    120
LFDIMKKAKL DKSNKVSKEL DKIQESTRKE IGKIFSSDMI YKDMLKADMI SKILPEYIVD    180
KYGDAASRIE AVKVFYGFSG YFIDFWASRK NVFSDKNIAS AIPHRIVNVN ARIHLDNITA    240
FNRIAEIAGD EVAGIAEDAC AYLQNMSLED VFTGACYGEF ICQKDIDRYN NICGVINQHM    300
NQYCQNKKIS RSKFKMERLH KQILCRSESG FEIPIGFQTD GEVIDAINSF STILEEKDIL    360
DRLRTLSQEV TGYDMERIYV SSKAFESVSK YIDHKWDVIA SSMYNYFSGA VRGKDDKKDV    420
KIQTEIKKIK SCSLLDLKKL VDMYYKMDGM CLEHEATEYV AGITEILVDF NYKTFDMDDS    480
VKMIQNEHMI NEIKEYLDTY MSIYHWAKDF MIDELVDRDM EFYSELDEIY YDLSDIVPLY    540
NKVRNYVTQK PYSQDKIKLN FGSPTLANGW SKSKEFDNNV VVLLRDEKIY LAILNVGNKP    600
SKDIMAGEDR RRSDTDYKKM NYYLLPGASK TLPHVFISSN AWKKSHGIPD EIMYGYNQNK    660
HLKSSPNFDL EFCRKLIDYY KECIDSYPNY QIFNFKFAAT ETYNDISEFY KDVERQGYKI    720
EWSYISEDDI NQMDRDGQIY LFQIYNKDFA PNSKGMQNLH TLYLKNIFSE ENLSDVVIKL    780
NGEAELFFRK SSIQHKRGHK KGSVLVNKTY KTTEKTENGQ GEIEVIESVP DQCYLELVKY    840
WSEGGVGQLS EEASKYKDKV SHYAATMDIV KDRRYTEDKF FIHMPITINF KADNRNNVNE    900
KVLKFIAEND DLHVIGIDRG ERNLLYVSVI DSRGRIVEQK SFNIVENYES SKNVIRRHDY    960
RGKLVNKEHY RNEARKSWKE IGKIKEIKEG YLSQVIHEIS KLVLKYNAII VMEDLNYGFK   1020
RGRFKVERQV YQKFETMLIN KLAYLVDKSR AVDEPGGLLK GYQLTYVPDN LGELGSQCGI   1080
IFYVPAAYTS KIDPVTGFVD VFDFKAYSNA EARLDFINKL DCIRYDAPRN KFEIAFDYGN   1140
FRTHHTTLAK TSWTIFIHGD RIKKERGSYG WKDEIIDIEA RIRKLFEDTD IEYADGHNLI   1200
GDINELESPI QKKFVGELFD IIRFTVQLRN SKSEKYDGTE KEYDKIISPV MDEEGVFFTT   1260
DSYIRADGTE LPKDADANGA YCIALKGLYD VLAVKKYWKE GEKFDRKLLA ITNYNWFDFI   1320
QNRRFAAAKR PAATKKAGQA KKKKASGSGA GSPKKKRKVE DPKKKRKV                1368

SEQ ID NO: 95           moltype = DNA  length = 4110
FEATURE                 Location/Qualifiers
misc_feature            1..4110
``` note         = Description of Artificial Sequence: Synthetic
               polynucleotide
source       1..4110
             mol_type = other DNA
             organism = synthetic construct
SEQUENCE: 95

```
atgggccacc atcatcatca tcatagcagc ggcctggtgc cgcgcggcag cggtaccatg    60
tgctacgact taaacaacat caagacaaag ttacgtgaac gcgaagtcga aactatgggc   120
aataacatgg ataatagctt cgagcctttt attggcggta atagtgtctc taaaacactt   180
cggaatgatg tgcgtgtagg ttccgaatat actggtaaac acattaaaga gtgcgcgatc   240
attgcagagg acgccgtgaa ggcggagaac cagtacatcg taaaagagat gatgacgac    300
ttttaccgtg acttcattaa tcgcaaactt gacgccttgc agggtattaa ttgggagcag   360
cttttttgaca ttatgaagaa ggcgaaattg ataagtcga ataagtcag caaagagtta    420
gacaagattc aagagtctac gcggaaagaa atcgggaaaa tcttctcatc cgatccaatc   480
tataaagaca tgctcaaagc ggacatgatc agcaaaattc tgccagagta tattgtcgac   540
aaatacggtg atgcagcctc gcggatcgaa gctgtaaagg tgttttacgg ctttcgggt    600
tatttttatcg acttctgggc atcgcgcaag aacgtcttct cagataagaa catcgcgtcg   660
gccattccgc accggattgt caatgtgaac gtcggatcc atctggacaa catcacggcc    720
ttcaaccgta tcgcagaaat tgcagggat gaagtcgccg gcattgctga agatgcttgt   780
gcttacctgc agaatatgag cttagaggat gtattcacgg gggcctgcta cggtgagttc    840
atctgtcaga aggatattga tcgttacaat aacatttgcg gtgttatcaa ccagcacatg   900
aatcaatact gccaaaacaa aaagatctca cgctcaaaat ttaagatgga acgtctgcac   960
aaacagatct tatgtcgctc tgagagtgg tttgagatcc cgattgggtt tcaaaccgac   1020
ggggaggtaa tcgatgctat caactccttt tctacgattc ttgaagagaa agatatcttg   1080
gatcgtctgc gcactttgtc gcaggaggta acaggttatg acatggagcg tatctatgta   1140
agttccaagg cgtttgagtc tgtatcaaag tacatcgatc acaaatggga cgtaattgca   1200
tcttccatgt acaattactt ttctggggct gttcgtggga aggacgacaa gaaagatgtc   1260
aagattcaga cggaaattaa aaagattaag tcatgttcgt tattggacct caaaaagctg   1320
gtagatatgt attataaaat ggatgggatg tgtttagagc acgaagcgac ggagtacgtg   1380
gcaggtatta cggagatcct ggttgacttt aactataaga cctttcgacat ggatgattcc   1440
gttaagatga ttcaaaatga gcacatgatt aatgaaatta agaatatttt agataccttat   1500
atgtctatct atcattgggc gaaggacttt atgatcgatg agctcgtaga tcgcgacatg   1560
gaattctaca gtgagctcga tgaaatctat tatgatttgt ccgacatcgt accactgtat   1620
aataaagtcc gcaactacgt cacgcaaaaa ccgtattccc aggataaaat caagttaaac   1680
tttggcagcc caaccttagc aaacggttgg agcaagtcga aagaatttga taacaacgtt   1740
gtagtattgt tgcgtgacga aaagatttat ctggccatct taaatgtggg gaataaaccg   1800
tcaaaggata tcatggcggg cgaagaccgt cgtcgtccg atactgatta caagaaaatg   1860
aattactatc tgctccctgg ggcaagcaaa acctgccac acgttttat ctctttcaat   1920
gcatggaaga aatcccacgg tatccctgac gagattatgt acggctataa ccaaaataag   1980
catttaaaat cttcgccaaa cttcgactta gagttttgtc gcaagctgat cgattattac   2040
aaagaatgta ttgacagcta tcctaactat cagatcttca atttcaaatt cgccgctacg   2100
gaaacttaca acgatatttc ggagttctac aaagatgttg aacgtcaggg gtacaagatt   2160
gaatgtcgt acatttcga ggacgatatt aatcagatgg atcgtgacgg ccagatttat   2220
cttttttcaaa tctacaacaa ggattttgcc ccaaactcta agggcatgca gaatttttat   2280
acactctatt taaaaatat ttttttcagag gaaaacctct ctgatgtcgt cattaaactg   2340
aatggcgagg ctgagctctt cttccgcaag agctcgatcc aacataaacg cggtcataag   2400
aagggtagtg tgttggtaaa taagacctat aaaaccacag aaaaaactga aaatggtcaa   2460
ggcgaaattg aagtaatcga gagcgtgccg gaccagtgtt acctggagct tgttaagtac   2520
tggtcagagg tgggtgtagg tcagttgtca gaagaggctt ccaaatacaa agataaagtc   2580
agccactacg ctgcaacaat ggatattgtc aaggaccggc ggtacacgga ggataagttc   2640
tttattcaca tgccgattac gattaatttt aaagctgata accggaacaa tgtcaacgag   2700
aaagtgctga gtttattgc agaaaacgat gatctccacg ttattggtat tgaccgtggg   2760
gaacgtaatc tcctgtacgt ctcagtaatt gattcacgtg ggcgtattgt tgagcagaag   2820
tcgtttaata ttgttgagaa ttacgagagc agtaaaaatg tgatccgccg ccatgattat   2880
cgtgggaaat tagtaaataa agagcactat cgtaatgagg cacgtaaggc ctggaaagaa   2940
atcggcaaaa tcaaggagat caagaaggt tatctcagtc aagttatcca tgagattagt   3000
aagttggtat taaagtataa cgccatcatc gtgatggaag atcttaatta tggcttcaaa   3060
cgcgggcggt ttaaagtcga gcggcaggta taccagaagt tcgagaccat gcttattaac   3120
aaattagcct acttagtgga caaatcacgc gcggtagacg aacgggtgg gttattaaaa   3180
ggctaccagc tgacatacgt gccagataac ttgggtgaac tggggtccca gtgcgggatc   3240
attttttatg tgccagcagc atacacttcg aaaatcgatc ctgttacggg ctttgtagac   3300
gtgtttgatt ttaaggcata ctccaatgcc gaagcacgtt tagatttcat caataaactg   3360
gactgcatcc ggtatgacgc gccgcgtaac aagtttgaaa ttgcttttcga ctacggtaac   3420
ttccgactc atcatcaac ccttgcaaag actagctgga ctattttat tcacggcgac   3480
cgtattaaaa aggagcgcgg ttcttacggc tggaaggacg aaattatcga tatcgaggcc   3540
cgtattcgta agctgtttga agacacagac atcgaatacg ccgatggtca aatttgatc    3600
ggtgacatta acgagctcga gagtccaatt caaaagaaat tcgttggtga gctgttcgac   3660
attatccgtt tcactgtcca actgcgcaac agcaaaagtg agaaatatga cggcaccgaa   3720
aaggagtatg acaaaattat ttcgccggta atggacgagg aggggttttt ctttacaacc   3780
gacagttata tccgcgcaga tggtactgaa ttacctaaag atgctgatgc taacgggggc   3840
tattgtatcg cgctgaaggg tctttacgac gtgctcgcgg taaagaaata ttggaaggag   3900
ggggagaagt tcgatcggaa gttacttgcc atcaccaatt acaactggtt tgatttcatt   3960
cagatcgtc gcttcgcggc cgcaaaaagg ccggcgccca cgaaaaggc cggccaggca   4020
aaaaagaaaa aggctagcgg cagcggcgcc ggatccccaa agaagaaaag gaaggttgaa   4080
gaccccaaga aaaagaggaa ggtgtgataa                                    4110
```

SEQ ID NO: 96         moltype = DNA   length = 4110
FEATURE               Location/Qualifiers
misc_feature          1..4110

```
                        note = Description of Artificial Sequence: Synthetic
                        polynucleotide
source                  1..4110
                        mol_type = other DNA
                        organism = synthetic construct
SEQUENCE: 96
atgggccacc atcatcatca tcatagcagc ggcctggtgc cgcgcggcag cggtaccatg    60
tgttatgacc tcaacaatat taagacaaag cttcgggagc gtgaggtgga gacgatgggc   120
aataatatgg acaatagttt cgagccattt atcggcggca attccgtaag caaaacgctt   180
cgtaatgagc ttcgtgtggg tagtgagtat accgggaaac atatcaagga atgtgccatt   240
atcgccgaag acgcgtaaa ggccgagaat caatatattg ttaaggagat gatggatgat    300
ttttatcgcg attttatcaa ccggaagctt gacgcgctgc aaggcattaa ctgggagcaa   360
ttgttcgaca tcatgaagaa ggcgaagctc gataaatcaa ataaagtctc gaaagaattg   420
gataaaatcc aagagtccac gcgcaaagaa attggtaaga ttttcagctc ggacccaatc   480
tataaggata tgctcaaagc cgacatgatc tcaaaaatct tgcctgaata tattgtagac   540
aaatacgggg atgccgcttc ccgtattgaa gccgtaaagg tattttatgg cttctcaggc   600
tattttatcg acttttgggc aagccgtaag aacgtgttct cagataagaa catcgcatca   660
gcaatccctc atcgcattgt caacgttaat gctcgtattc acttggacaa cattacagcc   720
tttaaccgca ttgcagaaat tgctggtgac gaggtcgcgg catcgcaga agacgcctgc    780
gcctaccttc agaatatgtc actcgaggat gtctttactg gcgcatgcta tggggaattc   840
atctgtcaga aggacattga tcgctataac aatatttgcg gtgtgattaa ccagcatatg   900
aatcagtatt gccagaataa gaagatttct cgctctaaat ttaagatgga agcttgcac    960
aagcaaatcc tgtgtcgctc ggaaagcggc tttgaaatcc ctatcggttt tcagactgat  1020
ggtgaggtca tcgatgctat caactcattt agcacgatct tagaggagaa ggatattctc  1080
gatcgtcttc gcacccttag ccaagaggtg acgggctacg atatggaacg catctacgtg  1140
agtagtaaag cttttgagag tgtgtcaaaa tatattgacc acaaatggga cgttattgcc  1200
tcctcgatgt acaactactt ctccggtgct gttcgcggta aagatgacaa aaaggacgtt  1260
aagatccaaa ctgagattaa aaagattaag agttgtagtt tattggattt aaagaaatta  1320
gtagacatgt attacaaaat ggacggtatg tgtcttgaac atgaggctac tgaatatgtt  1380
gcaggcatca ctgaaatcct cgtagacttt aattacaaga cttttgatat ggacgatagt  1440
gtcaaaatga tccaaaacga acatatgatt aacgaaatca aggagtacct tgacacatac  1500
atgtcaattt atcattgggc gaaggacttc atgatcgatg agttagtgga ccgcgacatg  1560
gaattctact cggagctgga tgagatctat tatgatctta gcgacatcgt tcctctctac  1620
aataaagtcc gcaactacgt aacacagaag ccgtactgga aggataaaat caagcttaac  1680
tttggttcgc cgacgttggc gaatgggtgg tccaagagta aggaatttga caacaatgta  1740
gttgtgttgc tgcgcgatga aaagatctac cttgcaatcc ttaatgtagg caataagcca  1800
tccaaggata tcatggccgg tgaagatcgc cgccgcagtg atacggacta aaaaaaatg   1860
aattattatc ttctcccggg ggcatctaaa accctccctc acgtgttcat ttctagcaac  1920
gcttggaaga aatcccacgg catcccagat gagatctata caggaacaag tcagaacaag  1980
catcttaagt ccagcccaaa tttcgacctc gagttctgcc gcaaattaat cgactattac  2040
aaagaatgca ttgattcgta tccgaactac cagatcttca actttaaatt cgctgccacg  2100
gaaacttaca acgacatttc agaattctac aaggatgtgg agcgtcaggg gtacaaaatc  2160
gaatggtcat atatttcgga ggatgacatt aaccaaatgg accgtgacgg ccaaatctat  2220
ttgttttcaga tctacaataa agactttgcg ccgaattcta aaggcatgca aaacttgcat  2280
accttatatt taaaaaacat cttttagtgag gaaaatttga gcgacgtcgt aatcaaactg  2340
aacggcgaag cagagttatt ttttcgtaag tcctctattc agcataagcg cgggcacaag  2400
aaaggctcgg tgctggtgaa caaaacatac aaaacaaccg aaaaaacaga aaacgggcaa  2460
ggggagattg aagtgatcga gagcgtgcct gaccagtgct atcttgagct tgtgaaatac  2520
tggtcagaaa ggggtgtagg tcagcttagc gaggaagcgt cgaaatacaa ggacaaagtc  2580
tcgcactatg ctgcgacaat ggacattgtc aaggatcgcc gctatacaga agataaattt  2640
tttatccata tgccgattac aatcaattt aaggccgata accgtaacaa tgttaacgag  2700
aaagttctca aatttatcgc ggaaaatgac gaccttcatg taattggtat cgaccggggg  2760
gaacggaact tgctttacgt atccggtcatt gattcccgtg gtcggatcgt ggagcaaaaa  2820
agcttcaaca tcgttgagaa ctatgagagc agcaagaacg taatccgtcg tcacgattac  2880
cggggggaaac ttgtgaacaa agaacactac cgcaacgagg cacggaaatc atggaaggag  2940
atcgggaaga tcaaagaaat taagagggt tatttaagtc aggtcattca tgagatttct   3000
aagcttgttc ttaagtataa tgctattatt gtcatggagg acctgaatta tgggtttaag  3060
cgtggccgct ttaaggtcga acggcaggtt taccaaaagt ttgaaactat gcttatcaat  3120
aaattggcgt atcttgtcga caagagccgt gcggtcgacg agcgggtgg tcttctgaaa   3180
gggtatcaac tcacttacgt tcctgataat ctcggcgagt tgggttcgca atgtggtatt  3240
atcttttacg tcccggccgc ctatacatca aaaatcgacc ctgttactgg ttttgtagat  3300
gttttttgact tcaaggctta ctcgaacgct gaggcacgcc tggattttat caataagctg  3360
gattgtatcc gttatgatgc accgcgcaac aagtttgaaa ttgcattcga ctacgggaat  3420
ttccgcacgc atcatactac gttagcaaag acatcatgga ctattttat tcatgggat   3480
cgcattaaaa aagagcgcgg tagctatggc tggaaagacg aaattatcga tatcgaagcc  3540
cggattcgta aactgttcga agatacagat atcgagtatg ccgacggcca taatttgatt  3600
ggcgatatca atgagctcga atccccgatt cagaagaaat ttgtcggcga gctgtttgac  3660
atcattcgct ttactgtaca gctgcgcaat tccaaatcgg aaaaatacga tggcactgaa  3720
aaagagtatg acaaaatcat ttctcctgta atggacaagg aaggcgtgtt tttcactact  3780
gacagttata tccgtgcgga cggcaccgag cttccaaagg acgccgatgc taatggcgct  3840
tattgcattg ccctcaaggg gctctacgat gttttagcag taaagaaata ttggaaggaa  3900
ggtgaaaaat tcgaccggaa attacttgcc attacaaact acaattggtt cgattttatc  3960
cagaaccgcc gctttggcgc gccaaaaagg ccggcggcca cgaaaaggc cggccaggca  4020
aaaaagaaaa aggctagcgg cagcggcgcc ggatccccaa agaagaaaag gaaggttgaa  4080
gaccccaaga aaagaggaa ggtgtgataa                                   4110
SEQ ID NO: 97          moltype = DNA   length = 4110
FEATURE                Location/Qualifiers
misc_feature           1..4110
```

|  | note = Description of Artificial Sequence: Synthetic polynucleotide |
|---|---|
| source | 1..4110<br>mol_type = other DNA<br>organism = synthetic construct |

SEQUENCE: 97

```
atgggccacc atcatcatca tcatagcagc ggcctggtgc cgcgcggcag cggtaccatg   60
tgttatgatc tgaacaatat taagacaaag ctgcgggagc gtgaagtgga dacgatgggt  120
aataacatgg ataattcgtt tgaacctttt attggtggga attcagtctc taagactctc  180
cgtaacgaac tccgtgtcgg cagtgaatac acaggcaaac acatcaagga atgcgcaatt  240
atcgcggagg acgcagttaa agccgagaac caatacatcg taaaggagat gatggacgac  300
ttttaccggg atttttattaa tcgtaagctt gatgccttgc aggggattaa ctgggagcag  360
ttattcgaca tcatgaaaaa agcaaagctt gacaagagta acaaagtgtc gaaggaattg  420
gataagatcc aagaaagcac tcgtaaggaa attggtaaga tttttagttc agatcctatt  480
tacaaggaca tgttgaaagc ggacatgatc agcaagattt tacctgagta catcgtggat  540
aaatacggtg atgctgctag tcggattgag gcggtaaaag tgttttacgg cttctctggc  600
tatttttattg atttttgggc gtcacggaaa aatgtgtttt ccgacaaaaa tattgctagt  660
gctattccgc atcgtattgt caatgtgaat gctcggatct atcttgataa tattacggcc  720
ttcaatcgca ttgccgaaat cgccggtgat gaagtagcgg gcattgcgga agatgcatgt  780
gcataccttc agaatatgtc ccttgaggat gtcttcacag gtgcatgcta cggggagttt  840
atttgccaga aggacattga ccgctacaac aatatttgtg gcgtaatcaa ccaacacatg  900
aatcaatatt gtcaaaacaa aaaaattttcc cgtagcaatc ttaagatgga gcgcttacat  960
aagcagattc tttgccgcag cgagtccggg ttcgagattc cgattggttt tcagaccgat 1020
ggggaagtaa ttgatgcgat taactccttc tcgacgattt tagaagagaa ggatatcttg 1080
gaccgtctcc gtacattaag ccaagaggta accgggtacg atatggaacg tatctatgta 1140
tcgagtaagg cgttcgaaag tgtcagcaaa tacatcgatc acaagtggga cgttattgcc 1200
tcgagcatgt acaattattt ctcaggcgcg gttcggggca agatgataaa gaaagatgtt 1260
aaaattcaaa cagaaatcaa gaaaatcaag tcgtgctcct tattagatct caagaagctg 1320
gtagacatgt actacaaaat ggacggtatg tgtttggaac acgaggcaac cgagtacgta 1380
gctggtatta cggagattct tgttgacttt aactacaaga cattcgacat ggatgactca 1440
gtgaagatga tccagaacga gcacatgatc aacgagatta aggaatattt agacacctac 1500
atgagcattt atcactgggc aaaagatttt atgattgatg agctcgtaga ccgtgatatg 1560
gaattctact ccgaacttga cgagatctat tatgatctta cgacattgt cccgctttat 1620
aataaggtac gtaattacgt cacccagaaa ccatactccc aggacaaaat taaattgaac 1680
tttgggtcac ctaccttagc gaacggctgg agtaagtcta aggaattcga taataacgtt 1740
gtggttctcc tgcgggatga aaagatctat ctcgcgatcc tgaatgtcgg gaacaaacct 1800
tccaaggaca ttatggcagg tgaggaccgc cgccggtcag acactgacta caagaaaatg 1860
aattattatc ttctgccagg ggcctcaaag acattgccgc acgtctttat cagtagcaat 1920
gcatggaaga agagtcacgg catcccagac gagatcatgt atgggtataa ccagaataag 1980
cacctgaagt cgtcgccaaa ctttgatttg gaattctgtc gcaaattgat cgactattat 2040
aaagaatgta ttgactcata cccgaactat caaattttta attttaagtt cgccgccaca 2100
gagacataca atgatatttc ggagttctat aaggacgtcg agcgtcaagg ctacaaaatt 2160
gagtggagtt acatctccga ggatgacatc aaccagatgg accgtgatgg ccaaatctac 2220
ttatttcaga tttacaacaa ggattttgca ccaaattcaa aggggatgca gaacttacac 2280
actctgtacc tcaagaatat ttttttctgag gaaaatctct ctgacgtagt tatcaaactc 2340
aatggtgaag cggagttgtt tttccggaag agctctattc agcataaacg tgggcacaag 2400
aagggttctg tgttggtaaa caaaacctat aaaacgaccg agaagaccga acaggccag 2460
ggtgagattg aggtaatcga atcggttccg gatcaatgct atcttgagct tgtgaagtac 2520
tggtcggaag gggcgtcgg gcaactttcg gaggaggcaa gcaaatataa agacaaagtc 2580
tcacattacg ctgcaacaat ggatatcgta aagaccgcc gttacacgga agataagttt 2640
ttcattcata tgcctatcac cattaattcc aaagccgata atcggaataa tgtcaatgaa 2700
aaggtcctta gtttatcgc agaaaatgac gaccttcacg tcatcggtat cgaccgcggc 2760
gagcgtaacc tcctctacgt atcagtaatt gactcccgcg gcggattgt cgagcagaag 2820
agcttcaata tcgttgaaaa ctatgagtcg tctaagaatg tgattcggcg ccatgattac 2880
cggggaaac tggtcaacaa ggagcactat cggaatgagg cgcgcaagtc ttggaaagag 2940
atcggtaaaa tcaaggaaat taagaagggt tatttgagtc aagtaattca tgagattagt 3000
aagcttgtct tgaaatataa tgcgattatt gttatggagg acctcaacta tgggttcaaa 3060
cgtggtcgtt tcaaagtcga gcgccaggtc taccaaagt tcgagaccat gcttattaat 3120
aaattagcgt acttggtgga caagtcacgc gctgttgatg agcgggcgg cctcttgaag 3180
ggttatcaat tgacatacgt tcctgacaac cttggtgagt tgggttcaca gtgtggtatc 3240
atcttctatg taccagcggc gtacacatca aagattacc cagtcacagg tttcgtggac 3300
gtctttgatt ttaaagcata cagcaatgcg gaggcccgct tagacttcat taacaagctc 3360
gactgtatcc ggtacgacgc tcctcgtaac aaattcgaga ttgccttcga ctacggtaat 3420
tttcgcactc accatacgac cctggctaaa acttcctgga tcttctttat tcatgtgac 3480
cgtatcaaaa aggagcgcgg gagctatggg tggaaagatg agattatcga cattgaggcc 3540
cggatccgca agcttttcga agataccgat atcgaatatg ctgatggtca aaccttatc 3600
ggtgacatca acgaattgga gagtccgatt cagaaaaagt ttgtagggga cttttcgat 3660
atcattcggt ttaccgtcca gttacgcaac tccaaatcgg agaagtacga cggcaccgaa 3720
aaggaatatg acaagatcat ttcacctgtc atggacgagg agggcgtgtt tttcactact 3780
gatagctata ttcgtgcgga cggcacgaaa cttccaaagg atgccgacgc caacggcgca 3840
tattgcattg ccttgaaggg cctctatgac gtcctggcag ttaaaaagta ctggaaagag 3900
ggtgaaaagt tcgaccgcaa attattggcc atcaccaatt acaactggtt cgactttatc 3960
caaaatcggg gttttggcgc gccaaaaagg ccggcggcca cgaaaaggc cggccaggca 4020
aaaaagaaaa aggtagcgg cagcggcgcc ggatccccaa agaagaaaag gaaggttgaa 4080
gaccccaaga aaaagaggaa ggtgtgataa                                  4110
```

| SEQ ID NO: 98 | moltype = DNA  length = 4110 |
|---|---|
| FEATURE | Location/Qualifiers |
| misc_feature | 1..4110 | note = Description of Artificial Sequence: Synthetic
polynucleotide
source          1..4110
                mol_type = other DNA
                organism = synthetic construct
SEQUENCE: 98

```
atgggccacc atcatcatca tcatagcagc ggcctggtgc cgcgcggcag cggtaccatg    60
tgctacgatc tcaataacat caagacaaaa ctgcgggagc gtgaagtgga aacgatgggg   120
aacaatatgg ataactcatt cgagccattt attggtggca actccgttag caaaactctc   180
cgcaatgaac tgcgggtagg gtcggaatat acaggtaaac acatcaagga gtgtgcaatt   240
attgcggaag acgcggtcaa agctgagaac cagtacatcg tgaaagaaat gatggacgac   300
ttttatcgtg atttcatcaa ccgcaaactt gacgcgcttc aaggtattaa ctgggaacag   360
ttattcgata ttatgaagaa agctaagctg ataagagca caaagtatc taaggaattg   420
gacaaaatcc aggaatccac acggaaggaa atcgggaaaa ttttttcgag cgatccaatc   480
tataaggaca tgctcaaagc ggatatgatc tccaagatcc tcccggaata tattgtggat   540
aagtatggcg atgccgccag tcggattgag gctgttaagg ttttctatgg tttcagtggc   600
tacttcatcg acttctgggc gagtcgcaaa aatgtattta gcgacaaaaa tattgcctcg   660
gcaattcctc accggattgt gaatgtcaat gctcgcatcc acttagataa cattacagcc   720
tttaaccgta ttgctgagat tgcagggac gaggtggccg gcatcgccga agacgcttgc   780
gcttaccttc agaatatgag cttggaggac gtctttacgg gcgcgtgtta cggtgagttt   840
atttgtcaaa aagtatcga ccggtataat aacatctgcg gggtcatcaa tcagcacatg   900
aaccaatact gccaaaacaa gaaaatttca cgtagtaaat tcaagatgga gcggctccaa   960
aagcagatct tgtgtcggtc cgagagtggt ttcgagatcc ctattggctt ccagaccgac  1020
ggggaggtca ttgacgccat taattccttt tccacgatcc tggaagaaaa ggacatcctt  1080
gaccggcttg gacgctttc ccaagaggtc acggttacg atatggaacg gatctacgtg  1140
tctagtaaag ctttcgaatc agtatctaag tatattgacg ataaagtgga cgtaattgcg  1200
tcctccatgt acaattattt ctctgggca gtacgtggga aggatgataa gaaggatgtg  1260
aaaatccaaa ccgaaattaa gaagattaaa tcatgtagtc tcttggacct caaaaagctg  1320
gtcgatatgt actacaaaat ggatgggatg tgtctcgagc atgaggctac agagtacgtc  1380
gctgggatca ctgagattct ggtggatttc aactacaaga cctttgacat ggatgatagt  1440
gtgaaaatga ttcagaatga gcatatgatt aatgaaatta agaataccct tgataccta  1500
atgtcaattt atcactggc aaaggacttt atgatcgatg aactcgttga ccgcgatatg  1560
gaattctatt ccgaattaga tgagatctac tacgaccttt cggatattgt tcctctctat  1620
aataaagtcc ggaactatgt aacccaaaag ccttactcac aagacaaaat caaactcaat  1680
ttcggcagcc ctacgctcgc taatgggtgg tcgaagagta aggaattcga taacaacgtg  1740
gtcgtgctgc ttcgggatga aaaaatttat ttagcgattt tgaacgttgg caacaagccg  1800
agtaaggata ttatggctgg tgaagaccgg cggcgctcgg acactgacta taaaaaaatg  1860
aactactacc ttcttccggg ggcgtcaaag acactcccgc acgtattcat ctcctcgaac  1920
gcatggaaga agagccacgg gatccctgat gaaatcatgt atggttacaa tcagaataag  1980
catttgaaat ccagcccaaa ttttgacctc gagttttgtc gcaaacttat tgattactat  2040
aaagaatgca tcgatagcta tccaaactat caaatcttta acttcaaatt cgctgcaaca  2100
gagacttata atgacatttc agaattctac aaggatgtcg aacgcagggg ctataaaatc  2160
gaatggtcct atatcagcga ggatgatatt aatcagatgg accgggacgg ccagatttat  2220
ttgttccaaa tttacaacaa ggatttcgca ccgaatagta agggtatgca aaacttgcac  2280
accctctatc ttaaaaatat cttcagtgag gaaaatttat cggacgttgt aatcaagttg  2340
aatgggagg cagagctttt cttccgtaag tcaagtatcc agcataagcg ggggcacaaa  2400
aagggctccg tactcgtgaa caaaacatat aaaaccacag agaagacgga aaatggccaa  2460
ggtgagattg aggtcatcga aagcgttccg gatcagtgct atctcgagct ggtcaagtac  2520
tggtctgagg gcggtgtcgg tcaactctct gaggaagcaa gcaagtacaa ggacaaagta  2580
tcccactacg ctgctacgat ggacattgtc aaagatcgtc gttacacaga ggataaattt  2640
tttatccata tgccaattac gatcaatttc aaggcggata atcggaataa cgtgaatgaa  2700
aaagtattaa aatttattgc ggaaaatgac gacctccacg ttatcggcat tgatcgcggg  2760
gagcgcaatt tactctatgt aagtgttatt gattcccggg gccgtattgt agaacagaaa  2820
agctttaaca ttgtagaaaa ttatgaatcc tccaagaatg tcattcgccg tcatgattac  2880
cgcggtaagc ttgtaaataa ggaacactat cgcaatgagg ctcggaagtc ttggaaggag  2940
atcgggaaaa tcaaggagat caagaaaggt taccttagcc aggtgattca tgagatctct  3000
aaactggttc ttaaatacaa cgcgatcatt gttatgaag acctgaatta tggttttaaa  3060
cgtgggcgct ttaagttga gcgtcaagtt taccaaaaat ttgaaactat gttgattaac  3120
aagttagcgt accttgttga caaaagtcgg gctgtaatga aacgggtgg cctgctcaaa  3180
gggtatcaac tcacttacgt cccggataat ttaggcgaat taggtagcca atgcggcatt  3240
atcttctacg taccggctgc atacacctca aagatcgacc cggtgacggg gtttgtggat  3300
gtctttgact tcaaagctta ctcaaatgct gaggcacggc tcgattttat taacaaactt  3360
gactgtatcc gttacgatgc accgcgtaac aaatttgaaa tcgcctttga ctacggtaat  3420
tttcggactc atcatcaac tcttgctaag acaagctgga ccatcttcat tcatggcgat  3480
cgcattaaaa aagagcgtgg cagctatggg tggaaagatg agattattga tatcgaagct  3540
cgcatccgca aactgtttga agataccgac atcgaatacg cggatgggca taatttgatc  3600
ggggacatca acgaattaga gagccctatc agaagaaat ttgtaggtga acttttgac  3660
attattcggt tcaccgtgca attgcgtaat tccaagagtg agaaatacga cggtaccgag  3720
aaggaatatg acaaaattat tagtccggta atggatgaag agggtgtctt cttcacaacc  3780
gacagttata ttcgggccga tggtacgaaa ttacctaagg atgcggacgc aaatgggggct  3840
tattgcattg ctctcaaagg tctctacgat gtgctggcag taaagaaata ctggaaggag  3900
ggcgagaaat tcgatcgcaa acttctcgca attaccaatt acaattggtt tgatttcatt  3960
caaaatcgtc ggtttggcgc gccaaaaaggg ccggcggcca cgaaaaggc cggccaggca  4020
aaaaagaaaa aggctagcgg cagcggcgcc ggatccccaa agaagaaaag gaaggttgaa  4080
gaccccaaga aaagaggaa ggtgtgataa                                    4110
```

SEQ ID NO: 99    moltype = DNA   length = 4110
FEATURE          Location/Qualifiers
misc_feature     1..4110 note = Description of Artificial Sequence: Synthetic
polynucleotide
source          1..4110
                mol_type = other DNA
                organism = synthetic construct
SEQUENCE: 99

```
atgggccacc atcatcatca tcatagcagc ggcctggtgc cgcgcggcag cggtaccatg   60
tgctacgacc ttaataacat taagactaaa ctgcgtgagc gcgaggtcga gacgatgggc  120
aataatatgg acaactcttt cgaacctttt atcgggggga actccgttag taaaaccttg  180
cggaatgagt tacgtgtggg gagtgaatat accggtaaac acatcaagga atgcgccatc  240
attgcagagg atgcagtgaa ggcggaaaat cagtatattg tcaaagagat gatggacgat  300
ttctatcgcg actttatcaa ccggaaactt gacgcgctgc agggcattaa ttgggagcag  360
ttattcgata tcatgaagaa agcaaagctt gataagtcga caaagtctc taaagaactc  420
gataagattc aggaatcaac ccggaaagaa attggtaaga tctttagcag tgatcctatt  480
tacaaagata tgttaaaagc tgatatgatc tccaaaatct tgcctgagta catcgtcgat  540
aagtatggcg acgccgcttc acgtatcgag gccgtgaaag tgttctatgg tttctcaggc  600
tatttcatcg acttttgggc tagtcggaaa aatgtcttct ccgacaaaaa catcgcttcc  660
gccattccac atcgcattgt aaacgttaat gcgcggatcc atctggacaa catcaccgcc  720
tttaatcgga ttgccgagat cgcaggtgac gaggtcgcgg gcatcgctga agatgcctgt  780
gcgtatctgc agaatatgag cttggaggac gtttttactg gcgcatgtta cggcgagttc  840
atctgccaga aggacattga ccgttacaat aacatctgcg gtgttatcaa tcagcatatg  900
aaccagtact gtcagaataa aaagtcagc cgcagcaata tcaagatgga acgtttacac  960
aagcaaatct tatgccggag cgaatcaggg tttgaaattc cgattggttt tcagacggat 1020
ggtgaagtaa tcgatgcaat taattctttc tctactatct tagaagagaa ggacatcctc 1080
gatcggcttc ggactcttag ccaggaggtg actgggtatg atatggagcg gatttatgtt 1140
tcgtccaagg cctttgagtc tgtcagcaaa tacatcgacc acaaaatgga tgtgatcgca 1200
tccagtatgt ataattactt ttctggcgcc gtgcgtggca agatgacaa aaggatgta 1260
aaaattcaga ccgaaatcaa aaagattaag tcttgttcgt tgctcgacct taaaaaactc 1320
gttgacatgt actataaaat ggatggcatg tgtttagagc atgaggccac ggagtatgtg 1380
gccggatca cggagatttt ggtagatttc aactacaaaa cttttcgacat ggatgattcc 1440
gttaagatga ttcagaatga gcatatgatt aacgaaatta agaatactt ggataccttc 1500
atgtccattt accactgggc gaaagacttc atgatcgacg aacttgtcga tcgcgatatg 1560
gagttttatt cagaattaga tgaaatttac tatgacttgt cggacatcgt accgctctat 1620
aataaggttc ggaattacgt cacccagaag ccatatagcg aagtaaagat caaattaaat 1680
ttcggagcc caacactcgc aaatggttgg tccaaatcga aggaattcga caataacgtt 1740
gtagtgctgc tgcgtgacga aagatttac cttgctatct taaacgtggg taacaagcca 1800
agcaaagaca ttatggcggg ggaagatcgt cggcgtagcg ataccgatta caagaaaatg 1860
aactactatt tattgcctgg ggctagcaaa acccttccgc acgttttcat tagctcaaat 1920
gcttggaaga agtcacatgg gattccagat gagatcatgt atggttataa ccagaacaaa 1980
catctgaaat caagtcctaa tttcgactta gaattctgcc gtaagttaat tgactactac 2040
aaagaatgca tcgacagtta tccgaattat caaattttta acttcaagtt tgcagcgacc 2100
gaaacctaca acgatatctc cgaatttac aaggatgttg agcggcaggg gtataaaatc 2160
gagtggagtt acatctctga agatgcatt aaccaaatgg accgtgatgg tcagatctac 2220
ctcttccaaa tttacaacaa ggacttcgca cctaattcga aaggcatgca aaatctgcac 2280
actttgtacc tgaagaacat cttctcggag gagaatttat ctgatgtagt gattaagctg 2340
aacgggagg ctgaactctt cttcgcaaa agttcgattc agcataaacg tgggcataag 2400
aagggcagtt tacttgtcaa caagacctat aagctaccg aaaagacaga gaacgggcag 2460
ggcgaaatcg aggttatcga gagtgttcct gatcagtcgt attttggagtt ggtaaaaat 2520
tggtccgaag ggggtgtagg ccagttgtcg gaggaggcta gcaaatacaa agacaaagtt 2580
tcccattatg ccgcgacgat ggacatcgtg aaggaccgtc gttatactga agacaaattc 2640
ttcatccata tgcctatcac tatcaacttc aaagctgata accggaacaa tgtaaacgaa 2700
aaggtgttaa aattcattgc ggaaaatgac gatctccatg tcatcggcat tgatcgtggt 2760
gagcgcaacc tgctttacgt gtcagtcatt gatagtcgcg gcggattgt ggagcaaaag 2820
agtttaaca ttgtggagaa ttacgagtcc tctaaaaatg tgattcgtcg ccatgattac 2880
cggggtaagc tcgtcaataa ggaacactat cggaatgagg ctcgcaaatc ttggaaggaa 2940
atcggtaaga tcaaggagat taaggagggc tatctctctc aagtcatcca cgagatctcg 3000
aagcttgtat taaagtacaa cgcgatcatt gtaatgaag atttgaacta tgggttcaag 3060
cgggggcggt tcaaagtgga gcggcaggtg taccaaaaat cgaaactat gttaatcaat 3120
aaactggctt acctggtcga taaatctcgc gcagtggatg aaccaggggg gcttttgaag 3180
gggtatcaac tcacttatgt tcctgacaac cttggggagc tcggttccca gtgcgggatt 3240
atcttttatg tgccagccgc atacacgagt aagatcgatc cggtaccgg ctttgtagac 3300
gtttttgact tcaaagcata tagtaacgca gaggcacgcc tcgatttcat caacaaactg 3360
gactgcattc gctacgatgc accacgtaat aagttcgaaa tcgcgtttga ttatggcaac 3420
tttcgcacgc accacgac ttagcgaaa acgtcttgga caattttcat tcacgcgat 3480
cgcatcaaga aggagcgcgg ctcgtacggg tggaaggacg aaattattga tatcgaggca 3540
cggattcgta aacttttga ggacacagat attgagtatg ctgacggcca taacctcatt 3600
ggcgatatca atgagcttga gtcacctatc caaaaaaat tcgttgggga acttttcgac 3660
attatccgtt ttacggtgca gctccgcaac tcgaaatcaa aaaatatga tggcacggag 3720
aaagagtacg ataagatcat ctctcctgtg atggatgaga agggcgtctt cttccaccac 3780
gattcgtaca ttcgtgcgga tgggacgag ttaccgaagg acgctgatgc taatggcgcc 3840
tactgtatcg cgctcaaggg cctgtacgac gtcttagctg tcaagaagta ttggaaggag 3900
ggtgagaaat tcgaccggaa gttactggcg atcactaact acaattggtt tgactttatc 3960
caaaatcgcc gttttggcgc gccaaaaagg ccggcggcca cgaaaaggc cggccaggca 4020
aaaaagaaaa aggctagcgg cagcggcgcc ggatccccaa agaagaaaag gaaggttgaa 4080
gaccccaaga aaaagaggaa ggtgtgataa                                  4110
```

SEQ ID NO: 100        moltype = DNA   length = 4110
FEATURE               Location/Qualifiers
misc_feature      1..4110

|  | note = Description of Artificial Sequence: Synthetic polynucleotide |
|---|---|
| source | 1..4110 |
|  | mol_type = other DNA |
|  | organism = synthetic construct |

SEQUENCE: 100

```
atgggccacc atcatcatca tcatagcagc ggcctggtgc cgcgcggcag cggtaccatg   60
tgttacgatc tgaacaacat caaaacgaag ctgcgcgagc gcgaagttga acgatgggg   120
aataacatgg ataattcgtt cgaaccgttc attgggggga attcagttag caagaccctg   180
cggaatgagt tacgtgttgg ctctgagtac acaggcaagc atattaagga atgcgctatc   240
attgctgagg acgccgtgaa agccgaaaac cagtatattg tgaaagagat gatggacgac   300
ttttaccgtg acttcattaa tcgtaagctg gatgcgctcc aggggattaa ttgggaacag   360
ctgttcgata tcatgaagaa ggccaaactc gataagtcga ataagttag caaagagctg    420
gacaagattc aggaatcgac tcggaaagag attggtaaaa tcttcagttc tgacccgatt   480
tacaaggata tgcttaaagc tgacatgatt tcaaaaatcc tgccagaata tattgttgat   540
aagtacggcg atgcggcatc acgtattgaa gctgttaaag tgttttatgg ttttttcgggg  600
tattttatcg attttttggc ttcacgcaaa aatgtgtttt cagataagaa catcgcgtcg   660
gcaattccgc accgcatcgt aaacgtcaat gctcgcattc acctcgacaa catcacggca   720
ttcaaccgca ttgcggagat cgcggggac gaagtcgctg cattgccga ggacgcttgc     780
gcatatctgc agaacatgag ccttgaagac gtattcactg gtgcctgtta tggcgagttt   840
atctgtcaaa aagacattga tcgctataat aacatttgcg gggtgatcaa ccagcatatg   900
aaccaatact gccaaaataa aaaaatctcc cgctcaaaat ttaagatgga gcgcctgcat   960
aaacaaatcc tttgtcggtc cgagagtggg ttcgagatcc caatcgggtt ccaaacggac  1020
ggcgaagtta ttgatgcgat caacagtttt tcaacaattc ttgaggagaa agacatcctt  1080
gaccgtcttc ggacattatc gcaagaggta accgggtacg acatggaacg tatttacgtc  1140
tcatcgaaag cgttcgagtc cgtctctaag tacatcgacc ataagtggga tgtcattgca  1200
tcatcgatgt acaattattt ttctggtgca gttcggggca aagatgataa aaaggacgtg  1260
aagatccaga cagaaattaa aaaaatcaag agctgttccc tgctcgactt aaagaaactt  1320
gtcgatatgt actacaagat ggacggtatg tgcttggagc atgaggccac ggagtatgtc  1380
gctggcatca ctgagattct ggatgatttt aactacaaga cctttgacat ggatgattcc  1440
gtcaaaatga ttcaaaacga acatatgatt aatgagatta aagagtacct ggatacctat  1500
atgtccattt atcattgggc aaaagatttt atgattgatg agctggtcga ccgtgacatg  1560
gagttctact cggaattgga cgaaatttac tatgatctgt cggatattgt accactttac  1620
aataaggttc ggaattatgt tacgcagaaa ccgtactctc aggataagat caaacttaat  1680
tttggctcgc cgactctcgc taatggttgg tcaaagtcca aagagttcga taacaacgta  1740
gtagttcttc tgcgggacga gaagatttac ctggcaatcc tcaatgtagg gaataaacct  1800
agtaaagata ttatggcggg ggaagaccgc cgccgcagtg atacggacta aaaaaaatg   1860
aattattacc tccttccggg tgcgtctaag accttgccac atgttttat ttcttccaac   1920
gcgtggaaaa agagtcacgg cattccggac gaaatcatgt atggttataa tcagaataaa  1980
cacctcaagt ccagccctaa cttgacctt gagttcgtcc ggaagctgat tgattattat   2040
aaggaatgta tcgattctta cccgaactat cagatcttta acttcaaatt tgccgcaact  2100
gaaacataca atgacatcag cgagttctat aaagatgtgg aacgccaagg gtacaaaatt  2160
gaatggtcat acatctccga ggacgacatt aatcaaatgg accgggatgg tcagatttca  2220
ttattccaga tttataacaa ggactttgcc ccaaattcaa aaggcatgca aaacctccta  2280
accttgtact tgaaaaatat cttctccgag gaaaatcttt ccgacgttgt gatcaaactt  2340
aacgggggaag cagagctttt cttcgtaag tcgtctatcc aacataaaacg ggggcacaaa  2400
aaaggcagcg ttctggtgaa taaaacgtac aagaccactg agaaaacggga gaatgggcaa  2460
ggcgaaattg aggtcatcga gtcggttcca gatcagtgct atctcgagct cgtaaaaatac  2520
tggtccgagg gtggtgtggg ccagttatca gaagaggcct cgaagtacaa agataaggtc  2580
tctcactacg ctgccacgat ggatattgtc aaggaccgcc gctacactga agacaaattt  2640
ttcattcaca tgccgatcac aatcaacttc aaggccgata accggaacaa cgtgaacgaa  2700
aaagtactga gtttatcgc cgaaaatgat gacttgcatg ttattggcat tgaccggggt   2760
gaacgcaatt tactctacgt atcggtgatt gacagtcggg gccgtatcgt tgagcagaag  2820
agtttcaaca tcgtggaaaa ttacgagtcc agtaaaaatg ttatccggcg tcacgattac  2880
cggggcaagc tggtgaataa ggagcattat cggaatgaag cgcgcaagtc ttggaaagaa  2940
attggcaaaa ttaaggagat taaagaaggt tatctctccc aagtaattca cgagatttca  3000
aagttggtct tgaagtataa cgcgattatt gtgatgaag acttgaacta cggttttaaa  3060
cgcggccgtt ttaaagtgga gcggcaggta taccagaaat ttgaaacaat gctgatcaac  3120
aagctggcgt atttggtgga taagtcgcgc gccgttagtg agctggggg gttgctgaag   3180
ggttaccaat taacttatgt tcctgataac ttggggggagt taggttcaca gtgtggcatt  3240
atcttctacg ttccagccgc ttatacttcc aaaattgacc cagtgacagg tttcgtcgat  3300
gtattcgatt tcaaggcata ttccaatgct gaggcgcgcc ttgatttcat taataaattg  3360
gattgcattc ggtatgatgc tccgcgtaac aagttcgaaa tcgccttcga ctacggtaac  3420
ttccggacac accataacaac cctggccaag actagctgga ccatcttcat ccacgggcac  3480
cggattaaaa aggaacgggg cagctatggt tggaaagacg aaattattga tattgaggcc  3540
cggatccgga agctgtttga agacaccgac attgaatacg ctgatggtca caatttaatt  3600
gggggatatca acgagctgga atcgccatt cagaaaaagt tcgtcggcga attattcgac  3660
atcattcggt tcaccgtgca actgcgcaac tccaaatcag aaaagtacga tggcacggag  3720
aaagagtacg acaaaattat ttccccggtg atggacgagg agggtgtttt tttcacaact  3780
gattcgtata tccggggcgga tggtaccgag cttccgaaag acgctgacgc caatggcgct  3840
tactgcattg ctttaaaggg cttgtatgat gtactgcggg tcaagaagta ctggaaggaa  3900
ggcgagaagt ttgatcgcaa gttgcttgcc atcactaact ataactggtt tgattttatc  3960
caaaaccgtc ggttcggcgc gccaaaaagg ccggcggcca cgaaaaggc cggccaggca   4020
aaaaagaaaa aggctagcgg cagcggcgcc ggatccccaa agaagaaaag gaaggttgaa  4080
gaccccaaga aaaagaggaa ggtgtgataa                                    4110
```

| SEQ ID NO: 101 | moltype = DNA   length = 4110 |
|---|---|
| FEATURE | Location/Qualifiers |
| misc_feature | 1..4110 |

```
                        note = Description of Artificial Sequence: Synthetic
                        polynucleotide
source                  1..4110
                        mol_type = other DNA
                        organism = synthetic construct
SEQUENCE: 101
atgggccacc atcatcatca tcatagcagc ggcctggtgc cgcgcggcag cggtaccatg    60
tgctacgatc ttaacaatat taaaactaag ttgcgcgaac gtgaggtaga aacaatgggt   120
aataacatgg ataattcgtt cgagcctttc atcggcggta atagcgtctc taagaccctc   180
cgtaatgagt tacgggtggg ctcagaatat accggcaagc atatcaagga gtgtgccatt   240
attgccgaag acgctgtgaa ggcggaaaat cagtatatcg tcaaagagat gatgacgat    300
ttttaccgcg actttatcaa tcgcaaatta gatgcgttac aaggcattaa ttgggagcaa   360
ttatttgaca ttatgaaaaa agcgaaactt gacaagtcaa acaaagtttc gaaagaactt   420
gacaaaatcc aagaatcgac gcgcaaaagg atcgggaaga tcttcagcag tgatccgatt   480
tacaaagaca tgttaaaagc ggacatgatc tcaaagatcc tccctgaata tatcgtagat   540
aagtatgggg atgcggcgtc acggattgaa gcggtgaaag tgttttacgg ttttagtggg   600
tatttcattg acttttgggc ctcgcgcaag aacgtcttt ccgacaaaaa tatcgcaagt   660
gccattccac atcggatcgt caatgttaac gctcgtattc atttggacaa cattacggcg   720
ttcaaccgga ttgcagaaat cgcaggtgat gaggtcgccg ggatcgctga agatgcttgc   780
gcataccttc agaatatgtc gctggaagac gtttttacgg gtgcatgtta cggtgagttt   840
atctgtcaga agatattga ccgttataat aacatctgcg gcgtcatcaa ccagcatatg    900
aatcaatatt gccaaaataa aaagattagc cgttccaagt tcaaaatgga gcgtcttcac   960
aaacaaatcc tgtgccggag cgaatcaggt ttcgaaattc cgattggctt ccaaacagat  1020
ggtgaagtga ttgacgctat taactcattc agcaccatct ggaagaaaa ggatattctc  1080
gatcgccttc ggacgttgtc tcaggaagtg actggttacg acatgaacg gatctatgtt  1140
tcatctaaag ctttcgagag tgtatcgaag tatatcgata ataaatggga tgtttatcga  1200
tcgtccatgt acaattactt tagcggggct gtccgcggca aggacgataa aaaggatgtc  1260
aagatccaga cggagattaa aaagattaaa tcgtgctctt tgctggattt gaaaaagctt  1320
gtggatatgt attataaaat ggacggtatg tgcctggaac atgaggcaac tgagtatgtg  1380
gcagggatca ctgagattct cgtcgacttc aattacaaca ccttcgatat ggacgattct  1440
gttaagatga tccaaaatga gcatatgatc aatgagatta agaatatct tgacacatac  1500
atgtcaatct accattgggc taaagacttc atgatcgacg agcttgtgga ccgggacatg  1560
gaatttata gcgaactcga tgagatctat tatgacctta gtgatattgt cccattgtat  1620
aataaggtcc ggaattacgt aactcaaaaa ccttattcac aagataaaat caagttgaac  1680
tttgggagcc caaccttggc gaatggttgg agtaagagta aagagttcga caataacgtc  1740
gtcgtcttgc tccgtgatga aaaaatttac ttagctattt taaacgttgg gaataagcct  1800
tctaaggata ttatggctgg ggaagaccgg cgccgttcag acaccgacta caaaaagatg  1860
aattactatc tccttccagg ggctagtaaa actctcccgc acgtgttcat ttcgtcaaac  1920
gcctggaaga aatcccatgg catcccagat gagattatgt atgggtacaa ccagaataaa  1980
catctgaaaa gctcgccaaa ttttgacttg gaattttgcc gcaaattaat cgattactac  2040
aaagaatgca ttgactcgta cccgaattat cagattttta acttcaaatt cgcagctacc  2100
gagacatata acgacatttc agagttctat aaagacgtcg aacggcaagg ttacaaaatc  2160
gaatggagct atattagtga agcgacatc aaccagatgg accgcgacgg ccaaatctat  2220
ttgttccaga tctataataa agacttcgca cctaattcga aaggcatgca aaacctccca  2280
acactgtatc ttaaaaacat cttcagcgaa gagaatctct cagacgttgt aattaaactt  2340
aacggtgaag ctgaactttt ctttcggaag tcttcgatcc aacataaacg tggccacaaa  2400
aagggttccg tgctcgtcaa taaaacgtac aagctactg agaaaacgga gaatgggcag  2460
ggggaaattg aggtcatcga aagcgttcca gatcaatgtt accttgaact cgtgaaatat  2520
tggtctgagg gcgggtagg tcagctgagc gaagaagcct cgaaatataa ggataaagtg  2580
agtcattacg ctgccaccat ggacatcgtg aaggaccgcc gttacacgga ggataagttc  2640
tttattcaca tgccgattac cattaacttc aaggccgaca atcgaaata cgtaaacgag  2700
aaggtcctga gtttatcgc ggaaaacgac gacttacacg tcattggcat tgatcggggt  2760
gagcggaatc tgttatatgt gtcagttatc gactcacgtg ggcggattgt ggaacagaaa  2820
agcttttaaca tcgtggaaaa ctacgagtcc tcaaaaaatg tgatccgccg ccatgattac  2880
cgtgccaagc tggttaacaa agagcactac cgcaatgaag cccgtaagag ctggaaagaa  2940
attggtaaaa tcaaggaaat caaagaaggg tatctgtccc aggtaattca cgagattagt  3000
aaattggtat tgaagtacaa tgcaatcatt gtgatggagg atttaaatta tgggttcaaa  3060
cggggccgtt ttaaggtgga gcgccaagtt tatcagaagt tcgaaccat gctcattaac  3120
aagttggcct atctcgtcga taagtctcgg gcggtagatg agccaggcgg gcttttaaaa  3180
ggctatcaat taacctacgt accggacaat tccggcgaac tcggtagtca atgcggtatt  3240
attttctacg taccagcggc gtacacctcg aaaatcgatc ctgtcacagg cttcgtggat  3300
gtattcgact ttaaagctta tagtaatgcg gaagcacgtt tagatttat taataaactt  3360
gattgtatcc gttatgatgc tccacgcaat aaatttgaaa ttgcctttga ctatgggaac  3420
ttccggacgc atcacacgac cctggccaaa acgagctgga ccatcttcat ccatggaacg  3480
cggatcaaaa aggagcgcgg tagctatggt tggaaagatg agattatcga tatcgaggct  3540
cgcattcgca agctgtttga agatacagat attgaatatg ctgacgggca taatctgatc  3600
ggcgacatca tgaattgga gtcacctatc cagaaaaagt ttgtcgggga gctcttcgac  3660
atcattcgct tcacggtaca attacggaat tcgaaatccg agaagtatga tggcactgag  3720
aaagagtatg acaaaattat ctcgccggtg ttggacgagg aagggtgtt ctttacaacg  3780
gatagctata ttcgtgccga tggcacggaa ttgccaaaag atgcagatgc aaatggtgcc  3840
tattgcattg ctctgaaggg tttatatgac gtcttggcgg ttaaaaaata ctggaaagag  3900
ggggagaagt tcgaccggaa actcctcgcc attacgaact acaattggtt cgatttttatc  3960
caaaaccggc ggttcggcgc gccaaaaagg ccggcggcca cgaaaaggc cggccaggca  4020
aaaaagaaaa aggctagcgg cagcggcgcc ggatccccaa agaagaaaag gaaggttgaa  4080
gaccccaaga aaaagaggaa ggtgtgataa                                   4110

SEQ ID NO: 102         moltype = DNA  length = 4110
FEATURE                Location/Qualifiers
misc_feature           1..4110
```

```
                    note = Description of Artificial Sequence: Synthetic
                    polynucleotide
source              1..4110
                    mol_type = other DNA
                    organism = synthetic construct
SEQUENCE: 102
atgggccacc atcatcatca tcatagcagc ggcctggtgc cgcgcggcag cggtaccatg    60
tgttatgacc tcaataacat taagactaag cttcgggaac gggaagtcga gactatgggt   120
aacaacatgg acaactcgtt tgagccgttc attggggggca attctgtctc gaagacgtta   180
cggaatgaat tacgcgtagg tagtgagtac acgggtaagc atattaaaga atgtgcgatt   240
atcgcggagg acgccgtgaa ggcggaaaat cagtacattg tgaaggagat gatggatgac   300
ttctaccgcg atttcatcaa ccggaagttg gatgccctcc aggggatcaa ctgggaacag   360
ctgtttgata ttatgaaaaa agctaaactc gacaaaagta ataaagtatc caagaatta   420
gataagattc aagaaagcac ccgcaaagag attggcaaga ttttctcgag tgatcctatt   480
tacaaggata tgttaaaagc tgatatgatc agcaaaattc tcccggaata cattgtggat   540
aaatatggtg acgcagcatc ccgcatcgag gcagtcaaag tattctatgg tttctcgggc   600
tatttcattg acttctgggc tagccgcaaa aatgtatttt ccgacaagaa tatcgccagc   660
gcgatcccac atcgcattgt aaatgtcaac gctcgtattc atcttgataa tatcacagct   720
ttcaaccgca tcgcagagat cgcagggat gaggtcgccg gcatcgctga agacgcctgc   780
gcttacttgc agaatatgtc ccttgaggac gttttcaccg gtgcctgcta tggggaattc   840
atctgccaga aagatattga tcgctataat aatatttgtg gtgtaatcaa tcaacatatg   900
aaccaatact gccaaaataa gaagatcagt cgttcgaaat tcaaaatgga aggctgcat   960
aagcaaatcc tctgccgctc agagtctggt ttcgaaatcc ctatcggttt tcaaacggat  1020
ggggaagtta tcgacgcgat caatagcttt tctacgatct tggaggaaaa ggatattctc  1080
gatcggttgc gcacgctgtc tcaagaggtg acggttacg atatggagcg tatctatgtt  1140
tcttcaaagg ccttcgaaag tgttagcaag tacatcgacc acaagtggga cgtgattgcc  1200
tctagcatgt acaactattt ctccggggcg gtccggggca aggatgataa aaaagatgtg  1260
aagattcaaa ctgaaattaa gaaaattaaa tcctgctctc tcctcgattt gaagaaactc  1320
gtcgacatgt attataagat ggatggcatg tgtcttgagc atgaggccac tgagtacgtt  1380
gcagggatca ctgaaatttt ggtcgatttc aactacaaga cttttgatat ggatgattcc  1440
gtcaagatga tccaaaacga gcatatgatt aacgaaatta agaatacct ggacacatat  1500
atgtcgattt tcattgggc caaagactc atgattgacg agctcgtgga ccgtgacatg  1560
gagttttact ccgagttaga tgagatctac tacgacctct cagatattgt tccattatac  1620
aacaaagttc gcaattacgt cacgcagaag ccttactcac aagataaaat caaactcaac  1680
ttcgggtctc caacattggc caacggctgg tccaagtcga agagtttga caataatgta  1740
gtagtgctgc tccgggatga gaaaatttat ctcgcgatct aaacgtagg taacaagccg  1800
tctaaggaca ttatggccgg cgaggaccgc cgccgttcag acacagatta caagaagatg  1860
aactattatc ttttaccagg ggcaagtaag acacttcctc atgttttcat ttcgtctaat  1920
gcgtggaaaa aaagccatgg catcccgac gaaatcatgt atggttataa ccaaaataag  1980
catctcaaat cgtcgccgaa cttcgatctg gaattttgcc gcaaattaat tgactactat  2040
aaaagagtgca tcgatagcta cccaaactac cagattttca actttaaatt cgctgcgaca  2100
gagacgtaca acgatattag tgagttctat aaagacgtgg aacgccaggg ttataaaatt  2160
gaatggagct atatctccga ggatgatatc aatcagatgg atcgcgacgg ccaaatttat  2220
ctcttccaaa tttacaacaa agatttcgca cctaactcaa agggcatgca gaatcttcac  2280
acgctttacc ttaagaatat cttcagcgaa gaaaatcttt ccgacgtcgt gatcaagctt  2340
aatgcggagg cagaacttttt ttttcggaaa tctagcatcc aacacaagcg tggccacaaa  2400
aaaggtagtg tgttagtaaa caaaacctac aagacgacgg aaaaaaccga gaacgggcaa  2460
ggcgagattg aggtaatcga atcggtacct gatcagtgct acctcgagct tgtaaaatat  2520
tggtcggagg gcggggtggg gcagttatcc gaggaggcct ccaaatataa agacaaagtt  2580
tcgcattatg ccgcaactat ggacattgtt aaagatcgtc gctacacaga ggataagttc  2640
tttattcaca tgcctatcac tattaatttt aaggctgata accgcaacaa tgttaatgaa  2700
aaggtgctga aatttatcgc ggaaaatgac gacttgcatg tcattggcat cgaccgtggc  2760
gaacgcaatc ttctctatgt atctgttatt gactcgcggg gcggatcgt ggagcaaaaa  2820
tctttcaata tcgtcgaaaa ctacgagtca tcaaaaaacg tgattcggcg gcatgattac  2880
cgcggtaacg tggtaaataa ggaacactat cgcaatgaag cacgtaaatc ctggaaagaa  2940
atcggcaaaa ttaaagagat taagagggc tatctttcgc aagtaattca cgaaatcagt  3000
aagctcgtat tgaagtacaa tgcgatcatc gtaatggagg acttaaacta tggttttaaa  3060
cggggccgtt tcaaagtgga gcgccaagtt tatcaaaagt tcgagacaat gcttatcaat  3120
aaattggctt atctggttga taaaagtcgc gctgttgatg agccaggtgg ccttctgaaa  3180
ggctatcagt tgacctatgt gcctgataac ttaggtgagc ttgggtctca gtgcgggatc  3240
attttctacg tcccagcggc ctatacgtcg aagattacc cggtgacggg gtttgtagac  3300
gtgtttgatt tcaaagcgta ctcgaacgct gaagctcgct tggatttcat taacaagctg  3360
gactgcatcc ggtacgatgc tccacggaac aagttcgaaa tcgcattcga ttatggcaat  3420
tttcgcacgc atcatacaac cttagctaaa acaagctgga caatcttttat ccatggatgc  3480
cgcattaaaa aagaacgcgg tagttacggt tggaaagacg aaatcatcga cattgaggct  3540
cgcattcgta aactcttcga agataccgat attgaatatg cggatgggca caatctgatc  3600
ggtgacatca atgaactcga aagtcctatt cagaagaaat tcgtggggga acttttttgac  3660
attatccgct ttactgtaca gttacgcaat tccaagagcg aaaagtatga cggcaccgag  3720
aaagagtacg ataaaattat ctcgcctgtg atggatgagg aaggggtttt cttcactacg  3780
gactcatata tccgcgctga cggcacggag ttgcctaagg acgctgatgc caatggcgcg  3840
tactgtatcg ctctcaaggg gctttatgat gtacttgccg taaaaaaata ctggaaggaa  3900
ggggagaagt ttgaccgtaa gttgttggcc attactaact acaattggtt tgatttcatc  3960
cagaaccgtc gtttcggcgc gccaaaaagg ccggcggcca cgaaaaggc cggccaggca  4020
aaaaagaaaa aggctagcgg cagcggcgcc ggatccccaa agaagaaaag gaaggttgaa  4080
gaccccaaga aaaagaggaa ggtgtgataa                                    4110

SEQ ID NO: 103       moltype = DNA   length = 4110
FEATURE              Location/Qualifiers
misc_feature         1..4110
```

```
                    note = Description of Artificial Sequence: Synthetic
                    polynucleotide
source              1..4110
                    mol_type = other DNA
                    organism = synthetic construct
SEQUENCE: 103
atgggccacc atcatcatca tcatagcagc ggcctggtgc cgcgcggcag cggtaccatg    60
tgctatgatc tcaacaacat caaaacaaag cttcgggaac gggaagtaga gactatgggc   120
aataacatgg ataactcttt tgaaccattc attggggta actccgtttc taagactctc    180
cgcaacgagt tacgcgtagg ctctgagtac accgggaaac acattaagga gtgcgctatt   240
atcgccgagg atgctgtgaa agccgaaaac cagtatattg ttaaagagat gatggacgat   300
ttctaccgtg acttcattaa ccggaaactt gacgccttc aggggatcaa ctggagcaa     360
ttattcgata ttatgaaaaa ggcaaagctt gataaaagca acaaggtttc aaaagaatta   420
gataaaattc aggaatccac ccgtaaggaa attggcaaga ttttctcatc ggatcctatc   480
tacaaagata tgctcaaagc cgatatgatc tccaaaattc tgccagaata catcgtagac   540
aagtatggcg atgctgcgtc ccgcattgag gcggttaaag tcttctatgg cttttctggg   600
tatttcatcg atttctgggc atctcgtaaa aatgttttta gcgacaagaa tatcgcttcc   660
gccattccgc atcgtattgt gaacgttaat gctcgcattc atttagataa tattactgcg   720
tttaatcgta tcgcagagat cgcggggat gaagtggcag ggattgcgga agacgcatgc    780
gcctacttgc aaaatatgtc attagaagac gttttacgg gtgcctgcta cggtgagttc    840
atctgtcaaa aagatatcga tcgttacaat aacatctgcg gtgtaattaa ccaacatatg   900
aaccagtact gccaaaataa gaaaattagc cgttcaaaat tcaagatgga acgcctccac   960
aagcagatcc tgtgtcggtc tgagtccggc ttcgaaattc cgatcggctt tcagactgat  1020
ggggaagtga ttgacgctat caactcattt tcgacaattc tcgaggaaaa ggacatcctc  1080
gatcgcttac gtactttatc tcaagaagtt accgggtatg atatgaacg catttatgta   1140
tcgagcaagg ccttcgagag cgtctcgaaa tatatcgaca ataagtggga cgtaatcgca  1200
tcgtctatgt acaattactt ctccggcgca gtgcgcggta aggatgataa aaaagacgta  1260
aaaatccaaa ctgagatcaa gaaaattaag agttgtagtc tcctcgacct caaaaaattg  1320
gtggatatgt attataaaat ggatgggatg tgcctcgaac acgaagccac agagtacgtc  1380
gcaggcatca ccgaaaatcct cgtagatttc aactataaga cgttcgatat ggatgactcc  1440
gtcaagatga tccagaacga acacatgatt aacgagatca aggagtacct cgataccat    1500
atgagcattt accactggc taaggatttc atgatcgatg agcttgtcga ccgggacatg  1560
gaattttatt ctgaacttga tgaaatctac tatgacttga gcgatattgt accactttat  1620
aacaaggtgc gtaattatgt cacccaaaag ccgtactccc aggataaaat caaacttaac  1680
tttggttcac caacgttggc caatggttgg tccaaatcaa aggaattcga taacaatgta  1740
gtggttctcc tccgggacga aaagatttat ctcgcaatcc ttaacgtggg taacaaaccg  1800
tctaaggaca ttatggctgg ggaggatcgt cgccggagcg acacagacta caaaaagatg  1860
aattattatt tactcccggg tgcgtccaag accttgccac atgttttcat cagttctaac  1920
gcatggaaga agtcacacg tatcccggat gaaattatgt atgggtataa ccagaacaaa   1980
catctcaaaa gtagtcctaa tttcgacttg gagttctgtc ggaaactgat cgattactac  2040
aaggaatgca tcgattctta tccaaattat cagatcttca atttcaagtt tgccgccaca  2100
gaaacgtata acgatatctc cgaattctac aaagatgtcg agcgcaggg gtacaagatc   2160
gagtggtctt atatttcgga ggatgatatt aaccagatgg accgtagtg ccagatttac   2220
cttttccaga tctacaacaa agattttgcc ccgaacagta aaggcatgca aaacctccat  2280
accttatact taagaatat cttctcggag gaaaatttgt cggacgtagt cattaaattg    2340
aatggtgagg ctgaattatt cttccggaag tcttcgatcc agcacaaacg cgggcacaag  2400
aaaggctcag tcttggtaaa taaaacttat aaaacaacgg aaaagacgga gaatggccag  2460
ggcgaaattg aagtgatcga gtcggtccca gaccaatgct acttggaact cgttaagtac  2520
tggtctgaag gtggggtcgg gcagctgtcg gaggaggcat cgaagtacaa ggacaaagtg  2580
agccactacg cggccacgat ggacattgta aaggatcgtc ggtatacaga agacaaattc  2640
tttattcata tgcctatcac aattaacttt aaagcggaca atcgtaataa cgtgaatgaa  2700
aaagtattga aattcattgc agaaaacgac gacttgcatg taattggtat cgaccgcggt  2760
gagcgcaacc tcctttacgt tagcgtgatc gattcacgtg ggcgtattgt ggagcaaaag  2820
tcgttcaata ttgtcgagaa ctatgaatca agtaaaaatg taatccggcg gcatgattac  2880
cggggtaagc ttgtcaacaa ggaacattac cgtaatgacg cccgcaagtc atggaaagaa  2940
atcggcaaga ttaaggagat caaggaaggt tatctcagtc aagtaatcca cgaaatctcc  3000
aagctcgtac tcaaatataa tgcaatcatt gtaatggaag atttgaatta cggttttaag  3060
cggggtcgct tcaaagtcga gcgccaagtt taccaaaaat tcgagacaat gctgatcaat  3120
aaattggctt acttagtgga taaagtcgt gctgttgacg agctggtgg tcttttgaag   3180
gggtatcagt tgacgtatgt gcctgacaat cttggtgcg tgggttctca gtgcggtatt   3240
attttttacg tgccggcagc atatacttcg aaaatcgacc ctgttaccgg tttcgtcgat  3300
gtattcgact ttaaagcgta ttccaatgcc gaggcccgtc tggactttat caacaaactt  3360
gactgtattc gttacgatgc gcctcggaat aaattcgaga ttgcgtttga ctatgggaat  3420
tttcggacgc atcataccac gttagccaag acgtcttgga ctatttttat ccatggactt  3480
cgcattaaaa aggaacgcgg ttcatacggc tggaaagatg agatcatcga tatcgaagct  3540
cgcatccgga agcttttcga agacaccgac atcgaatatg cagacgggca aacttgatt    3600
ggtgatatca atgaactgga atcccctatt caaaaaaaat tcgtgggtga gttgttcgac  3660
atcatccggt ttacggtcca gttacggaac tcgaagagtg agaaatacga tggtactgag  3720
aaagagtatg acaagatcat ctctccagtt atggatgagg agggcgtatt tttactacg   3780
gactcataca tccgcgcgga cggtacgaaa ttaccgaagg atgccgatgc aaatggcgca  3840
tactgtatcg cacttaaggg cctctacgac gttttagctg tgaagaaata ctggaaggag  3900
ggcgaaaaat ttgaccgcaa gttattagct attacgaatt acaactggtt cgatttatt   3960
caaaatcgtc ggttcggcgc gccaaaaagg ccggcggcca cgaaaaggc cggccaggca   4020
aaaaagaaaa aggctagcgg cagcggcgcc ggatccccaa agaagaaaag gaaggttgaa  4080
gaccccaaga aaagaggaa ggtgtgataa                                     4110

SEQ ID NO: 104    moltype = DNA   length = 4110
FEATURE           Location/Qualifiers
misc_feature      1..4110
```

|  |  |  |
|---|---|---|
| | note = Description of Artificial Sequence: Synthetic polynucleotide | |
| source | 1..4110 | |
| | mol_type = other DNA | |
| | organism = synthetic construct | |

SEQUENCE: 104

```
atgggccacc atcatcatca tcatagcagc ggcctggtgc cgcgcggcag cggtaccatg    60
tgctatgatt taaataacat caaaacgaag ctgcgggaac gcgaagtcga gacaatgggc   120
aacaatatgg ataattcttt tgagccattc attggcggta actccgtgtc taaaaccttg   180
cgtaacgagc ttcgggtagg gagtgagtat actgggaaac acattaaaga gtgcgcgatc   240
attgcggaag acgcgtaaa agccgaaaat cagtatatcg tcaaggagat gatggatgac   300
ttctaccgtt atttcattaa ccggaagctc gatgccctgc agggcattaa ttgggagcaa   360
ttatttgata tcatgaaaaa agcaaagttg gacaaatcaa acaaagtcag taaagagctc   420
gacaaaatcc aagagtccac ccgcaaggaa atcggtaaga ttttttagctc cgatcctatc   480
tataaagaca tgctgaaagc cgacatgatc tcaaagattt tgccggagta tattgtcgac   540
aaatatggcg acgcagcttc tcgtatcgaa gctgttaaag ttttttacgg tttctctggg   600
tattttattg attttttggc aagtcgcaaa aacgttttt cggataaaaa tattgcatcg   660
gcaatccctc atcggatcgt taacgtaaat gcccgaatcc acttggacaa cattacggct   720
tttaatcgca tcgccgaaat tgccggcgat gaagttgcgg gcattgccga ggatgcgtgt   780
gcctacttac aaaacatgtc tttagaggat gtgttttactg gtgcttgcta cggtgagttt   840
atttgccaaa aagatattga ccgttacaac aatatctgtg gggtcatcaa ccaacacatg   900
aaccaatatt gtcagaataa gaagattagc cggtcgaaat tcaaaatgga acgcctccac   960
aaacaaatcc tttgtcgcag tgagagcggc ttcgagattc cgatcgggtt ccaaaccgac  1020
ggcgaagtga tcgatgcgat taacagtttt tctactatct tggaagagaa ggacatcctg  1080
gaccggttac gcacgctttc ccaggaagtc acgggctatg acatgaacg gatttacgta  1140
tcaagtaagg cattcgaaag cgtgtcaaag tacattgacc ataaatggga cgtgattgcg  1200
agtagcatgt acaattattt ttcgggggct gtgcgtggga aagatgataa aaaggatgtt  1260
aagatccaga ctgagattaa aaaaatcaag tcctgttcgt tattagacct taagaaatta  1320
gtcgacatgt attacaaaat ggacgggatg tgcctcgagc acgaagctac tgagtacgta  1380
gctgcatcca ccgaaatttt agttgacttt aattataaaa cattcgacat ggatgattcc  1440
gtaaagatga tccagaatga acatatgatc aatgaaatta aggagtattt ggatacatat  1500
atgagcattt atcattgggc gaaggatttc atgattgacg aactggtgga tcgggacatg  1560
gaattctata gcgaattgga cgagatttat tacgatttat ctgacatcgt cccttttgtat  1620
aacaaagttc gtaactacgt gacccaaaag ccgtattcgc aagtaagat caagttgaat  1680
tttggttctc ctaccttagc aaatggctgg tctaaatcta aggaattcga caacaatgtg  1740
gtggtattgc tccgcgatga aagatttat cttgcaatcc tgaacgtcgg gaacaaaccg  1800
tcgaaggaca ttatggcggg ggaggaccgg cgccgctccg acacagatta agaagatg  1860
aactattatc tgttacctgg tgcctccaaa acactgccgc acgtatttat cagctctaac  1920
gcgtggaaga aatcacacgg gatcccggat gagatcatgt atggttataa ccaaaacaaa  1980
cacttaaaga gtagccctaa cttcgactta gaattctgcc ggaagttaat cgactattac  2040
aaaagagtgca ttgactcata tcctaattac caaattttca actttaagtt tgcgccaca  2100
gagacctaca acgacatcag tgagttctac aaagacgtcg agcgccaagg ctataagatt  2160
gagtggagtt atatcagtga agacgacatc aatcagatgg atcgcgacgg ccagatttat  2220
ttattccaga tttacaacaa agacttcgca ccaaactcta aaggcatgca aaaccttcac  2280
acgctctatc ttaagaatat tttttctgaa gagaacctga gtgacgtggt gattaagttg  2340
aacggtgaag cggaattgtt ctttcggaaa tcgagtatcc aacacaagcg cggccacaaa  2400
aaaggcagcg ttcttgtcaa caaaacttat aagactacgg agaagactga aaatggtcaa  2460
ggcgagattg aagtaattga atcggttcct gaccaatgct atctcgagtt agtaaaaatac  2520
tggtctgagg gggggtcgg ccaactgagt gaagaggcaa gcaaatacaa ggacaaggtc  2580
tcgcactacg cagccactat ggatatcgta aaagaccgcc ggtatacgga ggacaaattt  2640
ttcattcata tgccaatcac gattaacttt aaggcagata accgtaacaa cgtgaatgaa  2700
aaagtgctta aatttatcgc tgagaacgac gacctgcacg ttatcgggat tgaccgcggt  2760
gaacggaatc tcctttacgt tagtgtcatt gactccgcg gccgcatcgt tgaacaaaag  2820
tcattcaata tcgttgagaa ctacgagtct agtaagaatg tgatccgccg gcatgattac  2880
cgcggtaaat tagtgaacaa ggagcattat cgcaatgaag cccgtaagag ttggaaagaa  2940
atcgggaaga ttaaagagat caaagaaggg tacttgtcac aggttattca cgaaatctct  3000
aagttggttt taaatataaa cgcaatcatc gtaatggagg atcttaacta cgggtttaaa  3060
cgcgggcgct tcaaagtgga acgccaggtg tatcagaaat cgaaacgat gttgatcaat  3120
aagttggcat atcttgtaga taagagccgg gctgtcgacg aaccaggcgg cctcctgaaa  3180
ggttaccagt taacatatgt gccggacaat ttgggcgaat tgggttcaca gtgtgggatc  3240
atcttctacg ttccggccgc atacacgagc aaaatcgatc cagtcaccgg gtttgtcgac  3300
gtctttgact tcaaagccta tagtaacgcc gaagcccgcc tcgacttcat caataaatta  3360
gactgcatcc ggtatgacgc gcctcggaat aaattcgaaa ttgctttcga ctatgggaac  3420
ttccgcaccc accacacaac gttagctaag acgagttgga caatcttttat tcatggtgac  3480
cgcatcaaga aagaacgcgg ctcatacggc tggaaggatg aaatcattga catcgaggcg  3540
cgcatccgga agctgttcga ggataccgat attgagtacg cggatggcca taatctcatc  3600
ggggatatca acgagctcga atctccgatt cagaaaaaat ttgttgggga actctttgat  3660
attattcggt ttacagtgca attgcggaac agcaagagtg aaaaatacga cgggacggaa  3720
aaggaaatacg acaagatcat cagtcctgta atggacgagg aagtgtctt ctttaccact  3780
gattcttaca tccgcgccga cggcacagag ctcccgaagg acgcagacgc gaacggtgcg  3840
tactgcatcg cgttaaaagg cctgtatgac gtgctcgctg tcaaaaata ctggaaggaa  3900
gggaaaaat ttgatcggaa actttttagca atcactaact acaactggtt cgactttatc  3960
cagaaccggc gctttggcgc gccaaaaagg ccggcggcca cgaaaaaggc cggccaggca  4020
aaaaagaaaa aggctagcgg cagcggcgcc ggatccccaa agaagaaaag gaaggttgaa  4080
gaccccaaga aaaagaggaa ggtgtgataa                                    4110
```

|  |  |
|---|---|
| SEQ ID NO: 105 | moltype = AA length = 1463 |
| FEATURE | Location/Qualifiers |
| REGION | 1..1463 |

```
                        note = Description of Artificial Sequence: Synthetic
                        Cas12a/Cpf1 [Catenovulum sp. CCB-QB4] sequence
source                  1..1463
                        mol_type = protein
                        organism = synthetic construct
SEQUENCE: 105
MSDRLDVLTN QYPLSKTLRF ELKPVGATAD WIRKHNVIRY HNGKLVGKDA IRFQNYKYLK    60
KMLDEMHRLF LQQAVLEPN SNQAQELTAL LRAIENNYCN NNDLLAGDYP SLSTDKTIKI    120
SNGLSKLTTD LFDKKFEDWA YQYKEDMPNF WRQDIAELEQ KLQVSANAKD QKFYKGIIKK   180
LKNKIQKSEL KAETHKGLYS PTESLQLLEW LVRRGDIKLT YLEIGKENEK LNELVPLVEL   240
KDIHRNFNNF ATYLSGFSKN RENVYSTKFD RRSGYKATSV IARTFEQNLM FCLGNIAKWH   300
KVTEFINQAN NYELLQEHGI DWNKQIAALE HKLDVCLAEF FALNNFSQTL AQQGIEKYNQ   360
VLAGIAEIAG QPKTQGLNEL INLARQKLSA KRSQLPTLQL LYKQILSKGD KPFIDDFKSD   420
QELIAELNEF VSSQIHGEHG AIKLINHELE SFINEARAAQ QQIYVPKDKL TELSLLLTGS   480
WQAINQWRYK LFDQKQLDKQ QKQYSFSLAQ VERWLATEVE QQNFYQTEKE RQQHKDTQPA   540
NVTTSSDGHS ILTAFEQQVQ TLLTNICVAA EKYRQLSDNL TAIDKQRESE SSKGFEQIAV   600
IKTLLDACNE LNHFLARFTV NKKDKLPEDR AEFWNYEKLQ YIDAFPIYEL YNKVRNYLSK   660
KPFSTEKVKI NFDNSHFLSG WTADYERHSA LLFKFNENYL LGVVNENLSS EEEEKLKLVG   720
GEEEHAKRFIY DFQKIDNSNP PRVFIRSKGS SFAPAVEKYQ LPIGDIIDIY DQGKFKTEHK   780
KKNEAEFKDS LVRLIDYFKL GFSRHDSYKH YPFKWKASHQ YSDIAEFYAH TASFCYTLKE   840
ENINFNVLRE LSSAGKVYLF EIYNKDFSKN KRGQGRDNLH TSYWKLLFSA ENLKDVVLKL   900
NGQAEIFYRP ASLAETKAYT HKKGEVLHHK AYSKVWEALD SPIGTRLSWD DALKIPSITE   960
KTNHNNQRVV QYNGQEIGRK AEFAIIKNRR YSVDKFLFHC PITLNFKANG QDNINARVNQ  1020
FLANNKKINI IGIDRGEKHL LYISVINQQG EVLHQESFNT ITNSYQTANG EKRQVVTDYH  1080
QKLDMSEDKR DKARKSWSTI ENIKELKAGY LSHVVHRLAQ LIIEFNAIVA LEDLNHGFKR  1140
GRFKIEKQVY QKFEKALIDK LSYLAFKDRT SCLETGHYLN AFQLTSKFKG FNNLGKQSGI  1200
LFYVNADYTS TTDPLTGYIK NVYKTYSSVK DSTEFWQRFN SIRYIASENR FEFSYDLADL  1260
KQKSLESKTK QTPLAKTQWT VSSHVTRSYY NQQTKQHELF EVTARIQQLL SKAEISYQHQ  1320
NDLIPALASC QSKALHKELI WLFNSILTMR VTDSSKPSAT SENDFILSPV APYFDSRNLN  1380
KQLPENGDAN GAYNIARKGI MLLERIGDFV PEGNKKYPDL LIRNNDWQNF VQRPEMVNKQ  1440
KKKLVKLKTE YSNGSLFNDL AFK                                          1463

SEQ ID NO: 106          moltype = DNA   length = 4392
FEATURE                 Location/Qualifiers
misc_feature            1..4392
                        note = Description of Artificial Sequence: Synthetic
                        Cas12a/Cpf1 [Catenovulum sp. CCB-QB4] sequence
source                  1..4392
                        mol_type = other DNA
                        organism = synthetic construct
SEQUENCE: 106
atgagtgatc gtctagatgt tttaaccaac caatatccac tatctaaaac gttgcgtttc    60
gaattaaagc cagttggcgc aacagcagat tggattcgca agcacaatgt tatccgttat   120
cataacggta agttggttgg caaagatgcg attcgctttc aaaactacaa gtatcttaaa   180
aagatgcttg atgaaatgca tcgcttgttt ttacaacaag ctttagtgct agagccaaat   240
agcaatcaag cgcaagaact taccgcatta ttgcgcgcta tcgagaataa ctattgtaat   300
aacaatgacc tactggcagg agactatccg tcattaagca ctgataaaac cattaaaata   360
tcaaacgggt taagtaaatt aacgactgac ttattcgata aaaagtttga agattgggct   420
taccaatata agaggatat gcctaatttt tggcgccaag acattgcaga gcttgaacaa   480
aagttacaag tttcagctaa cgctaaagat caaaaattct ataaaggtat aattaaaaag   540
ctcaaaaata aaattcaaaa gagcgagttg aaagctgaaa cccataaagg attatactcg   600
cctacagaaa gcttacagct gctagagtgg ctagtcagac gaggtgatat taaattaacc   660
tatttggaaa taggtaagga gaatgaaaag ctaaacgagt tagtaccatt agttgaattg   720
aaggacatac atcgtaactt caataatttt gcgacctatc ttagtggctt tagtaaaaac   780
cgagagaatg tttactcaac taagtttgat aggcgaagtg gttacaaagc aacatctgtt   840
attgcgcgaa cgtttgaaca aaacttaatg ttttgtcttg gcaatattgc taagtgcat    900
aaggttacag aattattaa ccaagcgaat aattatgagc tattgcaaga acatggcatt   960
gactggaaca agcaaattgc cgcattagaa cacaagttag atgtatgtct tgccgaattt  1020
tttgcactaa acaacttcag tcaaactttg gctcaacagg gcattgaaaa atataaccaa  1080
gtgttagcgg gtattgctga aatagcagga cagcctaaaa cacaaggttt aaacgaatta  1140
attaaccttg cccgacaaaa attatcagct aagcgttcac aactgccaac gttgcaactt  1200
ctatacaaac aaattcttag caaggtgat aagccattta ttgatgattt taaatcagac  1260
caagagttga tcgccgagtt aaatgaattt gttagtagtc agatccacgg tgagcacggc  1320
gcgattaaat taatcaatca tgagttagaa agctttatca atgaagccag agcagcaag  1380
caacaaatat atgtgccaaa agataagtta actgagttgt cgttgttact gactggatct  1440
tggcaggcca ttaaccaatg gcgttacaag ctatttgacc aaaagcagtt ggataaacag  1500
caaaagcaat attcttttc gttagcacag gtagaacgat ggctcgcgac tgaggtagag  1560
caacagaact tctatcaaac agaaaaggaa cgccagcagc acaaggatac acagccagtc  1620
aatgtaacta caagtagtga cggtcattct attttgactg cgtttgagca gcaggtgcaa  1680
acgttattaa ccaatatttg cgtggctgct gaaaaatatc gccagttaag tgataactta  1740
acggccatag acaaacagcg agaaagtgag tcgagtaaag ggtttgagca aatcgccgtt  1800
attaaaacgt tactcgatgc ctgcaatgaa ctaaatcact ttttagcccg ttttacggtt  1860
aacaaaaaag ataaattacc ggaagataga gctgagtttt ggtacgaaaa actgcaagct  1920
tatattgatg cttttcctat ctatgagctt tacaacaagg ttagaaacta cctttcgaaa  1980
aagccatttt cgaccgaaaa agtaaaaatt aattttgata tagccatttt tttatccggt  2040
tggactgctg attatgaaag gcactctgct ctgctattta aatttaatga aaattattta  2100
cttggcgtag taaacgaaaa ccttagcagt gaagaagagg agaaacttaa attagttgga  2160
ggggaggaac atgcgaagcg atttatttat gattttcaaa aaatagataa ctcaaaccca  2220
ccaagagtat ttataagatc gaaaggtagt tcatttgctc cagcggttga aaaatatcaa  2280
```

-continued

```
ttgccaattg gtgacataat cgatatttac gatcaaggta aatttaaaac tgagcataag  2340
aaaaaaaatg aggccgagtt taaggacagc ctggttaggc taattgatta ttttaagcta  2400
ggttttagtc gccatgattc gtataagcat tacccattta aatggaaagc cagtcatcaa  2460
tattctgata tcgcagaatt ctatgctcat actgcaagct tttgctacac actaaaagaa  2520
gaaacataa attttaacgt gttgagggag ttatcaagtg caggaaaagt ttatttattt  2580
gaaatttaca acaaagactt ttctaaaaat aaacgaggtc aggggcgaga taacttacac  2640
accagttact ggaagctgct atttagcgca gaaaacctca aagacgtagt tctaaagctg  2700
aatgggcaag cggaaatttt ttacagacct gcaagtctcg ctgaaactaa agcatacacc  2760
cataaaaaag gcgaagtttt gaaacacaaa gcttacagca aagtatggga agcttttagat 2820
tctccaatag gaactcgatt aagctgggat gatgctttaa aaataccttc tatcactgaa  2880
aaaacgaatc ataataatca gagggtagtt caatataatg gtcaagaaat cgggcgaaaa  2940
gcagagttcg cgatcataaa aaatcgccgc tattcggtag acaagttttt atttcattgt  3000
ccaatcacct taaatttcaa ggcgaatggg caagacaata tcatgcccg tgttaatcag  3060
tttttagcga ataataaaaa aatcaacatt attggtattg atcggggtga aaagcactta  3120
ctgtatattt ctgttattaa tcaacaaggt gaagtgctgc accaagagtc gtttaatacc  3180
atcaccaaca gttatcaaac agctaacggt gaaaagcgcc aagtagtcac agactatcac  3240
caaaagcttg atatgagtga agataagcgt gacaaagccc gaaaatcttg gtcgacaatc  3300
gaaaatataa aagaactcaa ggctggctat ttgtcgcaatg ttgtccatcg actagcacaa  3360
ttgattattg agtttaatgc cattgttgcg ctcgaagatt taaatcatgg gtttaagcgt  3420
gggcgattta aaattgaaaa acaggttat caaaaatttg aaaagcgct tatcgataag  3480
cttagctacc ttgcgtttaa agacaggact tcctgtttag aaacaggcca ttatctcaat  3540
gcgtttcagc taactagtaa atttaaaggg tttaataacc tatcgggcatt  3600
ttgttctatg tgaatgccga ttacacctca accactgatc cactaacggg ctatattaaa  3660
aacgtttata aaacctatag cagcgtcaaa gacagtactg aatttttggca gcggtttaat  3720
agtattcgct atatcgcaag cgagaatcga tttgaattta gctacgactt agctgatctc  3780
aaacaaaaat cattagagag taaaaccaag caaacacctc ttgcgaaaac acaatggaca  3840
gtgagtagtc acgtgactcg ctcgtactat aaccaacaaa ctaaacagca tgagctgttt  3900
gaagtaacag ctcggataca acaattgctt agcaaagccg aataagtta ccagcaccaa  3960
aacgatttaa ttcctgcttt agccagttgc caatctaaag cgctacataa agagcttatt  4020
tggctattta acagcatttt gacaatgcgc gtgacagaca gcagcaagcc atcggcaacc  4080
agcgaaaacg actttatttt atcgccagtc gcgccttact ttgatagcag aaacttaaat  4140
aaacaactgc cagaaaatgg tgatgctaat ggcgcgtata acatagcgcg taaaggcatc  4200
atgctgttag aaaggattgg tgattttgtg ccagaaggta ataaaaaata tccagattta  4260
ctgatccgca ataatgattg gcagaacttt gttcagcgac cagagatggt caataagcaa  4320
aagaaaaaac tggttaaatt aaagacggaa tacagcaatg aagcttatt taatgatctc  4380
gcatttaaat ga                                                      4392
```

SEQ ID NO: 107       moltype = AA   length = 1525
FEATURE              Location/Qualifiers
REGION               1..1525
                     note = Description of Artificial Sequence: Synthetic
                     polypeptide
source               1..1525
                     mol_type = protein
                     organism = synthetic construct SEQUENCE: 107
```
MGHHHHHSS GLVPRGSGTM SDRLDVLTNQ YPLSKTLRFE LKPVGATADW IRKHNVIRYH   60
NGKLVGKDAI RFQNYKYLKK MLDEMHRLFL QQALVLEPNS NQAQELTALL RAIENNYCNN  120
NDLLAGDYPS LSTDKTIKIS NGLSKLTTDL FDKKFEDWAY QYKEDMPNFW RQDIAELEQK  180
LQVSANAKDQ KFYKGIIKKL KNKIQKSELK AETHKGLYSP TESLQLLEWL VRRGDIKLTY  240
LEIGKENEKL NELVPLVELK DIHRNFNNFA TYLSGFSKNR ENVYSTKFDR RSGYKATSVI  300
ARTFEQNLMF CLGNIAKWHK VTEFINQANN YELLQEHGID WNKQIAALEH KLDVCLAEFF  360
ALNNFSQTLA QQGIEKYNQV LAGIAEIAGQ PKTQGLNELI NLARQKLSAK RSQLPTLQLL  420
YKQILSKGDK PFIDDFKSDQ ELIAELNEFV SSQIHGEHGA IKLINHELES FINEARAAQQ  480
QIYVPDKLT ELSLLLTGSW QAINQWRYKL FDQKQLDKQQ KQYSFSLAQV ERWLATEVEQ  540
QNFYQTEKER QQHKDTQPAN VTTSSDGHSI LTAFEQQVQT LLTNICVAAE KYRQLSDNLT  600
AIDKQRESES SKGFEQIAVI KTLLDACNEL NHFLARFTVN KKDKLPEDRA EFWYEKLQAY  660
IDAFPIYELY NKVRNYLSKK PFSTEKVKIN FDNSHFLSGW TADYERHSAL LFKFNENYLL  720
GVVNENLSSE EEEKLKLVGG EEHAKRFIYD FQKIDNSNPP RVFIRSKGSS FAPAVEKYQL  780
PIGDIIDIYD QGKFKTEHKK KNEAEFKDSL VRLIDYFKLG FSRHDSYKHY PFKWKASHQY  840
SDIAEFYAHT ASFCYTLKEE NINFNVLREL SSAGKVYLFE IYNKDFSKNK RGQGRDNLHT  900
SYWKLLFSAE NLKDVVLKLN GQAEIFYRPA SLAETKAYTH KKGEVLKHKA YSKVWEALDS  960
PIGTRLSWDD ALKIPSITEK TNHNNQRVVQ YNGQEIGRKA EFAIIKNRRY SVDKFLFHCP 1020
ITLNFKANGQ DNINARVNQF LANNKKINII GIDRGEKHLL YISVINQQGE VLHQESFNTI 1080
TNSYQTANGE KRQVVTDYHQ KLDMSEDKRD KARKSWSTIE NIKELKAGYL SHVVHRLAQL 1140
IIEFNAIVAL EDLNHGFKRG RFKIEKQVYQ KFEKALIDKL SYLAFKDRTS CLETGHYLNA 1200
FQLTSKFKGF NNLGKQSGIL FYVNADYTST TDPLTGYIKN VYKTYSSVKD STEFWQRFNS 1260
IRYIASENRF EFSYDLADLK QKSLESKTKQ TPLAKTQWTV SSHVTRSYYN QQTKQHELFE 1320
VTARIQQLLS KAEISYQHQN DLIPALASCQ SKALHKELIW LFNSILTMRV TDSSKPSATS 1380
ENDFILSPVA PYFDSRNLNK QLPENGDANG AYNIARKGIM LLERIGDFVP EGNKKYPDLL 1440
IRNNDWQNFV QRPEMVNKQK KKLVKLKTEY SNGSLFNDLA FKAAAKRPAA TKKAGQAKKK 1500
KASGSGAGSP KKKRKVEDPK KKRKV                                      1525
```

SEQ ID NO: 108       moltype = DNA  length = 4581
FEATURE              Location/Qualifiers
misc_feature         1..4581
                     note = Description of Artificial Sequence: Synthetic
                     polynucleotide
source               1..4581

```
                mol_type = other DNA
                organism = synthetic construct
SEQUENCE: 108
atggggcatc accaccaca ccactcgtcg ggtcttgttc cacgtggttc tggtaccatg    60
tctgatcgcc tggacgtgct tactaaccaa tacccattat cgaaaacttt gcgcttcgaa   120
ttgaagccgg ttggagccac agctgactgg attcgcaaac acaacgttat ccgctatcat   180
aatggtaaac tggttggaaa ggatgcgatc cgttttcaaa attataagta tctgaagaaa   240
atgcttgatg agatgcatcg cttatttctt cagcaagcac tggtgttgga gccaaatagc   300
aaccaggcgc aggagttgac cgcactgctg cgtgctattg agaataatta ttgcaacaac   360
aacgacctgc tggcgggcga ttatcccagc ctctctaccg ataagaccat taaaatcagc   420
aacggcctta gcaagctgac cacggatctg ttcgataaga agttcgaaga ctgggcatac   480
caatacaaag aagatatgcc caatttctgg cgtcaagata ttgcggaatt agagcaaaag   540
cttcaggtga gtgcgaacgc aaaagatcaa aagttctaca aagggatcat caagaagctg   600
aagaataaga tccagaagtc tgaactgaaa gcggaaacgc acaagggctt atactcacct   660
acggagtcac tgcaactgct ggagtggctg gtacgtcgtg gcgatattaa actgacttac   720
ttagagattg gtaaagagaa cgagaaactt aatgaactgg tcccgctggt cgaacttaag   780
gacattcatc gcaatttcaa taatttcgcc acatatcttt ctggcttcag caagaatcgt   840
gagaatgtgt actcaaccaa atttgatcgt cgttcgggtt ataaagccac cagtgtaatc   900
gcacgcacgt tcgaacagaa tttaatgttc tgtcttggta acattgccaa gtggcacaag   960
gtgacagaat tcatcaacca ggcgaacaat tacgagctcc tgcaggagca cggcatcgat  1020
tggaataagc aaattgccgc gctggaacac aaactgacg tgtgtctcgc agagttcttc   1080
gcgcttaata acttctcaca aacccttgca caacagggta tcgaaaagta taaccaggtc  1140
ttggccggca tcgccgagat tgcaggccaa cccaagaccc agggcctgaa cgaactcatt  1200
aacctggccc gtcagaaatt gtctgccaaa cgctcacaac tgcctacgtt gcaactcctt  1260
tacaaacaaa tcttaagcaa gggtgataag ccattcatcg acgattttaa aagcgaccaa  1320
gagttgatcg ccgaattaaa tgagtttgta agcagccaga ttcacggaga gcatggtcag  1380
atcaaattaa ttaatcacga acttgaaagc tttatcaatg aagcccgtgc agcgcagcaa  1440
cagatttatg tgcccaagga caagcttacc gaattaagtc ttctcttaac gggcagttgg  1500
caagctatta atcaatggcg ttacaaactg ttcgaccaga aacagctgga taaacaacag  1560
aaacaatatt catttagcct ggcccaggtt gaacgctgac tggcaactga ggttgagcaa  1620
caaaacttct accaaaccga aaaggagcgc cagcagcata aagatacgca gccggcgaac  1680
gtcaccacca gcagcgatgg aacacagcat ttaacagcat ttgagcaaca ggtgcagacc  1740
ttattaacca acatctgtgt tgctgccgag aaatatcgcc aattaagtga taatctcaca  1800
gccatcgata aacaacgcga gagcgaatca agtaagggat tcgagcaaat cgcggtgatt  1860
aaaaccttgc tggacgcgtg taacgagctg aatcactttc tggcacgctt cacggtcaac  1920
aagaaggaca aactccccga agatcgcgca gaatttggt atgaaaagtt acaagcgtac   1980
attgacgcgt ttccgatcta cgagctgtat aataaagtgc gtaattactt aagcaagaag  2040
ccgtttagca ctgagaaagt caaaattaat tttgacaatt cccatttcct gtcgggttgg  2100
acggcggact atgagcgtca cagcgcctta ttattcaaat ttaatgaaaa ttacctgctg  2160
ggtgtagtga atgagaactt aagcagcgag gaagaagaaa agctgaagct cgtgggcggc  2220
gaagaacatg ccaagcgctt catttatgat tttcagaaaa tcgacaactc aaacccaccg  2280
cgcgttttca ttcgtagcaa ggggtcatcg ttcgcacctg cggtcgaaaa gtatcagtta  2340
ccgattggcg atatcattga catttacgat cagggtaaat taagacaga acacaagaag   2400
aagaatgagg ccgagtttaa agacagtctg gtacgtttga tcgattattt taagctgggc  2460
ttctctcgcc atgacagcta taagcactac ccattcaagt ggaaagccag tcatcaatat  2520
agcgacattg cggaatttta cgctcatacc gcctcatttt gttacacgct taaggaagaa  2580
aacatcaatt ttaacgttct gcgtgagttg tcgtcggcgg gcaaagtata tctcttcgaa  2640
atttacaata aggatttctc aaagaacaag cgcggccaag gacgcgacaa cttgcatacc  2700
agttattgga agttgctgtt ctcggctgag aacctgaagg atgttgtgct gaaattaaac  2760
ggccaagcgg agatctttta ccgcccagcg tctttggccg aaaccaaggc ctacacccat  2820
aagaaagggg aagtactgaa acataaggct tatagcaaga tgtgggaagc ctgggattct  2880
cccattggca cccgcctgag ctgggacgat gctttaaaga tcccgtctat taccgagaag  2940
accaatcaca ataatcagcg tgttgtccag tacaacggcc aagaaattgg ccgcaaagcg  3000
gagttcgcta ttatcaagaa ccgccgttat tccgtcgata aattcctctt tcactgcccg  3060
attacactca acttcaaggc gaacggccag gacaacatta acgcacgcgt taatcaattc  3120
ctggcaaata acaagaagat caacattatt ggaattgacc gtggtgaaaa gcatttactg  3180
tatatcagcg tgattaatca acaaggcgaa gtcctgcatc aggaaagctt caatacaatc  3240
acgaattcat atcagaccgc caatggcgag aaacgccaag tagtcactga ctatcaccag  3300
aagttggaca tgagcgagga caaacgcgat aaagcacgta agagctggag tacaatcgaa  3360
aatatcaaag agctgaaggc ggggtatctg agccacgttg tacatcgcct cgcgcaactg  3420
attatcgaat ttaatgccat tgttgcgttg gaagatctta ccacggggtt caaacgcgga  3480
cgttttaaaa tcgaaaagca agtgtatcag aagttcgaaa aggcgctgat cgacaaattg  3540
agctacttag cgtttaagga tcgcacgtcg tgtctggaaa ctggacatta cttgaatgcc  3600
tttcaattaa cctcaaagtt caaaggcttt aacaacctg cgcaggattt tg          3660
ttctacgtta acgccgatta cacgagcacc acggatccct aacaggcta tattaagaac   3720
gtatacaaaa cctactcctc ggtgaaggat tcgaccgaat tttggcagcg ctttaactct  3780
atccgctata ttgcgagcga gaaccgtttt gaatttagct acgacttagc ggacctgaaa  3840
cagaagtcgc tcgagagtaa aaccaaacag ccccctctcg ccaagcccca atggacggtc  3900
tctagccacg ttacccgttc ctattacaac cagcagacga agcaacatga gttattcgaa  3960
gtgacagcgc gcattcagca attgcttagc aaagcagaaa tcagctatca acatcaaaac  4020
gacttgatcc ctgcgttagc atcatgtcaa agtaaggcgt tacacaagga gttgatttgg  4080
ctgttcaaca gcatcctgac tatgcgcgtc acggactcaa gcaaaccgtc gcgacctcg   4140
gagaatgatt ttatcctgag cccggtagcg ccgtacttcg actccgcaa tctgaataag  4200
cagctgccgg aaaacgtcga cgcgaacggc gcataacaata tcgctcgtaa aggtatcatg  4260
cttctggaac gtatcgggga cttcgtcccg gaaggtaaca agaagtaccc cgatttactg  4320
atccgcaata atgactggca gaattttgta caacgcccgg agatggtgaa caagcagaag  4380
aagaaactcg tgaagttgaa aacggaatac tctaatggca gcctcttcaa tgatttggcg  4440
tttaaggcca cagctaagcg ccccgccgcg actaagaaag cgggtcaagc gaagaagaag  4500
aaagcgtcgg ggtcgggagc gggcagtccg aagaagaagc gtaaagtaga ggatccgaag  4560
```
aagaaacgca aagtataata a                                              4581

SEQ ID NO: 109         moltype = DNA   length = 4581
FEATURE                Location/Qualifiers
misc_feature           1..4581
                       note = Description of Artificial Sequence: Synthetic
                       polynucleotide
source                 1..4581
                       mol_type = other DNA
                       organism = synthetic construct SEQUENCE: 109
atgggccacc atcatcatca tcatagcagc ggcctggtgc cgcgcggcag cggtaccatg    60
tcggatcgtc ttgatgtact tacaaatcaa taccctctca gtaaaacttt acggttcgag   120
ctgaagccag ttggggcgac cgctgattgg attcgtaaac acaatgtaat ccgttatcac   180
aatggtaagt tagtgggcaa agacgccatt cgctttcaga actataagta cctgaagaaa   240
atgcttgacg agatgcaccg gctgtttttg cagcaagcac ttgtattaga gcctaattca   300
aaccaggccc aggaactcac cgccctctta cgcgcaatcg agaacaatta ttgcaacaac   360
aatgatttac tggcgggtga ctacccttct ctctcaacag acaagactat taaaatttca   420
aacggtttat caaaattaac cactgatctc tttgacaaaa agttcgaaga ctgggcgtat   480
caatataaag aagacatgcc taactttttgg cgtcaagaca ttgcggagct tgagcagaaa   540
ctgcaggttt cggcgaacgc taaagatcag aagtttttata aagggattat caaaaaactt   600
aagaataaaa ttcagaagtc ggaactcaag gccgaaaccc acaaggtgct ttattcaccg   660
acggagtctc tccagttact ggagtggctt gtacgtcgtg gcgacatcaa gttgacctat   720
ttagagattg gtaaggagaa cgagaaattg aatgagttag taccactggt agagctgaag   780
gacatccatc ggaactttaa caatttcgcc acataccttt ctgggttctc gaaaaaccgc   840
gagaatgttt actccacaaa gttcgaccgg cggagcgctc acaaggctac atccgttatc   900
gctcggacat tcgagcaaaa ccttatgttc tgtctcggga acatcgccaa atggcacaag   960
gttacggaat tatcaacca ggcgaacaac tacgaacttc ttcaggagca cggtattgat  1020
tggaacaaac aaatcgcggc cttagagcat aagtagacg tttgtctcgc agagtttttc  1080
gcgctcaata attttttcgca aacattagcc caacaaggca tcgaaaata caatcaggtc  1140
ttggctggta tcgcgaaaat cgccggtcaa ccgaagaccc agggcttgaa cgagctcatc  1200
aatttagcgc gtcaaaagct gtcggccaaa cggtcgcagc tcccaacgtt gcagttgctc  1260
tacaaacaga tcttgtcaaa aggcgacaag ccattcatcg acgatttcaa gagcgaccag  1320
gaattgattg cggaacttaa cgagttcgtc tcatcgcaaa ttcacgggga gcatggccga  1380
attaaactca tcaaccacga gttagaaagt ttcattaatg aagcccgtgc cgcgcaacag  1440
cagatctatg tacctaaaga taagcttact gaattatcat tgctcttgac gggttcctgg  1500
caggctatta tcaatggcg gtacaagtta tttgaccaaa agcagttaga caagcaacag  1560
aaacaatact ctttttcgct ggcgcaggtg gagcgctggt tggcgacgga ggtggagcag  1620
cagaactttt atcagacgga gaaagagcgc caacaacata aagcacgca gccagctaac  1680
gtcactacga gttctgatgg ccatagtatt cttactgctt tcgagcaaca agttcagacc  1740
ttacttacga atatctgcgt cgcggccgag aaatatcgtc agttatcaga taacctcacc  1800
gcgatcgaca agcagcggga gtccgagtcg agtaaggggt tcgaacaaat tgcggtcatt  1860
aagacactct tagacgcttg caacgaactt aatcatttcc ttctcggttt cacggtcaac  1920
aagaaggata aattaccgga ggaccgcgct gagttttggt acgagaaact ccaggcttac  1980
atcgatgcct tccctatttta tgaactctat aacaaggtcc ggaactactt aagtaagaag  2040
ccgttctcta cggaaaaagt gaaaatcaac tttgacaaca gccattttttt atccggttgg  2100
acagccgact acgaacggca ctcggctctc ctttttaatg aaaaa ctatctcctt  2160
ggcgttgtca atgaaaattt gagttccgaa gaagaggaaa agctgaagct cgtcggcggc  2220
gaagagcatg ctaagcggtt tatttacgac ttccagaaaa ttgataattc caaccctccg  2280
cggggttttca tccgtagcaa agggagctcc tttgctcctg ccgtcgaaaa ataccagctg  2340
cctatcgggg acattatcga catctatgac caaggcagt ttaaaacaga acacaaaaag  2400
aagaatgaag ctgagttcaa ggactccctg gttcgcttga tcgattactt caagctgggt  2460
tttagtcggc acgacagtta taagcactac ccttttaaat ggaaagcttc tcaccagtac  2520
agcgatatcg cggaattcta cgcgcatact gccagtttct gttatacttt gaaggaggaa  2580
aacattaact ttaatgtgct ccgtgagttg agttccgcag gtaaagtgta tctcttttgaa  2640
atctataaca aagatttctc taagaataag cgtgggcaag ggcgggataa tctccatacc  2700
agctattgga agctgctctt ctcggcggaa aatctcaaag acgtcgtctt aaaactgaac  2760
ggtcaagccg aaatcttcta ccggccagcc tccctcgcag aaaccaaagc ttacacccat  2820
aagaaaggtg aggttctcaa acataaagcc tacagcaagc tttgggaagc tctgactct  2880
ccgatcggga cacgtttgag ctgggacgat gctctcaaaa tccctagcat tacggagaaa  2940
accaatcata taaccaacg cgtggtgcaa tacaacgggc aagaaatcgg tcggaaggcg  3000
gagttcgcaa ttattaagaa tcgccggtac tcagttgata gtttctctt ccactgccct  3060
attacattga acttcaaagc taatggccaa gacaacatca tgcccgcgt aaatcaattc  3120
ctcgcgaata ataagaaaat taacattatc ggtatcgaca gggcgagaa gcacctcttg  3180
tatatctcag taattaatca acagggtgaa gtattgcacc aggagagctt aacacaatt  3240
accaactcgt atcagacagc taacggtgaa aagcggcaag tcgtaaccga ttaccatcaa  3300
aagctggata tgtcagaaga caagcgggat aaagcacgga aaagctggag tactatcgaa  3360
aatatcaagg aattgaaggc aggctatctt tcacacgtag tgcatcggtt agctcagttg  3420
atcattgaat ttaacgcgat cgtggcctta gggaccgaa accatggctt taaacgggac  3480
cgtttcaaaa tcgaaaagca agtataccag aagtttgaaa agcactgat cgataaattg  3540
tcatatcttg ctttttaaga ccggacatcg tgtttgaaaa ccgggcatta tctgaatgcc  3600
tttcagttga cctcaaaatt taagggcttt aacaatctgg gtaaacagtc cggtatcctt  3660
ttctacgtaa acgcagatta taccagtacg acagacccgc tcaccgggta tatcaaaaat  3720
gtgtataga cttacagttc ggttaaagac agtactgaat tttggcagcg gcttcaacagt  3780
atccggtata tcgccagcga gaatcgttt gagtttagtt atgacctcgc ggatcttaaa  3840
cagaagagcc tcgagtcgaa aacaaaacaa actccactgg caaaacccca atggacggtc  3900
agttcacacg taacacgtag ttactacaac cagcaaacaa acagcacga ttattcgaa  3960
gtaacagcgc ggatccagca actcctgagt aaggccgaaa tttcatatca acatcaaaac  4020
gacttgattc cggctcttgc atcatgccag tcgaaagctt gcacaaaga gctgatttgg  4080

```
ttattcaact cgattctcac tatgcgtgta accgactcta gtaaaccttc tgctacatcc    4140
gagaatgatt tcattttaag tcctgtcgcc ccatacttcg atagccgcaa tctgaataaa    4200
cagcttccag aaaatggtga cgcaaatggg gctataata ttgcacgtaa aggcattatg    4260
ttgctcgaac gcatcggcga ctttgtgcct gaaggtaaca agaagtaccc agatctgctc    4320
atccggaaca acgattggca aaatttcgtc cagcgcccgg aaatggttaa caaacaaaaa    4380
aaaaaattgg ttaagttaaa aacggagtac tcaaatggct cgctgttcaa tgatttagcg    4440
ttcaaaggcg cgccaaaaag gccggcggcc acgaaaaagg ccggccaggc aaaaaagaaa    4500
aaggctagcg gcagcggcgc cggatcccca agaagaaaaa ggaaggttga agaccccaag    4560
aaaaagagga aggtgtgata a                                             4581
```

SEQ ID NO: 110          moltype = DNA  length = 4581
FEATURE               Location/Qualifiers
misc_feature        1..4581
                        note = Description of Artificial Sequence: Synthetic
                        polynucleotide
source                 1..4581
                        mol_type = other DNA
                        organism = synthetic construct

```
SEQUENCE: 110
atgggccacc atcatcatca tcatagcagc ggcctggtgc cgcgcggcag cggtaccatg      60
tctgaccggc ttgacgtact cactaatcaa tacccattga gtaaaccct gcgtttcgag     120
ctcaagcctg ttggggcgac cgcagattgc attcgcaaac acaacgttat tcgctatcac     180
aatggtaaac tggtcgggaa agatgcaatt cggtttcaga attacaagta cctcaaaaag     240
atgctggatg agatgcatcg gttattcctt caacaggccc tggttttgga gccaaactca     300
aaccaagcgc aggaactgac agcgctgctt cgcgcaatcg agaacaatta ttgcaataat     360
aacgacttgc tcgcgggtca ctatccttct cttagtacga ataagacaat taaaatttca     420
aatgggttga gcaagttgac gacagatctg tttgataaaa agtttgaaga ctgggcgtac     480
cagtacaaag aggatatgcc taactttggt cgccaagaca ttgctgaatt ggaacagaag     540
ttgcaagtat ccgccaatgc gaaagatcag aaattctata aggtattat caagaagctc     600
aagaataaga tccaaaaatc tgagttaaag gcggaaacac acaagggct ttattcgcct     660
actgaatccc ttcagttgct cgaatggtta gttcgtcgtg gtgacatcaa gctgacatac     720
ctcgaaatcg gcaaggagaa cgagaagctc aacgaactcg ttccttttggt agagcttaag     780
gacattcatc gcaatttcaa caatttcgct acatacttaa gtgggttctc taaaaatcgc     840
gaaaatgtct attcaaccaa gttgaccgt cgctcgggct ataaagcaac atctgtcatt     900
gcgcgtacat ttgaacaaaa cttgatgttt tgtttgggga acattgcaaa gtggcataaa     960
gtgacagagt ttatcaacca agccaataat tacgagctcc ttcaagagca tggtattgat    1020
tggaataagc agatcgctgc attggagcat aaactcgatg tttgcttggc ggagttttt    1080
gctttaaata atttctcaca aacacttgca cagcagggca tcgaaaagta taatcaggta    1140
ctggccggta tcgcggagat cgccgggcaa cctaaaaccc aaggtcttaa tgagttaatc    1200
aatctcgccc gccagaagct cagtgcgaag cgctcccaat tgccaacgct tcagcttctt    1260
tataaacaga ttctcagcaa gggtgacaaa ccgttcatcg atgactttaa atcggaccag    1320
gaactgattg cggaacttaa cgagtttgta tcatcgcaaa tccacggcga gcatggtgcg    1380
attaaactta tcaaccacga attagagagc tttatcaacg aggctcgcgc tgcgcaacaa    1440
cagatctatg tcccaaagga caagttaacg gagcttttcct tattgctgac gggttcttgg    1500
caagcgatta tcaatggcg ttataagtta tttgaccaga gcaactggac aaacagcaa    1560
aagcagtaca gcttttctct tgctcaggtc gagcgttggc tggcgacgga ggttgagcag    1620
cagaacttt atcagacgga gaaagagcgc cagcaacaca aagtacgcgg accggctaat    1680
gttactacaa gctctgacgg ccatagtatt ttaaccgcct ttgaacaaca ggtacagaca    1740
cttcttacca atatttgtgt cgccgctgag aaatatcgtc aactctccga taacttaacc    1800
gcgattgaca agcagcgcga gtctgagtcg agtaaaggct tcgaacagat cgccgtaatc    1860
aaaacattgc tcgatgcgtg taatgagtta aaccatttc ttgcacgttt tactgtaaac    1920
aaaaagaca agttgcctga agaccgggcc gaattctggt acgagaaact gcaagcctat    1980
atcgatgctt ttcaatttta cgaattgtac aacaaggtcc ggaattattt gtccaaaaaa    2040
ccattctcta ccgaaaaagt gaagattaat tttgacaatt ctcattttct gtcgggctgg    2100
accgccgatt acgaacgcca tagcgccttg ctgttttaaa tcaacgagaa ctaccttttg    2160
ggcgtggtaa acgaaaatct ctcatccgaa gaagaggaga aattgaaatt agtcgggggc    2220
gaagagcatg cgaaacggtt tatttacgat tttcagaaaa tcgacaacag taacccacct    2280
cgtgtgttta ttcggtcgaa gggctctagt tttgctcctg ctgttgaaaa gtaccaatta    2340
ccgattggcg atatcatcga catctatgat caagggaaat tcaagacaga gcataaaaaa    2400
aaaaatgagg ccgagtttaa ggacagtta gtacgtctta tcgactattt caagttgggc    2460
ttctcccggc atgatagtta caagcattat ccttcaagt ggaaagcgtc tcaccagtat    2520
agcgacattg ctgaatttta cgcgcatacg gcttcattct gctatacgtt gaaggaagag    2580
aacatcaatt ttaacgtgct tcgtgagtta tctagtgccg gaaggtcta tcttttcgaa    2640
atttcaaaca aggatttcag caagaataag cgggggcagg ggcgggataa cttgcacacg    2700
tcgtattgga aactcttatt cagcgcgag aatttaaaag acgtggtgct taaactcaat    2760
ggccaggccg aaatcttcta ccgtcctgca agcctggctg aaacaaaagc gtatacccac    2820
aaaaagggtg aagtcttgaa gcacaaggct tacagcaaag tatgggaggc tttagactca    2880
cctattggca cgcgtctgtc ttgggacgat gcttttaaaa tccctagcat caccgaaaaa    2940
acgaaccaca ataatcaacg tgtggtacag tataacgggc aggagattgg gcgcaaggca    3000
gagttcgcga tcattaaaaa ccgtcgctat tcggtagata aattccttt ccattgccct    3060
attacgctga acttcaaggc taatgggcaa gataacatta acgcacgtgt aaaccagttc    3120
ttggcgaata caagaaaat caatatcatt ggtatcgacc ggggcgaaaa gcatcttctg    3180
tatatttctg ttatcaacca gcagggtgag gtgcttcacc aggaatcgtt taatacaatc    3240
accaattctt accagacggc taatggtgaa aaacgtcaga cttcaccacag    3300
aagttagaca tgtcagagga caaacgtgac aaggcgcgta atcatgtc aactattgag    3360
aacatcaagg aacttaaggc tggctacctc tcccacgtcg tccacggtt agcgcaattg    3420
attatcgagt tcaacgctat tgtagcgctc gaggacttga atcacgggtt caagcggggt    3480
cggttcaaaa tcgaaaaaca agtatatcag aagttcgaga aggcgcttat tgataagctg    3540
agttatcttg cgttcaagga tcgtacaagc tgcctctgaaa cgggtcacta tcttaatgcc    3600
```

```
tttcagctca catcgaaatt taagggggttc aacaatttgg gtaaacaatc aggcattttg   3660
ttctatgtaa atgctgacta cacctcgact acgatccgc tgacaggcta tatcaagaac    3720
gtctacaaaa cctatagcag tgtcaaagac tctacggagt tctggcaacg tttcaattcg   3780
atccgctata ttgcatccga aaatcggttt gagttttcgt acgaccttgc agacctcaag   3840
cagaagtccc tcgagagcaa aaccaagcaa actccacttg caaaaacgca atggactgtc   3900
tcatcgcatg ttacccgtag ctattataac cagcaaacaa aacaacacga attatttgaa   3960
gttaccgcac ggattcagca gttattaagt aaagcagaaa ttagctatca acatcaaaat   4020
gacctgatcc ctgcactcgc atcctgtcag agcaaagcac tgcataagga gttgatctgg   4080
ttattcaact ccattctcac tatgcgcgtc accgacagca gcaagccaag cgcaacctcc   4140
gaaaatgact ttattctgag ccctgtggcg ccatatttcg attcacgcaa tttgaacaaa   4200
caacttcctg aaaatggcga tgcaacgggc gcttataata ttgctcgcaa ggggattatg   4260
ttacttgagc ggattggtga tttcgtgcca aagggaata agaagtatcc agatcttttg    4320
attcgtaata atgattggca gaatttcgtc cagcgtcctg aaatggtgaa taagcagaag   4380
aagaaattag tgaaactgaa gacggaatat tctaacggga gcctgtttaa tgatttagca   4440
tttaagggcg cgccaaaaag gccggcggcc acgaaaaagg ccggccaggc aaaaaagaaa   4500
aaggctagcg gcagcggcgc cggatcccca aagaagaaaa ggaaggttga agaccccaag   4560
aaaaagagga aggtgtgata a                                             4581

SEQ ID NO: 111         moltype = DNA   length = 4581
FEATURE                Location/Qualifiers
misc_feature           1..4581
                       note = Description of Artificial Sequence: Synthetic
                       polynucleotide
source                 1..4581
                       mol_type = other DNA
                       organism = synthetic construct
SEQUENCE: 111
atgggccacc atcatcatca tcatagcagc ggcctggtgc cgcgcggcag cggtaccatg   60
tctgaccgtc tcgacgtact tactaatcaa tatccattat ccaaaacgct gcgcttcgag   120
ttgaaaccag tgggcgctac tgcggattgg atccggaagc acaacgtcat ccggtatcac   180
aacggcaagc tcgtcggcaa agatgctatc cggtttcaga attacaagta tttaaaaaaa   240
atgcttgatg aaatgcatcg gctctttctc caacaggctc tcgttttgga acctaacagc   300
aaccaggcgc aagaactcac ggcgctgctg cgcgccattg aaaacaacta ctgcaacaat   360
aatgacttgc tggctggtga ttacccgagt ttgagtacag ataagaccat caaaatttcg   420
aacgggttat caaaattaac aactgatctc tttgacaaaa agttcgagga ctgggcatac   480
cagtacaagg aggacatgcc aaatttctgg cggcaggata tcgcggagct ggaacaaaag   540
ttacaagtca gtcgaatgc caaagaccaa aaattctaca aagggattat caagaaactc    600
aaaaacaaga tccaaaaaag tgagttgaaa gctgaaaccc ataaagggtt gtattctcca   660
acggaatctc tgcaactgtt agaatggctg tccgccgcg gcgtatcaa gctgacttac    720
cttgagatcg gtaaggaaaa cgagaaactt aacgaattgg tcccgcttgt ggagttaaag   780
gatattcacc gcaatttcaa caatttcgcc acctatcttt ccggtttctc gaaaaaccgg   840
gagaacgtgt attcgacgaa gttcgaccgt cgttcaggtt acaaagcaac ctccgtgatc   900
gcgcgtacat tcgagcaaaa cttaatgttc tgtctgagca acattgcaaa atggcacaaa   960
gtaacggaat ttatcaatca agcgaataac tatgaactgc tccaagaaca tggtattgac   1020
tggaataagc agatcgccgc actcgagcac aagttagacg tatgtcttgc cgagtttttt   1080
gctttaaata attttttcgca gactctggcg caacaaggta ttgagaaata caaccaggtg   1140
cttgcgggta ttgccgagat cgcggggcaa cctaaaacgc aagggctgaa tgagttgatc   1200
aatcttgcac gtcagaagct gagtgccaag cgttctcaac ttccaacact gcaactcttg   1260
tacaagcaaa ttttgagtaa aggtgacaaa ccgttcattg atgacttcaa aagcgatcag   1320
gagttgatcg cggaattgaa tgagtttgta agcagtcaaa ttcatggtga gcatggcgcg   1380
atcaagctca tcaatcatga attgaatct tttattaacg aagcacgcgc tgctcagcag    1440
cagatctatg tcccgaagga caaattgacg gaattgtcac tgttacttac ggggtcctgg   1500
caggcgatca accagtggcg ttacaaactc ttcgatcaga aacagttgga caaacaacag   1560
aaacaatact ccttcagcct ggctcaagtc gagcgctggc tggcgacaga ggtcgaacag   1620
cagaatttct accaaaccga aaaggaacgc cagcagcata aagcacgcg gcctgcgaat    1680
gtaacaacct catcagacgg ccatagcatt ttgaccgctt ttgaacagca agttcgagct   1740
cttttgacta atatttgcgt agcagcgagg aagtatcgtc aattatcgga taatttaacc   1800
gctattgaca agcaacgtga gtccgaatcg tccaaggggt ttgaacaaat tgcagtcatc   1860
aagacgttat tagatgcctg taacgagctt aatcacttcc ttgcacggtt tacagttaac   1920
aagaaggaca aacttccgga agaccgtgct gaatttgtgt atgaaaagct ccaggcttac   1980
atcgacgctt ttccgattta cgagcttttac aataaagtgc gcaactacct ctcgaagaaa   2040
ccgttcagta ccgagaaggt gaagatcaat tttgacaatt cacactttct gtctggctgg   2100
accgccgatt acgagcggca tagtgcgtta ctctttaagt tcaacgaaaa ttacttgtta   2160
ggcgtggtga acgaaaattt gagttcggag gaggaagaaa agcttaagtt agtcgggcgg   2220
gaagagcacg cgaaacggtt tatttatgac ttccagaaaa tcgacaattc gaatccacct   2280
cgtgtattta tccgttctaa aggctcatca ttcgcaccag ccgtgaaaa gtatcaactc    2340
ccgattggcg acatcattga catttatgac cagggcaaat ttaaaacgga acacaagaag   2400
aaaaacgaag ccgagtttaa ggactcgtta gtccgcctca tcgactattt caagctgggc   2460
ttctcacgcc atgactctta taaacactac cctttcaaat ggaaagcgtc tcaccaatat   2520
tctgatattg cagaatttta cgcccacacc gcatcattct gctatacgct caaagaggaa   2580
aatatcaatt taacgtact ccgggagctc tcaagcgcag ggaaggtcta cctcttcgaa    2640
atctacaata aggatttctc caaaaacaag cgtggccaag gcgggacaa cctccacacg    2700
tcttactgga aactgttatt tagcgcagag aaccttaaag acgtggtgct gaaattgaac   2760
ggccaggcgg agattttcta tcggcctgca tctctggctg agactaaagc gtatactcac   2820
aagaagggtg aggtgttaaa gcataaggca tacagtaaag tgtgggaagc actggactct   2880
ccgattggca cacgcttatc gtgggatgat gcgctcaaga ttccgtctat tacggagaag   2940
actaatcata ataatcagcg ggtcgtccag tataatggtc aggagattgg tcgtaaggca   3000
gaatttgcga ttatcaagaa ccgccggtac agcgttgaca aatttctgtt tcattgtcct   3060
atcacgctga acttcaaagc gaacggtcag gataatatca acgcgcgcgt aaaccaattt   3120
```

```
ttagcaaaca ataaaaaaat taatatcatc gggattgacc gggggagaaa acacctctta 3180
tacatcagtg tcatcaacca acaaggcgag gtgttacacc aagaaagctt caatacgatc 3240
actaattcct accagactgc taacggggaa aaacgtcagg tggttactga ttatcatcaa 3300
aaacttgaca tgtctgaaga caagcgtgac aaagcgcgca agtcctggag cacgattgag 3360
aacattaagg agctcaaggc gggttactta tctcacgtcg tccatcggct ggcacagctt 3420
atcattgagt ttaatgctat tgttgccctc gaggacctca accacgggtt taaacgtggc 3480
cgctttaaaa ttgaaaagca agtttatcaa aaattcgaaa aggcgttaat tgacaagctc 3540
agttacctgc ctttcaagga ccggacaagt tgtctggaga ccgggcatta tcttaacgcc 3600
tttcaactta cgtcgaaatt caaaggtttt aacaattt ag ggaagcagtc gggcattta   3660
ttctacgtca acgcggatta cacatcaact acggatcctt tgacgggtta tatcaagaac 3720
gtatacaaaa cttactcgtc tgtaaaggat agcaccgagt tttggcaacg cttcaattcc 3780
attcggtata tcgcttcgga gaatcgtttt gaattttcgt atgacctggc cgacctgaag 3840
caaaagagtt tagaatcgaa gactaagcaa acgccgctcg ctaagacaca atggactgtc 3900
tctagtcatg ttacccggtc ctactataac cagcagacaa aacagcacga gttattcgag 3960
gtcaccgcac ggatccagca attgttatca aaagctgaaa tcagttatca gcaccagaac 4020
gaccttattc cggccctggc gtcttgtcag agcaaagctc tgcacaagga gctcatctgg 4080
cttttttaata gtattttgac catgcgggtc accgacagct ccaaaccatc cgcaacctcc 4140
gaaaatgatt ttatcctgag cccggtcgca ccatactttg actcccgcaa cctcaacaaa 4200
caacttcctg aaaatggtga tgcgaatggc gcttataaca tcgctcggaa aggcatcatg 4260
ctgcttgagc gcattggtga ttttgtacct gagggcaaca aaaagtatcc ggatttgttg 4320
attcgcaata atgactggca gaacttcgta cagcgtccgg agatggtgaa taagcagaaa 4380
aaaaagctgg tgaaactcaa gacggaatac tctaacggct cgctgtttaa cgatctggct 4440
tttaagggcg cgccaaaaag gccggcggcc acgaaaaagc ccggccaggc aaaaaagaaa 4500
aaggctagcg gcagcggcgc cggatcccca aagaagaaaa ggaaggttga agaccccaag 4560
aaaaagagga aggtgtgata a                                              4581

SEQ ID NO: 112        moltype = DNA  length = 4581
FEATURE               Location/Qualifiers
misc_feature          1..4581
                      note = Description of Artificial Sequence: Synthetic
                      polynucleotide
source                1..4581
                      mol_type = other DNA
                      organism = synthetic construct
SEQUENCE: 112
atgggccacc atcatcatca tcatagcagc ggcctggtgc cgcgcggcag cggtaccatg   60
agtgaccggt tggacgtgct gacaaaccaa tacccactga gtaagacgtt gcgtttcgaa  120
ctgaaaccgg tgggggccac tgctgattgg atccgtaagc acaacgtaat tcgctaccat  180
aacggtaagc ttgtaggcaa ggacgccatt cgcttccaga actacaaata ccttaagaaa  240
atgttggatg agatgcaccg cctgttcctg caacaggcgc tggttttaga gccgaattcc  300
aatcaggccc aagagctgac ggcttttgtta cgtgccatcg aaaacaatta ttgtaacaac  360
aacgacctct tggcagggga ttatccgagc ttaagtacaa acaagacgat caagatttcg  420
aacggttctt cgaagttaac tacagatctg tttgacaaaa aattcgagga ttgggcctaa  480
caatataagg aagatatgcc taactttttgg cgtcaagaca ttgccgagct tgaacaaaaa  540
ctgcaagtaa gcgcaaacgc gaaggaccag aagttctata agggatcat  caagaaactc    600
aagaacaaga tccaaaagtc agaactcaaa gctgagacgc ataagggcct gtattctccg  660
acagaatcac tgcaactctt ggaatggctt gtacgccgcg gcgatattaa gctgacgtac  720
cttgagatcg gtaaagaaaa tgagaagctc aatgaactgg tgcctctcgt agagttgaag  780
gatatccatc ggaacttcaa caattttcgcc acgtatcttt ccggcttttc gaaaaaccgt  840
gaaaatgttt acagtacgaa atttgatcgg cgttcagggt acaaagcgac gtcagtaatt  900
gcccggacct tcgaacagaa tttgatgttc tgcttaggaa acattgctaa gtggcacaaa  960
gtcactgaat ttatcaatca ggccaataat tacgaattat tacaggaaca tgggatcgat 1020
tggaacaaac aaaattgctgc tctgaacat aagcttgatg tctgtctcgc tgagttcttc  1080
gcgctgaaca acttttcaca aactctcgcg cagcaaggga ttgaaaagta caatcaagta  1140
ttagcgggca ttgcagagat tgctggtcag ccaaagaccc aaggccttaa tgaattaatt  1200
aatttagccc gccaaaagct gtcagccaaa cgcagtcagc tcccgacact tcaattatta  1260
tacaagcaaa tttatcaaa gggcgataaa ccgttcattg atgactttaa gtcggatcaa 1320
gagctgattc cggaactgaa cgaatttgtg agctctcaaa tccacggcga acatggtgct  1380
atcaagttaa ttaatcatga actcgaagtcg tttatcaatg aggctcgtgc cgcacaacag  1440
cagatttacg ttccgaagga caaactcact gagttgtctt tgcttctcac tggttcgtgg  1500
caagctatca atcaatggcg ctacaaactg ttcgaccaaa aacaactcga taacaacagg  1560
aagcagtaca gcttctcact ggcgcaagta gaacggtggc ttgctacgga ggttgaacaa 1620
cagaatttct accagacaga gaaagagcgc aacagcaca aggataccca accagcaaac  1680
gttacgacct cgagcgacgg ccacagtatt ctgacagctt tcgacgacga agttcaaact  1740
ctgctcacga acatttgtgt ggcagcagag aaataccggc aattatcgga taacctcacg  1800
gcaattgaca acaacgggga aagcgagtca agtaagggtt tcgagcaaat cgccgtaatt  1860
aaaactctgc tcgatgcgtg taatgaactc aatcatttct tagcgcggtt cacggtaaac  1920
aaaaaagaca agttgcctga agaccgggcg gaattctggt atgagaaact gcaggcttac  1980
atcgatgctt ttccaattta cgaactctac aacaaagttc gcaactatct tagtaaaaaa  2040
cctttctcga ccgaaaaggt taaaatcaat ttcgacaatt cacactttttt gagtggctgg  2100
acagcggatt atgaacgcca ttctgcactc ctgttcaagt tcaatgagaa ctaccttctt  2160
ggggtcgtta acgagaacct ttctagtgag gaggaagaaa agttaaagct cgtggggggc  2220
gaagagcacg cgaagcgctt tatctacgac tttcaaaaaa ttgataattc caaccgcca   2280
cgcgtcttta tccggtccaa aggcagcagt ttgtctcctg cagtcgaaaa gtatcaactc  2340
cctatcggtg atattattga catttatgat caaggcaagt ttaaaactga tgcacaaaaa  2400
aagaacgagg ccgagtttaa ggactccctg gttcgcctta tcgactattt taagttgggt  2460
ttcagccggc acgactcata taagcactac ccattcaaat ggaaggctag ccatcaatat  2520
tctgatattg ccgagttcta tgcgcacaca gcatccttct gttatactct gaaggaggag 2580
aatattaatt tcaacgttct gcgcgagtta agctcagcgg gcaaggtcta cttattcgaa  2640
```

```
atctacaaca aggatttcag taaaaataaa cggggccagg ggcgggataa tctccacacg   2700
agttattgga aactcttatt ctcggcggag aacctcaaag acgttgtttt aaaattaaat   2760
ggccaggctg aaatcttcta ccgtccagca agtctggctg aaactaaagc ctatacccac   2820
aagaaaggga aggttctgaa acataaagcc tactcgaaag tctgggaagc cttagactcc   2880
cctattggga ctcgtctttc atgggatgat gcgctgaaga tcccgagcat tacggagaag   2940
acaaatcata ataaccagcg ggtggtgcag tataacgggc aggagatcgg tcgtaaagcc   3000
gaatttgcga ttattaagaa tcgtcggtat tcggtggaca agttttttatt tcactgtccg   3060
atcacattaa acttcaaagc gaatgggcag gacaacatta atgcccgcgt taaccaattc   3120
cttgcaaata acaaaaagat taatattatc gggatcgatc gcggtgaaaa gcatttgttg   3180
tacatctctg tcatcaacca gcaggggag gtgctgcatc aagaatcgtt taacacaatt   3240
accaactcat atcagaccgc gaacggggag aaacgccaag ttgtgacaga ctaccatcag   3300
aagctggata tgagtgagga taaacgggat aaagcgcgta atcgtggag cacgattgag   3360
aatattaaag agttgaaagc agggtactta agtcacgtcg ttcatcggct cgcccaactc   3420
atcatcgaat tcaacgcgat cgtggcgtta gaggacctca accatgggtt caaacgcggt   3480
cggttcaaga ttgagaagca ggtatatcag aaattcgaga aagctttaat cgacaaactg   3540
agttatctcg ccttcaagga ccgcacgtcg tgcttggaaa cggggcacta tctgaacgcg   3600
ttccaactga catcgaaatt caaaggtttt aacaacttgg gcaagcagag cggcattctg   3660
ttctatgtca acgcggacta cacctctacc acggacccgc ttacggggta tatcaaaaac   3720
gtatataaga catattcgtc agtaaaggat tccacagagt tctggcaacg ctttaacagt   3780
attcggtaca ttgctagcga gaatcggttt gaatttagct acgatttggc agacttgaag   3840
caaaagtctt tggaatctaa aactaagcaa actccgcttg ctaaaaccca atggacagtt   3900
tcttcccatg ttacccgttc ctactataat cagcagacaa aacagcacga attgtttgaa   3960
gtcaccgcac gcattcagca attgttatca aaggccgaga tctcgtatca gcatcagaac   4020
gacttaattc cagcattagc gtcctgccag agcaaagcgt tacacaaaga gctgatctgg   4080
ctttttaatt ctatcttaac tatgcgggtg acggactcgt cgaagccgtc agcgacgagc   4140
gagaacgatt ttatcctgag tccggtggct ccgtattttg atagccgtaa tctcaacaaa   4200
caattgccgg aaaatggcga tgctaatggt gcctacaaca tcgcccgcaa aggcatcatg   4260
ctgttggagc ggatcgggga cttttgtgcct gagggcaata aaaaatatcc tgaccttctc   4320
attcgtaata acgattggca aaatttcgtg cagcgccctg agatggttaa caaacagaaa   4380
aagaagctcg tgaagctgaa gactgagtac agtaatgact cattgttcaa tgatttagcc   4440
tttaaaggcg cgccaaaaag gccggcggcc acgaaaaagg ccggccaggc aaaaaagaaa   4500
aaggctagcg gcagcggcgc cggatcccca aagaagaaaa ggaaggttga agaccccaag   4560
aaaaagagga aggtgtgata a                                           4581

SEQ ID NO: 113         moltype = DNA  length = 4581
FEATURE                Location/Qualifiers
misc_feature           1..4581
                       note = Description of Artificial Sequence: Synthetic
                        polynucleotide
source                 1..4581
                       mol_type = other DNA
                       organism = synthetic construct
SEQUENCE: 113
atgggccacc atcatcatca tcatagcagc ggcctggtgc cgcgcggcag cggtaccatg     60
tcggatcgcc tcgatgtact tacgaatcag tatccgttgt caaagacgct tcggtttgag    120
ttgaaacctt ttggtgccac agcggactgg attcggaaac ataacgtgat tcgttatcat    180
aacggtaaac tcgtaggcaa agacgcaatt cgctttcaga attataagta tcttaaaaag    240
atgctcgacg aaatgcatcg gctttttttta cagcaggcac ttgtgctcga accgaattgc    300
aaccaagcac aagaacttac ggcgctgctc cgggcgattg aaaataacta ctgcaacaac    360
aatgacctcc tggctggcga ctatccgagt ctcagcactg acaaaacgat caaaatcagc    420
aacgggtctct ccaagctgac aactgacctg ttcgataaaa agttcgaaga ttgggcatat    480
cagtataagg aggacatgcc aaacttctgg cggcaagata tcgcagagct tgagcagaag    540
ttgcaggtca gcgccaacgc aaaggatcaa agttttttata agggcatcat caagaagctc    600
aaaaataaga tccagaaaag cgagctgaaa gccgaaacgc acagggggtt gtacagtcca    660
acggagagtc tgcaactctt ggaatggctt tacggcggg gggatatcaa gcttacatat    720
ttagagatcg ggaaagagaa tgagaaattg aacgagttag ttccactcgt agagcttaaa    780
gacatccatc gcaatttcaa taactttgct acctatcttt cggggttttc aaaaaaccgc    840
gagaacgtgt attcgacaaa attcgatcgt cgcagcgggt ataaagcaac atccgtcatc    900
gcccgtacct ttgaacagaa tttgatgttt tgtttaggga acatcgccaa gtggcacaag    960
gtgactgaat tcatcaatca ggccaataat tacgaacttc tccaagaaca cgggattgat   1020
tggaacaaac agatcgcagc gttggagcac aagctggacg tatgtctcgc cgaattcttt   1080
gcactcaata atttttctca aaccctcgca caacaaggta tcgagaaata caaccaggtg   1140
cttgcgggga ttgcagagat tgctggccag cctaaaacgc aaggtctgaa cgagcttatt   1200
aaccttgcac ggcaaaagtt aagcgcgaaa cggagtcagt ttgccaactct tcagctccct   1260
tataagcaga ttcttttctaa gggtgataag ccattcatcg acgatttcaa atccgatcaa   1320
gaattgatcg cagaattgaa tgaattcgtc tcgtctcaga ttcatggcga gcatggcgcc   1380
attaagctta ttaaccatga gttagagagt tttattaacg aagcacgggc tgcccaacag   1440
cagatctatg tcccaaaaga caagctcacc gaactttctc tcctgttaac gggttcatgg   1500
caagcaatta atcagtggcg gtataaattg tttgatcaaa agcaacttga caaacaacaa   1560
agcaatactt ccttttcttt ggcgcaagtg gaacgttggt tagcaacaga agtagaacga   1620
cagaattttt atcagacaga aaggagcgca aacagcacaa aagacaccca accggctaac   1680
gtaacaacgt cgtcagacgg gcattcaatt ttaacagctt tcgagcagca ggtccaaact   1740
ttgttgacca acatctgcgt agcagcagag aaatatcgcc agttgagtga caatttgacg   1800
gcgattgata agcaacggga aagcaatcc tctaaaggtt ttgacaaat cgctgtcatc   1860
aagaccttat tggacgcgtg taacgaactg aatcattttt tggcacgctt tacggtcaac   1920
aagaaggata agctgcctga ggatcgggca gagtttggt atgagaagct ccaagcttac   1980
attgacgcat ttccaattta tgaattatat aataaagtgc gcaattatct gagtaaaaag   2040
ccattctcta ctgaaaaagt gaagatcaac tttgacaact cacactttct gtccggttgg   2100
acagccgatt acgaacggca ctcggcctta cttttttaagt tcaatgaaaa ttatctgtta   2160
```

```
ggcgttgtca acgagaacct ctcgagtgag gaggaagaaa aacttaaatt ggtaggcggt   2220
gaagagcatg cgaagcgctt catctacgat ttccagaaga tcgacaactc aaacccacct   2280
cgcgtcttca tccgttctaa aggtagctca tttcgcctg ccgttgaaaa atatcagctc    2340
cctattggcg atatcatcga catttatgat caggggaaat tcaaaacgga gcacaagaaa   2400
aaaaacgagg cggaattcaa agattctttg gttcgtttga tcgactattt taagctcggt   2460
tttagccggc acgacagtta caaacactac ccatttaagt ggaaggcgtc tcatcaatat   2520
tctgatatcg cggagttcta tgcccacacg gcgagcttct gctacaccct caaggaggag   2580
aatattaatt tcaacgtact gcgcgaactc agttcggcag gtaaagtata ccttttcgag   2640
atttataaca aagactttag taagaataag cgtggtcaag gccgggacaa ccttcataca   2700
tcttattgga agcttctttt tagtgctgaa aatctcaaag acgtcgtctt aaagctcaat   2760
ggtcaggcgg agattttcta tcgtccagca agcctcgcag agaccaaagc atacacgcat   2820
aagaaaggtg aagtgcttaa acataaggcc tattcaaaag tatgggaagc tctgacagc    2880
ccaatcggga cgcgcctcag ctgggatgac gcgcttaaaa tcccaagtat cacagagaaa   2940
acgaatcaca ataaccagcg tgtagtgcag tataacgggc aggagattgg tcgcaaagcc   3000
gagttcgcaa tcattaaaaa ccgtcgctat agtgtggata agttcctttt ccattgtccg   3060
attaccttga atttcaaggc taatggccag gacaacatca acgcccgtgt caatcaattt   3120
ttagccaaca ataagaaaat taatatcatc ggcatcgatc gcggcgagaa gcatttgctt   3180
tatatctcgg taattaacca gcaaggcgaa gttctccaac aagagtcatt caatactatc   3240
accaacagtt atcagacagc caacggtgag aaacgccaag tagtgacaga ctaccaccag   3300
aagctcgata tgagtgaaga taagcgtgat aaagcccgga gtcctggtc gacaatcgaa    3360
aatattaaag aacttaaggc gggttatctc tcacacgtgg tccaccgttt ggcacagctc   3420
atcatcgaat ttaacgcaat cgtagccttg gaggatctta accacggttt caagcggggt   3480
cgtttcaaaa tcgaaaaaca ggtgtatcag aagttcgaga aagcattaat tgacaagctg   3540
agttatttag cgttcaagga ccgtactagt tgtttggaga ctggtcacta cttaaatgcg   3600
ttccagctta cctccaaatt taagggcttt aataaccttg gtaagcagtc gggcatcttg   3660
ttttacgtta acgccgatta cacgtccact acagacccac tcactgggta tattaaaaac   3720
gtctataaaa cgtatagcag tgtgaaggac tctacggagt tctggcaacg ctttaactct   3780
attcggtata tcgcatccga aaatcgcttt gaattctcct atgacttggc agatttaaaa   3840
caaaaatctc tcgagagtaa aacaaagcaa acacctctcg caaaaactca atggacagtt   3900
tccagccatg tcactcggtc ctattacaac cagcagacta aacaacatga attattcgaa   3960
gtcacggccc gcattcaaca gctgcttagc aaagcggaaa ttagttacca gcatcagaat   4020
gacttaatcc cagcacttgc gtcgtgtcag agtaaggctc tccacaaaga gcttatttgg   4080
ttattcaact caattctgac tatgcgggtg actgatagta gtaaaccgtc tgcgactagt   4140
gagaacgatt tcatcctttc gcctgttgcg ccgtatttcg actctcggaa ccttaataaa   4200
cagttaccag agaacggcga tgccaatggt gcttacaata tcgcacggaa agggattatg   4260
cttctggaac ggattggcga tttcgtacca gaaggtaaca aaaaatatcc agacctgctc   4320
atccggaaca acgattggca gaactttgta caacgccctg agatggtgaa taagcaaaaa   4380
aagaagctcg tcaagctgaa gacagagtac agcaacggga gtttatttaa tgatttagca   4440
ttcaaaggcg cgccaaaaag gccggcggcc acgaaaaagg ccggccaggc aaaaaagaaa   4500
aaggctagcg gcagcggcgc cggatcccca aagaagaaaa ggaaggttga agaccccaag   4560
aaaaagagga aggtgtgata a                                             4581

SEQ ID NO: 114        moltype = DNA  length = 4581
FEATURE               Location/Qualifiers
misc_feature          1..4581
                      note = Description of Artificial Sequence: Synthetic
                       polynucleotide
source                1..4581
                      mol_type = other DNA
                      organism = synthetic construct
SEQUENCE: 114
atgggccacc atcatcatca tcatagcagc ggcctggtgc cgcgcggcag cggtaccatg   60
tccgaccggc tggatgtact cactaatcaa tatccgttat ccaagacatt acggttcgag   120
ttgaaaccga tagggccac agcggactgg attcgtaaac acaatgtaat ccgctatcac    180
aacggcaagt tggtggggaa agacgcaatt cgctttcgaa actataagta tcttaaaaaa   240
atgttagatg aaatgcaccg gcttttcctg cagcaggcac tggtgctgga gccgaactcc   300
aatcaagccc aggaactgac cgcattgtta cgtgcaatcg aaaacaatta ttgtaataat   360
aatgatttgt tagctggtga ctatccatcg ctttcaaccg ataagaccat taagatctca   420
aacggcttaa gcaaattaac gaccgatctg ttcgataaaa agttcgaaga tttgggcctat   480
cagtataaag aagacatgcc aaacttctgg cgccaagaca ttgccgaact cgaacagaaa   540
ctgcaagtat cggccaacgc taaagaccaa aagttttata aagtatcat caaaaagctt     600
aagaacaaga tccagaaaag tgagttgaaa gcagaaactc ataaagggct gtattcccca   660
actgaatccc tgcaactctt ggaatggctc gttcgccggg cgacattaa attgacgtac     720
ttagaaattg gtaaggaaaa cgaaaaactc aacgagttga taccgctcgt tgaactcaaa   780
gatattcatc gtaactttaa caactttgcg acttacctct caggcttcag caaaaatcgt   840
gaaaatgtat actcgactaa gttcgatcgg cggtccggtt acaaggccac atccgttatc   900
gctcgcactt ttgagcaaaa cctcatgttt tgtcttggca atattgctaa atggcataaa   960
gtcacagaat tcattaatca ggctaataac tacgaacttt tgcaagaaca cggatcgac   1020
tggaataagc aaattgctgc cttggagcat aaattagatg ttgtgccttgc agaattttc    1080
gcgctgaaca attttttcgca gacattagcg cagcagggca tcgaaaagta caaccaggtg   1140
ctcgcgggga ttgcagaaat cgcaggccaa ccaaaacac agggtctcaa cgagctgatc     1200
aacttagctc ggcaaaagtt gtccgctaag cgctcacaac ttccgacctt gcaactcctg   1260
tataaacaaa tcctctcaaa gggcgataag cctttatcg atgatttaa atcggatcaa     1320
gaactgatcg cagagttaaa cgagttcgtg agtagccaga ttcaccagaa gcatgggtga   1380
attaaactca tcaaccacga actggagagc tttatcaatg aggctcgcgc agcgcagcag   1440
cagatctatg taccaaagga taaacttaca gaactgtcgt tgctcctgac ggggtcatgg   1500
caggcaatta ccagtggcg gtataaattg ttcgaccaga agcaattaga caagcaacaa    1560
aagcaatatt ccttcagcct cgctcaggtc gagcgttggc tggctacgga agtcgagcaa   1620
cagaactttt accaaacgga gaaagaacgc cagcaacata aagatacgca gccagctaat   1680
```

```
gtcacaacct cttctgatgg gcactcaatc ctgaccgctt tcgaacaaca agtccaaact   1740
ctgttgacga acatttgtgt ggctgcggag aagtaccggc aactgagtga caaccttact   1800
gcaatcgata agcagcgtga atccgagagt tctaagggt ttgagcagat tgcggttatc    1860
aaaacacttc tggacgcctg caacgagctg aaccatttcc tggctcgctt cactgtcaac   1920
aagaaggata agctgccgga ggatcgcgct gaattctgat atgagaagct gcaggcgtac   1980
atcgatgcgt tcccaatcta cgagttgtac aacaaggtcc gtaactacct ttcgaaaaaa   2040
ccattctcaa ctgagaaagt aaagatcaat tttgacaatt ctcacttctt gtcgggctgg   2100
accgccgatt atgaacgtca ttctgccctt ctcttcaaat tcaacgagaa ttatcttttg   2160
ggggttgtaa atgagaactt gagctccgag gaagaggaaa agttgaaact tgtcggtggt   2220
gaagaacatg caaaacgctt tatctatgac ttccaaaaaa tcgacaacag taaccctcca   2280
cgggtgttca tccggagcaa gggtagttct tttgcaccgg ccgttgaaaa atatcaattg   2340
ccaatcgggg acattattga tatttatgac caagggaagt ttaagaccga gcacaagaaa   2400
aaaaatgaag ccgagttcaa ggatagtttg gtgcgcttga ttgactattt taagctgggt   2460
ttcagtcgcc acgacagcta caaacactat cctttcaaag ggaaggcctc tcaccaatat   2520
tctgatatcg ctgaattcta cgcccatacg gcttcctttt gctacacact taaagaggag   2580
aatatcaatt ttaacgttct ccgggagtta tcctctgctg ggaaggttta cttatttgaa   2640
atttacaaca aagatttctc taagaacaag cgtggccaag gccgcgacaa cctccatacc   2700
tcctactgga agctcttgtt ctccgcagaa aatttgaagg atgttgtcct taaacttaac   2760
gggcaagccg agatcttcta ccggccagcg agtctggccg aaactaaggc ttatactcat   2820
aaaaagggcg aagtcttgaa acacaaggca tactcaaagg tttgggaggc ccttgacagc   2880
cctattggca cgcggttgtc atgggacgac gcacttaaaa tcccttcaat caccgaaaag   2940
acgaaccata acaatcagcg cgtggtgcaa tataatgacg aagaaatcgg tcggaaagcc   3000
gaattcgcga tcattaagaa ccgccgttat agcgtggaca aattcctctt tcactgtcca   3060
atcacattaa acttcaaggc aaacggtcaa gataacatta acgcgcgtgt aaatcaattc   3120
ctcgcgaata acaagaaaat taacatcatc gggattgatc gtggtgagaa acatctgtta   3180
tatctctg tcattaatca gcagggcgaa gtacttcaca aggagtcctt taataccatc    3240
acgaatagct accagacggc aaatggcgag aagcggcagg tggttacaga ctaccatcag   3300
aaactggata tgtccgagga taagcgggac aaagcgcgca agagctggtc cactatcgag   3360
aacatcaagg agttaaaagc tgggtaccctt agccacgtcg tacatcgcct cgcacagttg   3420
attatcgat tcaatgcaat cgttgcgttg gaagacttga accatggttt taagcgggggt   3480
cggtttaaga tcgaaaagca ggtgtatcaa aaatttgaaa aagcactgat cgataagctg   3540
agttatctcg cattcaaaga tcgcactagc tgtctggaga ctggccacta cctcaatgcc   3600
tttcaactga cctcaaagtt caaggggttt aataatcttg ggaaacaaag tggtattttg   3660
ttttatgtta atgcggatta cacttcaact accgatcctc tgaccgggta tatcaagaac   3720
gtctataaaa cgtacagtag cgtcaaggac agtacggagt tctggcaacg cttcaacagt   3780
attcggtata ttgcgtcgga gaaccggttt gaattctctt atgacctggc ggatctcaag   3840
cagaaaagcc tggaatccaa aacaaaacag actccgctcg ccaagacaca gtggacggtt   3900
tcatcgcacg ttacgcggtc atactataac aacagacga aacaacacga gcttttcgaa    3960
gtaactgcac gtatccagca gttgctgtca aaggcggaga tttcctatca gcaccaaaac   4020
gaccttatcc cggcactcgc tagttgccaa agcaaagcgc ttcataaaga gctgatctgg   4080
ctcttcaata gtatcttaac catgcgtgta actgacagca gtaaacctag cgccacaagc   4140
gaaaacgact ttatcttaag ccctgtagca ccttatttcg attcacgcaa tttgaataaa   4200
cagctgcctg agaatggcga tgcaaacggt gcgtataata tcgcccggaa gggcatcatg   4260
ttattggaac ggattggcga tttcgtcccg gaggggaata agaagtatcc tgatctctta   4320
attcgtaata atgattggca aaattttgtg caacggccctg agatggtgaa caagcagaaa   4380
aaaaaactgg ttaagttaaa aactgaatat tcaaatggta gcttgtttaa cgacttagca   4440
tttaagggcg cgccaaaaag gccggcggcc acgaaaaagg ccggcaggc aaaaagaaa    4500
aaggctagcg gcagcggcgc cggatcccca aagaagaaaa ggaaggttga agaccccaag   4560
aaaaagagga aggtgtgata a                                             4581

SEQ ID NO: 115      moltype = DNA  length = 4581
FEATURE             Location/Qualifiers
misc_feature        1..4581
                    note = Description of Artificial Sequence: Synthetic
                    polynucleotide
source              1..4581
                    mol_type = other DNA
                    organism = synthetic construct
SEQUENCE: 115
atgggccacc atcatcatca tcatagcagc ggcctggtgc cgcgcggcag cggtaccatg     60
tccgaccgtt tagatgtctt gactaaccag tatccactct cgaagacact ccgtttcgag    120
ttaaaacctg taggcgcaac ggcagactgg attcggaaac acaatgtcat ccgctatcac    180
aacggcaagt tggtgggcaa ggatgcgatt cggttccaga attacaagta tctcaaaaaa    240
atgctcgacg agatgcatcg cctgtttctc cagcaggctt tagtattgga accaaactcc    300
aatcaggcac aggagttgac ggccctcttg cgtgctatcg agaataatta ttgtaataac    360
aatgacctgt tggcgggtga ctaccgtct ttatcaacag acaaaacgat taaaattcc     420
aacggggttg ccaaattaac taccgattta ttcgacaaga aattcgagga ctgggccat    480
cagtacaaag aagacatgcc taatttctgg cgccaagaca tcgcagaatt ggaacaaaca    540
cttcaagtct ccgcaaacgc taaggaccaa aaattctata agggtattat caagaagctc    600
aagaataaaa ttcagaagtc agaattaaag gccgagacgc acaaaggtct ttattcccct    660
actgaatcgc ttcaattact tgagtggttg gtgcgtcgtg gtgatatcaa gttaacgtac    720
ctggagattg caagagaa tgaaaaactg aacgagttgg taccttagt ggaattaaag      780
gacatccacc gcaactttaa caacttcgct acatatctta gcgggttctc taaaaaccgg    840
gagaacctga attctacgca attcgatcgt cgtagcggct acaaggcgac aagcgtcatt    900
gctcgtacat tcgaacagaa cctgatgttc tgtctgggta acatcgcaa atggcacaaa     960
gtaaccgaat tcattaacca ggccaataac tatgaattat acaggaaca cggcattgat    1020
tggaacaagc agatcgccgc cttagagcat aagctggacg tttgccttgc ggaatttttt    1080
gcgttgaaca atttcagtca aaccttagcc caacagggga ttgaaaagta taatcaggtg   1140
ttggctggta tcgcagaaat cgcggggcag ccaaaaaccc aaggcctcaa cgagctcatt   1200
```

```
aacttggctc gtcaaaagtt gtcggcgaag cgtagccaac tgccgaccct ccagttatta    1260
tataaacaga ttctgagtaa aggcgacaag cctttcattg acgatttcaa gtcggatcaa    1320
gagctcattg ccgagttgaa tgagtttgtg agctcccaaa ttcacggtga acacggtgcg    1380
atcaaattga ttaaccacga gttggagtcg tttattaatg aggcacgggc ggctcaacaa    1440
caaatttacg taccaaaaga caaacttact gagctgtccc ttcttctcac ggggtcatgg    1500
caagccatca atcaatggcg gtataaactg tttgatcaga agcagctcga caaacaacag    1560
aagcagtatt cgttttcgct cgcgcaagtg gaacgctggc tcgcgactga agttgaacaa    1620
caaaacttct accagacaga aaaagagcgc cagcagcaca aggacaccca acctgcgaac    1680
gtaactacga gttccgatgg tcattccatc ttaacggcct tcgagcagca agtccaaacg    1740
ctgctcacta atatctgcgt tgccgcagag aagtatcgcc aactgagcga taatctgacc    1800
gccatcgata agcaacggga gagcgagtct tctaaagggt tcgaacagat cgcggttatt    1860
aagaccctcc ttgatgcgtg caacgagctt aatcatttcc tcgcgcgttt tactgtcaat    1920
aagaaagaca aattgccaga agaccgcgct gaattttggt acgaaaaact ccaggcttat    1980
atcgatgcct tcccaattta cgaactctac aacaaagttc gcaactactt atccaagaag    2040
cctttctcta ccgagaaagt taagattaac ttcgacaact cgcacttcct ttccgggtgg    2100
acagcggact atgagcggca ctctgcgtta cttttttaagt ttaacgaaaa ttatctgttg    2160
ggggtcgtca acgaaaactt aagctctgag gaggaggaga agctcaagtt agtgggcggc    2220
gaagagcacg ctaagcggtt tatctacgat tttcaaaaga ttgataatag taatccacct    2280
cgcgtattta ttcggtcgaa aggctcttca ttcgcgcctg cggtggaaaa gtaccagttg    2340
cctatcggtg atatcattga tatctacgac cagggtaagt ttaagacgga gcacaaaaaa    2400
aagaatgagg cagagtttaa ggacagtctt gttcggctca ttgattattt taagttgggt    2460
ttttctcgtc atgacagcta taagcattac ccattcagtg gaaggcaag ccaccagtac    2520
tcggacattg cagaattcta cgctcatacg gcgtcattct gttatacact caaggaggag    2580
aacattaatt tcaacgtcct gcggaatta tcgtctgccg gtaaagtcta tcttttttgaa    2640
atttacaata aggacttctc gaaaaacaag cggggccaag gtcgcgataa tttacatact    2700
agttactgga agctgttatt tagcgcggag aaccttaagg acgtcgtgct gaaactgaac    2760
ggtcaggccg agatctttta ccgcccagcg agccttgcag aaacaaaagc ttatacacat    2820
aaaaaagggg aggtgcttaa gcataaggct tactcgaaag tgtgggaagc acttgatagc    2880
cctattggga cccgtctcag ctgggacgat gcgctcaaaa ttccttcgat tacggaaaag    2940
acgaatcata ataatcaacg ggtcgttcag tacaatggcc aagaaatcg tcggaaagcc    3000
gagtttgcaa ttatcaaaaa ccgccgttac tcggtggaca aattcctctt ccattgtcca    3060
atcactctta acttcaaagc caatgggcaa gacaatatca acgcgcgcgt caaccaattt    3120
cttgcaaata ataaaaagat taatattatt gggattgatc ggggtgaaaa acacctcctc    3180
tacatctcgg ttatcaacca gcaaggcgaa gtgcttcacc aagagagtt taatacgatt    3240
actaatagct atcagacagc caatggtgag aagcggcagg tggttacgga ttaccaccag    3300
aaacttgaca tgagtgagga caagcgcgat aaggcgcgta agtcatgag tacaattgaa    3360
aatattaaag aactcaaagc aggttatttg tcacatgtag tgcaccggtt agcccaattg    3420
attatcgagt ttaatgcaat tgtcgcgttg gaggacctca atcacggctt caagcgcggc    3480
cgctttaaaa tcgaaaaaca ggtttatcag aagtttgaga aggctctcat tgacaaactg    3540
agctatttag cttttaaaga ccgtacgtct tgcctcgaaa caggccatta tctgaatgct    3600
ttccaattaa caagtaagtt caagggtttt aacaacctcg ggaagcaaag tggtattctc    3660
ttctacgtaa atgcggatta caccctccact acggatcctt tgacgggcta catcaaaaac    3720
gtatacagaa cgtactcgtc agttaaggat tccacagagt tttggcaacg ctttaacagt    3780
atccgttata tcgcatctga gaaccgtttc gaattcagct acgatttagc tgatttaaag    3840
cagaaatcgt tagagtctaa aactaagcaa acgccacttg cgaagaccca atggacagtt    3900
agtagtcacg tgacccggtc ttattataac cagcaaacta agcagcacga actctttgaa    3960
gtgaccgcac ggattcaaca actgctttcc aaggctgaga ttagttacca acatcagaac    4020
gacttgattc cggcactcgc gagctgtcag tcaaaagctc tccataaaga gcttatctgc    4080
ctgttcaata gtatcttgac aatgcgtgtc acagattcgt cgaaaccttc tgccacgtcc    4140
gaaaacgatt tcatcttatc acctgtagct ccttactttg actcccgtaa tctgaataaa    4200
caactcccag aaaatgggga cgcaaacggt gcatacaaca ttgcgcgtaa aggcattatg    4260
ttgctggaac gtatcggcga cttcgttcct gaaggtaaca aaaagtaccc ggatttactg    4320
attcgcaata atgattggca gaatttcgtt caacggccag agatggtcaa taagcagaaa    4380
aaaaaattgg tgaaactgaa gactgaatat agcaatgggt cgctgtttaa tgatttggca    4440
ttcaaaggcg cgccaaaaag gccggcggcc acgaaaaagg ccggcaggc aaaaaagaaa    4500
aaggctagcg gcagcggcgc cggatcccca aagaagaaaa ggaaggttga agaccccaag    4560
aaaaagagga aggtgtgata a                                             4581

SEQ ID NO: 116        moltype = DNA   length = 4581
FEATURE               Location/Qualifiers
misc_feature          1..4581
                      note = Description of Artificial Sequence: Synthetic
                      polynucleotide
source                1..4581
                      mol_type = other DNA
                      organism = synthetic construct
SEQUENCE: 116
atgggccacc atcatcatca tcatagcagc ggcctggtgc cgcgcggcag cggtaccatg     60
tccgaccggc ttgatgtgct tactaaccaa tatccgcttt ccaagacctt acgctttgag    120
cttaaacctg tcggtgccac cgctgactgg attcggaaac ataacgttat ccggtaccac    180
aatgggaaac tggtaggtaa ggatgcgatc cgttttcaaa attacaagta tctgaaaaag    240
atgctggatg aaatgcatcg gttgtttttg cagcaagcct tggttctgga acctaactcg    300
aaccaagcac aagaactcac cgctctcctg cgcgcaatcg aaaataacta ctgtaacaac    360
aacgatttgc ttgcagggga ctatccgtca ttgagtacgg acaagaccat caaaatttct    420
aatgggctct caaaactcac caccgatttg tttgacaaaa aattcgagga ttgggcgtat    480
caatacaagg aggacatgcc gaactctggg cgtcaggata ttgcggagtt ggaacaaaag    540
cttcaagtgt ccgcaaacgc caaagatcaa aagttctata aggggatcat taaaaaattg    600
aaaaataaga ttcaaaagtc ggagcttaag gccgaaacac ataaagggtt atatagcccg    660
acggaaagtc tccagctcct tgagtggtta gtccgccgtg gtgatatcaa actcacatac    720
```

```
ttagaaattg gtaaagagaa cgaaaaactt aatgaacttg tacctttggt agagttgaaa    780
gatattcacc gtaattttaa caatttcgct acatacttga gtgggttctc caagaatcgt    840
gagaacgtat attcgactaa attcgaccgc cggtcgggtt acaaggcgac ttcagttatt    900
gcgcgtacgt ttgaacagaa cttgatgttc tgtctgggta acattgcaaa gtggcataaa    960
gtcaccgagt tcattaatca ggcaaacaac tatgagttac tgcaagaaca tggtattgac   1020
tggaataagc aaaattgcag cacttgaacat aagttggacg tatgtctggc tgagttttc   1080
gcgctgaata atttctcaca aactcttgcg cagcaaggca tcgagaagta caaccaggtc   1140
ctcgccgta tcgcggagat tgcaggtcaa ccaaaaactc aaggtctcaa cgaattaatc   1200
aacctggctc ggcaaaagtt gtcagccaag cgttcgcagt tacctacatt acaactgtta   1260
tacaaacaga ttctctcaaa aggcgataag ccgtttattg acgacttcaa gtctgatcaa   1320
gagttgattg cagaactgaa cgaattcgtc agcagccaaa tccacgggga acatggcgca   1380
attaagctta ttaaccatga actcgagtcg tttatcaatg aagctcgtgc tgcccagcaa   1440
cagatttatg ttcctaagga taaactcaca gaactgagtt tactcctcac ggggtcctgg   1500
caggcgatta accagtggcg gtacaagctc ttcgacgaga aacaactcga caagcagcaa   1560
aagcaatact cattctcgtt agctcaagtg gaacgctggt tggcaacaga agtcgagcaa   1620
cagaactttt atcagactga gaaagagcgc cagcaacata aggatacgca gccagctaat   1680
gtcacaacat cctctgacgg ccactccatc ctcaccgcat tcgagcaaca ggtacaaacc   1740
ttgttaacaa acatttcgt cgctgcggaa aagtaccgtc aactgtcgga taacttaacc   1800
gcaattgata aacagcgcga gtccgaatcg agcaaagggt tcgagcagat tgcggtaatt   1860
aaaacgctct tggacgcgtg caatgagtta aaccactttc tcgcacgttt tactgttaat   1920
aaaaaggaca agttgccaga ggaccgggct gaattttggt atgagaaatt gcaggcctat   1980
atcgacgcgt tcccaattta tgaactgtac aataaagtcc ggaactatct ttccaagaaa   2040
ccgttcagta cagaaaaggt aaagatcaat tttgataatt cacatttcct ctccggttgg   2100
acggctgact atgagcggca tagcgccta ttgtttaaat taatgagaa ttatttatta   2160
ggtgtggtta acgaaaatct gtccagtgaa gaggaagaaa agcttaaact tgttggcggt   2220
gaagagcacg cgaaacgttt tatttacgac tttcagaaaa tcgataatag taacccacca   2280
cgggtcttca tccggtcgaa aggctcgtcc ttcgctccgg cggtggaaaa gtatcaactt   2340
ccgatcgggg acattatcga tatttatgac caaggcaagt tcaagactga acacaaaaag   2400
aaaaatgagg cggagtttaa agattcactt gtccgcttga tcgattactt caagctcggc   2460
ttttcacgtc acgactcata taagcattat ccatttaagt ggaaggcgtc ccaccagtac   2520
tctgacattg cagaattcta cgcgcataca gcttcgttct gctacacttt aaaagaagag   2580
aatattaact ttaatgttt gcgtgaatta tcgagcgcag ggaaggttta tcttttcgag   2640
atttataata aggactttag taagaataaa cgtggtcaag tcgggataa tcttcatact   2700
tcttattgga agttactttt ctcagcagaa aatttaaaag atgttgtact gaaacttaat   2760
ggccaagccg aaatcttcta tcgcccggca agcttagcga aaacgaaagc gtacacccac   2820
aagaaagggg aggtacttaa gcataaagct tactcaaaag tgtgggaggc actcgactcc   2880
ccaattggga cccgcctctc atgggacgat gcattgaaaa ttccatctat cacagaaaag   2940
acaaaccata ataaccagcg cgttgtccag tataacgggc aggaaattgg tcggaaagcc   3000
gagtttgcca tcattaagaa ccgccgttac agcgtagata agttcttatt tcactgccct   3060
attactctga acttcaaagc caatgggcag gataacatta acgctcgggt taatcagttc   3120
ctcgccaaca acaaaaagat taacattatc gggatcgatc gtgggaaaa acaccttctt   3180
tatatctcgg tgatcaatca acaaggcgaa gtgctgcacc aggaaagctt caatacgatt   3240
accaactctt accaaacggc aaacgggcaa ggcgtcaaca ttgtaacaga ctaccaccag   3300
aaattagaca tgtccgagga taagcgcgac aaggcacgta agtcttggtc aacgattgaa   3360
aacatcaaag agttgaaagc cggctacttg agccatgttg ttcatcggct cgcccagctg   3420
attatcgagt ttaacgcgat tgtggcactg gaagacctga accatggctt caaacgcggc   3480
cgctttaaaa tcgagaaaca ggtttatcaa aaattcgaag agcccttat tgataagttg   3540
agttatttag catttaaaga tcggacatca tgtctggaaa cagggcacta tctcaatgcc   3600
ttccaactca caagcaaatt taagggcttt aataacctcg gaagcaatc tgggatcttg   3660
ttttatgtca atgcggacta tacgtccacg actgacccctt tgacgggta catcaaaaac   3720
gtgtataaga cgtacagcag tgtcaaggac tcgacagaat tttggcaacg ctttaactcg   3780
attcggtaca tcgctagtga gaaccgtttt gaatttcgt acgatcttgc agatttaaaa   3840
cagaagtctc ttgaatccaa aactaaacaa actccgcttg cgaagacgca gtggacggtt   3900
tcgtcacatg taacgcgctc ttattataat caacaaacaa agcaacatga actgttcgaa   3960
gtaaccgccc ggattcagca gctgctttcc aaggctgaga tttcctacca acaccagaac   4020
gatctgatcc cggctctcgc ctcgtgccaa agcaaagctc tgcataaaga gttaatttgga   4080
ctgtttaact cgatcctgac catgcgggtt acagactctt caaagccttc tgcgacatca   4140
gagaacgact ttatcctgtc acctgtcgct ccttattttg attcccggaa tttgaacaag   4200
caactcccag aaaaacggtga cgcgaatggt gcctataaca ttgctcgcaa gggcattatg   4260
ctgttagaac gcattgggga tttcgtgccg gagggcaaca aaaatacccc agcctctta   4320
attcggaata atgattggca aaactttgtt cagcgccctg aaatggtgaa caaacaaaaa   4380
aaaaaacttg ttaagctgaa gacggaatat tccaacggga gcctgtttaa cgatctcgct   4440
tttaaaggcg cgccaaaaag gccggcggcc acgaaaaagg ccggccaggc aaaaaagaaa   4500
aaggctagcg gcagcggcgc cggatcccca aagaagaaaa ggaaggttga agaccccaag   4560
aaaaagagga aggtgtgata a                                             4581

SEQ ID NO: 117          moltype = DNA   length = 4581
FEATURE                 Location/Qualifiers
misc_feature            1..4581
                        note = Description of Artificial Sequence: Synthetic
                        polynucleotide
source                  1..4581
                        mol_type = other DNA
                        organism = synthetic construct
SEQUENCE: 117
atgggccacc atcatcatca tcatagcagc ggcctggtgc cgcgcggcag cgtaccatg     60
agtgatcggc tcgacgttct gacgaaccag tatcctctgt ctaagacact ccggttcgaa   120
ttaaagcctg tcggcgcaac ggctgattgg atccgcaaac ataacgttat tcggtatcat   180
aacggcaaat tagtaggtaa agatgcaatc cgctttcaaa attataaata tttgaaaaaa   240
```

```
atgttggacg agatgcaccg tcttttctta caacaggcct tagttttaga gccaaactca    300
aaccaagccc aggaattaac tgcgcttttc cgcgcgattg aaaataatta ttgtaacaat    360
aacgatctcc ttgccgggga ctatccttca ctttcaactg ataaaaccat caaaatcagc    420
aatggtctgt cgaagttaac aaccgacctg tttgacaaga agtttgagga ttgggcgtat    480
caatacaaag aggacatgcc aaacttctgg cgtcaagata tcgctgaact tgaacagaag    540
ctgcaagtgt ctgcaaacgc caaagatcaa aagttttata aaggtatcat taaaaagtta    600
aaaaacaaaa tccaaaagtc cgagttaaag cagaaaccc ataaggggtt atacagtcct    660
acagaatctc tgcaactgtt ggagtggttg gttcggcggg gggacattaa attaacatac    720
ctggaaatcg ggaaagagaa tgaaaagctt aatgaacttg taccacttgt tgaactcaag    780
gatattcacc gcaattttaa taattttgca acgtacctct ctggtttttc caagaaccgc    840
gagaatgtgt attcgacaaa gttcgatcgg cggtcgggt ataaagcgac ttcggtcatt    900
gcccgtactt cgagcagaa cttgatgttt tgcctcggca acatcgcgaa atggcataaa    960
gtgacggagt tcatcaatca ggccaataac tacgaactgc tccaagaaca cggcatcgac   1020
tggaacaagc agatcgcggc tctggagcat aagttggatg tgtgtcttgc agaatttttt   1080
gcgttgaata acttttccca aactcttgca caacaaggta ttgaaaagta caatcaagtt   1140
ttggctggga tcgcagaaat tgctgggcaa ccaaagacac aggggcttaa tgaacttatt   1200
aacttggccc gccaaaaact tagcgcgaaa cgcagtcagc tcccgacctt acagctgctt   1260
tacaagcaaa tccttagcaa aggcgataaa ccgttcattg acgacttcaa gtccgatcaa   1320
gagctgatcg cagagctgaa tgaatttgtc tcgtcgcaaa tccacggcga gcatggcgcc   1380
atcaagctta tcaatcatga actcgaatcg ttcatcaacg aggcccgtgc agcgcagcaa   1440
caaatttacg tccctaaaga caaacttact gaattgtctc ttttactcac cgggagttgg   1500
caagcaatta atcagtggcg ctataagctg ttcgatcaga acaacttga caaacaacag   1560
aagcaataca gtttctcgct ggcgcaagtc gaacggtggc tggctacgga agtagagcag   1620
caaaatttct accagacaga aaagaacgg caacagcaca aagatccca accagcgaac   1680
gttacgactt cctcagacgg gcactctatt ctcaccgcct tcgaacagca ggtacagacc   1740
ctgctcacta atatctgcgt cgccgcagag aagtaccggc aacttagtga caattcttacg   1800
gcgattgaca aacaacggga gagtgagtca agcaagggct tcgagcaaat cgccgtaatc   1860
aaaaccttgc ttgacgcctg caatgagctt aaccatttcc tggcgcggtt cactgtgaat   1920
aaaaaagaca agctcccaga agaccgtgcc gagttttggt atgaaaagct tcaagcatac   1980
attgatgcat tcccgattta cgaactttac aacaaggtgc ggaattacct ctctaaaaag   2040
cctttcagca cggaaaaagt aaagatcaat tttgataatt ctcactttct ctctggttgg   2100
actgcggact acgagcggca tagtgcttta ttgtttaagt tcaacgagaa ttatcttctg   2160
ggcgtggtga acgaaaacct ttcttccgag gaagaagaaa agttgaagct cgttggtggc   2220
gaggagcacg caaagcggtt tatttacgat tttcagaaga ttgataactc aaatccaccg   2280
cgggtattca tccgcagcaa aggcagttca tttgctcctg cagttgagaa ataccaactc   2340
ccaattgggg acatcatcga tatctatgac caaggcaagt ttaaaacaga acacaaaaag   2400
aagaatgaag ctgaatttaa agactccctt gttcgcttaa tcgactactt taagttgggt   2460
ttcagccggc acgactccta caagcattac ccatttaaat ggaaggccag tcaccagtat   2520
tctgatattg ccgaattcta cgcgcacact gcaagtctct gttatacttt gaaagaagag   2580
aacatcaact ttaatgtact tcgtgagtta tcgtctgcag gcaaggttta tttatttgaa   2640
atctacaata aggatttctc caagaacaaa cgcgggcaag ggcgtgataa ccttcatact   2700
tcctattgga agttactgtt ttctgcggag aaccttaaag acgtcgtgtt aaagctgaac   2760
ggccaggccg agatcttta ccggccagca tcgctgacgc agctaaggc gtatacccac   2820
aaaaaaggtg aagtcctgaa gcacaaagcc tacagcaagg tttgggaagc tcttgattcg   2880
ccgattggga cgcgtttatc ttgggatgac gctttgaaga ttccaagcat cacggagaaa   2940
actaaccaca ataatcagcg cgtagttcag tacaatgggc aagagatcgg ccgcaaggcg   3000
gagtttgcta ttatcaaaaa tcgtcggtat tccgtcgaca aattcttgtt ccactgcccg   3060
attacattga actttaaggc aaacggtcaa gacaatatta acgctcgtgt gaatcaattc   3120
ctcgctaaca ataaaaaaat taacattatt gggattgatc gtggggagaa gcacctgctg   3180
tacatctcag taattaatca gcagggcgag gtgttgcatc aagagagttt caatacgatc   3240
acgaactctt atcaaacggc caacggggaa aagcgtcaac tcgtaaccga tcatcaccag   3300
aaactggata tgtcggagga taagcgggac aaggctcgca aatcctggag cacaatcgag   3360
aacattaaag aactgaaggc tgggtactta agtcacgtgg ttcaccgctt agcccaattg   3420
attatcgaat ttaatgcgat tgtggctctc gaggatctga accatggctt caaacgcggt   3480
cggtttaaga ttgaaaagca agtataccaa aagttcgaga aggcactgat cgataagctg   3540
tcctaccttg cgttcaaaga ccgtacctcg tgtttggaaa cggggcacta tctcaatgcc   3600
tttcagttga cctcgaagtt taagggcttt aataatttag gaagcaaag tgggatcctc   3660
ttttatgtaa atgctgatta cacttcaact accgatcctt tgactggtta catcaagaac   3720
gtgtataaaa cctatagctc cgttaaagac tctacggaat tctggcagcg cttcaattca   3780
attcgttaca tcgcttcaga aatcgctttt gaattctcat acgatcttgc tgacttgaag   3840
cagaaatcgc ttgaatcaaa aaccaagcag acgcctttag ctaaaactca gtggaccgtg   3900
agttctcatg tgactcggag ttattataat cagcagacta acaacacga actctttgaa   3960
gtcacggccc ggatccaaca gctgttatca aaagccgaga ttagttacca gcatcagaat   4020
gatctgattc cagcgcttgc gagctgccag tcgaaggccg tgcataaaga attaatttgg   4080
cttttaact cgatcctgac aatgcgcgtc acagattctt cgaagccaag tgcaactagc   4140
gaaaatgact tcatcctcag cccagtagcc cctattttg attcgcgcaa tcttaacaaa   4200
cagcttcctg agaacggcga tgcgaacggg gcatataata ttgcacgaa agggatcatg   4260
ctgttagagc ggatcggtga ttttgtacca gaagtaata aaaagtaccc ggatttgctc   4320
atccggaaca acgactggca gaactttgtc caacgtccgg agatggtcaa taaacaaaaa   4380
aagaagctgg ttaagctgaa aactgaatat tctaatggtt cattatttaa cgacctggca   4440
ttcaaaggcg cgccaaaaag gccggcgcc acgaaaaagg ccggcaggc aaaaaagaaa   4500
aaggctagcg gcacggcgc cggatcccca aagaagaaaa ggaaggttga agaccccaag   4560
aaaaagagga aggtgtgata a                                             4581
```

SEQ ID NO: 118      moltype = RNA   length = 56
FEATURE              Location/Qualifiers
misc_feature      1..56
                     note = synthetic sequence
misc_difference   37..56

```
                    note = misc_feature - n is a, c, g, or u
source              1..56
                    mol_type = other RNA
                    organism = synthetic construct
SEQUENCE: 118
gtctaaaaga ccatatgaat ttctactttc gtagatnnnn nnnnnnnnnn nnnnnn          56

SEQ ID NO: 119      moltype = RNA   length = 56
FEATURE             Location/Qualifiers
misc_feature        1..56
                    note = synthetic sequence
misc_difference     37..56
                    note = misc_feature - n is a, c, g, or u
source              1..56
                    mol_type = other RNA
                    organism = synthetic construct
SEQUENCE: 119
gtctaaaggc cttataaaat ttctactgtc gtagatnnnn nnnnnnnnnn nnnnnn          56

SEQ ID NO: 120      moltype = RNA   length = 56
FEATURE             Location/Qualifiers
misc_feature        1..56
                    note = synthetic sequence
misc_difference     37..56
                    note = misc_feature - n is a, c, g, or u
source              1..56
                    mol_type = other RNA
                    organism = synthetic construct
SEQUENCE: 120
gtctatacag acactttaat ttctactatt gtagatnnnn nnnnnnnnnn nnnnnn          56

SEQ ID NO: 121      moltype = RNA   length = 56
FEATURE             Location/Qualifiers
misc_feature        1..56
                    note = synthetic sequence
misc_difference     37..56
                    note = misc_feature - n is a, c, g, or u
source              1..56
                    mol_type = other RNA
                    organism = synthetic construct
SEQUENCE: 121
gtctgaaaga caagtataat ttctactatt gtagatnnnn nnnnnnnnnn nnnnnn          56

SEQ ID NO: 122      moltype = RNA   length = 56
FEATURE             Location/Qualifiers
misc_feature        1..56
                    note = synthetic sequence
misc_difference     37..56
                    note = misc_feature - n is a, c, g, or u
source              1..56
                    mol_type = other RNA
                    organism = synthetic construct
SEQUENCE: 122
ggctataagc cttgtataat ttctactatt gtagatnnnn nnnnnnnnnn nnnnnn          56

SEQ ID NO: 123      moltype = RNA   length = 56
FEATURE             Location/Qualifiers
misc_feature        1..56
                    note = synthetic sequence
misc_difference     37..56
                    note = misc_feature - n is a, c, g, or u
source              1..56
                    mol_type = other RNA
                    organism = synthetic construct
SEQUENCE: 123
gttgaaactg taagcggaat gtctacttgg gtagatnnnn nnnnnnnnnn nnnnnn          56

SEQ ID NO: 124      moltype = RNA   length = 56
FEATURE             Location/Qualifiers
misc_feature        1..56
                    note = synthetic sequence
misc_difference     37..56
                    note = misc_feature - n is a, c, g, or u
source              1..56
                    mol_type = other RNA
                    organism = synthetic construct
SEQUENCE: 124
gcatgagaac catgcatttc taaggtactc caaaacnnnn nnnnnnnnnn nnnnnn          56
```

```
SEQ ID NO: 125           moltype = RNA   length = 56
FEATURE                  Location/Qualifiers
misc_feature             1..56
                         note = synthetic sequence
misc_difference          37..56
                         note = misc_feature - n is a, c, g, or u
source                   1..56
                         mol_type = other RNA
                         organism = synthetic construct
SEQUENCE: 125
gttgagtaac cttaaataat ttctactgtt gtagatnnnn nnnnnnnnnn nnnnnn        56

SEQ ID NO: 126           moltype = RNA   length = 56
FEATURE                  Location/Qualifiers
misc_feature             1..56
                         note = synthetic sequence
misc_difference          37..56
                         note = misc_feature - n is a, c, g, or u
source                   1..56
                         mol_type = other RNA
                         organism = synthetic construct
SEQUENCE: 126
atctacaaca gtagaaattt aagctaaggc ttagacnnnn nnnnnnnnnn nnnnnn        56

SEQ ID NO: 127           moltype = RNA   length = 40
FEATURE                  Location/Qualifiers
misc_feature             1..40
                         note = synthetic sequence
misc_difference          21..40
                         note = misc_feature - n is a, c, g, or u
source                   1..40
                         mol_type = other RNA
                         organism = synthetic construct
SEQUENCE: 127
taatttctac tcttgtagat nnnnnnnnnn nnnnnnnnnn                          40

SEQ ID NO: 128           moltype = RNA   length = 40
FEATURE                  Location/Qualifiers
misc_feature             1..40
                         note = synthetic sequence
misc_difference          21..40
                         note = misc_feature - n is a, c, g, or u
source                   1..40
                         mol_type = other RNA
                         organism = synthetic construct
SEQUENCE: 128
taatttctac tcttgtagat nnnnnnnnnn nnnnnnnnnn                          40

SEQ ID NO: 129           moltype = RNA   length = 64
FEATURE                  Location/Qualifiers
misc_feature             1..64
                         note = Synthetic Sequence
misc_difference          37..64
                         note = misc_feature - n is a, c, g, or u
source                   1..64
                         mol_type = other RNA
                         organism = synthetic construct
SEQUENCE: 129
gtctaaaaga ccatatgaat ttctactttc gtagatnnnn nnnnnnnnn nnnnnnnnnn     60
nnnn                                                                64

SEQ ID NO: 130           moltype = RNA   length = 63
FEATURE                  Location/Qualifiers
misc_feature             1..63
                         note = Synthetic Sequence
misc_difference          37..63
                         note = misc_feature - n is a, c, g, or u
source                   1..63
                         mol_type = other RNA
                         organism = synthetic construct
SEQUENCE: 130
gtctaaaggc cttataaaat ttctactgtc gtagatnnnn nnnnnnnnn nnnnnnnnnn     60
nnn                                                                 63

SEQ ID NO: 131           moltype = RNA   length = 62
FEATURE                  Location/Qualifiers
misc_feature             1..62
                         note = Synthetic Sequence
misc_difference          37..62
```

```
                        note = misc_feature - n is a, c, g, or u
source                  1..62
                        mol_type = other RNA
                        organism = synthetic construct
SEQUENCE: 131
gtctatacag acactttaat ttctactatt gtagatnnnn nnnnnnnnnn nnnnnnnnnn   60
nn                                                                 62

SEQ ID NO: 132          moltype = RNA   length = 62
FEATURE                 Location/Qualifiers
misc_feature            1..62
                        note = Synthetic Sequence
misc_difference         37..62
                        note = misc_feature - n is a, c, g, or u
source                  1..62
                        mol_type = other RNA
                        organism = synthetic construct
SEQUENCE: 132
gtctgaaaga caagtataat ttctactatt gtagatnnnn nnnnnnnnnn nnnnnnnnnn   60
nn                                                                 62

SEQ ID NO: 133          moltype = RNA   length = 61
FEATURE                 Location/Qualifiers
misc_feature            1..61
                        note = Synthetic Sequence
misc_difference         37..61
                        note = misc_feature - n is a, c, g, or u
source                  1..61
                        mol_type = other RNA
                        organism = synthetic construct
SEQUENCE: 133
ggctataagc cttgtataat ttctactatt gtagatnnnn nnnnnnnnnn nnnnnnnnnn   60
n                                                                  61

SEQ ID NO: 134          moltype = RNA   length = 61
FEATURE                 Location/Qualifiers
misc_feature            1..61
                        note = Synthetic Sequence
misc_difference         37..61
                        note = misc_feature - n is a, c, g, or u
source                  1..61
                        mol_type = other RNA
                        organism = synthetic construct
SEQUENCE: 134
gttgaaactg taagcggaat gtctacttgg gtagatnnnn nnnnnnnnnn nnnnnnnnnn   60
n                                                                  61

SEQ ID NO: 135          moltype = RNA   length = 61
FEATURE                 Location/Qualifiers
misc_feature            1..61
                        note = Synthetic Sequence
misc_difference         37..61
                        note = misc_feature - n is a, c, g, or u
source                  1..61
                        mol_type = other RNA
                        organism = synthetic construct
SEQUENCE: 135
gcatgagaac catgcatttc taaggtactc caaaacnnnn nnnnnnnnnn nnnnnnnnnn   60
n                                                                  61

SEQ ID NO: 136          moltype = RNA   length = 60
FEATURE                 Location/Qualifiers
misc_feature            1..60
                        note = Synthetic Sequence
misc_difference         37..60
                        note = misc_feature - n is a, c, g, or u
source                  1..60
                        mol_type = other RNA
                        organism = synthetic construct
SEQUENCE: 136
gttgagtaac cttaaataat ttctactgtt gtagatnnnn nnnnnnnnnn nnnnnnnnnn   60

SEQ ID NO: 137          moltype = RNA   length = 61
FEATURE                 Location/Qualifiers
misc_feature            1..61
                        note = Synthetic Sequence
misc_difference         37..61
                        note = misc_feature - n is a, c, g, or u
source                  1..61
```

```
                        mol_type = other RNA
                        organism = synthetic construct
SEQUENCE: 137
atctacaaca gtagaaattt aagctaaggc ttagacnnnn nnnnnnnnnn nnnnnnnnnn    60
n                                                                   61

SEQ ID NO: 138          moltype = RNA   length = 56
FEATURE                 Location/Qualifiers
misc_feature            1..56
                        note = Synthetic Sequence
misc_difference         36..56
                        note = misc_feature - n is a, c, g, or u
source                  1..56
                        mol_type = other RNA
                        organism = synthetic construct
SEQUENCE: 138
gtcaaaagac ctttttaatt tctactcttg tagatnnnnn nnnnnnnnnn nnnnnn        56

SEQ ID NO: 139          moltype = RNA   length = 44
FEATURE                 Location/Qualifiers
misc_feature            1..44
                        note = Synthetic Sequence
misc_difference         21..44
                        note = misc_feature - n is a, c, g, or u
source                  1..44
                        mol_type = other RNA
                        organism = synthetic construct
SEQUENCE: 139
taatttctac tcttgtagat nnnnnnnnnn nnnnnnnnnn nnnn                     44

SEQ ID NO: 140          moltype = RNA   length = 56
FEATURE                 Location/Qualifiers
misc_feature            1..56
                        note = synthetic sequence
source                  1..56
                        mol_type = other RNA
                        organism = synthetic construct
SEQUENCE: 140
gtctaaaaga ccatatgaat ttctactttc gtagatctga tggtccatgt ctgtta        56

SEQ ID NO: 141          moltype = RNA   length = 56
FEATURE                 Location/Qualifiers
misc_feature            1..56
                        note = synthetic sequence
source                  1..56
                        mol_type = other RNA
                        organism = synthetic construct
SEQUENCE: 141
gtctaaaggc cttataaaat ttctactgtc gtagatctga tggtccatgt ctgtta        56

SEQ ID NO: 142          moltype = RNA   length = 56
FEATURE                 Location/Qualifiers
misc_feature            1..56
                        note = synthetic sequence
source                  1..56
                        mol_type = other RNA
                        organism = synthetic construct
SEQUENCE: 142
gtctatacag acactttaat ttctactatt gtagatctga tggtccatgt ctgtta        56

SEQ ID NO: 143          moltype = RNA   length = 56
FEATURE                 Location/Qualifiers
misc_feature            1..56
                        note = synthetic sequence
source                  1..56
                        mol_type = other RNA
                        organism = synthetic construct
SEQUENCE: 143
gtctgaaaga caagtataat ttctactatt gtagatctga tggtccatgt ctgtta        56

SEQ ID NO: 144          moltype = RNA   length = 56
FEATURE                 Location/Qualifiers
misc_feature            1..56
                        note = synthetic sequence
source                  1..56
                        mol_type = other RNA
                        organism = synthetic construct
SEQUENCE: 144
ggctataagc cttgtataat ttctactatt gtagatctga tggtccatgt ctgtta        56
```

```
SEQ ID NO: 145          moltype = RNA   length = 56
FEATURE                 Location/Qualifiers
misc_feature            1..56
                        note = synthetic sequence
source                  1..56
                        mol_type = other RNA
                        organism = synthetic construct
SEQUENCE: 145
gttgaaactg taagcggaat gtctacttgg gtagatctga tggtccatgt ctgtta        56

SEQ ID NO: 146          moltype = RNA   length = 56
FEATURE                 Location/Qualifiers
misc_feature            1..56
                        note = synthetic sequence
source                  1..56
                        mol_type = other RNA
                        organism = synthetic construct
SEQUENCE: 146
gcatgagaac catgcatttc taaggtactc caaaacctga tggtccatgt ctgtta        56

SEQ ID NO: 147          moltype = RNA   length = 56
FEATURE                 Location/Qualifiers
misc_feature            1..56
                        note = synthetic sequence
source                  1..56
                        mol_type = other RNA
                        organism = synthetic construct
SEQUENCE: 147
gttgagtaac cttaaataat ttctactgtt gtagatctga tggtccatgt ctgtta        56

SEQ ID NO: 148          moltype = RNA   length = 56
FEATURE                 Location/Qualifiers
misc_feature            1..56
                        note = synthetic sequence
source                  1..56
                        mol_type = other RNA
                        organism = synthetic construct
SEQUENCE: 148
atctacaaca gtagaaattt aagctaaggc ttagacctga tggtccatgt ctgtta        56

SEQ ID NO: 149          moltype = RNA   length = 40
FEATURE                 Location/Qualifiers
misc_feature            1..40
                        note = synthetic sequence
source                  1..40
                        mol_type = other RNA
                        organism = synthetic construct
SEQUENCE: 149
taatttctac tcttgtagat ctgatggtcc atgtctgtta                          40

SEQ ID NO: 150          moltype = RNA   length = 40
FEATURE                 Location/Qualifiers
misc_feature            1..40
                        note = synthetic sequence
source                  1..40
                        mol_type = other RNA
                        organism = synthetic construct
SEQUENCE: 150
taatttctac tcttgtagat ctgatggtcc atgtctgtta                          40

SEQ ID NO: 151          moltype = AA    length = 6
FEATURE                 Location/Qualifiers
source                  1..6
                        mol_type = protein
                        organism = synthetic construct
SEQUENCE: 151
HHHHHH                                                                6

SEQ ID NO: 152          moltype = AA    length = 7
FEATURE                 Location/Qualifiers
source                  1..7
                        mol_type = protein
                        organism = synthetic construct
SEQUENCE: 152
GHHHHHH                                                               7
```

What is claimed is:

1. A nucleic acid-guided nuclease system comprising:
   an engineered nucleic acid-guided nuclease, wherein the engineered nucleic acid-guided nuclease comprises a polypeptide sequence having at least 100% homology to a polypeptide consisting of SEQ ID NO: 94 (ABW8), 29 (ABW3), 81 (ABW7), 107 (ABW9), 3 (ABW1), 16 (ABW2), 42 (ABW4), 55 (ABW5), or 68 (ABW6), or a polynucleotide encoding the sequence; and
   a guide nucleic acid compatible with the nucleic acid-guided nuclease and comprising a guide sequence complementary to a target sequence in a target polynucleotide, or a polynucleotide encoding the guide nucleic acid.

2. The system of claim 1 comprising the polynucleotide encoding the nuclease sequence, wherein the polynucleotide has at least 100% homology to one of the polynucleotides consisting of one of SEQ ID NO: 95-104 (ABW8 variants 1-10), 30-39 (ABW3 variants 1-10), 82-91 (ABW7 variants 1-10), 108-117 (ABW9 variants 1-10), 4-13 (ABW1 variants 1-10), 17-26 (ABW2 variants 1-10), 43-52 (ABW4 variants 1-10), 56-65 (ABW5 variants 1-10), or 69-78 (ABW6 variants 1-10).

3. The system of claim 1 wherein the guide nucleic acid is a guide RNA (gRNA).

4. The system of claim 3 wherein the gRNA is a split gRNA.

5. The system of claim 3 wherein the gRNA comprises one or more chemical modifications.

6. The system of claim 1 further comprising an editing sequence.

7. The system of claim 6 wherein the editing sequence comprises a sequence to be integrated into the target polynucleotide.

8. The system of claim 6 wherein the target polynucleotide is contained within a cell and the sequence to be integrated is exogenous to the cell.

9. A method of modifying a target polynucleotide comprising a target sequence comprising contacting the target polynucleotide with a system comprising an engineered nucleic acid-guided nuclease, wherein the engineered nucleic acid-guided nuclease comprises a polypeptide sequence having 100% homology to a polypeptide consisting of SEQ ID NO: 94 (ABW8), 29 (ABW3), 81 (ABW7), 107 (ABW9), 3 (ABW1), 16 (ABW2), 42 (ABW4), 55 (ABW5), or 68 (ABW6); and a guide nucleic acid compatible with the nucleic acid-guided nuclease and comprising a guide sequence complementary to the target sequence in the target polynucleotide; and
   allowing the nuclease and the guide nucleic acid to modify the target polynucleotide.

10. The method of claim 9 wherein the guide nucleic acid is a guide RNA (gRNA).

11. The method of claim 10 wherein the gRNA is a dual gRNA.

12. The method of claim 10 wherein the gRNA comprises one or more chemical modifications.

13. The method of claim 9 wherein the target polynucleotide is contained in a cell.

14. The method of claim 13 wherein the nuclease and guide nucleic acid are combined outside the cell to form a ribonucleoprotein (RNP) and the RNP is transfected into the cell.

15. The method of claim 14 wherein the RNP is transfected by electroporation.

16. The method of claim 9 wherein the modification comprises a strand break in the target polynucleotide.

17. The method of claim 16 further comprising contacting the target polynucleotide with an editing template comprising a polynucleotide having a change in sequence relative to the sequence of the portion of the target polynucleotide comprising the strand break.

18. The method according to claim 17 wherein the guide nucleic acid and the editing template are provided as a single nucleic acid.

19. The method according to claim 17 wherein the editing template comprises a sequence that is exogenous to a cell comprising the target polynucleotide.

* * * * *